US012531156B2

(12) United States Patent
Shelton, IV et al.

(10) Patent No.: US 12,531,156 B2
(45) Date of Patent: Jan. 20, 2026

(54) METHOD FOR ADVANCED ALGORITHM SUPPORT

(71) Applicant: Cilag GmbH International, Zug (CH)

(72) Inventors: Frederick E. Shelton, IV, Hillsboro, OH (US); Aaron Chow, Cincinnati, OH (US); Kevin M. Fiebig, Cincinnati, OH (US); Shane R. Adams, Lebanon, OH (US); David C. Yates, Marrow, OH (US); Jason L. Harris, Lebanon, OH (US); Taylor W. Aronhalt, Loveland, OH (US); Jacqueline Corrigan Aronhalt, Loveland, OH (US)

(73) Assignee: Cilag GmbH International, Zug (CH)

( * ) Notice: Subject to any disclaimer, the term of this patent is extended or adjusted under 35 U.S.C. 154(b) by 0 days.

(21) Appl. No.: 18/092,025

(22) Filed: Dec. 30, 2022

(65) Prior Publication Data

US 2024/0221937 A1 Jul. 4, 2024

(51) Int. Cl.
*G16H 50/20* (2018.01)
*G16H 50/70* (2018.01)

(52) U.S. Cl.
CPC ............. *G16H 50/20* (2018.01); *G16H 50/70* (2018.01)

(58) Field of Classification Search
CPC ........ G16H 50/20; G16H 50/70; G16H 20/40; G16H 40/20; G16H 40/40; G16H 40/63; G16H 40/67
USPC .......................................................... 705/2, 3
See application file for complete search history.

(56) References Cited

U.S. PATENT DOCUMENTS

| | | | |
|---|---|---|---|
| 1,015,727 | A | 1/1912 | Drury |
| 6,463,417 | B1 | 10/2002 | Schoenberg |
| 7,093,147 | B2 | 8/2006 | Farkas et al. |
| 7,515,094 | B2 | 4/2009 | Keller, III |
| 7,555,787 | B2 | 6/2009 | Clercq |
| 7,853,437 | B2 | 12/2010 | Seguin et al. |
| 7,869,977 | B2 | 1/2011 | Lewis et al. |
| 7,877,621 | B2 | 1/2011 | Jacoby et al. |
| 8,069,490 | B2 | 11/2011 | Gross et al. |
| 8,122,498 | B1 | 2/2012 | Gordon et al. |

(Continued)

FOREIGN PATENT DOCUMENTS

| | | | |
|---|---|---|---|
| CN | 108430339 | A | 8/2018 |
| WO | 2021113168 | A1 | 6/2021 |

OTHER PUBLICATIONS

Ahmadi, Elsevier, 2018, pp. 48-53.

(Continued)

*Primary Examiner* — Jason S Tiedeman
(74) *Attorney, Agent, or Firm* — Condo Roccia Koptiw LLP

(57) ABSTRACT

A surgical computer-implement surgical system may include a surgical computing system (e.g., a surgical hub), one or more surgical data sources in communication with the surgical computing system, a surgical device in communication with the surgical computing system, and a processor. Data generated by the one or more surgical data sources may be received by the processor. Such data may be used, by the processor, to train a machine learning (ML) model (e.g., a neural network). ML model may be deployed to affect an operation of the surgical device. For example, the ML model may be deployed to the surgical hub to affect an operation of the surgical device.

20 Claims, 74 Drawing Sheets

(56) References Cited

U.S. PATENT DOCUMENTS

| | | | |
|---|---|---|---|
| 8,242,793 B2 | 8/2012 | Kumhyr et al. | |
| 8,245,295 B2 | 8/2012 | Park et al. | |
| 8,255,341 B2 | 8/2012 | Gross et al. | |
| 8,332,945 B2 | 12/2012 | Kim et al. | |
| 8,457,913 B2 | 6/2013 | Zwinger et al. | |
| 8,537,050 B2 | 9/2013 | Freeman et al. | |
| 8,643,539 B2 | 2/2014 | Pauly et al. | |
| 8,825,823 B2 | 9/2014 | Keller, III | |
| 8,892,903 B1 | 11/2014 | Trimberger | |
| 9,059,189 B2 | 6/2015 | Keller, III et al. | |
| 9,202,008 B1 | 12/2015 | Frederick et al. | |
| 9,262,632 B2 | 2/2016 | Reed et al. | |
| 9,268,938 B1 | 2/2016 | Aguayo Gonzalez et al. | |
| 9,345,481 B2 | 5/2016 | Hall et al. | |
| 9,411,009 B1 | 8/2016 | Aguayo Gonzalez et al. | |
| 9,558,349 B2 | 1/2017 | Reed et al. | |
| 9,558,350 B2 | 1/2017 | Reed et al. | |
| 9,687,230 B2 | 6/2017 | Leimbach et al. | |
| 10,157,278 B2 | 12/2018 | Aguayo Gonzalez et al. | |
| 10,390,895 B2 | 8/2019 | Henderson et al. | |
| 10,412,071 B2 | 9/2019 | Maher et al. | |
| 10,695,081 B2 | 6/2020 | Shelton, IV et al. | |
| 10,713,540 B2 | 7/2020 | Zhang et al. | |
| 10,729,502 B1 | 8/2020 | Wolf et al. | |
| 10,842,523 B2 | 11/2020 | Shelton, IV et al. | |
| 10,859,609 B2 | 12/2020 | Aguayo Gonzalez et al. | |
| 10,872,140 B2 | 12/2020 | Aguayo Gonzalez et al. | |
| 10,881,399 B2 | 1/2021 | Shelton, IV et al. | |
| 10,902,944 B1 | 1/2021 | Casey et al. | |
| 10,932,808 B2 | 3/2021 | Shelton, IV et al. | |
| 10,970,387 B2 | 4/2021 | Aguayo Gonzalez et al. | |
| 11,144,632 B2 | 10/2021 | Aguayo Gonzalez et al. | |
| 11,202,570 B2 | 12/2021 | Shelton, IV et al. | |
| 11,389,164 B2 | 7/2022 | Yates et al. | |
| 11,389,188 B2 | 7/2022 | Gee et al. | |
| 11,399,858 B2 | 8/2022 | Sawhney et al. | |
| 11,406,382 B2 | 8/2022 | Shelton, IV et al. | |
| 11,410,259 B2 | 8/2022 | Harris et al. | |
| 11,413,042 B2 | 8/2022 | Shelton, IV et al. | |
| 11,419,606 B2 | 8/2022 | Overmyer et al. | |
| 11,419,630 B2 | 8/2022 | Yates et al. | |
| 11,419,667 B2 | 8/2022 | Messerly et al. | |
| 11,423,007 B2 | 8/2022 | Shelton, IV et al. | |
| 11,424,027 B2 | 8/2022 | Shelton, IV | |
| D964,564 S | 9/2022 | Boudreaux | |
| 11,432,885 B2 | 9/2022 | Shelton, IV et al. | |
| 11,446,052 B2 | 9/2022 | Shelton, IV et al. | |
| 11,457,944 B2 | 10/2022 | Scoggins | |
| 11,464,511 B2 | 10/2022 | Timm et al. | |
| 11,464,513 B2 | 10/2022 | Shelton, IV et al. | |
| 11,464,514 B2 | 10/2022 | Yates et al. | |
| 11,464,532 B2 | 10/2022 | Nott et al. | |
| 11,464,535 B2 | 10/2022 | Shelton, IV et al. | |
| 11,464,559 B2 | 10/2022 | Nott et al. | |
| 11,464,590 B1 | 10/2022 | Roh et al. | |
| 11,464,971 B2 | 10/2022 | Schepis et al. | |
| 11,471,156 B2 | 10/2022 | Shelton, IV et al. | |
| 11,471,206 B2 | 10/2022 | Henderson et al. | |
| 11,478,244 B2 | 10/2022 | Dinardo et al. | |
| 11,504,191 B2 | 11/2022 | Mccloud et al. | |
| 11,504,192 B2 | 11/2022 | Shelton, IV et al. | |
| 11,510,671 B2 | 11/2022 | Shelton, IV et al. | |
| 11,510,675 B2 | 11/2022 | Shelton, IV et al. | |
| 11,510,720 B2 | 11/2022 | Morgan et al. | |
| 11,510,741 B2 | 11/2022 | Shelton, IV et al. | |
| 11,517,309 B2 | 12/2022 | Bakos et al. | |
| 11,517,315 B2 | 12/2022 | Huitema et al. | |
| 11,529,187 B2 | 12/2022 | Shelton, IV et al. | |
| 11,534,196 B2 | 12/2022 | Black | |
| 11,540,824 B2 | 1/2023 | Shelton, IV et al. | |
| 11,540,855 B2 | 1/2023 | Messerly et al. | |
| 11,547,468 B2 | 1/2023 | Shelton, IV et al. | |
| 11,559,307 B2 | 1/2023 | Shelton, IV et al. | |
| 11,559,308 B2 | 1/2023 | Yates et al. | |
| 11,564,703 B2 | 1/2023 | Shelton, IV et al. | |
| 11,564,756 B2 | 1/2023 | Shelton, IV et al. | |
| 11,571,210 B2 | 2/2023 | Shelton, IV et al. | |
| 11,571,212 B2 | 2/2023 | Yates et al. | |
| 11,571,234 B2 | 2/2023 | Nott et al. | |
| 11,576,677 B2 | 2/2023 | Shelton, IV et al. | |
| 11,602,612 B2 | 3/2023 | Hara et al. | |
| 11,607,239 B2 | 3/2023 | Swensgard et al. | |
| 11,659,023 B2 | 5/2023 | Shelton, IV et al. | |
| 11,723,642 B2 | 8/2023 | Shelton, IV et al. | |
| 11,771,419 B2 | 10/2023 | Shelton, IV et al. | |
| 11,801,098 B2 | 10/2023 | Stokes et al. | |
| 11,809,552 B2 | 11/2023 | Aguayo Gonzalez et al. | |
| 11,818,052 B2 | 11/2023 | Shelton, IV et al. | |
| 11,871,901 B2 | 1/2024 | Shelton, IV et al. | |
| 11,937,769 B2 | 3/2024 | Shelton, IV et al. | |
| 11,969,142 B2 | 4/2024 | Harris et al. | |
| 12,003,594 B2 | 6/2024 | Mirth et al. | |
| 12,035,983 B2 | 7/2024 | Shelton, IV et al. | |
| 12,165,200 B1 | 12/2024 | Tilly et al. | |
| 12,334,200 B2 | 6/2025 | Wolf et al. | |
| 2001/0033180 A1 | 10/2001 | Swart et al. | |
| 2001/0037458 A1 | 11/2001 | Kean | |
| 2001/0051881 A1 | 12/2001 | Filler | |
| 2002/0001337 A1 | 1/2002 | Chauncey et al. | |
| 2002/0061668 A1 | 5/2002 | Fujimura | |
| 2002/0079881 A1 | 6/2002 | Hiromatsu | |
| 2003/0070105 A1 | 4/2003 | Launiainen | |
| 2004/0068386 A1 | 4/2004 | Smith et al. | |
| 2005/0144612 A1 | 6/2005 | Wang et al. | |
| 2005/0184028 A1 | 8/2005 | Baur et al. | |
| 2005/0184236 A1 | 8/2005 | Baur et al. | |
| 2006/0082488 A1 | 4/2006 | Keller | |
| 2006/0164115 A1 | 7/2006 | Komiya et al. | |
| 2006/0253762 A1 | 11/2006 | Schalick | |
| 2007/0024293 A1 | 2/2007 | Kosaka et al. | |
| 2007/0027459 A1* | 2/2007 | Horvath | A61B 90/98 606/147 |
| 2007/0028129 A1 | 2/2007 | Schumacher et al. | |
| 2007/0192140 A1 | 8/2007 | Gropper | |
| 2007/0220263 A1 | 9/2007 | Ziener et al. | |
| 2007/0257025 A1 | 11/2007 | Nordstrom et al. | |
| 2007/0283166 A1 | 12/2007 | Yami et al. | |
| 2008/0049853 A1 | 2/2008 | Franceschini et al. | |
| 2008/0054925 A1 | 3/2008 | Ohkura | |
| 2008/0088336 A1 | 4/2008 | Pommerenke | |
| 2008/0091975 A1 | 4/2008 | Kladko et al. | |
| 2008/0115001 A1 | 5/2008 | Schuette | |
| 2008/0191726 A1 | 8/2008 | Ku et al. | |
| 2008/0276111 A1 | 11/2008 | Jacoby et al. | |
| 2008/0285626 A1 | 11/2008 | Ma et al. | |
| 2008/0312953 A1 | 12/2008 | Claus | |
| 2009/0019546 A1 | 1/2009 | Park et al. | |
| 2009/0044057 A1 | 2/2009 | Choate et al. | |
| 2009/0049549 A1 | 2/2009 | Park et al. | |
| 2009/0088815 A1 | 4/2009 | Kalgren et al. | |
| 2009/0099830 A1 | 4/2009 | Gross et al. | |
| 2009/0172773 A1 | 7/2009 | Moore | |
| 2009/0216498 A1 | 8/2009 | Seguin et al. | |
| 2009/0306920 A1 | 12/2009 | Zwinger et al. | |
| 2010/0030497 A1 | 2/2010 | Zavadsky et al. | |
| 2010/0033199 A1 | 2/2010 | Komatsu et al. | |
| 2010/0033386 A1 | 2/2010 | Lewis et al. | |
| 2010/0100694 A1 | 4/2010 | Hwang et al. | |
| 2010/0100964 A1 | 4/2010 | Mahaffey et al. | |
| 2010/0123453 A1 | 5/2010 | Pauly et al. | |
| 2010/0132048 A1 | 5/2010 | Hall et al. | |
| 2010/0161525 A1 | 6/2010 | Gross et al. | |
| 2010/0213960 A1 | 8/2010 | Mok et al. | |
| 2010/0228222 A1* | 9/2010 | Williams | A61M 3/0202 604/113 |
| 2010/0237854 A1 | 9/2010 | Kumhyr et al. | |
| 2010/0313270 A1 | 12/2010 | Kim et al. | |
| 2010/0332199 A1 | 12/2010 | Dhanekula et al. | |
| 2011/0002186 A1 | 1/2011 | Buonpane et al. | |
| 2011/0095934 A1 | 4/2011 | Freeman et al. | |
| 2011/0112384 A1 | 5/2011 | Eisenhardt et al. | |
| 2012/0179812 A1 | 7/2012 | Keller, III | |
| 2012/0223403 A1 | 9/2012 | Keller, III et al. | |
| 2012/0226463 A1 | 9/2012 | Keller, III et al. | |

(56) References Cited

U.S. PATENT DOCUMENTS

| | | | |
|---|---|---|---|
| 2012/0278893 | A1 | 11/2012 | Jyothi et al. |
| 2013/0044003 | A1 | 2/2013 | Eguro et al. |
| 2013/0108145 | A1 | 5/2013 | Cobb et al. |
| 2013/0127442 | A1 | 5/2013 | Satoh et al. |
| 2013/0211792 | A1 | 8/2013 | Kang et al. |
| 2013/0218163 | A1 | 8/2013 | Frey |
| 2013/0318607 | A1 | 11/2013 | Reed et al. |
| 2014/0005743 | A1* | 1/2014 | Giuffrida ........... A61N 1/37247 607/45 |
| 2014/0100807 | A1 | 4/2014 | Rosenblatt et al. |
| 2014/0182373 | A1 | 7/2014 | Sbihli et al. |
| 2014/0195184 | A1 | 7/2014 | Maeda et al. |
| 2014/0218229 | A1 | 8/2014 | Pauly et al. |
| 2014/0223554 | A1 | 8/2014 | Roden, III |
| 2014/0259161 | A1 | 9/2014 | Kastner et al. |
| 2014/0263552 | A1 | 9/2014 | Hall et al. |
| 2014/0270423 | A1 | 9/2014 | Zellner et al. |
| 2014/0304826 | A1 | 10/2014 | Bytheway et al. |
| 2014/0309660 | A1 | 10/2014 | Yoon |
| 2015/0009073 | A1 | 1/2015 | Keller, III |
| 2015/0182694 | A1 | 7/2015 | Rosinko |
| 2016/0342791 | A1 | 11/2016 | Aguayo Gonzalez et al. |
| 2017/0068792 | A1 | 3/2017 | Reiner |
| 2017/0161485 | A1 | 6/2017 | Aguayo Gonzalez et al. |
| 2017/0202605 | A1 | 7/2017 | Shelton, IV et al. |
| 2017/0296213 | A1 | 10/2017 | Swensgard et al. |
| 2017/0310482 | A1 | 10/2017 | Reed et al. |
| 2017/0360512 | A1* | 12/2017 | Couture ................. A61B 34/30 |
| 2018/0011130 | A1 | 1/2018 | Aguayo Gonzalez et al. |
| 2018/0013779 | A1 | 1/2018 | Aguayo Gonzalez et al. |
| 2018/0049822 | A1 | 2/2018 | Henderson et al. |
| 2018/0221093 | A1 | 8/2018 | Hladio |
| 2018/0260665 | A1 | 9/2018 | Zhang et al. |
| 2018/0349212 | A1 | 12/2018 | Liu et al. |
| 2018/0360452 | A1 | 12/2018 | Shelton, IV et al. |
| 2019/0006047 | A1 | 1/2019 | Gorek et al. |
| 2019/0059929 | A1 | 2/2019 | Shelton, IV et al. |
| 2019/0073632 | A1 | 3/2019 | Laster et al. |
| 2019/0104437 | A1 | 4/2019 | Bartfai-walcott et al. |
| 2019/0104919 | A1 | 4/2019 | Shelton, IV et al. |
| 2019/0125455 | A1 | 5/2019 | Shelton, IV et al. |
| 2019/0197237 | A1 | 6/2019 | Aguayo Gonzalez et al. |
| 2019/0200844 | A1 | 7/2019 | Shelton, IV et al. |
| 2019/0200977 | A1 | 7/2019 | Shelton et al. |
| 2019/0200981 | A1 | 7/2019 | Harris et al. |
| 2019/0200997 | A1* | 7/2019 | Shelton, IV ........... G16H 20/40 |
| 2019/0201047 | A1 | 7/2019 | Yates et al. |
| 2019/0201102 | A1 | 7/2019 | Shelton, IV et al. |
| 2019/0201119 | A1 | 7/2019 | Harris et al. |
| 2019/0201123 | A1 | 7/2019 | Shelton, IV et al. |
| 2019/0201136 | A1 | 7/2019 | Shelton, IV et al. |
| 2019/0201137 | A1 | 7/2019 | Shelton, IV et al. |
| 2019/0201144 | A1 | 7/2019 | Shelton, IV et al. |
| 2019/0205441 | A1 | 7/2019 | Shelton et al. |
| 2019/0205567 | A1 | 7/2019 | Shelton, IV et al. |
| 2019/0206555 | A1 | 7/2019 | Morgan et al. |
| 2019/0206562 | A1 | 7/2019 | Shelton, IV et al. |
| 2019/0206564 | A1 | 7/2019 | Shelton, IV et al. |
| 2019/0206565 | A1 | 7/2019 | Shelton, IV |
| 2019/0206569 | A1 | 7/2019 | Shelton, IV et al. |
| 2019/0207857 | A1 | 7/2019 | Shelton, IV et al. |
| 2019/0272917 | A1 | 9/2019 | Couture et al. |
| 2020/0015901 | A1 | 1/2020 | Scheib et al. |
| 2020/0066391 | A1 | 2/2020 | Sachdeva et al. |
| 2020/0089866 | A1 | 3/2020 | Aguayo Gonzalez et al. |
| 2020/0168334 | A1 | 5/2020 | Mowery |
| 2020/0197592 | A1 | 6/2020 | Leinfellner et al. |
| 2020/0237452 | A1* | 7/2020 | Wolf ....................... G06F 3/048 |
| 2020/0246568 | A1 | 8/2020 | Steinhauer et al. |
| 2020/0268457 | A1 | 8/2020 | Wolf et al. |
| 2020/0273581 | A1 | 8/2020 | Wolf et al. |
| 2020/0345431 | A1 | 11/2020 | Patton |
| 2020/0405296 | A1 | 12/2020 | Shelton, IV et al. |
| 2021/0046280 | A1 | 2/2021 | Inukai et al. |
| 2021/0076966 | A1 | 3/2021 | Grantcharov et al. |
| 2021/0082579 | A1 | 3/2021 | Grady et al. |
| 2021/0128244 | A1 | 5/2021 | Couture et al. |
| 2021/0151146 | A1 | 5/2021 | Gupta et al. |
| 2021/0196302 | A1 | 7/2021 | Shelton, IV et al. |
| 2021/0196384 | A1 | 7/2021 | Shelton, IV et al. |
| 2021/0196386 | A1 | 7/2021 | Shelton, IV et al. |
| 2021/0210189 | A1 | 7/2021 | Casey et al. |
| 2021/0244290 | A1 | 8/2021 | Tan et al. |
| 2021/0244487 | A1 | 8/2021 | Beck |
| 2021/0298734 | A1 | 9/2021 | Jaramaz et al. |
| 2021/0307765 | A1 | 10/2021 | Dumpe et al. |
| 2021/0307833 | A1 | 10/2021 | Farley et al. |
| 2021/0313052 | A1 | 10/2021 | Makrinich et al. |
| 2021/0315579 | A1 | 10/2021 | Shelton, IV et al. |
| 2021/0322014 | A1 | 10/2021 | Shelton, IV et al. |
| 2021/0343017 | A1* | 11/2021 | Jordan ................... G16H 50/30 |
| 2021/0344880 | A1* | 11/2021 | Katra .................... G06T 7/0012 |
| 2021/0370790 | A1 | 12/2021 | Feldman |
| 2021/0375439 | A1 | 12/2021 | Mckinnon et al. |
| 2021/0391058 | A1 | 12/2021 | Kostrzewski et al. |
| 2022/0037011 | A1 | 2/2022 | Fryman et al. |
| 2022/0039822 | A1 | 2/2022 | Huang et al. |
| 2022/0075869 | A1 | 3/2022 | Aguayo Gonzalez et al. |
| 2022/0096163 | A1 | 3/2022 | Payyavula et al. |
| 2022/0104822 | A1 | 4/2022 | Shelton, IV et al. |
| 2022/0160443 | A1 | 5/2022 | Spykerman et al. |
| 2022/0189604 | A1 | 6/2022 | El-Khatib et al. |
| 2022/0230738 | A1 | 7/2022 | Shelton, IV et al. |
| 2022/0233119 | A1 | 7/2022 | Shelton, IV et al. |
| 2022/0233191 | A1 | 7/2022 | Shelton et al. |
| 2022/0238216 | A1 | 7/2022 | Shelton, IV et al. |
| 2022/0241027 | A1 | 8/2022 | Shelton, IV et al. |
| 2022/0249097 | A1 | 8/2022 | Shelton, IV et al. |
| 2022/0249168 | A1 | 8/2022 | Besier et al. |
| 2022/0265233 | A1 | 8/2022 | Boddington et al. |
| 2022/0286687 | A1 | 9/2022 | Bishop et al. |
| 2022/0313362 | A1 | 10/2022 | Casey et al. |
| 2022/0318270 | A1 | 10/2022 | Safary et al. |
| 2022/0323092 | A1 | 10/2022 | Shelton, IV et al. |
| 2022/0323095 | A1 | 10/2022 | Nott et al. |
| 2022/0323150 | A1 | 10/2022 | Yates et al. |
| 2022/0331011 | A1 | 10/2022 | Shelton, IV et al. |
| 2022/0331018 | A1 | 10/2022 | Parihar et al. |
| 2022/0331047 | A1 | 10/2022 | Shelton, IV et al. |
| 2022/0346792 | A1 | 11/2022 | Shelton, IV et al. |
| 2022/0367040 | A1 | 11/2022 | Sutherland et al. |
| 2022/0370117 | A1 | 11/2022 | Messerly et al. |
| 2022/0370126 | A1 | 11/2022 | Shelton, IV et al. |
| 2022/0370138 | A1 | 11/2022 | Shelton, IV et al. |
| 2022/0374414 | A1 | 11/2022 | Shelton, IV et al. |
| 2022/0387711 | A1 | 12/2022 | Caudill |
| 2022/0392621 | A1* | 12/2022 | George .................. G16H 20/60 |
| 2022/0395276 | A1 | 12/2022 | Yates et al. |
| 2022/0401099 | A1 | 12/2022 | Shelton, IV et al. |
| 2022/0406452 | A1 | 12/2022 | Shelton, IV |
| 2022/0409140 | A1 | 12/2022 | Cordonnier et al. |
| 2022/0409302 | A1 | 12/2022 | Shelton, IV et al. |
| 2023/0000518 | A1 | 1/2023 | Nott et al. |
| 2023/0020732 | A1 | 1/2023 | Guim et al. |
| 2023/0027978 | A1 | 1/2023 | Gaborit et al. |
| 2023/0028948 | A1 | 1/2023 | Rolls et al. |
| 2023/0037577 | A1 | 2/2023 | Kimball et al. |
| 2023/0057949 | A1 | 2/2023 | Tallent et al. |
| 2023/0064821 | A1 | 3/2023 | Shelton, IV |
| 2023/0092371 | A1 | 3/2023 | Yates et al. |
| 2023/0095002 | A1 | 3/2023 | Shelton, IV et al. |
| 2023/0097906 | A1 | 3/2023 | Shelton, IV et al. |
| 2023/0098538 | A1 | 3/2023 | Shelton, IV et al. |
| 2023/0098870 | A1 | 3/2023 | Harris et al. |
| 2023/0116571 | A1 | 4/2023 | Shelton, IV et al. |
| 2023/0146947 | A1 | 5/2023 | Shelton, IV et al. |
| 2023/0171266 | A1 | 6/2023 | Brunner et al. |
| 2023/0171304 | A1 | 6/2023 | Shelton, IV et al. |
| 2023/0187060 | A1 | 6/2023 | Morgan et al. |
| 2023/0190390 | A1 | 6/2023 | Shelton, IV et al. |
| 2023/0200889 | A1 | 6/2023 | Shelton, IV et al. |
| 2023/0210611 | A1 | 7/2023 | Shelton, IV et al. |
| 2023/0233245 | A1 | 7/2023 | Nott et al. |
| 2023/0263548 | A1 | 8/2023 | Shelton, IV et al. |

(56) References Cited

U.S. PATENT DOCUMENTS

| | | | | |
|---|---|---|---|---|
| 2023/0306296 | A1 | 9/2023 | Mukherjee | |
| 2023/0320792 | A1 | 10/2023 | Shelton, IV et al. | |
| 2023/0326193 | A1* | 10/2023 | Zia | G16H 40/63 705/2 |
| 2023/0334868 | A1 | 10/2023 | Hashimoto et al. | |
| 2023/0352133 | A1* | 11/2023 | Chen | G16H 30/20 |
| 2023/0355265 | A1 | 11/2023 | Nott et al. | |
| 2023/0377709 | A1 | 11/2023 | Shelton, IV et al. | |
| 2023/0389796 | A1 | 12/2023 | Shelton, IV et al. | |
| 2023/0395250 | A1 | 12/2023 | Denzinger et al. | |
| 2023/0396680 | A1 | 12/2023 | Kim | |
| 2023/0397960 | A1 | 12/2023 | Shelton, IV et al. | |
| 2024/0013895 | A1 | 1/2024 | Jin et al. | |
| 2024/0024027 | A1* | 1/2024 | Shelton | A61B 18/22 |
| 2024/0029858 | A1 | 1/2024 | Upadrasta et al. | |
| 2024/0049944 | A1 | 2/2024 | Kobayashi et al. | |
| 2024/0065550 | A1* | 2/2024 | Connor | A61M 60/546 |
| 2024/0065767 | A1 | 2/2024 | Cordonnier et al. | |
| 2024/0112768 | A1 | 4/2024 | Shelton, IV et al. | |
| 2024/0138919 | A1 | 5/2024 | Casey et al. | |
| 2024/0197173 | A1 | 6/2024 | Kok et al. | |
| 2024/0216065 | A1 | 7/2024 | Shelton, IV et al. | |
| 2024/0216081 | A1 | 7/2024 | Shelton, IV et al. | |
| 2024/0220763 | A1 | 7/2024 | Shelton, IV et al. | |
| 2024/0221878 | A1 | 7/2024 | Shelton, IV et al. | |
| 2024/0221892 | A1 | 7/2024 | Shelton, IV et al. | |
| 2024/0221893 | A1 | 7/2024 | Shelton, IV et al. | |
| 2024/0221894 | A1 | 7/2024 | Shelton, IV et al. | |
| 2024/0221895 | A1 | 7/2024 | Shelton, IV et al. | |
| 2024/0221896 | A1 | 7/2024 | Shelton, IV et al. | |
| 2024/0221897 | A1 | 7/2024 | Shelton, IV et al. | |
| 2024/0221923 | A1 | 7/2024 | Shelton, IV et al. | |
| 2024/0221924 | A1 | 7/2024 | Shelton, IV et al. | |
| 2024/0221931 | A1 | 7/2024 | Shelton, IV et al. | |
| 2024/0221960 | A1 | 7/2024 | Shelton, IV et al. | |
| 2024/0265536 | A1 | 8/2024 | Watanabe et al. | |
| 2024/0346374 | A1 | 10/2024 | Ni et al. | |
| 2025/0000510 | A1 | 1/2025 | Creamer et al. | |
| 2025/0127670 | A1 | 4/2025 | Sukumaran et al. | |
| 2025/0142289 | A1 | 5/2025 | Seo et al. | |

OTHER PUBLICATIONS

Alsallal et al., "A Machine Learning Technique to Detect Counterfeit Medicine Based on X-Ray Fluorescence Analyser", International Conference on Computing, Electronics & Communications Engineering (ICCECE), IEEE, 2018, pp. 118-122.

Anonymous, "Cloud computing", Wikipedia, the free encyclopedia, Dec. 22, 2022, pp. 1-24.

Asadizanjani, et al., "Counterfeit Electronics Detection Using Image Processing and Machine Learning", Journal of Physics Conference Series, vol. 787, 2017, pp. 1-6.

Domingues, et al., "Using Deep Learning Techniques in Medical Imaging: A Systematic Review of Applications on CT and PET", Artificial Intelligence Review, Nov. 21, 2019, pp. 4093-4160.

Qayyum et al., "Secure and Robust Machine Learning for Healthcare: A Survey", IEEE, Reviews in Biomedical Engineering, vol. 14, 2021, pp. 156-180.

Ralston et al., "Defeating Counterfeiters with Microscopic Dielets Embedded in Electronic Components", IEEE Computer Society, Computer, Aug. 2016, pp. 18-26.

Unberath et al., "The Impact of Machine Learning on 2D/3D Registration for Image-Guided Interventions: A Systemic Review and Perspective", Frontiers in Robotics and AI, vol. 8, No. 716007, Aug. 30, 2021, pp. 1-24.

Brownlee, Jason "Dynamic Ensemble Selection (DES) for Classification in Python—MachineLearningMastery.com", Retrieved from the Internet: URL: https://web.archive.org/web/20221206025245/https://machinelearningmastery.com/dynamic-ensemble-selection-in-python/XP093167838, Dec. 6, 2022, pp. 1-3.

Charriere, Katia et al., "Real-time analysis of cataract surgery videos using statistical models", Multimed Tools Appl (2017) 76:22473-22491; Springer Science+Business Media New York 2017, May 23, 2017, 19 pages.

Park, Sang-Min et al., "Data Throttling for Data-Intensive Workflows", Department of Computer Science, University of Virginia, Charlottesville, VA, 2008, 11 pages.

International Search Report and Written Opinion received for PCT Application No. PCT/IB2023/063313, Mailed on Apr. 5, 2024, 11 pages.

International Search Report and Written Opinion received for PCT Application No. PCT/IB2023/063314, Mailed on Jun. 11, 2024, 25 pages.

International Search Report and Written Opinion received for PCT Application No. PCT/IB2023/063316, Mailed on Apr. 10, 2024, 12 pages.

International Search Report and Written Opinion received for PCT Application No. PCT/IB2023/063317, Mailed on Apr. 25, 2024, 11 pages.

International Search Report and Written Opinion received for PCT Application No. PCT/IB2023/063320, Mailed on Mar. 25, 2024, 17 pages.

International Search Report and Written Opinion received for PCT Application No. PCT/IB2023/063321, Mailed on Apr. 8, 2024, 13 pages.

International Search Report and Written Opinion received for PCT Application No. PCT/IB2023/063322, Mailed on Jun. 19, 2024, 20 pages.

International Search Report and Written Opinion received for PCT Application No. PCT/IB2023/063324, Mailed on Apr. 10, 2024, 14 pages.

Invitation to Pay Additional Fees received for PCT Application No. PCT/IB2023/063314, Mailed on Mar. 22, 2024, 13 pages.

Invitation to Pay Additional Fees received for PCT Application No. PCT/IB2023/063318, Mailed on Apr. 12, 2024, 14 pages.

Invitation to Pay Additional Fees received for PCT Application No. PCT/IB2023/063322, Mailed on Apr. 16, 2024, 11 pages.

ISO 26262-1, "Road Vehicles—Functional Safety—Part 1: Vocabulary", International Organization for Standardization, Edition 2, Dec. 2018, 13 pages.

Zhao, et al., "Tracking-by-detection of Surgical Instruments in Minimally Invasive Surgery via the Convolutional Neural Network Deep Learning-based Method", Computer Assisted Surgery, vol. 22, No. S1, Dec. 2017, 11 pages.

* cited by examiner

METHOD FOR ADVANCED ALGORITHM SUPPORT

CROSS-REFERENCE TO RELATED APPLICATIONS

This application is related to the concurrently filed U.S. Patent Applications, the content, in its entirety, of each is hereby incorporated by reference herein:

- U.S. patent application Ser. No. 18/092,025, entitled, A METHOD FOR ADVANCED ALGORITHM SUPPORT;
- U.S. patent application Ser. No. 18/092,015, entitled, SURGICAL COMPUTING SYSTEM WITH SUPPORT FOR INTERRELATED MACHINE LEARNING MODELS;
- U.S. patent application Ser. No. 18/092,019, entitled, SURGICAL COMPUTING SYSTEM WITH SUPPORT FOR MACHINE LEARNING MODEL INTERACTION;
- U.S. patent application Ser. No. 18/092,023, entitled, SURGICAL COMPUTING SYSTEM. WITH SUPPORT FOR INTERRELATED MACHINE LEARNING MODELS;
- U.S. patent application Ser. No. 18/092,032, entitled, DETECTION OF KNOCK-OFF OR COUNTERFEIT SURGICAL DEVICES;
- U.S. patent application Ser. No. 18/092,041, entitled, ADAPTABLE OPERATION RANGE FOR A SURGICAL DEVICE;
- U.S. patent application Ser. No. 18/092,026, entitled, SURGICAL COMPUTING SYSTEM WITH INTERMEDIATE MODEL SUPPORT;
- U.S. patent application Ser. No. 18/092,027, entitled, ADVANCED DATA TIMING IN A SURGICAL COMPUTING SYSTEM;
- U.S. patent application Ser. No. 18/092,031, entitled, SURGICAL DATA SPECIALTY HARMONIZATION FOR TRAINING MACHINE LEARNING MODELS;
- U.S. patent application Ser. No. 18/092,036, entitled, DATA VOLUME DETERMINATION FOR SURGICAL MACHINE LEARNING APPLICATIONS;
- U.S. patent application Ser. No. 18/092,038, entitled, ADAPTIVE SURGICAL DATA THROTTLE;
- U.S. patent application Ser. No. 18/092,047, entitled, SURGICAL DATA PROCESSING ASSOCIATED WITH MULTIPLE SYSTEM HIERARCHY LEVELS;
- U.S. patent application Ser. No. 18/092,049, entitled, PEER-TO-PEER SURGICAL INSTRUMENT MONITORING;
- U.S. patent application Ser. No. 18/092,055, entitled, MODIFYING GLOBALLY OR REGIONALLY SUPPLIED SURGICAL INFORMATION RELATED TO A SURGICAL PROCEDURE; and
- U.S. patent application Ser. No. 18/092,056, entitled, SURGICAL DATA PROCESSING ASSOCIATED WITH MULTIPLE SYSTEM HIERARCHY LEVELS.

BACKGROUND

Patient care is generally improved when tailored to the individual. Every person has different needs, so surgical and interventional solutions that center on the unique journey of every patient may represent efficient, groundbreaking pathways to healing. At the same time, the high stakes of patient care, in particular surgical processes, often drive a focus on conservative, repeatable activities.

Innovative medical technology, such as advanced surgical support computing systems and intelligent surgical instruments for example, may improve approaches to patient care and address the particular needs of health care providers.

The ever-increasing availability data and computing resources have made non-traditional algorithms, such as machine learning algorithms, a specific technical opportunity in health care systems. But incorporating such non-traditional algorithms into any medical technology presents many challenges.

SUMMARY

Surgical data may be obtained. For example, surgical data may be obtained from a surgical hub device. The surgical data may be processed for use.

A first machine learning model maybe trained based on the surgical data. And the first machine learning model may be deployed. For example, the first machine learning model may be deployed on a computing element.

An output may be generated by the first machine learning model. For example, the output may be generated based on an input associated with a surgical task.

For example, systems, methods, and instrumentalities are disclosed for using interrelated machine learning (ML) models (e.g., algorithms). The interrelated ML models may act collectively to perform complimentary portions of a surgical analysis. The ML models may be used at various locations. For example, ML models may be implemented in a facility network, a cloud network, an edge network, and/or the like. The location of the ML models may influence the type of data the ML models process. For example, ML models used outside a HIPAA boundary (e.g., cloud network) may process non-private and/or non-confidential information. The ML models may be used to feed their respective results into other ML models to provide a more complete result.

For example, systems, methods, and instrumentalities are disclosed for aggregating and/or apportioning available surgical data into a more usable dataset for machine learning (ML) model (e.g., algorithm) interaction. A ML model may be more accurate and/or reliable if using complete and/or regular data. Aggregating and/or apportioning available surgical data may enable a more complete and/or regular dataset for ML model analysis.

For example, systems, methods, and instrumentalities are disclosed for a surgical computing system with support for machine learning model interaction. Data exchange behavior between machine learning (ML) models and data storages may be determined and implemented. For example, data exchange may be determined based on privacy implications associated with a ML model and/or data storage. Data exchange may be determined based on processing goals associated with ML models.

For example, disclosed herein are methods, systems, and apparatus for a computing system and/or a computing device to determine whether a device is an authentic original equipment manufacturer (OEM) device or a counterfeit device, e.g., using machine learning (ML). A computing device may utilize ML and/or a ML algorithm to improve artificial intelligence algorithms, may reduce the iterations used to train artificial intelligence algorithms, and/or may make training machine learning less timing consuming. Adaptive learning algorithms may be used to aggregation one or more data streams. Adaptive learning algorithms may be used to generate and/or determine meta-data from a data collection. Adaptive learning may be used to determine one or more improvements from a previous machine learning analysis. Improvements in the collection and or processing of data feeds may be used to determine whether a device is an OEM device or a counterfeit device.

For example, disclosed herein are methods, systems, and apparatus for a device, such as a computing device or a surgical device, to determine an allowable operation range to control an input associated with a surgical device. A device may use data from a machine learning (ML) model to determine an allowable operation range associated with a surgical device. A device may utilize the data from a ML model to improve artificial intelligence algorithms, may reduce the iterations used to train artificial intelligence algorithms, and/or may make training machine learning less timing consuming. Adaptive learning algorithms may be used to aggregation one or more data streams. Adaptive learning algorithms may be used to generate and/or determine meta-data from a data collection. Adaptive learning may be used to determine one or more improvements from a previous machine learning analysis. Improvements in the collection and or processing of data feeds may be used to determine allowable operation range, e.g., to control one or more surgical devices.

For example, a surgical computing device may include a processor. The processor may be configured to implement two neural networks, a primary neural network trained with a procedure focus and support neural network trained with a patient focus. Data indicative of a surgical patient, a target procedure, and a proposed procedure plan may be input to the support neural network. The support neural network may generate a patient specific mapping from this data. The patient specific mapping and the data indicative of a surgical patient, a target procedure, and a proposed procedure plan may be input to the primary neural network. The primary neural network may output a modified procedure plan that is different from the proposed procedure plan.

For example, a surgical computing system may employ a machine learning model to modify the temporal characteristics of data collection and use during surgery. Such a model may recommend a data collection framework, specific to an individual's surgery, in view of the outcomes of surgeries with similarly situated patients, procedures, surgical equipment, and the like. The capability of a surgical computing system to identify and modify the temporal characteristics of data collection across a diverse array of surgical devices may facilitate the use of such a model. And a surgical computing system that enables the collection of data with a common reference time across that diverse array of surgical devices may facilitate the training of such a model.

For example, data, derived from one type or specialty of surgery, may be used to provide surgical recommendations for a different specialty. Surgical data may be received from surgical procedures (e.g., from a first surgical procedure and a second surgical procedure) to derive a common data set. The common data set may include related surgical data between related sub-tasks (e.g., a first sub-task associated with the first surgical procedure and a second sub-task associated with the second surgical procedure). The common data may be derived via a neural network that is trained to determine the common data set. The common data set between the related sub-tasks (e.g., first sub-task associated with the first surgical procedure and a second sub-task associated with the second surgical procedure) may include common procedure plans from the different surgical procedure(s), common data from different procedure(s), or common surgeon recorded interaction(s) from different procedure(s). Surgical data within the common data set between the related sub-tasks (e.g., first sub-task and a second sub-task) may be compared. A surgical recommendation may be provided for a surgical task based on the comparison of the data between the related sub-tasks (e.g., first sub-task and a second sub-task). The surgical recommendation may be provided via a neural network (e.g., a second neutral network) that is trained to provide the surgical recommendation for the surgical task. The surgical recommendation may be outputted for performing the surgical task.

For example, systems, methods, and instrumentalities may be described herein associated with allometry (e.g., growth and/or decay) of surgical data as it moves up or down various hierarchical levels. A surgical device (e.g., a surgical hub) may receive a plurality of surgical data parameters associated with a first patient. The plurality of surgical data parameters may be of a first data magnitude (e.g., a first data size) and of a first data individuality level.

For example, systems, methods, and instrumentalities may be described herein associated with surgical data processing at various system hierarchical levels. A surgical hub/edge server may obtain surgical data associated with a surgical task. The surgical data may include a data magnitude and a data form data individuality level. The data magnitude may be the extent the portion of the surgical data is to be processed. The data form may be the individuality level of the portion of the surgical data to be processed. The surgical hub/edge device may determine sets of parameters associated with a first surgical data subblock of the surgical data and a second surgical subblock of the surgical data. For example, the surgical hub/edge device may determine a first set of parameters associated with a first surgical data subblock of the surgical data and a second set of parameters associated with a second surgical data subblock of the surgical data.

For example, systems, methods, and instrumentalities may be described herein associated with adjusting/scaling of at least one surgical data attribute to be analyzed by a machine learning (ML) algorithm based on a resource-time relationship associated with a computing resource. The resource-time relationship may be determined based on at least one of timeliness of a needed result, computational processing level associated with the surgical computing device, or a computational memory associated with the surgical computing device, a network bandwidth between the surgical computing device and where the needed result it to be sent, one or more communication parameters, risk level of functioning without obtaining the needed result, importance level of the surgical data or a surgical task associated with the surgical task, or availability of other data that may be used as a substitution. The communication parameters may include a throughput rate at the surgical computing device or a latency between the surgical computing device and where the needed result is to be sent.

For example, systems, methods, and instrumentalities may be provided for a smart surgical instrument or a surgical device monitoring other surgical instruments or surgical devices in a peer-to-peer interconnected surgical ecosystem. The monitoring and/or recording may be performed by a surgical device that may be configured as a monitoring surgical device. The monitoring surgical device may use peer-to-peer surgical ecosystem to monitor and/or record surgical information associated with a surgical task on a peer surgical instrument, for example, without a central surgical hub.

For example, systems, methods, and instrumentalities may be described herein associated with modification of global or regional information related to a surgical procedure. A surgical computing device/edge computing device may receive global or regional surgical information associated with a surgical procedure (e.g., one or more surgical tasks of a surgical procedure) from an enterprise cloud server. In an example, the surgical computing device/edge computing device may receive the global or regional surgical information in response to a request message sent by the surgical computing device/edge computing device to the enterprise cloud server. The request message may be generated based on a trigger event occurring.

DETAILED DESCRIPTION

Figure 1:
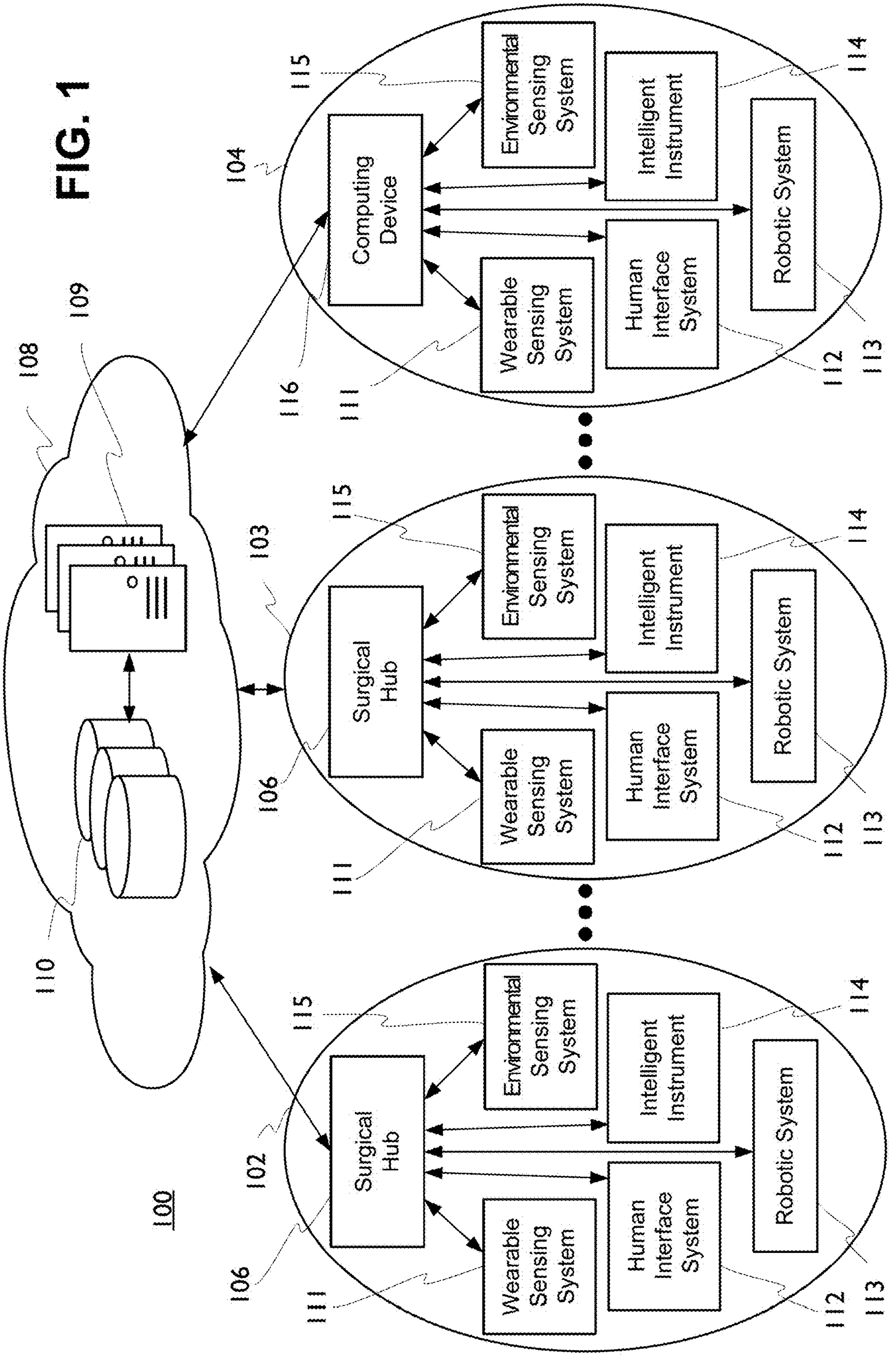
FIG. 1 is a block diagram of a computer-implemented surgical system.

Computing systems, which may include surgical hubs, may configure data to train a machine learning model(s) and use the machine learning model(s) to detect whether one or more devices are knock-off or counterfeit devices. Machine learning/machine learning model may be used to improve data, such as to determine whether a device is an original equipment manufacturer device or a counterfeit device. But using data to train a machine learning model may be timing consuming and may be inconvenient.

Computing systems, which may include surgical devices and/or surgical hubs, may configure machine learning to train data and provide allowable control input ranges to control one or more surgical devices. Allowable control input ranges may provide recommended input ranges to control the one or more surgical devices for a health care provider (HCP) during a surgical operation. Machine learning may be used to improve data, such as allowable control input ranges for surgical devices. But training machine learning may be timing consuming and may be inconvenient.

Surgical data may be prepared, or received from surgical data sources, and processed in order to determine surgical performance, surgical data trends, or surgical recommendations, for example, to inform one or more steps of future surgical procedures to improve surgical outcomes. However, surgical data encompasses a wide range of data types from a myriad of data sources, including data related to the context and scope of the surgery, data related to the configuration and/or control of the devices to be used in surgery and/or data generated/collected during surgery. The amount and variation of surgical data makes such data difficult to process for the purposes of determining surgical performance, surgical data trends and surgical recommendations. Historic surgical data may be used for these purposes. For example, historical surgical data may be used to make surgical recommendations, including for one or more steps of future surgical procedures, based on how the one or more steps were previously performed. Yet, using traditional analysis of surgical data, it can often be difficult to identify trends, particularly complex trends, in the data. For this reason, surgical performance, surgical data trends and surgical recommendations determined using traditional techniques may lack accuracy.

Some surgical systems may include a centralized surgical computing device that may be interacting with a plurality of surgical devices. It may be desirable to have surgical system configured in a manner that may avoid or partially avoid the use of a centralized computing device.

A surgical computer-implement surgical system may include a surgical computing system (e.g., a surgical hub), one or more surgical data sources in communication with the surgical computing system, a surgical device in communication with the surgical computing system, and a processor. Data generated by the one or more surgical data sources may be received by the processor. Such data may be used, by the processor, to train a machine learning (ML) model (e.g., a neural network). The ML model may be deployed to affect an operation of the surgical device. For example, the ML model may be deployed to the surgical hub to affect an operation of the surgical device.

FIG. 1 is a block diagram of a computer-implemented surgical system 100. An example surgical system, such as the surgical system 100, may include one or more surgical systems (e.g., surgical sub-systems) 102, 103, 104. For example, surgical system 102 may include a computer-implemented interactive surgical system. For example, surgical system 102, 103, 104 may include a surgical computing system, such as surgical hub 106 and/or computing device 116, in communication with a cloud computing system 108. The cloud computing system 108 may include a cloud server 109 and a cloud storage unit 110.

Surgical systems 102, 103, 104 may each computer-enabled surgical equipment and devices. For example, surgical systems 102, 103, 104 may include a wearable sensing system 111, a human interface system 112, a robotic system 113, one or more intelligent instruments 114, environmental sensing system 115, and/or the like. The wearable sensing system 111 may include one or more devices used to sense aspects of individuals status and activity within a surgical environment. For example, the wearable sensing system 111 may include health care provider sensing systems and/or patient sensing systems.

The human interface system 112 may include devices that enable an individual to interact with the surgical system 102, 103, 104 and/or the cloud computing system 108. The human interface system 112 may include a human interface device.

The robotic system 113 may include surgical robotic devices, such a surgical robot. The robotic system 113 may enable robotic surgical procedures. The robotic system 113 may receive information, settings, programming, controls and the like from the surgical hub 106 for example, the robotic system 113 may send data, such as sensor data, feedback information, video information, operational logs, and the like to the surgical hub 106.

Figure 2:
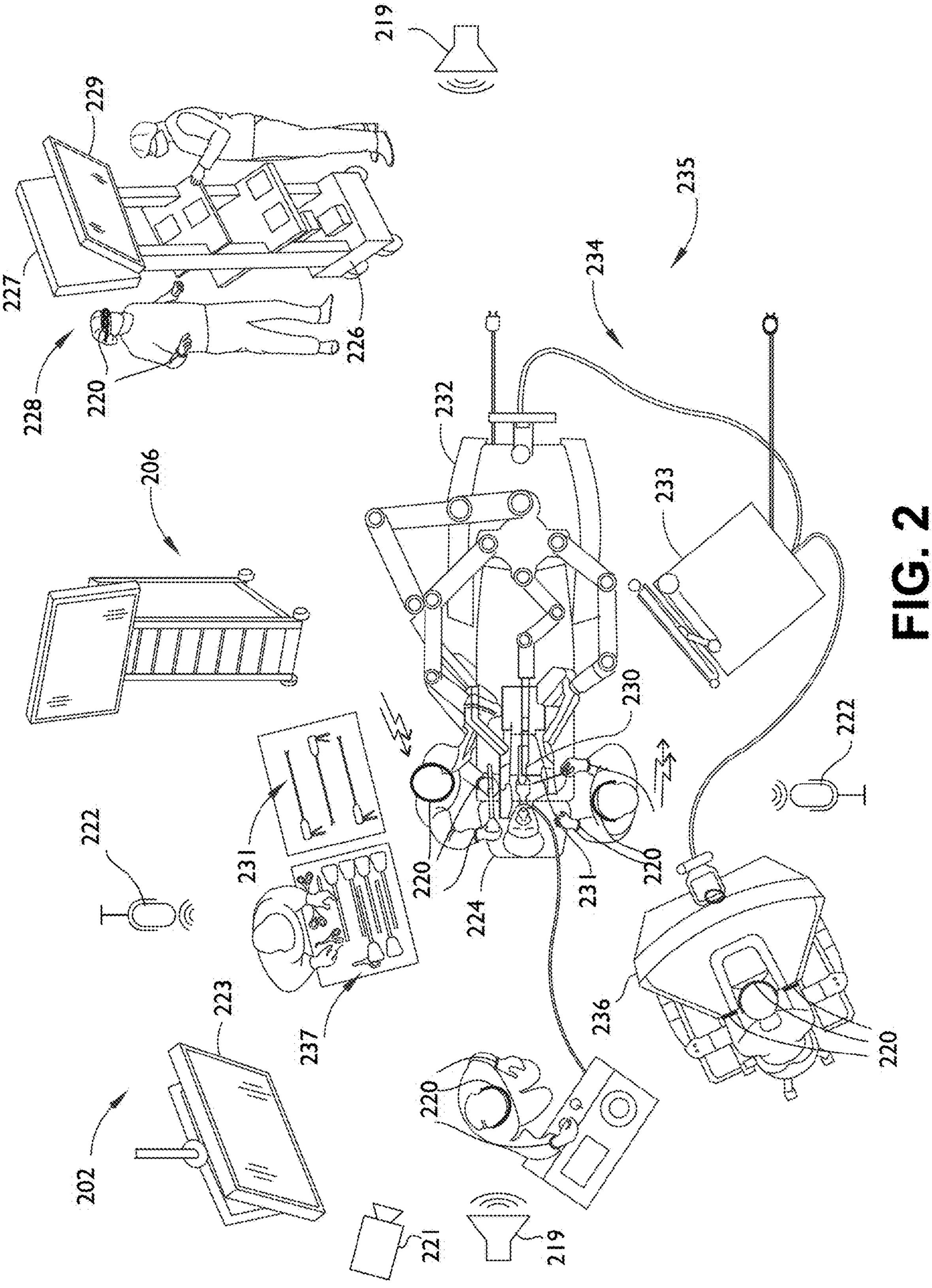
FIG. 2 shows an example surgical system in a surgical operating room.

The environmental sensing system 115 may include one or more devices, for example, used for measuring one or more environmental attributes, for example, as further described in FIG. 2. The robotic system 113 may include a plurality of devices used for performing a surgical procedure, for example, as further described in FIG. 2.

The surgical system 102 may be in communication with a remote server 109 that may be part of a cloud computing system 108. In an example, the surgical system 102 may be in communication with a remote server 109 via networked connection, such an internet connection (e.g., business internet service, T3, cable/FIOS networking node, and the like). The surgical system 102 and/or a component therein may communicate with the remote servers 109 via a cellular transmission/reception point (TRP) or a base station using one or more of the following cellular protocols: GSM/GPRS/EDGE (2G), UMTS/HSPA (3G), long term evolution (LTE) or 4G, LTE-Advanced (LTE-A), new radio (NR) or 5G.

In an example, the surgical hub 106 may facilitate displaying the image from a surgical imaging device, like a laparoscopic scope for example. The surgical hub 106 have cooperative interactions with the other local systems to facilitate displaying information relevant to those local systems. The surgical hub 106 may interact with one or more sensing systems 111, 115, one or more intelligent instruments 114, and/or multiple displays. For example, the surgical hub 106 may be configured to gather measurement data from the one or more sensing systems 111, 115 and send notifications or control messages to the one or more sensing systems 111, 115. The surgical hub 106 may send and/or receive information including notification information to and/or from the human interface system 112. The human interface system 112 may include one or more human interface devices (HIDs). The surgical hub 106 may send and/or receive notification information or control information to audio, display and/or control information to various devices that are in communication with the surgical hub.

For example, the sensing systems 111, 115 may include the wearable sensing system 111 (which may include one or more HCP sensing systems and one or more patient sensing systems) and the environmental sensing system 115. The one or more sensing systems 111, 115 may measure data relating to various biomarkers. The one or more sensing systems 111, 115 may measure the biomarkers using one or more sensors, for example, photosensors (e.g., photodiodes, photoresistors), mechanical sensors (e.g., motion sensors), acoustic sensors, electrical sensors, electrochemical sensors, thermoelectric sensors, infrared sensors, etc. The one or more sensors may measure the biomarkers as described herein using one of more of the following sensing technologies: photoplethysmography, electrocardiography, electroencephalography, colorimetry, impedimentary, potentiometry, amperometry, etc.

The biomarkers measured by the one or more sensing systems 111, 115 may include, but are not limited to, sleep, core body temperature, maximal oxygen consumption, physical activity, alcohol consumption, respiration rate, oxygen saturation, blood pressure, blood sugar, heart rate variability, blood potential of hydrogen, hydration state, heart rate, skin conductance, peripheral temperature, tissue perfusion pressure, coughing and sneezing, gastrointestinal motility, gastrointestinal tract imaging, respiratory tract bacteria, edema, mental aspects, sweat, circulating tumor cells, autonomic tone, circadian rhythm, and/or menstrual cycle.

The biomarkers may relate to physiologic systems, which may include, but are not limited to, behavior and psychology, cardiovascular system, renal system, skin system, nervous system, gastrointestinal system, respiratory system, endocrine system, immune system, tumor, musculoskeletal system, and/or reproductive system. Information from the biomarkers may be determined and/or used by the computer-implemented patient and the surgical system 100, for example. The information from the biomarkers may be determined and/or used by the computer-implemented patient and the surgical system 100 to improve said systems and/or to improve patient outcomes, for example. The one or more sensing systems 111, 115, biomarkers, and physiological systems are described in more detail in U.S. application Ser. No. 17/156,287, titled METHOD OF ADJUSTING A SURGICAL PARAMETER BASED ON BIOMARKER MEASUREMENTS, filed Jan. 22, 2021, the disclosure of which is herein incorporated by reference in its entirety.

FIG. 2 shows an example of a surgical system 202 in a surgical operating room. As illustrated in FIG. 2, a patient is being operated on by one or more health care professionals (HCPs). The HCPs are being monitored by one or more HCP sensing systems 220 worn by the HCPs. The HCPs and the environment surrounding the HCPs may also be monitored by one or more environmental sensing systems including, for example, a set of cameras 221, a set of microphones 222, and other sensors that may be deployed in the operating room. The HCP sensing systems 220 and the environmental sensing systems may be in communication with a surgical hub 206, which in turn may be in communication with one or more cloud servers 209 of the cloud computing system 208, as shown in FIG. 1. The environmental sensing systems may be used for measuring one or more environmental attributes, for example, HCP position in the surgical theater, HCP movements, ambient noise in the surgical theater, temperature/humidity in the surgical theater, etc.

As illustrated in FIG. 2, a primary display 223 and one or more audio output devices (e.g., speakers 219) are positioned in the sterile field to be visible to an operator at the operating table 224. In addition, a visualization/notification tower 226 is positioned outside the sterile field. The visualization/notification tower 226 may include a first non-sterile human interactive device (HID) 227 and a second non-sterile HID 229, which may face away from each other. The HID may be a display or a display with a touchscreen allowing a human to interface directly with the HID. A human interface system, guided by the surgical hub 206, may be configured to utilize the HIDs 227, 229, and 223 to coordinate information flow to operators inside and outside the sterile field. In an example, the surgical hub 206 may cause an HID (e.g., the primary HID 223) to display a notification and/or information about the patient and/or a surgical procedure step. In an example, the surgical hub 206 may prompt for and/or receive input from personnel in the sterile field or in the non-sterile area. In an example, the surgical hub 206 may cause an HID to display a snapshot of a surgical site, as recorded by an imaging device 230, on a non-sterile HID 227 or 229, while maintaining a live feed of the surgical site on the primary HID 223. The snapshot on the non-sterile display 227 or 229 can permit a non-sterile operator to perform a diagnostic step relevant to the surgical procedure, for example.

In one aspect, the surgical hub 206 may be configured to route a diagnostic input or feedback entered by a non-sterile operator at the visualization tower 226 to the primary display 223 within the sterile field, where it can be viewed by a sterile operator at the operating table. In one example, the input can be in the form of a modification to the snapshot displayed on the non-sterile display 227 or 229, which can be routed to the primary display 223 by the surgical hub 206.

Referring to FIG. 2, a surgical instrument 231 is being used in the surgical procedure as part of the surgical system 202. The hub 206 may be configured to coordinate information flow to a display of the surgical instrument 231. For example, in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. A diagnostic input or feedback entered by a non-sterile operator at the visualization tower 226 can be routed by the hub 206 to the surgical instrument display within the sterile field, where it can be viewed by the operator of the surgical instrument 231. Example surgical instruments that are suitable for use with the surgical system 202 are described under the heading “Surgical Instrument Hardware” and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 2 illustrates an example of a surgical system 202 being used to perform a surgical procedure on a patient who is lying down on an operating table 224 in a surgical operating room 235. A robotic system 234 may be used in the surgical procedure as a part of the surgical system 202. The robotic system 234 may include a surgeon’s console 236, a patient side cart 232 (surgical robot), and a surgical robotic hub 233. The patient side cart 232 can manipulate at least one removably coupled surgical tool 237 through a minimally invasive incision in the body of the patient while the surgeon views the surgical site through the surgeon’s console 236. An image of the surgical site can be obtained by a medical imaging device 230, which can be manipulated by the patient side cart 232 to orient the imaging device 230. The robotic hub 233 can be used to process the images of the surgical site for subsequent display to the surgeon through the surgeon’s console 236.

Other types of robotic systems can be readily adapted for use with the surgical system 202. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud computing system 208, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, the imaging device 230 may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device 230 may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is the portion of the electromagnetic spectrum that is visible to (i.e., can be detected by) the human eye and may be referred to as visible light or simply light. A typical human eye will respond to wavelengths in air that range from about 380 nm to about 750 nm.

The invisible spectrum (e.g., the non-luminous spectrum) is the portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device 230 is configured for use in a minimally invasive procedure. Examples of imaging devices suitable for use with the present disclosure include, but are not limited to, an arthroscope, angioscope, bronchoscope, choledochoscope, colonoscope, 9epresent9, duodenoscope, enteroscope, esophagogastro-duodenoscope (gastroscope), endoscope, laryngoscope, nasopharyngo-neproscope, sigmoidoscope, thoracoscope, and uretero-scope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information that the human eye fails to capture with its receptors for red, green, and blue. The use of multi-spectral imaging is described in greater detail under the heading “Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device 230 and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

Wearable sensing system 211 illustrated in FIG. 1 may include one or more sensing systems, for example, HCP sensing systems 220 as shown in FIG. 2. The HCP sensing systems 220 may include sensing systems to monitor and detect a set of physical states and/or a set of physiological states of a healthcare personnel (HCP). An HCP may be a surgeon or one or more healthcare personnel assisting the surgeon or other healthcare service providers in general. In an example, a sensing system 220 may measure a set of biomarkers to monitor the heart rate of an HCP. In an example, a sensing system 220 worn on a surgeon's wrist (e.g., a watch or a wristband) may use an accelerometer to detect hand motion and/or shakes and determine the magnitude and frequency of tremors. The sensing system 220 may send the measurement data associated with the set of biomarkers and the data associated with a physical state of the surgeon to the surgical hub 206 for further processing. One or more environmental sensing devices may send environmental information to the surgical hub 206. For example, the environmental sensing devices may include a camera 221 for detecting hand/body position of an HCP. The environmental sensing devices may include microphones 222 for measuring the ambient noise in the surgical theater. Other environmental sensing devices may include devices, for example, a thermometer to measure temperature and a hygrometer to measure humidity of the surroundings in the surgical theater, etc. The surgical hub 206, alone or in communication with the cloud computing system, may use the surgeon biomarker measurement data and/or environmental sensing information to modify the control algorithms of hand-held instruments or the averaging delay of a robotic interface, for example, to minimize tremors. In an example, the HCP sensing systems 220 may measure one or more surgeon biomarkers associated with an HCP and send the measurement data associated with the surgeon biomarkers to the surgical hub 206. The HCP sensing systems 220 may use one or more of the following RF protocols for communicating with the surgical hub 20006: Bluetooth, Bluetooth Low-Energy (BLE), Bluetooth Smart, Zigbee, Z-wave, IPv6 Low-power wireless Personal Area Network (6LoWPAN), Wi-Fi. The surgeon biomarkers may include one or more of the following: stress, heart rate, etc. The environmental measurements from the surgical theater may include ambient noise level associated with the surgeon or the patient, surgeon and/or staff movements, surgeon and/or staff attention level, etc.

The surgical hub 206 may use the surgeon biomarker measurement data associated with an HCP to adaptively control one or more surgical instruments 231. For example, the surgical hub 206 may send a control program to a surgical instrument 231 to control its actuators to limit or compensate for fatigue and use of fine motor skills. The surgical hub 206 may send the control program based on situational awareness and/or the context on importance or criticality of a task. The control program may instruct the instrument to alter operation to provide more control when control is needed.

Figure 3:
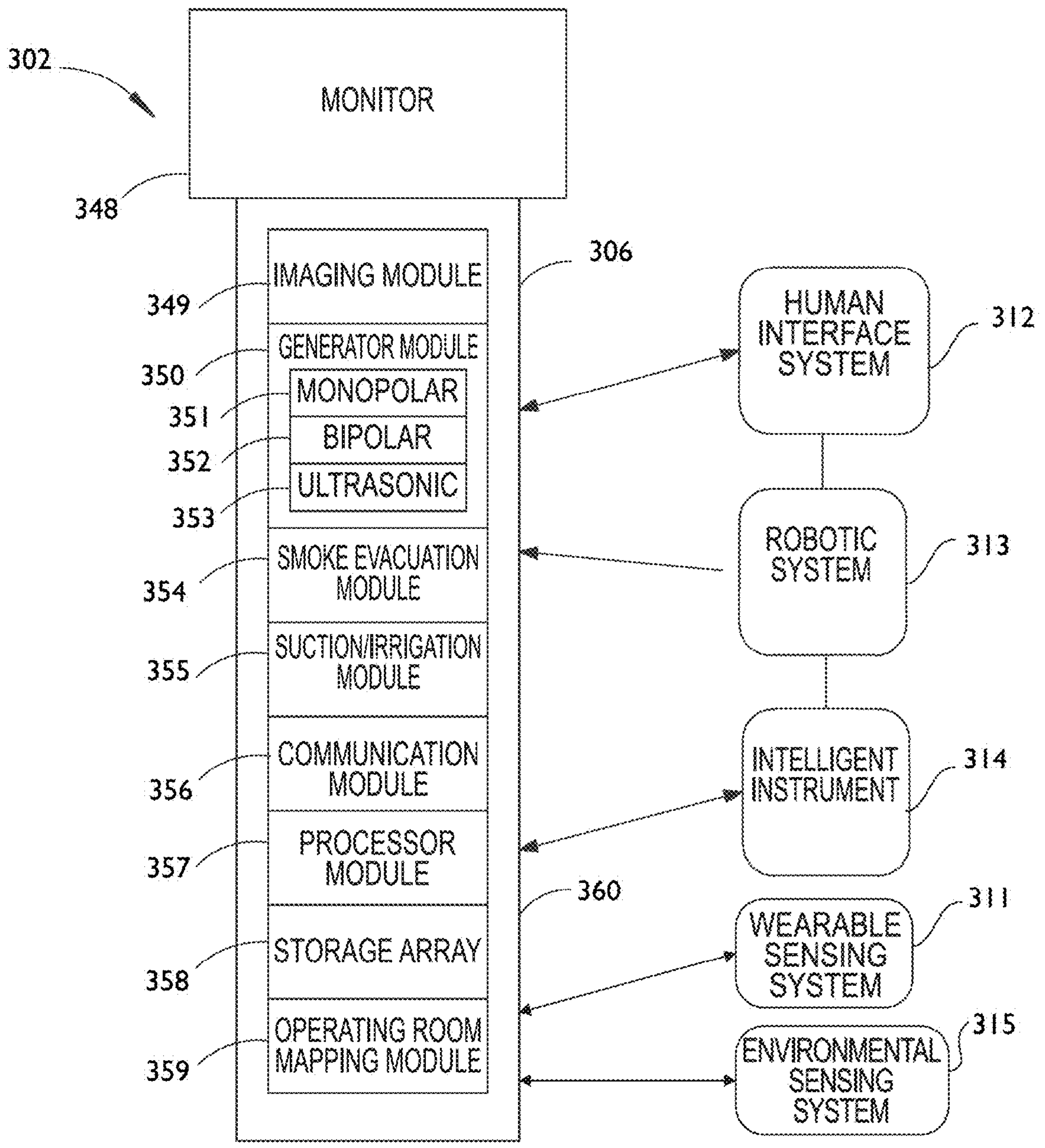
FIG. 3 illustrates an example surgical hub paired with various systems.

FIG. 3 shows an example surgical system 302 with a surgical hub 306. The surgical hub 306 may be paired with, via a modular control, a wearable sensing system 311, an environmental sensing system 315, a human interface system 312, a robotic system 313, and an intelligent instrument 314. The hub 306 includes a display 348, an imaging module 349, a generator module 350, a communication module 356, a processor module 357, a storage array 358, and an operating-room mapping module 359. In certain aspects, as illustrated in FIG. 3, the hub 306 further includes a smoke evacuation module 354 and/or a suction/irrigation module 355. The various modules and systems may be connected to the modular control either directly via a router or via the communication module 356. The operating theater devices may be coupled to cloud computing resources and data storage via the modular control. The human interface system 312 may include a display sub-system and a notification sub-system.

The modular control may be coupled to non-contact sensor module. The non-contact sensor module may measure the dimensions of the operating theater and generate a map of the surgical theater using, ultrasonic, laser-type, and/or the like, non-contact measurement devices. Other distance sensors can be employed to determine the bounds of an operating room. An ultrasound-based non-contact sensor module may scan the operating theater by transmitting a burst of ultrasound and receiving the echo when it bounces off the perimeter walls of an operating theater as described under the heading "Surgical Hub Spatial Awareness Within an Operating Room" in U.S. Provisional Patent Application Ser. No. 62/611,341, titled INTERACTIVE SURGICAL PLATFORM, filed Dec. 28, 2017, which is herein incorporated by reference in its entirety. The sensor module may be configured to determine the size of the operating theater and to adjust Bluetooth-pairing distance limits. A laser-based non-contact sensor module may scan the operating theater by transmitting laser light pulses, receiving laser light pulses that bounce off the perimeter walls of the operating theater, and comparing the phase of the transmitted pulse to the received pulse to determine the size of the operating theater and to adjust Bluetooth pairing distance limits, for example.

During a surgical procedure, energy application to tissue, for sealing and/or cutting, is generally associated with smoke evacuation, suction of excess fluid, and/or irrigation of the tissue. Fluid, power, and/or data lines from different sources are often entangled during the surgical procedure. Valuable time can be lost addressing this issue during a surgical procedure. Detangling the lines may necessitate disconnecting the lines from their respective modules, which may require resetting the modules. The hub modular enclosure 360 offers a unified environment for managing the power, data, and fluid lines, which reduces the frequency of entanglement between such lines. Aspects of the present disclosure present a surgical hub 306 for use in a surgical procedure that involves energy application to tissue at a surgical site.

The surgical hub 306 includes a hub enclosure 360 and a combo generator module slidably receivable in a docking station of the hub enclosure 360. The docking station includes data and power contacts. The combo generator module includes two or more of an ultrasonic energy generator component, a bipolar RF energy generator component, and a monopolar RF energy generator component that are housed in a single unit. In one aspect, the combo generator module also includes a smoke evacuation component, at least one energy delivery cable for connecting the combo generator module to a surgical instrument, at least one smoke evacuation component configured to evacuate smoke, fluid, and/or particulates generated by the application of therapeutic energy to the tissue, and a fluid line extending from the remote surgical site to the smoke evacuation component. In one aspect, the fluid line may be a first fluid line, and a second fluid line may extend from the remote surgical site to a suction and irrigation module 355 slidably received in the hub enclosure 360. In one aspect, the hub enclosure 360 may include a fluid interface.

Certain surgical procedures may require the application of more than one energy type to the tissue. One energy type may be more beneficial for cutting the tissue, while another different energy type may be more beneficial for sealing the tissue. For example, a bipolar generator can be used to seal the tissue while an ultrasonic generator can be used to cut the sealed tissue. Aspects of the present disclosure present a solution where a hub modular enclosure 360 is configured to accommodate different generators and facilitate an interactive communication therebetween. The hub modular enclosure 360 may enable the quick removal and/or replacement of various modules. Aspects of the present disclosure present a modular surgical enclosure for use in a surgical procedure that involves energy application to tissue. The modular surgical enclosure includes a first energy-generator module, configured to generate a first energy for application to the tissue, and a first docking station comprising a first docking port that includes first data and power contacts, wherein the first energy-generator module is slidably movable into an electrical engagement with the power and data contacts and wherein the first energy-generator module is slidably movable out of the electrical engagement with the first power and data contacts. Further to the above, the modular surgical enclosure also includes a second energy-generator module configured to generate a second energy, different than the first energy, for application to the tissue, and a second docking station comprising a second docking port that includes second data and power contacts, wherein the second energy generator module is slidably movable into an electrical engagement with the power and data contacts, and wherein the second energy-generator module is slidably movable out of the electrical engagement with the second power and data contacts. In addition, the modular surgical enclosure also includes a communication bus between the first docking port and the second docking port, configured to facilitate communication between the first energy-generator module and the second energy-generator module. Referring to FIG. 3, aspects of the present disclosure are presented for a hub modular enclosure 360 that allows the modular integration of a generator module 350, a smoke evacuation module 354, and a suction/irrigation module 355. The hub modular enclosure 360 further facilitates interactive communication between the modules 359, 354, and 355. The generator module 350 can be with integrated monopolar, bipolar, and ultrasonic components supported in a single housing unit slidably insertable into the hub modular enclosure 360. The generator module 350 can be configured to connect to a monopolar device 351, a bipolar device 352, and an ultrasonic device 353. Alternatively, the generator module 350 may comprise a series of monopolar, bipolar, and/or ultrasonic generator modules that interact through the hub modular enclosure 360. The hub modular enclosure 360 can be configured to facilitate the insertion of multiple generators and interactive communication between the generators docked into the hub modular enclosure 360 so that the generators would act as a single generator.

Figure 4:
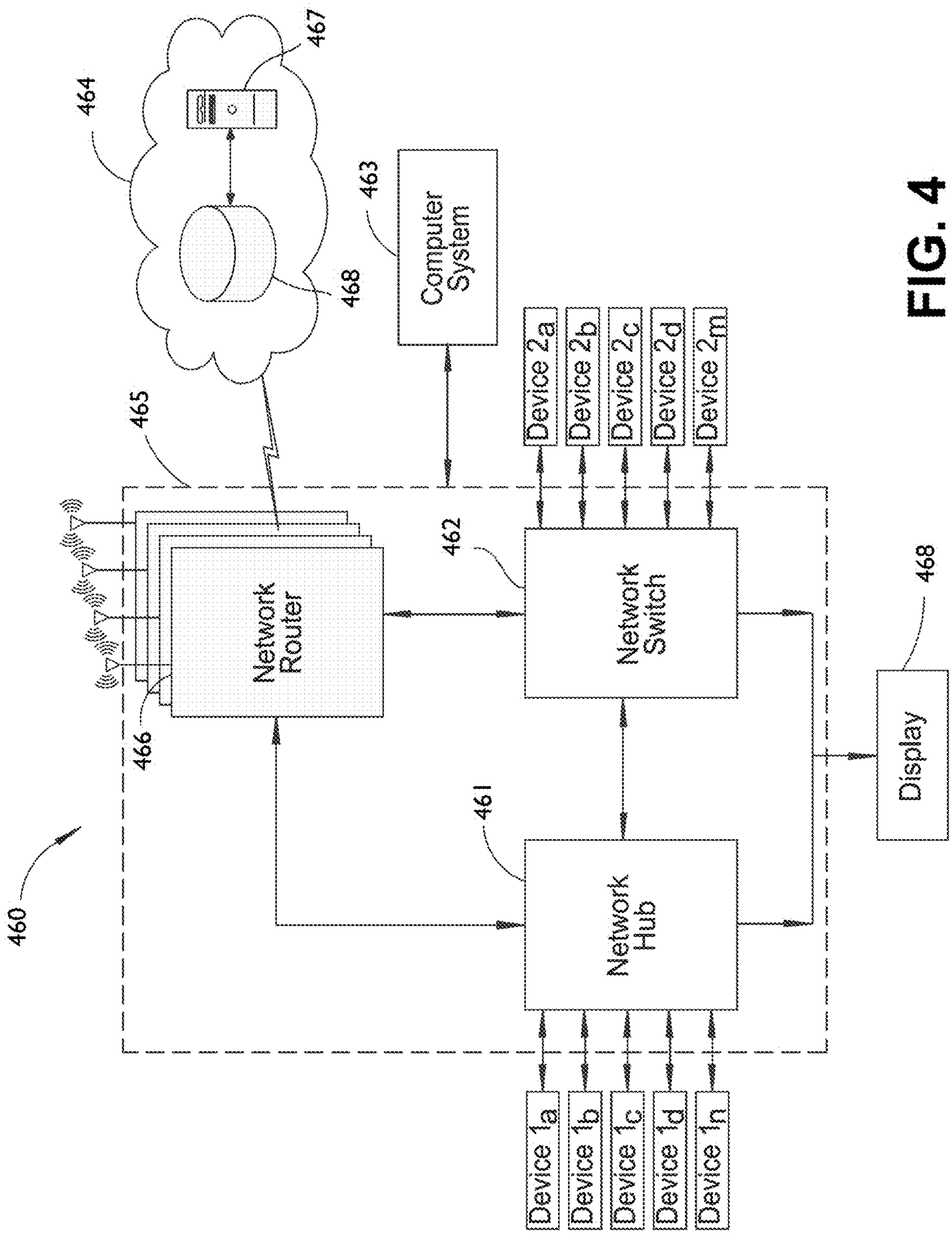
FIG. 4 illustrates a surgical data network having a set of communication surgical hubs configured to connect with a set of sensing systems, an environmental sensing system, a set of devices, etc.

FIG. 4 illustrates a surgical data network having a set of communication hubs configured to connect a set of sensing systems, environment sensing system(s), and a set of other modular devices located in one or more operating theaters of a healthcare facility, a patient recovery room, or a room in a healthcare facility specially equipped for surgical operations, to the cloud, in accordance with at least one aspect of the present disclosure.

As illustrated in FIG. 4, a surgical hub system 460 may include a modular communication hub 465 that is configured to connect modular devices located in a healthcare facility to a cloud-based system (e.g., a cloud computing system 464 that may include a remote server 467 coupled to a remote storage 468). The modular communication hub 465 and the devices may be connected in a room in a healthcare facility specially equipped for surgical operations. In one aspect, the modular communication hub 465 may include a network hub 461 and/or a network switch 462 in communication with a network router 466. The modular communication hub 465 may be coupled to a local computer system 463 to provide local computer processing and data manipulation.

The computer system 463 may comprise a processor and a network interface. The processor may be coupled to a communication module, storage, memory, non-volatile memory, and input/output (I/O) interface via a system bus. The system bus can be any of several types of bus structure(s) including the memory bus or memory controller, a peripheral bus or external bus, and/or a local bus using any variety of available bus architectures including, but not limited to, 9-bit bus, Industrial Standard Architecture (ISA), Micro-Charmel Architecture (MSA), Extended ISA (EISA), Intelligent Drive Electronics (IDE), VESA Local Bus (VLB), Peripheral Component Interconnect (PCI), USB, Advanced Graphics Port (AGP), Personal Computer Memory Card International Association bus (PCMCIA), Small Computer Systems Interface (SCSI), or any other proprietary bus.

The processor may be any single-core or multicore processor such as those known under the trade name ARM Cortex by Texas Instruments. In one aspect, the processor may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHz, a 32 KB single-cycle serial random access memory (SRAM), an internal read-only memory (ROM) loaded with StellarisWare® software, a 2 KB electrically erasable programmable read-only memory (EEPROM), and/or one or more pulse width modulation (PWM) modules, one or more quadrature encoder inputs (QEI) analogs, one or more 12-bit analog-to-digital converters (ADCs) with 12 analog input channels, details of which are available for the product datasheet.

In an example, the processor may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

It is to be appreciated that the computer system 463 may include software that acts as an intermediary between users and the basic computer resources described in a suitable operating environment. Such software may include an operating system. The operating system, which can be stored on the disk storage, may act to control and allocate resources of the computer system. System applications may take advantage of the management of resources by the operating system through program modules and program data stored either in the system memory or on the disk storage. It is to be appreciated that various components described herein can be implemented with various operating systems or combinations of operating systems.

A user may enter commands or information into the computer system 463 through input device(s) coupled to the I/O interface. The input devices may include, but are not limited to, a pointing device such as a mouse, trackball, stylus, touch pad, keyboard, microphone, joystick, game pad, satellite dish, scanner, TV tuner card, digital camera, digital video camera, web camera, and the like. These and other input devices connect to the processor through the system bus via interface port(s). The interface port(s) include, for example, a serial port, a parallel port, a game port, and a USB. The output device(s) use some of the same types of ports as input device(s). Thus, for example, a USB port may be used to provide input to the computer system 463 and to output information from the computer system 463 to an output device. An output adapter may be provided to illustrate that there can be some output devices like monitors, displays, speakers, and printers, among other output devices that may require special adapters. The output adapters may include, by way of illustration and not limitation, video and sound cards that provide a means of connection between the output device and the system bus. It should be noted that other devices and/or systems of devices, such as remote computer(s), may provide both input and output capabilities.

The computer system 463 can operate in a networked environment using logical connections to one or more remote computers, such as cloud computer(s), or local computers. The remote cloud computer(s) can be a personal computer, server, router, network PC, workstation, microprocessor-based appliance, peer device, or other common network node, and the like, and typically includes many or all of the elements described relative to the computer system. For purposes of brevity, only a memory storage device is illustrated with the remote computer(s). The remote computer(s) may be logically connected to the computer system through a network interface and then physically connected via a communication connection. The network interface may encompass communication networks such as local area networks (LANs) and wide area networks (WANs). LAN technologies may include Fiber Distributed Data Interface (FDDI), Copper Distributed Data Interface (CDDI), Ethernet/IEEE 802.3, Token Ring/IEEE 802.5, and the like. WAN technologies may include, but are not limited to, point-to-point links, circuit-switching networks like Integrated Services Digital Networks (ISDN) and variations thereon, packet-switching networks, and Digital Subscriber Lines (DSL).

In various examples, the computer system 463 may comprise an image processor, image-processing engine, media processor, or any specialized digital signal processor (DSP) used for the processing of digital images. The image processor may employ parallel computing with single instruction, multiple data (SIMD) or multiple instruction, multiple data (MIMD) technologies to increase speed and efficiency. The digital image-processing engine can perform a range of tasks. The image processor may be a system on a chip with multicore processor architecture.

The communication connection(s) may refer to the hardware/software employed to connect the network interface to the bus. While the communication connection is shown for illustrative clarity inside the computer system 463, it can also be external to the computer system 463. The hardware/software necessary for connection to the network interface may include, for illustrative purposes only, internal and external technologies such as modems, including regular telephone-grade modems, cable modems, optical fiber modems, and DSL modems, ISDN adapters, and Ethernet cards. In some examples, the network interface may also be provided using an RF interface.

Surgical data network associated with the surgical hub system 460 may be configured as passive, intelligent, or switching. A passive surgical data network serves as a conduit for the data, enabling it to go from one device (or segment) to another and to the cloud computing resources. An intelligent surgical data network includes additional features to enable the traffic passing through the surgical data network to be monitored and to configure each port in the network hub 461 or network switch 462. An intelligent surgical data network may be referred to as a manageable hub or switch. A switching hub reads the destination address of each packet and then forwards the packet to the correct port.

Modular devices 1*a*-1*n* located in the operating theater may be coupled to the modular communication hub 465. The network hub 461 and/or the network switch 462 may be coupled to a network router 466 to connect the devices 1*a*-1*n* to the cloud computing system 464 or the local computer system 463. Data associated with the devices 1*a*-1*n* may be transferred to cloud-based computers via the router for remote data processing and manipulation. Data associated with the devices 1*a*-1*n* may also be transferred to the local computer system 463 for local data processing and manipulation. Modular devices 2*a*-2*m* located in the same operating theater also may be coupled to a network switch 462. The network switch 462 may be coupled to the network hub 461 and/or the network router 466 to connect the devices 2*a*-2*m* to the cloud 464. Data associated with the devices 2*a*-2*m* may be transferred to the cloud computing system 464 via the network router 466 for data processing and manipulation. Data associated with the devices 2*a*-2*m* may also be transferred to the local computer system 463 for local data processing and manipulation.

As illustrated in FIG. 4 a computing system, such as a surgical hub system 460, may include a modular communication hub 465 that is configured to connect modular devices (e.g., surgical devices) located in a healthcare facility to a cloud-based system (e.g., a cloud computing system 464 that may include a remote server 467 coupled to a remote storage 468). The modular communication hub 465 and the devices may be connected in a room in a healthcare facility specially equipped for surgical operations. In one aspect, the modular communication hub 465 may include a network hub 461 and/or a network switch 462 in communication with a network router 466. The modular communication hub 465 may be coupled to a local computer system (e.g., a computing device) to provide local computer processing and data manipulation.

Figure 5:
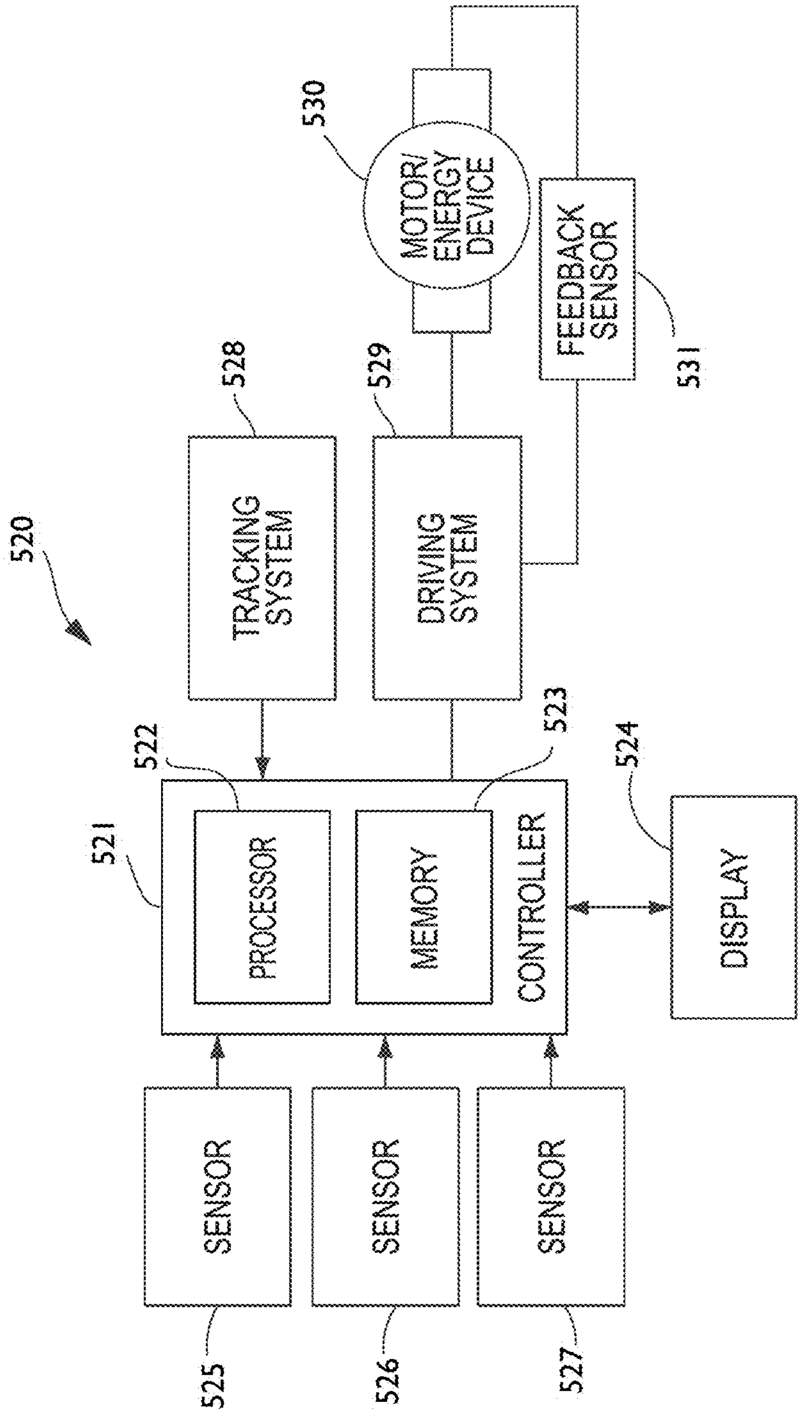
FIG. 5 illustrates a logic diagram of a control system of a surgical instrument.

FIG. 5 illustrates a logical diagram of a control system 520 of a surgical instrument or a surgical tool in accordance with one or more aspects of the present disclosure. The surgical instrument or the surgical tool may be configurable. The surgical instrument may include surgical fixtures specific to the procedure at-hand, such as imaging devices, surgical staplers, energy devices, endocutter devices, or the like. For example, the surgical instrument may include any of a powered stapler, a powered stapler generator, an energy device, an advanced energy device, an advanced energy jaw device, an endocutter clamp, an energy device generator, an in-operating-room imaging system, a smoke evacuator, a suction-irrigation device, an insufflation system, or the like. The system 520 may comprise a control circuit. The control circuit may include a microcontroller 521 comprising a processor 522 and a memory 523. One or more of sensors 525, 526, 527, for example, provide real-time feedback to the processor 522. A motor 530, driven by a motor driver 529, operably couples a longitudinally movable displacement member to drive the I-beam knife element. A tracking system 528 may be configured to determine the position of the longitudinally movable displacement member. The position information may be provided to the processor 522, which can be programmed or configured to determine the position of the longitudinally movable drive member as well as the position of a firing member, firing bar, and I-beam knife element. Additional motors may be provided at the tool driver interface to control I-beam firing, closure tube travel, shaft rotation, and articulation. A display 524 may display a variety of operating conditions of the instruments and may include touch screen functionality for data input. Information displayed on the display 524 may be overlaid with images acquired via endoscopic imaging modules.

The microcontroller 521 may be any single-core or multicore processor such as those known under the trade name ARM Cortex by Texas Instruments. In one aspect, the main microcontroller 521 may be an LM4F230H5QR ARM Cortex-M4F Processor Core, available from Texas Instruments, for example, comprising an on-chip memory of 256 KB single-cycle flash memory, or other non-volatile memory, up to 40 MHz, a prefetch buffer to improve performance above 40 MHZ, a 32 KB single-cycle SRAM, and internal ROM loaded with StellarisWare® software, a 2 KB EEPROM, one or more PWM modules, one or more QEI analogs, and/or one or more 12-bit ADCs with 12 analog input channels, details of which are available for the product datasheet.

The microcontroller 521 may comprise a safety controller comprising two controller-based families such as TMS570 and RM4x, known under the trade name Hercules ARM Cortex R4, also by Texas Instruments. The safety controller may be configured specifically for IEC 61508 and ISO 26262 safety critical applications, among others, to provide advanced integrated safety features while delivering scalable performance, connectivity, and memory options.

The microcontroller 521 may be programmed to perform various functions such as precise control over the speed and position of the knife and articulation systems. In one aspect, the microcontroller 521 may include a processor 522 and a memory 523. The electric motor 530 may be a brushed direct current (DC) motor with a gearbox and mechanical links to an articulation or knife system. In one aspect, a motor driver 529 may be an A3941 available from Allegro Microsystems, Inc. Other motor drivers may be readily substituted for use in the tracking system 528 comprising an absolute positioning system. A detailed description of an absolute positioning system is described in U.S. Patent Application Publication No. 2017/0296213, titled SYSTEMS AND METHODS FOR CONTROLLING A SURGICAL STAPLING AND CUTTING INSTRUMENT, which published on Oct. 19, 2017, which is herein incorporated by reference in its entirety.

The microcontroller 521 may be programmed to provide precise control over the speed and position of displacement members and articulation systems. The microcontroller 521 may be configured to compute a response in the software of the microcontroller 521. The computed response may be compared to a measured response of the actual system to obtain an "observed" response, which is used for actual feedback decisions. The observed response may be a favorable, tuned value that balances the smooth, continuous nature of the simulated response with the measured response, which can detect outside influences on the system.

The motor 530 may be controlled by the motor driver 529 and can be employed by the firing system of the surgical instrument or tool. In various forms, the motor 530 may be a brushed DC driving motor having a maximum rotational speed of approximately 25,000 RPM. In some examples, the motor 530 may include a brushless motor, a cordless motor, a synchronous motor, a stepper motor, or any other suitable electric motor. The motor driver 529 may comprise an H-bridge driver comprising field-effect transistors (FETs), for example. The motor 530 can be powered by a power assembly releasably mounted to the handle assembly or tool housing for supplying control power to the surgical instrument or tool. The power assembly may comprise a battery which may include a number of battery cells connected in series that can be used as the power source to power the surgical instrument or tool. In certain circumstances, the battery cells of the power assembly may be replaceable and/or rechargeable. In at least one example, the battery cells can be lithium-ion batteries which can be couplable to and separable from the power assembly.

The motor driver 529 may be an A3941 available from Allegro Microsystems, Inc. A3941 may be a full-bridge controller for use with external N-channel power metal-oxide semiconductor field-effect transistors (MOSFETs) specifically designed for inductive loads, such as brush DC motors. The driver 529 may comprise a unique charge pump regulator that can provide full (>10 V) gate drive for battery voltages down to 7 V and can allow the A3941 to operate with a reduced gate drive, down to 5.5 V. A bootstrap capacitor may be employed to provide the above battery supply voltage required for N-channel MOSFETs. An internal charge pump for the high-side drive may allow DC (100% duty cycle) operation. The full bridge can be driven in fast or slow decay modes using diode or synchronous rectification. In the slow decay mode, current recirculation can be through the high-side or the low-side FETs. The power FETs may be protected from shoot-through by resistor-adjustable dead time. Integrated diagnostics provide indications of undervoltage, overtemperature, and power bridge faults and can be configured to protect the power MOSFETs under most short circuit conditions. Other motor drivers may be readily substituted for use in the tracking system 528 comprising an absolute positioning system.

The tracking system 528 may comprise a controlled motor drive circuit arrangement comprising a position sensor 525 according to one aspect of this disclosure. The position sensor 525 for an absolute positioning system may provide a unique position signal corresponding to the location of a displacement member. In some examples, the displacement member may represent a longitudinally movable drive member comprising a rack of drive teeth for meshing engagement with a corresponding drive gear of a gear reducer assembly. In some examples, the displacement member may represent the firing member, which could be adapted and configured to include a rack of drive teeth. In some examples, the displacement member may represent a firing bar or the I-beam, each of which can be adapted and configured to include a rack of drive teeth. Accordingly, as used herein, the term displacement member can be used generically to refer to any movable member of the surgical instrument or tool such as the drive member, the firing member, the firing bar, the I-beam, or any element that can be displaced. In one aspect, the longitudinally movable drive member can be coupled to the firing member, the firing bar, and the I-beam. Accordingly, the absolute positioning system can, in effect, track the linear displacement of the I-beam by tracking the linear displacement of the longitudinally movable drive member. In various aspects, the displacement member may be coupled to any position sensor 525 suitable for measuring linear displacement. Thus, the longitudinally movable drive member, the firing member, the firing bar, or the I-beam, or combinations thereof, may be coupled to any suitable linear displacement sensor. Linear displacement sensors may include contact or non-contact displacement sensors. Linear displacement sensors may comprise linear variable differential transformers (LVDT), differential variable reluctance transducers (DVRT), a slide potentiometer, a magnetic sensing system comprising a movable magnet and a series of linearly arranged Hall effect sensors, a magnetic sensing system comprising a fixed magnet and a series of movable, linearly arranged Hall effect sensors, an optical sensing system comprising a movable light source and a series of linearly arranged photo diodes or photo detectors, an optical sensing system comprising a fixed light source and a series of movable linearly, arranged photodiodes or photodetectors, or any combination thereof.

The electric motor 530 can include a rotatable shaft that operably interfaces with a gear assembly that is mounted in meshing engagement with a set, or rack, of drive teeth on the displacement member. A sensor element may be operably coupled to a gear assembly such that a single revolution of the position sensor 525 element corresponds to some linear longitudinal translation of the displacement member. An arrangement of gearing and sensors can be connected to the linear actuator, via a rack and pinion arrangement, or a rotary actuator, via a spur gear or other connection. A power source may supply power to the absolute positioning system and an output indicator may display the output of the absolute positioning system. The displacement member may represent the longitudinally movable drive member comprising a rack of drive teeth formed thereon for meshing engagement with a corresponding drive gear of the gear reducer assembly. The displacement member may represent the longitudinally movable firing member, firing bar, I-beam, or combinations thereof.

A single revolution of the sensor element associated with the position sensor 525 may be equivalent to a longitudinal linear displacement d1 of the displacement member, where d1 is the longitudinal linear distance that the displacement member moves from point "a" to point "b" after a single revolution of the sensor element coupled to the displacement member. The sensor arrangement may be connected via a gear reduction that results in the position sensor 525 completing one or more revolutions for the full stroke of the displacement member. The position sensor 525 may complete multiple revolutions for the full stroke of the displacement member.

A series of switches, where n is an integer greater than one, may be employed alone or in combination with a gear reduction to provide a unique position signal for more than one revolution of the position sensor 525. The state of the switches may be fed back to the microcontroller 521 that applies logic to determine a unique position signal corresponding to the longitudinal linear displacement d1+d2+ . . . dn of the displacement member. The output of the position sensor 525 is provided to the microcontroller 521. The position sensor 525 of the sensor arrangement may comprise a magnetic sensor, an analog rotary sensor like a potentiometer, or an array of analog Hall-effect elements, which output a unique combination of position signals or values.

The position sensor 525 may comprise any number of magnetic sensing elements, such as, for example, magnetic sensors classified according to whether they measure the total magnetic field or the vector components of the magnetic field. The techniques used to produce both types of magnetic sensors may encompass many aspects of physics and electronics. The technologies used for magnetic field sensing may include search coil, fluxgate, optically pumped, nuclear precession, SQUID, Hall-effect, anisotropic magnetoresistance, giant magnetoresistance, magnetic tunnel junctions, giant magnetoimpedance, magnetostrictive/piezoelectric composites, magnetodiode, magnetotransistor, fiber-optic, magneto-optic, and microelectromechanical systems-based magnetic sensors, among others.

The position sensor 525 for the tracking system 528 comprising an absolute positioning system may comprise a magnetic rotary absolute positioning system. The position sensor 525 may be implemented as an AS5055EQFT single-chip magnetic rotary position sensor available from Austria Microsystems, AG. The position sensor 525 is interfaced with the microcontroller 521 to provide an absolute positioning system. The position sensor 525 may be a low-voltage and low-power component and may include four Hall-effect elements in an area of the position sensor 525 that may be located above a magnet. A high-resolution ADC and a smart power management controller may also be provided on the chip. A coordinate rotation digital computer (CORDIC) processor, also known as the digit-by-digit method and Volder's algorithm, may be provided to implement a simple and efficient algorithm to calculate hyperbolic and trigonometric functions that require only addition, subtraction, bit-shift, and table lookup operations. The angle position, alarm bits, and magnetic field information may be transmitted over a standard serial communication interface, such as a serial peripheral interface (SPI) interface, to the microcontroller 521. The position sensor 525 may provide 12 or 14 bits of resolution. The position sensor 525 may be an AS5055 chip provided in a small QFN 16-pin 4×4×0.85 mm package.

The tracking system 528 comprising an absolute positioning system may comprise and/or be programmed to implement a feedback controller, such as a PID, state feedback, and adaptive controller. A power source converts the signal from the feedback controller into a physical input to the system: in this case the voltage. Other examples include a PWM of the voltage, current, and force. Other sensor(s) may be provided to measure physical parameters of the physical system in addition to the position measured by the position sensor 525. In some aspects, the other sensor(s) can include sensor arrangements such as those described in U.S. Pat. No. 9,345,481, titled STAPLE CARTRIDGE TISSUE THICKNESS SENSOR SYSTEM, which issued on May 24, 2016, which is herein incorporated by reference in its entirety; U.S. Patent Application Publication No. 2014/0263552, titled STAPLE CARTRIDGE TISSUE THICKNESS SENSOR SYSTEM, which published on Sep. 18, 2014, which is herein incorporated by reference in its entirety; and U.S. patent application Ser. No. 15/628,175, titled TECHNIQUES FOR ADAPTIVE CONTROL OF MOTOR VELOCITY OF A SURGICAL STAPLING AND CUTTING INSTRUMENT, filed Jun. 20, 2017, which is herein incorporated by reference in its entirety. In a digital signal processing system, an absolute positioning system is coupled to a digital data acquisition system where the output of the absolute positioning system will have a finite resolution and sampling frequency. The absolute positioning system may comprise a compare-and-combine circuit to combine a computed response with a measured response using algorithms, such as a weighted average and a theoretical control loop, that drive the computed response towards the measured response. The computed response of the physical system may take into account properties like mass, inertia, viscous friction, inductance resistance, etc., to predict what the states and outputs of the physical system will be by knowing the input.

The absolute positioning system may provide an absolute position of the displacement member upon power-up of the instrument, without retracting or advancing the displacement member to a reset (zero or home) position as may be required with conventional rotary encoders that merely count the number of steps forwards or backwards that the motor 530 has taken to infer the position of a device actuator, drive bar, knife, or the like.

A sensor 526, such as, for example, a strain gauge or a micro-strain gauge, may be configured to measure one or more parameters of the end effector, such as, for example, the amplitude of the strain exerted on the anvil during a clamping operation, which can be indicative of the closure forces applied to the anvil. The measured strain may be converted to a digital signal and provided to the processor 522. Alternatively, or in addition to the sensor 526, a sensor 527, such as, for example, a load sensor, can measure the closure force applied by the closure drive system to the anvil. The sensor 527, such as, for example, a load sensor, can measure the firing force applied to an I-beam in a firing stroke of the surgical instrument or tool. The I-beam is configured to engage a wedge sled, which is configured to upwardly cam staple drivers to force out staples into deforming contact with an anvil. The I-beam also may include a sharpened cutting edge that can be used to sever tissue as the I-beam is advanced distally by the firing bar. Alternatively, a current sensor 531 can be employed to measure the current drawn by the motor 530. The force required to advance the firing member can correspond to the current drawn by the motor 530, for example. The measured force may be converted to a digital signal and provided to the processor 522.

For example, the strain gauge sensor 526 can be used to measure the force applied to the tissue by the end effector. A strain gauge can be coupled to the end effector to measure the force on the tissue being treated by the end effector. A system for measuring forces applied to the tissue grasped by the end effector may comprise a strain gauge sensor 526, such as, for example, a micro-strain gauge, that can be configured to measure one or more parameters of the end effector, for example. In one aspect, the strain gauge sensor 526 can measure the amplitude or magnitude of the strain exerted on a jaw member of an end effector during a clamping operation, which can be indicative of the tissue compression. The measured strain can be converted to a digital signal and provided to a processor 522 of the microcontroller 521. A load sensor 527 can measure the force used to operate the knife element, for example, to cut the tissue captured between the anvil and the staple cartridge. A magnetic field sensor can be employed to measure the thickness of the captured tissue. The measurement of the magnetic field sensor also may be converted to a digital signal and provided to the processor 522.

The measurements of the tissue compression, the tissue thickness, and/or the force required to close the end effector on the tissue, as respectively measured by the sensors 526, 527, can be used by the microcontroller 521 to characterize the selected position of the firing member and/or the corresponding value of the speed of the firing member. In one instance, a memory 523 may store a technique, an equation, and/or a lookup table which can be employed by the microcontroller 521 in the assessment.

The control system 520 of the surgical instrument or tool also may comprise wired or wireless communication circuits to communicate with a surgical hub, such as surgical hub 460 for example, as shown in FIG. 4.

Figure 6:
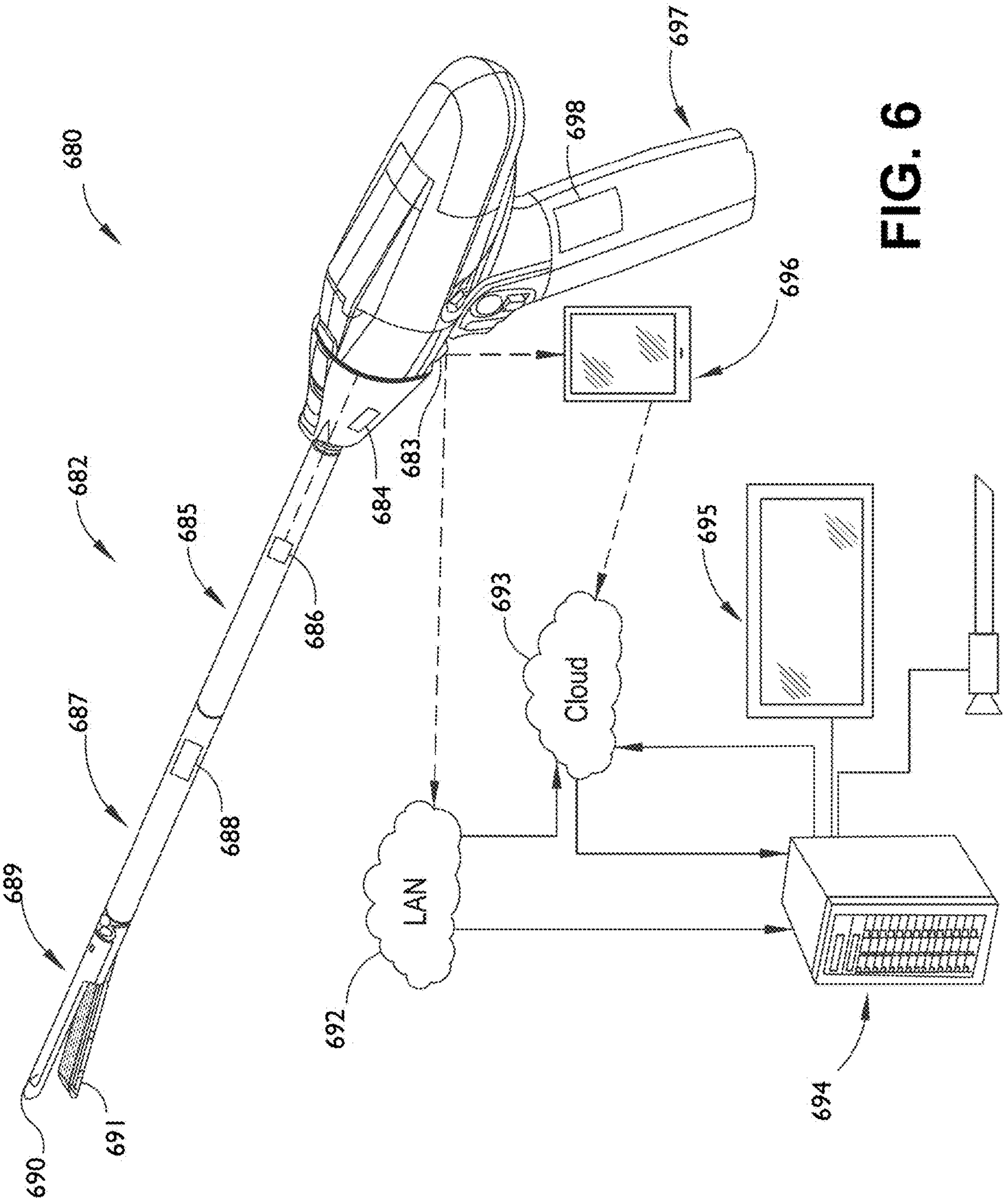
FIG. 6 shows an example surgical system that includes a handle having a controller and a motor, an adapter releasably coupled to the handle, and a loading unit releasably coupled to the adapter.

FIG. 6 illustrates an example surgical system 680 in accordance with the present disclosure and may include a surgical instrument 682 that can be in communication with a console 694 or a portable device 696 through a local area network 692 and/or a cloud network 693 via a wired and/or wireless connection. The console 694 and the portable device 696 may be any suitable computing device. The surgical instrument 682 may include a handle 697, an adapter 685, and a loading unit 687. The adapter 685 releasably couples to the handle 697 and the loading unit 687 releasably couples to the adapter 685 such that the adapter 685 transmits a force from a drive shaft to the loading unit 687. The adapter 685 or the loading unit 687 may include a force gauge (not explicitly shown) disposed therein to measure a force exerted on the loading unit 687. The loading unit 687 may include an end effector 689 having a first jaw 691 and a second jaw 690. The loading unit 687 may be an in-situ loaded or multi-firing loading unit (MFLU) that allows a clinician to fire a plurality of fasteners multiple times without requiring the loading unit 687 to be removed from a surgical site to reload the loading unit 687.

The first and second jaws 691, 690 may be configured to clamp tissue therebetween, fire fasteners through the clamped tissue, and sever the clamped tissue. The first jaw 691 may be configured to fire at least one fastener a plurality of times or may be configured to include a replaceable multi-fire fastener cartridge including a plurality of fasteners (e.g., staples, clips, etc.) that may be fired more than one time prior to being replaced. The second jaw 690 may include an anvil that deforms or otherwise secures the fasteners, as the fasteners are ejected from the multi-fire fastener cartridge.

The handle 697 may include a motor that is coupled to the drive shaft to affect rotation of the drive shaft. The handle 697 may include a control interface to selectively activate the motor. The control interface may include buttons, switches, levers, sliders, touchscreens, and any other suitable input mechanisms or user interfaces, which can be engaged by a clinician to activate the motor.

The control interface of the handle 697 may be in communication with a controller 698 of the handle 697 to selectively activate the motor to affect rotation of the drive shafts. The controller 698 may be disposed within the handle 697 and may be configured to receive input from the control interface and adapter data from the adapter 685 or loading unit data from the loading unit 687. The controller 698 may analyze the input from the control interface and the data received from the adapter 685 and/or loading unit 687 to selectively activate the motor. The handle 697 may also include a display that is viewable by a clinician during use of the handle 697. The display may be configured to display portions of the adapter or loading unit data before, during, or after firing of the instrument 682.

The adapter 685 may include an adapter identification device 684 disposed therein and the loading unit 687 may include a loading unit identification device 688 disposed therein. The adapter identification device 684 may be in communication with the controller 698, and the loading unit identification device 688 may be in communication with the controller 698. It will be appreciated that the loading unit identification device 688 may be in communication with the adapter identification device 684, which relays or passes communication from the loading unit identification device 688 to the controller 698.

The adapter 685 may also include a plurality of sensors 686 (one shown) disposed thereabout to detect various conditions of the adapter 685 or of the environment (e.g., if the adapter 685 is connected to a loading unit, if the adapter 685 is connected to a handle, if the drive shafts are rotating, the torque of the drive shafts, the strain of the drive shafts, the temperature within the adapter 685, a number of firings of the adapter 685, a peak force of the adapter 685 during firing, a total amount of force applied to the adapter 685, a peak retraction force of the adapter 685, a number of pauses of the adapter 685 during firing, etc.). The plurality of sensors 686 may provide an input to the adapter identification device 684 in the form of data signals. The data signals of the plurality of sensors 686 may be stored within or be used to update the adapter data stored within the adapter identification device 684. The data signals of the plurality of sensors 686 may be analog or digital. The plurality of sensors 686 may include a force gauge to measure a force exerted on the loading unit 687 during firing.

The handle 697 and the adapter 685 can be configured to interconnect the adapter identification device 684 and the loading unit identification device 688 with the controller 698 via an electrical interface. The electrical interface may be a direct electrical interface (i.e., include electrical contacts that engage one another to transmit energy and signals therebetween). Additionally, or alternatively, the electrical interface may be a non-contact electrical interface to wirelessly transmit energy and signals therebetween (e.g., inductively transfer). It is also contemplated that the adapter identification device 684 and the controller 698 may be in wireless communication with one another via a wireless connection separate from the electrical interface.

The handle 697 may include a transceiver 683 that is configured to transmit instrument data from the controller 698 to other components of the system 680 (e.g., the LAN 20292, the cloud 693, the console 694, or the portable device 696). The controller 698 may also transmit instrument data and/or measurement data associated with one or more sensors 686 to a surgical hub. The transceiver 683 may receive data (e.g., cartridge data, loading unit data, adapter data, or other notifications) from the surgical hub 670. The transceiver 683 may receive data (e.g., cartridge data, loading unit data, or adapter data) from the other components of the system 680. For example, the controller 698 may transmit instrument data including a serial number of an attached adapter (e.g., adapter 685) attached to the handle 697, a serial number of a loading unit (e.g., loading unit 687) attached to the adapter 685, and a serial number of a multi-fire fastener cartridge loaded into the loading unit to the console 694. Thereafter, the console 694 may transmit data (e.g., cartridge data, loading unit data, or adapter data) associated with the attached cartridge, loading unit, and adapter, respectively, back to the controller 698. The controller 698 can display messages on the local instrument display or transmit the message, via transceiver 683, to the console 694 or the portable device 696 to display the message on the display 695 or portable device screen, respectively.

Figure 7A:
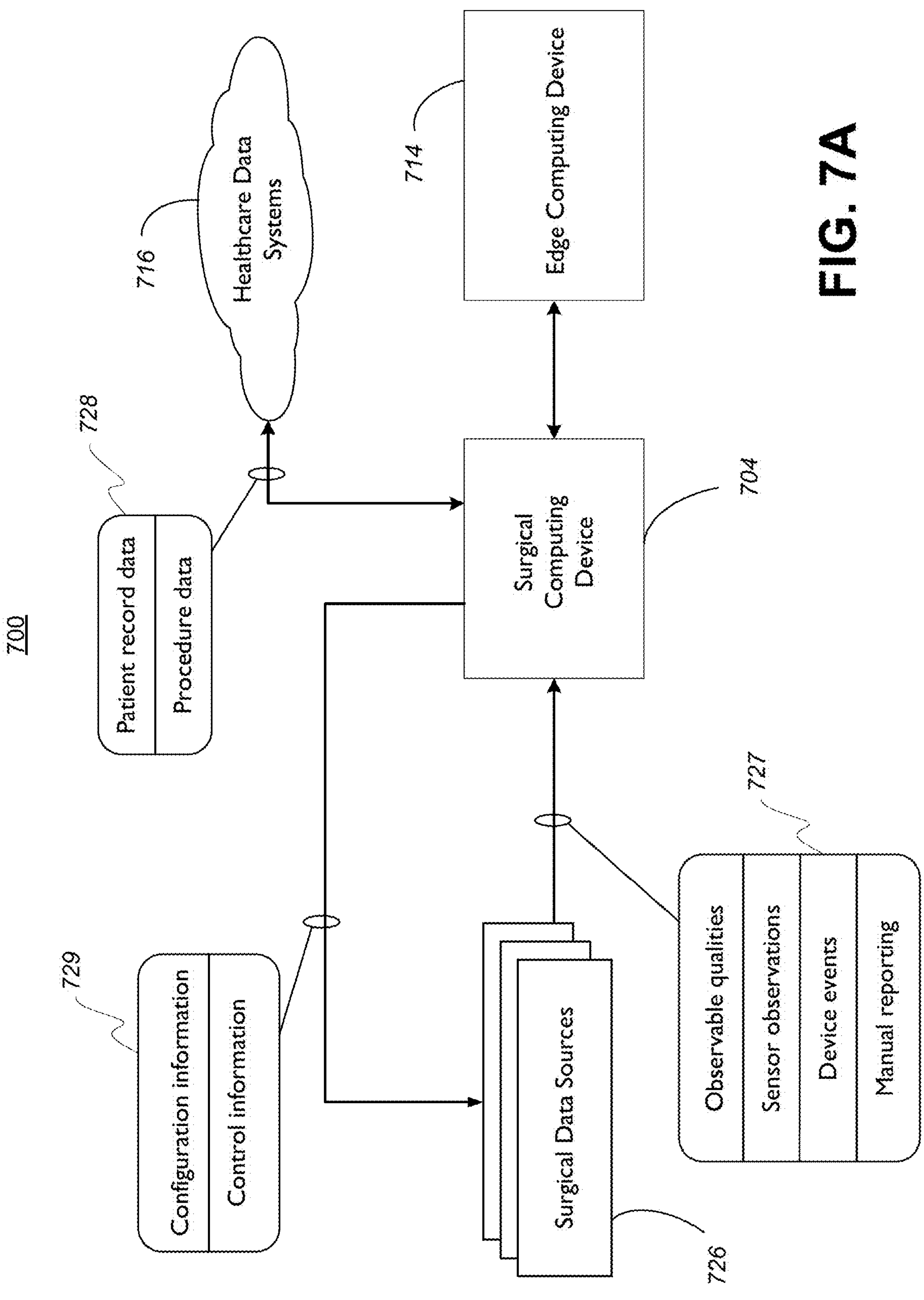
FIG. 7A-D show an example surgical system information matrix, an example information flow in a surgical system, an example information flow in a surgical system with a surgical robot, and an illustration of surgical information in the context of a procedure, respectively.

FIG. 7A illustrates a surgical system 700 that may include a matrix of surgical information. This surgical information may include any discrete atom of information relevant to surgical operation. Generally described, such surgical information may include information related to the context and scope of the surgery itself (e.g., healthcare information 728). Such information may include data such as procedure data and patient record data, for example. Procedure data and/or patient record data may be associated with a related healthcare data system 716 in communication with the surgical computing device 704.

The procedure data may include information related to the instruments and/or replaceable instrument components to be employed in a given procedure, such as a master list for example. The surgical computing device 704 may record (e.g., capture barcode scans) of the instruments and/or replaceable instrument components being put to use in the procedure. Such surgical information may be used to algorithmically confirm that appropriate configurations of surgical instruments and/or replaceable components are being used. See U.S. Patent Application Publication No. US 2020-0405296 A1 (U.S. patent application Ser. No. 16/458,103), titled PACKAGING FOR A REPLACEABLE COMPONENT OF A SURGICAL STAPLING SYSTEM, filed Jun. 30, 2019, the contents of which is hereby incorporated by reference herein in its entirety.

For example, patient record data may be suitable for use in changing the configurations of certain surgical devices. For example, patient data may be used to understand and improve surgical device algorithmic behavior. In an example, surgical staplers may adjust operational parameters related to compression, speed of operation, location of use, feedback based on information (e.g., information indicative of a specific patient's tissue and/or tissue characteristics) in the patient record. See U.S. Patent Application Publication No. US 2019-0200981 A1 (U.S. patent application Ser. No. 16/209,423), titled METHOD OF COMPRESSING TISSUE WITHIN A STAPLING DEVICE AND SIMULTANEOUSLY DISPLAYING THE LOCATION OF THE TISSUE WITHIN THE JAWS, filed Dec. 4, 2018, the contents of which is hereby incorporated by reference herein in its entirety The surgical information may include information related to the configuration and/or control of devices being used in the surgery (e.g., device operational information 729). Such device operational information 729 may include information about the initial settings of surgical devices. Device operational information 729 may include information about changes to the settings of surgical devices. Device operational information 729 may include information about controls sent to the devices from the surgical computing device 704 and information flows related to such controls.

The surgical information may include information generated during the surgery itself (e.g., surgery information 727). Such surgery information 727 may be include any information generated by a surgical data source 726. The data sources 726 may include any device in a surgical context that may generate useful surgery information 727. This surgery information 727 may present itself as observable qualities of the data source 726. The observable qualities may include static qualities, such as a device's model number, serial number, and the like. The observable qualities may include dynamic qualities such as the state of configurable settings of the device. The surgery information 727 may present itself as the result of sensor observations for example. Sensor observations may include those from specific sensors within the surgical theatre, sensors for monitoring conditions, such as patient condition, sensors embedded in surgical devices, and the like. The sensor observations may include information used during the surgery, such as video, audio, and the like. The surgery information 727 may present itself as a device event data. Surgical devices may generate notifications and/or may log events, and such events may be included in surgery information 727 for communication to the surgical computing device 704. The surgery information 727 may present itself as the result of manual recording, for example. A healthcare professional may make a record during the surgery, such as asking that a note be taken, capturing a still image from a display, and the like The surgical data sources 726 may include modular devices (e.g., which can include sensors configured to detect parameters associated with the patient, HCPs and environment and/or the modular device itself), local databases (e.g., a local EMR database containing patient records), patient monitoring devices (e.g., a blood pressure (BP) monitor and an electrocardiogramonitor), HCP monitoring devices, environment monitoring devices, surgical instruments, surgical support equipment, and the like.

Intelligent surgical instruments may sense and measure certain operational parameters in the course of their operation. For example, intelligent surgical instruments, such as surgical robots, digital laparoscopic devices, and the like, may use such measurements to improve operation, for example to limit over compression, to reduce collateral damage, to minimize tissue tension, to optimize usage location, and the like. See U.S. Patent Application Publication No. US 2018-0049822 A1 (U.S. patent application Ser. No. 15/237,753), titled CONTROL OF ADVANCEMENT RATE AND APPLICATION FORCE BASED ON MEASURED FORCES, filed Aug. 16, 2016, the contents of which is hereby incorporated by reference herein in its entirety. Such surgical information may be communicated to the surgical computing device 704.

The surgical computing device 704 can be configured to derive the contextual information pertaining to the surgical procedure from the data based upon, for example, the particular combination(s) of received data or the particular order in which the data is received from the data sources 726. The contextual information inferred from the received data can include, for example, the type of surgical procedure being performed, the particular step of the surgical procedure that the surgeon is performing, the type of tissue being operated on, or the body cavity that is the subject of the procedure. This ability by some aspects of the surgical computing device 704 to derive or infer information related to the surgical procedure from received data can be referred to as "situational awareness." For example, the surgical computing device 704 can incorporate a situational awareness system, which is the hardware and/or programming associated with the surgical computing device 704 that derives contextual information pertaining to the surgical procedure from the received data and/or a surgical plan information received from the edge computing system 714 or a healthcare data system 716 (e.g., enterprise cloud server). Such situational awareness capabilities may be used to generation surgical information (such as control and/or configuration information) based on a sensed situation and/or usage. See U.S. Patent Application Publication No. US 2019-0104919 A1 (U.S. patent application Ser. No. 16/209,478), titled METHOD FOR SITUATIONAL AWARENESS FOR SURGICAL NETWORK OR SURGICAL NETWORK CONNECTED DEVICE CAPABLE OF ADJUSTING FUNCTION BASED ON A SENSED SITUATION OR USAGE, filed Dec. 4, 2018, the contents of which is hereby incorporated by reference herein in its entirety.

In operation, this matrix of surgical information may be present as one or more information flows. For example, surgical information may flow from the surgical data sources 726 to the surgical computing device 704. Surgical information may flow from the surgical computing device 704 to the surgical data sources 726 (e.g., surgical devices). Surgical information may flow between the surgical computing device 704 and one or more healthcare data systems 716. Surgical information may flow between the surgical computing device 704 and one or more edge computing devices 714. Aspects of the information flows, including, for example, information flow endpoints, information storage, data interpretation, and the like, may be managed relative to the surgical system 700 (e.g., relative to the healthcare facility) See U.S. Patent Application Publication No. US 2019-0206564 A1 (U.S. patent application Ser. No. 16/209,490), titled METHOD FOR FACILITY DATA COLLECTION AND INTERPRETATION, filed Dec. 4, 2018, the contents of which is hereby incorporated by reference herein in its entirety.

Surgical information, as presented in its one or more information flows, may be used in connection with one or more artificial intelligence (AI) systems to further enhance the operation of the surgical system 700. For example, a machine learning system, such as that described herein, may operate on one or more information flows to further enhance the operation of the surgical system 700.

Figure 7B:
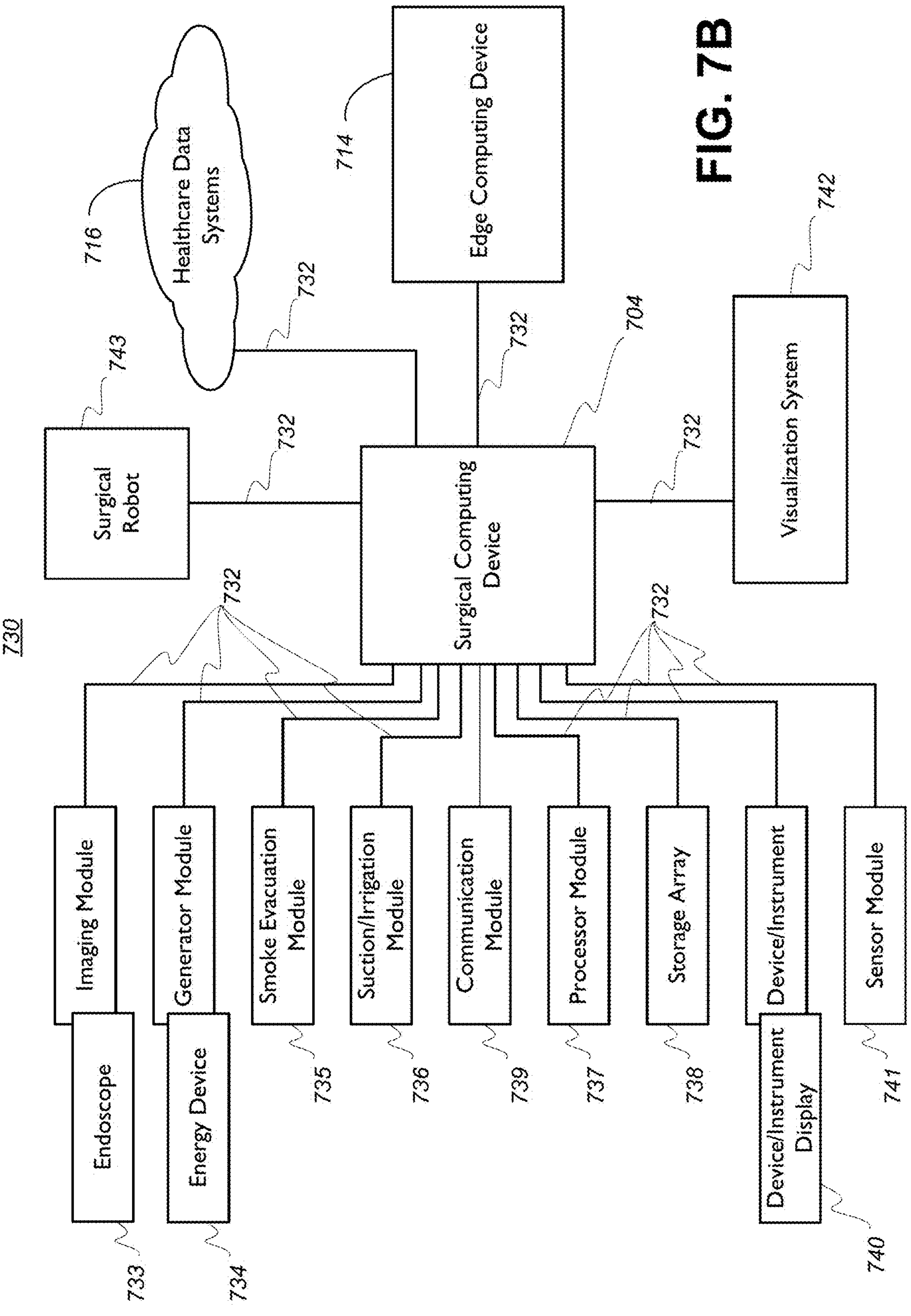

FIG. 7B shows an example computer-implement surgical system 730 with a plurality of information flows 732. A surgical computing device 704 may communication with and/or incorporate one or more surgical data sources. For example, an imaging module 733 (and endoscope) may exchange surgical information with the surgical computing device 704. Such information may include information from the imaging module 733 (and endoscope), such as video information, current settings, system status information, and the like. The imaging module 733 may receive information from the surgical computing device 704, such as control information, configuration information, operational updates (such as software/firmware), and the like.

For example, a generator module 734 (and corresponding energy device) may exchange surgical information with the surgical computing device 704. Such information may include information from the generator module 734 (and corresponding energy device), such as electrical information (e.g., current, voltage, impedance, frequency, wattage), activity state information, sensor information such as temperature, current settings, system events, active time duration, and activation timestamp, and the like. The generator module 734 may receive information from the surgical computing device 704, such as control information, configuration information, changes to the nature of the visible and audible notifications to the healthcare professional (e.g., changing the pitch, duration, and melody of audible tones), electrical application profiles and/or application logic that may instruct the generator module to provide energy with a defined characteristic curve over the application time, operational updates (such as software/firmware), and the like.

For example, a smoke evacuator 735 may exchange surgical information with the surgical computing device 704. Such information may include information from the smoke evacuator 735, such as operational information (e.g., revolutions per minute), activity state information, sensor information such as air temperature, current settings, system events, active time duration, and activation timestamp, and the like. The smoke evacuator 735 may receive information from the surgical computing device 704, such as control information, configuration information, operational updates (such as software/firmware), and the like.

For example, a suction/irrigation module 736 may exchange surgical information with the surgical computing device 704. Such information may include information from the suction/irrigation module 736, such as operational information (e.g., liters per minute), activity state information, internal sensor information, current settings, system events, active time duration, and activation timestamp, and the like. The suction/irrigation module 736 may receive information from the surgical computing device 704, such as control information, configuration information, operational updates (such as software/firmware), and the like.

For example, a communication module 739, a processor module 737, and/or a storage array 738 may exchange surgical information with the surgical computing device 704. In an example, the communication module 739, the processor module 737, and/or the storage array 738 may constitute all or part of the computing platform upon which the surgical computing device 704 runs. In an example, the communication module 739, the processor module 737, and/or the storage array 738 may provide local computing resources to other devices in the surgical system 730. Information from the communication module 739, the processor module 737, and/or the storage array 738 to the surgical computing device 704 may include logical computing-related reports, such as processing load, processing capacity, process identification, CPU %, CPU time, threads, GPU %, GPU time, memory utilization, memory thread, memory ports, energy usage, bandwidth related information, packets in, packets out, data rate, channel utilization, buffer status, packet loss information, system events, other state information, and the like. The communication module 739, the processor module 737, and/or the storage array 738 may receive information from the surgical computing device 704, such as control information, configuration information, operational updates (such as software/firmware), and the like. The communication module 739, the processor module 737, and/or the storage array 738 may also receive information from the surgical computing device 704 generated by another element or device of the surgical system 730. For example, data source information may be sent to and stored in the storage array. For example, data source information may be processed by the processor module 737.

For example, an intelligent instrument 740 (with or without a corresponding display) may exchange surgical information with the surgical computing device 704. Such information may include information from the intelligent instrument 740 relative to the instrument's operation, such as device electrical and/or mechanical information (e.g., current, voltage, impedance, frequency, wattage, torque, force, pressure, etc.), load state information (e.g., information regarding the identity, type, and/or status of reusables, such as staple cartridges), internal sensor information such as clamping force, tissue compression pressure and/or time, system events, active time duration, and activation timestamp, and the like. The intelligent instrument 740 may receive information from the surgical computing device 704, such as control information, configuration information, changes to the nature of the visible and audible notifications to the healthcare professional (e.g., changing the pitch, duration, and melody of audible tones), mechanical application profiles and/or application logic that may instruct a mechanical component of the instrument to operate with a defined characteristic (e.g., blade/anvil advance speed, mechanical advantage, firing time, etc.), operational updates (such as software/firmware), and the like.

For example, in a surgical stapling and cutting instrument, control and configuration information may be used to modify operational parameters, such as motor velocity for example. Data collections of surgical information may be used to define the power, force, and/or other functional operation and/or behavior of an intelligent surgical stapling and cutting instrument. See U.S. Pat. No. 10,881,399 B2 (U.S. patent application Ser. No. 15/628,175), titled TECHNIQUES FOR ADAPTIVE CONTROL OF MOTOR VELOCITY OF A SURGICAL STAPLING AND CUTTING INSTRUMENT, filed Jun. 20, 2017, the contents of which is hereby incorporated by reference herein in its entirety.

For example, in energy devices, control and configuration information (e.g., control and configuration information based on a situational awareness of the surgical computing device 704) may be used to adapt the function and/or behavior for improved results. See U.S. Patent Application Publication No. US 2019-0201047 A1 (U.S. patent application Ser. No. 16/209,458), titled METHOD FOR SMART ENERGY DEVICE INFRASTRUCTURE, filed Dec. 4, 2018, the contents of which is hereby incorporated by reference herein in its entirety. Likewise, in combo energy devices (e.g., devices which may use more than one energy modality) such control and/or configuration information may be used to select an appropriate operational mode. For example, the surgical computing device 704 may use surgical information including information being received from patient monitoring to send control and/or configuration information to the combo energy device. See U.S. Patent Application Publication No. US 2017-0202605 A1 (U.S. patent application Ser. No. 15/382,515), titled MODULAR BATTERY POWERED HANDHELD SURGICAL INSTRUMENT AND METHODS THEREFOR, filed Dec. 16, 2016, the contents of which is hereby incorporated by reference herein in its entirety.

For example, a sensor module 741 may exchange surgical information with the surgical computing device 704. Such information may include information from the sensor module 741 relative to its sensor function, such as sensor results themselves, observational frequency and/or resolution, observational type, device alerts such as alerts for sensor failure, observations exceeding a defined range, observations exceeding an observable range, and the like. The sensor module 741 may receive information from the surgical computing device 704, such as control information, configuration information, changes to the nature of observation (e.g., frequency, resolution, observational type etc.), triggers that define specific events for observation, on control, off control, data buffering, data preprocessing algorithms, operational updates (such as software/firmware), and the like.

For example, a visualization system 742 may exchange surgical information with the surgical computing device 704. Such information may include information from the visualization system 742, such visualization data itself (e.g., still image, video, advanced spectrum visualization, etc.), visualization metadata (e.g., visualization type, resolution, frame rate, encoding, bandwidth, etc.). The visualization system 742 may receive information from the surgical computing device 704, such as control information, configuration information, changes to the video settings (e.g., visualization type, resolution, frame rate, encoding, etc.), visual display overlay data, data buffering size, data preprocessing algorithms, operational updates (such as software/firmware), and the like.

Surgical information may be exchanged and/or used with advanced imaging systems. For example, surgical information may be exchanged and/or used to provide context for imaging data streams. For example, surgical information may be exchanged and/or used to expand the conditional understanding of such imaging data streams. See U.S. patent application Ser. No. 17/493,904, titled SURGICAL METHODS USING MULTI-SOURCE IMAGING, filed Oct. 5, 2021, the contents of which is hereby incorporated by reference herein in its entirety. See U.S. patent application Ser. No. 17/493,913, titled SURGICAL METHODS USING FIDUCIAL IDENTIFICATION AND TRACKING, filed Oct. 5, 2021, the contents of which is hereby incorporated by reference herein in its entirety.

For example, a surgical robot 743 may exchange surgical information with the surgical computing device 704. In an example, surgical information may include information related to the cooperative registration and interaction of surgical robotic systems. See U.S. patent application Ser. No. 17/449,765, titled COOPERATIVE ACCESS HYBRID PROCEDURES, filed Oct. 1, 2021, the contents of which is hereby incorporated by reference herein in its entirety. Information from the surgical robot 743 may include any aforementioned information as applied to robotic instruments, sensors, and devices. Information from the surgical robot 743 may also include information related to the robotic operation or control of such instruments, such as electrical/mechanical feedback of robot articulators, system events, system settings, mechanical resolution, control operation log, articulator path information, and the like. The surgical robot 743 may receive information from the surgical computing device 704, such as control information, configuration information, operational updates (such as software/firmware), and the like.

Surgical devices in communication with the surgical computing device 704 may exchange surgical information to aid in cooperative operation among the devices. For example, with the surgical robot 743 and the energy generator 734 may exchange surgical information with each other and/or the surgical computing device 704 for cooperative operation. Cooperative operation between the cooperatively the surgical robot 743 and the energy generator 734 may be used to minimize unwanted side effects like tissue sticking for example. Cooperative operation between the cooperatively the surgical robot 743 and the energy generator 734 may be used to improve tissue welding. See U.S. Patent Application Publication No. US 2019-0059929 A1 (U.S. patent application Ser. No. 15/689,072), titled METHODS, SYSTEMS, AND DEVICES FOR CONTROLLING ELECTROSURGICAL TOOLS, filed Aug. 29, 2017, the contents of which is hereby incorporated by reference herein in its entirety. Surgical information may be generated by the cooperating devices and/or the surgical computing device 704 in connection with their cooperative operation.

The surgical computing system 704 may be record, analyze, and/or act on surgical information flows, like those disclosed above for example. The surgical computing system 704 may aggregate such data for analysis. For example, the surgical computing system 704 may perform operations such as defining device relationships, establishing device cooperative behavior, monitoring and/or storing procedure details, and the like. Surgical information related to such operations may be further analyzed to refine algorithms, identify trends, and/or adapt surgical procedures. For example, surgical information may be further analyzed in comparison with patient outcomes as a function of such operations. See U.S. Patent Application Publication No. US 2019-0206562 A1 (U.S. patent application Ser. No. 16/209,416), titled METHOD OF HUB COMMUNICATION, PROCESSING, DISPLAY, AND CLOUD ANALYTICS, filed Dec. 4, 2018, the contents of which is hereby incorporated by reference herein in its entirety.

Figure 7C:
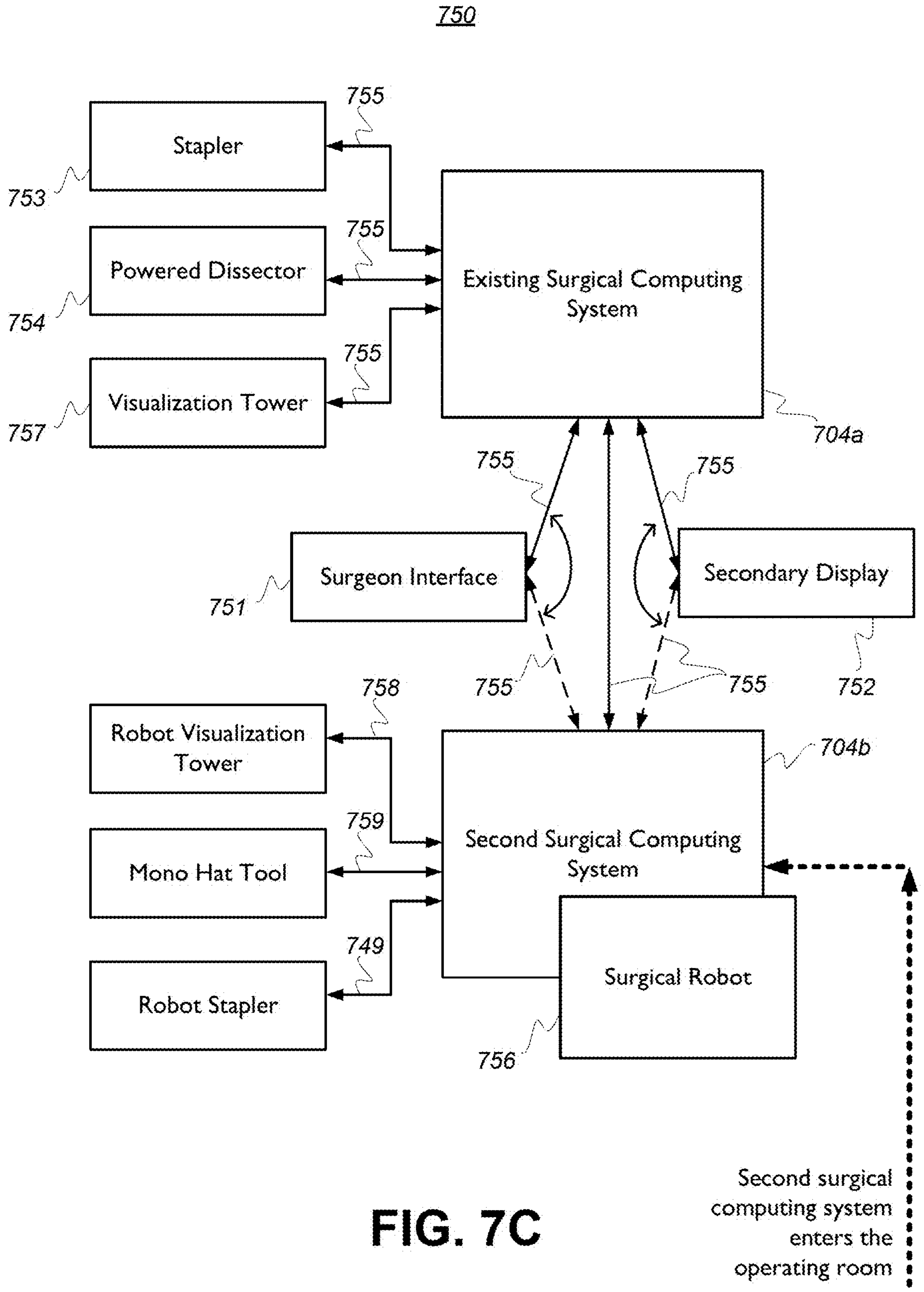

FIG. 7C illustrates an example information flow associated with a plurality of surgical computing systems 704*a*, 704*b* in a common environment. When the overall configuration of a computer-implement surgical system (e.g., computer-implement surgical system 750) changes (e.g., when data sources are added and/or removed from the surgical computing system, for example), further surgical information may be generated to reflect the changes. In this example, a second surgical computing system 704*b* (e.g., surgical hub) may be added (with a corresponding surgical robot) to surgical system 750 with an existing surgical computing system 704*a*. The messaging flow described here represents further surgical information flows 755 to be employed as disclosed herein (e.g., further consolidated, analyzed, and/or processed according to an algorithm, such as a machine learning algorithm).

Here, the two surgical computing systems 704*a*, 704*b* request permission from a surgical operator for the second surgical computing system 704*b* (with the corresponding surgical robot 756) to take control of the operating room from the existing surgical computing system 704*a*. The second surgical computing system 704*b* presents in the operating theater with control of the corresponding surgical robot 756, a robot visualization tower 758, a mono hat tool 759, and a robot stapler 749. The permission can be requested through a surgeon interface or console 751. Once permission is granted, the second surgical computing system 704*b* messages the existing surgical computing system 704*a* a request a transfer of control of the operating room.

In an example, the surgical computing systems 704*a*, 704*b* can negotiate the nature of their interaction without external input based on previously gathered data. For example, the surgical computing systems 704*a*, 704*b* may collectively determine that the next surgical task requires use of a robotic system. Such determination may cause the existing surgical computing system 704*a* to autonomously surrender control of the operating room to the second surgical computing system 704*b*. Upon completion of the surgical task, the second surgical computing system 704*b* may then autonomously return the control of the operating room to the existing surgical computing system 704*a*.

As illustrated in FIG. 7C, the existing surgical computing system 704*a* has transferred control to the second surgical computing system 704*b*, which has also taken control of the surgeon interface 751 and the secondary display 752. The second surgical computing system 704*b* assigns new identification numbers to the newly transferred devices. The existing surgical computing system 704*a* retains control the handheld stapler 753, the handheld powered dissector 754, and visualization tower 757. In addition, the existing surgical computing system 704*a* may perform a supporting role, wherein the processing and storage capabilities of the existing surgical computing system 704*a* are now available to the second surgical computing system 704*b*.

Figure 7D:
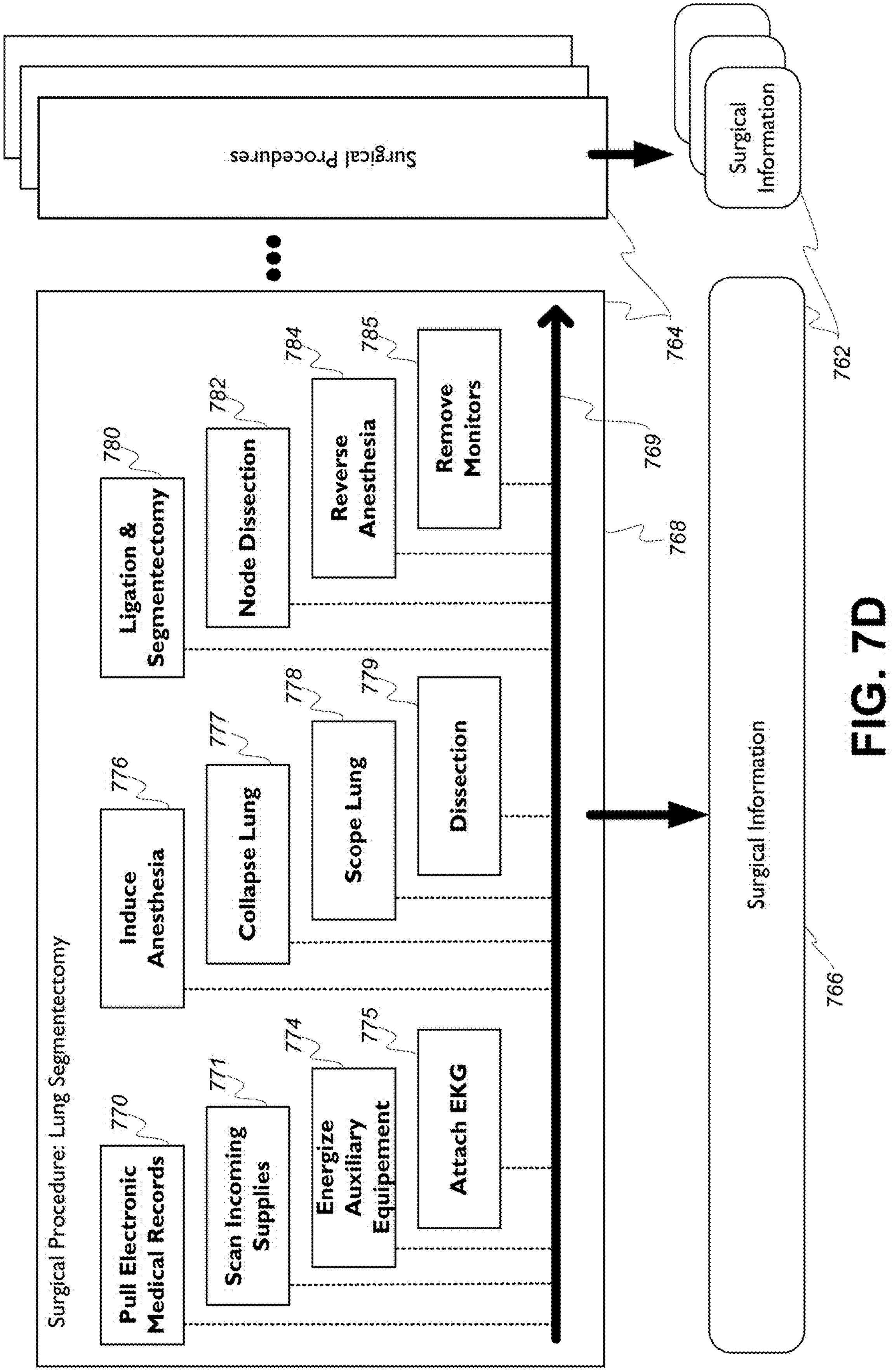

FIG. 7D illustrates an example surgical information flow in the context of a surgical procedure and a corresponding example use of the surgical information for predictive modeling. The surgical information disclosed herein may provide data regarding one or more surgical procedures, including the surgical tasks, instruments, instrument settings, operational information, procedural variations, and corresponding desirable metrics, such as improved patient outcomes, lower cost (e.g., fewer resources utilized, less surgical time, etc.). The surgical information disclosed herein (e.g., that disclosed in regard to FIGS. 7A-C) in the context of one or more surgical systems and devices disclosed herein, provides a platform upon which the specific machine learning algorithms and techniques disclosed herein may be used.

Surgical information 762 from a plurality of surgical procedures 764 (e.g., a subset of surgical information from each procedure) may be collected. The surgical information 762 may be collected from the plurality of surgical procedures 764 by collecting data represented by the one or more information flows disclosed herein, for example.

To illustrate, example instance of surgical information 766 may be generated from the example procedure 768 (e.g, a lung segmentectomy procedure as shown on a timeline 769). Surgical information 766 may be generated during the preoperative planning and may include patient record information. Surgical information 766 may be generated from the data sources (e.g., data sources 726) during the course of the surgical procedure, including data generated each time medical personnel utilize a modular device that is paired with the surgical computing system (e.g., surgical computing system 704). The surgical computing system may receive this data from the paired modular devices and other data sources The surgical computing system itself may generate surgical information as part of its operation during the procedure. For example, the surgical computing system may record information relating to configuration and control operations. The surgical computing system may record information related to situational awareness activities. For example, the surgical computing system may record the recommendations, prompts, and/or other information provided to the heathcare team (e.g., provided via a display screen) that may be pertinent for the next procedural step. For example, the surgical computing system may record configuration and control changes (e.g., the adjusting of modular devices based on the context). Such configuration and control changes may include activating monitors, adjusting the field of view (FOV) of a medical imaging device, changing the energy level of an ultrasonic surgical instrument or RF electrosurgical instrument, or the like.

At 770, the hospital staff members retrieve the patient's EMR from the hospitals EMR database. Based on select patient data in the EMR, the surgical computing system determines that the procedure to be performed is a thoracic procedure.

At 771, the staff members scan the incoming medical supplies for the procedure. The surgical computing system may cross-reference the scanned supplies with a list of supplies that are utilized in various types of procedures. The surgical computing system may confirm that the mix of supplies corresponds to a thoracic procedure. Further, the surgical computing system may determine that the procedure is not a wedge procedure (because the incoming supplies either lack certain supplies that are necessary for a thoracic wedge procedure or do not otherwise correspond to a thoracic wedge procedure). The medical personnel may also scan the patient band via a scanner that is communicably connected to the surgical computing system. The surgical computing system may confirm the patient's identity based on the scanned data.

At 774, the medical staff turns on the auxiliary equipment. The auxiliary equipment being utilized can vary according to the type of surgical procedure and the techniques to be used by the surgeon. In this example, the auxiliary equipment may include a smoke evacuator, an insufflator, and medical imaging device. When activated, the auxiliary equipment may pair with the surgical computing system. The surgical computing system may derive contextual information about the surgical procedure based on the types of paired. In this example, the surgical computing system determines that the surgical procedure is a VATS procedure based on this particular combination of paired devices. The contextual information about the surgical procedure may be confirmed by the surgical computing system via information from the patient's EMR.

The surgical computing system may retrieve the steps of the procedure to be performed. For example, the steps may be associated with a procedural plan (e.g., a procedural plan specific to this patient's surgery, a procedural plan associated with a particular surgeon, a procedural plan template for the procedure generally, or the like).

At 775, the staff members attach the EKG electrodes and other patient monitoring devices to the patient. The EKG electrodes and other patient monitoring devices pair with the surgical computing system. The surgical computing system may receive data from the patient monitoring devices.

At 776, the medical personnel induce anesthesia in the patient. The surgical computing system may record information related to this procedural step such as data from the modular devices and/or patient monitoring devices, including EKG data, blood pressure data, ventilator data, or combinations thereof, for example.

At 777, the patient's lung subject to operation is collapsed (ventilation may be switched to the contralateral lung). The surgical computing system may determine that this procedural step has commenced and may collect surgical information accordingly, including for example, ventilator data, one or more timestamps, and the like At 778, the medical imaging device (e.g., a scope) is inserted and video from the medical imaging device is initiated. The surgical computing system may receive the medical imaging device data (i.e., video or image data) through its connection to the medical imaging device. The data from the medical imaging device may include imaging data and/or imaging metadata, such as the angle at which the medical imaging device is oriented with respect to the visualization of the patient's anatomy, the number or medical imaging devices presently active, and the like. The surgical computing system may record positioning information of the medical imaging device. For example, one technique for performing a VATS lobectomy places the camera in the lower anterior corner of the patient's chest cavity above the diaphragm. Another technique for performing a VATS segmentectomy places the camera in an anterior intercostal position relative to the segmental fissure.

Using pattern recognition or machine learning techniques, for example, the surgical computing system may be trained to recognize the positioning of the medical imaging device according to the visualization of the patient's anatomy. For example, one technique for performing a VATS lobectomy utilizes a single medical imaging device. Another technique for performing a VATS segmentectomy uses multiple cameras. Yet another technique for performing a VATS segmentectomy uses an infrared light source (which may be communicably coupled to the surgical computing system as part of the visualization system).

At 779, the surgical team begins the dissection step of the procedure. The surgical computing system may collect data from the RF or ultrasonic generator indicating that an energy instrument is being fired. The surgical computing system may cross-reference the received data with the retrieved steps of the surgical procedure to determine that an energy instrument being fired at this point in the process (i.e., after the completion of the previously discussed steps of the procedure) corresponds to the dissection step. In an example, the energy instrument may be an energy tool mounted to a robotic arm of a robotic surgical system.

At 780, the surgical team proceeds to the ligation step of the procedure. The surgical computing system may collect surgical information 766 with regard to the surgeon ligating arteries and veins based on receiving data from the surgical stapling and cutting instrument indicating that such instrument is being fired. Next, the segmentectomy portion of the procedure is performed. The surgical computing system may collect information relating to the surgeon transecting the parenchyma. For example, the surgical computing system may receive surgical information 766 from the surgical stapling and cutting instrument, including data regarding its cartridge, settings, firing details, and the like.

At 782, the node dissection step is then performed. The surgical computing system may collect surgical information 766 with regard to the surgical team dissecting the node and performing a leak test. For example, the surgical computing system may collect data received from the generator indicating that an RF or ultrasonic instrument is being fired and including the electrical and status information associated with the firing. Surgeons regularly switch back and forth between surgical stapling/cutting instruments and surgical energy (i.e., RF or ultrasonic) instruments depending upon the particular step in the procedure. The surgical computing system may collect surgical information 766 in view of the particular sequence in which the stapling/cutting instruments and 37epresenl energy instruments are used. In an example, robotic tools may be used for one or more steps in a surgical procedure. The surgeon may alternate between robotic tools and handheld surgical instruments and/or can use the devices concurrently, for example.

Next, the incisions are closed up and the post-operative portion of the procedure begins. At 784, the patient's anesthesia is reversed. The surgical computing system may collect surgical information regarding the patient emerging from the anesthesia based on ventilator data (e.g., the patient's breathing rate begins increasing), for example.

At 785, the medical personnel remove the various patient monitoring devices from the patient. The surgical computing system may collect information regarding the conclusion of the procedure. For example, the surgical computing system may collect information related to the loss of EKG, BP, and other data from the patient monitoring devices.

The surgical information 762 (including the surgical information 766) may be structured and/or labeled. The surgical computing system may provide such structure and/or labeling inherently in the data collection. For example, in surgical information 762 may be labeled according to a particular characteristic, a desired result (e.g., efficiency, patient outcome, cost, and/or a combination of the same, or the like), a certain surgical technique, an aspect of instrument use (e.g., selection, timing, and activation of a surgical instrument, the instrument's settings, the nature of the instrument's use, etc.), the identity of the health care professionals involved, a specific patient characteristic, or the like, each of which may be present in the data collection.

Surgical information (e.g., surgical information 762 collected across procedures 764) may be used in connection with one or more artificial intelligence (AI) systems. AI may be used to perform computer cognitive tasks. For example, AI may be used to perform complex tasks based on observations of data. AI may be used to enable computing systems to perform cognitive tasks and solve complex tasks. AI may include using machine learning (e.g., machine learning algorithms and/or machine learning techniques/models). ML models (e.g., ML techniques) may perform complex tasks, for example, without being programmed (e.g., explicitly programmed). For example, a ML model may improve over time based on completing tasks with different inputs (e.g., by retraining the ML model or using reinforcement learning). An ML algorithm (e.g., process) may train the ML model, for example using input data and/or a learning dataset. When using reinforcement learning, the ML algorithm may train itself.

Machine learning (ML) algorithms and/or models may be employed, for example, in the medical field. For example, an ML model may be used on a set of data (e.g., a set of surgical data) to produce an output (e.g., reduced surgical data, processed surgical data). In examples, the output of a ML model may include identified trends or relationships of the data that were input for processing. The outputs may include verifying results and/or conclusions associated with the input data. In examples, an input to an ML model may include medical data, such as surgical images and patient scans. The ML model may output a determined medical condition based on the input surgical images and patient scans. The ML model may be used to diagnose medical conditions, for example, based on the surgical scans.

ML models may be improved iteratively, for example, by reusing the historic data that trained the ML model and/or the input data. Therefore, ML models may be constantly improving with added inputs and processing. The ML models may be updated based on input data. For example, over time, a ML process that produces medical conclusions based on medical data may improve and become more accurate and consistent in medical diagnoses with additional input data.

ML models may be used to solve different complex tasks (e.g., medical tasks). For example, ML models may be used for data reduction, data preparation, data processing, trend identification, conclusion determination, surgical recommendations, surgical classifications, medical diagnoses, and/or the like. For example, ML models may take in surgical data as input data and process the data to generate output data to be used for medical analysis. The output data of the ML models may be used to determine a medical diagnosis. In the end, the ML models may take raw surgical data and generate useful medical information (e.g., medical trends and/or diagnoses) associated with the raw surgical data. Further details on ML models are described herein.

ML models may be combined to perform different discrete tasks on input data. For example, different combinations of ML models (e.g., sub-models) performing discrete tasks may be analyzed (e.g., using a further ML model) to determine which combination of ML models performs the best (e.g., competitive usage of different algorithm types and training to determine the best combination for a dataset). For example, the ML models may include model control and monitoring to improve and/or verify results and/or conclusions (e.g., error bounding).

A ML model may be initialized and/or setup to perform tasks prior to training using an ML algorithm. For example, the ML model may be initialized based on initialization configuration information. The initialized ML model may be untrained and/or a base ML model for performing the task (e.g., already trained ML model for performing the task). The untrained ML model may be inaccurate in performing the designated tasks. As the ML model becomes trained through the ML algorithm, the tasks may be performed more accurately.

The initialization configuration information for a ML model may include initial settings and/or parameters. For example, the initial settings and/or parameters may include defined ranges for the ML model to employ. The ranges may include ranges for manual inputs and/or received data. The ranges may include default ranges and/or randomized ranges for portions of the dataset not received, for example, which may be used to complete a dataset for processing. For example, if a dataset is missing a data range, the default data range may be used as a substitute to perform the ML algorithm.

The initialization configuration information for a ML model may include data storage locations. For example, locations or data storages and/or databases mapping the data relationships may be included. The databases mapping the data relationships may be used to identify trends in datasets. The databases mapping the data relationships may include mappings of data to a medical condition. For example, a database associated with data interactions may include a mapping for heart rate data to medical conditions, such as, for example, arrythmia and/or the like.

The initialization configuration information may include parameters associated with defining the system. The initialization configuration information may include instructions (e.g., methods) associated with displaying, confirming, and/or providing information to a user. For example, the initialization configuration may include instructions to the ML model to output the data in a specific format for visualization for a user.

ML models may be trained using one or more ML algorithms. ML models may be trained using one or more of the following types of ML algorithm: supervised learning; unsupervised learning; semi-supervised learning; reinforcement learning; and/or the like.

Figure 8A:
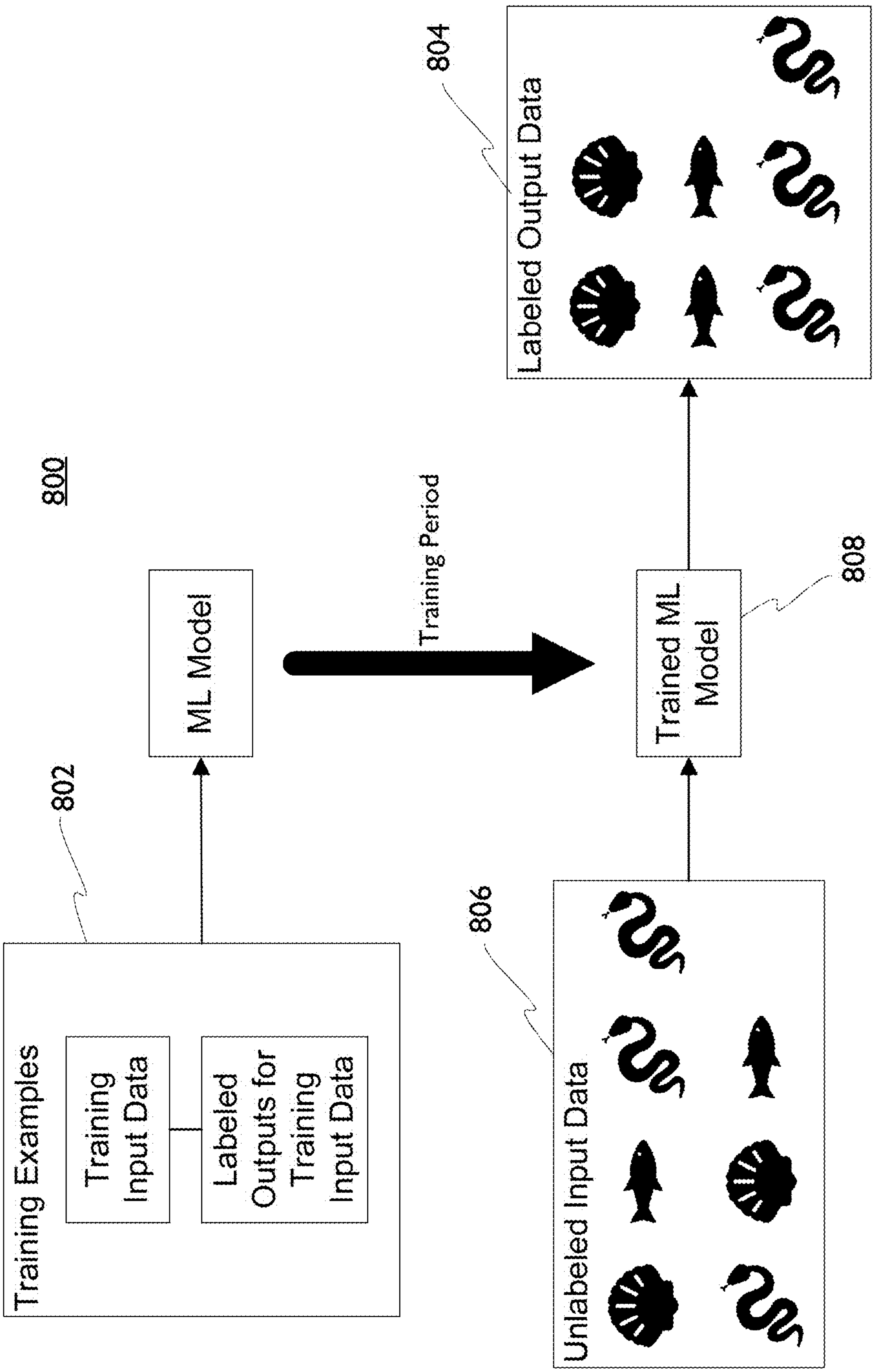
FIGS. 8A&B show an example supervised learning framework and an example unsupervised learning framework, respectively.

Machine learning algorithms may be supervised (e.g., supervised learning). A supervised ML algorithm creates a mathematical model (e.g., ML model) from training a dataset (e.g., training data). FIG. 8A illustrates an example supervised ML framework 800. The training data (e.g., training examples 802, for example, as shown in FIG. 8) may consist of a set of training examples (e.g., input data mapped to labeled outputs, for example, as shown in FIG. 8). A training example 802 may include one or more inputs and one or more labeled outputs. The labeled output(s) may serve as supervisory feedback. In a mathematical model, a training example 802 may be represented by an array or vector, sometimes called a feature vector. The training data may be represented by row(s) of feature vectors, constituting a matrix. Through iterative optimization of an objective function (e.g., cost function), a supervised learning algorithm may learn a function (e.g., a prediction function) that may be used to predict the output associated with one or more new inputs. A suitably trained prediction function (e.g., a trained ML model 808) may determine the output 804 (e.g., labeled outputs) for one or more inputs 806 that may not have been a part of the training data (e.g., input data without mapped labeled outputs, for example, as shown in FIG. 8). Example algorithms may include linear regression, logistic regression, neural network, nearest neighbor, Naive Bayes, decision trees, SVM, and/or the like. Example problems solvable by supervised learning algorithms may include classification, regression problems, and the like.

Linear regression may be used to predict continuous outcomes. For example, linear regression may be used to predict the value of a variable (e.g., dependent variable) based on the value of a different variable (e.g., independent variable). Linear regression may apply a linear approach for modeling a relationship between a scalar response and one or more explanatory variables (e.g., dependent and/or independent variables). Linear regression may be a polynomial where the coefficients of each term of the polynomial are the unknown model parameters, that is, the model is linear in the unknown variables that are to be trained. Other basis functions other than polynomials may be used in linear regression provided that the model is still linear in the unknown parameters. Simple linear regression may refer to linear regression use cases associated with one explanatory variable. Multiple linear regression may refer to linear regression use cases associated with more than one explanatory variables. Linear regression may model relationships, for example, using linear predictor functions. The linear predictor functions may estimate unknown model parameters from a data set.

Logistic regression may be used, for example, as a classifier. A weighted sum of the explanatory variables are input into a non-linear function such as a sigmoid, softmax, hyperbolic tangent or other function that can map continuous inputs into discrete labels or discrete probability distributions. The explanatory variables may be put through a basis function, such as a radial basis function or polynomial, before being weighted and summed. The weights of the model can then be trained using an optimization algorithm such as gradient descent, stochastic gradient descent or expectation maximization by comparing the predicted labels with the true labels and evaluating them in a cost function.

Nearest neighbor may be used as a classifier, in regression or in clustering (see further discussion related to clustering below). When a point is input into the model, the model looks for the nearest training data point to the provided input. The model then outputs the labelled output corresponding to the nearest training data point as being the predicted output of the input point. This model can be extended by instead looking at the K-Nearest-Neighbors and instead outputting either the mean, mode, median or other combination or function of the K nearest training data points to the provided input.

A Naive Bayes model may be used, for example, to construct classifiers. A Naive Bayes model may be used to assign class labels to problem instances (e.g., represented as vectors of feature values). The class labels may be drawn from a set (e.g., finite set). Different processes (e.g., algorithms) may be used to train the classifiers. A family of processes (e.g., family of algorithms) may be used. The family of processes may be based on a principle where the Naive Bayes classifiers (e.g., all the Naive Bayes) classifiers assume that the value of a feature is independent of the value of a different feature (e.g., given the class variable).

Decision trees may be used, for example, as a framework to quantify values of outcomes and/or the probabilities of outcomes occurring. Decision trees may be used, for example, to calculate the value of uncertain outcome nodes (e.g., in a decision tree). Decision trees may be used, for example, to calculate the value of decision nodes (e.g., in a decision tree). A decision tree may be a model to enable classification and/or regression (e.g., adaptable to classification and/or regression problems). Decision trees may be used to analyze numerical (e.g., continuous values) and/or categorical data. Decision trees may be more successful with large data sets and/or may be more efficient (e.g., as compared to other data reduction techniques).

SVMs may be used in a multi-dimensional space (e.g., high-dimensional space, infinite-dimensional space). SVCs may be used to construct a hyper-plane (e.g., set of hyper-planes). A hyper-plane that has the greatest distance (e.g., compared to the other constructed hyper-planes) from a nearest training data point in a class (e.g., any class) may achieve a strong separation (e.g., in general, the greater the margin, the lower the classifier's generalization error). SVMs may be effective in high-dimensional spaces. SVMs may behave differently, for example, based on different mathematical functions (e.g., the kernel, kernel functions). For example, kernel functions may include one or more of the following: linear, polynomial, radial basis function (RBF), sigmoid, etc. The kernel functions may be used as a SVM classifier. SVM may be limited in use cases, for example, where a data set contains high amounts of noise (e.g., overlapping target classes).

Figure 8B:
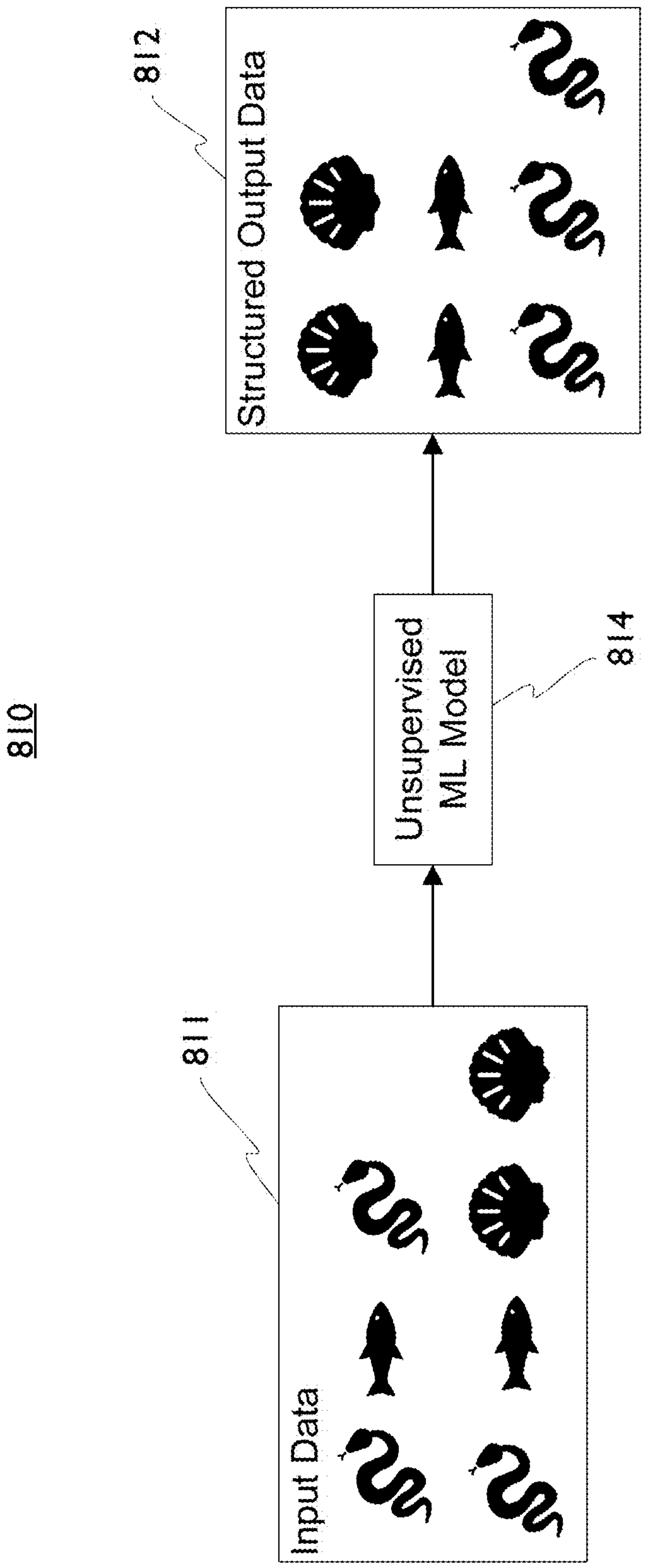

Machine learning algorithms may be unsupervised (e.g., unsupervised learning). FIG. 8B illustrates an example unsupervised learning framework 810. An unsupervised ML algorithm 814 may train on a dataset that may contain inputs 811 and may find a structure 812 (e.g., pattern detection and/or descriptive modeling) in the data. The structure 812 in the data may be similar to a grouping or clustering of data points. As such, the algorithm 814 may learn from training data that may not have been labeled. Instead of responding to supervisory feedback, an unsupervised learning algorithm may identify commonalities in training data and may react based on the presence or absence of such commonalities in each training datum. For example, the training may include operating on a training input data to generate an ML model and/or output with particular energy (e.g., such as a cost function or probability distribution), where such energy may be used to further refine the ML model (e.g., to define the ML model that minimizes the cost function or probability of an output in view of the training input data). Example algorithms may include a priori algorithm, K-Means, K-Nearest Neighbors (KNN), K-Medians, and the like. Example problems solvable by unsupervised learning algorithms may include clustering problems, anomaly/outlier detection problems, and the like Further to the nearest neighbor discussion above, K-means clustering may be used for vector quantization. K-means clustering may be used in signal processing. K-means clustering may be aimed at partitioning n observations into k clusters, for example, where each observation is classified into a cluster with the closest mean. K-medians is similar in that each observation is classified into a cluster with the closest median.

K-means clustering may include K-Nearest Neighbors (KNN) learning. KNN may be an instance-based learning (e.g., non-generalized learning, lazy learning). KNN may refrain from constructing a general internal model. KNN may include storing instances corresponding to training data in an n-dimensional space. KNN may use data and classify data points, for example, based on similarity measures (e.g., Euclidean distance function). Classification may be computed, for example, based on a majority vote of the k nearest neighbors of a (e.g., each) point. KNN may be robust for noisy training data. Accuracy may depend on data quality (e.g., for KNN). KNN includes choosing a number of neighbors to be considered (e.g., optimal number of neighbors to be considered). KNN may also be used for classification and/or regression.

Machine learning algorithms may be semi-supervised (e.g., semi-supervised learning). A semi-supervised learning algorithm may be used in scenarios where a cost to label data is high (e.g., because it requires skilled experts to label the data) and there are limited labels for the data. Semi-supervised learning models may exploit an idea that although group memberships of unlabeled data are unknown, the data still carries important information about the group parameters.

Machine learning algorithms may use reinforcement learning, which may be an area of machine learning that may be concerned with how software agents may take actions in an environment to maximize a notion of cumulative reward. Reinforcement learning algorithms may not assume knowledge of an exact mathematical model of the environment (e.g., represented by Markov decision process (MDP) and may be used when exact models may not be feasible. Reinforcement learning algorithms may be used in autonomous vehicles or in learning to play a game against a human opponent. Examples algorithms may include Q-Learning, Temporal Difference (TD), Deep Adversarial Networks, and/or the like.

Reinforcement learning may include an algorithm (e.g., agent) continuously learning from the environment in an iterative manner. In the training process, the agent may learn from experiences of the environment until the agent explores the full range of states (e.g., possible states). Reinforcement learning may be defined by a type of problem. Solutions of reinforcement learning may be classed as reinforcement learning algorithms. In a problem, an agent may decide an action (e.g., the best action) to select based on the agent's current state. If a step if repeated, the problem may be referred to as a Markov Decision Process (MDP).

For example, reinforcement learning may include operational steps. An operation step in reinforcement learning may include the agent observing an input state. An operation step in reinforcement learning may include using a decision making function to make the agent perform an action. An operation step may include (e.g., after an action is performed) the agent receiving a reward and/or reinforcement from the environment. An operation step in reinforcement learning may include storing the state-action pair information about the reward.

Machine learning may be a part of a technology platform called cognitive computing (CC), which may constitute various disciplines such as computer science and cognitive science. CC systems may be capable of learning at scale, reasoning with purpose, and interacting with humans naturally. By means of self-teaching algorithms that may use data mining, visual recognition, and/or natural language processing, a CC system may be capable of solving problems and optimizing human processes.

The output of the training process (e.g., the ML algorithm) may be a model (e.g., a ML model) for predicting outcome(s) on a new dataset. For example, a linear regression learning algorithm may involve a cost function that may be used to assess the prediction errors of a prediction function that is linear in the model parameters during the training process. The training process then adjusts the coefficients and constants (e.g., the model parameters) of the prediction function to minimize the cost function. When a minimum may be reached, the prediction function with adjusted coefficients may be deemed trained and constitute the model the training process has produced. In another example, a neural network (NN) algorithm (e.g., multilayer perceptrons (MLP)) for classification may include a hypothesis function represented by a network of layers of nodes that are assigned with biases and interconnected with weight connections. The hypothesis function may be a non-linear function (e.g., a highly non-linear function) that may include linear functions and logistic functions nested together with the outermost layer consisting of one or more logistic functions. The NN algorithm may include a cost function that assesses classification errors and is minimized by adjusting the biases and weights through a process of feedforward propagation and backward propagation. When a global minimum may be reached, the optimized hypothesis function with its layers of adjusted biases and weights may be deemed trained and constitute the model the training process has produced.

Often it is not possible to minimize the cost function directly during the training process and so other optimization algorithms must be used to train the mode. An example of an optimization algorithm is stochastic gradient descent (SGD). SGD may include an iterative process used to optimize a function (e.g., objective or cost function). SGD may be used to optimize an objective function, for example, with certain smoothness properties. Stochastic may refer to random probability. SGD may be used to reduce computational burden, for example, in high-dimensional optimization problems. SGD may be used to enable faster iterations, for example, while exchanging for a lower convergence rate. A gradient may refer to the slope of a function, for example, that calculates a variable's degree of change in response to another variable's changes. Gradient descent may refer to a convex function that outputs a partial derivative of a set of its input parameters. For example, a may be a learning rate and Ji may be a training example cost of the ith iteration. The equation may represent the stochastic gradient descent weight update method at the jth iteration. In large-scale ML and sparse ML, SGD may be applied to problems in text classification and/or natural language processing (NLP). SGD may be sensitive to feature scaling (e.g., may need to use a range of hyperparameters, for example, such as a regularization parameter and a number of iterations).

ML algorithms may be used independently of each other or in combination. Different problems and/or datasets may benefit from using different ML algorithms (e.g., combinations of ML algorithms). Different training types for models may be better suited for a certain problem and/or dataset. An optimal algorithm (e.g., combination of ML algorithms) and/or training type may be determined for a specific usage, problem, and/or dataset.

In some examples, adaptive boosting (e.g., AdaBoost) may be used. Adaptive boosting may include creating a classifier (e.g., powerful classifier). Adaptive boosting may include creating a classier by combining multiple classifiers (e.g., poorly performing classifiers), for example, to obtain a resulting classifier with high accuracy. AdaBoost may be an adaptive classifier that improves the efficiency of a classifier. AdaBoost may trigger overfits. AdaBoost may be used (e.g., best used) to boost the performance of decision trees, base estimator(s), binary classification problems, and/or the like. AdaBoost may be sensitive to noisy data and/or outliers.

In examples, a ML algorithm and/or combination of ML algorithms may be determined for a particular problem and/or use case. Multiple data reduction and/or data analysis processes may be performed to determine accuracy, efficiency, and/or compatibility associated with a dataset. For example, a first ML algorithm (e.g., first set of combined ML algorithm) may be used on a dataset to perform data reduction and/or data analysis. The first ML algorithm may produce a first output. Similarly, a second ML algorithm (e.g., second set of combined ML algorithm) may be used on the dataset (e.g., same dataset) to perform data reduction and/or data analysis. The second ML algorithm may produce a second output. The first output may be compared with the second output to determine which ML algorithm produced more desirable results (e.g., more efficient results, more accurate results). Multiple ML algorithm may be compared with the same dataset to determine the optimal ML technique(s) to use on a future similar dataset and/or problem.

In examples, in a medical context, a surgeon or healthcare professional may give feedback to ML algorithm and/or ML models used on a dataset. The surgeon may input feedback to weighted results of a ML model.

In examples, a data analysis method (e.g., ML algorithm to be used in the data analysis method) may be determined based on the dataset itself. For example, the origin of the data may influence the type of data analysis method to be used on the dataset. System resources available may be used to determine the data analysis method to be used on a given dataset. The data magnitude, for example, may be considered in determining a data analysis method. For example, the need for datasets exterior to the local processing level or magnitude of operational responses may be considered (e.g., small device changes may be made with local data, major device operation changes may require global compilation and verification).

Data collection may be performed as a first stage of a machine learning pipeline. Data collection may include steps such as identifying various data sources, collecting data from the data sources, integrating the data, and the like. For example, for training a machine learning model for predicting surgical complications and/or post-surgical recovery rates, data sources containing pre-surgical data, such as a patient's medical conditions and biomarker measurement data, may be identified. Such data sources may be a patient's electronical medical records (EMR), a computing system storing the patient's pre-surgical biomarker measurement data, and/or other like datastores. The data from such data sources may be retrieved and stored in a central location for further processing in the machine learning lifecycle. The data from such data sources may be linked (e.g. logically linked) and may be accessed as if they were centrally stored. Surgical data and/or post-surgical data may be similarly identified, collected. Further, the collected data may be integrated. In examples, a patient's pre-surgical medical record data, pre-surgical biomarker measurement data, pre-surgical data, surgical data, and/or post-surgical may be combined into a record for the patient. The record for the patient may be an EMR. In examples, the relationships between the data types may be identified. The relationships between he data types may be identified manually, for example, by an HCP.

Data preparation may be performed as another stage of the machine learning pipeline. Data preparation may include data preprocessing steps such as data formatting, data cleaning, and data sampling. For example, the collected data may not be in a data format suitable for training a model. Such data record may be converted to a flat file format for model training. Such data may be mapped to numeric values for model training. Such identifying data may be removed before model training. For example, identifying data may be removed for privacy reasons. As another example, data may be removed because there may be more data available than may be used for model training. In such case, a subset of the available data may be randomly sampled and selected for model training and the remainder may be discarded.

Data preparation may include data transforming procedures (e.g., after preprocessing), such as scaling and aggregation. For example, the preprocessed data may include data values in a mixture of scales. These values may be scaled up or down, for example, to be between 0 and 1 for model training. For example, the preprocessed data may include data values that carry more meaning when aggregated.

Model training may be another aspect of the machine learning pipeline. The model training process as described herein is dependent on the ML algorithm used. A model may be deemed suitably trained after it has been trained, cross validated, and tested. Accordingly, the dataset from the data preparation stage (e.g., an input dataset) may be divided into a training dataset (e.g., 60% of the input dataset), a validation dataset (e.g., 20% of the input dataset), and a test dataset (e.g., 20% of the input dataset). After the model has been trained on the training dataset, the model may be run against the validation dataset to identify overfitting. If accuracy of the model were to decrease when run against the validation dataset when accuracy of the model has been increasing, this may indicate a problem of overfitting. The test dataset may be used to test the accuracy of the final model to determine whether it is ready for deployment or more training may be required.

Model deployment may be another aspect of the machine learning pipeline. The model may be deployed as a part of a standalone computer program. The model may be deployed as a part of a larger computing system. A model may be deployed with model performance parameters(s). Such performance parameters may monitor the model accuracy as it is used for predicating on a dataset in production. For example, such parameters may keep track of false positives and false positives for a classification model. Such parameters may further store the false positives and false positives for further processing to improve the model's accuracy.

Post-deployment model updates may be another aspect of the machine learning pipeline. For example, a deployed model may be updated as false positives and/or false positives are predicted on production data. In an example, for a deployed MLP model for classification, as false positives occur, the deployed MLP model may be updated to increase the probably cutoff for predicting a positive to reduce false positives. In an example, for a deployed MLP model for classification, as false negatives occur, the deployed MLP model may be updated to decrease the probably cutoff for predicting a positive to reduce false negatives. In an example, for a deployed MLP model for classification of surgical complications, as both false positives and false negatives occur, the deployed MLP model may be updated to decrease the probably cutoff for predicting a positive to reduce false negatives because it may be less critical to predict a false positive than a false negative.

For example, a deployed model may be updated as more live production data become available as training data. In such case, the deployed model may be further trained, validated, and tested with such additional live production data. In an example, the updated biases and weights of a further-trained MLP model may update the deployed MLP model's biases and weights. Those skilled in the art recognize that post-deployment model updates may not be a one-time occurrence and may occur as frequently as suitable for improving the deployed model's accuracy.

Such machine learning pipelines may be applied to surgical information (e.g., a combination of information flows of surgical information in FIG. 7) to generate useful ML models. For example, such machine learning pipelines may be used to generate ML models to make surgical classifications, identify surgical data trends, or make surgical recommendations. In another example, such machine learning pipelines may be applied to surgical information to generate ML models to perform data reduction. In another example, a pre-processing ML model may be generated using such machine learning pipelines.

ML algorithms may be used to train ML models to perform data reduction. ML algorithms for data reductions may include using multiple different data reduction algorithms. For example, ML algorithms for data reductions may include using one or more of the following: CUR matrix decomposition; a decision tree; mixture of gaussian algorithms; explicit semantic analysis (ESA); generalized linear model; Naive Bayes; neural networks; a multivariate analysis; an o-cluster; a singular value decomposition; Q-learning; a temporal difference (TD); deep adversarial networks; support vector machines (SVM); linear regression; reducing dimensionality; linear discriminant analysis (LDA); outlier detection; and/or the like.

Data reduction generally refers to the process of reducing the complexity of the data and pre-processing the data before it is input into a model or training algorithm. This could be through dimensionality reduction, that is, consolidating the information stored in a data point from, for example, 100 dimensions, to fewer dimensions that are some combination of the original 100 dimensions. Alternatively, data reduction can be summarizing the data in some way. For example, a linear regression model provides a single line that can summarize any of the data points as an approximation. Other forms of data reduction could be noise reduction, or outlier identification that filters the input data to only the most useful and relevant.

ML algorithms may be used to perform data reduction, for example, using CUR matrix decompositions. A CUR matrix decomposition includes using a matrix decomposition model (e.g., process, algorithm), such as a low-rank matrix decomposition model. For example, CUR matrix decomposition includes a low-rank matrix decomposition process that is expressed (e.g., explicitly expressed) in a number (e.g., small number) of columns and/or rows of a data matrix (e.g., the CUR matrix decomposition may be interpretable). CUR matrix decomposition may include selecting columns and/or rows associated with statistical leverage and/or a large influence in the data matrix. Using CUR matrix decomposition may enable identification of attributes and/or rows in the data matrix. The simplification of a larger dataset (e.g., using CUR matrix decomposition) may enable review and interaction (e.g., with the data) by a user. CUR matrix decomposition may facilitate regression, classification, clustering, and/or the like.

ML algorithms may be used to perform data reduction, for example, using decision trees (e.g., decision tree model). Decision trees may be used in combination with other decision trees. For example, a random forest may refer to a collection of decision trees (e.g., ensemble of decision trees). A random forest may include a collection of decision trees whose results may be aggregated into a result. A random forest may be a supervised learning algorithm. A random forest may be trained, for example, using a bagging training process.

A random decision forest (e.g., random forest) may add randomness (e.g., additional randomness) to a model, for example, while generating the trees. A random forest may be used to search for a best feature among a random subset of features, for example, rather than searching for the most important feature (e.g., while splitting a node). Searching for the best feature among a random subset of features may result in a wide diversity that may result in a better (e.g., more efficient and/or accurate) model.

A random forest may include using parallel ensembling. Parallel ensembling may include fitting (e.g., several) decision trees in parallel, for example, on different data set sub-samples. Parallel ensembling may include using majority voting or averages for outcomes or final results. Parallel ensembling may be used to minimize overfitting and/or increase prediction accuracy and control. A random forest with multiple decision trees may (e.g., generally) be more accurate than a single decision tree-based model. A series of decision trees with controlled variation may be built, for example, by combining bootstrap aggregation (e.g., bagging) and random feature selection.

ML algorithms may be used to perform data reduction, for example, using a mixture of Gaussians or some other statistical clustering. Such statistical clustering assigns, for each data point, a probability that the data point was generated by the cluster. Such clustering models can be trained using an expectation maximization (EM) algorithm may be used to find a likelihood (e.g., local maximum likelihood) parameter of a statistical model such as the likelihood (or probability) a point is associated with a given cluster. An EM algorithm may be used for cases where equations may not be solved directly. An EM algorithm may consider latent variables and/or unknown parameters and known data observations. For example, the EM model may determine that missing values exist in a data set. The EM model receive configuration information indicating to assume the existence of missing (e.g., unobserved) data points in a data set. Examples of missing data may be a collection of results from a patient survey where not every question has been answered by every patient. Due to the probabilistic nature of models that can be trained using an EM algorithm, it is possible to calculate probabilities without knowledge of the unknown parameters since the conditional probabilities can be adjusted accordingly based on fewer observations.

ML algorithms may be used to perform data reduction, for example, using explicit semantic analysis (ESA). ESA may be used at a level of semantics (e.g., meaning) rather than on vocabulary (e.g., surface form vocabulary) of words or a document. ESA may focus on the meaning of a set of text, for example, as a combination of the concepts found in the text. ESA may be used in document classification. ESA may be used for a semantic relatedness calculation (e.g., how similar in meaning words or pieces of text are to each other). ESA may be used for information retrieval.

ESA may be used in document classification, for example. Document classification may include tagging documents for managing and sorting. Tagging a document (e.g., with a keyword) may allow for easier searching. Keyword tagging (e.g., only using keyword tagging) may limit the accuracy and/or efficiency of document classification. For example, using keyword tagging may uncover (e.g., only uncover) documents with the keywords and not documents with words with similar meaning to the keywords. Classifying text semantically (e.g., using ESA) may improve a model's understanding of text. Classifying text semantically may include representing documents as concepts and lowering dependence on specific keywords.

ML techniques algorithms may be used to perform data reduction, for example, using linear regression. Linear regression may be used to identify patterns within a training dataset. The identified patterns may relate to values and/or label groupings. The ML model may learn a relationship between the (e.g., each) label and the expected outcomes. After training, the model may be used on raw data outside the training data set (e.g., data without a mapped and/or known output). The trained model using linear regression may determine calculated predictions associated with the raw data, for example, such as identifying seasonal changes in sales data.

ML algorithms may be used to perform data reduction, for example, a generalized linear model (GLM). A GLM may be used as a flexible generalization of linear regression. GLM may generalize linear regression, for example, by enabling a linear model to be related to a response variable.

ML algorithms may be used to perform data reduction, for example, using a neural network. Neural networks may learn (e.g., be trained) by processing training data, for example, to perform other tasks (e.g., similar tasks). Training data may include input data and corresponding output data (e.g., an input mapped to an output). The neural network may learn by forming probability-weighted associations between the input and the output. The probability-weighted associations may be stored within a data structure of the neural network. The training of the neural network from a given piece of training data may be conducted by determining the difference between a processed output of the network (e.g., prediction) and a target output. The difference may be the error. The neural network may adjust the weighted associations (e.g., stored weighted associations), for example, according to a learning rule and the error value.

ML algorithms may be used to perform data reduction, for example, using multivariate analysis. Multivariate analysis may include performing multivariate state estimation and/or non-negative matrix factorization.

ML algorithms may be used to perform data reduction, for example, such as reducing dimensionality. Reducing dimensionality of a sample of data (e.g., unlabeled data) may help refine groups and/or clusters. Reducing a number of variables in a model may simplify data trends. Simplified data trends may enable more efficient processing. Reducing dimensionality may be used, for example, if many (e.g., too many) dimensions are clouding (e.g., negatively affecting) insights, trends, patterns, conclusions, and/or the like.

ML algorithms may be used to perform data reduction, for example, linear discriminant analysis (LDA). LDA may refer to a linear decision boundary classifier, for example, that may be created by fitting class conditional densities to data (e.g., and applying Bayes' rule). LDA may include a generalization of Fisher's linear discriminant (e.g., projecting a given dataset into lower-dimensional space, for example, to reduce dimensionality and minimize complexity of a model and reduce computational costs). An LDA model (e.g., standard LDA model) may suit a class with a Gaussian density. The LDA model may assume that the classes (e.g., all clases) share a covariance matrix. LDA may be similar to analysis of variance (ANOVA) processes and/or regression analysis. For example, LDA may be used to express a dependent variable as a linear combination of other features and/or measurements.

ML algorithms may be used to perform data reduction, for example, such as using outlier detection. An outlier may be a data point that contains information (e.g., useful information) on an abnormal behavior of a system described by the data. Outlier detection processes may include univariate processes and multivariate processes. An example of outlier detection is the RANdom SAmple and Consensus algorithm (RANSAC). This algorithm randomly samples a set of training data points and fits a model to it. The rest of the training data points are then classified as being outliers or inliers based on how big the prediction error between the model output and the training point. The process is then repeated with a separate sample of points until a certain proportion of points are classified as inliers (i.e. 70%) or certain number of loops of the process have occurred. For example, a set of data points is to have a straight line fit through it. The minimum number of points required to fit a straight line is two. The RANSAC algorithm repeatedly samples two of the data points and fits a line through them before comparing the rest of the data points to the line to classify each of the remaining points as inliers and outliers. The final model is then fit to all the points that are then considered inliers.

Additionally or alternatively to using a ML algorithm to perform data reduction, reducing dimensionality may include using principal component analysis (PCA). PCA may be used to establish principal components that govern a relationship between data points. PCA may focus on simplifying (e.g., only simplifying) the principal components. Reducing dimensionality (e.g., PCA) may be used to maintain the variety of data grouping in a data set, but streamline the number of separate groups. Principle component analysis aims to find the combination of features in a data point that show the most variance. For example a collection of data points in 3D space will have three features associated with each point—one for each dimension in space. If those data points form a roughly linear trend, principle component analysis will enable the data points to be approximated by a single number that represents the position of the point on the straight line in the 3D space. Of course, high dimensional data can be used, and the data does not have to be roughly linear for PCA to be valuable in reducing dimensionality ML algorithms may be used, for example, to perform surgical recommendation. For example, an ML model may receive raw surgical data and generate surgical recommendations. Raw surgical data may include surgical procedure data, patient-specific data, HCP data, surgical instrument data, and/or the like. For example, during a surgical procedure, an ML model may receive heart rate data and patient specific data. The ML model may determine that a surgical complication may occur, for example, if the surgical procedure continues as planned. The ML model may generate a recommendation (e.g., for the HCP) to alter the surgical procedure plan, for example, to avoid the surgical complication.

ML algorithms may be used, for example, to perform surgical classification. For example, an ML algorithm may determine surgical complications, surgical events, surgical procedure step (e.g., step transitions), surgical data type, and/or the like. The ML algorithm may use raw surgical data to determine, for example, a current surgical procedure step in the live surgical procedure. For example, the ML algorithm may determine that a transition between surgical steps in a surgical procedure has occurred. The ML algorithm may determine that a surgical complication has occurred (e.g., is likely to occur).

ML algorithms may be used, for example, to perform surgical trend identification.

Such ML models may be applied to surgical information (e.g., a combination of information flows of surgical information in FIGS. 7A-D) to generate useful ML models.

Systems, methods, and instrumentalities are disclosed for using interrelated machine learning (ML) models (e.g., algorithms). The interrelated ML models may act collectively to perform complimentary portions of a surgical analysis. The ML models may be used at various locations. For example, ML models may be implemented in a facility network, a cloud network, an edge network, and/or the like. The location of the ML models may influence the type of data the ML models process. For example, ML models used outside a HIPAA boundary (e.g., cloud network) may process non-private and/or non-confidential information. The ML models may be used to feed their respective results into other ML models to provide a more complete result.

For example, a computing system may include a processor that may implement interrelated ML models. The computing system may determine sets of data (e.g., first set of data, second set of data, etc.) to be sent to ML models for processing. The sets of data may be determined, for example, based on the processing task associated with the ML model the set of data is to process. The computing system may generate (e.g., using a machine learning model) an output based on a set of data. Multiple ML models may process different sets of data. The outputs from the different ML models may be fed into subsequent ML model(s), for example, for additional processing. The subsequent ML model(s) may receive the outputs from the interrelated ML models and/or other sets of data. The subsequent ML model(s) may generate a result based on the received outputs and/or sets of data.

The processing tasks associated with the ML model(s) may be associated with surgical data processing. For example, the ML model(s) may be associated with data preparation, data reduction, trend analysis, recommendation determination, and/or the like.

Surgical data may be prepared and/or processed to provide medical insights on the surgical data. For example, surgical data for a live surgical procedure may provide insights on the live surgical procedure. The insights may give context to health care professionals (HCPs) in the surgical theater performing the live surgical procedure. For example, the HCPs may be informed by the insights about certain events and/or recommendations associated with the live surgical procedure. Insights on the surgical data may indicate that a patient is experiencing a higher heart rate than may be normal for the surgical procedure and/or surgical procedure step. Insights may be valuable to HCPs and/or medical training. Insights give context to surgical procedures and the medical field.

Machine learning (ML) may be used, for example, in the medical field to receive raw surgical data for processing to produce helpful information. For example, machine learning may be used to pre-process the surgical data for HCPs to perform analyses. Pre-processing data may include data reduction, data clean up, and/or data completion. Machine learning may be used on prepared surgical data, for example, to perform surgical analysis on the prepared surgical data. For example, ML may be used to identify trends, patterns, and/or relationships in the data. ML may be used, for example, to determine methodologies on how to communicate the identified trends, patterns and/or relationships. For example, ML may be used to determine surgical recommendations (e.g., on the fly adaptations of control programs)

based on surgical data, and the ML may be used to communicate the recommendations to a user (e.g., HCP, surgeon, nurse).

Multiple ML processes (e.g., techniques, algorithms, models) may be used on the surgical data. For example, separate but interrelated ML models may be used in conjunction with each other to identify different portions of a surgical analysis (e.g., data preparation, relationships within the data, methodologies of how to communicate the recommendations, or on the fly adapatations of control programs. For example, a first ML model may be used to prepared raw surgical data and output a first set of data to be used for pattern identification. A second ML model may use the first set of data to identify patterns within the first set of data. The second ML model may output a second set of data that indicates relationships within the first set of data. A third ML model may receive the second set of data and determine a method of communicating the data, which may be output to as a third set of data. In the end, the identified patterns of the surgical data may be communicated to a user. The ML models in conjunction may be used to take raw surgical data and produce helpful surgical insights in a digestible manner to a user.

Figure 9:
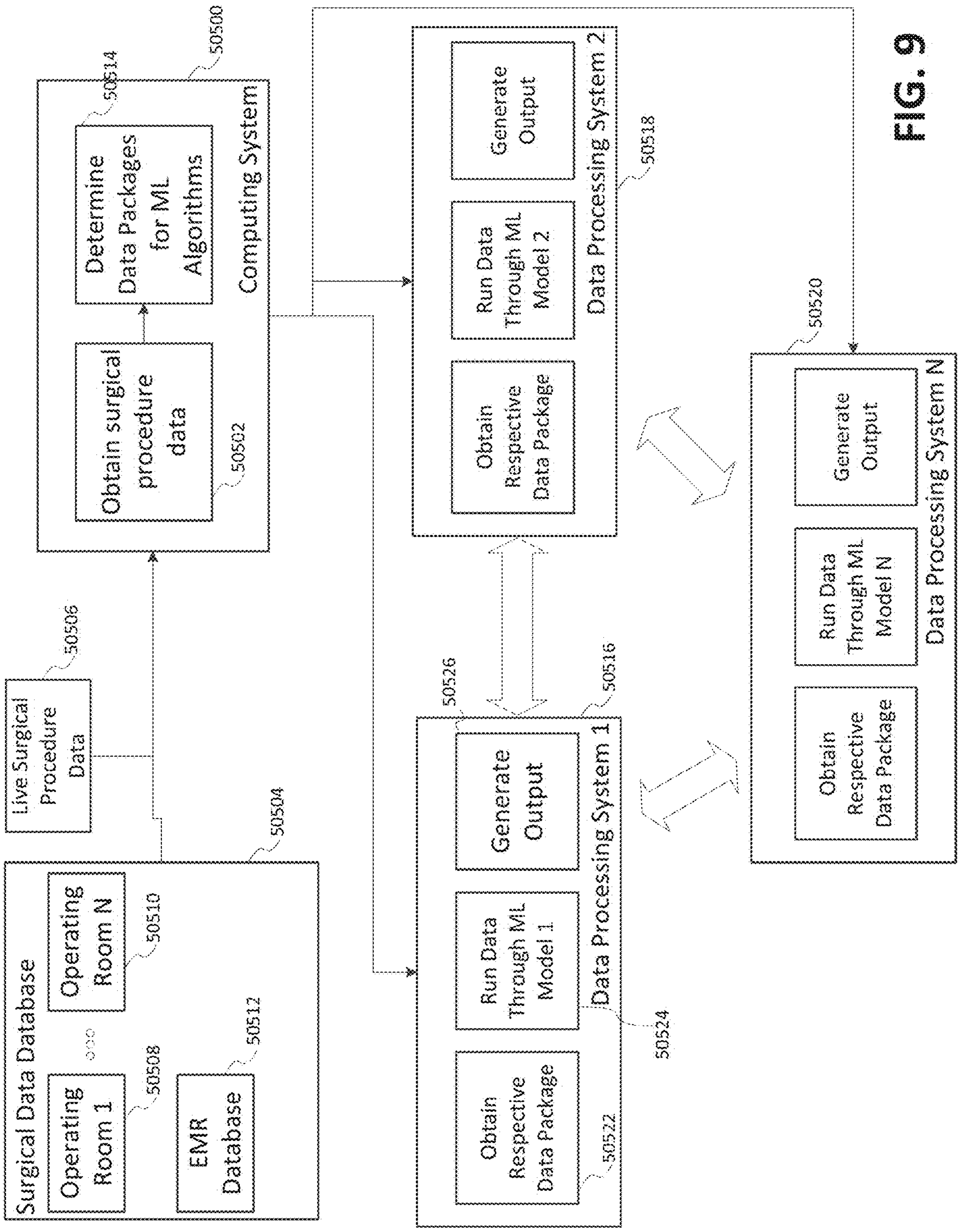
FIG. 9 illustrates an example of using interrelated ML algorithms to perform different portions of analysis for surgical data

FIG. 9 illustrates an example of using interrelated ML algorithms to perform different portions of analysis for surgical data. As shown in FIG. 9 at 50502, a computing system 50500 may receive surgical data (e.g., surgical procedure data). The surgical procedure data may include surgical data from a surgical data database 50504 and/or live surgical procedure data 50506. Surgical data from the surgical data database 50504 may include surgical data from different operating rooms (e.g., such as Operating Room 1 50508, Operating Room N 50510, etc.), data from an electronic medical record database (e.g., associated with a particular patient) 50512, and/or the like. As shown in FIG. 9 at 50514, data packages (e.g., comprising sets of the obtained surgical data) may be determined, for example, to be sent to different interrelated ML models (e.g., algorithms) for processing. For example, data packages may be sent to a first data processing system 50516, a second data processing system 50518, an Nth data processing system 50520, and/or the like.

The respective data processing systems (e.g., ML models, ML algorithms, etc.) may process their respectively obtained data packages (e.g., using ML). The first data processing system A50516 may obtain its respective data package (e.g., as shown at 50522). The first data processing system may process the data package (e.g., run data through a ML model), for example, as shown at 50524. The ML model may used to perform one or more of the data processing goals (e.g., data reduction, trend identification, recommendation determination, etc.) as described herein. The ML model may output a set of data associated with the ML model's processing goals. For example, the ML model may be used to reduce raw surgical data. The output may comprise reduced surgical data, for example, that may be used by a user and/or other ML models to produce surgical insights and/or recommendations.

As shown at 50514, the data packages for the respective data processing systems (e.g., ML models) may be determined. The data packages may be determined, for example, based on the processing task and/or goal of the respective data processing systems and/or ML models. For example, a data package for a ML model that is associated with performing data reduction may include raw surgical data that needs to be sifted through before performing accurate trend analysis. For example, raw surgical data may include various data outliers that may occur due to improper calibration of instruments and/or sensors, and/or other data collection errors. The data outliers (e.g., if considered/used during data analysis) may produce inaccurate results and/or conclusions. Removing the data outliers may allow for more accurate analysis. The ML model may identify and remove outlier data during data reduction, for example, before sending the cleaned data for analysis using a different ML model.

In examples, a data package for a data processing system (e.g., ML model) that is associated with determining a baseline surgical procedure plan may include data associated with historic surgical procedure performed on patients with similar biometrics and/or body compositions. Data from historic surgical procedures may be used to influence future surgical procedures. The data package may comprise different data that may be used to map out an optimal surgical procedure plan.

In examples, the data packages may be determined based on the processing capabilities of the ML models and/or data processing systems. For example, a data processing system may be limited based on its processing capabilities. Higher amounts of data to be processed and/or complexity of the processing task may use more processing resources. For example, a data processing system may be limited to using a threshold number of processing resources for a given task. The data packages may be determined by considering the processing power of the data processing system. For example, a local data processing system that is associated with processing lower amounts of data in a non-complex manner may receive a smaller data package than a cloud based data processing system equipped to handle databases of data for complex processing. The computing system 50500 may determine the processing capabilities associated with ML models and the data processing systems, for example, before sending the data packages.

The data processing systems may (e.g., also, in addition to the data packages from the computer system) receive outputs from the other data processing systems (e.g., interrelated ML models) as (e.g., additional) inputs for their respective processing. For example, the first data processing system 50516 may process the received data such that the output comprises reduced data (e.g., first ML algorithm performs data reduction). The reduced data may be an input to the second data processing system AA045. The reduced data may be used (e.g., in conjunction with the respective data package obtained by the second data processing system) to perform the ML algorithm associated with the second data processing system. The reduced data may enhance the outputs produced by the second data processing system (e.g., provide more accurate results, and/or allow for more efficient processing).

In examples, outputs may be determined by ML models and/or data processing systems in anticipation of sending the output to a different interrelated ML model and/or data processing system. For example, a first data processing system may process a first set of data and output a second set of data intended for a second data processing system. The second set of data may be generated based on the determined processing capabilities associated with the intended recipient of the second set of data. For example, a second data processing system may be limited to handling only non-complex processing tasks. The output of the first data processing system may take into consideration the lower processing power of the second data processing system and reduce the complexity of the data in the out and/or the amount of data in the output.

Figure 10:
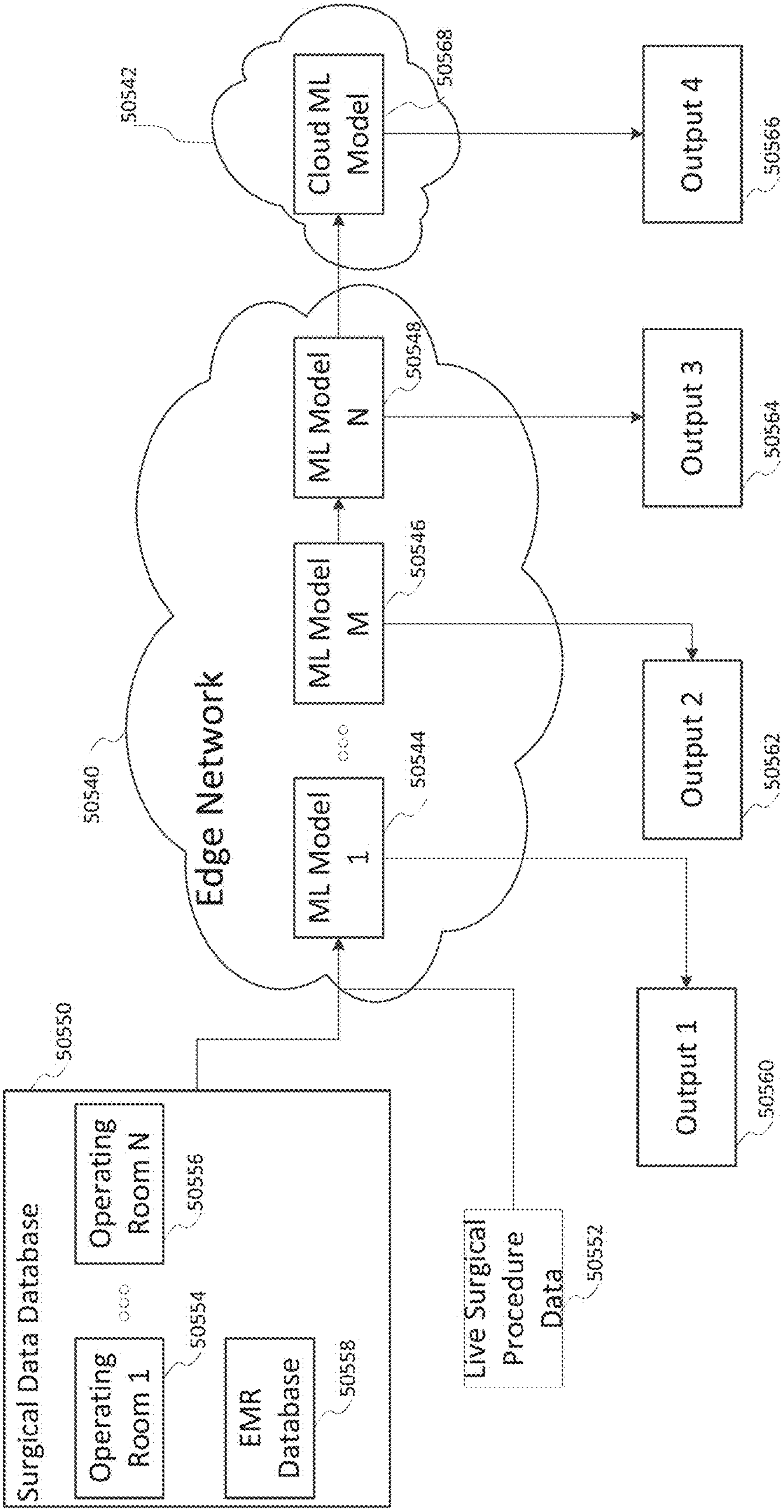
FIG. 10 illustrates an example of interrelated ML models processing data in different locations.

FIG. 10 illustrates an example of interrelated ML models processing data in different locations. As shown in FIG. 10, ML models may be used to process surgical data in an edge network 50540 or a cloud network 50542. In examples, ML models may be used to process surgical data locally (e.g., in a facility, such as a medical facility, an operating room, and/or the like). As shown in FIG. 10, surgical data may be transmitted to ML models (e.g., algorithms) for processing within different networks. The ML models (e.g., each ML model) may generate an output (e.g., and send the output to a user, storage, or further ML model for processing). The location of the data processing (e.g., ML model) may affect the type of data received for processing.

The Health Information Portability and Accountability Act may provide guidelines for handling medical data. For example, a HIPAA boundary may restrict private and/or confidential data from being sent between a protected area and an unprotected area. In examples, confidential data may be transmitted locally in a facility network and/or an edge network hosted within the facility. However, private and/or confidential data may be restricted from being transmitted beyond the HIPAA boundary (e.g., a cloud network).

Data obtained for processing may include data from a surgical data database 50550 and/or live surgical procedure data 50552. Data obtained from the surgical data database 50550 may include data from operating rooms in a medical facility (e.g., operating room 1 50554, operating room N 50556, etc.), data from electronic medical records 50558, and/or the like. The surgical data database 50550 may include at least some data classified as private and/or confidential (e.g., under HIPAA guidelines).

In examples, the data packages may be determined based on privacy concerns associated with the surgical data and the ML models (e.g., location of the ML models processing the data). Data tagged with a confidential and/or private type indicator may be refrained from being transmitted beyond the HIPAA boundary.

For example, ML models within the edge network and/or local network (e.g., of a medical facility) may receive private and/or confidential data for processing. As shown in FIG. 10, multiple ML models may be located in the edge network for processing data, such as ML Model 1 50544, ML Model M 50546, and ML Model N 50548. Based on the location of the ML models (e.g., within the HIPAA boundary in the edge network), the data received for processing may include data tagged as private and/or confidential. For example, the surgical data received for processing at ML model 1 50544, ML Model M 50546, ML Model N 50548, and/or other ML models within the edge network may receive surgical data that includes confidential and/or private data.

ML models in the cloud network (e.g., outside the HIPAA boundary) may receive surgical data that excludes confidential and/or private data. The data received as an output from a different ML model (e.g., within the HIPAA boundary) may not include the confidential and/or private data.

In examples, an ML model may generate an output specific to the destination the output is to be sent to. For example, ML Model 1 50544 may produce a first output 50560. The first output may be an input to a ML Model M 50546. ML The input to ML Model M 50546 may include private and/or confidential data, for example, because it is located within the HIPAA boundary (e.g., permitted to receive such data). Similarly, ML Model M 50546 may produce a second output 50562 (e.g., based on the input from ML Model 1 and/or an input from another source) that considers ML Model N 50548. The input to ML Model N 50548 may include private and/or confidential data, for example, because it is similarly located within the HIPAA boundary. ML Model N 50548 may generate a third output 50564 (e.g., based on the input received from ML Model M and/or a different source). The third output 50564 may be generated, for example, as an input to a Cloud ML Model 50568. The output 50564 may consider that Cloud ML Model 50568 is located in a cloud network (e.g., outside the HIPAA boundary). The Cloud ML Model 50568 may be restricted to data not containing private and/or confidential information. ML Model N 50548 may redact (e.g., remove) any confidential and/or private information in the third output 50564 (e.g., before sending to the Cloud ML Model 50568). A fourth output 50566 may be generated, for example, using the Cloud ML Model 50568.

Figure 11:
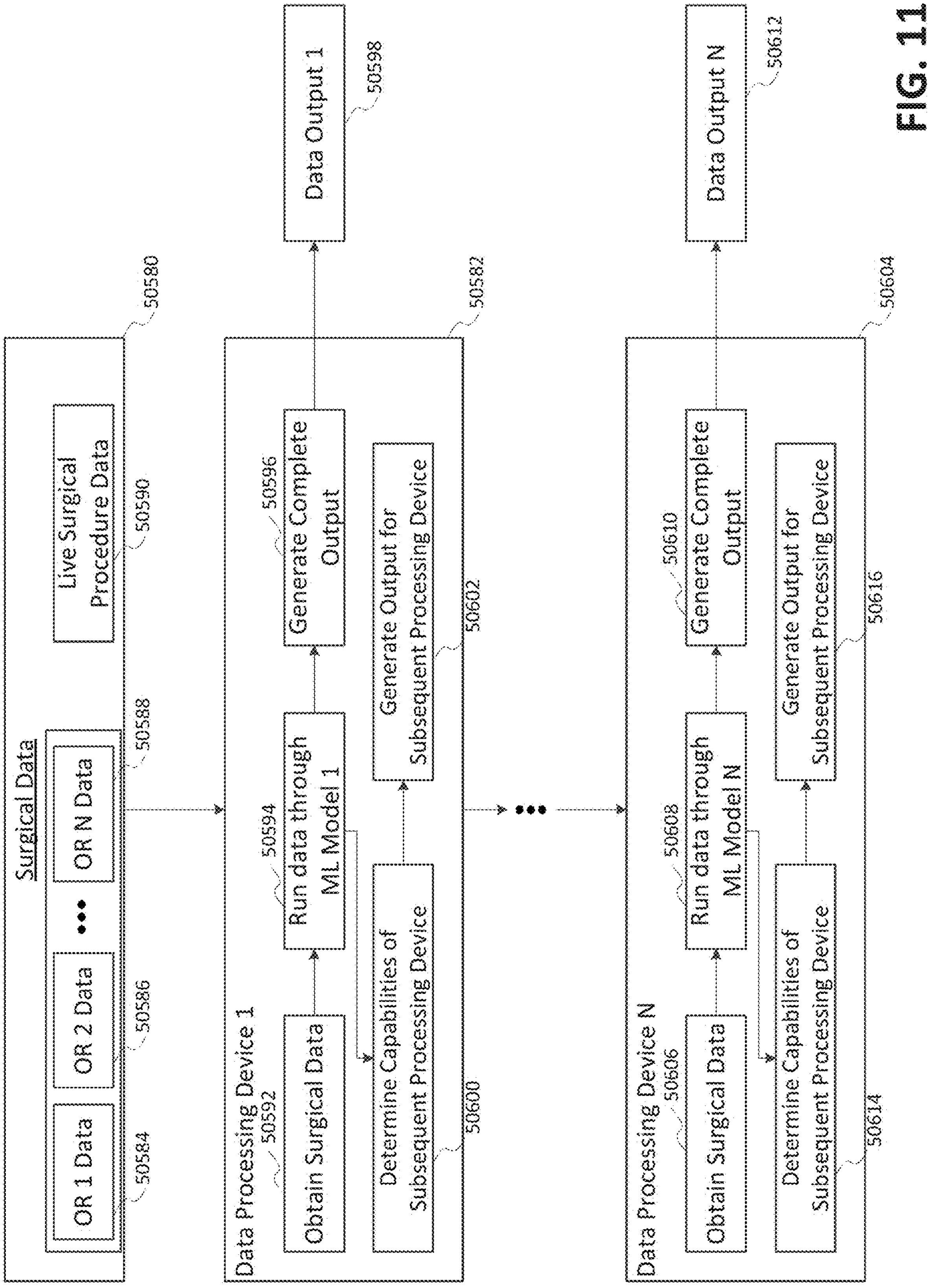
FIG. 11 illustrates an example flow of interrelated ML models generating processed data for other ML models and generating a completed set of processed data.

FIG. 11 illustrates an example flow of interrelated ML models generating processed data for other ML models and generating a completed set of processed data. ML models may process data and generate an output intended for a subsequent use and/or ML model (e.g., as described herein with respect to FIGS. 9 and 10). The ML models may general multiple outputs (e.g., different data packages). For example, a first ML model may generate a first output (e.g., to be transmitted to a second ML model) and a second output (e.g., to be transmitted to a third ML model). The first output may be generated based on the second ML model (e.g., capabilities, processing goal, etc.). The second output may be generated based on the second ML model. The first ML model may produce a third output, for example, that may include the entire output of the ML model processing. For example, a first data set may be input to the first ML model. The ML model may process the first data set. Based on the processing, the ML model may generate a complete result including all the processed data. The ML model may further determine data packages (e.g., subsets of the complete result of the processed data), for example, to be generated for other uses (e.g., other ML models to use). For example, a first data package may be generated and output for a second ML model. The first data package may be a subset of the complete result of the processed data. A second data package may be generated and output for a third ML model. The second data package may be a subset of the complete result of the processed data (e.g., including at least a portion of different data from the first data package).

As shown in FIG. 11, surgical data 50580 may be input to a first data processing device (e.g., first ML model) 50582. The surgical data may include data (e.g., as described herein), for example, such as data associated with an operating room (e.g., OR 1 data 50584, OR 2 data 50586, OR N data 50588, etc.), live surgical procedure data 50590, and/or the like. As shown at 50592, the first data processing device 50582 may obtain the surgical data 50580 (e.g., a portion of the surgical data). The obtained surgical data may be processed, for example, using an ML model (e.g., as shown at 50594). A complete result 50596 may be generated, for example, based on the using the ML model on the obtained surgical data. The complete result 50596 may be output as a first output (e.g., as shown at 50598). The data processing device may determine capabilities (e.g., processing capabilities, privacy capabilities, etc.) associated with a subsequent processing device (e.g., subsequent ML model), for example, as shown at 50600. Based on the determined capabilities associated with the subsequent processing device, a data package (e.g., output) may be generated to be transmitted to the subsequent data processing device (e.g., as shown at 50602). The data package may be transmitted to the subsequent data processing device (e.g., as shown in FIG. 11). The subsequent data processing device may be, for example, data processing device N 50604.

Data processing device N 50604 may obtain surgical data (e.g., an output from a previous ML model and/or data processing device, such as the output from data processing device 1 50582), for example, as shown at 50606. Data processing device N 50608 may process the obtained surgical data (e.g., as shown at 50608). Similar to the previous data processing devices, a complete result may be generated based on the processing using the ML model (e.g., as shown at 50610). The complete result may be output (e.g., as shown at 50612). Similarly, data processing device N 50604 may determine a capability associated with a subsequent processing device (e.g., as shown at 50614) to generate an output for the subsequent processing device (e.g., as shown at 50616).

Figure 12:
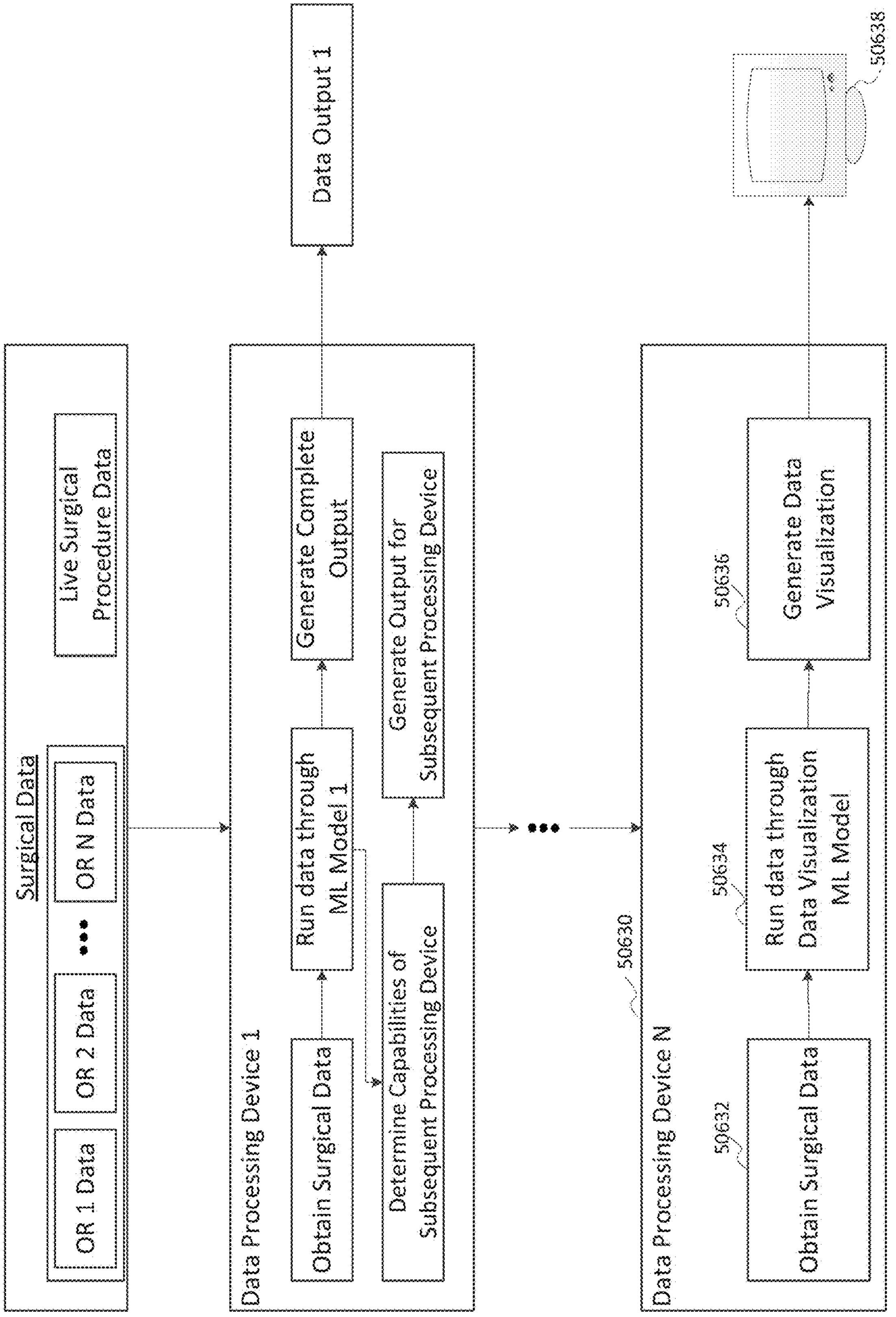
FIG. 12 illustrates an example flow of generating a data visualization using interrelated ML models.

FIG. 12 illustrates an example flow of generating a data visualization using interrelated ML models. Data processing devices may obtain surgical data and process the surgical data using ML models (e.g., as described herein). Outputs may be generated for subsequent data processing devices (e.g., as described herein). A data processing device may include a processing device using a ML model associated with generating a data visualization of input data. For example, surgical data may be input to a ML model to generate a graphic for a user that may indicate insights, trends, patterns, recommendations, etc. A data visualization of surgical data may be informative to HCPs, for example, performing a live surgical procedure.

As shown in FIG. 11, a data processing device N 50630 may include a processing device associated with data visualization. The data processing device N 50630 may obtain surgical data (e.g., as shown at 50632), for example, from previous ML models, surgical databases, and/or the like. The data processing device N 50630 may use an ML model to perform a data visualization processing task (e.g., as shown at 50634). For example, the ML model may be used to generate a graphic, chart, recommendation, etc. based on the obtained surgical data (e.g., as shown at 50636). The data visualization may be sent as an output to a user. For example, the data visualization may be sent to and displayed on a display (e.g., as shown at 50638). The display may be used, for example, in an operating room during a live surgical procedure by an HCP. The display may be used, for example, by an HCP in planning a surgical procedure.

The ML models (e.g., algorithms) may be used (e.g., within the same data processing device or within different data processing devices) to take on different portions of data reduction, data interaction, and/or data analysis. The outputs of the ML models may be fed as inputs to the other interrelated ML models (e.g., to be used for processing). The ML models may process data in different portions of a network ecosystem. For example, the network ecosystem may include data processing at a surgical hub level, an edge-network level, a cloud network level, etc. The outputs generated at the different levels of the network ecosystem may be fed to the different ML models present at varying levels of the network ecosystem. The outputs may pass conclusions, results, and/or supporting metadata to the other ML models. The outputs may be a portion of the complete dataset used in previous ML model processing. For example, multiple ML models may be processing data in different hub networks. The different hub ML models may feed their results to ML models in the edge-network and/or cloud network. The information feeding from one system to a subsequent system may be variable (e.g., dependent on the capacities of the receiving system). The information feeding from one system to a subsequent system may be variable, for example, based on the privacy level of the data and the receiving system's status within a protected HIPAA network. Multiple interrelated ML models (e.g., algorithms) may be used (e.g., in conjunction with each other) to identify different portions of data analysis (e.g., data preparation, identifying relationships in data, communicating recommendations, communicating adaptations of control programs, etc.)

In examples, the interrelated ML models may include nested ML models (e.g., algorithms) to process discrete and/or separate tasks for full processing of the data. Nested and/or hierarchical ML models may be used to prepared and process data (e.g., biomarker data).

For example, the interrelated ML models may include an ML model associated with pre-processing the data. The pre-processing ML model may be used to determine one or more of the following: integrity of the data, organizational state of the data, completeness of the data, and/or the like. The pre-processing ML model may be used to determine whether data is ready for data reduction.

For example, the pre-processing ML model may compare available datasets, for example, to look for differences in completeness, depth, annotation level, surgical task/aspects tagging, and/or the like. The identified differences may be compared with known (e.g., valid, preconfigured) interactions and/or relationships. The identified differences may be compared against a validation set of data. The identified differences may be compared against a suspected interrelationship listing. Portions of the data may be (e.g., may need to be) combined, linked, associated, etc., for example, to complete the dataset to be ready for further processing.

Datasets available for ML models may be incomplete based on policy implementations. For example, datasets available for ML models may be incomplete due to HIPAA limitations, consent issues, and/or limitations imposed on the collection of data from a surgery, patient, and/or devices. The incomplete dataset may create an issue for the ML model to use (e.g., ML models may not perform accurately on incomplete datasets). ML models may (e.g., need to) combined multiple (e.g., two or more) incomplete datasets into a complete set, for example, to perform an accurate analysis.

Preprocessing ML models may be assisted, for example, based on a directionality analysis (e.g., whether the trends generally are getting better or worse). For example, the directionality analysis may assist the pre-processing ML model to determine the weight of subjective assessments. The more iterations in combination with subject assessments may reduce the impact of subjectivity in base data that is analyzed. For outcomes, recovery, and/or treatment analysis, the processing may involve subjective appraisals (e.g., which may create a repeatable link between results from causes which are improper or questionable).

In examples, missing or combined datasets may be tagged (e.g., indicated as such), for example, to track the impact on results, outcomes recommendations, etc. For example, a post-processing check may be run (e.g., using an ML model) to ensure that no absent, marginal, or interwoven data affected (e.g., substantially affected) the results (e.g., as compared with the data set being removed instead of combined). A flag may be indicated, for example, if the tagged data did impact (e.g., substantially impact, impact beyond a threshold) a relationship, result, and/or trend based on the completeness of the data and/or the validity of the data. The flag may allow an end user to input (e.g., make a call) on the final results (e.g., the recommendations provided by the analysis generated by the ML model).

ML models may be used as a gatekeeper and/or a validity check on a fresh (e.g., new, non-training) data set. The ML model may be trained on training datasets to act as a validity check on input data. For example, the ML model may be used (e.g., depending on the confidence in the ML model) to take in input data, process the data (e.g., run a transform on the data), and determine a result based on the processing. The ML model may determine whether the result is within an acceptable level (e.g., threshold range) of deviation from data that is measured and/or recorded. The data going into the ML model may be trusted if the result is accurate. The validity check may be multiple layers deep (e.g., start with height and weight to predict basic metrics and then use complex metrics to determine complex outputs and/or medical classifications.

For example, a body mass index (BMI) may be determined for a patient. Data on co-morbidities and intensity of diabetes, blood sugar levels, and/or blood pressure may be used in conjunction with the medications the patient is taking, for example, top determine whether the combinations are within the expected and/or predicted bounds (e.g., including the current standard deviation associated with the ML model). The data may be treated as valid (e.g., ready) to be added to other data sets for reduction, for example, if the data is determined to be within the accuracy bounds. If the data is outside the accuracy bounds, the ML model may request or seek confirmations of the out of bounds (e.g., outlier) data. If the data is outside the accuracy bounds and an outside user confirms that the data is correct, the ML model may adjust the bounding check for future data sets (e.g., further training the ML model for better accuracy). This may lead to the ML model resulting in tighter or looser constraints on the other datasets. In examples (e.g., associated with multiple levels of validity checks using the ML model), a BMI may be checked first, a heart rate and health block pressure may be checked second, the trending of biomarkers with respect to weight gain or loss may be checked third, and/or the like. The different levels (e.g., each of the different levels) may confirm conformance to the pre-established trends or ranges (e.g., trained trends or ranges), and the data may be used to adjust the ranges and calculate future relationships and/or patterns (e.g., train the ML model to be more accurate for future data analyses).

For example, base medical measurements may be input to a ML model (e.g., height, weight, demographics, gender, previous conditions, etc.) A first (e.g., basic) processing layer may be used to link the data with more complex conditions and/or outcomes. If an ML model takes in certain input data for an analysis but a portion of the input data is missing (e.g., incomplete), the input data may be run through a different ML model to produce a complete (e.g., synthesized) dataset to be run through the complex ML model. For example, the incomplete dataset may be completed. Protocols may be set in place that may allow for the completed data to be input to the complex ML model if the completed dataset (e.g., synthesized data) is trustworthy The pre-processing ML model may be used to identify incorrect and/or erroneous data, for example, by parsing available data into sub-groups that are run through a similar ML model to determine if the data is correct and/or good data.

Grouping data sets may enable a ML model to determine whether datasets contain incorrect and/or erroneous data. In examples, available data may be parsed into multiple (e.g., three) groups based on a predefined order (e.g., all even, all odd, etc.) The groups (e.g., each group) may be processed using an ML model (e.g., the same ML model). If the results are similar between the datasets, the datasets may be determined to be good (e.g., accurate, complete, etc.). For example, if results from two of the three groupings produce similar results and results from the third grouping is not similar, the third grouping may be flagged (e.g., indicated as irregular). The irregular dataset may be dissected and/or decomposed, for example, to identify the datapoints that may cause the irregular output. The datapoints determined to cause the irregular output may be flagged to the user to confirm the accuracy. The irregular data point may be confirmed, for example, by re-choosing the three data set sub-groups and re-running the ML model (e.g., calculations/analysis) to confirm that the irregular data point is the cause of the irregular result and/or conclusion.

In examples, if two sources of the same and/or related biomarkers do not provide the same result for the same patient, a separate sub-algorithm (e.g., different ML model) may be used to perform comparison and pattern identifications in related data, for example, to distinguish which of the conflicting data sets is more correct (e.g., the dataset closer to the verified set is determined to be more correct). The sub-algorithm may be enabled to return the result and/or identified pattern to a higher layer of processing (e.g., which may resolve the conflicting datapoints issue). The problematic datapoint may be discarded. Discarding a reading may be considered, for example, based on an input from an HCP. HCPs may look at the entirety of a dataset and determine that a problematic datapoint does not fit or does not have a rational explanation. The problematic datapoint may be overridden but still allow for the collection of the semi-erroneous data. For example, HCPs may determine that datapoints are irregular but there are enough regular datapoints to continue. For example, an anesthesiologist may determine that a surgical procedure is in a critical step and the data is needed to perform the step. The anesthesiologist may determine that there are sufficient accurate datapoints to make logical conclusions (e.g., based on knowledge, intuition, other data) in order to continue the procedure in a safe manner.

For example, the interrelated ML models may include an ML model associated with performing data reduction. The data reduction ML model may operate on surgical procedure data (e.g., completed, master, ready surgical procedure data). The data reduction ML model may perform a reduction methodology (e.g., as described herein) to identify trends, generate relationships, identify patterns, create recommendations, and/or the like.

The data reduction ML model may use a history of past datapoints (e.g., that map historic inputs to history outputs), for example to determine an unknown output given a complex input. During a training phase of the ML model, the model may generate relationships between inputs and outputs. The ML model may be used to predict outputs based on the complex input and previous training on mapped data. Trends, recommendations, conclusions, and/or relationships may be determined based on the training dataset. The trained ML model may, for example, take an unknown image as an input, and determine a classification associated with the unknown image with a certain degree of confidence (e.g., based on historic data that trained the ML model). The model may not identify trends not identified in the training dataset (e.g., new trends). The model may focus on mapped trends based on the training.

For example, the interrelated ML models may include an ML model associated with data display and/or visualization. The data display ML model may combine the recommendations, conclusions, trends, relationships, and/or other results it has determined, for example, in combination with a decomposed manifestation (e.g., visualization) of the data. The visualization of the data may be presented to a user, for example, so the user can see the recommendation and at least some supporting metadata supporting the determined trends and/or conclusions.

Data visualization may be used to learn about the available data and identify main patterns in the data. Data visualizations may be represented by one or more of the following: a parallel coordinates plot, a prediction table, a hierarchical segmented plotting of decision tree results, decision boundaries, and/or the like.

For example, data visualization ML models may include using a parallel coordinates plot. The parallel coordinates plot may enable a user to compare different variables (e.g., features) together to discover possible relationships. For example, in the scenario of hyperparameters optimization, a parallel coordinates plot may be used to inspect what combination of parameters may give the greatest test accuracy. For example, parallel coordinates plots may be used in data analysis to inspect relationships in values between the different features in a data frame.

For example, data visualization ML models may include using a prediction table. Prediction tables may be used for time-series data. Prediction tables may be used to identify on which datapoints (e.g., in time-series data) the ML model may be underperforming. The prediction tables may be used to identify the limitations the ML model may be facing. Creating a prediction table may include creating a summary table that includes actual and predicted values and a form of metrics summarizing how well and/or bad a data point has been predicted.

For example, data visualization ML models may include using hierarchical segmented plotting of decision tree results. Linked bar charts and/or pie graphs may be used, for example, based on the level of the decision tree. The visualization may illustrate overall trends (e.g., plotted trends) identified by the ML model.

Figure 13:
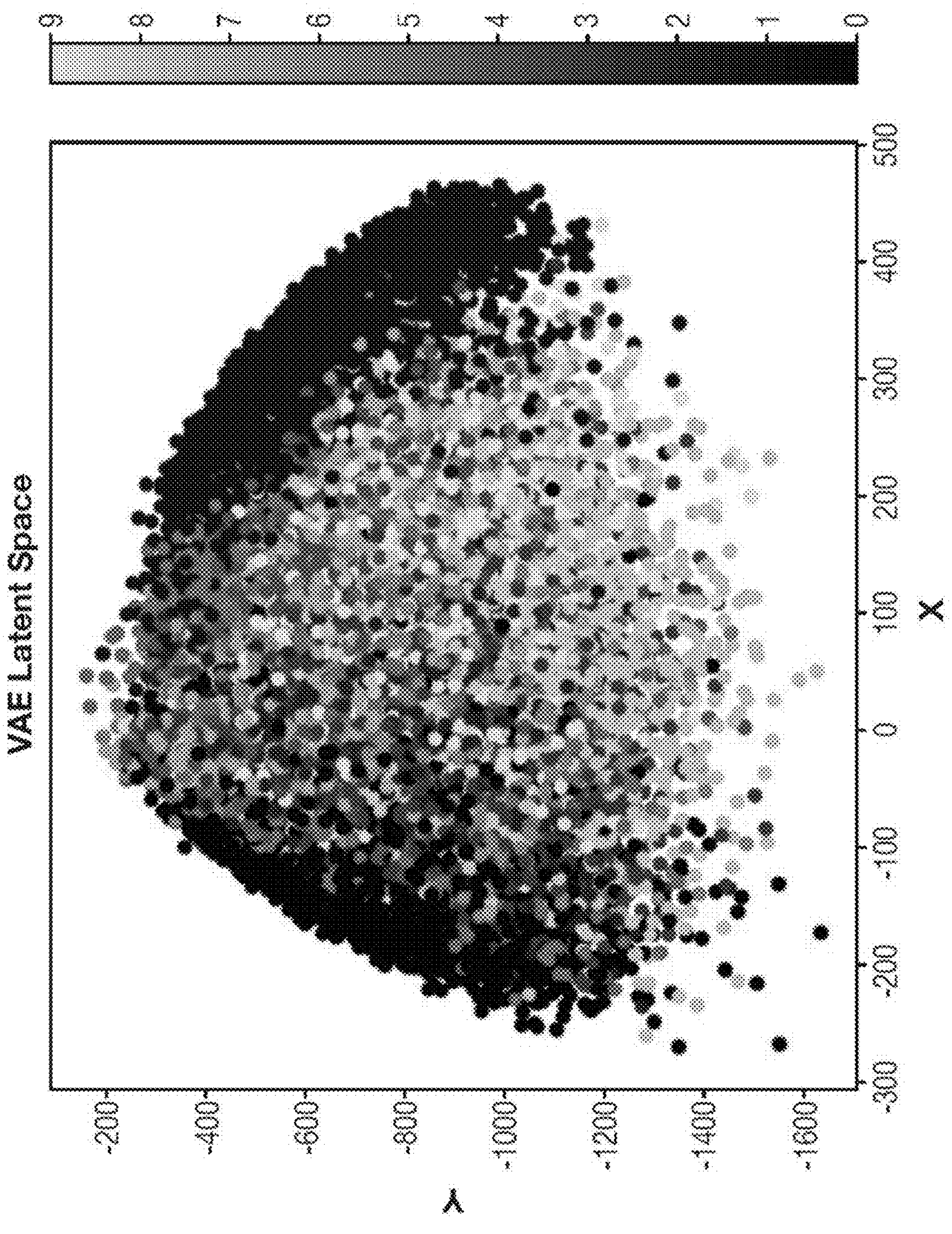
FIG. 13 illustrates an example plot point graph for VAE latent space.
Figure 14:
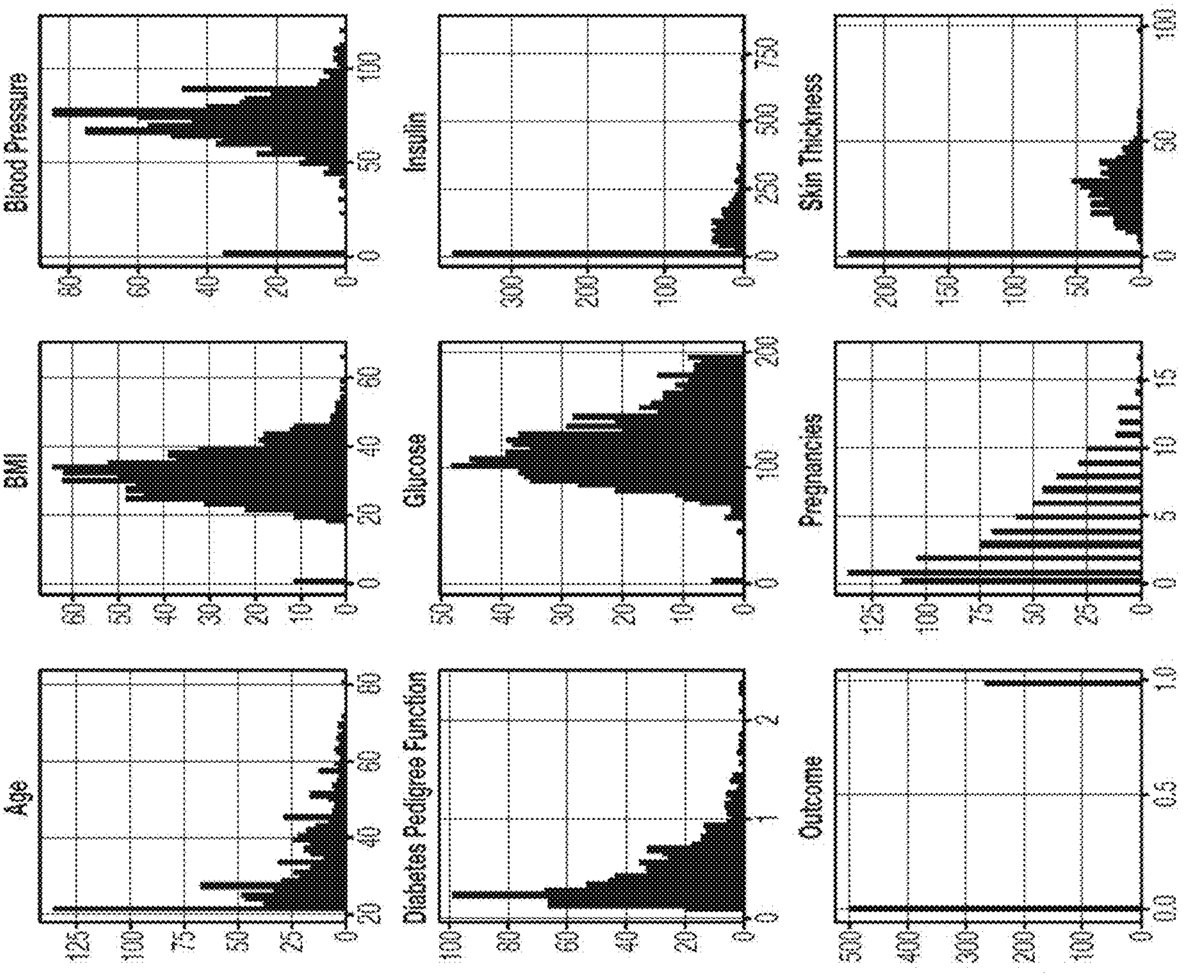
FIG. 14 illustrates an example of implementing decision boundaries for the VAE latent space data plot.

For example, data visualization ML models may include using decision boundaries. Decision boundaries may enable graphical understanding on how a ML makes its predictions. Decision boundaries associated with the ML model process may be plotted. FIG. 13 illustrates an example plot point graph for VAE latent space. FIG. 14 illustrates an example of implementing decision boundaries for the VAE latent space data plot. As shown in FIG. 14, comparative trending used with decision boundaries on key variables may be used to identify relationships within the data.

Data visualization performed by ML models may enable trend identification that may not be captured by human analysis, for example, based on the multidimensional optimization performed by the ML models.

For example, the interrelated ML models may include an ML model associated with performance. For example, after a conclusion and/or recommendation is determined (e.g., agreed on) and permitted to adjust the behavior of an attached system, a ML model may collect on-the-fly datasets that may enable small additional customizations within the predefined threshold range defined by the data reduction recommendation.

For example, the interrelated ML models may include an ML model associated with determining whether data should be substituted. For example, the ML model may determine data boundaries that may be used to determine whether data should be substituted. For example, an ML model may determine if a baseline (e.g., standard) control algorithm (e.g., parameter) should be substituted with a different (e.g., irregular) control algorithm (e.g., parameter). The ML model may determine that the different (e.g., irregular) control algorithm may enable a surgical instrument to operate in a manner adapting to the surgical procedure. The ML model may determine to use a different control algorithm, for example, based on a different biomarker of a functional instrument measurement. The ML model may determine errant data sets relative to the ML boundary (e.g., as a separate process/computation), for example, to enable the ML model to determine if a baseline control algorithm should be substituted for a different control algorithm.

For example, a low impendence measure on a bipolar radio frequency device may indicate one or more conditions (e.g., low impendence tissue, immersion in a conductive fluid, a physical short in the electrical path, and/or the like). The ML model may receive (e.g., compile) weld capacity data associated with the tissue and biomarker data (e.g., link the data together), for example, to determine different control parameters (e.g., different temperature and/or power level control of a generator) that may enable a better surgical step (e.g., better welds performed based on different temperature and/or power level control of the generator). The ML model may determine that a zone of the dataset (e.g., low impendence) does not fit within the pattern and/or groupings. The ML model may process the irregular zone in a different (e.g., separate, independent) process with a direction (e.g., goal) to find a different control means and/or pattern (e.g., to run the instrument when in the irregular zone). The ML model separately processing the irregular zone may enable adaptively changing control parameters for surgical instruments and/or equipment being used in a surgical procedure. The different control parameters may be used for the irregular zone (e.g., only).

For example, the interrelated ML models may include a secondary ML model to oversee a primary real-time ML operation. For example, the nested ML algorithms may be statically sequential and/or have a real-time component (e.g., aspect). A command structure may be implemented, for example, to control interactions between a number of ML algorithms (e.g., independently processing ML algorithms) reporting on status for systems and/or ML processes performed (e.g., data validity, model selection, result verification, etc.). The primary command algorithm may use the summarized data and determined command decisions. The primary command algorithm may request status data from a system (e.g., any system) to use the data for a decision. Other ML systems may interrupt the primary algorithm with data, for example, if the system meets a condition (e.g., reaches a ready status, disabled status, etc.).

Multiple ML models (e.g., algorithms) may be combined, for example, to be used in concert. ML models used in concern may achieve a better, faster, or more accurate result (e.g., pattern), for example, as compared with separate, independent ML models. ML models may back stacked. Stacking models may improve performance metrics for large models. Stacking ML models may benefit from obtaining known relationships between outputs that can already be computed (e.g., adding additional speed and reliability to the model).

For example, stacked ML models may be used in parallel (e.g., parallel utilization of stacked ML algorithms). Stacking models may enable training using the same training dataset with multiple types of modeling techniques. The predictions of the different models may be used as input features for a meta-classifier. The meta-classifier may minimize the weaknesses and maximize the strengths of the individual models. Different types of models may have different strengths associated with their predictive capacity. Stacking multiple models on a single dataset and using a meta-classifier on the outputs may enable parallel utilization of stacked models. The result may be more robust, for example, as compared to if the model was run multiple times and/or was more complex. Utilization of a stacked model may enable better predictions and/or faster predictions, for example, compared to standard computations. The stacked ML models may boost (e.g., convert) weak learners to strong learners faster than other techniques. Ensembled learning may enable the combining of several learners for improved efficiency and accuracy.

For example, stacked ML models may be used in series (e.g., serial utilization of stacked ML algorithms). Serial use of models may include feeding results from a first ML model into a second ML model, for example, to compartmentalize the stages of an analysis. Serial use of models may be useful, for example, if the stages produce meaningful trends the user may use as insight. Serial use of models may be useful, for example, if there are checks along the stages to ensure that errors are more propagated within the several layers into the algorithm (e.g., in case the data is unbalanced or flawed). Serial use of models may allow separation of overall processing resources, for example, such that multiple systems, locations, and/or separate networks may be used (e.g., to determine the overall trending/pattern identification), as shown in FIG. 10. Separation of processing resources may be used, for example, if a primary system has insufficient physical resource and/or time to achieve the processing goals.

For example, serial utilization of stacked ML algorithms may include training the ML models on the same set of training data. The ML algorithms may include using a layer (e.g., additional layer) of a meta-classifier that takes in predicted values of the model and processes the predicted results, for example, to reduce error and strengthen the best outcomes from the different modeling techniques. The data may be fed through the same level ML models separately with the outputs compared and adjusted by a meta-classifier.

Serial utilization of stacked ML algorithms may include using different parts of different models at different stages of an analysis (e.g., a layer of a first model that is taking in data to predict a second layer, where there may be a device that directly measures the result associated with the second layer). Collected data may be used to override part of the first layer of the ML algorithm (e.g., saving resources and/or reducing drift in the final layer of the model). Collected data may be used to compare with the predicted results (e.g., to check prediction quality and the quality of the data being measured, for example, whether the instrument is malfunctioning due to the model predicting an output that is different than expected). Systematic errors may be detected (e.g., errors in collection and/or recordation) based on the predicted results. The systematic errors may be corrected (e.g., using the instruments differently).

Figure 15:
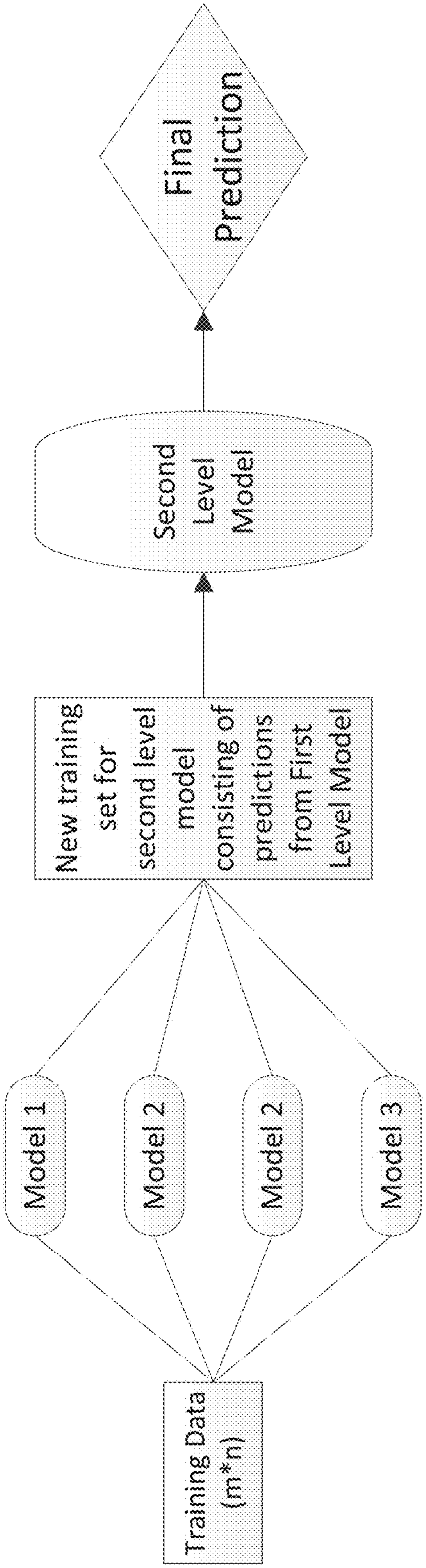
FIG. 15 illustrates an example of using ML models in series and parallel.

A combination of serial utilization and parallel utilization of stacked ML algorithms may be used. FIG. 15 illustrates an example of using ML models in series and parallel.

Incomplete and/or inconsistent data may be adapted to be used by ML models, for example, by using related but independent available data. Datasets may be flawed (e.g., partially flawed). Data preparation may include processing data to be more suitable for ML. Data preparation may include establishing a data collection process. The ability to resolve incomplete data sets may enable better use and more reliable computation using ML models. For example, incomplete and/or inconsistent data may be prepared to be better suited for ML processing using one or more of the following techniques: data consolidation, leveling data quality, data consistency, and/or the like.

Data consolidation may be used, for example, to make data more suitable for ML models. Data consolidation may use data warehouses and an extract, transform, and load (ETL) process. For example, data may be deposited in warehouses (e.g., storages). The storages may be created for structured records (e.g., SQL). The records may be suitable for standard table formats. Warehouses may load (e.g., store) data after transforming the data (e.g., to a more usable format).

Data consolidation may use data lakes and an extract, load, and transform (ELT) process. Data lakes may be a storage capable of keeping structured and unstructured data (e.g., images, videos, sounds, records, PRDF files, etc.). Data may not be transformed before storing, for example, if it is structured. Data may be stored as is, and the determination on how to use and process the data may be performed later (e.g., on demand). Data lakes may be used for ML (e.g., better fit as compared to data warehouses).

Leveling data quality may be performed, for example, to make data more suitable for ML models. Leveling data quality may include dealing with omitted data. For example, omitting data may be associated with record sampling. Removing dataset records (e.g., objects) that contain missing, erroneous, and/or representative values may level data quality. Record sampling may be performed to form datasets that may be reduced (e.g., to identify key variables of data that need to be present to make a set more representative). For example, a system may determine to refrain from discarding data that has omitted data in categories and/or portions of the data that are not influential in the determination of trends and/or results (e.g., missing data would not affect overall processing task). Algorithmic templates may be created using base datasets, for example, to evaluate a final value. Adding amounts of data that are properly mapped (e.g., accurate) may allow for evaluation of a trained ML model to see if the prediction (e.g., output) is correct.

Leveling data quality may include aggregating datasets. For example, a pool of data may be combined for records (e.g., objects) pulling averages, means, random entries, and/or the like, to create datasets that represents a composite of the dataset. Aggregating may enable determining an average patients and/or randomized patients that may be representative of a broader dataset (e.g., but reflect complete records of the larger dataset). A dataset may be used (e.g., or another aspect of the data that is related to the missing data) to fill in (e.g., synthesize) the missing data, for example, which may enable inclusion of the incomplete dataset in an analysis while avoiding driving the calculation off the average (e.g., as a result of the missing data). For example, missing values may be substituted with dummy values (e.g., N/A for categorical values, 0 for numerical values). Missing numerical values may be substituted with mean figured. Categorical values may be substituted with the most frequent items.

Leveling data quality may include joining transactional and/or attribute data. Transaction data may include events that snapshot moments (e.g., the price of boots at a given time, when a user with a certain IP clicking on the "Buy Now" button). Attribute data may be static (e.g., more static). For example, attribute data may include user demographics and/or age. Attribute data may not relate to specific events. Data sources and/or logs may include both transaction and attribute data. Attribute data and transaction data may enhance each other, for example, to provide more predictive power (e.g., compared to using the data types separately). For example, if machinery sensor readings are being tracked to enable predictive maintenance, logs of transactional data may be generated. Qualities (e.g., attributes) may be added, for example, such as equipment model, batch, location, etc. Dependencies between the transaction data and the attribute data may be analyzed to determine dependencies (e.g., between equipment behavior and its attributes. Transaction data may be aggregated into attributes.

Leveling data quality may include use of clinical scoring systems to complete missing data. For example, pre-existing operative scoring systems may be used to align missing aspects. For example, mortality statistics may be used as a means to link outcomes with procedure steps (e.g., order, difficult, etc.) to complete missing nominal monitored statistics. For example, an APHAR risk score may be used by HCPs to estimate post-operative outcomes as a means for using the combined output of the lower fidelity clinical model as a means to determine a missing piece of data the higher fidelity ML model uses to make a prediction. For example, bariatric suitability pre-operational scoring may be used to complete data sets.

In examples, using one combined measure in combination to another combined measure to fill in missing aspects of either or another combined biometric aspect may be performed. For example, a patient's APGAR and prolonged air leak risk scoring may be used to determine secondary uncollected data that in turn could be used by the machine learning to identify potential post-operative infection risk.

Clinical scoring systems may be limited by subjective limitations. For example, clinical scoring systems may employ subjective rating scales (e.g., patient's pain level may differ between patients). Subjective rating scales may be difficult to evaluate.

Leveling data quality may include fixing imbalanced data, for example, by rescaling the data. Data rescaling may include data normalization. Data rescaling may improve the quality of a dataset by reducing dimensions and/or avoiding situations where some values overweight other values. Min-max normalization may be used. Min-max normalization may include transforming numerical values to ranges (e.g., from 0.0 to 1.0 where 0.0 represents a minimal value and 1.0 represents a maximum value), for example, that may even out the weight of an attribute compared to other attributes in the dataset. Decimal scaling may be used to perform data rescaling. Decimal scaling may include moving decimal points in a direction to rescale the data.

ML processes may be used to ensure that the data is within a threshold amount of rescaling, for example, before further analysis. Data may be entered incorrectly (e.g., decimal point may be omitted). An ML process may detect that the incorrectly entered data is beyond a reasonable range and should be flagged for further analysis and/or review.

Leveling data quality may include fixing inadequate data, for example, using synthetic data. Synthetic data may include artificially generated samples that mimic real-world data. Synthetic data may induce bias in data. The impact of synthetic data may be limited and/or determined, for example, to minimize inadvertent data shifting due top the use and/or inclusion of the synthetic data. ML models may experience drift in predicting outputs for base datasets with the inclusion of synthetic data. The output of the ML model synthesizing data may be input to another ML model, for example, to ensure the synthetic data is not producing inappropriate results.

Leveling data quality may include fixing inconsistent medical term interchangeability. For example, a natural language filter may be used. A natural language filter may be used on medical implication terms within a dataset. The search may adjust variants and semi-interchangeable medical terms into a consistent descriptive result.

For example, a system may use an ML process to determine terms that are effectively interchangeable within the medical literature and/or billing codes. The pattern or trend may group and/or cluster the terms that are close to the same meaning. The ML process may use a boundary algorithm to device terms that may be grouped into one group and other in another near group. The listing may be used to adjust the language within the medical records to a constant terminology set. The system may run a verification on the synonym aggregation, for example, by looking at outliers along the boundary within a known teaching dataset. The adjustments may allow the system to enlarge, combine, and/or separate boundaries to better represent the information to a common language.

Natural language processing (NLP) may be used, for example, as a second ML process layer for performing classification for models. The NLP models may use information (e.g., additional information), for example, such as the background of the author, local terms, phrases, region specific words. Pairing data about the users with how the data was gathered and the history of the data may enable creating an ML model that classifies the author as a certain thing and then use the classification to further influence the sentiment analysis. Language trends may be determined, for example, using NLP models.

Sentiment analysis may be used, for example, to evaluate sentiments associated with wordings. For example, a sentiment analysis may be used to determine the happiness of populations based on the wordings of messages. Sentiment analysis may be paired with geotracking to model how happy a population is.

Leveling data quality may include ensuring data consistency. For example, data formatting may be used to ensure data consistency. Data formatting may include date formats, money denominations and symbols, numeric range settings, and/or the like. Discretizing data may be used to ensure data consistence. Predictions may be more effective, for example, based on turning numerical values into categorical values. Turning numerical values into categorical values may be performed by dividing the range of values into a number of groups.

Data structure may be used to compensate for data incompleteness. For example, consistency of a classification of learned instances may be improved and/or ensured, for example, to ensure conclusions are trustworthy and/or reliable. In examples, the measure of subjectivity may be used to report probabilities of results to be accurate and/or predictive. Individual comparison of user measured subjectivity may be used as a check and/or probability of the result of an ML process. Determination of a drift of a measurement may be used to identify uncontrolled measurements of biomarkers. For example, a drift measurement may be used to identify a potential cause of an inconsistent result. The HCPs may then identify how to modify control parameters and/or instrument configuration (e.g., to prevent the inconsistent result).

Using the structure of the data (e.g., procedure plan of the steps, the instrument usage, the HCP stress level, imaging results, combining images, and/or the like) may be used to compensate for lack of data completeness. Context of the surgical procedure, patient, and/or surgical step may be used to assist an ML model in determining a floating boundary for groupings. For example, different (e.g., ten different) liver resection procedures may be recorded using a monitored scope. The system may be aware that the data is associated with liver resection jobs. The system may determine that the instruments are being used at the liver at predefined steps of the procedure. The steps may be used to identify the liver (e.g., color, shape, location, etc.), for example, which may enable ML processes to define an accurate range of acceptable elements and/or aspects.

Systems, methods, and instrumentalities are disclosed for aggregating and/or apportioning available surgical data into a more usable dataset for machine learning (ML) model (e.g., algorithm) interaction. A ML model may be more accurate and/or reliable if using complete and/or regular data. Aggregating and/or apportioning available surgical data may enable a more complete and/or regular dataset for ML model analysis.

For example, a computing system may include a processor that may be configured to aggregate and/or apportion available surgical data into a more usable dataset for ML model analysis. The computing system may obtain a first set of surgical data associated with a surgical procedure (e.g., performed or live surgical procedure). The computing system may obtain a master set of surgical data (e.g., from a surgical database). The master set of surgical data may include a verified set of data. The master set of surgical data may be associated with historic surgical procedures. The computing system may determine that the first set of surgical data is problematic (e.g., incomplete, erroneous, irregular, etc.) The computing system may determine the first set of surgical data is problematic, for example, based on comparison to the master set of data. The computing system may generate substitute data. The substitute data may be generated based on the master set of data and the first set of data. The substitute data may be generated based on a data type that is problematic in the first set of data. The computing system may generate a second dataset (e.g., revised first set of surgical data), for example, that includes the substitute data and a portion of the first set of data (e.g., the non-problematic portion of the first set of data).

Data may be apportioned and/or aggregated, for example, to combine and/or verify incomplete datasets. Apportionment of surgical data may optimize usage of the data for comprehensiveness, accuracy, and/or verification of ML models. The combination, substitution, and/or integration of different datasets from different procedures, devices, and/or sources into a combined master set of data may be performed to enable analysis (e.g., using an ML model) to determine relationships, control program adaptations, recommendations of functional changes in surgical behavior, and/or the like. For example, a first incomplete dataset and a second incomplete data set may have related outcomes and/or procedure constraints that may be combined to generate a more complete dataset for an ML model to interpret. Segmented datasets from differing sources may be used in combination with a separate verification data set, for example, to ensure adequate combination of the datasets to draw conclusions from. Data within a portion of a protected dataset (e.g., HIPAA controlled) may be combined with a different portion of a different dataset, for example, without either dataset contributing too much identifier data that may trigger privacy controls.

ML models (e.g., algorithms) may produce more accurate and/or relatable results, for example, using a complete and accurate data set (e.g., data set with consistent data, data set without missing data, etc.). ML models may be used to ensure that a dataset for processing (e.g., using subsequent ML model(s)) may be complete and/or adequate (e.g., able to provide reliable conclusions). The ML model may (e.g., based on a determination that a dataset is incomplete or contains inaccurate data) revise the dataset (e.g., complete the dataset and/or remove outlier data) to be better suited for ML model processing.

Figure 16:
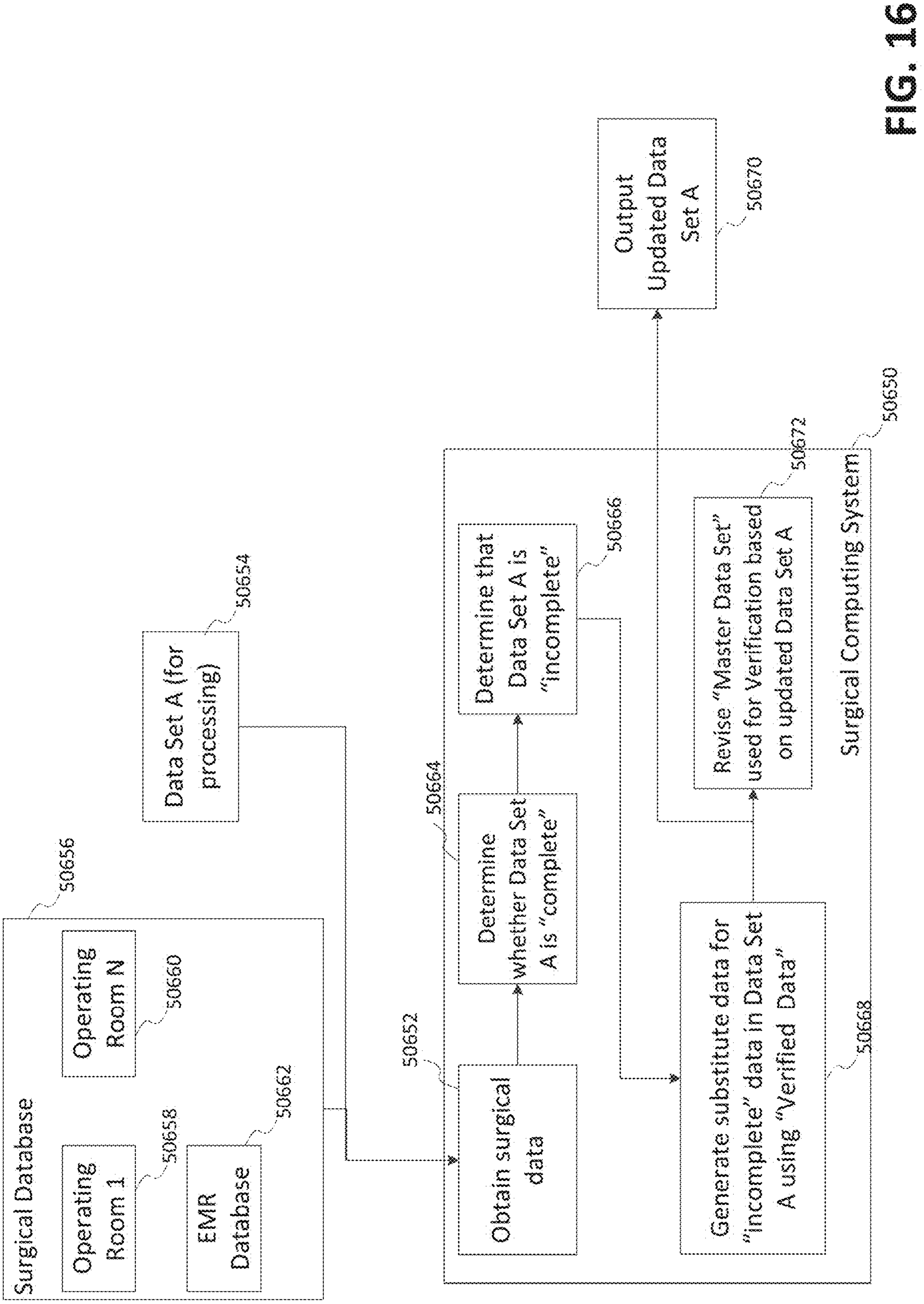
FIG. 16 illustrates an example of revising an incomplete dataset and updating a master data set for verification.

FIG. 16 illustrates an example of revising an incomplete dataset and updating a master data set for verification. As shown in FIG. 16, a surgical computing system 50650 may obtain surgical data (e.g., as shown at 50652). The surgical data may include a data set (e.g., Data Set A) for processing 50654 and/or data from a surgical database 50656. Data from a surgical database 50656 may include data associated with an operating room (e.g., operating room 1 50658, operating room N 50660, etc.), an electronic medical records database 50662, and/or the like. The surgical data from the surgical database may include data from historic surgical procedures and/or processes. The surgical computing system 50650 may determine (e.g., as shown at 50664) whether Data Set A 50654 is a complete dataset (e.g., whether the dataset is missing data, whether the dataset contains irregular data, etc.). As shown at 50666, the surgical computing system 50650 may determine that Data Set A 50654 is incomplete. The surgical computing system 50650 may rectify the incomplete dataset (e.g., using an ML model). For example (e.g., as shown at 50668), the surgical computing system 50650 may generate substitute data (e.g., using an ML model) to insert into the incomplete Data Set A (e.g., to complete the dataset). The substitute data may be generated using verified data (e.g., confirmed data, accurate data from previous confirmation), for example, from the surgical data base or ML model storage. The surgical computing system 50650 may output the updated (e.g., completed) Data Set A (e.g., as shown at 50670). Additionally, the surgical computing system 50650 may revise a master data set (e.g., data set that is used for training the ML model, data set from the surgical database, verified dataset, and/or the like), for example, based on the updated Data Set A. The updating of the master data set may enable the ML model to constantly improve its accuracy in its predictions.

For example, the surgical computing system may obtain a first set of surgical data associated with a first surgical procedure. The first set of surgical data may include data from surgical instruments, surgical equipment, patient data, HCP data, and/or the like. The first surgical procedure may be a live surgical procedure. The first set of surgical data may include incomplete data. For example, data collection at a surgical instrument may be inaccurate. The first set of surgical data may be missing data for certain portions of a surgical procedure, for example. The missing surgical data and/or erroneous surgical data may cause issues in an analysis performed using an ML model.

The surgical computing system may determine that the first set of surgical data is incomplete. The surgical computing system may determine that the first set of surgical data is incomplete using an ML model. The ML model may determine that there is missing data and/or erroneous data. The ML model may determine that there is missing data and/or erroneous data based on comparison to historic surgical data (e.g., data from a surgical database) The ML model may determine that there is missing data, for example, if there are gaps in the dataset.

The ML model may determine there is erroneous data if the dataset includes data inconsistent with the rest of the dataset. For example, the ML model may determine a heartrate measurement is inconsistent with the rest of the data based on the heartrate at a first time spiking to a level that is not within an average deviation of the time points surrounding the data point. For example, the ML model may determine that a heartrate measurement is erroneous, for example, based on the measurement exceeding normal human values.

The ML model may determine there is erroneous data if the dataset includes data inconsistent with historic surgical data (e.g., data from the surgical database). For example, a ML model may determine a landmark position in a patient's body is erroneous based on comparison to landmark positions in other patients from similar surgical procedures where the patients are similarly situated.

The ML model may determine the dataset is incomplete and/or erroneous, for example, based on comparison to a master data set (e.g., verified dataset). A verified dataset may include data that is confirmed as accurate data. The verified dataset may include a training dataset for a ML model. The ML model may determine the dataset is incomplete and/or erroneous, for example, if it contains data that is inconsistent with the master data set.

The completeness of a dataset may be determined, for example, based on a pre-processing ML model (e.g., algorithm). The pre-processing ML model may examine data looking for incomplete, irregular, and/or erroneous data.

In examples, a data reduction ML model may determine conclusions that may not be validated (e.g., conclusions are not reliable) based on comparison to a validation dataset. The data reduction ML model may determine that the ML model is unable to identify stable conclusions on a dataset. Based on a determination that the conclusions may not be reliable, the input data may be input to a pre-processing ML model, for example, to determine the integrity of the data. The pre-processing model may look for trends within the data, for example, that may imply errors, omissions, and/or mis-classifications. The pre-processing model may determine recommendations based on identified issues with the data.

The pre-processing ML model may obtain data characterized as irregular, unstable, and/or errant. The ML model may discover issues with the data, for example, such as calibration errors with surgical instruments, failure of sensors, and/or data recordation issues.

The pre-processing ML model may determine that a dataset is problematic (e.g., incomplete, irregular, erroneous, etc.), for example, based on the sampling rate. For example, a sampling rate (e.g., Nyquist sampling rate) may affect data collection. Data may be irregular and/or incomplete based on the sampling frequency.

For example, a data reduction ML model may be used to analyze data associated with force-to fire, outcomes, complications, a procedure plan, complaints, force-to-close, visible staple form, bleeding, and/or the like. The ML model may determine (e.g., while performing data reduction on the data) that the ML model is unable to reach a conclusion that can be verified (e.g., based on a validation dataset) and/or the ML model cannot identify reliable and/or repeatable relationships. The data reduction model may pass the data to a pre-processing ML model to verify the integrity of the data. The pre-processing ML model may identify that there are irregularities in the dataset. The pre-processing ML model may identify issues with the data. For example, the pre-processing ML model may check for completeness, comprehensiveness, and/or erroneousness. The pre-processing ML model may identify a product inquiry classification of the failure was incorrect. The pre-processing ML model may recommend re-classification of a number of the misclassified failures. The recommendations may be confirmed, for example, by HCPs and/or an independent system. The fixed data may be returned for data reduction trending.

The pre-processing ML model may determine the amount of drift that occurs in the data that is fed into the system. For example, the pre-processing ML model may determine that irregularities are in the data due to a detected drift. For example, if a 9V battery is actually measured as 8.7V and a 60 mm measurement is actually 59 mm, and the operating temperature is actually 60 degrees as opposed to the assumed 58 degrees, etc, then the drift may be determined to account for data irregularity. For example, the drift may be tagged in the data for consideration during data reduction.

The pre-processing ML model may identify data that is damaged and/or incomplete as a result from issues with communication models (e.g., algorithms), reduction models (e.g., algorithms), wireless buffer sizes in communication devices (e.g., if someone has a high frequency sensor polling faster than Bluetooth low energy buffer can dump data to a processor, then bits may be lost, overwritten, and/or messed up), and/or the like. The pre-processing ML model may identify the error and determine the occurrence and frequency of the error to track a pattern to identify potential causes. The identified patterns may be used to send a notification about the error and/or may resolve the issue.

The ML model (e.g., a subsequent ML model) may improve and/or rectify the incomplete and/or erroneous data set. For example, the ML model may generate substitute data (e.g., synthesize data, for example, as described herein) for the incomplete and/or erroneous dataset. The ML model may generate substitute data, for example, based on the non-incomplete and/or non-erroneous portions of data in the dataset. The ML model may generate substitute data, for example, based on the master set of data (e.g., data from a surgical database).

Additional data may be incorporated into a data set, for example, to complete a dataset for ML processing. For example, incorporation of instrumentation having incomplete and/or a limited subset of its functional operation (e.g., based on the instrumentation of the device and/or the motorization of the device) may result in a portion (e.g., only a portion) of the overall data being collected.

An ML model may be used to determine available data and the circumstances under which the data was collected. The ML model may be enabled to aggregate datasets, for example, that have missing data aspects. In examples, ML models may encounter scenarios where the models do not perform as expected (e.g., edge cases). An edge case may be a problem and/or situation that occurs (e.g., only) at a certain operating parameter (e.g., minimum or maximum operating parameter). An edge case may involve input values that may use special handling in an ML model. Unit tests may be created, for example, to validate the behavior of ML models in edge cases. The unit tests may test the boundary conditions of an algorithm, function, and/or method. A series of edge cases around a boundary may be used to give reasonable coverage and confidence (e.g., using an assumption that if it behaves correctly at the edges, it should behave correctly everywhere else).

Edge cases may occur, for example, based on a bias, variance, unpredictability, and/or the like. A bias may be associated with the ML model being simple (e.g., too simple). Bias may occur, for example, if an ML model cannot achieve good performance on a training data set. Bias may indicate that the architecture of an ML model does not have a structure that can represent nuances in training data.

Variance may occur, for example, if the ML model is inexperienced (e.g., too inexperienced). If an ML model achieves good performance on its training data but performs poorly in testing, the training data set may be too small to adequately reflect the range of variability in a ML model's operational environment.

Unpredictability may occur, for example, if the ML model operates in an environment experiencing variability and/or surprises. ML may rely on finding regular patterns in input data. A statistical variation may exist in data, but a ML model with an appropriate architecture and trained using enough training data may be able to find enough data regularity (e.g., achieve small enough bias and variance), for example, to make reliable decisions and minimizer edge cases.

A system may run multiple models (e.g., ML models) on differing portions of an incomplete dataset, for example, to determine which parameters have and do not have impacts (e.g., significant impacts) on outcomes. The ML models may run metadata related to the portions of the data that are impactful but missing portions of the data, for example, to determine if there is metadata around the data collection that may help fill in the data (e.g., intelligent substitution or averaging) or determine trends that may be used in substitution to the primary missing data.

For example, bleeding events may have a direct relationship to blood pressure of a patient. Blood pressure may not be tracked in real-time within the operating room during a surgical procedure. An electrocardiogram (EKG) version of heart rate monitoring may be used, for example, as a proxy for portions of the dataset that is missing blood pressure measurements with a nominal heart rate being set to a nominal blood pressure. The evaluation of an advanced energy device may be compared with bleeding results and using the blood pressure of the patient event, for example, if some of the patients did not have active blood pressure monitoring at the time of the surgery and imaging of the surgical site with the laparoscope.

The computing system may create a separate (e.g., independent) more complete dataset, for example, generated from and/or synthetically created and compared to the incomplete data set. The separately generated dataset may be used to ensure regularity and can be using in ML models for processing.

For example, similar datasets with similar outcomes and backgrounds may be combined into a more complete dataset for later analysis. Utilization of outcomes resulting from similar procedures, patient biomarkers, and/or predictive trend measures may be used to create directional synthetic data and/or substitution of data (e.g., to complete an incomplete dataset). This may differ from random data generation because it is based on a known and/or measured aspect of the patient, HCP, procedure, and/or outcome. The generated data may be supported by pre-established relationships of measured factors.

For example, a first patient with irregular blood sugar may be tagged with a related stress level, which may be associated with high heart rate, which may result in difficult to manage bleeding issues. A second patient may have similar difficult to managed bleeding, for example, as an event resulting from the same manger of advanced energy device usage. The second patient may not have data associated with blood sugar and/or diabetes co-morbidities. The heart rate variability may be a related measure of stress and/or pain, for example, which may be used to indicate both incomplete sets of data are resulting from stress or paint (e.g., not the blood sugar level, which may be a result, not a cause, of the stress). Both datasets may be made more complete with the measure of stress as the additional tag and/or category, for example, allowing both to be more complete and included with the analysis.

Synthetic data may be determined, for example, based on a probabilistic map of expected values from training data. A probabilistic map may be generated, for example, by running known numbers through a trained ML model and recording the data outputs as a result. The generated map may be used as a search reference, for example, to predict missing portions of data.

The ML model may compartmentalize relationships of limited datasets collected to the interrelated but isolated outcomes of sub-functions, for example, which may enable the use of the more limited dataset directly. The ML model may related the results higher into more advanced combined relationships.

The ML model may insert the generated substitute data into the dataset (e.g., to complete the dataset). The ML model may determine that the initially incomplete and/or erroneous dataset is ready for subsequent processing (e.g., complete and/or regular). The ML model may output the updated data set.

The master data set may be updated, for example, as more input data (e.g., from future surgical procedures) are fed into the ML model for processing. The ML model may learn and constantly improve with each surgical procedure dataset input to the ML model. The ML model may insert the revised dataset into the master dataset (e.g., to be used for future processing). With each iteration of processing data, the master data set may be updated and/or improved.

A validation set may be used, for example, to verify outputs (e.g., from ML models). For example, a portion of a dataset may be set aside as validation data. The validation dataset may be used on control algorithms, for example, that are generated from a cloud network and/or hospital network level cloud.

Validation datasets may be datasets that record data with a higher quality data than a standard procedure is expected to collect. Validation data sets may be generated using surgical devices in the operating room and/or using heavily instrumented devices in the operating room (e.g., non-"smart" devices, such as, for example, a thermometer that may send time stamped data to be collected with the rest of the operating room data).

Validation datasets may be confirmed and/or vetted, for example, to ensure that the correct data is received (e.g., data that falls within the bounds of expected constraints, such as, for example, patient outcomes, instrument performance, tissue performance, etc.). The validation datasets may include high quality data that may enable better analysis. The validation datasets may be cherry picked for unit tests. Certain data may be generated, such as, for example, jamming a device, and/or operating outside of standard bounds, to put into the validation data set. Devices and systems may be loaded and/or overloaded to account for possible outcomes (e.g., including failure outcomes). The validation dataset may be used to train ML models for multiple possible outcomes.

Validation datasets may be used to probe control algorithms (e.g., from other sources). For example, if a validation dataset is returned with predicted results that are different than what occurred in the procedure, the indication may be used to correct an error before deployment of the algorithm and/or a modification of the algorithm. If the validation dataset is returned with the correct predicted results from different control algorithms, an indication may be used to indicate there is a different insight due to some factor recorded in the dataset. The flagged control algorithm may be a candidate for further review to investigate why there is a difference in the controls and if the difference in the control algorithm is another way to perform the process.

A validation dataset may be created (e.g., artificially created) using a simulator and/or bench top datasets that express a known relationship of the instrument and its operation. For example, relationship data may be generated on the assembly line with defined combinations of parts leading to a specific device configuration and the resulting operational behavior. Bench top data may be generated, for example, using a user defined device and/or generator setup that may result in a device behavior that is predefined as beneficial and/or unacceptable. The unacceptable behaviors may result from a product inquiry and/or design validation testing.

Partial datasets may be used for confidence in ML model output predictions. For example, a master output may be used to check against an ML model output to confirm validation. The master output may take timing to process the (e.g., all) applicable data sets to confirm validation. For example, portions of the algorithm and/or datasets may be validated (e.g., as opposed to the entire composition of the algorithm), for example, based on a risk-based approach. The risk-based approach may expedite the results (e.g., while limited confidence in the output). The faster the output is produced may be associated with the higher the risk associated with the output.

A full master set of datasets may be created, for example, using highly instrumented procedures with exhaustive data collection and/or annotation practices (e.g., to ensure quality of data). The master dataset may be used to train the first iteration(s) of an ML model, for example, before the ML model is deployed for use in operating theaters.

Additional data may be collected for the master dataset, for example, after the deployment of the product. Additional data may be collected from controlled and/or singled out procedures that may be tooled for comprehensive data acquisition and/or labeling. System directed investigation of possible but inconclusive relationships from the original data may be performed. The additional data may be directed by a first ML model related to relationships that it identified that could have an interrelationship but the dataset was inconclusive. Targeted data collection and/or analysis may be used to seek information and/or interrelationships of a sub-portion of a primary set of information.

Preliminary relationship adjustment of some of the instruments within its reach may be used to result in minor changes in operation, for example, to monitor resulting behavior within the normal operation parameters of the device and/or subsystem to extract relationship data. For example, an RF Bipolar device may use tissue impendence and terminations of a weld. The triggering points may have a target impendence with a standard deviation that is acceptable for the triggering event to change the behavior. If the system identifies a potential relationship between the impedance value, the tissue type, the tissue thickness, and/or the resulting weld integrity, the system may direct generators that identify this set of parameters to adjust the impendence level trigger within its predefined acceptable range to one side or another side of the range (e.g., to validate or refute the potential relationship). The results may be communicated to the cloud system that may provide the resulting understanding to the other operational connected generators to further validate the result. The adjustment may be performed with micro changes that may produce (e.g., only) directional outcomes without affecting overall outcome and/or may be used to dramatically adjust the parameter to monitor larger effects.

In examples, an ML model may monitor relationships identified through a dataset to determine (e.g., with more, additional information) whether the relationships become stronger or weaker. The ML model may be enabled to re-enforce and/or adjust device control algorithms based on the initial learning.

Figure 17:
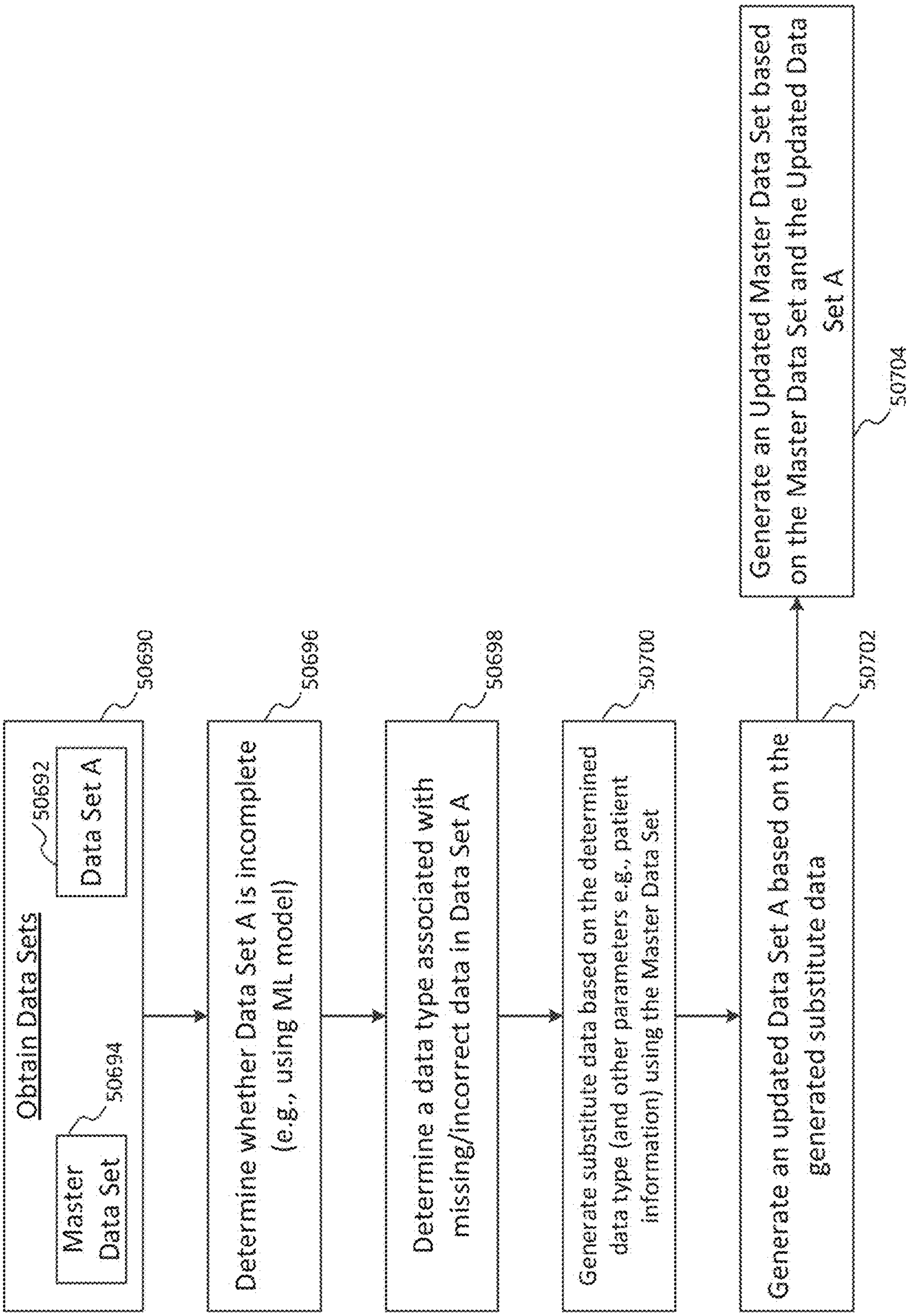
FIG. 17 illustrates an example of using a ML model to complete a dataset based on data type.

FIG. 17 illustrates an example of using a ML model to complete a dataset based on data type. As shown at 50690, surgical data sets may be obtained. The surgical data sets may include a data set to be processed (e.g., Data Set A 50692) and/or a master data set 50694. As shown at 50696, a ML model may be used to determine whether Data Set A 50692 is incomplete, irregular, and/or erroneous (e.g., as described herein). As shown at 50698, a data type associated with missing and/or incorrect data in Data Set A may be determined. As shown at 50700, substitute data (e.g., to insert in place of the missing data and/or replace the irregular and/or erroneous data) may be generated (e.g., using an ML model). As shown at 50702, Data Set A may be updated, for example, based on the generated substitute data. Additionally, the master data set may be updated (e.g., a revised master data set may be generated) based on the updated Data Set A (e.g., as shown at 50704).

The ML model may determine a data type associated with portions of data in the data set. For example, a data type may be one or more of the following: surgical instrument parameters, surgical equipment parameters, patient information, patient biomarkers, HCP information, and/or the like. For example, a data type may indicate that a piece of data is a patient biomarker, such as heart rate, for example. The ML model may determine that there is a missing portion of heart rate data during a surgical procedure. Based on the determination that the missing data is a heart rate (e.g., data type), the ML model may determine to generate substitute data of the same type (e.g., substitute heart rate data).

In examples, ML models may be used to take multiple sets of problematic (e.g., incomplete, irregular, and/or erroneous) data and generate an independent complete dataset. For example, an ML model may receive a first dataset and a second dataset. The ML model may be used to determine that the first and second datasets are problematic. The ML model may determine that the first and second datasets are problematic (e.g., incomplete, irregular, and/or erroneous), for example, based on comparison to a verified data set (e.g., master data set). The ML model may determine to aggregate the datasets and/or generate a third dataset using the first and second datasets.

The ML model may confirm that the generated independent dataset (e.g., generated based on the multiple problematic datasets) is valid for analysis. The ML model may confirm the generated independent dataset is valid for analysis, for example, based on a comparison to verified datasets and/or a master data set. The ML model may confirm that the generated independent dataset is accurate and/or reliable.

For example, a surgical computing system may determine data exchange behaviors for ML models and processing systems. The surgical computing system may obtain surgical data. The surgical data may include subsets of surgical data. The subsets of surgical data may be associated with respective classifications (e.g., privacy classifications). For example, the respective classifications may be determined for each of the subsets of surgical data. The surgical computing system may determine processing goal(s) associated with processing systems (e.g., ML models), for example, in a hierarchy. The hierarchy may include multiple processing systems in a level-based system. The higher processing systems in the hierarchy may process non-private data. The lower processing systems may use increasingly more private data.

The surgical computing system may determine classification threshold associated with processing tasks associated with the ML models (e.g., processing systems). The processing tasks may include data preparation, reduction, analysis, and/or the like. The surgical computing system may determine whether a subset of data is above or below the classification threshold. The surgical computing system may determine data packages to send to the ML models. The data packages may be determined based on the classification threshold, processing goals, data needs, and/or the like, associated with the ML models. For example, a data package may refrain from including data that is below (e.g., or above) the classification threshold.

The classification threshold may be associated with a privacy level. For example, privacy may be balanced with processing task importance to determine data exchange and data packages. For example, private data may be refrained from being sent to a processing system associated with a minimally important processing task. However, private data may be sent to a processing system associated with an important processing task.

Data exchange between systems performing processing (e.g., ML processing) may be performed. For example, a surgical computing system may determine data sets (e.g., data packages) to be sent for processing. The surgical computing system may send discrete data packages to different processing systems based on one or more of the following: processing goals, processing location, data type, data classification, processing capability, and/or the like. Data exchange between systems may be triggered, for example, based on an event (e.g., triggering event).

Data exchange between systems may be triggered based on privacy concerns. For example, a trigger for data exchange may be limited based on privacy concerns. A trigger for data exchange may be expanded based on a processing system's data needs (e.g., integral analysis needs). The data exchange may consider both the privacy concerns and the processing system's data needs. For example, a balancing test may be performed (e.g., considering the privacy concerns and the processing system's data needs) to determine the data exchange behavior between systems. Different systems performing different processing tasks may interact, for example, to determine data exchange behavior.

Data exchange between systems may be determined, for example, to meet processing goals of different processing systems. For example, processing systems (e.g., ML models) may use different data packages to perform various processing tasks (e.g., reduction, preparation, trend analysis, recommendation determination, etc.). Data exchange between systems may enable data storage and/or data compartmentalization. For example, organization of datasets may be determined based on the use of the data for ML model usage. For example, data exchange may provide a secure data storage. Compartmentalization of data may allow for more security in the event of a data breach, for example, because the data is located in various locations. Different locations may store different levels of private data.

In examples, data exchange may enable compartmentalization in a hierarchy of data storages and/or systems that process the data. For example, a first data storage and/or first processing system (e.g., at the highest level) may receive a first data package including data associated with a minimal privacy level (e.g., not private, not confidential information, for example, as determined by HIPAA guidelines). The data received at the first data storage and/or first processing system may include non-private data and/or redacted data (e.g., data with private and/or confidential data removed). A second data storage and/or second processing system (e.g., a level below the first data storage and/or first processing system, for example, in the hierarchy) may receive a second data package. The second data package may include the data in the first data package. The second data package may include data associated with a privacy level higher than the privacy level in the first data package (e.g., the data in the second data package may have a low private information level). The second data storage and/or second processing system may be enabled to store and/or process data associated with a higher privacy level than the first data storage and/or first processing system. The second data package may be a more complete set of data as compared to the first data package.

In examples, a data storage and/or processing system in the hierarchy may be aware of the other data storages and/or processing systems in the hierarchy. The data storage and/or processing system in the hierarchy may be aware of the privacy level, processing goals, data needs, and/or the like associated with the other data storages and/or processing systems in the hierarchy. For example, a first data storage may be aware that a second data storage is associated with storing more private information as compared with the first data storage. A lower level storage (e.g., in a hierarchy) may be aware of subsequent levels in the hierarchy (e.g., processing goals and/or data storage) and/or the criticality of the patient privacy aspects associated with the subsequent levels. The lower level storage may (e.g., using the awareness of the subsequent levels in the hierarchy) determine the amount of data, data type, and/or storage location of the data. For example, a first processing system with a first processing goal and first data needs associated with the first processing goal may be aware that a second processing system is associated with a second processing goal and a second data needs associated with the second processing goal.

In examples, data classifications (e.g., privacy level classifications) may be determined for portions of surgical data. For example, privacy level classifications for data may be determined based on HIPAA boundaries and/or considerations. For example, data storages within a facility may be enabled to store private and/or confidential data. For example, data storages within an edge network (e.g., associated with a medical facility) may be enabled to store private and/or confidential data. For example, data storages in a cloud network (e.g., outside the facility network and/or edge network) may store non-private and/or non-confidential information (e.g., restricted from storing confidential information), for example, based on HIPAA guidelines.

The privacy level classifications for portions of surgical data may be compared to thresholds (e.g., privacy level thresholds) associated with data storages and/or processing systems, for example, to determine whether the portion of surgical data can be stored and/or processed at the respective data storages and/or processing systems. For example, the thresholds may be predefined (e.g., based on HIPAA boundaries). The thresholds may be used to balance privacy concerns with processing data needs, for example. For example, a data storage and/or processing system within a controlled data network may have a privacy threshold that enables receiving more private and/or confidential data. A data storage and/or processing system outside a controlled data network may have a privacy threshold that restricts receiving private and/or confidential data (e.g., receives only non-private data).

Figure 18:
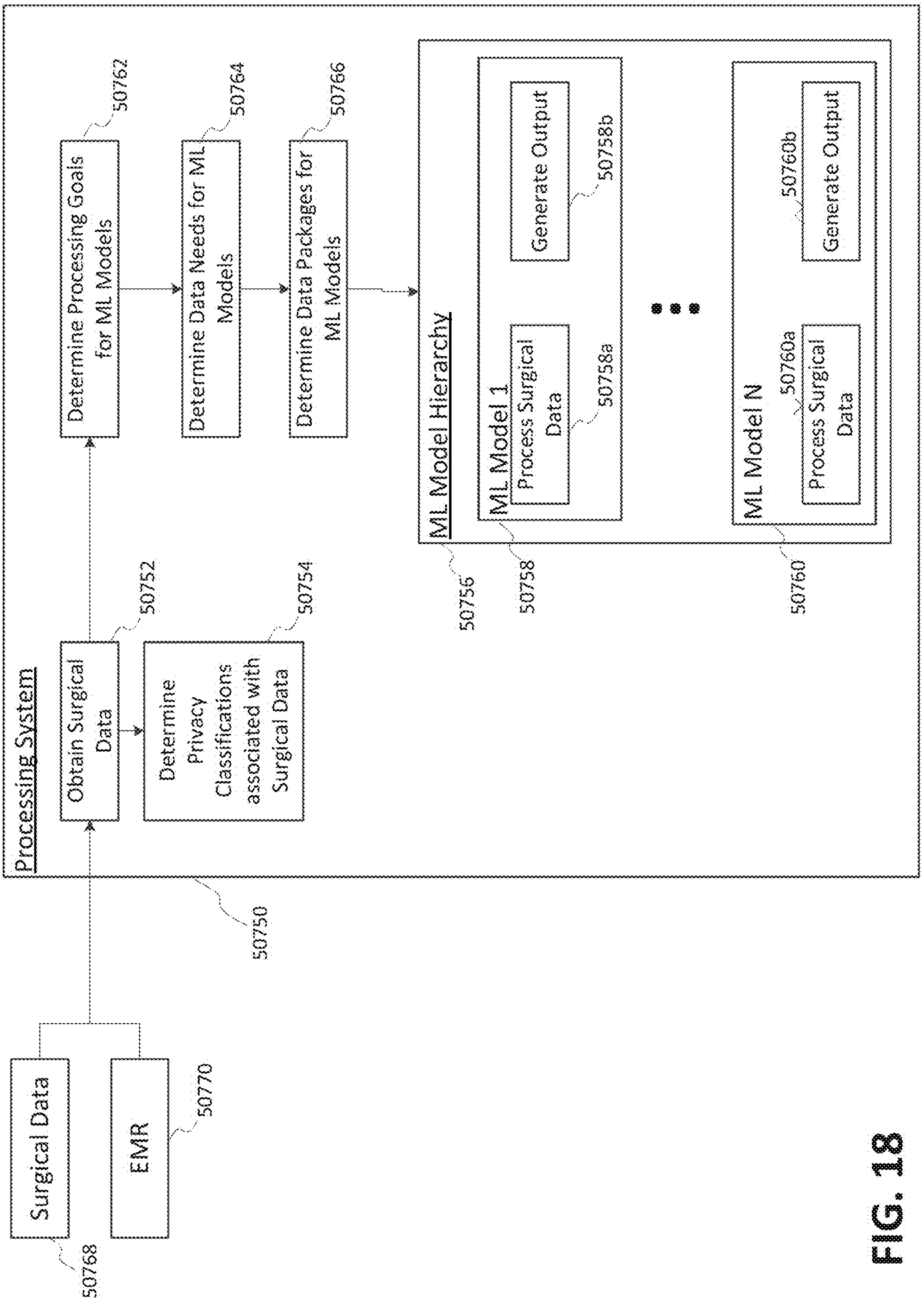
FIG. 18 illustrates an example of determining data exchange for a hierarchy of data processing systems.

FIG. 18 illustrates an example of determining data exchange for a hierarchy of data processing systems. As shown in FIG. 18, a processing system (e.g., surgical processing system) 50750 may obtain surgical data (e.g., as shown at 50752) and determine data exchange behavior (e.g., for a hierarchy of data storages and/or processing systems). The processing system 50750 may determine classifications (e.g., privacy classifications) associated with the obtained surgical data (e.g., as shown at 50754 in FIG. 18). The processing system 50750 may be aware of a hierarchy of processing systems (e.g., ML models) and/or data storages. For example, the processing system 50750 may be aware of a ML model hierarchy 50756 (e.g., for processing surgical data). The ML model hierarchy 50756 may include multiple ML models (e.g., for processing data at different levels), for example, such as a first ML model 50756 and an Nth ML model 50758. The hierarchy may include data storages, for example. The ML models may be used in the processing system 50750. The ML models may be used outside the processing system 50750 (e.g., in a different processing system, for example, within the same network or outside the computing system's network). The processing system may determine processing goals associated with the ML models in the ML model hierarchy 50756 (e.g., as shown at 50762). The processing goals may be associated with data needs associated with the ML models in the ML model hierarchy 50756. The data needs associated with the ML models may be determined, for example, based on the processing goals associated with the ML models (e.g., as shown at 50764). Data packages for the ML models may be determined (e.g., as shown at 50766), for example, by the processing system. The data packages may be sent to the ML models (e.g., within the processing system or to different processing systems).

The obtained surgical data (e.g., as shown at 50752) may include surgical data 50768, electronic medical records (EMR) 50770, and/or the like. For example, the obtained surgical data may include data associated with a surgical procedure, data associated with a specific patient, data associated with similar patients, and/or the like. The obtained surgical data may be associated with a privacy level. For example, privacy levels may be determined based on HIPAA guidelines (e.g., as described herein). For example, surgical data may be determined to be private information if the data contains identifying information. Privacy classifications may include (e.g., but is not limited to) one or more of the following: not private and/or confidential, low privacy, medium privacy, high privacy, critical privacy, and/or the like. For example, portions of surgical data that are associated with data that identifies a patient may be classified with a high privacy or critical privacy level. Surgical data associated with a high privacy or critical privacy level may be refrained from being transmitted (e.g., transmitted without redaction) to a location outside the facility network and/or cloud network. Surgical data associated with a low privacy level or not private level may be enabled to be transmitted to (e.g., any) data storage and/or processing system (e.g., outside the facility and/or edge network).

Private information in surgical data may be redacted, for example, to lower the privacy concerns associated with data. For example, surgical data associated with a high privacy level may be redacted (e.g., the identifying information may be redacted), for example, so the surgical data can be classified as a lower privacy level. The redacted surgical data may conform to privacy limitations associated with a data storage and/or processing system (e.g., outside the facility and/or edge network), for example, because it does not contain the identifying information (e.g., anymore).

The processing system may determine subsets of surgical data from the obtained surgical data. For example, subsets of surgical data may be discretized portions of the obtained surgical data. The subsets of surgical data may determined, for example, based on the type of data, data format, data contents, and/or the like. For example, a subset of data may include data (e.g., only data) associated with a specific surgical instrument. A subset of data may be a table of records (e.g., with fields as columns) associated with a specific patient. A subset of data may include a particular column of data within a table of records, for example. A subset of data may include any portion of the obtained surgical data (e.g., a specific data entry in a table of data, a row of data in a table of data, a column of data in a table of data). For example, a subset of data may include data associated with a specific surgical procedure. A subset of data may include data associated with a specific surgical procedure for a specific patient, for example.

The processing system 50750 may determine respective classifications (e.g., privacy level classifications) for each determined subset of surgical data. For example, different subsets may be associated with different classifications. A first subset of data may (e.g., be determined to) contain non-private and/or non-confidential data (e.g., as determined with respect to HIPAA guidelines). The first subset of data may not have privacy implications associated with transmittal. The first subset of data may be transmitted to a data storage and/or processing system within the facility network, edge network, cloud network, and/or the like. A second subset of data may (e.g., be determined to) contain data associated with a high and/or critical privacy level classification (e.g., includes patient identifying data). The second subset of data may be subjected to restrictions on transmittal (e.g., HIPAA restrictions). For example, the second subset of data may be refrained from being sent to a data storage and/or processing system outside the facility network and/or edge network (e.g., refrained from being sent to a cloud network).

The processing system 50750 may determine processing goal(s). For example, the processing goal(s) may include an overarching processing goal (e.g., associated with a ML model hierarchy 50756). The processing goal(s) may include separate processing goals for each ML model in the ML model hierarchy. For example, a first ML model may be associated with data reduction and/or data preparation and a second ML model may be associated with trend analysis and/or the like. The ML models may perform processing tasks as described herein with respect to FIGS. 9-17.

As shown at 50764, a data needs (e.g., for each ML model) may be determined based on a determined processing goal (e.g., for each of the ML models). The data needs may include the data used (e.g., needed) to perform and/or complete the processing goal. For example, a processing goal may be data reduction to perform trend analysis. The data needs associated with the processing goal may include data used to perform the trend analysis. The data needs may consider subsequent ML models (e.g., the subsequent ML model's processing goals). For example, a first ML model may perform preprocessing and data reduction on data and a second ML model may perform trend analysis for a specific biomarker. The data needs for the first ML model may consider the data used in the second ML model.

As shown at 50766, data packages may be determined, for example, for the ML models in the ML model hierarchy 50756. Different data packages may be determined and sent to the ML models. For example, a first data package may be determined for ML Model 1 50758 and an Nth data package may be determined for ML Model N 50760. ML Model N 50760 may be the lowest level in the ML Model Hierarchy 50756. The lowest level in the ML Model Hierarchy 50756 (e.g., ML Model N 50760) may receive the most complete data package (e.g., as compared to the other data packages determined for the other ML models in the ML Model Hierarchy). For example, the lower the level in the ML Model Hierarchy, the more complete the data package may be. The more complete data packages may include more surgical data (e.g., private and/or confidential data) as compared with data packages determined for higher level ML models. The level-based system may be designed, for example, to limit private information from being sent to specific levels in the ML Model Hierarchy. For example, the lowest level ML model (e.g., only the lowest level ML model) may receive highly classified and/or private data for processing. The level-based system may provide added security precautions, for example, in the event of a data breach.

For example, the processing system may determine a first data package for a first ML model and a second data package for a second ML model. The second ML model may be a lower level ML model in the ML Model Hierarchy as compared to the first ML model. The first data package may be determined based on the data needs and/or processing goals associated with the first ML model. The second data package may be determined based on the data needs and/or processing goals associated with the second ML model. The output of the first ML model may be sent to the second ML model, for example. The first data package may be determined based on considering that the output of the first ML model will be sent to the second ML model. The second data package may include the data included in the first data package. The second data package may include at least a portion of the data included in the first data package.

Figure 19:
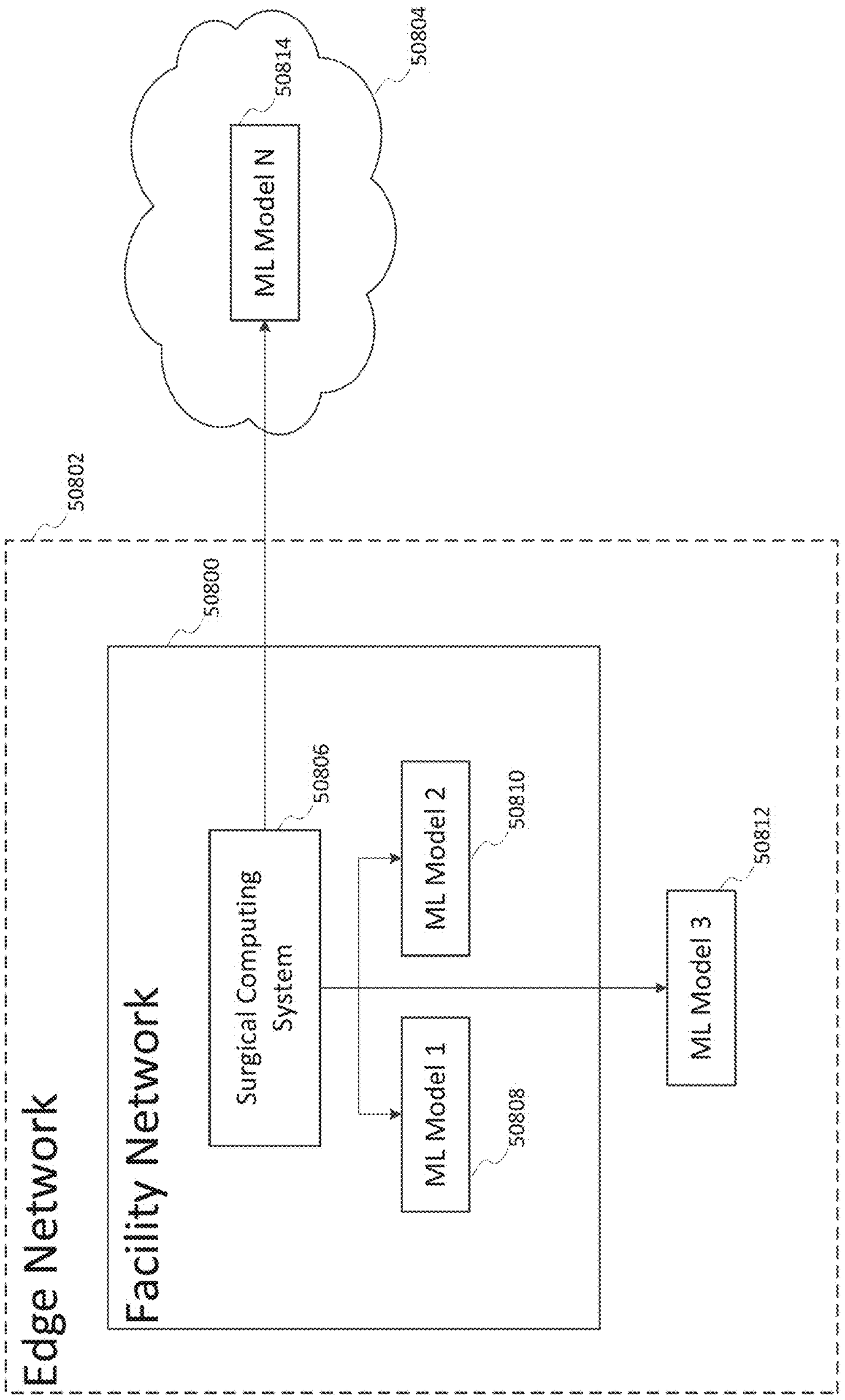
FIG. 19 illustrates example ML models in located in the facility network, edge network, and cloud network.
Figure 20:
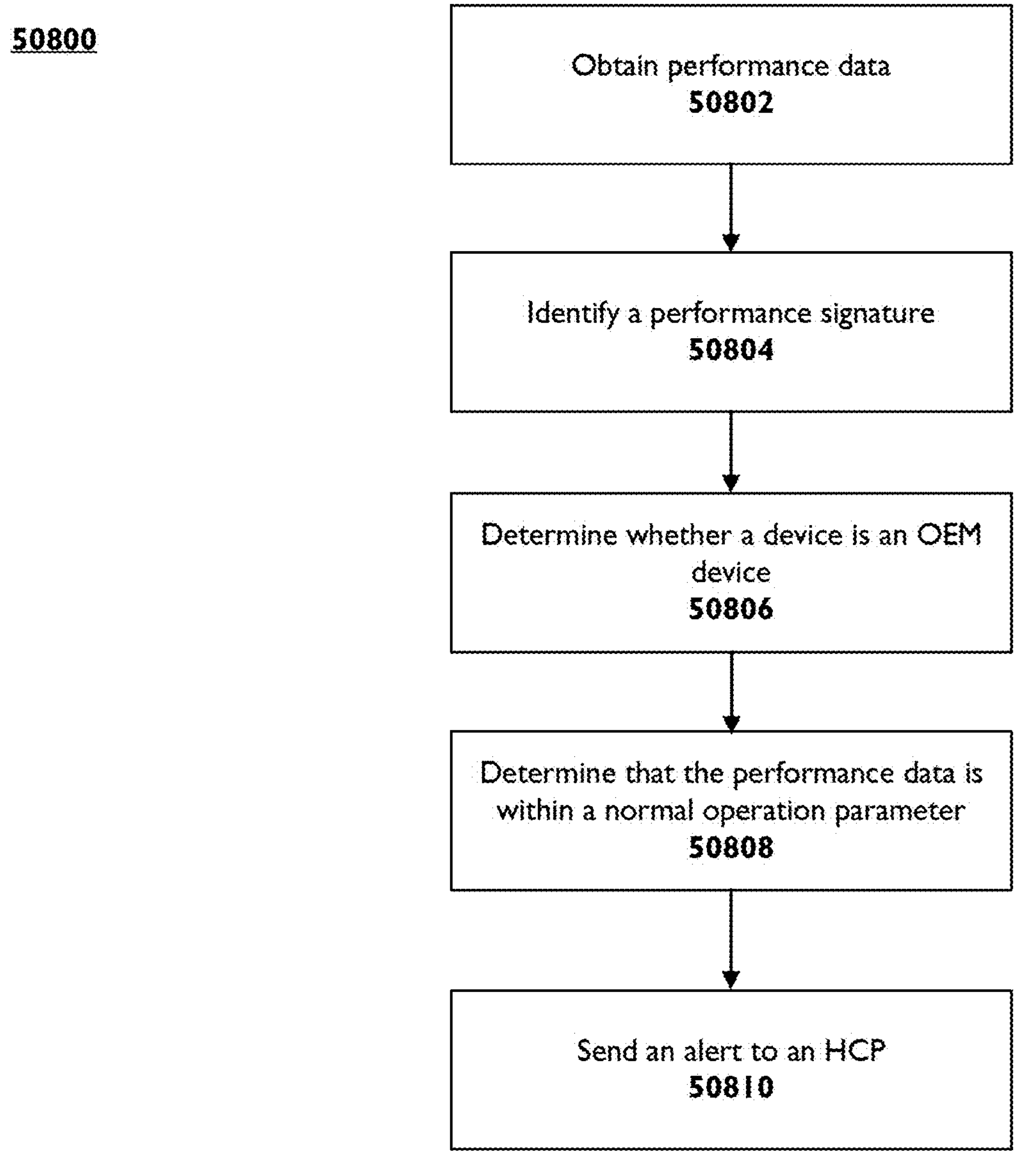
FIG. 20 illustrates a flow diagram of a computing device determining whether a surgical device is an original equipment manufacturer (OEM) device.
Figure 21:
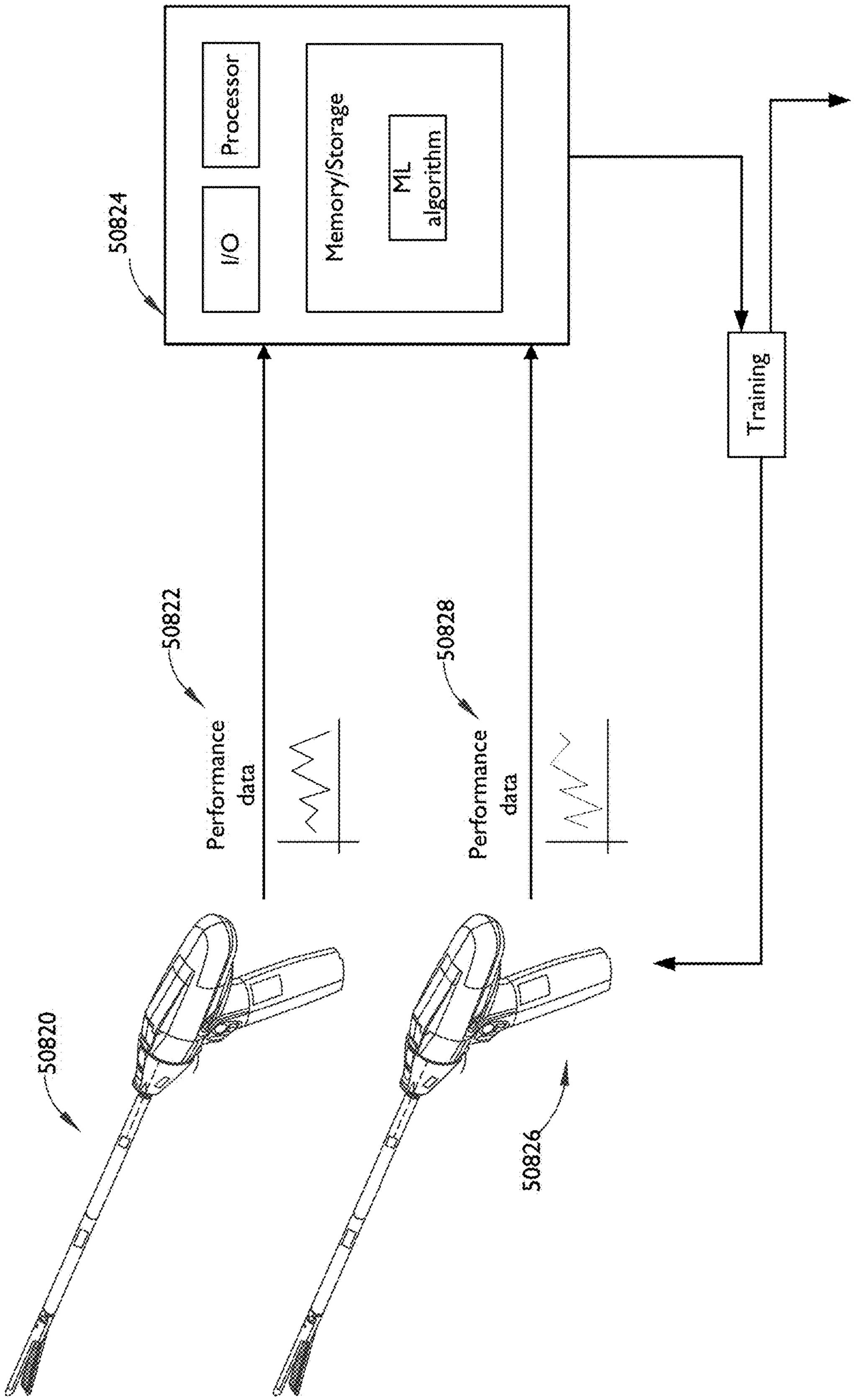
FIG. 21 illustrates an authentic OEM device sending performance data and a counterfeit device sending performance data to a computing device.

The ML Model Hierarchy may include ML models outside of the processing system 50750. FIG. 19 illustrates example ML models in located in the facility network, edge network, and cloud network. For example, the ML models may process data at a different location and/or in a different processing system. For example, the processing system 50750 may be located in a medical facility (e.g., within a facility network 50800 as shown in FIG. 19 and/or within an edge network 50802 as shown in FIG. 19). The facility network may be contained within the edge network (e.g., as shown in FIG. 19). The ML Model Hierarchy may include ML models within the facility network, edge network, cloud network, and/or the like. For example, a first ML model may be located in the edge network and a second ML model may be located in the cloud network. Different privacy implications may affect the data exchange between the ML models. As shown in FIG. 19, a first ML model 50808 and a second ML model 50810 may be located in the facility network (e.g., and within the edge network). A third ML model 50812 may be located within the edge network, for example, outside the facility network. An Nth ML Model 50814 may be located in a cloud network, for example, outside the edge network. A HIPAA boundary may affect data exchange between ML Models. For example, the HIPAA boundary may restrict confidential information from being transmitted outside the edge network and/or facility network (e.g., restricted from transmitting confidential information to the cloud network). The cloud network may be outside the HIPAA boundary, for example.

The ML models may process obtained surgical data (e.g., data packages, for example, as shown at 50758*a* and 50760*a* in FIG. 19). The ML models may generate an output (e.g., as shown at 50758*b* and 50760*b* in FIG. 19). The generated outputs from the ML models may be sent to subsequent ML models (e.g., in the hierarchy). The generated outputs may be stored and/or sent to HCP for review. The generated outputs may be stored, for example, to train the ML model for subsequent inputs.

In examples, the ML models may send discretized data packages to subsequent ML models. For example, a first ML model may receive a first data package for processing. The first ML model may generate a first output based on processing the first data package. The first ML model may identify a second ML model (e.g., subsequent ML model). The first model may determine a data needs and/or processing goal associated with the second ML model. The first model may generate a second data package (e.g., to be sent to the second ML model for processing). The second data package may include at least a portion of the first output. For example, the second data package may include the entire first output. The second data package may be determined based on the privacy concerns associated with the second ML model. The second data package may be determined based on the processing capabilities associated with the second ML model. The second data package may be determined based on a balancing analysis between the processing goal and the privacy implications associated with the second ML model.

Data exchange between processing systems (e.g., ML models) may be performed, for example, based on privacy level classifications and/or processing goals for surgical data. For example, a surgical computing system may obtain surgical data (e.g., a set of surgical data). The surgical data may include at least one subset of surgical data (e.g., as described herein). The subsets of surgical data may be grouped, for example, based on data type, data format, data source, data classification (e.g., privacy classification), surgical procedure type, patient, surgical instrument, and/or the like. The surgical computing system may determine processing goal(s) associated with the surgical data. For example, the surgical computing system may determine an overarching processing goal associated with the surgical data and different processing goals associated with individual processing systems (e.g., ML models), for example, in a ML model hierarchy. The processing goal(s) may be associated with a respective data needs and/or processing task. For example, the processing goal may be achieved based on performing the processing task. For example, the processing task may be achieved based on using data fulfilling the processing task's data needs.

The surgical computing system may determine a classification threshold associated with the ML models (e.g., processing tasks associated with the ML models). For example, a classification threshold may include a privacy level threshold. In examples, a first ML model may be associated with a first privacy level threshold. The first privacy level threshold may be associated with the location and/or security associated with the ML model. For example, a ML model within the facility network may be enabled to handle and/or process data that is private and/or confidential (e.g., under HIPAA guidelines). For example, a ML model in the cloud network (e.g., outside the HIPAA boundary) may be restricted from receiving data that is classified as private and/or confidential. For example, a privacy level may be low if the data contains information that is not likely able to be used to identify confidential information (e.g., a patient's identity). A privacy level may be critical and/or high if the data is associated with information that would reveal confidential information (e.g., identifies a patient).

The classification threshold may be used to determine data packages sent to the ML models. For example, a data that is below or above the classification threshold may be refrained from being sent to the ML model associated with the classification threshold. For example, if a subset of data is determined to have a high and/or critical privacy level classification and the ML model is determined to have a classification threshold of a medium privacy level classification, the subset of data may be refrained from being sent to the ML model (e.g., because it is beyond the privacy scope of the ML model). For example, if the subset of data is determined to have a low privacy level classification and the ML model is determined to have a classification threshold of a medium privacy level classification, the subset of data may be sent to the ML model for processing.

In examples, classification thresholds associated with ML models in a ML model hierarchy may be level-based. For example, a first ML model (e.g., highest level ML model) in a ML model hierarchy may have a classification threshold associated with a zero-privacy level. The first ML model may be enabled to receive subsets of data associated with zero privacy implications (e.g., no private and/or confidential information). The first ML model may be refrained from being sent and/or receiving subsets of data with any privacy implications. Subsequent ML models (e.g., lower level models) in the ML model hierarchy may have privacy classification thresholds that are associated with receiving more private data. For example, a second ML model may be a second level in the ML model hierarchy and have a privacy level classification threshold that enables a subset of data tagged as a medium privacy level to be received by the second ML model. An Nth ML model may be the lowest level ML model in the ML model hierarchy. The Nth ML model may be associated with the most secure and private data collection and/or processing. The Nth ML model may have a privacy level threshold that enables the most private data to be received.

In examples, the classification threshold associated with ML models may be determined based on the processing goal and the privacy implications. For example, the importance of the processing goal may outweigh the privacy concerns. The classification threshold may enable more private information to be exchanged, for example, if the importance of the processing goal outweighs certain privacy concerns.

Data packages for data exchange may be determined, for example, based on the classification thresholds and/or data processing goals (e.g., data needs associated with the data processing goals). For example, data packages may be determined based on balancing privacy concerns with processing goals. A processing goal may be important, for example, to provide critical surgical procedure information regarding a patient. The processing goal's needs may outweigh privacy concerns associated with data used for the processing goal. In examples, a processing goal may be determined to have low importance and the privacy implications associated with data used to achieve the processing goals may outweigh the processing goal's needs. The data package may be determined to refrain from including the private information. The determined data package(s) may be sent to the ML models.

In examples, the surgical computing system may determine whether classifications associated with subset(s) of data are above or below a first privacy classification threshold (e.g., associated with a first ML model) and/or above or below a second privacy classification threshold (e.g., associated with a second ML model). The data packages determined for each ML model may be determined based on whether a particular subset of data has a determined classification above or below the ML model's respective privacy classification threshold. For example, a first data package may be determined to include a first portion of data that is below (e.g., or alternatively above) the first privacy classification threshold. The second data package may be determined to include a second portion of data that is below (e.g., or alternatively above) the first privacy classification threshold.

Data exchange behavior may be dynamic. For example, processing goals associated with ML models may change. The changed processing goals may affect how data is exchanged between systems (e.g., ML models). For example, a change in processing goals (e.g., in a ML model hierarchy) may be determined. Based on the change in processing goals, an updated processing goal may be determined (e.g., for a ML model). The change in processing goal in a first ML model may affect the processing goals and/or data exchange of other ML models in the ML model hierarchy.

An updated classification threshold (e.g., updated privacy classification threshold) may be determined based on the updated processing goal. Data exchange may be affected based on the updated processing goal. For example, an updated data package may be determined for a ML model based on the updated processing goal (e.g., updated data needs) and/or updated classification threshold.

A computing device, such as a surgical hub, may use data to train a ML model and detect a change in a device and/or a health care professional (HCP). A computing device may detect if a device and/or a surgeon is performing differently in a typical operation using data from the operation. For example, a computing device may data to train a ML model. The trained ML model may be or may include gathered performance data associated with a device and/or an HCP. The computing device may compare how a device and/or an HCP is performing to other data, such as other trained ML model that are associated with a normal performance data for a device and/or other HCPs. The computing device may determine that the current performance associated with the device and/or the HCP differs from the generated ML performance data. The generated ML performance data may include and/or may be configured to indicate aggregated typical operation data generated by the ML process and/or the ML algorithm (e.g., the ML model associated with a normal performance data for a device and/or other HCPs). Based on the comparison, the computing device may determine whether a device and/or an HCP has improved or degraded performance.

In examples, a computing device may compare performance data to detect and/or localize groups of devices and/or HCPs that preformed differently than the aggregate typical operation ML gathered data. The computing device may itemize the detected/localized groups of devices and/or HCPs that preformed differently. The computing device may use the itemized performance data to identify a trend, e.g., using ML algorithm and/or configuring the ML. Examples of the trend and/or the pattern for the ML algorithm and/or the ML to identify may further be described in at least one of U.S. Pat. No. 11,410,259, entitled "Adaptive Control Program Updates For Surgical Devices" issued Aug. 9, 2022, U.S. Pat. No. 11,423,007, entitled "Adjustment Of Device Control Programs Based On Stratified Contextual Data In Addition To The Data" issued Aug. 23, 2022, U.S. Pat. No. 10,881,399, entitled "Techniques For Adaptive Control Of Motor Velocity Of A Surgical Stapling And Cutting Instrument" issued Jan. 5, 2021, U.S. Pat. No. 10,695,081, entitled "Controlling A Surgical Instrument According To Sensed Closure Parameters" issued Jun. 30, 2020, or U.S. patent application Ser. No. 15/940,649, entitled "Data Pairing To Interconnect A Device Measured Parameter With An Outcome" filed Mar. 29, 2018, which are hereby incorporated by references in their entireties. Additionally and/or alternatively, examples of the trend and/or the pattern for the ML algorithm and/or the ML to identify may further be described in at least one of U.S. patent application Ser. No. 16/209,423, entitled "Method Of Compressing Tissue Within A Stapling Device And Simultaneously Displaying The Location Of The Tissue Within The Jaws" filed Dec. 4, 2018, U.S. Pat. No. 10,881,399, entitled "Techniques For Adaptive Control Of Motor Velocity Of A Surgical Stapling And Cutting Instrument" issued Jan. 5, 2021, U.S. patent application Ser. No. 16/458,103, entitled "Packaging For A Replaceable Component Of A Surgical Stapling System" filed Jun. 30, 2019, U.S. Pat. No. 10,390,895, entitled "Control Of Advancement Rate And Application Force Based On Measured Forces" issued Aug. 27, 2019, U.S. Pat. No. 10,932,808, entitled "Methods, Systems, And Devices For Controlling Electrosurgical Tools" issued Mar. 2, 2021, U.S. patent application Ser. No. 16/209,458, entitled "Method For Smart Energy Device Infrastructure" filed Dec. 4, 2018, U.S. Pat. No. 10,842,523, entitled "Modular Battery Powered Handheld Surgical Instrument And Methods Therefor" issued Nov. 24, 2020, U.S. Pat. No. 9,687,230, entitled "Articulatable Surgical Instrument Comprising A Firing Drive" issued Jun. 27, 2017, which are incorporated by references herein in their entireties.

In examples, a computing device may detect a device in an operating room (e.g., for a surgical operation). The computing device may receive identification information from the device. For example, a device may send identification information to the computing device and the computing device may use the identification information received from the device to ID the device. Based on the identified device, the computing device may use the ML algorithm and/or the aggregated ML performance data to determine if the device is performing differently than the aggregated typical operation performance.

In examples, a computing device may detect a device in an operating room. A device may be or may include a surgical device to be used for a surgical procedure in an operating room. A device may not send identification information. For a non-self IDed device, the computing device may monitor the performance of the device to determine performance data over time. The computing device may input (e.g., feed) the monitored performance data (e.g., surgical information as disclosed with regard to FIGS. 7A-D) of the non-self IDed device to identify the device. For example, the computing device may configure ML process and/or use the ML algorithm to compare the monitored performance data with the gathered/aggregated ML performance data of a group of devices. Based on the comparison, the computing device may identify the non-self IDed device.

A computing device may identify a trend, e.g., a performance trend, associated with the identified non-self ID device. Based on the identified trend, the computing device may determine that a non-self IDed device is performing differently than the aggregated typical operation ML gathered data. For example, as described herein, the computing device may determine that a non-self IDed device may have an improved or degraded performance, e.g., in comparison to the aggregated ML generated data. The computing device may monitor the performance of the non-self IDed device and determine a relationship between the difference of the non-self IDed device to the aggregated ML performance data. For example, the computing device may monitor and/or determine that the non-self IDed device may account for the differences in outcome, usage, time-in-use, and/or performance.

A computing device may analyze one or more different outputs between current performance data associated with a device and/or an HCP and aggregated data, e.g., based on a comparison as described herein. Based on the comparison of the differing outputs, the computing device may determine that the variance is improving or degrading operation performance of the device.

In examples, the computing device may determine that the performance data of the device (e.g., current performance data associated with the device used for a surgery) has shorter time-in-use in comparison to the aggregated data of a group of the same devices. The computing device may determine, e.g., using the ML algorithm, that the performance data of the device has the same or higher success rate for a surgical procedure in comparison to the aggregated data of a group of the same devices. Based on the information (e.g., shortened time-in-use and the same/higher success rate), the computing device may determine that the performance data of the device is improving the operation performance of the device.

The data and/or the aggregated data may be determined from a ML model. For example, the aggregated data of a group of the same devices may be determined from information from a ML model associated with the group of the same devices. For example, a ML model associated with the group of the same devices may be configured to indicate information for the aggregated data of the group of the same devices.

In examples, the computing device may determine that the performance data of the device (e.g., current performance data associated with the device used for a surgery) has longer time-in-use in comparison to the aggregated data of a group of the same devices. The computing device may determine, e.g., using the ML algorithm, that the performance data of the device has the same or lower success rate for a surgical procedure in comparison to the aggregated data of a group of the same devices. Based on the information (e.g., longer time-in-use and the same/lower success rate), the computing device may determine that the performance data of the device is degrading the operation performance of the device.

In addition to and/or alternatively, a computing device may gather information associated with a device being monitored (e.g., for performance data) as described herein. For example, the computing device may gather regional data associated with the device, other procedure(s) using similar function(s) and/or sub-function(s), or other local hospital(s). The computing device may use the gathered information as a benchmark to compare performance data associated with a device. For example, the computing device may use the information as a benchmark to compare at least one of an outcome, a complication, throughput, efficiency, and/or cost relative to the device. The computing device may use the gathered information to determine (e.g., further determine) improved or degraded operation of the device.

A computing device may determine a configuration associated with a device. For example, a computing device, such as a hub or a surgical hub, may determine a current configuration associated with a surgical device in an operating room that is being used for a surgery. The computing device may determine a configuration, e.g., a current configuration, associated with a device based on the device sending information to the computing device.

In examples, a device may establish a connection with a computing device and/or may self-ID to the computing device. The device may send current configuration information to the computing device.

In examples, a device may not self-ID to a computing device. The computing device may determine and/or record configuration of a non-self IDed device. As described herein, the computing device may identify the non-self ID device. For example, the computing device may obtain performance data, such as configuration associated with the non-self IDed device. The computing device may record and/or monitor the performance data (e.g., the configuration) associated with the non-self IDed device. As described herein, the device may be a surgical device that is being used in a surgical procedure and an HCP, such as a surgeon, is performing the surgical procedure using the surgical device.

Based on the obtained performance data, the computing device may identify a performance signature associated with the device. A performance signature may be or may include at least one of a trend, a characteristic, and/or configuration information associated with the device. Based on the identified performance signature, the computing device may determine whether the non-self IDed device is an authentic original equipment manufacturer (OEM) device or a counterfeit device (e.g., an imitator device). For example, the computing device may compare the identified performance signature (e.g., using the recorded and/or monitored configuration associated with the non-self IDed device as described herein) to configurations of a known authentic OEM device. For example, the computing device may compare the recorded and/or monitored configuration associated with the non-self IDed device to a predefined list of configurations of a known authentic OEM device. The computing device may identify the non-self IDed device, e.g., based on the comparison.

In examples, a computing device may use a ML algorithm to identify a non-self IDed device. The computing device may utilize a ML algorithm that is capable of reviewing data from the non-self ID device. For example, the computing device may configure a ML algorithm to analyze the data from the non-self ID device to look for trend, such as a performance signature as described herein. As described herein, the computing device may compare the identified trend, such as the performance signature, associated with the device to a predefined list of known configurations of a known device. Based on the comparison, the computing device may determine if the non-self ID'ed device is an authentic OEM device or an imitator. For example, if the computing device determines that the identified trend is similar with (e.g., matches with) the predefined list of known configurations of a known device, the computing device may determine that the non-self ID'ed device is an authentic OEM device. If the computing device determines that the identified trend is not similar with (e.g., does not match with) the predefined list of known configurations of a known device, the computing device may determine that the non-self ID'ed device is an imitator. The computing device may continue to monitor and/or record the configuration of the non-self ID'ed device.

In examples, a computing device may use data, such as ML model and/or data using a ML algorithm, to identify a non-self ID'ed device. The computing device may configure a ML algorithm to analyze the data from the non-self ID'ed device (e.g., to train a ML model). The data from the non-self ID'ed device may be associated with the surgical information as described herein (e.g., with regards to FIGS. 7A-D). The computing device may use and/or may be configured to use data to train a ML model (e.g., using ML process and/or a ML algorithm) as described herein. For example, the computing device may use the surgical information, such as the data from the non-self ID'ed device, as input to the ML process and/or the ML algorithm. The computing device may use the surgical information to train a ML model, e.g., using ML process and/or the ML algorithm. The computing device may use the one or more training methods appropriate for using the surgical information (e.g., with regards to FIGS. 8A-B) to train a ML model. For example, the data from the non-self ID'ed device may be used to train a ML model using supervised learning, such as a supervised learning algorithm as described herein. The output data from the ML process and/or the ML algorithm (e.g., the trained ML model) may be or may include data that is appropriate for the computing device to identify a trend(s) associated with the non-self ID'ed device. For example, the trained ML model (e.g., the output data from the ML process and/or the ML algorithm) may be or may provide information (e.g., comparable information) to the computing device that, based on the data from the non-self ID'ed device, the non-self ID'ed device is artificial, tampered with, or irregular (e.g., data associated with a counterfeit device). As described herein, the computing device may configure a ML algorithm to look for a trend(s) and determine a validity and/or identify a likelihood that the data from the device is artificial, tampered with, or irregular. The computing device may configure a ML algorithm (e.g., enable the ML algorithm) to identify a source of an error if the computing device and/or the ML algorithm determines that the data for the device is tampered with and/or irregular. The computing device may configure a ML algorithm (e.g., enable the ML algorithm) to adjust and/or remove suspect data, such as artificial and/or tampered with. Based on the adjustment and/or removal of the suspected data, the computing device may process other data and may improve processing the data, e.g., to identify the device.

ML process and/or a ML algorithm may use data from a device, such as a surgical device. For example, the data from a device may be or may include surgical information as described with regards to FIGS. 7A-D. The ML process and/or the ML algorithm may train the data, e.g., using a supervised training as described with respect to FIGS. 8A-B. For example, the ML process and/or the ML algorithm may use the data from the surgical device and may train a ML model to output the trained model data (e.g., a ML model data). The trained model data may be or may include information associated with a normal parameter(s) associated with the surgical device. For example, the computing device may use a list of configurations from a known device (e.g., an authentic OEM device) and train a ML model. The trained ML model may be or may include information associated with a normal parameter(s) for the known device. Based on the trained model and/or the ML model data, the computing device may identify, and/or aware a normal parameter(s) associated with a known device, such as an authentic OEM device. For example, the computing device may analyze the data from the surgical device (e.g., the monitored/recorded data from a device and/or the ML trained data associated with the device as described herein). The computing device may compare the data for the device to other data (e.g., information associated with a normal parameter(s) for the known device(s) and/or other ML trained data for the known device(s) as described herein). Based on the comparison, the computing device may determine if the data from a device is irregular and/or if the data from the device is out of bound(s). The computing device may have a trained model for data of an authentic OEM device with one or more of normal operation data, catastrophic failure data, device failure data, and/or the like. As described herein, the computing device may use one or more trained models to determine whether a device, such as a non-self ID'ed device, is an authentic OEM device, an imitator device, operating under normal parameter, operating irregularly, such as in catastrophic failure and/or device failure.

In examples, a computing device may use at least one of a Kriging model technique, a x^k factorial design, and/or the like to determine whether monitored/recorded data from a device is normal performance data, out of bounds data, or irregular data. The computing device may use one or more techniques described herein based on analysis of the monitored/recorded data from a device that the data is bad, corrupt, or out of the normal parameter(s).

In examples, a computing device may use a ML algorithm to gather information associated with a device, such as a non-self ID'ed device, a determined imitator device, and/or an authentic OEM device that has been determined to operate abnormally. As described herein, a computing device may determine that a device has been acting abnormally. If a computing device determines that a device does not conform to a normal performance, a computing device may identify at least one of a facility associated with the device, an HCP(s) who has been using the device, a surgical procedure(s) that do not conform to a normal performance of the device. The computing device may use the gathered information to generate a trained model, e.g., using the ML process and/or a ML algorithm as described herein.

A computing device may use gathered information, e.g., as described herein, to identify and/or pinpoint a pool (e.g., a sub-pool) of devices that is performing abnormally. For example, a computing device may use the gathered information as a means to identify a pool of devices for additional in-servicing and/or reuse of the devices.

A computing device may gather data/information associated with a device. A computing device may gather data and/or information for a device to establish and/or update a normal operating envelope of a device(s). In examples, a computing device may gather data generated from an engineering trial(s). In examples, a computing device may gather data associated with a device during usage by an HCP(s). For example, the device may upload the usage and/or performance data to a computing device periodically, upon a request from a computing device, and/or the like. An HCP(s) may upload the data to a computing device manually. Based on the data, a computing device may determine product reliability and/or break period(s). The data from the device may be or may include normal use situation data, catastrophic failure situation data, device failure situation data, and/or the like. As described herein, a computing device may use the gathered data, e.g., to train a model using a ML process and/or a ML algorithm as described herein.

In examples, a computing device may gather information for a device(s) if one or more conditions are met. For example, a computing device may gather controlled sample (s) and/or partner operation(s) where one or more factors are controlled (e.g., based on one or more conditions being met).

In examples, a computing device may gather information for a device(s) based on region. For example, a computing device may gather information for a device(s) for regional specific operation. A computing device may use a ML algorithm to determine that one particular region has degraded device performance. Based on such analysis, a computing device may gather information for a device(s) for the identified region where the device has been experiencing degraded performance.

In examples, a computing device may automate data gathering of a device. For example, a computing device may generate one or more boundaries. If a computing device determines that the one or more generated boundaries have been reached or is reaching the boundaries, the computing device may autonomously gather data associated with the device.

Based on gathered/recorded data associated with a device, a computing device may determine whether the device is known. For example, as described herein, a computing device may compare the gathered/recorded data associated with a device to a list of configurations associated with a known authentic OEM device to determine whether the device is an authentic OEM device. In examples, a computing device may compare the gathered/recorded data associated with a device to a list of configurations associated with known counterfeit devices to determine whether the device is a counterfeit device.

In examples, a computing device may compare the gathered/recorded data associated with a device to a list of configurations associated with quasi-unknown devices. For example, a computing device may have a list of configurations for quasi-known devices that is neither known authentic OEM devices nor known counterfeit devices. The computing device may continue to gather information associated with a device if the computing device determines that the device is a quasi-known device. The computing device may send data for the quasi-known device to other computing device, an edge device, and/or a cloud for a user to investigate and/or generate a group for quasi-known devices.

In examples, a computing device may compare the gathered/recorded data associated with a device to a list of configurations associated with known authentic OEM devices, known counterfeit devices, and/or quasi-unknown devices. If a computing device determines that the gathered/recorded data associated with a device is not similar with (e.g., does not match with) at least one of the lists of configurations for known authentic OEM devices, known counterfeit devices, and/or quasi-unknown devices, the computing device may identify the device as an unknown device, such as a questionable device. The computing device may send the data to other computing device, an edge device, and/or a cloud for a user to investigate and/or classify the device as unknown device.

A ML model may determine and/or classify data that the ML model and/or an ML algorithm has seen before. The ML algorithm may attempt to make a guess on what the algorithm best thinks something is. For example, the ML algorithm may not be able to discover and/or classify gathered and/or recorded data as an unknown device as described herein. A computing device may send the gathered and/or recorded data to other computing device, an edge device, and/or a cloud for a user to investigate and/or to further classify the device.

A computing device may use geographical data to determine and/or identify a device. For example, a computing device may utilize regional specific data, such as electrical operating frequency and/or voltage to determine a geographical region. If a computing device determines that an electrical operating frequency is 50 Hz, the computer device may identify that a device is located in Europe or Asia. If a computing device determines that an electrical operating frequency is 60 Hz, the computer device may identify that a device is located in North America.

FIG. 9 illustrates a flow diagram 50800 of a computing device determining whether a surgical device is an OEM device. As illustrated in 50802 and/or as described herein, a computing device, such as a surgical hub, may obtain performance data of one or more devices, such as one or more surgical devices, in an operating room. The performance data may be or may include status information associated with a device, usage information associated with a device, an HCP using a device, and/or the like.

As illustrated in 50804, a computing device may identify a performance signature of a surgical device. For example, as described herein, a computing device may identify a performance signature of a surgical device based on the obtained performance data associated with the surgical device. Based on the identified performance signature of the surgical device, a computing device may determine whether the surgical device is an OEM device or a counterfeit device, e.g., as illustrated in 50806. For example, as described herein, a computing device may compare the obtained performance data (e.g., 50802) and/or the identified performance signature (e.g., 50804) to data that has a list of normal performance information associated with a surgical device. The data and/or ML generated data (e.g., information from a ML trained model) may be or may include a list of capabilities associated with a list of OEM devices and/or a list of capabilities associated with counterfeit devices.

A computing device may compare obtained performance data and/or identified performance signature to data (e.g., information and/or data from a trained ML model). Based on the comparison, a computing device may determine whether a device is an OEM device or a counterfeit device. In examples, if a computing device determines that the obtained performance data and/or the identified performance signature is similar with (e.g., matches with) and/or is within a predetermined threshold (e.g., associated with OEM devices), the computing device may determine that the device is an OEM device. If a computing device determines that the obtained performance data and/or the identified performance signature is not similar with (e.g., does not match with) and/or exceeds a predetermined threshold (e.g., associated with OEM devices), the computing device may determine that the device is a knock off device or a counterfeit device. In examples, if a computing device determines that the obtained performance data and/or the identified performance signature is similar with (e.g., matches with) and/or is within a predetermined threshold (e.g., associated with counterfeit devices), the computing device may determine that the device is a counterfeit device. If a computing device determines that the obtained performance data and/or the identified performance signature is not similar with (e.g., does not match with) and/or exceeds a predetermined threshold (e.g., associated with counterfeit devices), the computing device may determine that the device is an OEM device.

In examples, based on a comparison, a computing device may determine that obtained performance data and/or identified performance signature is not similar with (e.g., does not match with) data associated with OEM devices and/or counterfeit devices. For example, a computing device may determine that the obtained performance data and/or the identified performance signature is not similar with (e.g., may not match with) data associated with OEM devices and/or counterfeit devices. A computing device may determine that the device may be an unknown device and/or an unidentified device. A computing device may monitor and obtain performance data associated with the surgical device. Based on the monitored/obtained data, the computing device may use and/or configure the data to train a ML model. The computing device may configure the ML trained model to identify and/or generate a list to categorize the unknown/unidentified device.

In examples, a computing device may determine that a surgical device is a counterfeit device and/or a knock off device. The computing device may continue to obtain and/or monitor performance data associated with the surgical device. The computing device may input (e.g., feed) the performance data associated with the identified counterfeit surgical device and train a ML model (e.g., using a ML process and/or a ML algorithm) to determine (e.g., further determine) information associated with the counterfeit surgical device. For example, the information associated with the counterfeit surgical device may be or may include a manufacturing facility of the counterfeit device, the HCP using the counterfeit device, the surgical procedure associated with the counterfeit device, a medical facility that has been using the counterfeit device, and/or the like.

As shown in 50808, a computing device may determine that the performance data is within a normal operation parameter (e.g., if the computing device determines that the computing device is determined to be an OEM device).

In examples, a computing device may determine that a surgical device is an OEM device. If the computing device identifies a surgical device to an OEM device, the computing device may obtain a ML model (e.g., data) associated with authentic OEM devices. The data from the ML model associated with authentic OEM devices may be or may include data associated with normal operation parameter for authentic OEM devices. Based on the obtained data associated with authentic OEM devices, the computing device may determine (e.g., based on a comparison) that the performance data is within a normal operation parameter.

If a computing device determines that the performance data is outside of a normal operation parameter, the computing device may send an alert to an HCP, e.g., as shown in 508010. In examples, a computing device may receive data (e.g., information associated with a ML model) associated with a list of OEM devices. The data (e.g., a ML model information) may be or may include a list of gathered performance data associated with the list of OEM devices. The list of gathered performance data may be or may include a list of normal performance data, a list of catastrophic failure performance data, a list of device failure performance data, and/or the like. Based on the data, the computing device may compare the obtained performance data to the machine learning data. If the computing device determines that the obtained performance data is similar with (e.g., matches with) the data (e.g., being and/or including the list of catastrophic failure performance data or the list of device failure performance data) and/or is within a threshold level, the computing device may determine a potential source of error. The computing device may provide a potential solution based on the data. For example, the computing device may send an alert message to an HCP. The alert message may be or may include the identified potential source of error and/or a potential solution.

FIG. 10 illustrates an authentic OEM device sending performance data and a counterfeit device sending performance data to a computing device. For examples, as described herein, a computing device may obtain performance data from one or more devices in an OR (e.g., 50802). In examples, a computing device 50824 may obtain performance data 50822 from an authentic OEM surgical stapler 50820. In examples, a computing device 50824 may obtain performance data 50828 from a counterfeit surgical stapler 50826. As described herein, the performance data 50822, 50828 may be or may include structured data (e.g., serial number associated with a surgical stapler) and/or unstructured data (e.g., force to fire curves associated with a surgical stapler, access change in frequency of force peaks associated with a surgical stapler, and/or the like).

As described herein, an authentic OEM surgical stapler 50820 and/or a counterfeit surgical stapler 50826 may send self-ID information in the performance data 50822, 50828. For example, an authentic OEM surgical stapler 50820 may include serial number associated with the surgical stapler in the performance data 50822 for self-ID. The counterfeit surgical stapler 50826 may include serial number associated with the surgical stapler in the performance data 50828 for self-ID and may act (e.g., mimic) an authentic OEM surgical stapler.

A computing device 50824 may identify a performance signature associated with one or more devices (e.g., 50804). For example, based on the obtained performance data 50822 from an authentic surgical stapler 50820 and based on the obtained performance data 50828 from a counterfeit surgical stapler 50826, a computing device 50824 may identify performance signature associated with the authentic surgical stapler 50820 and the counterfeit surgical stapler 50826. The obtained performance data 50822, 50828 may be or may include unstructured data. For example, unstructured data may be or may include force to fire curves associated with a surgical stapler, access change in frequency of force peaks associated with a surgical stapler, and/or the like.

As described herein, the computing device 50824 may configure a processor to run a ML algorithm to identify the performance signature associated with the authentic surgical stapler 50820 and/or the counterfeit surgical stapler 50826. For example, based on the unstructured data in the performance data 50822, 50828, the computing device 50824 may identify performance signature associated with the authentic surgical stapler 50820 and/or the counterfeit surgical stapler 50826. The computing device 50824 may use the identified performance data and train a ML model. The computing device 50824 may use the trained ML data to determine whether one or more devices, such as a surgical stapler, are authentic OEM devices or counterfeit devices.

As described herein, a computing device may use data from the trained ML model (e.g., the output from the ML algorithm) and to compare the identified performance signature of the surgical stapler to a list of configurations and/or performance data for an authentic OEM surgical stapler. Based on the comparison, the computing device 50824 may determine that the identified performance signature and/or the obtained performance data 50822 is similar with (e.g., matches) with the list of configurations and/or performance data for an authentic OEM surgical stapler. Based on the determination (e.g., the similarity and/or the match), the computing device 50824 may determine that the surgical stapler is an authentic OEM surgical stapler 50820.

As described herein, a computing device may compare the identified performance signature of the surgical stapler to a list of configurations and/or performance data for a counterfeit surgical stapler. Based on the comparison, the computing device 50824 may determine that the identified performance signature and/or the obtained performance data 50828 is similar with (e.g., matches with) the list of configurations and/or performance data for a counterfeit surgical stapler. Based on the determination (e.g., the similarity and/or the match), the computing device 50824 may determine that the surgical stapler is a counterfeit surgical stapler 50828.

In examples, a computing device may identify a device for a surgical operation in an operating room. For example, a computing device may detect a surgical stapler connected to the computing device. As described herein, the computing device may obtain performance data associated with the surgical stapler, e.g., while an HCP uses the surgical stapler. Based on the obtained performance data, the computing device may identify a performance signature associated with the surgical stapler. The computing device may use a ML algorithm to compare the identified performance signature of the surgical stapler to a list of configurations and/or performance data for an authentic OEM surgical stapler. In examples, the computing device may determine force to fire a curve(s) and access change in frequency of a force peak(s) based on the performance data associated with the surgical stapler. The computing device may compare the force to fire curve(s) and/or the force peak(s) associated with the surgical stapler to data (e.g., data from a ML trained model). For example, the data (e.g., the data from the ML trained model) may be or may include a list of force to a fire curve(s) and/or a force peak(s) associated with a group of authentic OEM surgical staplers. Based on the comparison of the curve and/or the force peak, the computing device may determine whether the surgical stapler being used is an authentic OEM surgical stapler. In examples, as described herein, if the computing device determines that the curve and/or the force peak of the surgical stapler (e.g., based on the performance data) is similar with (e.g., matches with) and/or within a threshold difference with the data (e.g., the data from the ML trained model) for authentic OEM surgical staplers, the computing device may determine that the surgical stapler is an authentic OEM device. In examples, as described herein, if the computing device determines that the curve and/or the force peak of the surgical stapler (e.g., based on the performance data) differs from (e.g., greater than a threshold difference) the data (e.g., the data from the ML trained model) for authentic OEM surgical staplers, the computing device may determine that the surgical stapler is a counterfeit surgical stapler. As described herein, the computing device may compare the performance data (e.g., the curve and/or the force peak) of the surgical stapler to other data (e.g., authentic OEM surgical stapler not functioning properly, such as in catastrophic and/or device failure situations) and determine if the surgical stapler is not functioning properly.

In examples, a computing device may obtain performance data of a surgical stapler. The computing device may identify a magnitude of buckling load(s) of the surgical stapler. The magnitude of buckling load(s) may be affected by buckling characteristics of a staple wire, such as a wire diameter and/or unsupported length of wire. The computing device may compare the performance data (e.g., the magnitude of buckling load(s) of the surgical stapler) to data (e.g., data from a ML trained model) that is or includes a list of magnitude of buckling load of authentic OEM surgical staplers. Based on the comparison, the computing device may determine relative peaks between a single driver and a double driver of the surgical device. Based on the different buckling loads of staple wire(s) (e.g., between an authentic OEM surgical stapler and a counterfeit surgical stapler), the computing device may identify whether the surgical stapler being used is an authentic OEM device or a counterfeit device.

In examples, a computing device may obtain performance data associated with a device, such as a surgical device, as loads are increased, the time at which buckling occurs. Based on the comparison to data (e.g., data from a ML trained model) that may be or may include performance data associated with authentic OEM devices and the time to achieve a different load, the computing device may determine whether the device is an OEM device or a counterfeit device.

In examples, a computing device may compare operation data of a device, such as a surgical stapler. The operation data may be or may include a firing load(s) and/or motor current(s) associated with the surgical stapler. The computing device may access characteristic(s) (e.g., the firing load(s) and/or motor current(s) and determine an expected outcome of the surgical stapler (e.g., expected firing timing, range, frequency, etc.) based on data (e.g., data and/or data from a ML trained model associated with authentic OEM devices). As described herein, the computing device may compare an actual outcome and based on the difference, the computing device may determine whether the device is an OEM device or a counterfeit device.

In examples, a computing device may obtain operation data of a device, such as a radio frequency (RF) handpiece device. For example, a computing device may obtain the operation data for a RF handpiece device that is connected to a generator. The computing device may obtain and/or determine a performance signature of the RF handpiece device that is connected to a generator. In examples, the computing device may obtain circuit impedance (e.g., measuring capacitance). In examples, the computing device may leverage powered closure, e.g., as part of a wake-up cycle, to ping a motor (e.g., again while closed). Based on the obtained performance signature of the RF handpiece device, the computing device may compare the obtained performance signature to data (e.g., data from a ML trained model) for groups of authentic OEM RF handpiece devices. As described herein, the computing device may determine whether the RF handpiece device is an authentic OEM RF handpiece device or a counterfeit RF handpiece device, e.g., based on the comparison. The data (e.g., data from a ML trained model) for groups of authentic OEM RF handpiece devices may be or may include performance data for circuit impedance in a narrow band. The computing device may flag (e.g., send an alert message) if the device is a counterfeit device. For example, as described herein, if the computing device determines that the device is a counterfeit device, the computing device may send an alert to an HCP and/or continue to monitor the performance data of the determined counterfeit device.

In examples, a computing device may obtain operation data of a device, such as a surgical incision device, that is connected to a generator. The computing device may ping a blade associated with the surgical incision device and may obtain a frequency associated with the ping, e.g., as the operation data. As described herein, the computing device may have data (e.g., data from a ML trained model) of frequency information associated with authentic OEM surgical incision device. The computing device may compare the operation data of the surgical incision device to the data (e.g., the data from the ML trained model) and determine whether the surgical incision device is an OEM device or a counterfeit device.

A computing device may determine that a device is a counterfeit device (e.g., a non-OEM device). If a computing device determines that a device is a counterfeit device, the computing device may flag the device as a knock off device, a counterfeit device, an imitator device, and/or the like. The computing device may continue to obtain performance data of the counterfeit device. In examples, the computing device may use the obtained performance data and generate data (e.g., data from a ML trained model) for configuration information associated with a counterfeit device.

Alternatively and/or additionally, a computing device may inform an HCP that the device that the HCP is using is a counterfeit device. For example, a computing device may send an alert to an HCP that the device is a counterfeit device. The computing device may send an alert and inform the HCP about a potential danger associated with using a counterfeit device.

Alternatively and/or additionally, a computing device may prevent an HCP from using a counterfeit device. As described herein, a counterfeit device may have different performance data in comparison to authentic OEM devices. The difference in the performance data may generate an unexpected outcome (e.g., timing delay, providing over current, providing under current, using different frequencies, etc.) and may pose danger to a patient and/or to an HCP. The computing device may prevent an HCP from using the counterfeit device. For example, the computing device may block a control input of the identified counterfeit device.

As described herein, a computing device may compare performance data of a device to data (e.g., data from a ML trained model). The computing device may compare the performance data of a device to data (e.g., data from a ML trained model) associated with authentic OEM devices. Based on the comparison (e.g., if the comparison data is similar with, e.g., matches with, and/or within a threshold boundary), the computing device may determine whether a device is an authentic OEM device or a counterfeit device. The computing device may use data (e.g., data from a ML trained model) associated with authentic OEM devices in different situations. For example, as described herein, the data (e.g., the data from the ML trained model) may be or may include situations where authentic OEM devices are malfunctioning, such as in catastrophic failure situations, device failure situations, etc. If the computing device compares operation data associated with a device to data (e.g., data from a ML trained model) and determines that the device does is not similar with (e.g., not match) with the data associated with authentic OEM devices (e.g., normal use situations, catastrophic failure situations, device failure situations, and/or the like), the computing device may classify the device as an unknown device.

As described herein, a computing device may continue to monitor the unknown device. The computing device may send the operation data associated with the unknown device to other computing device, an edge device, cloud, and/or the like for others to investigate. The computing device may use the operation data associated with the unknown device and train a ML model (e.g., using a ML process and/or ML algorithm). The trained ML model may be configured to classify an unknown device as a category for future identification.

A computing device may determine whether operation data from a device is bad data. For example, if a computing device determines that operation data from a device may be compromised and/or bad data, the computing device may attempt to identify a source of error and/or provide troubleshooting information to an HCP(s). For example, a computing device may detect if operation data from a device is corrupt and/or incompatible with data (e.g., data from a ML trained model) associated with a group of devices under normal operation situations. Based on the detection, the computing device may adjust a surgical plan and/or may provide best information available for the surgical plan. The computing device may inform an HCP(s) about the incompatible data from the device and/or send an alert to the HCP(s), e.g., a potential avenue(s) to look out for or pay more attention.

In examples, a computing device may receive operation data from a device, such as a foot switch. The foot switch may be using the same plug. Wires associated with the foot switch may be switched. The foot switch may be mechanically integrated. Because the wires got switched, the foot switch may not operate or may operate in an errant fashion. A computing system may determine that the operation data from the foot switch may be bad data (e.g., malfunctioning data) and identify a potential source of error. The computing device may send the potential source of error to an HCP(s). For example, as described herein, the computing device may send an alert to an HCP(s) that the device that is being used is not operating properly (e.g., incompatible data and/or bad data). The computing device may provide a checklist for the HCP(s) to pay more attention to and/or a potential troubleshooting guide to fix the incompatible data and/or bad data associated with the device.

In examples, a computing device may utilize a ML algorithm to determine a potential source of error. A computing device may find a source of error within device compatibility based on a probabilistic hierarchy data from a ML algorithm. For example, a computing device may use a ML algorithm and/or ML probabilistic hierarchy data and may determine that a competitor product is plugged into an OEM generator. The computing device may send an alert to an HCP(s) that a high probability exist that the competitor product may not work and may provide a place to start for troubleshooting.

A computing device, such as a surgical hub, may configure an operation range (e.g., allowable operation range) associated with a surgical device. An operation range may be or may include an upper envelope and a lower envelope of allowable input to control a surgical device. A computing device may determine an operation range to control a surgical device for a surgical step associated with a surgical procedure. A computing device may analyze data (e.g., gathered data associated with an operation range for a surgical step performed by one or more health care professionals (HCPs). A computing device may use the data to train machine learning and may provide an operation range that is suitable for a surgical step. A computing device may provide an operation range, e.g., an allowable operation range, to an HCP who is about to perform a surgical step.

A device, such as a surgical device, may receive and/or be configured with an operation range, e.g., an allowable operation range, to control a surgical device for a surgical step. For example, a surgical device that is being used for a surgical procedure in an operating room may be configured with an operation range. The operation range may have an upper range and a lower range to control a surgical device. A configured operation range described herein may be or may include a predefined envelope.

A configured operation range and/or a predefined envelope may be associated with a magnitude of function adaptation. For example, a device may be a motor controlled surgical device. A motor controlled surgical device may have a predefined operation program and have a capability to change the operation of the motor controlled surgical device based on a current surgical step and/or a current situation during a surgical operation. The motor controlled surgical device may be bounded by an operation range, a predefined envelope, and/or a window of adjustment. For example, the motor controlled surgical device may allow a change of the operation of the device that is within an operation range, a predefined envelope, and/or a window of adjustment. If the motor controlled surgical device determines that the change of the operation of the device falls outside of an operation range, a predefined envelope, and/or a window of adjustment, the motor controlled surgical device may block the change of the operation. The motor controlled surgical device may send an alert (e.g., an alert message) to an HCP.

A device may have different an operation range, a predefined envelope, and/or a window of adjustment. For example, a device may have a larger range adjustment for an operation range, a predefined envelope, and/or a window of adjustment for an HCP initiated updates and/or after receiving an affirmative response from an HCP. A device may have a smaller range of adjustment (e.g., smaller than controls involving an HCP) if the adjustment is generated based on a ML model (e.g., using a ML algorithm.

In examples, a device may collect operation data. The device may use the collected operation data to train a ML model. Based on the ML trained model, the device may generate configuration information associated with an operation range, a predefined envelope, and/or a window of adjustment. In addition to and/or alternatively, one or more other devices may receive aggregated data associated with a surgical device. The one or more other devices may use the aggregated data to train a ML model. The device may use the ML model and generate configuration information associated with an allowable operation range, an allowable predefined envelope, and/or an allowable window of adjustment.

In examples, a device may receive configuration information from a computing device, such as a surgical hub. For example, a computing device may send configuration information that includes an operation range, a predefined envelope, and/or a window of adjustment information to the device. Based on the configuration information, the device may operate within an operation range, a predefined envelope, and/or a window of adjustment.

In examples, a device may determine and/or receive a determination from a computing device that an increased risk resulting a collateral injury is imminent. In examples, a device may determine that a condition of a patient changes (e.g., changes suddenly) and/or if an emergency arises. Based on the determination, a device may have adaptive configuration information associated with an operation range, a predefined envelope, and/or a window of adjustment. For example, the device may allow larger window of an operation range, a predefined envelope, and/or a window of adjustment if a condition of a patient changes and/or if an emergency arises.

A device, such as a surgical device, may receive and/or be configured with an allowable operation range for a surgical procedure, e.g., based on a trained ML model. For example, a surgical device may receive and/or be configured with an allowable operation range to control a device based on a trained ML model. An allowable operation range may be generated based on and/or using data from the trained ML model. An allowable operation range may change (e.g., adaptively change) based on data available to a device (e.g., a computing device) and/or to information from a trained ML model (e.g., generated using a ML process and/or a ML algorithm). An allowable operation range may be used and/or may configure a device to provide a predetermined and/or an estimated allowable control range to control a device during a surgical procedure, e.g., based on information from a trained ML model.

Data being used for an allowable operation range may be from a ML trained model. For example, data from a ML trained model may be based on data associated with at least one of a patient, an HCP, a surgical device, a current surgical procedure, a risk involved in a surgical procedure, a user input, a magnitude of a risk of failure, a risk of anticipated and/or unanticipated consequence, and/or like.

In examples, data associated with a patient may be or may include body mass index (BMI), height, weight, medical history, and/or the like. In examples, data associated with an HCP may be or may include an experience, such as a number of time performing a surgical procedure, a success and/or a failure rate, a preferred setting using a device, a tendency to adjust device configuration and/or data associated with success rate, data of other HCP(s) performing the same surgical procedure, and/or the like.

A ML process and/or a ML algorithm may be used to analyze the data as described herein. For example, a device may use the data to train a ML model and to provide an allowable operation range. An allowable operation range, generated by a trained ML model and/or a ML algorithm, may limit controlling a device, e.g., based on frequency, success rate, past magnitude of the change, and/or the like. For example, an allowable operation range may be used to prevent a change in controlling a device from a cascading effect (e.g., causing an unintentionally large effect and/or a self-propagating issue).

In examples, a device may be configured with an estimated allowable operation range to control the device. For example, a surgical device may receive an estimated allowable operation range to control the surgical device for a surgical procedure externally (e.g., from a computing device, a surgical hub, a cloud network, and/or the like). In examples, a device may configure and/or use a ML algorithm and determine an estimated allowable operation range to control the device, e.g., as described herein.

In examples, a device may configure a ML algorithm to analyze data, such as an operation data. Based on the analysis of the data, a device may use the data to train a ML model. The device may use the data from the ML model to adjust (e.g., automatically adjust) a behavior of control algorithm operation. A control algorithm operation may be used and/or configured to provide an allowable operation range as described herein. For example, a device may configure a ML algorithm to adjust a behavior of future control algorithm operation providing an allowable operation range based on a pattern determined from the data. A device may configure a ML algorithm to have a magnitude and/or a frequency limit on the adjustment. In examples, a device may configure a ML algorithm to have a fixed limit on the adjustment. For example, a device may configure a ML algorithm that no more than two adjustments per week, no more than a 5% adjustment up, a 10% adjustment slower are allowed, and/or the like. A device may configure a ML algorithm to limit the adjustment based on an aspect of a surgical procedure, such as a risk, an overall benefit, an issue with a user interface operation, and/or the like. In examples, a device may configure a ML algorithm to have an adjustable limit (e.g., an adaptive limit) based on an aspect of a surgical procedure as described herein.

In examples, a device may configure a ML algorithm to limit an adjustment based on an effect and/or a frequency of previous adjustment. For example, if a device determines that one or more large magnitude adjustments occurred in the past (e.g., recently), the device may configure a ML algorithm to limit an adjustment (e.g., one or more future adjustments). Based on the limit on the adjustment, the device may reduce a potential impact of a previous adjustment for a predetermine amount of time. For example, the limit on the adjustment may limit a detrimental magnitude of previous adjustment, type and/or timing of future adjustment, and/or the like. The limit on the adjustment may provide an improvement and/or make a larger directional adjustment, e.g., using the past adjustment.

In examples, a device may configure a ML algorithm to limit an adjustment based on a historic adaptation. For example, a device may configure to limit an adjustment based on a user, a surgical procedure, past usage data of a device, and/or like. A device may configure a ML algorithm to compare an output (e.g., actual performance of a device using a configured allowable operation range) to one or more similar previous outputs. Based on the comparison, the device determine that the current output is within a normal bound (e.g., a threshold and/or an acceptable operation bound). For example, a device may be configured (e.g., initially configured) that for a surgical knife device, an allowable operation range may be 30 mm/s. The device may compare the allowable operation range of 30 mm/s to one or more historical output change recommendations of the same surgical knife device used in the same surgical procedure. For example, the device may compare the allowable operation range, e.g., prior to displaying the allowable operation range to an HCP. The device may compare the historical output change recommendations from a local database, an edge and/or a fog network, a cloud network, and/or the like. Based on a comparison, the device may perform a check (e.g., an additional check) on an allowable operation range. The device may adjust and/or compensate the allowable operation range based on the comparison and present the adjusted/compensated allowable operation range to an HCP. For example, as described herein, a device may be configured with (e.g., initially configured with) an allowable operation range of 30 mm/s to control a surgical knife. Based on a comparison to historical data associated with a device, a patient, targeted action, the device may determine that the allowable operation range may be adjusted to 18 mm/s, e.g., to have a higher success rate.

Figure 22:
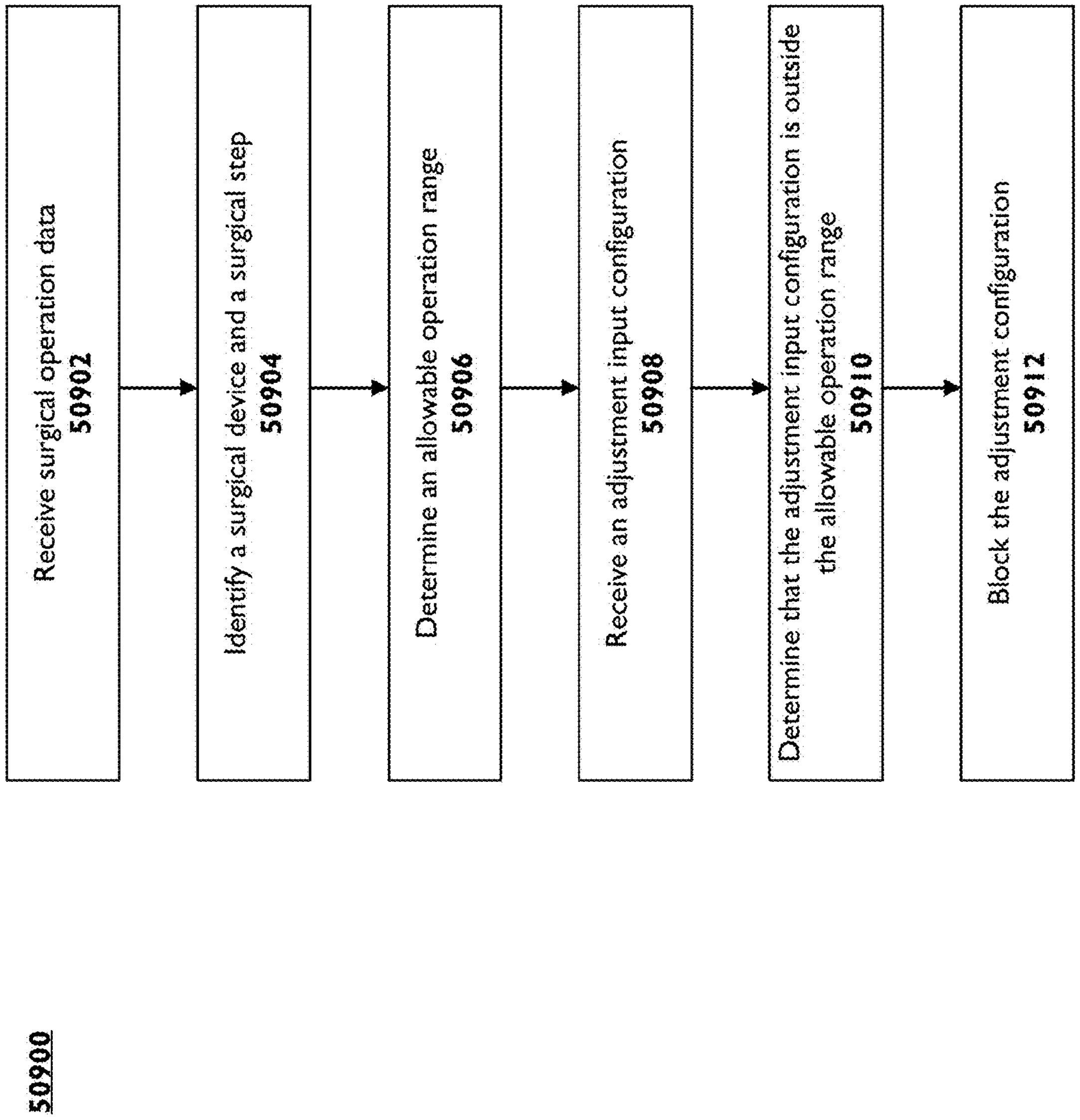
FIG. 22 illustrates a flow diagram of a device, such as a computing device, determining an allowable operating range to control a surgical device.

FIG. 22 illustrate a flow diagram 50900 of a device, such as a computing device, determining an allowable operating range to control a surgical device. As illustrated in 50902, a computing device, such as a surgical hub, may receive surgical operation data. Surgical operating data may be or may include data and/or information associated with a surgical operation. For example, the surgical operation data may be associated with and/or may include surgical information (e.g., with regard to FIGS. 7A-D). In examples, surgical operating data may be or may include at least one of patient information, HCP information, surgical operation information, information associated with a surgical device to be used for a surgical operation, and/or the like.

As described herein, patient information may be or may include BMI, weight, height, blood type, medical history, a scan, a lab result, and/or the like. HCP information may be or may include an experience associated with an HCP, an expertise associated with an HCP, a number of times an HCP has performed a current surgical operation, a preferred setting for an HCP, and/or the like. Surgical operation information may be or may include one or more surgical procedures associated with a surgical operation, one or more surgical devices associated with a surgical operation, patient information associated with a surgical operation, one or more HCPs associated with a surgical operation, and/or the like. Information associated with a surgical device may be or may include a manufacturer, a history of usage (e.g., a number of failure associated with the device), service history of the surgical device, battery level, and/or the like.

As illustrated in 50904, a computing device may identify a surgical device to be used for a surgical operation and/or a surgical step to be performed in a surgical operation. For example, based on the surgical operation data, a computing device may identify a surgical device to be used for a surgical operation and/or a surgical step to be performed in a surgical operation.

A computing device may determine an allowable operation range associated with a surgical device that is to be used for a surgical operation. For example, as illustrated in 50906, a computing device may determine an allowable operation range based on at least one of an identified surgical device (e.g., as illustrated in 50904), an identified surgical step (e.g., as illustrated in 50904), and/or received surgical operation data (e.g., as illustrated in 50902). As described herein, a computing device may use the surgical operation data, the identified surgical device, and/or the identified surgical step to train a ML model (e.g., using a ML algorithm and/or a ML process). Based on the data associated with the ML model, the computing device may to determine an allowable operation range. For example, based on the data from the ML trained model, a computing device may analyze history of usage associated with a surgical device for a surgical step performed by HCPs. The trained ML model data may provide a range of control input that has a high success rate for a current surgical step. Based on the analysis, a computing device may provide an allowable operation range to control a surgical device for a surgical step. Providing the allowable operation range to control a surgical device disclosed herein may be further described in at least one of U.S. patent application Ser. No. 16/209,423, entitled "Method Of Compressing Tissue Within A Stapling Device And Simultaneously Displaying The Location Of The Tissue Within The Jaws" filed Dec. 4, 2018, U.S. Pat. No. 10,881,399, entitled "Techniques For Adaptive Control Of Motor Velocity Of A Surgical Stapling And Cutting Instrument" issued Jan. 5, 2021, U.S. patent application Ser. No. 16/458,103, entitled "Packaging For A Replaceable Component Of A Surgical Stapling System" filed Jun. 30, 2019, U.S. Pat. No. 10,390,895, entitled "Control Of Advancement Rate And Application Force Based On Measured Forces" issued Aug. 27, 2019, U.S. Pat. No. 10,932,808, entitled "Methods, Systems, And Devices For Controlling Electrosurgical Tools" issued Mar. 2, 2021, U.S. patent application Ser. No. 16/209,458, entitled "Method For Smart Energy Device Infrastructure" filed Dec. 4, 2018, U.S. Pat. No. 10,842,523, entitled "Modular Battery Powered Handheld Surgical Instrument And Methods Therefor" issued Nov. 24, 2020, which are incorporated by references herein in their entireties.

As described herein, a computing device may use and/or configured to use data to train a ML model, and the computing device may utilize the data from the trained ML model to determine an allowable operation range. Surgical information (e.g., 726, 727, 762, 766 as described herein regarding FIGS. 7A-D) associated with the same surgical operation using the same surgical device performed by other HCPs may be configured as one or more inputs to the ML model. The inputs may be used to train the ML model, e.g., using the one or more training methods appropriate for training the surgical information. For example, the computing device may use the surgical information to train a ML model using supervised learning, such as a supervised learning algorithm as described herein (e.g., with regard to FIGS. 8A-B). The output of the ML trained model (e.g., the supervised learning algorithm) may be or may include appropriate information for a computing device to determine an allowable operation range for a surgical operation using a surgical device as described herein. For example, the output of the ML trained model may be or may include labeled outputs providing supervisory feedback(s) providing an allowable operation range for a surgical operation using a surgical device.

As shown in 50908, a computing device may receive an adjustment input configuration. An adjustment input configuration may be configured to control a surgical device for a surgical step. In examples, the adjustment input configuration may be an input to increase/decrease a motor associated with a surgical stapler. In examples, the adjustment input configuration may be an input to increase/decrease current associated with a surgical cutter and/or cauterize device. The adjustment input configuration may be generated by a ML trained model. As described herein, a computing device may use and/or may be configured to use data from the ML trained model and generate/receive an adjustment input configuration. A computing device may use appropriate data and/or surgical information (e.g., with regard to FIGS. 7A-D) as input to train the ML model. For example, the computing device may use surgical data associated with a surgical device used by other HCPs for the same surgical step to train the ML model. The computing device may use and/or the input surgical data associated with a surgical device to train the ML Model. As described herein, the computing device may use one or more training methods appropriate for training the ML model. For example, the computing device may use the surgical data associated with a surgical device and train the ML model using supervised learning, such as a supervised learning algorithm as described herein (e.g., with regard to FIGS. 8A-B). The output of the ML trained model (e.g., the supervised learning) may be or may include adjustment input configuration appropriate for a current surgical step. For example, the output of the ML data may be configured to provide an adjustment input configuration to control a surgical device for a current surgical step. The output of the ML model may provide an adjustment input configuration to increase or decrease control input for a surgical device.

As shown in 50910, a computing device may determine that the adjustment input configuration is outside of the determined allowable operation range. A computing device may determine that the adjustment input configuration is within of the determined allowable operation range.

As illustrated in 50912, if a computing device determines that the adjustment input configuration is outside of the determined allowable operation range, the computing device may block the adjustment input configuration to control the surgical device. A computing device may send an alert (e.g., an alert message) to an HCP. In examples, a computing device may send an alert message indicating that an adjustment input configuration is outside of the allowed operation range. In examples, a computing device may send an alert message indicating that an adjustment input configuration is outside of the allowed operation range. The computing device may send an alert message indicating a risk associated with adjusting an input to the adjustment input configuration that is outside of the allowed operation range. In examples, a computing device may send a message indicating that an adjustment input configuration is within of the allowed operation range.

A computing device may determine an origin of an adjusted input configuration. For example, a computing device may determine whether an adjusted input configuration is from an HCP, e.g., a surgeon using a surgical device, or generated by a ML data, e.g., by other computing device, a remote server, a cloud, and/or the like.

In examples, if a computing device determines that an adjustment input configuration is from the HCP, the computing device may send a message to the HCP. The message may include whether to adjust an input to control a surgical device, e.g., using the adjustment input configuration that is outside of the allowed operation range. A computing device may receive a feedback message and/or a response from the HCP. For example, the feedback message and/or the response may confirm that the adjustment input configuration should be used (e.g., despite being outside of the allowable operation range). As described herein, a computer device may request a justification for the HCP's confirmation (e.g., to use the adjustment input configuration that is outside of the allowable operation range). For example, a computing device may ask/request additional information for the adjustment input configuration (e.g., a change in patient's condition, a surgical device malfunction, switched and/or wrong scan data, wrong patient information, etc.).

A computing device may allow the adjustment input configuration as an input to control a surgical device for a current surgical step, e.g., based on the feedback message, response from the HCP, and/or the justification. A computing device may send a request message to the HCP. The request message may indicate whether the allowable operation range needs to be revised, e.g., based on the adjustment input configuration. In examples, the HCP may indicate that the adjustment input configuration is temporary (e.g., one time) and the allowable operation range does not need a revision. In examples, the HCP may indicate that the adjustment input configuration is permanent, and the allowable operation range needs a revision, e.g., based on the adjustment input configuration and/or current operation data.

In examples, if a computing device determines that an adjustment input configuration is generated by a ML model, the computing device may send ML data to an HCP. The ML data may be or may include information and/or analysis that caused the adjustment input configuration. For example, the ML data may be or may include at least one of frequency information of other HCPs using the adjusted input configuration for the current surgical step or a success rate of the surgical operation using the adjusted input configuration.

If a computing device determines that the adjustment input configuration is within the allowable operation range, the computing device may adjust an input to control a surgical device for a surgical step, e.g., using the adjustment input configuration.

Figure 23:
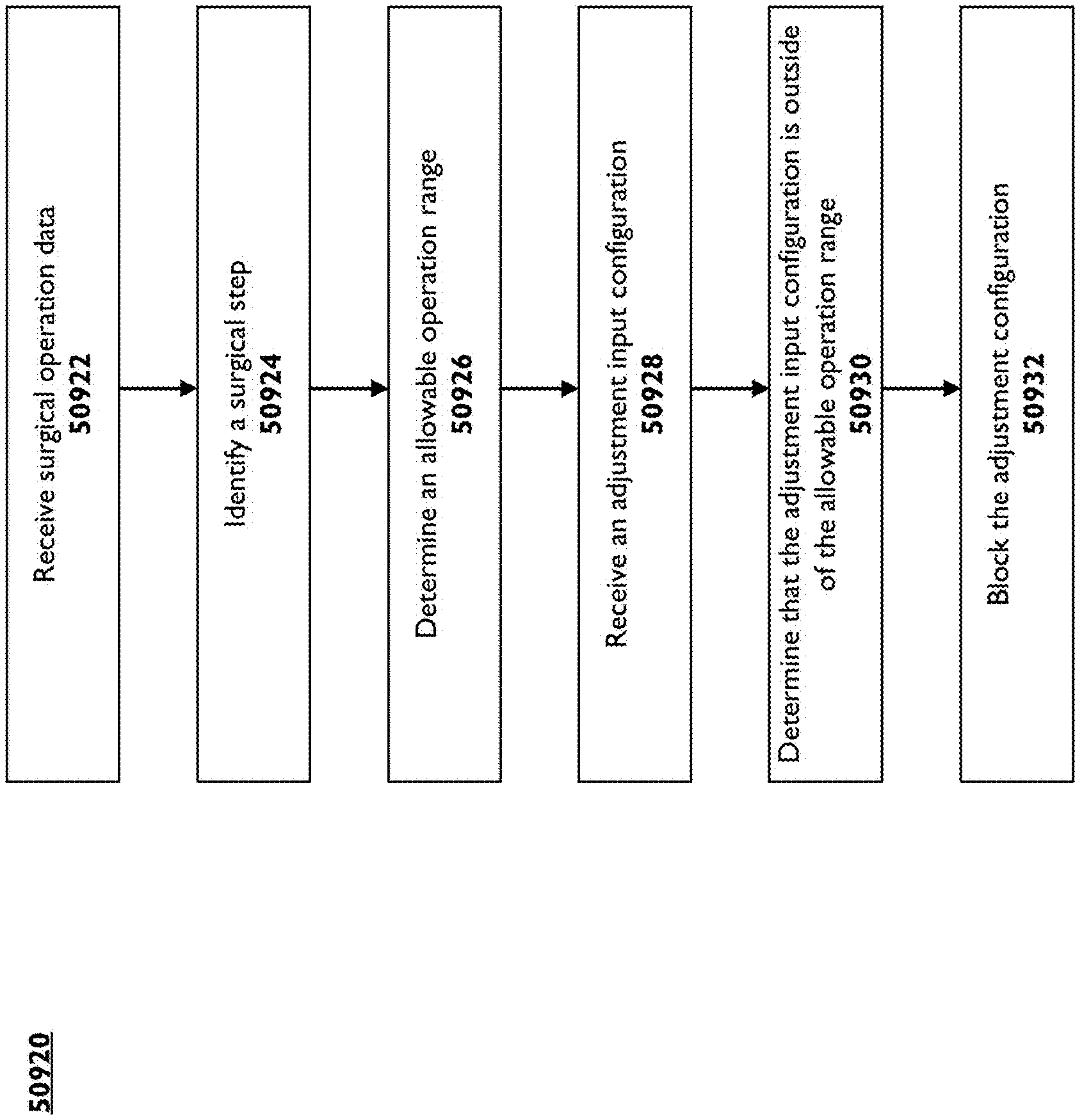
FIG. 23 illustrates a flow diagram of a device, such as a surgical device, determining an allowable operating range to control the surgical device.

FIG. 23 illustrate a flow diagram 50920 of a device, such as a surgical device, determining an allowable operating range to control the surgical device. As illustrated in 50922, a device, such as a surgical device, may receive surgical operation data. Surgical operating data may be or may include data and/or information associated with a surgical operation. In examples, surgical operating data may be or may include at least one of patient information, HCP information, surgical operation information, and/or the like.

As described herein, patient information may be or may include BMI, weight, height, blood type, medical history, a scan, a lab result, and/or the like. HCP information may be or may include an experience associated with an HCP, an expertise associated with an HCP, a number of times an HCP has performed a current surgical operation, a preferred setting for an HCP, and/or the like. Surgical operation information may be or may include one or more surgical procedures associated with a surgical operation, one or more surgical devices associated with a surgical operation, patient information associated with a surgical operation, one or more HCPs associated with a surgical operation, and/or the like.

As illustrated in 50924, a surgical device may identify a surgical step to be performed in a surgical operation. For example, based on the surgical operation data, a surgical device may identify a surgical step to be performed in a surgical operation.

A surgical device may determine an allowable operation range to control the surgical device that is to be used for a surgical operation. For example, as illustrated in 50926, a surgical device may determine an allowable operation range based on an identified surgical step (e.g., as illustrated in 50924) and/or received surgical operation data (e.g., as illustrated in 50922). As described herein, a surgical device may use the data (e.g., the surgical step and/or surgical operation data) to train a ML model. The surgical device may use data from the ML trained model to determine an allowable operation range. For example, based on the data from the ML trained model, a surgical device may analyze history of usage associated with the surgical device for a surgical step performed by HCPs. The data from the ML model may be configured to provide a range of control input that has a high success rate for a current surgical step. Based on the analysis, a surgical device may provide an allowable operation range to control the surgical device for a surgical step.

As shown in 50928, a surgical device may receive an adjustment input configuration. An adjustment input configuration may be configured to control the surgical device for a surgical step. In examples, the adjustment input configuration may be an input to increase/decrease a motor associated with a surgical stapler. In examples, the adjustment input configuration may be an input to increase/decrease current associated with a surgical cutter and/or cauterize device.

As shown in 50930, a surgical device may determine that the adjustment input configuration is outside of the determined allowable operation range. A surgical device may determine that the adjustment input configuration is within the determined allowable operation range.

As illustrated in 50932, if a surgical device determines that the adjustment input configuration is outside of the determined allowable operation range, the surgical device may block the adjustment input configuration to control the surgical device. A surgical device may send an alert (e.g., an alert message) to an HCP. In examples, a surgical device may send an alert message indicating that an adjustment input configuration is outside of the allowed operation range. In examples, a surgical device may send an alert message indicating that an adjustment input configuration is outside of the allowed operation range. A surgical device may send an alert message indicating that a risk associated with adjusting an input to the adjustment input configuration that is outside of the allowed operation range. In examples, a surgical device may send a message indicating that an adjustment input configuration is within of the allowed operation range.

A surgical device may determine an origin of an adjusted input configuration. For example, a surgical device may determine whether an adjusted input configuration is from an HCP, e.g., a surgeon using a surgical device, or generated by a ML model, e.g., by a computing device, a remote server, a cloud, and/or the like.

In examples, if a surgical device determines that an adjustment input configuration is from the HCP, the surgical device may send a message to the HCP. The message may include whether to adjust an input to control a surgical device, e.g., using the adjustment input configuration that is outside of the allowed operation range. A surgical device may receive a feedback message and/or a response from the HCP. For example, the feedback message and/or the response may confirm that the adjustment input configuration should be used (e.g., despite being outside of the allowable operation range). As described herein, a surgical device may request a justification for the HCP's confirmation (e.g., to use the adjustment input configuration that is outside of the allowable operation range). For example, a surgical device may ask/request additional information for the adjustment input configuration (e.g., a change in patient's condition, a surgical device malfunction, switched and/or wrong scan data, wrong patient information, etc.).

A surgical device may allow the adjustment input configuration as an input to control a surgical device for a current surgical step, e.g., based on the feedback message, response from the HCP, and/or the justification. A surgical device may send a request message to the HCP. The request message may indicate whether the allowable operation range needs to be revised, e.g., based on the adjustment input configuration. In examples, the HCP may indicate that the adjustment input configuration is temporary (e.g., one time) and the allowable operation range does not need a revision. In examples, the HCP may indicate that the adjustment input configuration is permanent, and the allowable operation range needs a revision, e.g., based on the adjustment input configuration and/or current operation data.

In examples, if a surgical device determines that an adjustment input configuration is generated by ML model, the surgical device may send ML data to an HCP. The ML data may be or may include information and/or analysis that caused the adjustment input configuration. For example, the ML data may be or may include at least one of frequency information of other HCPs using the adjusted input configuration for the current surgical step or a success rate of the surgical operation using the adjusted input configuration.

If a surgical device determines that the adjustment input configuration is within the allowable operation range, the surgical device may adjust an input to control a surgical device for a surgical step, e.g., using the adjustment input configuration.

Figure 24:
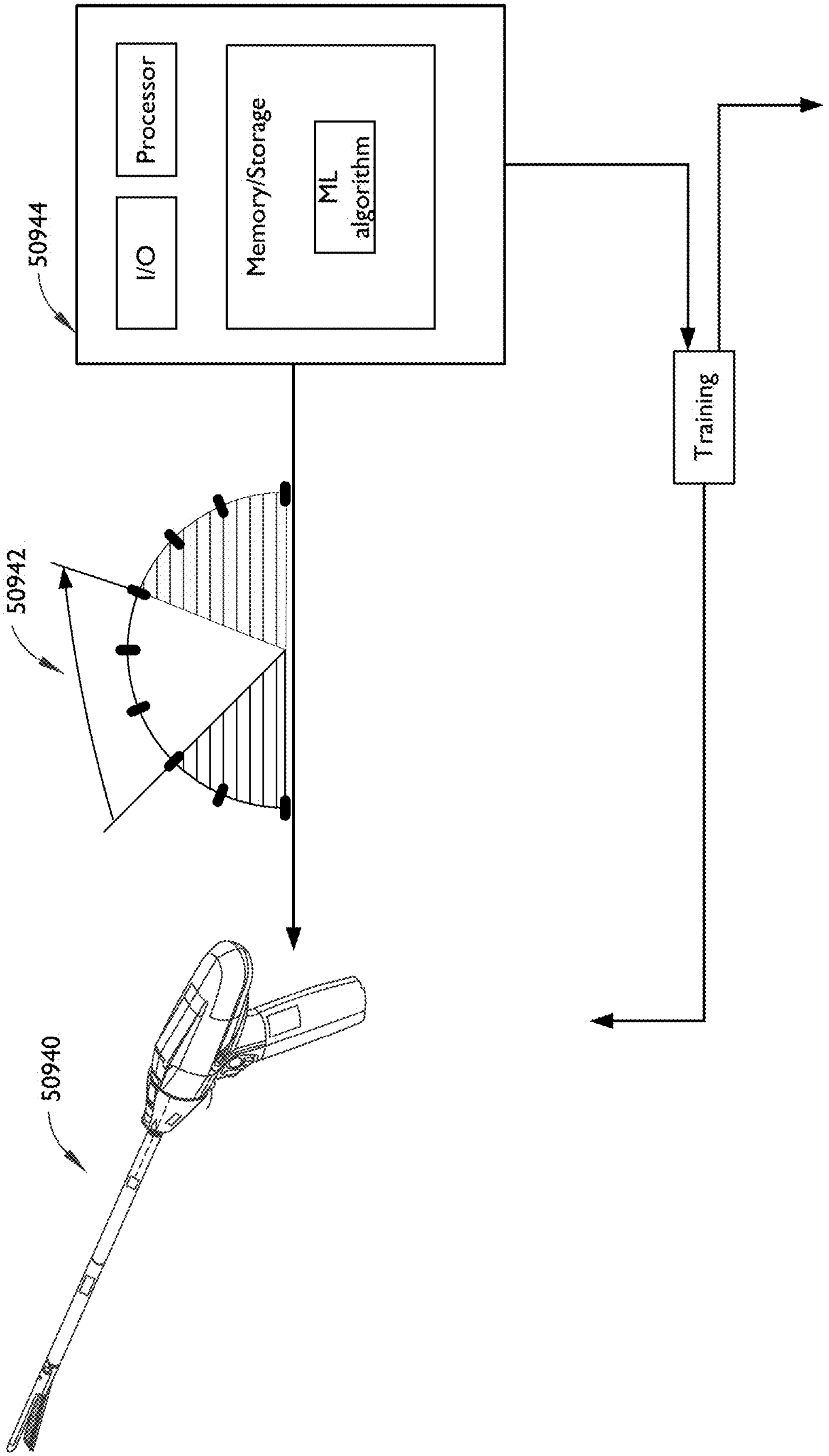
FIG. 24 illustrates a computing device determining an allowable operation range associated with a surgical device.

FIG. 24 illustrates a computing device determining an allowable operation range associated with a surgical device. For example, as described herein, a surgical hub 50944 may determine an allowable operation range 50942 associated with a surgical stapler 50940. The allowable operation range 50942 may be an allowable input range to control the surgical stapler 50940. As described herein, the computing device, such as the surgical hub 50944, may configure the data described herein to train a ML model and use the data from the ML model to determine an allowable operation range 50942, e.g., based on the surgical stapler 50942, a surgical step, and/or surgical operation data.

Figure 25:
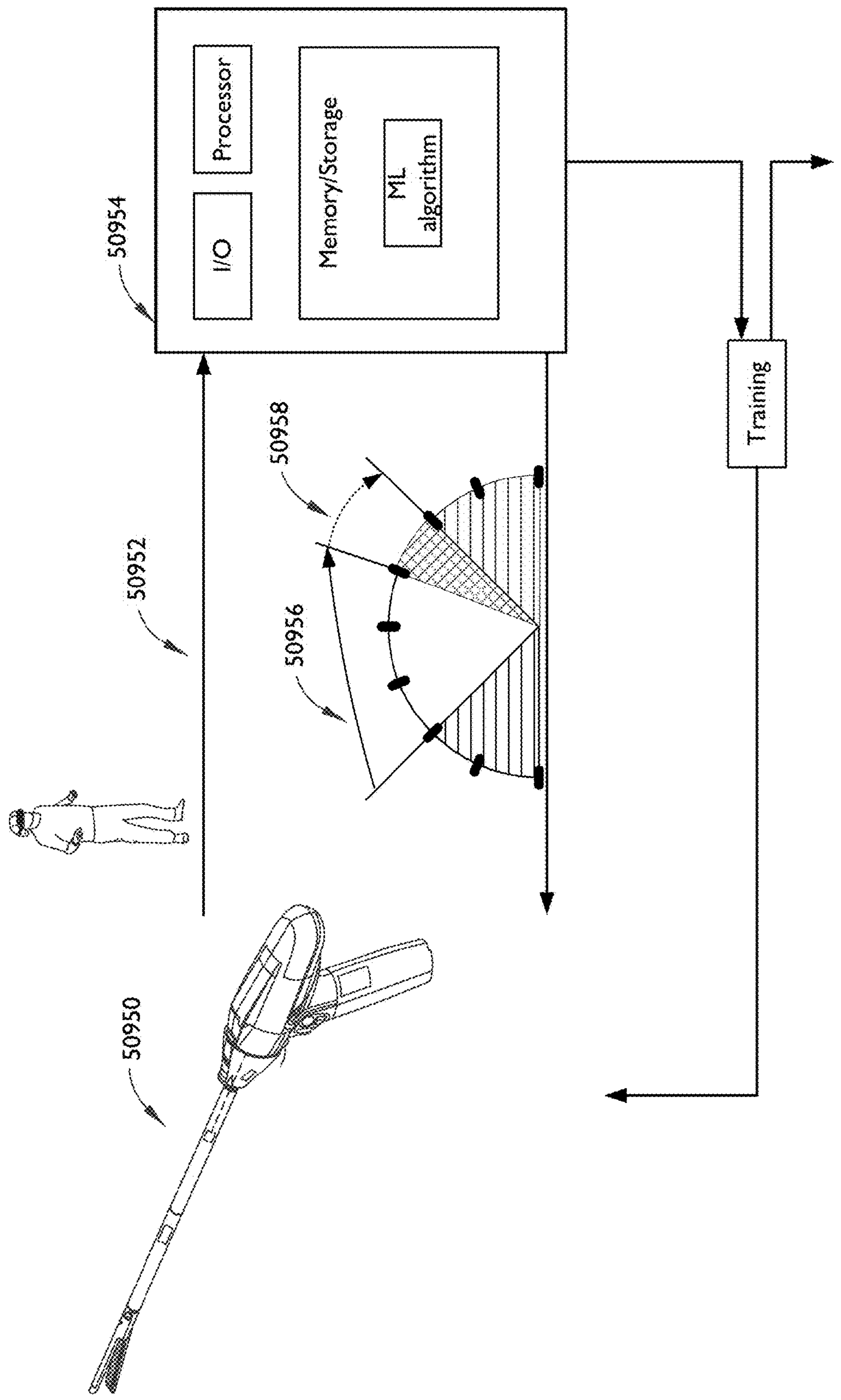
FIG. 25 illustrates a computing device adjusting an allowable operation range associated with a surgical device based on an adjustment input configuration from a health care professional.

FIG. 25 illustrates a computing device adjusting an allowable operation range associated with a surgical device based on an adjustment input configuration from a health care professional. For example, a surgical hub 50954 may receive an adjustment input configuration 50952 from a surgical stapler 50950. As described herein, the surgical hub 50954 may determine whether the adjustment input configuration 50952 is outside of an allowable operation range 50956. If the surgical hub 50954 determines that the adjustment input configuration 50952 is outside of the allowable operation range 50956, the surgical hub 50954 may determine whether the adjustment input configuration 50952 may be initiated by an HCP, such as a surgeon who is using the device. If the surgical hub 50954 determines that the adjustment input configuration 50952 is initiated by a surgeon, the surgical hub 50954 may adjust the allowable operation range 50956. For example, the surgical hub 50954 may configure a revised allowable operation range 50958 that extends from the allowable operation range 50956 and account for the adjusted input configuration 50952 from the surgeon.

Figure 26:
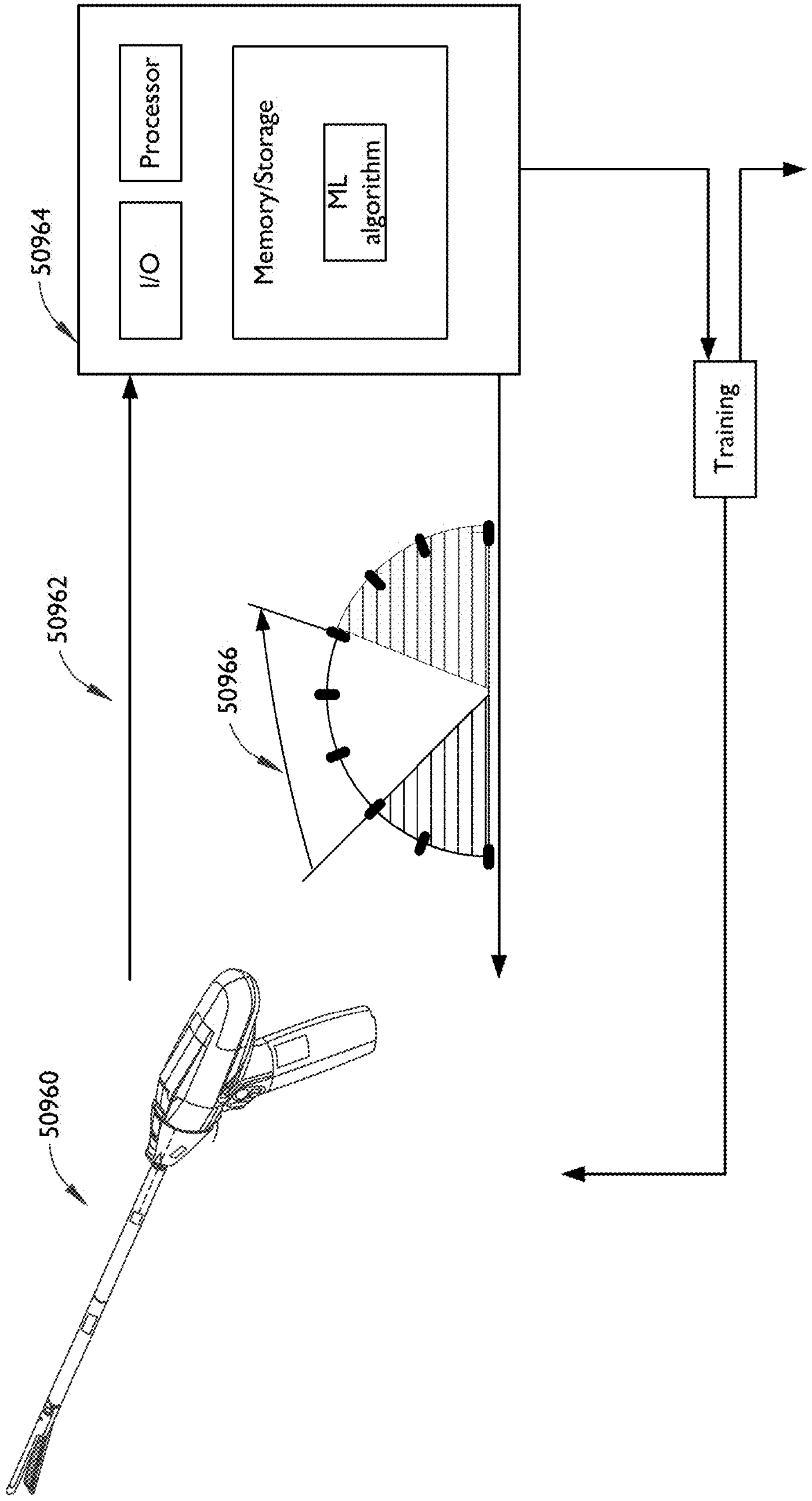
FIG. 26 illustrates a computing device receiving an adjustment input configuration that is outside of an allowable operation range and the adjustment input configuration is from machine learning (ML) trained data and/or a ML algorithm.

FIG. 26 illustrates a computing device receiving an adjustment input configuration that is outside of an allowable operation range and the adjustment input configuration is from a ML model (e.g., trained model using a ML process and/or a ML algorithm as described herein). For example, a surgical hub 50964 may receive an adjustment input configuration 50962 from a surgical stapler 50960. As described herein, the surgical hub 50964 may determine whether the adjustment input configuration 50962 is outside of an allowable operation range 50966. If the surgical hub 50964 determines that the adjustment input configuration 50962 is outside of the allowable operation range 50966, the surgical hub 50964 may determine whether the adjustment input configuration 50962 may be initiated by a ML trained model. As described herein, if the surgical hub 50964 determines that the adjustment input configuration 50962 is based on the ML trained model and is outside of the allowable operation range 50966, the surgical hub 50964 may block the adjustment input configuration 50962. For example, the surgical hub 50964 may configure the surgical stapler 50960 maintain the allowable operation range 50966 and block the adjustment input configuration 50962. In examples, the surgical hub 50964 may resend the allowable operation range 50966 to the surgical stapler 50960, e.g., confirming that the allowable operation range 50966 has not changed based on the adjustment input configuration 50962.

In examples, as described herein, a device may receive and/or be configured with an allowable operation range. In examples, as described herein, a device may determine an allowable operation range, e.g., using data from a ML trained model. A device, such as a surgical device, may receive a control input from an HCP and/or an original equipment manufacturer (OEM) intermediary device to control the surgical device for a surgical procedure. The device may include a process to determine and/or a user to permit, refuse, limit, and/or adjust the received/configured and/or determined allowable operation range.

A device may receive a control input to control the device. For example, a surgical device may receive a control input to control the device from an HCP who is performing a current surgical step. As described herein, the surgical device may be configured with and/or determined an allowable operation range to control the surgical device. The surgical device may determine whether a control input from an HCP is within an allowable operation range or outside of an allowable operation range. If the surgical device determines that the control input is within the allowable operation range, the surgical device may allow the control input to control the device. If the surgical device determines that the control input is outside of the allowable operation range, the surgical device may block the control input to control the device. The surgical device may send an alert (e.g., an alert message) to the HCP, indicating that the control input provided is outside of the allowable operation range.

The surgical device may receive feedback from an HCP. The feedback from the HCP may indicate an acknowledgement from the HCP that the control input is outside of the allowable operation range. The feedback may include a confirmation to allow the control input (e.g., that is outside of the allowable operation range) and/or revise the allowable operation range based on the HCP's acknowledgement.

In examples, an HCP may receive an allowable operation range, e.g., before providing a control input. As described herein, the HCP may accept the configured allowable operation range. In examples, the HCP may reject the configured allowable operation range. The HCP may provide an updated operation range. The device may use the updated operation range and configure the data to train the ML model and configure to provide an updated allowable operation range.

In examples, a device may use a third-party confirmation. For example, a device may use a third-party confirmation to enable one or more sequential algorithmic adjustments. A device may display data from a ML trained model, a result (e.g., relationships, recommendations, control system changes, etc.), and/or the like. In addition to and/or alternatively, the device may display data (e.g., a reduced composition of the data) and enable a third-party (e.g., a third-party device) to decide if utilization of the result is valid and/or warranted.

In examples, a device may show a result (e.g., data) of a ML trained model recommended output parameter, such as an allowable operation range, to complete a task. For example, the device may show a minimize drive time, a step shift in an output parameter, one or more adjustments made by an HCP based on the HCP's experience, visual, hepatic, and/or device feedback, sensory feedback, and/or the like. The illustration may allow a third-party (e.g., a third-party device) and/or an HCP to override, reduce, or eliminate the proposed adjustment data from the ML model (e.g., an allowable operation range). The feedback from the third-party and/or the user may be provided to a device through a display, such as a screen associated with the device and/or through a computing device, such as a hub and/or a display associated with the hub.

A device may interact with an HCP if the device determines an adjustment from the HCP is over a preconfigured adjustment (e.g., a large adjustment). A device may inquire an HCP, an overseer, and/or the like for a confirmation of the adjustment as described herein. A device may request a justification for such adjustment. In examples, during a surgical procedure, a device may provide an allowable operation range for the device based on the device moving to right. The device may receive an adjustment from an HCP that is over a preconfigured threshold (e.g., a large adjustment). The device may request a justification from the HCP for the adjustment. The device may ask the HCP whether the device is moving to left (e.g., instead of recommended right). If the device receives an affirmative answer from the HCP, the device may provide an updated allowable operation range (e.g., based on the entire position being reversed from right to left). In examples, the device may inquire the HCP whether the switch in motion (e.g., right to left) is one time incident or whether the procedure and/or the allowable operation range needs to be updated (e.g., before the next step proceed).

In examples, a device may request a justification from an HCP if the HCP makes an adjustment greater than a preconfigured threshold as described herein. A device may ask if scan data was improperly tagged and/or inputted into the device. A device may inquiry if right and left are switched and the change was not in time as being mislabeled (e.g., before the data was inputted into the device). A device may ask to confirm if the patient had a surgery before that was not logged, inputted, and/or forgot about. A device may ask if one or more markers that should exist for a patient are not present. For example, the device may ask for confirmation that the patient is missing a kidney and/or if the kidney is being used as a reference for another procedure. A device may ask if a wrong patient is on an operating table. A device may display that a surgical plan and/or a scan does not match with the input to the device. The device may ask for a confirmation to an HCP and/or the device may ask whether to continue with the surgical plan or adjust based on the input.

A device may determine that a potential input from an HCP may have a catastrophic consequence. The device may notify an HCP about a possibility of a catastrophic consequence and/or indicate that the potential input may be outside of a standard operational range. A device may inquire if the device determines that a change in a patient's condition between a scan and/or an evaluation has happened and when a surgical procedure is occurring.

A device may ask for an HCP's feedback if a surgical plan needs to be updated. In examples, based on an MRI scan, a device may determine that a patient is suffering from a meniscus tear and provide a surgical plan and/or an allowable operation range for a meniscus tear repair. After the scan and/or during a surgery, the device may determine that the rest of the meniscus completely tears apart. The device may confirm with an HCP that the surgical plan and/or the allowable operation range need to be updated.

In examples, a device may provide a surgical plan and/or an allowable operation range for a gallbladder surgery for a patient. During the surgery, based on the input, the device may determine that the patient has cancer. The device may ask an HCP to confirm that a surgical plan and/or an allowable operation range need to be updated.

A device may configure data from a ML model to determine a weighted adjustment (e.g., adjustment to an allowable operation range). For example, a device may configure the data from a ML model to determine a weighted adjustment based on one or more feedbacks from an HCP and/or a third-party as described herein. The weighted adjustment may be based on a temporal aspect and/or frequency. In examples, if a device determines that one or more adjustments provide an improvement, the device may increase the frequency of the adjustments and/or allow less time for the adjustments. In examples, if a device determines that one or more adjustments result in a detrimental and/or failed results, the device may decrease the frequency of the adjustments and/or allow more time for the adjustments.

A device may determine a weighted adjustment (e.g., adjustment to an allowable operation range) based on a type of change. In examples, a device may determine that an allowable operation range for a procedure step (e.g., less critical and/or non-life threatening) may be needed. The device may provide an adjusted allowable operation range (e.g., more frequently and/or less checklist). In examples, a device may determine that an allowable operation range for a critical step and/or an important procedure (e.g., a procedure that may involve a risk and/or non-procedural step). The device may require more information, one or more confirmation steps, and/or more user confirmations before the device provides an adjusted allowable operation range.

A device may utilize a weighted response, e.g., to control a magnitude of an algorithmic adaptation. For example, a device may compile and/or aggregate one or more results (e.g., the ideal results). A device may use the compiled and/or aggregated results to have a weighted and/or a predefined aggregate listing. The device may combine the weighted and/or the predefined aggregate listing to current data (e.g., a portion of the current data). The device may request a verification (e.g., a remote verification) and/or a validation. The device may need the verification and/or the validation and may upload the data to a cloud and/or a remote server for review and/or combination with other system results (e.g., results from other locations and/or facilities).

A device, such as a computing device, may collect the data in the remote server and/or the cloud. A computing device may use a ML model to provide a conclusion and provide a global device operation change (e.g., a global allowable operation range). A global device operation change (e.g., a global allowable operation range) may control a device (e.g., one or more facilities that are using the device). A global device operation change (e.g., a global allowable operation range) may validate an allowable operation range to a device recommendation and/or provide one or more proposed changes to the device in a controlled and/or a global manner. The global device operation change may prevent an inadvertent and/or an uncontrolled change to a local device (e.g., a local operational and/or a local environment).

A computing device may compare a proposed change (e.g., a global device operation change) with a competing change, e.g., suggested for a related device, a related step, a related technique, and/or the like. The computing device may prevent a constant cycling of change, e.g., based on the comparison and/or an alteration from related device.

In examples, a device may configure data from a ML trained model and process an output based on a collected parameter. If a device determines that the output is completed, the device may have one or more parameters (e.g., one or more additional parameters). The device may go back and weigh one or more parameters (e.g., including the one or more additional parameters) and/or defined parameters. The device may alter an output based on a weighted factor. For example, a device may have a tissue disease state and/or an identification of a vessel and/or arteries. The disease state and/or the identification may alter and/or weight an output, e.g., to compensate for the parameter.

A device may determine a threshold (e.g., a threshold function) that limits a viable adjustment bounding. A device may determine a threshold bounding of a magnitude of algorithmic change(s). For example, a device may configure a functional algorithm to determine one or more bounds of a functional range(s). A device may determine whether an adjustment is out of bound or within bound. For example, a device may determine whether an adjustment is out of bound based on data (e.g., data coming in/out of a ML model). A ML model may use patient information, such as BMI, height, weight, and/or like. The ML model may be use the patient information and generate a predictive model configuration. For example, the ML model may be configured to guess what properties of the tissues will be, what a functional range may be appropriate for the device to be operating within, and/or the like based on the patient information before a surgical procedure. During a surgical procedure, the device may compare performance data of a device to the predictive modeled configuration. The device may determine whether a drift and/or an error exist in the predicted model and/or the procedure. Based on a determination that a drift and/or an error exist, the device may adjust the predicted model to an acceptable bound.

In examples, the device may determine if a patient's tissue is more difficult to transect once or consistently more difficult to transect. In examples, the device may determine if a problem exists with the device and/or a sensor. In examples, the device may determine if a problem exists with a predictive model for a tissue composition of the patient. Based on the determination, a device may give an alert to an HCP. For example, a device may give a warning to an HCP that a different cartridge is recommended for a current surgical procedure (e.g., versus what a cartridge being used for the current surgery).

A device may use historical data and predict one or more devices that are most effective for one or more surgical steps. Based on the historical data, the device may provide and/or integrate a product recommendation to a purchasing and hospital inventory management system. For example, the device may make sure enough cartridges (e.g., blue, white, gold, and/or the like cartridges) are in stock for a hospital. The device may send an alert (e.g., an alert message) if one or more cartridges are low in stock. The device may make an adjustment(s) in the event of a supply chain disruption(s). The device may change one or more recommendations, e.g., in order to be more effectively allocate resources. For example, if procedure A uses blue and/or gold cartridges and procedure B will be more effective with a gold cartridge, the device may recommend using a blue cartridge for procedure A (e.g., instead of using a gold cartridge). The device may integrate and/or provide a product recommendation to a higher level management, e.g., for an entire hospital network, to more effectively deploy resources and/or supplies where needed.

Figure 27:
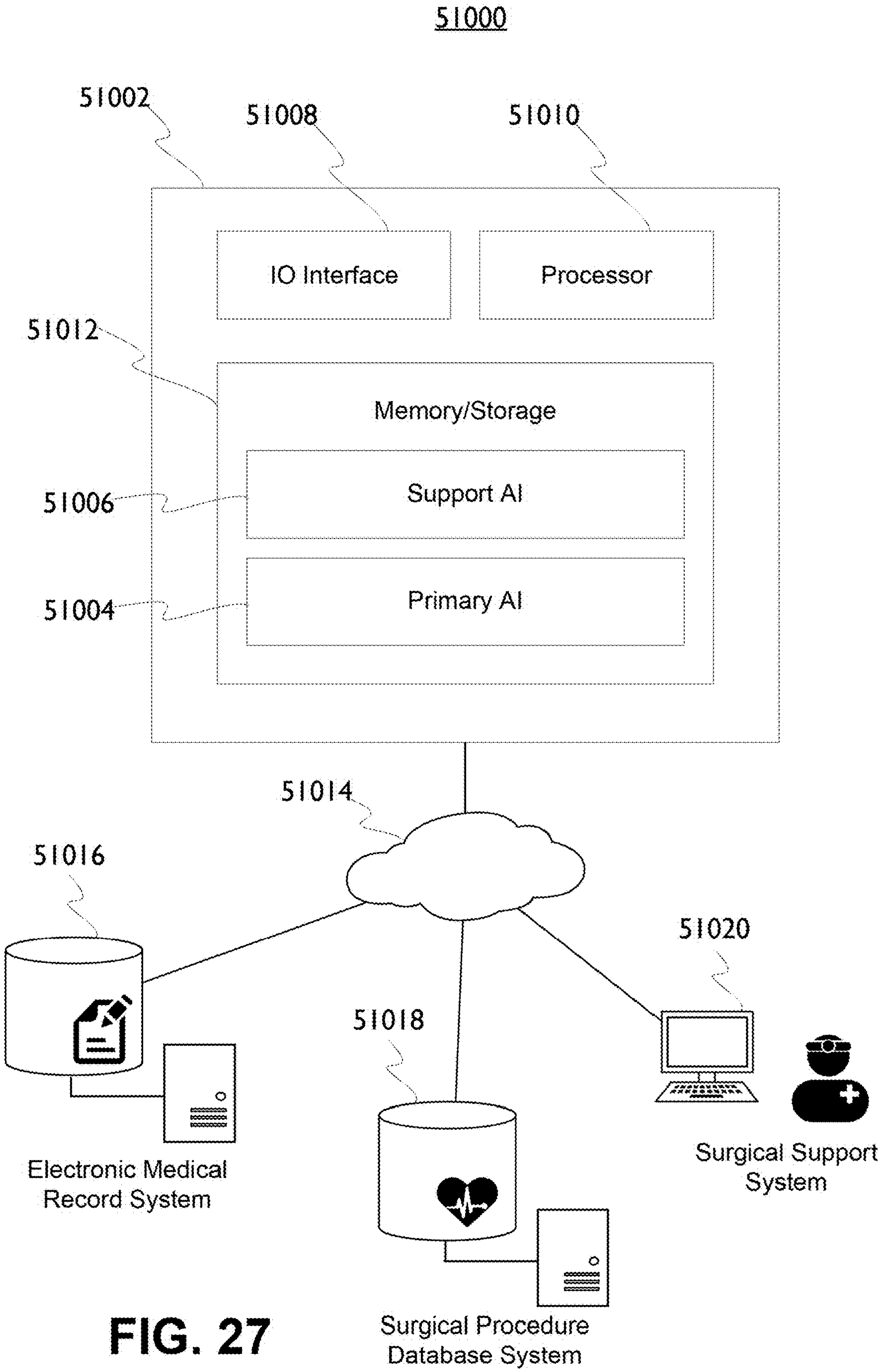
FIG. 27 is a block diagram of an example computing system with example primary and support artificial intelligence (AI) models.

FIG. 27 is a block diagram of an example computing system 51000 with an example primary artificial intelligence (AI) model 51004 (e.g., a primary neural network) and an example support AI model 51006 (e.g., a support neural network). A computing device 51002 may be used to enhance the preparation of a surgical procedure plan. The device 51002 may include an IO interface 51008, a processor 51010, memory/storage 51012, and the like.

The IO interface 51008 may include any hardware, software, or combination thereof, suitable for providing input and/or output of data or information. The IO interface 51008 may include a human interface device such as a display, keyboard, mouse, and the like. The IO interface 51008 may include a computer network input/output interface, such as an ethernet interface, for example.

The processor 51010 may include any hardware, software, or combination thereof suitable for processing data. The processor 51010 may operate according to a set of computer instructions to perform computer tasks. For example, the processor 51010 may include an Intel based general purpose processor, for example. The processor 51010 may operate in accordance with instructions and/or data stored in the memory/storage, for example. The processor 51010 may include an AI accelerator, such as an application-specific integrated circuit or other hardware specialized for AI processing. For example, the processor 51010 may include a Tensor Processing Unit (TPU).

The memory/storage 51012 may include any software, hardware, or combination thereof suitable for retaining information. The memory/storage 51012 may include volatile memory, non-volatile memory, and the like. For example, the memory/storage may include random access memory, and/or solid-state drive memory, or the like. The memory/storage memory/storage 51012 may have stored therein instructions and data suitable for implementing one or more artificial intelligence algorithms. For example, the memory/storage 51012 may include and/or retain a primary AI model 51004 and a support AI model 51006.

The primary AI model 51004 and support AI model 51006 may include AI models with the functionality disclosed herein. For example, the primary AI model 51004 and support AI model 51006 may work cooperatively to provide improved surgical support recommendations. The primary AI model 51004 and support AI model 51006 may have any AI architecture and training suitable for recommending surgical procedure information based on training of earlier patient-focused and procedure-focused training data, for example. For example, the primary AI model 51004 and support AI model 51006 may operate based on surgical information, such as the surgical information disclosed with reference, for example, to FIGS. 7A-D herein. For example, the primary AI model 51004 and support AI model 51006 may operate based on surgical information, such as surgical information obtainable via an electronic medical records (EMR) system 51016, a surgical procedure database system 51018, or the like for example.

The device 51002 may interact with a network 51014. For example, the device 51002 may interact with the network 51014 via the IO interface 51008. The network 51014 may provide connectivity between the device 51002 and/or one or more other computing devices, such as the EMR system 51016, the surgical procedure database system51018, a surgical support system 51020, and the like.

The EMR system 51016 may include any computing system suitable for receiving, managing, retaining, and/or editing electronic medical records. The EMR system 51016 may include features for storing, retrieving, and using patient data. For example, the EMR system 51016 may include features for storing, retrieving, and using patient data in a manner that complies with patient privacy regulations and/or policies. For example, the EMR system 51016 may include the features disclosed in U.S. patent application Ser. No. 17/958,230, titled METHOD FOR HEALTH DATA AND CONSENT MANAGEMENT, filed Sep. 30, 2022, the contents of which are hereby incorporated by reference herein.

For example, EMR system 51016 may include patient data. Patient data may patient-identifying information, healthcare data, and the like. Example patient-identifying information may include, but not limited to, names or part of names, information that may indicate unique identifying characteristic, geographical identifiers, dates directly related to a person, phone number details, fax number details, details of email addresses, social security details, medical record numbers, health insurance beneficiary numbers, account details, certificate or license numbers, vehicle license plate details, device identifiers and serial numbers, website URLs, IP address details, fingerprints, retinal and voice prints, complete face or any comparable photographic images, and/or the like.

The patient data may include general and administrative information, such as patient management information, provider administrative information relating to the patient, billing data, patient demographics, and the like.

Healthcare data may include personal data relating to the physical or mental health of an individual, including the provision of health care services, which reveals information about their health status. Health data may include data collected when a patient has an interaction with a health care provider (e.g., a primary physician, hospital or an organization, such as a universal health service. The health data may include information related to the patient's medical care, including for example, progress notes, vital signs, medical histories, diagnoses, medications, immunizations, allergies, imaging (e.g., radiology images), laboratory and test results, past medical procedures (e.g., past surgical procedures), planned medical procedures (e.g., planned surgical procedures), and the like. The health data may include pre- and post-operative scan data and/or peri-operative imaging data. Such can data and imaging data may be classified and aggregated for analysis and inclusion in an training data set.

The surgical procedure database system 51018 may include any computing systems suitable for maintaining information related to surgical procedures. For example, the surgical procedure database system 51018 may include one or more surgical procedure plans. Surgical procedure plan may include a data structure that incorporates one or more surgical tasks. The surgical procedure database system 51018 may incorporate information related to the performance of various surgical procedures. For example, the surgical procedure database system 51018 may indicate the instruments, surgical setup, specific procedures, anatomical landmarks, and supporting and clinical staff support related information for a particular procedure.

In an example, a surgical procedure plan may include information that outlines the staff, equipment, technique, and steps that may be used to perform a surgical procedure. For example, the procedure plan may include a staff manifest indicating what roles and/or what specific health care professionals are to be involved in the procedure. The procedure plan may include a listing of equipment, such as durable surgical equipment, imaging equipment, instruments, consumables, etc. that may be used during the procedure. For example, the procedure plan may include a pick list for a surgical technician to use to assemble the appropriate tools and materials for the surgeon and the surgery when prepping the operating theater. The procedure plan may include information about the procedure's expected technique. For example, the procedure plans for the same surgical goal may include different methods of access, mobilization, inspection, tissue joining, wound closure, and the like.

The procedure plan may reflect a surgeon's professional judgement with regard to an individual case. The procedure plan may reflect a surgeon's preference for and/or experience with a particular technique. The procedure plan may map specific surgical tasks to roles and equipment. The procedure plan may provide an expected timeline for the procedure.

The procedure plan may include one or more decision points and/or branches. Such decision points and/or branches may provide surgical alternatives that are available for particular aspects of the procedure, where selection of one of the alternatives may be based on information from the surgery itself. For example, the choice of one or more alternatives may be selected based on the particular planes of the particular patient's anatomy, and the surgeon may select an alternative based on her assessment of the patient's tissue during the live surgery.

The procedural plan may include one or more contingencies. These may include information about unlikely but possible situations that may arise during the live surgery. The contingencies may include one or more surgical tasks that may be employed if the situation does occur. The contingencies may be used to ensure that adequate equipment, staff, and/or consumables are at the ready during the procedure.

The procedure plan may be recorded in one or more data structures. A procedure plan data structure may be used to record data about a future live surgery, about a completed live surgery, about a future simulated surgery, about a completed simulated surgery, and the like. A procedure plan data structure for live surgeries may be used by the computer-implemented interactive surgical system, such as the surgical computing system 704 disclosed herein. For example, the procedure plan data structure for live surgeries may be used by surgical computing system 704 to enhance situational awareness and/or the operational aspects of a computer-implemented interactive surgical system 730. The procedure plan data structure for live surgeries may be used by the surgical computing system 704 to record discrete elements of the live surgery for structured analysis.

The procedure plan may be stored in any data structure suitable for storing, adding, removing, editing, and processing structured information. For example, the procedure plan may be stored in a data structure disclosed in U.S. patent application Ser. No. 17/332,594, titled METHODS FOR SURGICAL SIMULATION, filed May 27, 2021, the contents of which are hereby incorporated by reference herein. For example, the procedure plan may be stored in a relational database, such as one or more tables of a relational database for example.

The surgical support terminal 51020 may include a user interface terminal suitable for presenting and receiving information. For example, the surgical support terminal 51020 may provide an interface for a surgeon to prepare for a particular surgery. For example, the surgical support terminal 51020 may query the electronic medical record system 51016 for information regarding a patient who will undergo a particular procedure. The surgical support system 51020 may query the surgical procedure database system 51018 for information related to the surgical procedure to be performed on that patient.

The surgical support system 51020 may enable the surgeon to refine, edit, modify, adjust the surgical procedure plan. For example, the surgeon may add surgical tasks, remove surgical tasks, modify surgical tasks, and the like. The surgical support system 51020 may enable the surgeon to modify the surgical procedure plan by incorporating particular surgical instruments, by modifying the staff required, by revising surgical steps, by adjusting one or more parameters associated with the surgical steps, and the like. The surgical support system 51020 may provide the surgeon with various medical imaging related to the procedure. For example, the surgical support system 51020 may provide a 2D and/or 3D image to the surgeon for preparing for a surgical procedure.

The surgical support system 51020 may interact with the device 51002 to further modify and/or enhance the surgical procedure plan. For example, the device 51002 may provide a primary AI model 51004 and a support AI model 51006 to generate an output indicative of a recommended, modified procedure plan based on an initial proposed procedure plan. The recommended, modified procedure plan may be outputted at the surgical support system 51020, for example. The recommended, modified procedure plan may be outputted at the surgical support system 51020, for example, for further review, analysis, revision, and the like.

Figure 28:
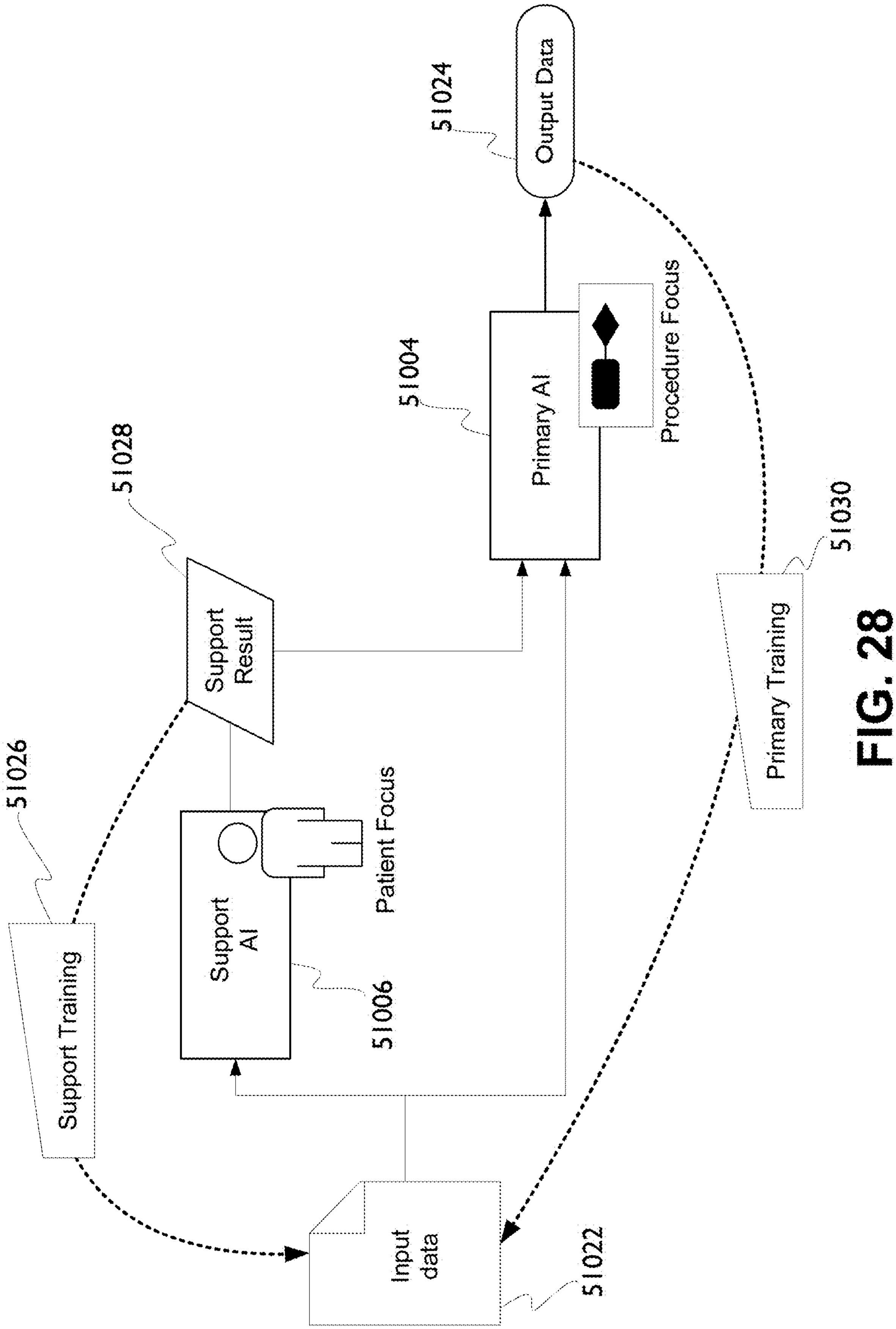
FIG. 28 is an architecture diagram illustrating the use and training of example primary and support AI models.

FIG. 28 is an architecture diagram illustrating the use and training of example primary AI model 15004 and a support AI model 51006 for modifying a procedure plan. Here, input data 51022 may be provided to a primary AI model 51004 and a support AI model 51006. The primary AI model 51004 may be implemented as a primary neural network. The support AI model 51006 may be implemented as a secondary neural network. The input data may include information suitable for the primary AI model 51004 and support AI model 51006 to generate a recommendation. For example, the input data may include information indicative of a surgical patient. For example, the input data may include information indicative of a target procedure. For example, the input data may include information indicative of a surgical patient a proposed procedure plan. For example, the input data may include information indicative of a surgical patient, and target procedure, and a proposed procedure plan. The input data may be received from the surgical support system 51020, for example.

In an example, the input data 51022 may include basic patient demographic information, information indicative of the patient's tissue condition, patient imaging, prescription information, a procedure identifier, a data structure defining the proposed procedure plan (including, for example, procedure steps, instruments, and parameters related to instrument settings and use), and the like.

The support AI model 51006 may include a model trained according to support training data 51026 with a patient focus. For example, the support AI model 51006 may a include a neural network, such as recommendation engine. The support AI model 51006 may be trained to provide an intermediate output, such as a support result 51028. The support result may represent a refined aspect of the patient data presented at the input data 51022. In effect, for example, the support training data 51026 may provide "gap filling" for the input patient data based on the model's representation of similarly situated patients in the training data 51026.

In an example, the support AI model 51006 may be trained to isolate anatomical elements. The support AI 51006 may generate one or more support results 51028. For example, the support results 51028 may include an isolated version of the patient-specific anatomy. In this example, the isolated version of the patient-specific anatomy may include one or more data elements indicative of the patient anatomy targeted by the target procedure. For example, the support AI 51006 may include elements of architecture and training like that disclosed in Domingues, I., Pereira, G., Martins, P. et al. Using deep learning techniques in medical imaging: a systematic review of applications on CT and PET. Artif Intell Rev 53, 4093-4160 (2020), the contents of which are hereby incorporated by reference.

In an example, the support AI model 51006 may be trained to provide anatomical landmarks relevant to the patient anatomy. For example, the support results 51028 may include registration information. For example, the registration information may be one or more anatomical landmarks. Here, the support AI may be trained using support training data 51026 that is independent of the target procedure (i.e., support training data need not be taken from surgical information associate with procedures that match the target procedure). For example, the support AI 51006 may include elements of architecture and training like that disclosed in Unberath M, Gao C, Hu Y, Judish M, Taylor R H, Armand M and Grupp R., The Impact of Machine Learning on 2D/3D Registration for Image Guided Interventions: A Systematic Review and Perspective. Front. Robot. AI 8:716007 (2021), the contents of which are hereby incorporated by reference.

The input data 51022 and the support results 51028 may be provided to the primary AI model 51004. The primary AI model 51004 may process the support result and some or all of the input data. The support results 51028 may be modified by expert intervention. For example, the support results 51028 may be presented separately to a surgeon at a surgical support system 51020, for example. The support result 51028 may be input to the primary AI model 51004 to further enhance the prediction/recommendation with regard to providing a modified procedure plan.

The primary AI model 51004 may be trained with primary training data 51030 based on data associated with procedure plans and corresponding patient outcomes. For example, the support AI model 51006 and the primary AI model 51004 may be trained independently. The training data 51030 may include data with a procedure focus. For example, the training data 51030 may include information regarding procedure plans and corresponding patient outcomes with patients that are similar and dissimilar to the patient represented by the patient information int the input data 51022. For example, the primary AI model 51004 may employ one or more elements of architecture and training like that disclosed in U.S. Patent Application Publication US2019/0073632A1, titled PROVIDING IMPLANTS FOR SURGICAL PROCEDURES, filed Oct. 30, 2018, the contents of which are hereby incorporated by reference.

The primary AI model 51004 may generate output data 51024 which may represent one or more recommendations and/or modifications to the proposed procedure plan provided in the input data 51022. For example, the primary AI model 51030 may output a modified procedure plan that is different from the proposed procedure plan. The differences may include differences in surgical steps, instrumentation, instrumentation use and/or settings, anatomical references (such as dissection paths and/or port placement for example), and the like. In an example, the modified procedure plan may identify a surgical instrument. The modified procedure plan may identify a surgical instrument that is different than that identified by the proposed procedure plan. In an example, the modified procedure plan may identify tumor margins. For example, the tumor margins may be different than that identified by the proposed procedure plan. In an example, the modified procedure plan may identify a mobilization approach. This mobilization approach may be different than that identified by the proposed procedure plan.

Such modifications to the procedure plan may be a product of the input data 51022 and the support result 51028. For example, the support result 51028 may include a patient specific mapping, such as a patient specific anatomy associated with a target procedure. And the primary AI model 51004 may leverage the patient specific anatomy to modify aspects of the procedure plan for the particular patient. The primary AI model 51004 may recommend a procedure plan in view of the support results 51028 which is different than had the support results 51028 not been used.

As illustrated here, in FIG. 28, the support AI model 51006 is trained in view of patient focused training data 51026 and the primary AI model 51004 is trained in view of procedure focused training data 51030, such that the support results 51028 represent patient focused input to the primary AI model. In an example, the support AI model may be designed and trained in view of procedure focused training data and the primary AI model may be designed and trained in view of patient focused training data, such that the support results, in this example, may represent procedure focused input to the primary AI model.

Figure 29:
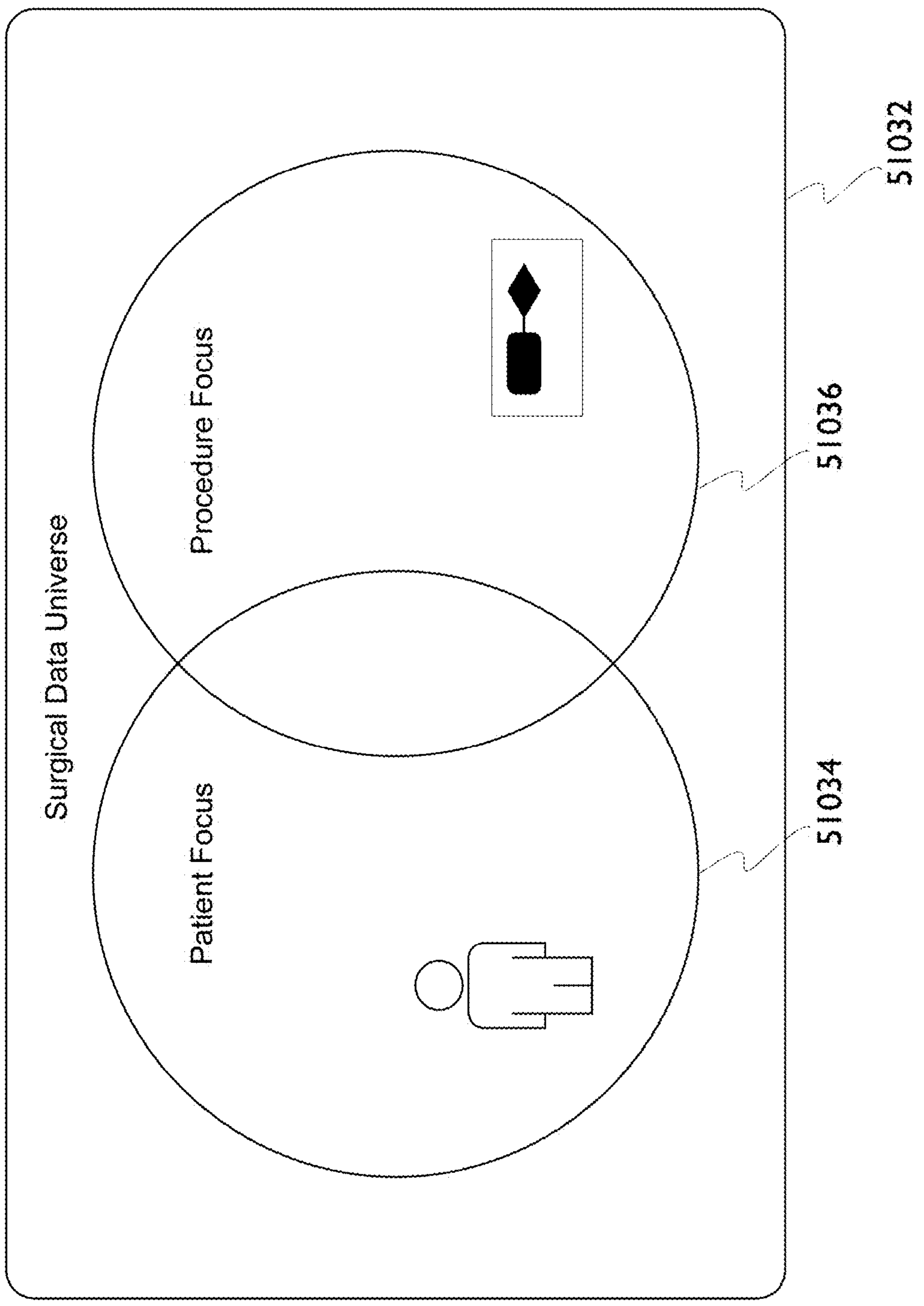
FIG. 29 illustrates a logic view of the universe of surgical data.

FIG. 29 illustrates a logic view of the universe of surgical data 51032. The AI approach disclosed herein, advantageously uses differently focused data sets for each module to provide a modified procedure plan that takes advantage of the distinct learning available from the differently focused data sets. For example, one model may be trained in view of data selected from a patient focused subset 51034 of universe of available surgical data 51032, and another model may be trained in view of data selected from a procedure focused subset 51036 of the universe of available surgical data 51032. In an example, and as illustrated in FIG. 29, the patient focused subset 51034 and the procedure focused subset 51036 may be partially overlapping subsets. In an example, the patient focused subset 51034 and the procedure focused subset 51036 may be fully distinct from each other.

In an example, multiple versions of the support AI model and the primary AI model may be used, with an analysis of their respective outputs to identify a preferred combination. By leveraging at least two versions of models on a same or similar dataset may be used to determine relationships each could identify from surgical and/or interventional data. The results may be then used to produce a hybrid composite algorithm. Such an approach may be used to defining which module is positioned in which role (e.g., support or primary). In an example, such a hybridization may generate different composite algorithm steps for use for each distinct data set.

In an example, multiple versions of the support AI model and the primary AI model may be used, with an analysis of their respective outputs to group models that achieved similar results. And other models may be highlighted based on outputs that that result in divergent results. Here, such divergent outputs may identify outliers that are relevant (e.g., not merely noise). Such models may be incorporated as support AI models, as disclosed herein, to enable the overall system to take advantage of such relevant outliers.

To illustrate, Korean-based surgical data may represent an improved outcome regarding colon cancer due to diet, such a data set may drive results in outlier output data. Japanese-based surgical data, by contrast, may present a similar outlier effect for gastric cancer, but here not because of diet, but because of the meticulousness of dissection and additional surgical efforts to prevent mobilization of cancer cells. Such an outlier may be difficult to identify appropriate by traditional means. Here, for example, the beneficial learning available in the Japanese-based data set may be overshadowed by a regional confounding factor (e.g., H-pyloi bacteria may increase ulceration because of inadequate water supply treatments, which degrade the surgical outcomes in the gastric cancer data). The architecture disclosed herein may enable the identification and use of beneficial data sets apart from mere regional differences.

In another example, data extracted, such as the support results disclosed herein, may be used to determine a vector directionality of improved performance. For example, localized and/or patient specific data may be approximate and/or may correlate a directional result (e.g., indicating better or worse results) based on the specifics of the patient (e.g., physiology, anatomy, disease state, etc.) and the constraints of the surgery itself (e.g., surgical approach, disease intensity, secondary comorbidities, complications, etc.). Here, a base case may be used based on global and/or regional outcomes. And the base case may be adjusted with the patient specific extracted data to provide an improved result.

For example, the primary AI may be trained according to such global and/or region outcomes and the support AI may be trained according to such patient specific information. Such an approach may enable the surgeon to allow for a directionality and magnitude impact based on these input aspects.

Figure 30:
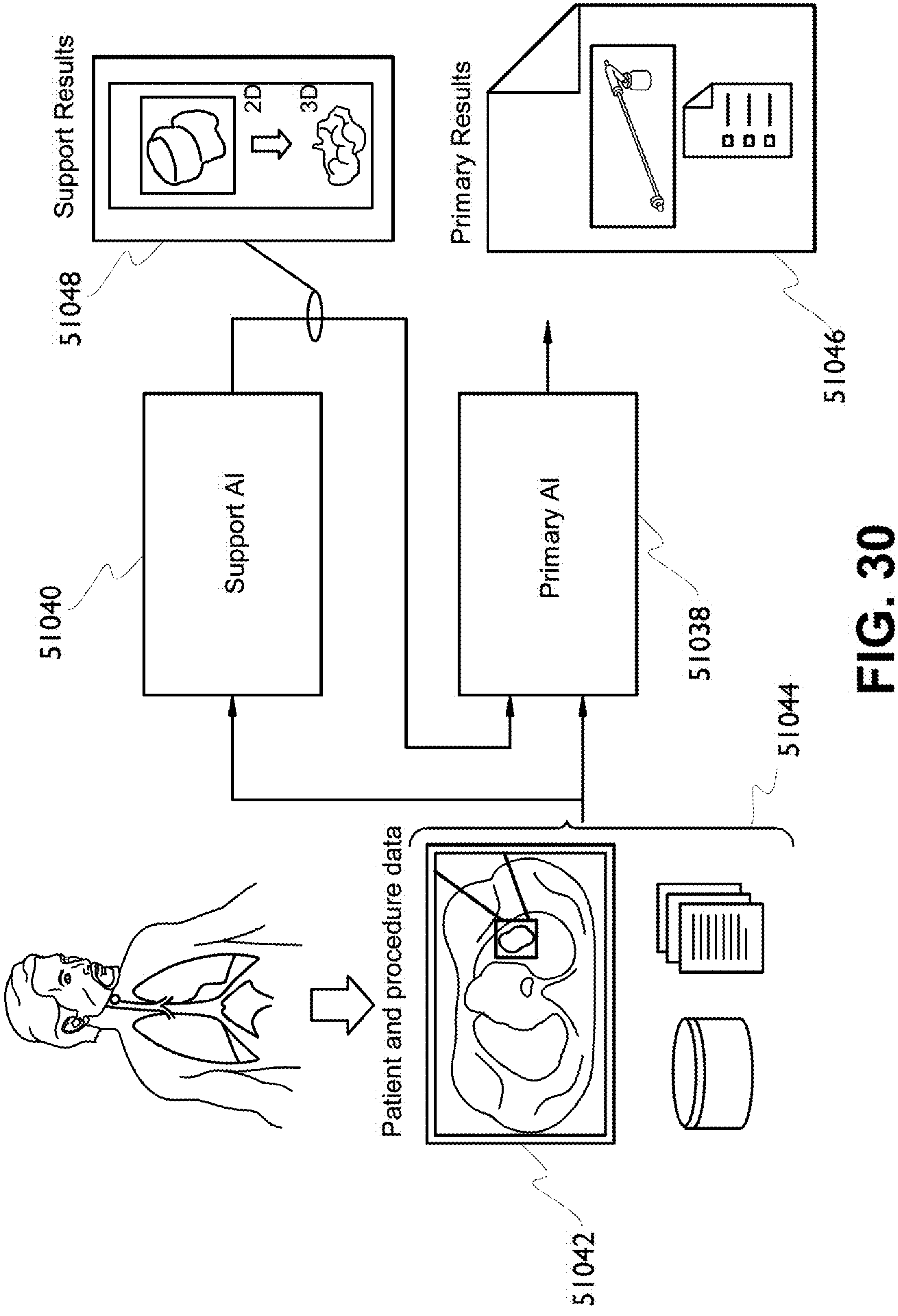
FIG. 30 illustrates the use of example primary and support artificial intelligence AI models in thoracic surgery planning.

FIG. 30 illustrates the use of example primary 51038 and support 51040 AI models in thoracic surgery planning. Here, a patient may undergo additional imaging 51042, consistent with views used in the support AI training data. The support AI 51040 may provide support results 51048 that better identify the relevant anatomy.

In an example, the support AI may include training data including 2D and 3D (e.g., taken via laparoscopic imaging systems with structured light. See: Locally displayed coordinate system is further described in U.S. patent application Ser. No. 16/729,747, titled DYNAMIC SURGICAL VISUALIZATION SYSTEMS, filed Dec. 31, 2019, which is incorporated by reference herein in its entirety) pairs.

In an example, such additional imaging 51042, taken over time, in combination with the support AI 51040 may generate support results that better evaluate the volume of a tumor over time. The support AI 51040 may leverage landmarks within the images and the training data to assess volume, which may be available in the support results 51048. Further, this approach (and/or an automated segmentation of scan data) may ultimately be used to evaluate the effectiveness of non-surgical therapies, e.g., pharmaceutical therapies. The primary AI training set, in turn, may be expanded to incorporate such non-surgical therapies generally.

The primary/support approach may be used to leverage alternative treatment options, incorporated into the primary AI training data, to determine if there is a more optimal treatment. The primary AI output data 51046 may highlight modifications to the procedure plan impacts issues such as complication rates, specialized tools, or the like.

Figure 31:
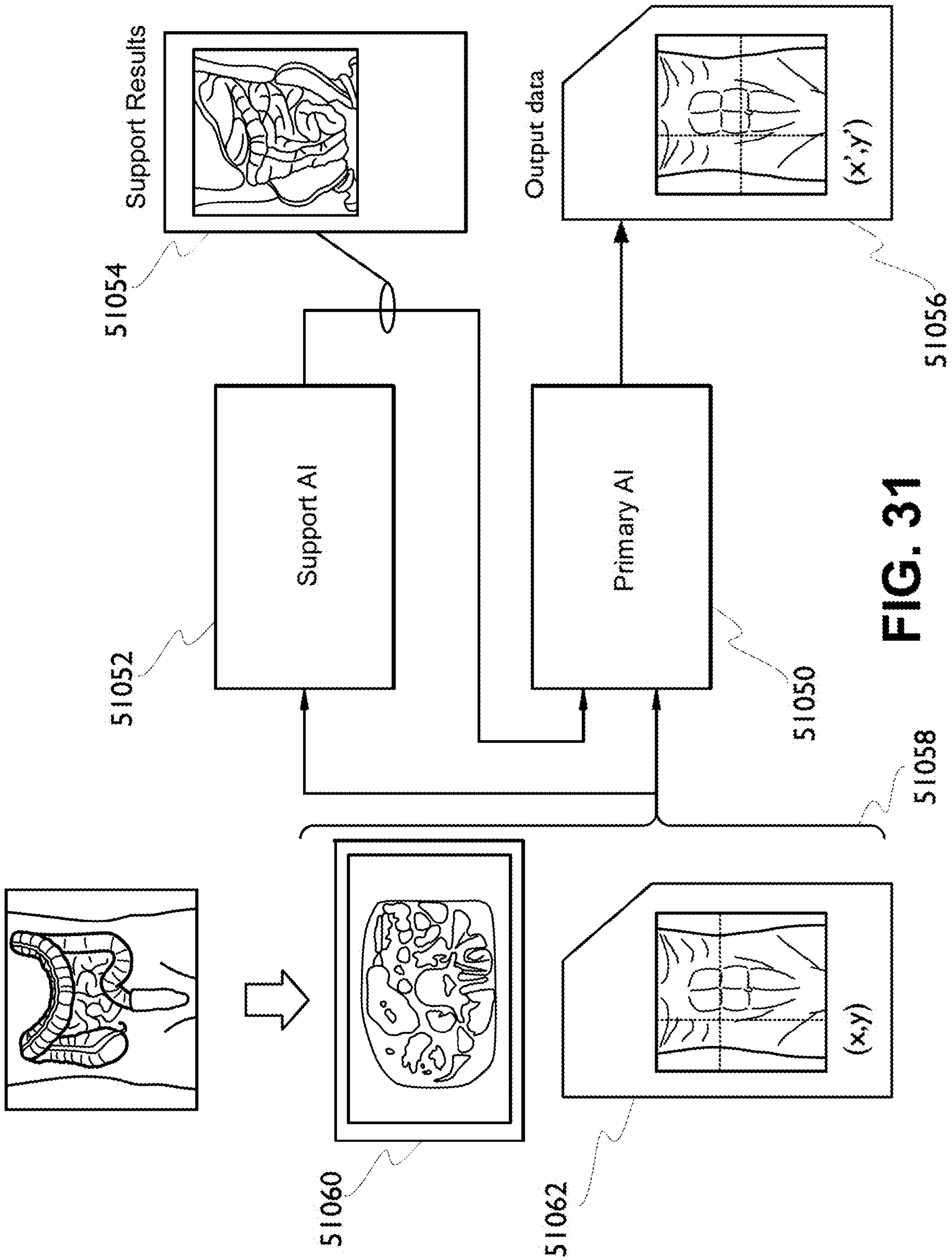
FIG. 31 illustrates use of example primary and support artificial intelligence AI models in abdominal surgery planning.

FIG. 31 illustrates use of example primary 51050 and support 51052 artificial intelligence AI models in abdominal surgery planning. Here, the support AI 51052 may be used to extract geometry data as support results 51054 that may be leveraged in the selection of procedure step parameters, such as the selection of instrumentation, implant sizing, configuration, usage location (primary results 51056, illustrated in FIG. 31)

For example, the input data 51058 may include preoperative imaging 51060 and a proposed procedure plan 51062 with procedure step parameters such as coordinates indicating a usage location. The support results 51054 may provide a more robust and granular understanding of the patient's relevant anatomy. And the primary AI 51050 may be trained with procedural data that includes coordinates. Accordingly, the output data 51056 may include a resultant modification to the procedure plan that includes a second set of coordinates that is different from those provided in the proposed procedure plan 51062.

For example, the overall operational cavity and/or gross parameters may be used to determine the diameter size of a device modification. For example, the patient's anatomical geometry (e.g., colon size) may be enhanced by the support AI 51052 and may facilitate the primary AI 51050 to recommend a more appropriate procedure step parameter (e.g., a modified sized diameter of the head of the circular stapler for the anastomotic reconnection step). In another example, enhanced determination of bone size, defect size, and/or orientation by the support AI 51052 may facilitate definition of an orthopaedic implant by the primary AI 51050. In another example, enhanced determination of the size of the esophageal sphincter region of the unsupported opening (resting size) of the sphincter by the support AI 51052 may facilitate selection of a Torax LINX device size and/or collapsing force by the primary AI 51050.

In another example, enhanced determination of the size of a tumor by the support AI 51052 may facilitate selection of a Torax LINX device size and/or collapsing force by the primary AI 51050.

In another example, enhanced determination of the size of the esophageal sphincter region of the unsupported opening (resting size) of the sphincter by the support AI 51052 may facilitate selection extraction pouch size and/or insertion location/orientation by the primary AI 51050.

In another example, enhanced determination anatomical geometry by the support AI 51052 may facilitate selection of the correct sizing/version of implants and/or selection of instruments and/or access ports by the primary AI 51050.

In another example, enhanced determination anatomical geometry by the support AI 51052 may facilitate the automatic registration and adaptation of related imaging means or images to coalesce them into a single overlaid image. Here, the support AI 51052 may identify salient geometry, extractions of which may be used to identify perspective, scaling, distortion, foal length, and the like. In turn, the primary AI 51050 may be trained to apply filters to the imaging, preparing it for cooperative use with other imaging with common salient geometry In another example, enhanced determination anatomical geometry by the support AI 51052 may facilitate identification of anatomical landmarks by the primary AI 51050 for aspects of the modified procedure plan in the output data 51056, such as orientation, direction instructions, identification of tissue and/or organ planes, and the like. Such modifications being exceptionally useful to the surgeon for navigation of dissection during the surgery.

Figure 32:
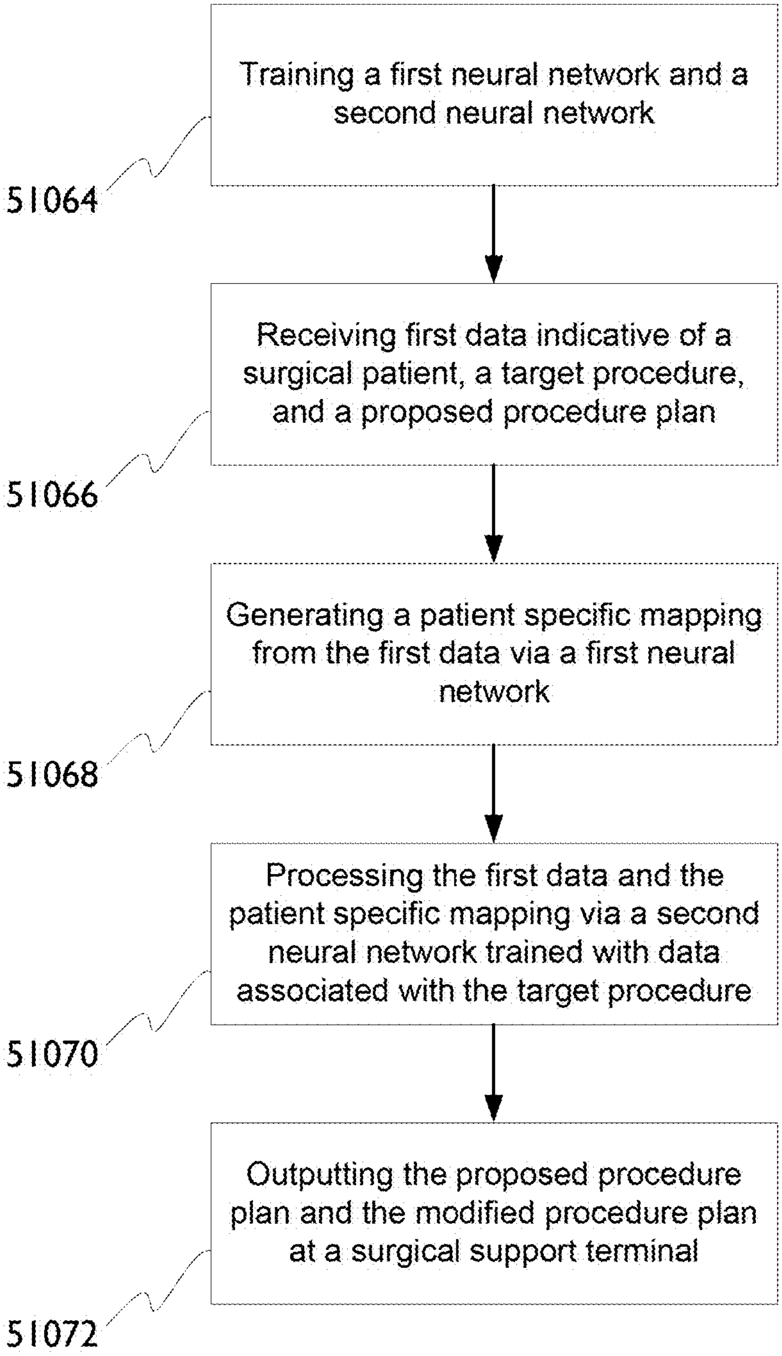
FIG. 32 is a flow diagram of an example process employing primary and support artificial intelligence AI models in surgical planning.

FIG. 32 is a flow diagram of an example process employing primary and support artificial intelligence AI models in surgical planning. At 51064, a first neural network and a second neural network may be trained. For example, the first neural network and a second neural network may be trained independently of each other. For example, the first neural network may be trained to isolate anatomical elements. For example, the first neural network may be trained to generate relative anatomical positioning.

The second neural network may be trained to recommend procedure plans associated with improved patient outcomes. For example, the second neural network may be trained with procedure plans from previously performed procedures and their corresponding patient outcomes. The second neural network may also be trained according to anatomical mapping associated with those previously performed procedures. The second neural network may be trained with data associated with a target procedure. For example, the second neural network may be associated with a particular general class of procedures.

The first neural network may be trained with patient focus (e.g., training data may be used from surgical data with relevant patient attributes regardless of the particular procedures associated with the source training data). The second neural network may be trained with a procedure focus (e.g., training data may be used from surgical data with a common procedure type regardless of the particular patients associated with the source training data). In an example, in the context of lung surgery or a lung resection surgery, the second neural network may be trained with procedure plans, patient specific mappings, and patient outcomes of other lung resection surgeries, and the first neural network may be trained with patient imaging and corresponding anatomical isolated information, regardless of the procedure being performed. Here, the patient specific mapping associated with the first neural network may be used as a data element by the second neural network.

At 51066, the first data may be received. The first data may be indicative of a surgical patient, a target procedure, and a proposed procedure plan, for example. Here, the target procedure may be used to associate the first data with a particular second neural network. The surgical patient aspect of the first data may include patient bibliographic data and/or patient imaging data. The procedure plan may include one or more data elements that indicate and characterize a particular instance of the target procedure.

At 51068, a patient specific mapping may be generated. For example, the patient specific mapping may represent support results generated from the first neural network to support operation of the second neural network. The patient specific mapping may be generated from the first data. The patient specific mapping may be generated from the first data via the first neural network.

At 51070, the first data and the patient specific mapping may be processed. The first data and the patient specific mapping may be processed via the second neural network. The first data and the patient specific mapping may be processed via the second network in accordance with the techniques disclosed herein. And at 51072, a modified procedure plan may be outputted. For example, the modified procedure plan may be outputted at a surgical support system. In an example, the output of the surgical support system may include both the modified procedure plan and a copy of the original procedure plan.

Figure 33A:
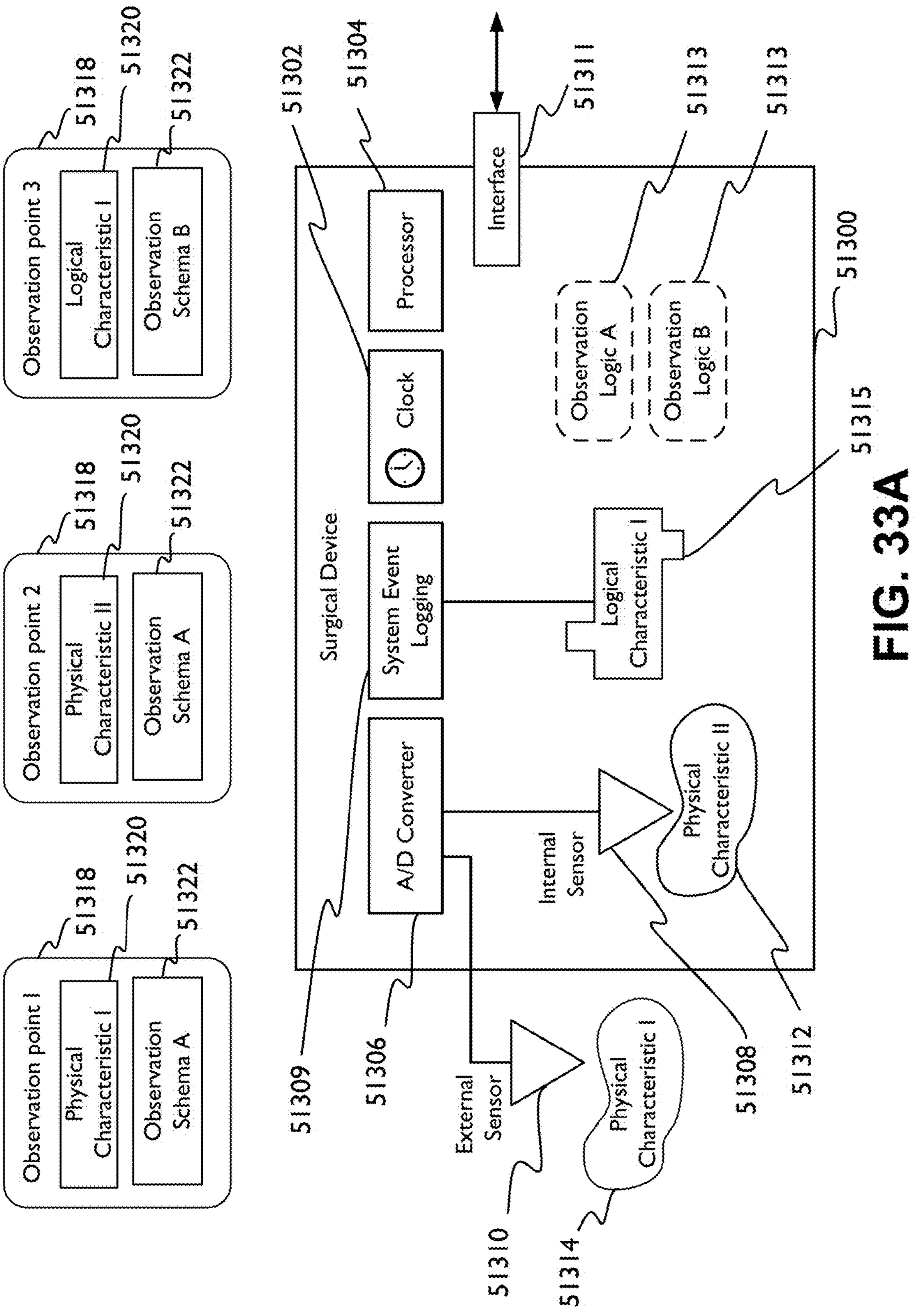
FIGS. 33A&B are block diagrams illustrating example surgical devices with observations points and time domains.
Figure 33B:
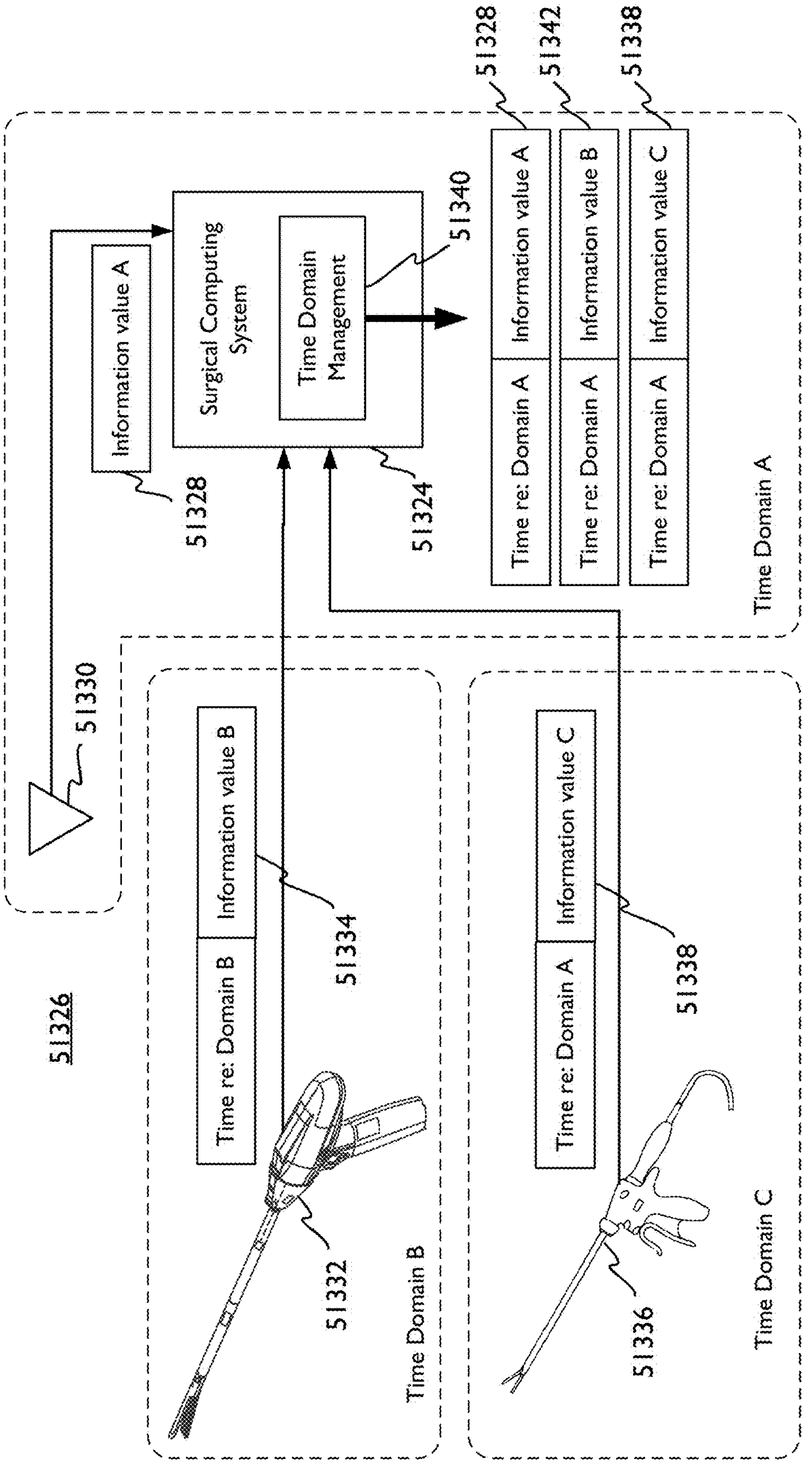

FIGS. 33A-B are block diagrams illustrating example surgical devices with observations points and time domains. In FIG. 33A, a surgical device 51300 may include a clock 51302, a processor 51304, an analog-to-digital (A/D) converter 51306, and one or more sensors, such as an internal sensor 51308 and/or an external sensor 51310, and an interface 51311. The surgical device 51300 may have a system event logging 51309. The surgical device 51300 may have a primary surgical function (not shown), for example as a surgical instrument, a display, a computerized surgical equipment, and the like. For example, the surgical device 51300 may a surgical information source as disclosed with reference to FIG. 7A-D.

The clock 51302 may include any device, component, or subsystem suitable for providing a time source to the surgical device 51300. In some types of surgical devices, such as surgical devices with embedded and/or microcontroller systems for example, the clock 51302 may include a hardware time clock. The time clock (e.g., real time clock) may include an integrated circuit configured to keep time. The hardware time clock may be powered, e.g., by an internal lithium battery. The hardware clock may include an oscillator, such as an external 32.768 kHz crystal oscillator circuit, an internal capacitor-based oscillator, an embedded quartz crystal, or the like. The integrated circuit uses the regular oscillations to track time. In some types of surgical devices, such as surgical devices with software and/or firmware operating systems, a software clock may be used. Here, the system clock of the processor, used for control of processor circuit-level timing, may provide timing information to the operating system that be configured to keep time. The surgical device 51300 may include a hardware time clock, a software clock, and/or a combination of a hardware time clock and a software clock, for example.

Operation of the clock 51302 may be made with a local time reference. For example, an initial time may be established locally to the surgical device 51300, for example, as entered by a user with initializing the surgical device 51300. From that initialization forward, the clock 51302 keeps time relative to that local reference. Operation of the clock 51302 may be with an external time reference. For example, an initial and/or subsequent time may be established externally, for example, as communicated to the surgical device 51300 by another clock. For example, the clock 51302 may be influenced by time information received from a surgical computing system (such as surgical computing system 704, for example). The clock 51302 may be influenced by time information received from a network time server, via Network Time Protocol (NTP), for example.

The processor 51304 may include and hardware, software, or combination thereof suitable for processing information in furtherance of the operation of the surgical device. The processor may be a microcontroller, a general-purpose computing processor, an application specific integrated circuit (ASIC), or the like. The processor 51304 may include any of the processors and processor types disclosed herein.

The interface 51311 may include any hardware, software, and combination thereof suitable for communicating information to and/or from the surgical device 51300. For example, the interface 51311 may include a human user interface. For example, the interface 51311 may include a network interface for communicating with other devices, such as other surgical devices, a surgical computer system, such as the surgical computer system disclosed with reference to FIGS. 7A-D. The interface 51311 may send messages (including observations, e.g., surgical information). The interface 51311 may receive messages (including, e.g., configuration and/or control messages).

The sensors 51308, 51310 may include any electrical, electromechanical, electrochemical, or the like device suitable for observing and/or measuring a physical characteristic of the real world and converting that observation into an electrical signal.

The external sensor 51310 may consider an external physical characteristic 51314, such as any observable aspect of the real world outside of the boundaries of the surgical device. For example, an external sensor 51310 may include sensors for patients, including probes for surgical monitoring equipment, such as electrocardiogram probes, vital sign probes, sensors associated with pulse oximetry, and the like. For example, an external sensor 51310 may include sensors for healthcare professionals, such as those used in wearable heartrate monitors, activity monitors, galvanic skin response monitors, and the like. For example, the external sensor 51310 may include sensors for environmental characteristics, such as those sensors used for digital thermometers, digital barometers, air quality monitors, sound and noise monitors, and the like. Sensors associated with use in a computer-interactive surgical system are disclosed in U.S. Patent Application Publication No. US 2022-0233119 A1 (U.S. patent application Ser. No. 17/156,287), titled METHOD OF ADJUSTING A SURGICAL PARAMETER BASED ON BIOMARKER MEASUREMENTS, filed Jan. 22, 2021, the contents of which are hereby incorporated by reference.

The internal sensor 51308 may observe an internal physical characteristic 51312, such as any observable physical aspect of the real world inside the device and/or associated with a physical aspect of the device itself. For example, surgical device 51300 with an internal sensor 51308 may be used to consider internal chassis temperature, internal component pressure (e.g., operating pressure of an insufflator, a smoke evacuation system, or the like), revolutions-per minute (e.g., operating RPM of a smoke evacuation device's motor), an internal flow rate sensor (e.g., measuring liters-per-minute of liquid or gas flow), and the like. Observations from the internal sensor 51308 may appear to the user via a system status display and may be considered part of the surgical device status information, for example.

The A/D converter 51306 converts electrical signals from the sensors 51308, 51310 into a digital signal for use by the processor 51304. In an example, the A/D converter 51306 (and/or the sensors 51308, 51310 themselves) may operate at the instruction of the processor 51304 to establish the conditions under which observations (e.g., measurements) are made and/or reported. Such conditions may be established by the observation logic 51313 of the surgical device 51300.

The system event logging 51309 may represent another source of surgical information with timing aspects. The system event logging 51309 may observe an internal logical characteristic 51315 of the surgical device 51300. A logical characteristic 51315 may include any measurable aspect of the logical environment of the surgical device 51300. For example, a logical characteristic may include measurements related to device bandwidth capacity/utilization, memory capacity/utilization, processor capacity/utilization, software events and notifications, reporting of setting information, and the like.

Observation logic 51313 may be associated with one or more sources of observation, such as the sensors 51308, 51310, the system event logging 51309, etc. The observation logic 51313 may present as instructions and/or operations coded into software and/or firmware, as hardware components (such as logic components), as an integrated circuit, or the like. The implementation of the observation logic 51313 may be consistent with the architecture of the surgical device 51300. The observation logic 51313 may dictate when and under what conditions the sensors 51308, 51310 are used to measure the corresponding physical characteristic 51310, 51312. The observation logic 51313 may dictate when and under what conditions the system event logging 51309 is used to measure the corresponding logical characteristic 51315. The observation logic 51313 may control one or more aspects of the observation and/or measurement itself, including the timing of observations, the frequency of observations, the effective resolution and/or range of the measurements, and the like. The observation logic 51313 may provide higher-level control of the observations with hardware, coding, logic techniques (such as hardware interrupt triggers), application-level triggers, if/then statements, case statements, and the like. The observation logic 51313 may coordinate observations among the other internal operations of the surgical device 51300. Notably, the observation logic 51313 may coordinate observations with operations outside the surgical device 51300. For example, the observation logic 51313 may be configured to coordinate observations based on information received via the interface 51311. For example, the observation logic 51313 may be configured to coordinate observations based on information received via the interface 51311 from another surgical device. For example, the observation logic 51313 may be configured to coordinate observations based on information received via the interface 51311 from surgical computer system, such as surgical computer system 704, for example. In an example, the observation logic 51313 may be implemented by the processor 51304.

A systems framework for sensor operation may employ one or more observation points 51318. An observation point 51318 may logically represent the object of observation, the sensor 51308, 51310, the corresponding observation logic 51313, and/or the like. For example, an observation point 51318 may be a data representation of the object of observation, the corresponding observation logic 51313, and the like.

In an example, the observation point 51318 may include a multipart data structure. For example, the observation point 51318 may include information (e.g., a label) that represents the objection of observation. Such representation may be in a human readable form, in a computer readable form, in a look-up form (e.g., with a unique identifier of the object of observation). The observation point 51318 may include information (e.g., a schema 51322) that represents the observation logic 51313 that is used to observe the object of observation. Such representation may be in a human readable form, in a computer readable form, in a look-up form (e.g., with a unique identifier of the observation logic). A device that receives the observation point 51318 will learn what is being observed in the corresponding flow of surgical information and, importantly, the details of the processing causing it to be observed.

A surgical device 51300 may be associated with one or more observation points 51318. The surgical device 51300 may have one or more observation points 51318 associated with common observation logic. The surgical device 51300 may have one or more observation points 51318 associated with different and/or independent observation logic.

The observation point 51318 may facilitate the exchange of information. In an example, the observation point 51318 may represent metadata that characterizes the data of the observation/measurements themselves-explaining the particular physical characteristic being observed and explaining the circumstances (e.g., configurations and settings for example) under which the observation was made. In an embodiment, the observation point 51318 may include an application programming interface (API) providing a platform by which surgical devices may have interactions regarding observations and configurations associated with how those observations are made.

FIG. 33B illustrates a surgical computing system with multiple time domains. A time domain may represent the reference and/or variability of a clock source for one or more devices. Generally, a surgical device (and its corresponding observation points) having time locally will be in its own time domain. Surgical devices that receive network time and/or have time synchronization capabilities may share a time domain. Analysis of surgical information from observation points with different time domains may be less effective in view of the differences in timing. For example, with devices in different time domains, two observations may be reported as having been made at the same time but had actually been made at different times. The difference may be a static difference. The difference may be a dynamic difference. A surgical computing system with the capability to resolve these timing differences may enable and/or facilitate advanced analysis of generated surgical data.

To illustrate, a surgical computing system 51324 may operate in Time Domain A. Time Domain A may represent a reference time domain for the surgical system 51326. Observations 51328 received from a directly connected sensor 51330 are timestamped by the surgical computing system 51324. Such surgical data is also in Time Domain A.

The first surgical device 51332 may be Time Domain B. Surgical data sent from the first surgical device 51332 to the surgical computing system 51324 may include observation values 51334 that are timestamped with reference to Time Domain B. The differences in the time domains may reflect the differences in clock time of the various elements in the surgical system 51326 relative to a reference time.

To mitigate such differences (e.g., to mitigate such time differences for purposes of the later application of machine learning to data collected across time domains), the surgical computing system 51324 may include a time domain management function 51340. The time domain management function 51340 may be responsible for normalizing the information values collected across diverse time domains into a common (e.g., reference) time domain.

As illustrated, the surgical computing system 51324 may designate Time Domain A as a reference time domain for the overall system 51326. The surgical computing system 51324 may determine a corrective timing adjustment associated with a time domain other than the reference time domain. Subsequent observations may be processed according to the timing adjustment to put them into the reference time domain.

In an example, the corrective adjustment may be used by the surgical computing system 51324 to translate received timestamped observations from their source time domain into the reference time domain. As illustrated, observation values 51334 from the first surgical device 51332 that are timestamped with reference to Time Domain B may be translated by the time domain management 51340 to result in the observation value 51342.

In an example, the corrective timing adjustment may be communicated to and applied by the surgical device prior to sending timestamped observations. As illustrated, a second surgical device 51336 may be in Time Domain C. The second surgical device 51336 may receive one or more queries and/or one or more configuration updates from the surgical computing system 51324. Such interaction may communicate a timing adjustment to the second surgical device 51336. Such interaction may instruct the second surgical device 51336 to apply the timing adjustment to the subsequent observation values 51338. Accordingly, surgical data sent from the second surgical device 51336 to the surgical computing system 51324 may include observation values 51338, originally generated in Time Domain C, but having been adjusted and properly timestamped with reference to Time Domain A.

The surgical computing system 51324 may determine the corrective adjustment by any timing logic suitable for synchronizing computing systems. For example, the surgical computing system 51324 may perform a synchronization procedure where the surgical computing system 51324 requests an information value to be sent to the surgical computing system 51324 from an observation point with a defined duration of time from the request. The device in the non-reference time domain may receive the request, place the receive time (in the non-reference time domain) into the information value field, wait the instructed duration (again in the non-reference time domain), and then timestamp and send the information value (containing the receive time) to the surgical computing system 51324. The surgical computing system 51324 may compare the received time data (the "sent" timestamp and the "received" time) to what would be expected had the same request been made of an element in the reference time. Based on such a comparison, a timing adjustment may be determined. Subsequent queries may be made with variously instructed wait-time durations to further refine the timing adjustment. Queries may be made at intervals to adapt to non-static differences among the time domains.

The time domain management function 51340 may store the determined corrective adjustments associated with each time domain in the surgical system 51326. In an embodiment, the surgical computing system 51324 may perform a translation function associated with the individual timing adjustments. Here, the devices send information to the surgical computing system 51324 in their own local time domains, and it is the surgical computing system 51324 that applies the corrective adjustment to the timestamp and information value to establish a common reference time for the received values.

In an embodiment, the time domain management 51340 may provide configuration instructions to devices in other time domains. The instructions may include the timing adjustment and instruct the device to provide information values relative in accordance with that timing adjustment. Such a configuration instruction may, in effect, move a device from one time domain to the reference time domain. Having a common time domain may better enable analysis of information values received from devices in different time domains.

Figure 34:
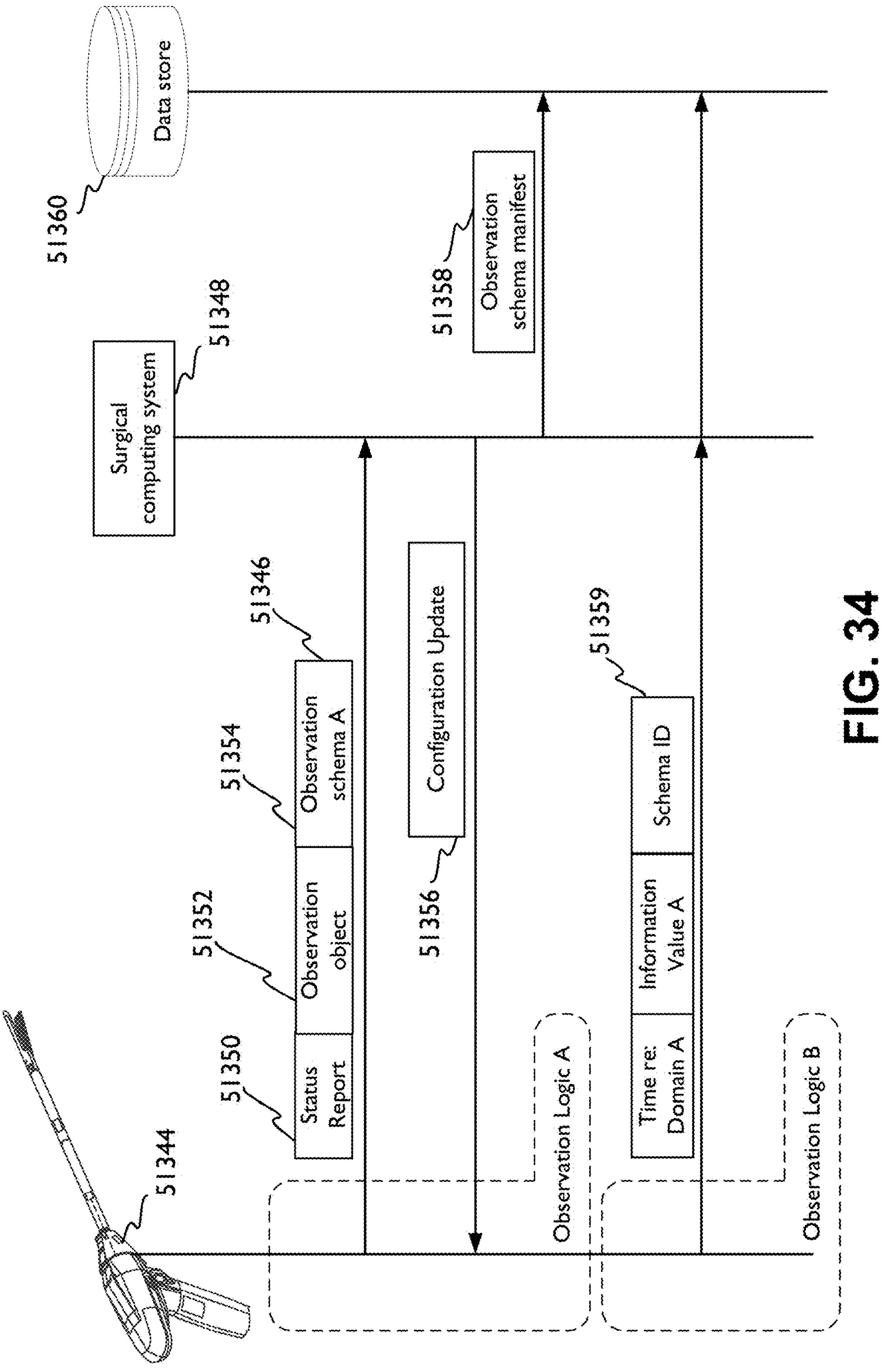
FIG. 34 is a message flow illustrating an example control to provide a common time domain and/or configure an observation point schema.

FIG. 34 is a message flow illustrating an example control to provide a common time domain and/or configuration of an observation point schema. A surgical device 51344 may begin in a non-reference time domain. The surgical device 51344 may provide first information 51346 to a surgical computing system 51348 (e.g., to the time domain management function of the surgical computing system 51348). For example, the first information 51346 may include aspects of the device's operations, such as a status report 51350, a listing of observation points (including, for example, one or more observation objects 51352 and one or more corresponding observation schema 51354), and the like. In an example, the surgical device 51344 may provide such first information 51346 as part of an initial activation for use in a surgical procedure.

Such first information 51346 may be provided to the surgical computing system 51348. In an embodiment, the surgical computing system 51348 may perform a query (not shown) to determine a timing offset. In an embodiment, the surgical computing system 51348 may receive information in the status report 51350 to determine a timing offset.

The surgical computing system 51348 may consider present observation points as reported by the first information 51346. The surgical computing system 51348 may determine a recommend observation point schema or one or more observation points. For example, the surgical computing system 51348 may determine the recommended observation point schema from a look-up table containing the recommended observation point schema for a particular patient's surgical procedure. For example, the surgical computing system 51348 may determine the recommended observation point schema from a look-up table containing the recommended observation point schema for a type of surgical procedure. For example, the surgical computing system 51348 may determine the recommended observation point schema from a look-up table containing the recommended observation point schema, where the look-up table is based on the surgical devices to be used in the surgical procedure.

In an example, the surgical computing system 51348 may determine the recommended observation point schema in the context of a machine learning platform, further disclosed herein. For example, the surgical computing system 51348 may determine the recommended observation point schema based on a look-up table curated to develop training data for the machine learning platform. For example, the surgical computing system 51348 may determine the recommended observation point schema based on one or more outputs from a trained machine learning model.

The surgical computing system 51348 may generate and/or send one of more configuration updates 51356 to the surgical device 51344. The configuration update 51356 may include an instruction to change the observation logic associated with an observation point to an observation logic that reflects the recommended observation point schema. The configuration update 51356 may include the recommended observation point schema. The configuration update 51356 may include information indicative of the recommended observation point schema. The surgical device 51344 may use the recommended observation schema to update its observation logic accordingly. As now configured, the surgical device 51344 may report observations in accordance with the updated observation point schema (illustrated in FIG. 34 as moving from Observation Logic A to Observation Logic B).

The configuration update 51356 (and/or other configuration updates) may include the timing adjustment. As now configured, the surgical device 51344 may report observations in with the reference time domain (e.g., Time Domain A, as shown). For example, the surgical device 51344 may send second information 51359 to the surgical computing system 51348. The second information 51359 may include one or more observations. The second information 51359 may include one or more observations timestamped in accordance with a timing adjustment. The second information 51359 may include one or more observations timestamped with reference to a reference time domain. The second information 51359 may include one or more observations made in accordance with the recommended observation schema.

In an example, a surgical computing system 51348 may send a timing adjustment and a recommended observation point schema to a surgical device 51344, together, in a configuration update 51356. In an example, a surgical computing system 51348 may send a timing adjustment and a recommended observation point schema to a surgical device 51344 in separate configuration updates 51356. In an example, a surgical computing system 51348 may send a timing adjustment without a recommended observation point schema (e.g., in the case where there is no change to the observation point logic recommended for the surgical procedure). In an example, a surgical computing system 51348 may send a recommended observation point schema without a timing adjustment (e.g., in the case where the surgical device is already operating in the reference time domain).

The surgical computing system generate 51348 an observation point manifest 51358 to document the observation points. In an example, the observation point manifest 51358 may be sent to server, such as a data store 51360, for example. The observation point manifest 51358 may include a listing of the domain information, timing adjustments, original observation logic (e.g., via the received observation point schema), observation logic changes (e.g., via the recommended observation schema), and the like. The observation point manifest 51358 may be used in the training of a machine learning model, for example.

Figure 35:
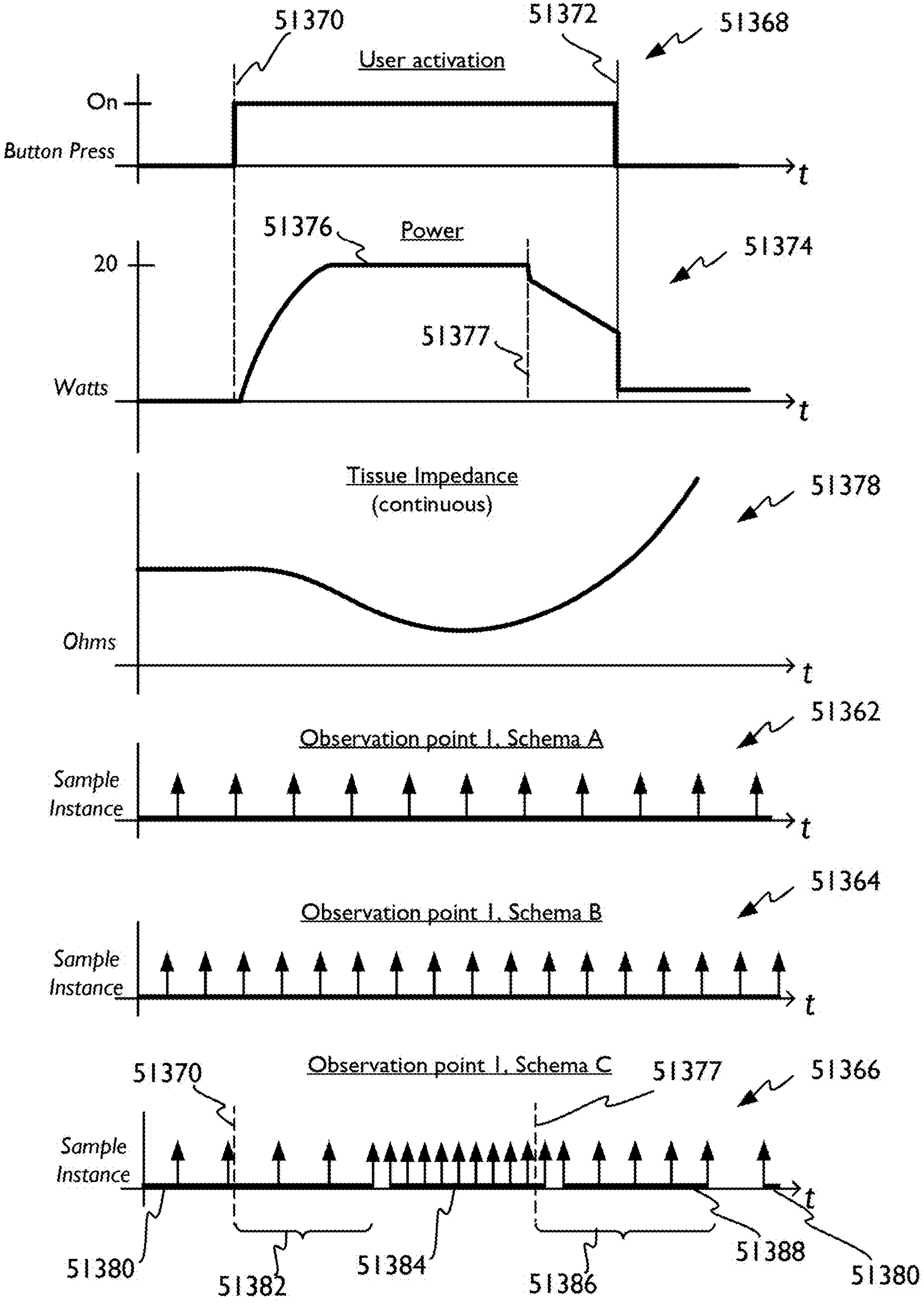
FIG. 35 includes timing diagrams depicting three example observation point schemas for a surgical device.

FIG. 35 includes timing diagrams depicting three example observation point schemas 51362, 51364, 51366 for a surgical device. To illustrate the variability and flexibility of the observation point capabilities disclosure herein, FIG. 35 illustrates different observation point logic/schema that may be used in connection with a surgical device, such as an energy device. The dynamic configurability of the observation point logic/schema for the device may facilitate more advanced analysis and refining of the device's operation (via a machine learning model, disclosed herein, for example).

Chart 1 51368 illustrates the timing associated with an example user activation of the surgical device. At 51370, the user may press an activation mechanism, such as a button on the surgical device, to cause application of power to a tissue during a surgical procedure. The button press may continue until 51372, at which the button may be released causing the surgical device to cease application of power to the tissue.

Chart 2 51374 illustrates the power applied by the energy device, including a ramping up of wattage at the onset of the button press 51370 and a plateauing of the power at a steady wattage 51376, for example. The surgical device may, based on observed tissue impedance, begin to ramp down the power (at 51377). For example, the surgical device may ramp down power when tissue impedance drops below a threshold. The power may cease at release of the button press 51372.

Chart 3 51378 illustrates the corresponding real world physical characteristic of tissue impedance. Before the application power tissue impedance is generally constant (e.g., as a function of the tissue type for example). At the onset of application of power, the tissue impedance may drop. As power continues to be applied, the tissue impedance may reach a minimum such that further application of power may cause the tissue impedance to rise.

The surgical device may observe this continuous change in tissue impedance with one or more sensors and/or one or more corresponding observation points. Other surgical devices may observe other aspects of the operation of the surgical device during this time. And further, other surgical devices may be observing other characteristics in the operating room during this time as well. Such timestamped observations may be included in the surgical information provided to the surgical computing system (e.g., as disclosed with regard to FIGS. 7A-D). To provide flexibility in timing of observations for operation of the surgical device and to improve cooperative operation among surgical devices, the surgical device may support configurable observation timing and methodology, such as the three observation point logic/schemas 51362, 51364, 51366 illustrated here.

In logic/schema A 51362, the observation point measuring tissue impedance does so by making observations (and sending such timestamped observations to the surgical computing system) at a fixed frequency. The logic/schema A 51362 may represent a methodology that generates less communication volume (e.g., and less required bandwidth), but does so with corresponding reduction of temporal granularity.

By contrast, in logic/schema B 51364, the observation point measuring tissue impedance does so by making observations (and sending such timestamped observations to the surgical computing system) at a fixed frequency that is greater than that of logic/schema A 51362. Accordingly, logic/schema B 51364 may represent a methodology with greater temporal granularity than logic/schema A 51362 but does so at a corresponding increase in communication volume (e.g., required bandwidth).

In an example, the surgical computing system may use configuration updates to have the surgical device transfer from one logic/schema to another as appropriate for the data needs of the surgical computing system and the network as a whole.

In logic/schema C 51366, the observation logic applied at the surgical device may include one or more modes and/or triggers. Such complex logic may enable sophisticated observation options to be performed (and, in an embodiment, recommended by a machine learning model, for example). Here, the observation point measuring tissue impedance does so in a first mode 51380 by making observations (and sending such timestamped observations to the surgical computing system) at a fixed frequency like that of logic/schema A 51362.

Logic/schema C 51366 may include a first trigger, for example, upon detection of the button press 51370, the schema C 51366 may include a duration of time 51382 or offset at the end of which observation of the tissue impedance transitions from the rate of the first mode 51380 to a rate of a second mode 51384. Here the rate of the second mode 51384 may be a rate even higher than that associated with schema B 51364, for example. Such a high temporal resolution in this second mode 51384 may enhance the surgical device's resolution of identifying a local minimum of the tissue impedance and may be used to more quickly adapt to the tissue impedance dropping below a threshold, for example.

The logic/schema C 51366 may include a second trigger, for example, upon detection of the power ramp down 51377. At this point, the schema C 51366 may provide a second duration 51386 during which the observation of the tissue enters a third mode 51388 performed at a third data rate that is between the first data rate and the second data rate. Such a third data rate may provide granularity during the ramp down duration.

As shown in FIG. 35, the triggers associated with schema C 51366 may be from the surgical device via which the tissue impedance is being measured. In an example, one or more triggers of the observation point schema may be derived from surgical devices other than that making the observation. For example, a trigger in an observation point schema may include messaging from another device within the system, control information from the surgical computing system, for example, and/or manual indications from one or more user interfaces associated with a display or other equipment within the surgical system, for example.

The dynamic configurability of the observation point logic/schema and/or the ability to derive inter-device coordination of observation timing facilitate the use of a machine learning platform to further refine the operation of the one or more surgical devices and the surgical computing system, for example.

For example, a machine learning algorithm monitoring such measured parameters (e.g., observation point schemas) over time may determine temporal implications, interactions, and the like. Such a machine learning model may be used to improve data utilization, consistency, accuracy, and/or desired outcomes, and the like. The flexible observation point schema (e.g., the ability to specify when a surgical device makes the measurement, how often it checks, its wait times, its rate of change over time, and the like) may enable such improvements.

For example, a machine learning algorithm, like that disclosed herein, may be used to determine the optimal time to collect the data based on temporal relationships determined from previous acquisitions. For example, the algorithm may compile the acquisition of data and may compares it with resulting device behavior, outcomes, operation, and the like. Such comparisons may be focused on aspects of observation point schema, such as the time-till-collection (e.g., latency), frequency of collection, collection logic, and/or any other time-dependent aspect of the collection. The comparisons may determine relationships between the usefulness and/or viability of the data with the time dependent property of its collection. Such a relationship, embodied by the machine learning process, for example, may be to change (e.g., via a configuration update) the time dependent aspect of the collection in order to improve functional use of the data.

Such time dependent aspects may reflect repeatable time dependent behaviors within a surgery. For example, such time dependent aspects may be the result of nature of tissue being operated on (e.g., the viscoelastic behavior of the tissue). For example, such time dependent aspects may be the result of a surgical treatment of the tissue effect on the tissue (e.g., the effect of coagulation, electroporation, and the like on tissue impedance). For example, such time dependent aspects may be reflected in the effect of the number and/or frequency of data points to capture the result of such effects tissue and/or any other surgical interaction that may drive such repeatable time dependent behaviors. As disclosed herein, surgical data may be used to determine a timing (e.g., an optimal timing) from a surgical procedure and/or the operation of other devices in the surgical theater. And, such determination may be influenced by a historic timing or trend, for example.

The flexible timing approach disclosed herein may be used in connection with medically related time-based decisions, such a that associated with time-dependent tissue relationships, such as visco-elastic tissue creep, tissue impendence changes in relation to coagulation and/or force, viscous fluid flow impacts (e.g., viscous fluid flow rate, viscous fluid flow range, viscous fluid flow penetration, and the like) of electro-poration and/or ablation.

In an example, various observation point schema across various observation points may be used to monitor tissue compression and/or load to determine a recommended timing (e.g., a feedback control) for control of a powered actuator in a surgical device.

In an example, various observation point schema across various observation points may be used to determine a recommended timing for measuring a tissue property for use in controlling a surgical device. As shown in FIG. 35, the relationship among surgical device control, power, and tissue impendence may be associated with various observation point schemas. Similarly, observation point schemas may be used in the context of other tissue/device interactions, such as load stroke and force, surgical stapler firing time, force vs time in tissue viscoelasticity, micro tissue tension load for energy sealing, and the like.

For example, in the context of energy sealing, such observation point schemas may be used to refine how to monitor the micro tissue tension load over a time period to determine the ideal time to apply energy for sealing. For example, optimal energy sealing may generally occur when micro tissue tension (e.g., internal forces within the tissue due to compression, welding, and/or induced forces from the jaws) is at a minimum. Vector forces placed on an anatomic structure due to moving or pulling on the structure tend may be force magnitude dependent making coordination of observation point schema between tissue measurement and internal measurement of mechanical force being applied particularly relevant for application of a machine learning model. For example, any relevant parameter monitored may be suitable for observation point schema changes, such as type of tissue, pressure between jaws, articulation angle, amount of tissue in jaws, weight of tissue outside of jaws, diseased state of tissue, instrument operation, and the like.

For example, observation point schema changes may be used to address various timing relations to surgeon input. For example, observation point schema with triggers may be used to assess wait-times relative to suggested surgeon pauses for tissue relaxation. In an example, such observation point schema changes may be used to assess an auto-pause, where the device pauses operation until one or more tissue characterizations are met.

The flexible nature of the observation point schema and their amenability to analysis, as disclosed herein, may aid in advanced coordination among surgical devices, such as an identification of a wait time between a trigging event and the biomarker measurement to provide a control response (e.g., an optimal control response). For example, using both a recommended timing and a rate-of-change parameter in the observation point schema, a subsequent task, event, and/or monitoring event may be determined. For example, a recommended observation point schema may address both a time (e.g., time range) for monitoring and a rate-of-change (e.g., range of rate-of-change) that may be used to ultimately forecast such an upcoming event.

Further, the flexible nature of the observation point schema may enable assessment of a forward time proroga-tion of an event relative to it causing measurable effects. For example, tissue properties encountered in previous surgical phase may be used to adjust parameters in upcoming instrument activations. In an example, surgical technique from previous steps may be monitored within same procedure as a predictive means for time or future steps. Such observation point schema may be used to develop a display of current job within the procedure plan and a projection of the time between tasks and/or operations. Such observation point schema may be used to develop a display of current job within the procedure plan and a highlight of upcoming difficult tasks. Such observation point schema may be used to develop recommendations of technique adaptation and/or the impacts on forecasted outcomes, time to accomplish, impact on further future tasks, and the like. For example, in the context of a liver resection pringle maneuver, timing relevant to the pattern of on/off hepatic artery occlusion may be considered.

In an example, such observation point schema may be used to better monitor HCP (e.g., surgeon) stress level, comfort level, fatigue level, and the like relative to difficult procedural steps. Such observation point schema may be useful in forecasting and/or recommending changes in approach, changes in instruments, changes in technique (e.g., based on monitoring such HCP reactions to previous steps withing the same procedure).

For example, how a surgeon reacts to a predefined surgical step relative to their peers or previous operations may be used to determine improved upcoming procedural steps within that same procedure to minimize the impacts on time or stress level. To illustrate, surgical information that indicates a surgeon takes twice as long as usual or twice as long as an average surgeon to accomplish a tissue plane separation and/or skeletonization of a tumor and/or an artery to a tumor may imply complications with the anatomy. Such an assessment may be used to identify more aggressive techniques and/or more exacting tissue separations tools (e.g., ultrasonic scalpel rather than a monpolar dissector).

In an example, in the context of a lower-anterior resection (LAR) procedure, a surgeon may have to be in positions that are not ergonomically friendly on the body causing stress and/or fatigue on the surgeon. Observation point schemas that enable the adjustment of monitoring in view of surgical information, such as operating table position and/or procedural step, may be used to identifies such a position and/or determine positional shifts that could reduce the stress/fatigue.

In an example, the operation and/or timing of information to display may be influenced by surgical information such as that related to user interaction and/or responses of the user receiving the information. For example, observation point schema may be used to adapt the operation of a display based on the timeliness of the user response. For example, display operations associated with negative reactions (e.g., ignoring suggestions, difficulty executing suggestions, reduced outcomes, longer than forecasted time-to-complete, etc.) may be reduced. And display operations associated with positive reactions (e.g., improved technique, improved outcome of task, positive response from user, etc.) may be increased.

In an example, such observation point schemas may be used to identify high-sampling-rate measures that use significant resources without an improved outcome. For example, a determination of when to measure a biomarker or event could be based on numerous different surgical/patient/user parameters, as assessed by the machine learning model in view of patient outcome. Biomarkers being sampled at an unnecessarily high sampling rate may reduced, alleviating load on the system and overall cost without an impact to patient outcomes.

In an example, such observation point schema may be used to assess a rate of change of a combined medical algorithm. For example, appropriate timing of measurements may facilitate the determination of the preferred time to measure biomarkers contributing such an algorithm (e.g., a patient scoring system). For example, appropriate timing of measurements may facilitate the correlation an HCP-selected desired outcome to the specific timing, when to measure, what to measure, the pattern of measurement, and the like.

In an example, such observation point schemas may be used in the improved operation and/or assessment of operation in a powered surgical stapler. For example, in a powered stapler the first detected contact of tissue may signify a jaw approximation such that forces are beginning to induce a creep response on tissue. To illustrate, the tissue could be initially 6 mm thick (e.g., well above the 2 mm indicated limit of a cartridge, e.g., a green cartridge, in use). Using such a first detected contact as the point at which the device measures the duration of force applied may enable a determination of the resulting effective tissue height. A machine learning approach, enabled by the flexible observation point schemas disclosed herein, may be used to hone in on the most appropriate moment to start the measurement of the duration of force applied. Here, an outcome may include a resultant staple height, effectiveness of the staple line, surgeon input, or the like. And the machine learning approach is useful in such optimization problems-setting the firing rate and/or pausing schedule, in view of such a multivariable system.

Figure 36:
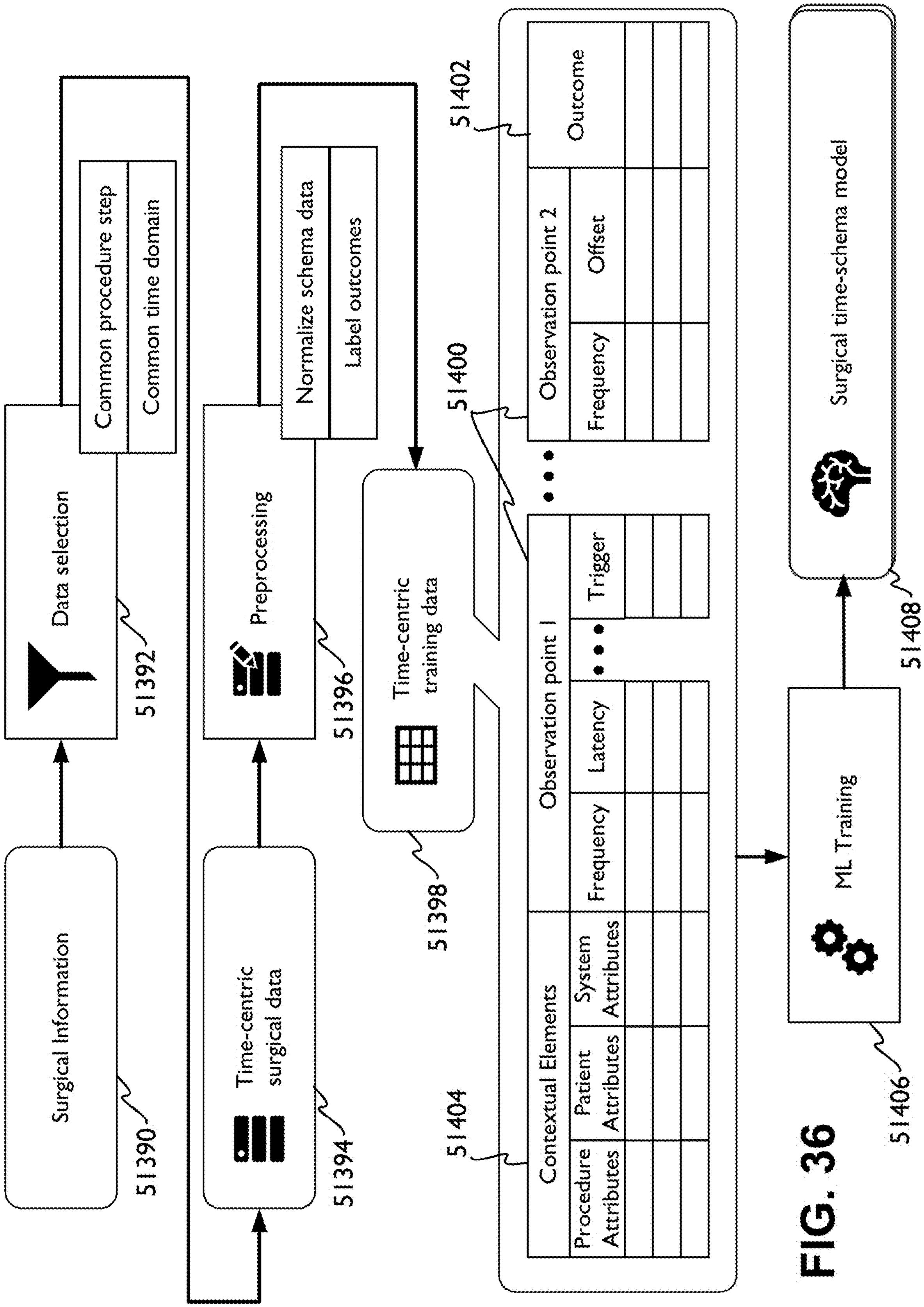
FIG. 36 illustrates a data processing pipeline for training an example surgical time-schema model.

FIG. 36 describes or illustrates the data processing and training of a machine learning model. At 51390, surgical information, including observations and their associated observation point information may be collected (e.g., collected at a surgical computing system). For example, the surgical information collected at 51390 may include the surgical information disclosed with reference to FIGS. 7A-D. For example, the surgical information may include observations, procedure data, patient data, and the like. The surgical information may be collected from one or more surgeries, for example. The surgical information may be collected from one or more different procedures, for example. The surgical information may be collected from one or more surgical facilities, for example.

At 51392, the collected surgical data may be filtered via a data selection process. The data selection process may organize the collected data into data groups associated with common surgical procedure steps and/or common reference time domains. The data selection process may be a manual process, an automated process, a batch process, a real-time process, or the like. The data selection process may incorporate the observation point manifest, for example, associated with a surgical procedure step.

The surgical procedure steps may include any identifiable segment of surgical procedure data with an associated outcome by which the relative success of the surgical procedure may be assessed. For example, the surgical procedure steps may include steps decerned by a situational awareness function of the surgical computing system (e.g., surgical hub). For example, the surgical procedure steps may include steps associated with a defined surgical plan. The data selection process may result in time-centric surgical data at 51394. The time-centric surgical data may include information, in a common time domain, that represents the timing of observations in the surgical system.

At 51396, the time-centric surgical data may be preprocessed. For example, the time-centric surgical data may be preprocessed to normalize the various schema and/or label outcomes. The preprocessing may result in time-centric training data at 51398. Regarding normalization, for each surgery-instance of the one or more procedures steps present in the time centric data, the present observation schema may be preprocessed into one or more columns of normalized characteristics. The preprocessing may include any data normalization process suitable for organizing data for machine learning training. In an embodiment, the surgical computing system may, in effect, pre-normalize the data by configuring surgical devices with schema in a normalized manner. In an embodiment, the preprocess may consider the various schema characteristics, identify the unique types of schema characteristics, and populate one or more tables with columns associated with the schema characteristic. The normalizing of the schema data may include a transform of the individual observation point schemas to a common structure, for example. To illustrate, the resultant time-centric training data may include a listing of observation points 51400 and their corresponding timing characteristics, such as latency, frequency, presence of triggers, and the like.

Regarding labeling, the result time-centric training data, being consolidated into records associated with surgery-instance procedural step(s), include one or more assessments of the corresponding surgery-instance procedural step(s). The assessment may for the content of the label 51402. For example, each surgery-instance procedural step(s) record may be assessed according to one or more metrics, such as a manually entered success metric, an automatically recorded duration, an assessment of whether the procedure proceeded to the next planned step or if it deviated, and the like.

The resultant time-centric training data may represent data pairs suitable for a supervised machine learning training algorithm. For example, the time-centric training data may include contextual information 51404 related to the surgery-instance procedure step(s), such as information related to, for example, the procedure performed, the patient on which the procedure was performed, and/or the system in which the procedure was performed. Such data may be used to define the context for each record. The contextual information 51404 may include details about the procedure, including, for example, an identifier of the procedure, the instruments used, a listing of surgical tasks, staffing, and the like. The contextual information 51404 may include details about the patient, including, for example, age, weight, demographic information, vital signs, lab work values, assessments of tissue type/tissue quality, and the like. The contextual information 51404 may include details about the system including, for example, listing of surgical devices and support equipment, the system location, and the like. The time-centric training data may include information related to the observation point(s) 51400 used. And the time-centric training data may include information related the one or more labels 51402.

At 51406 the machine learning platform may be used to train a model 51408 in view of the time-centric training data (e.g., recommending observation schema). The training may include any suitable technique, including those disclosure with reference to FIGS. 8A&B for example. For example, the training may include a supervised learning technique. The volume of the time-centric training data may include any number of records suitable for a consistent convergence of the machine learning training. For example, a time-centric training data implementation associated with an advanced energy device may include surgical information from over a hundred surgery-instance procedure steps data records. For example, the output of the ML training process may result in a surgical time-schema model 51408. For example, the machine learning platform may be used to train a surgical time-schema model 51408 in view of the timing alternatives of observation points based on data with a common time reference.

Figure 37:
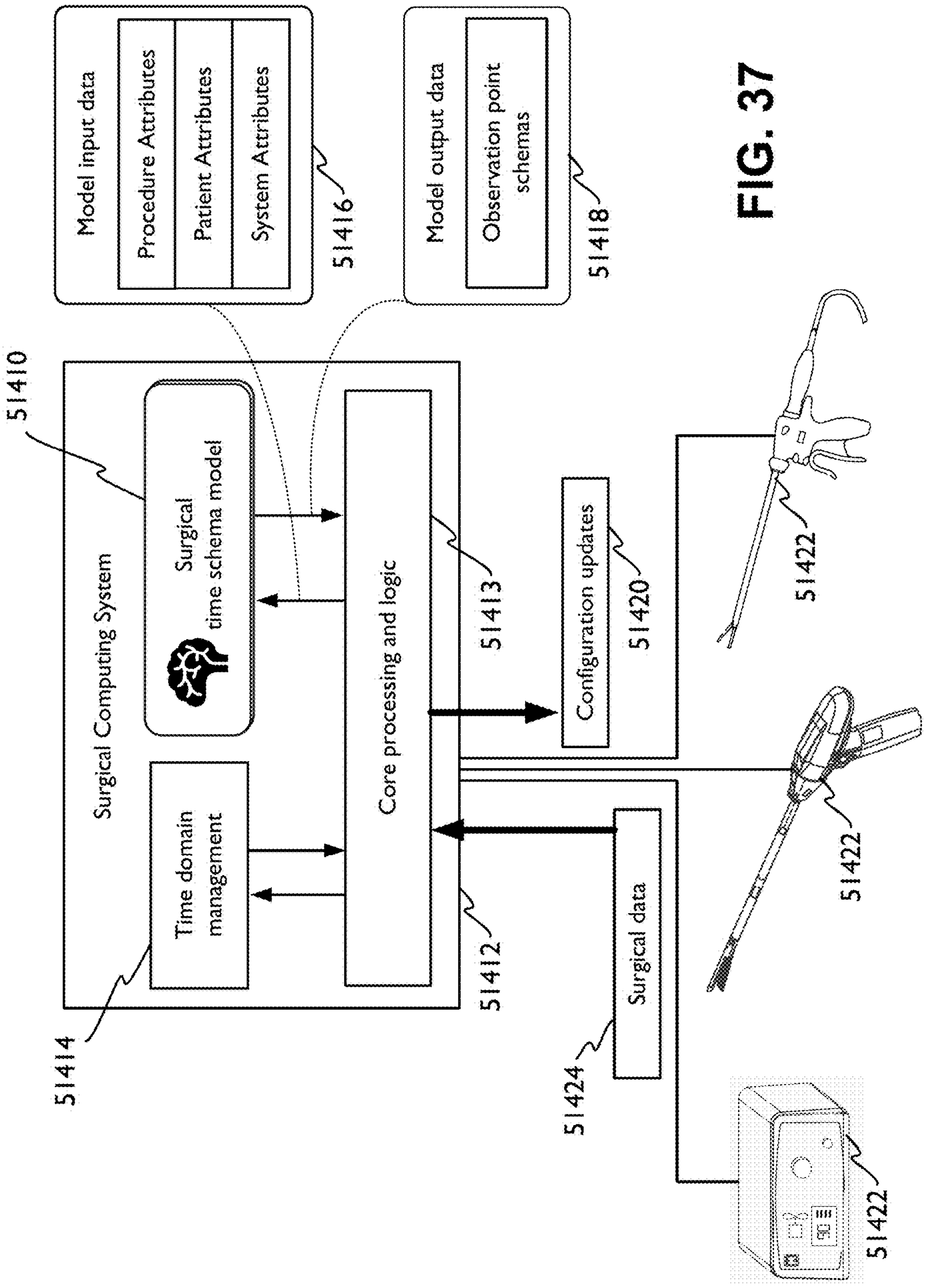
FIG. 37 is a block diagram illustrating an example surgical time-schema model in a surgical computing system.

FIG. 37 illustrates an example surgical time-schema model 51410 deployed for use in a surgical computing system 51412. The surgical computing system 51412 may include a core processing and logic component 51413, a time domain management function 51414, and the surgical time schema model 51410, for example.

The surgical computing system 51412 may receive surgical information for use as input to the surgical time schema model 51410. For example, the surgical computing system 51412 may receive surgical information for use as input data 51416, such procedural attributes, patient attributes, and system attributes, and the like. The input data 51416 may correspond in type to the contextual information 51404 used in training, for example.

The surgical time schema model 51410 may generate output data 51418. The output data 51418 may include one or more recommended observation point schemas for use in a particular procedure. The output data 51418 may correspond in type with the one or more observation points 51400 used in training, for example.

The input 51416 and/or output 51418 of the surgical time schema model 51410 may occur at the outset of a surgical procedure, for example (e.g., the outset of a surgical procedure as shown in FIG. 7D. At the outset of a procedure, the surgical computing system 51412 may initialize the environment and may learn system attributes associated with the identity and nature of the devices and surgical equipment to be used. The surgical computing system 51412 may initialize the environment and may learn information relevant to the patient from the patient's electronic medical record, for example. The surgical computing system 51412 may initialize the environment and may learn information relevant to the procedure (e.g., as derived from a procedure plan and/or by situational awareness capabilities of the surgical computing system).

Based on this input data 51416, the surgical time schema model 51410 may recommend on or more observation point schemas. In an example, the surgical computing system 51412 include a human interface confirmation process (not shown) to evaluate, confirm, and/or edit the recommended observation point schemas. After confirmation of such recommended observation point schemas, the surgical computing system 51412 may send one or more configuration updates 51420 to the surgical devices 51422.

In an example, the surgical computing system 51412 may send one or more configuration updates 51420 to the surgical devices 51422 to implement recommended observation point schemas without a human interface confirmation.

In an example, the surgical computing system 51412 may engage a human interface confirmation process based on the difference between the present observation points (e.g., as reported by the surgical instruments and/or via the observation point manifest) and the recommended observation point schema. For example, changes that differ by more than a configurable confirmation threshold may prompt human confirmation. For example, changes that are below a configurable confirmation threshold may be implemented without human confirmation, for example.

In an embodiment, the surgical computing system 51412 may include a real-time machine learning model suitable for displaying recommendations and/or alternative techniques based on time-dependent activities and their relationship with future outcomes or steps or use.

The configuration updates 51420 may include one or more of the recommended observation point. Subsequent to the configuration updates, the surgical devices 51422 may send surgical data 51424 to the surgical computing system 51412 in accordance with the recommended observation point schemas. The configuration updates 51420 may include updates to provide a common time domain for subsequent observations. Subsequent to the configuration updates, the surgical devices 51422 may send surgical data 51424 to the surgical computing system 51412 in accordance with the common time domain.

Figure 38:
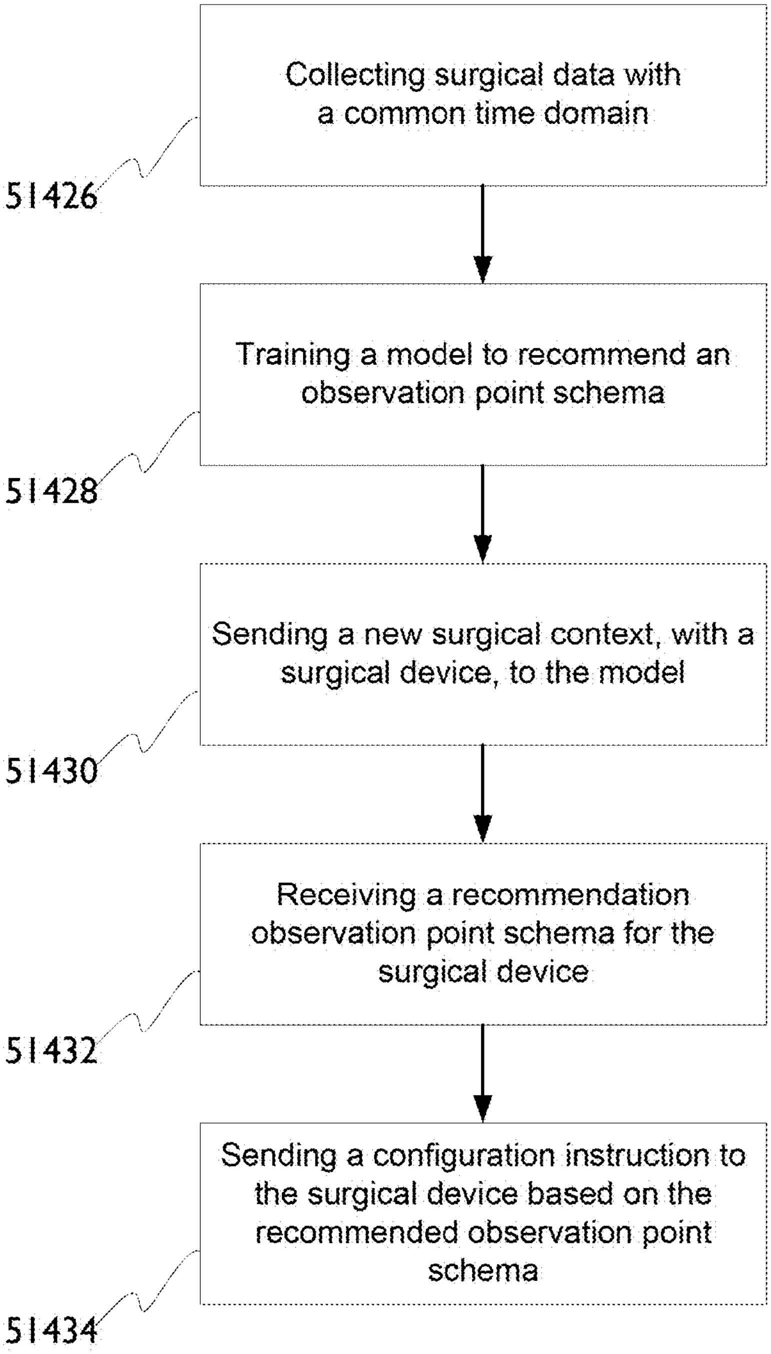
FIG. 38 is a process flow diagram illustrating operation of a surgical computing system having an example surgical time-schema model.

FIG. 38 is a process flow diagram illustrating the collection of surgical data and the updating of observation point schema in surgical devices. At 51426, surgical data may be collected in a common time domain. For example, the surgical data may be collected in time domain in view of the process disclosed in FIG. 33B. A common time domain for collecting surgical data may facilitate the identification of observation timing relationships across devices in the surgical system. For example, providing a common time domain of collected surgical data may facilitate the operation of the machine learning training of the model, for example.

At 51428, a model (e.g., such as model disclosed in FIGS. 36&37) may be trained to recommend an observation point schema in view of input data. The model, as trained and deployed, may receive input at 51430. The input may include the surgical context, the patient attributes, the system attributes, and the procedure attributes, for example. The model may receive input at 51430 because the surgical computing system and/or another device may send such an input. For example, for a model deployed in a surgical computing system itself, the surgical computing system may send such input data internally. For example, for a model deployed on a computing system other than the surgical computing system, the surgical computing system may send such input via a network, for example. In an example, the model may be deployed at an edge network server, a local server, a cloud server, or the like.

In response to the input, the model may recommend an observation point schema for a surgical device, at 51432. The surgical computing system may receive such output data (e.g., internally and/or via a network from the deployed model). And, at 51434, configuration instructions, consistent with a recommended observation point schema, may be sent a surgical device for implementation.

Examples herein may utilize data derived from one type or specialty of surgery to provide surgical recommendations for a different specialty. Surgical data may be received from surgical procedures (e.g., from a first surgical procedure and a second surgical procedure) to derive a common data set. The common data set may include related surgical data between related sub-tasks (e.g., a first sub-task associated with the first surgical procedure and a second sub-task associated with the second surgical procedure). The common data may be derived via a neural network (e.g., a first neural network) that is trained to determine the common data set. The common data set between the related sub-tasks (e.g., first sub-task associated with the first surgical procedure and a second sub-task associated with the second surgical procedure) may include common procedure plans from the different surgical procedure(s), common data from different procedure(s), or common surgeon recorded interaction(s) from different procedure(s). Surgical data within the common data set between the related sub-tasks (e.g., first sub-task and a second sub-task) may be compared. A surgical recommendation may be provided for a surgical task based on the comparison of the data between the related sub-tasks (e.g., first sub-task and a second sub-task). The surgical recommendation may be provided via a neural network (e.g., a second neutral network) that is trained to provide the surgical recommendation for the surgical task. The surgical recommendation may be outputted for performing the surgical task.

Figure 39:
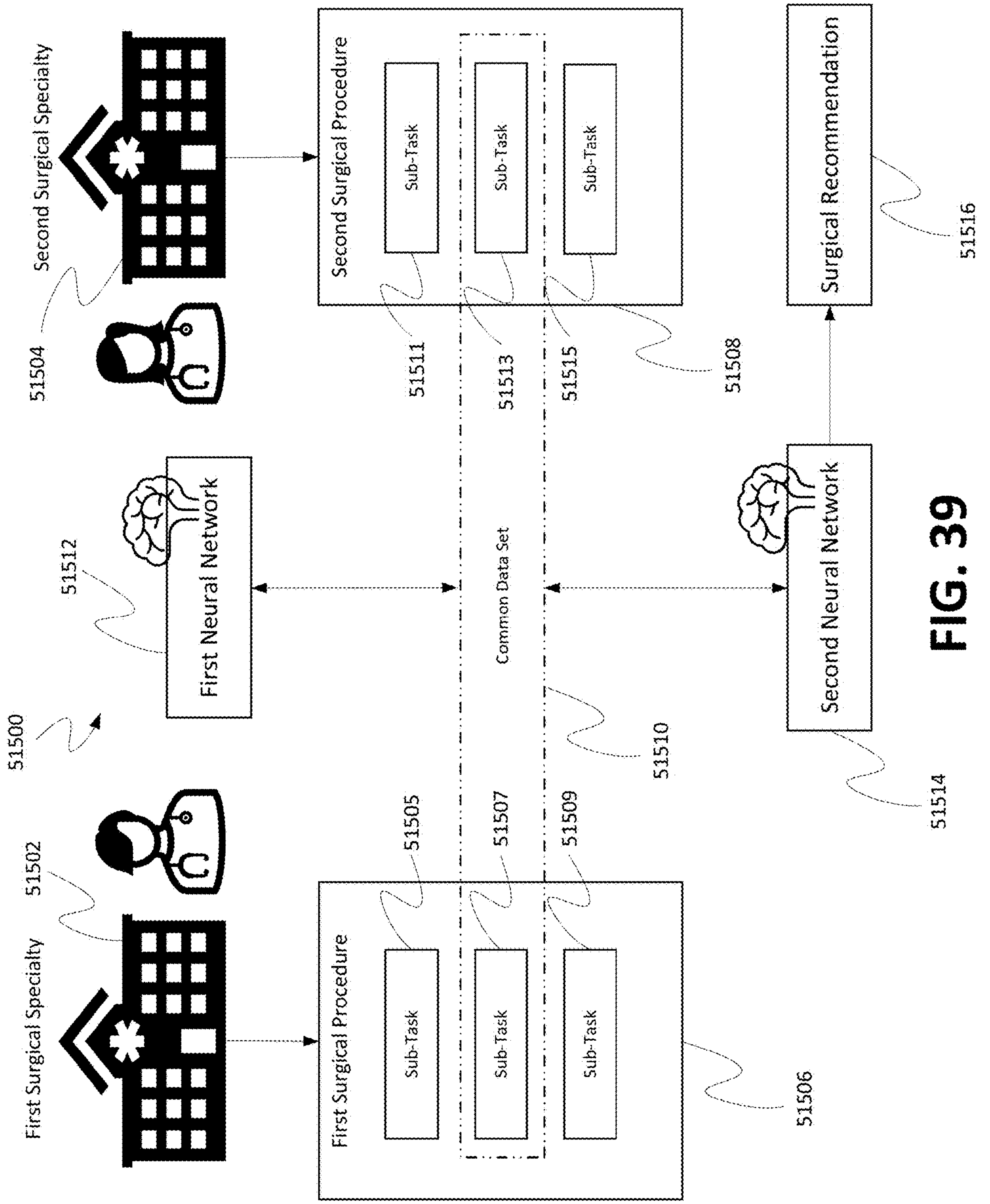
FIG. 39 illustrates an example for determining common data sets between different surgical specialties.

FIG. 39 illustrates an example 51500 for determining common data sets between different surgical specialties. The example 51500 may include a first surgical specialty 51502 and a second surgical specialty 51504. Surgical data may be provided from a first surgical procedure 51506 related to the first surgical specialty 51502. Surgical data may be provided from a second surgical procedure 51508 related to the second surgical specialty 51504. Surgical data from the first surgical procedure 51506 may be divided into sub tasks 51505, 51507, 51509. Surgical data from the second surgical procedure 51508 may be divided into sub tasks 51511, 51513, 51515. Sub tasks 51507 of the first surgical procedure 51506 and sub task 51513 of the second surgical procedure 51508 may be related. Although 51507 and 51513 are shown as related in this example, any one or more of the sub tasks 51505, 51507, 51509 of the first surgical procedure 51506 may be related to any one or more the sub tasks 51511, 51513, 51515 of the second surgical procedure 51508. The related sub-tasks may include common procedure plan(s), common data, or common surgeon recorded interaction(s) between the first surgical procedure 51506 related to the first surgical specialty 51502 and the second surgical procedure 51508 related to the second surgical specialty 51504. A common data set 51510 may be determined between the first surgical procedure 51506 and the second surgical procedure 51508 via a first neural network 51512. The first neural network 51512 may be trained to determine the common data set 51510. The common data set 51510 may include surgical data associated with the sub task 51507 of the first surgical procedure 51506 and surgical data associated with the sub task 51513 of the second surgical procedure 51508.

A surgical recommendation 51516 for performing a surgical task may be provided via a second neural network 51514. The surgical recommendation 51516 may be based on comparing data associated with the sub task 51507 of the first surgical procedure 51506 with data associated with the sub task 51513 of the second surgical procedure 51508. The second neural network 51514 may be trained to determine the surgical recommendation 51516. The surgical recommendation 51516 for performing the surgical tasks may be outputted.

The common data set 51510 between the related sub-tasks 51507 and 51513 across the first surgical procedure 51506 and the second surgical procedure 51508 may include similar surgical aspects. The first neural network 51512 may be trained to determine the common data 51510 set using the similar surgical aspects between the first surgical procedure 51506 and the second surgical procedure 51508. The common data set 51510 between the related sub-tasks 51507 and 51513 may include at least one of similar surgical jobs, similar intended outcomes, similar constraints, similar device utilization, similar surgical approaches, similar procedure, and/or similar patient complications. The first surgical procedure 51506 and the second surgical procedure 51508 may be surgical procedures in different geographic regions (e.g., different surgical techniques by country). The first surgical procedure 51506 and the second surgical procedure 51508 may be robotic vs. laparoscopic vs. open. The first surgical procedure 51506 and the second surgical procedure 51508 may involve different disciplines, different disease types, and/or different manifestations. Improvements from one or more distinct groups may be used from the first surgical procedure 51506 to improve similar situations for the second surgical procedure 51508 and vice versa.

In examples, databases of cases may be automatically arranged by specialty, initial diagnosis, and/or machine-predicted diagnosis across different surgical procedures (e.g., the first surgical procedure 51506 and the second surgical procedure 51508). In examples, collected datasets may be arranged into sub-tasks that may be used as building blocks of common tasks or common jobs that enable comparison of data from different surgical procedures (e.g., the first surgical procedure 51506 and the second surgical procedure 51508). Surgical data may be received across the different surgical procedures (e.g., the first surgical procedure 51506 and the second surgical procedure 51508). The surgical data may be grouped into sub tasks, such as sub-tasks 51505, 51507, 51509 associated with the first surgical procedure 51506 and sub-tasks 51511, 51513, 51515 associated with the second surgical procedure 51508. In examples, data from the sub-tasks may overlap. A common data set 51510 from related sub tasks (e.g., such as sub-tasks 51507 and 51513 as shown in FIG. 39) may be determined (e.g., from the data from the sub-tasks that may overlap).

The first neural network 51512 may be trained to determine the common data set 51510 by determining related patient data between the different surgical procedures (e.g., the first surgical procedure 51506 and the second surgical procedure 51508). The common data set 51510 may include related patient data associated with related sub-tasks (e.g., sub-task 51507 and sub-task 51513). In examples, the related sub-tasks may be grouped based on patient placement on a bed (e.g., supine position, prone position, lateral position). In examples, related sub-tasks may be grouped based on patient information (e.g., patent age, patient weight, patient co-mobility/position limitations, etc.).

The first neutral network 51512 may be trained to determine the common data set 51510 by determining related surgeon data between the different surgical procedures (e.g., the first surgical procedure 51506 and the second surgical procedure 51508). The common data set 51510 may include related surgeon data associated with related sub-tasks (e.g., sub-task 51507 and sub-task 51513). In examples, the related sub-tasks may be grouped based on surgeon preferences (e.g., right/left-handed surgeons, surgeon bed side preference). In examples, the related sub-tasks may be grouped based on surgeon body characteristics (e.g., surgeon height, surgeon arm length, surgeon muscle strength, etc.).

The first neutral network 51512 may be trained to determine the common data set 51510 by determining data associated with related surgical instruments between the different surgical procedures (e.g., the first surgical procedure 51506 and the second surgical procedure 51508). The common data set 51510 may include data associated with related surgical instruments associated with related sub-tasks (e.g., sub-task 51507 and sub-task 51513). In examples, the related sub-tasks may be grouped based on surgical instrument characteristics (e.g., short vs long shafts, end-effector-curved vs straight, articulating vs straight, powered vs manual, etc.).

The first neutral network 51512 be trained to determine the common data set 51510 by determining data associated with related surgical approaches between the different surgical procedures (e.g., the first surgical procedure 51506 and the second surgical procedure 51508). The common data set 51510 may include data associated with related surgical approaches associated with related sub-tasks (e.g., sub-task 51507 and sub-task 51513). In examples, the related sub-tasks may be grouped based on surgical approaches used for surgery types (e.g., robotic, laparoscopic, open, flexible endoscopic/natural orifice, etc.). Some of the related surgical jobs or sub-tasks used in the first surgical procedure 51506 may be used in the second surgical procedure 51508 and vice versa. The common data set 51510 may include interchangeable jobs for analyses and relationship generation. In examples, common tissue mobilization, dissection, or margin identification examples may be used in thoracic (e.g., parenchyma resection, artery/vein transection), colorectal (e.g., sigmoid resection, anastomosis), or bariatric (e.g., roux-y, sleeve gastrectomy) procedures.

The first neutral network 51512 may be trained to determine the common data set 51510 by determining data associated with related surgical approaches between the different surgical procedures (e.g., the first surgical procedure 51506 and the second surgical procedure 51508). The first neutral network 51512 may determine the common data set 51510 by analyzing surgical outcomes, tool usage, or procedural examples of use. In examples, the first neutral network 51512 may use the procedure plan and the normal descriptive examples of the procedure as a means for comparing similar jobs or surgical outcomes from one procedure type to another to enable sub-division of the larger order tasks into more common groupable tasks for analysis. In examples, the first neural network 51512 may use a lookup table or supervised learning as a means for defining combinable datasets from different procedures, different regions, different specialties, and/or different surgical approaches (e.g., robotic, lap, etc.).

In examples, the first neural network 51512 may be trained to determine common data sets (e.g., the common data set 51510) based on the surgical outcomes, intended results, or constraints of the sub-tasks. In examples, adjustments or additional ports may be based on patient driven factors. The patient driven factors may be body mass index (BMI) (e.g., which may require driving to additional ports or locations) or co-mobility/other injuries that would prevent normal patient placement on the bed (e.g., which would require alterations to ports/access based on patient alterations on the bed). In examples, instrument selection adjustments may be based on new patient information compared to the standard/generic plan. BMI/obesity could require alteration to standard setup/instruments and suggest alternative instruments (e.g., longer instruments, short vs curve tip for end-effectors, lap vs open). In examples, adjustments to surgical sequences may be based on co-mobilities, patient anatomy, and/or organ variability. Patient vitals pre/during/post may alter the sequence of the surgery (e.g., sequence of dissection and/or mobilization of anatomy). In examples, adjustments to post operation recovery may be based on the time in recovery, post operation infection(s) or subtopic(s). In examples, adjustments to rehabilitation plans may be based on progress, setbacks, time gap(s) between post-surgery and starting rehab, and/or refinements to the plan based on patient response/recovery.

In examples, neural networks (e.g., the first neural network 51512) may be trained to break down surgical data sets into smaller manageable chucks based on a generic procedure plan or outline. In examples, neural networks (e.g., the first neural network 51512) may use data cataloging in the process of making an organized inventory of data (e.g., all data assets) in an organization, which may be designed to help data professionals quickly find the most appropriate data for any analytical or business purpose. If data mapping is completed, a data catalog (e.g., such as a think card catalog in a library) may be used to index where information (e.g., all information) is stored. The data catalog may use metadata to collect, tag, and store datasets. Datasets may be stored in a data warehouse, data lake, master repository, or another storage location. Cloud storage may be used for data.

Examples of data curation may be provided herein. Data curation may manage data through its life cycle for interest and usefulness. Data curation may organize and manage a collection of datasets to meet the needs and interests of a specific groups of people. Data curation may minimize the manifestation of data swamps which may be unstructured, ungoverned, and out of control data lakes. Due to a lack of process, standards, and governance, data swamps may make data hard to find, hard to use, and may be consumed out of context. A data lake may include raw unstructured or multi-structured data that may have unrecognized value for the firm. While traditional data warehouses may clean up and convert incoming data for specific analysis and applications, the raw data residing in data lakes may be (e.g., may still be) waiting for applications to discover ways to manufacture insights.

Examples of data mapping may be provided herein. Data mapping may be the process of matching fields from one database to another. Data mapping may be the first step to facilitate data migration, data integration, and other data management tasks. Examples of data migration may be provided herein. Data migration may be the process of moving data from one system to another as a one-time event.

Examples of data integration may be provided herein. Data integration may be an ongoing process of regularly moving data from one system to another. The integration may be scheduled, such as quarterly or monthly, or may be triggered by an event. Data may be stored and maintained at both the source and destination. Data maps, (e.g., like data migration) for integrations, may match source fields with destination fields.

For example, gastric cancer treatments in Japan may have meaningfully different outcomes from other parts of the world. Identification of patterns from surgeries performed in that region may be analyzed for sharing and sharing recommendations for better patient outcomes elsewhere. For example, laparoscopic surgical approach results in a procedure may require a quantifiable number of steps and a time duration (e.g., anesthesia time linked to patient outcomes). Robotic surgical approaches may have quantifiable differences in these and other measures.

Surgeon observation, health care professional (HCP) tracking, instrument tracking, or site visualization may be used as a means for identifying common data sets (e.g., the common data set 51510). Neural networks (e.g., the first neural network 51512) may be trained to use the user motions, grip orientation, device usage, or imaging of the surgical site as a means for determining the generic job being conducted and tag the information with this summary/conclusion in a manner that may allow later algorithm analysis to combine data from differing sources to be compiled together. This may leverage answers or relationships in one discipline or procedure type (e.g., the first surgical procedure) for use in other disciplines or procedures (e.g., the second surgical procedure).

For example, a system may monitor thoracic parenchyma tissue plane dissection to skeletonize the artery, vein, and bronchus for a segmentectomy of the lung. The task may involve repeated use of advance energy and traditional dissectors to gain access to the critical structures in order to uncover them and allow access for the transection of the structures before the segment can be transected. The system may (e.g., may then) compare these user hand motions, instrument choices, and end-effector motions to those of the mobilization procedure of colorectal surgery. In the mobilization procedure, (e.g., similar) repetitive dissections may be done to free up the colon for movement while maintaining the blood supply in its new position. Even though one task may be meant to cut off arteries and the other may maintain them, the task sub-set is very similar which may allow the system to tag them both as "tissue plane separation," "artery skeletonization," or "fine dissection." This may allow the two very different procedures the ability to combine the data into one group and may allow its conclusions from one procedure to be ported to the other. Local techniques of how to separate convoluted tissue planes, adhesions, or disorganized remodeled tissues in the lung may be directly used in the mesentery attachment of the colon.

Examples described herein provide the ability to build data in such a way that may be classifiable and comparable. Examples herein provide formats/data structures that may classify more complex motions/actions/device usage in a clear, repeatable, and measurable way, which may be different from application to application.

Figure 40:
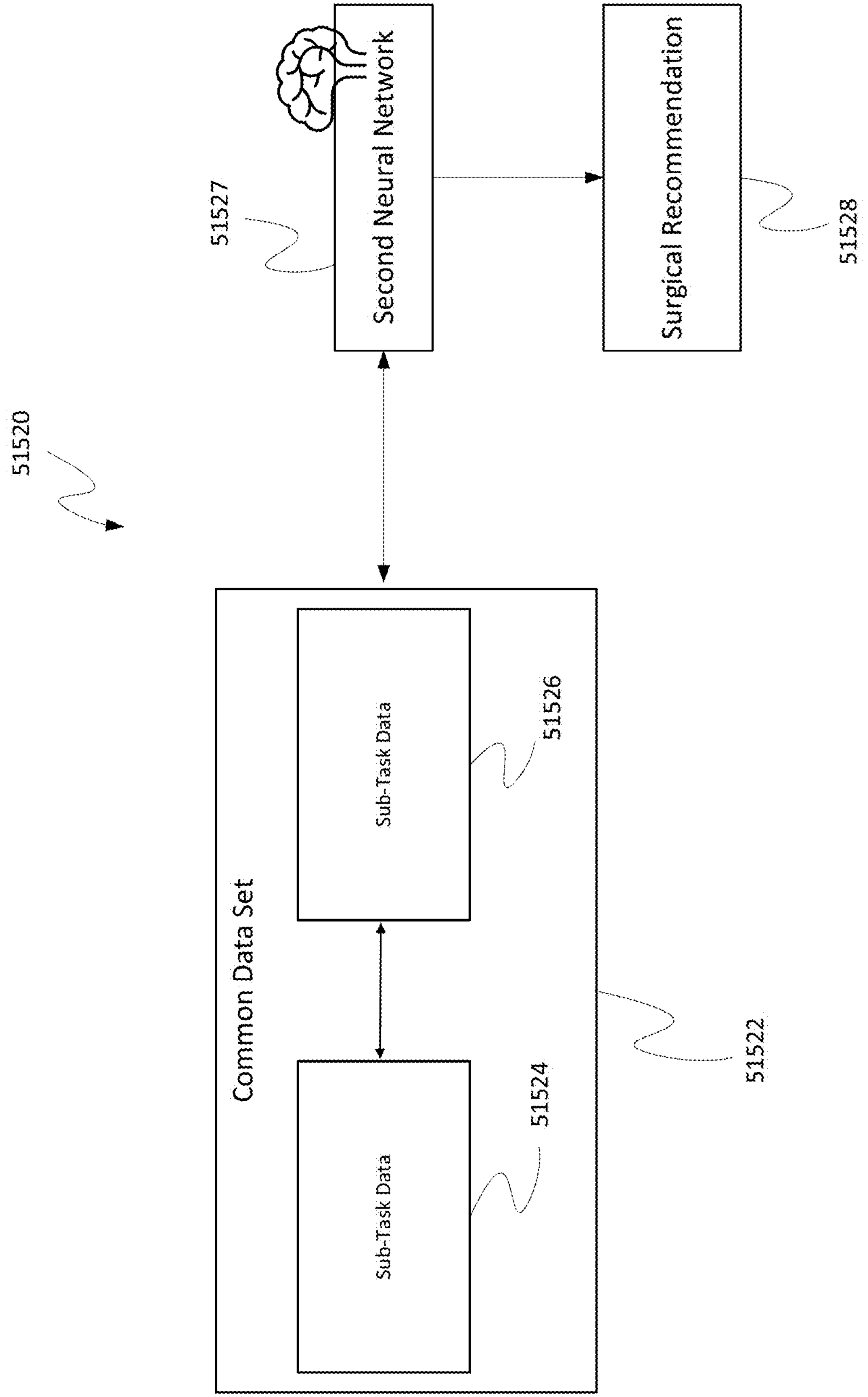
FIG. 40 illustrates an example block diagram for providing a surgical recommendation from a common data set.

FIG. 40 illustrates an example block diagram 51520 for providing a surgical recommendation from a common data set 51522. The common data set 51522 may include sub-task data 51524 and sub-task data 51526. The sub-task data 51524 may be associated with a first surgical procedure 51506 (shown in FIG. 39) and sub-task data 51256 may be associated with a second surgical procedure 51508 (shown in FIG. 39). The sub-task data 51254 and the sub-task data 51256 may be related sub-tasks. A second neural network 51527 may be trained to compare the sub-task data 51254 and the sub-task data 51246 within the common data set 51522 to provide a surgical recommendation 51526 for a surgical task. The surgical task may be related to the sub-task data 51524 and sub-task 51526. The surgical task may be performed within one of the same surgical procedures (e.g., the first surgical procedure 51506 or the second surgical procedure 51508 in FIG. 39) or may be performed within a different surgical procedure. The surgical recommendation 51528 for performing the surgical task may outputted for a surgeon or health care provider to perform.

Figure 41:
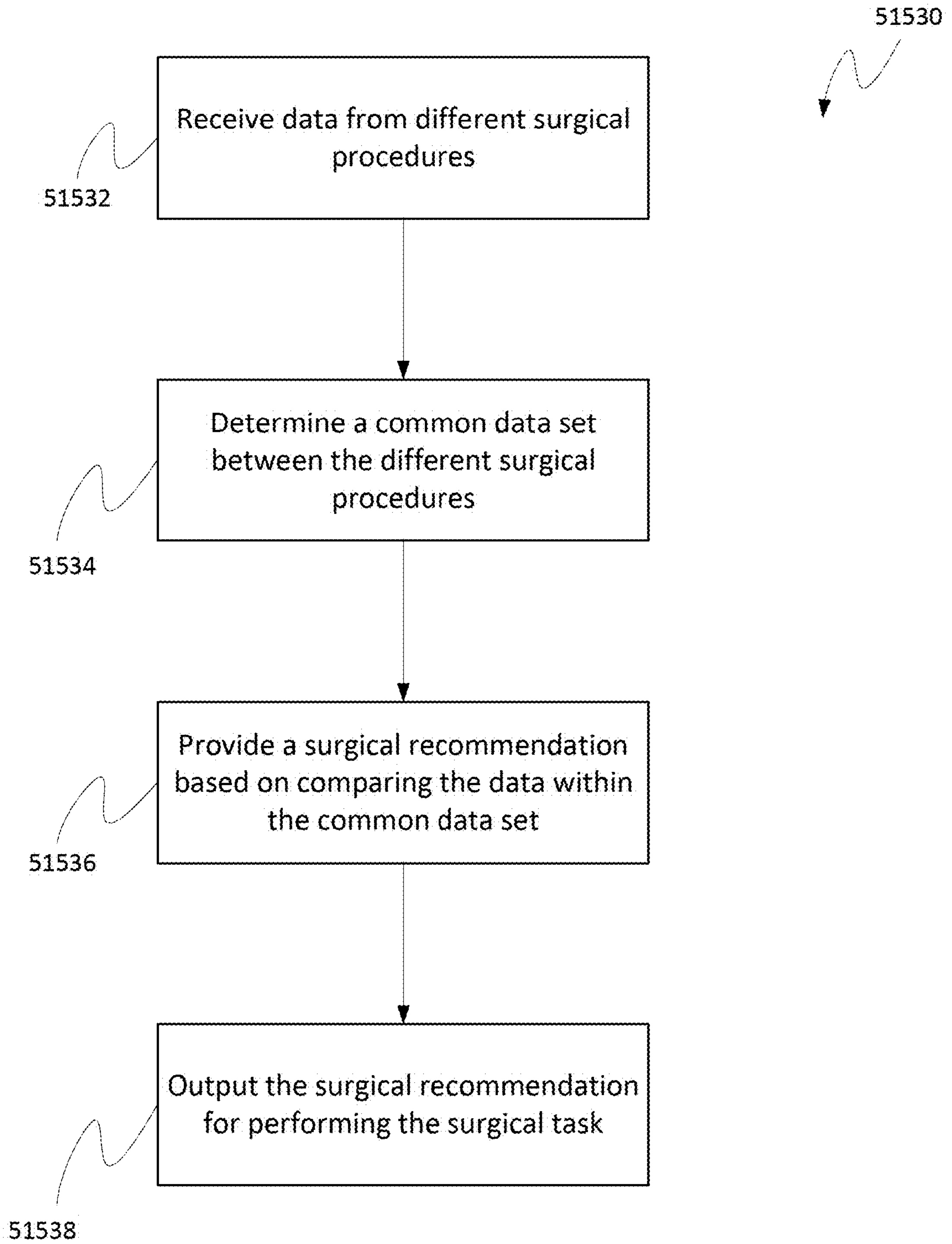
FIG. 41 illustrates an example flow chart for determining a common data set between multiple surgical procedures to provide a surgical recommendation.

FIG. 41 illustrates an example flow chart 51530 for determining a common data set between multiple surgical procedures to provide a surgical recommendation. At 51532, data may be received from different surgical procedures (e.g., the first surgical procedure 51506 and the second surgical procedure 51508 shown in FIG. 39). At 51534, a common data set may be determined from the received data. The common data set may be determined between data from the different surgical procedures (e.g., the first surgical procedure 51506 and the second surgical procedure 51508 shown in FIG. 39) via a first neural network (e.g., the first neural network 51512 as shown in FIG. 39). The first neural network may be trained to determine the common data set. The common data set may include data associated with different subtasks (e.g., sub-task data 51524 associated with the first surgical procedure and sub-task data 51526 associated with the second surgical procedure shown in FIG. 40). At 51536, a surgical recommendation for a surgical task may be provided based on comparing the data associated with the different sub tasks (e.g., sub-task data 51524 and sub-task data 51526 shown in FIG. 40) within the common data set between the different surgical procedures (e.g., the first surgical procedure and the second surgical procedure shown in FIG. 39) via a second neural network (e.g., the second neural network 51527 shown in FIG. 40). The second neural network may be trained to provide the surgical recommendation. At 51538, the surgical recommendation for performing the surgical task may be outputted.

Examples herein may include a neural network to determine an amount of data needed for performing a surgical task while maintaining the privacy of HCPs (e.g., making the HCPs unidentifiable). A first data set may be received for performing a surgical task. The first data set may be evaluated to determine how it performs the surgical task. Based on the evaluation of the first data set performing the surgical task, data from the first data set may be filtered to determine a second data set for performing the surgical task via a neural network. The neural network may be trained to filter the data from the first data set to determine the second data set for performing the surgical task. The data filtered from the second data set may be data that can identify HCPs. The second data set may have a lower amount of data than the first data set.

Figure 42:
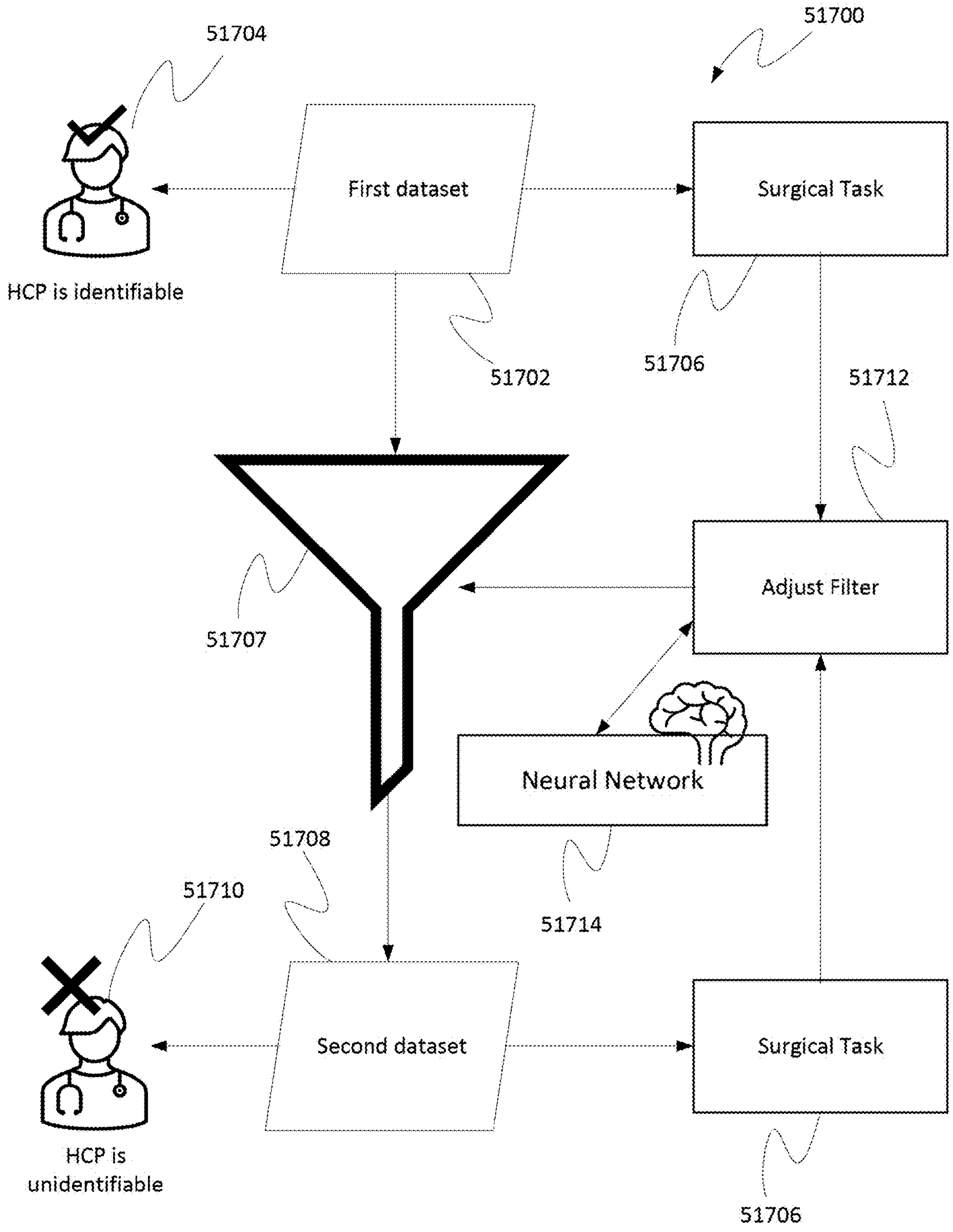
FIG. 42 illustrates an example for filtering a surgical data set.

FIG. 42 illustrates an example for filtering a surgical data set. The example 51700 may include a first dataset at 51702, which may be received to perform a surgical task 51706. The first data set 51702 may include surgical data that identifies an HCP at 51704. The first data set 51702 may be evaluated to determine to how the first data set 51702 performs the surgical task 51706. Based on the evaluation of the first data set 51702 performing the surgical task 51706, the first data set 51702 may be filtered at 51707 to determine a second dataset 51708 for performing the surgical task 51706 via a neutral network 51714. The neural network 51714 may be trained to adjust the data filtered at 51712 for performing the surgical task 51706. The surgical data included in the second data set 51708 (e.g., that is filtered from the first data set 51702) may not identify the HCP as shown at 51710. The second data set 51708 may have a lower amount of data than the first data set 51702. The surgical data filtered from the first data set 51702 may include identifiable data that may be used to identify HCPs. This may protect the privacy of HCPs while still successfully performing the surgical task 51706. The second data set 51708 may be outputted to perform the surgical task 51706.

Figure 43:
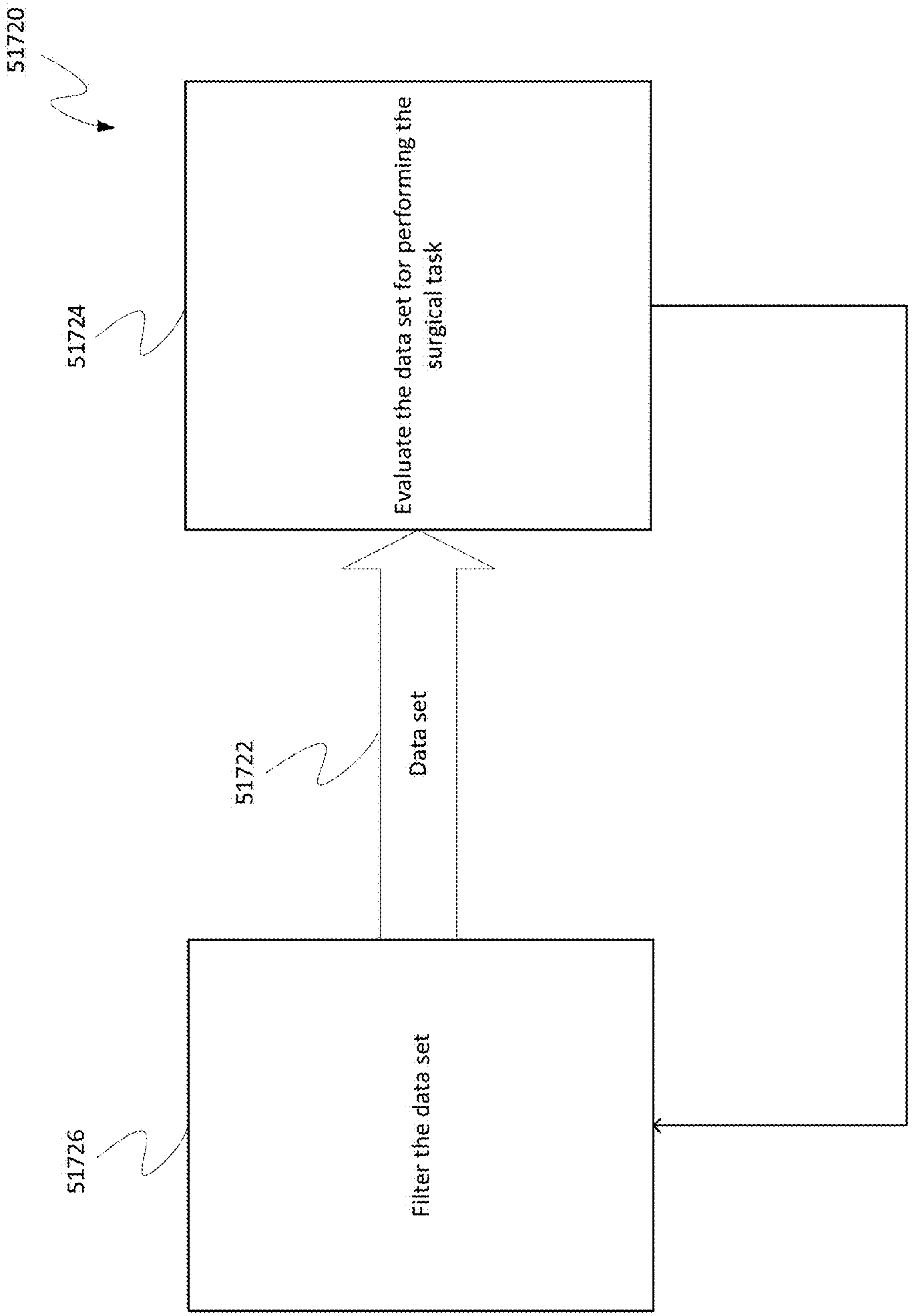
FIG. 43 illustrates an example block diagram for filtering a data set.

FIG. 43 illustrates an example block diagram 51720 for filtering a data set. The block diagram 51720 may include a data set at 51722. At 51724, the data set 51722 (e.g., the first data set) may be evaluated to determine how the data set 51722 (e.g., the first data set) performs the surgical task. Based on the evaluation of the data set 51722 (e.g., the first data set) performing the surgical task, at 51726, data from the data set 51722 (e.g., the first data set) may be filtered to determine a second data set for performing the surgical task via a neural network (e.g., the neural network 51714 shown in FIG. 42). Neural networks (e.g., the neural network 51714 shown in FIG. 42) may be trained to filter the data from the first data set to determine the second data set for performing the surgical task.

Neural networks (e.g., the neural network 51714 shown in FIG. 42) may be trained to balance the collection of health care provider specific data needed to perform a surgical task with the need to limit data collection to maintain the privacy of the HCPs. In examples, neural networks may evaluate data and identify relationships within the data. Based on the evaluated data and the relationships within the data, neutral networks may determine whether certain data sets can successfully perform surgical tasks. If a data set can successfully perform a surgical task, neural networks may be trained to determine how much data from the data set can may be filtered while still successfully performing the surgical task. Neural networks may be trained to filter as much data from the data set as possible while successfully performing the surgical task. Filtering as much data as possible while still successfully performing the surgical task may maximize the privacy of the HCPs. Based on filtering the data sets, neural networks may (e.g., may then) be trained to adjust the amount, frequency, or intensity of the data collection of the HCPs to balance the need for privacy with the need for complete datasets to successfully perform surgical tasks.

Neural networks (e.g., the neural network 51714 shown in FIG. 42) may be trained to monitor HCP data collection systems to optimize an amount of surgical data and surgical data collection parameters for performing a surgical task (e.g., sampling frequency, data exchange, choice of device best capable of capturing the job) with the constraints of privacy, storage capacity requirements, compilation level vs raw data, etc. In examples, neural networks may be trained to identify a relationship between surgical data needed to differentiate key surgical jobs and interactions while minimizing the collection of personal information.

Neural networks (e.g., the neural network 51714 shown in FIG. 42) may start with access to a larger more complete dataset (e.g., a first data set) of the HCP data and metadata. As the patterns or trends become clearer, neural networks (e.g., the neural network 51714 shown in FIG. 42) may be trained to filter out the collection or storage of future data to a smaller dataset (e.g., a second data set) to limit the unrelated or non-correlate able data. This may balance HCP privacy with the ability to improve efficiency and outcomes of surgical tasks. In examples, neural networks (e.g., the neural network 51714 shown in FIG. 42) may be trained to aggregate staff data to determine an average of the operation group to identify the first order important data sources to collect.

Neural networks (e.g., the neural network 51714 shown in FIG. 42) may be trained to determine patterns and trends within data sets (e.g., the first data set). If neural networks identify potentially important trends or patterns, they may (e.g., may then) be trained to instruct the system to collect more individualized data in (e.g., only in) the key areas of the first data set to refine the pattern or trends. Filtering the data from the first data set to determine the second data set for performing the surgical task may be based on the determined key areas within the first data set.

Neural networks (e.g., the neural network 51714 shown in FIG. 42) may be trained to determine personalized or individualized data within the first data set. Filtering the data from the first data set to determine the second data set for performing the surgical task may be based on the determined personalized or individualized data within the first data set. In examples, the neural networks may be trained to collect a limited amount of personalized or individualized data until there is proof the neural networks could be more specific in their recommendations.

Neural networks (e.g., the neural network 51714 shown in FIG. 42) may be trained to pre-identify areas to filter data within data sets (e.g., the first data set). The pre-identified data from the first data set may be the minimum amount of surgical data needed to perform the surgical task. If the neural network was trained to be able to collect more specific data in (e.g., only in) the pre-identified areas, the amount of personalized or individualized data could be further limited.

Neural networks (e.g., the neural network 51714) may be built out to low fidelity low effort models first (e.g., if 5 pieces of data are used in a simple model, there may be 80% accuracy, but the inclusion of 100 pieces of data and an advanced model may provide an additional 10-15% accuracy of the model.) This low fidelity model may provide the basis for a deterministic model that may want to run less data when comparing the amount of personal tracking it may have to do to gather the additional 95 data points over the 5 data points it has for its 80% accuracy.

Collected surgical data may be monitored, tracked, and paired with utilization metrics in order to determine how much usage is derived from the collection of a certain type of data. This may (e.g., may then) be a layer to figuring out how useful collecting a piece of data could be, based on how much it is actually used, what predictions it is needed for, the difficulty of recording and storing the data, and/or the accuracy and reliability of the data.

Neural networks (e.g., the neural network 51714 shown in FIG. 42) may be trained to identify the least invasive combination of surgical data within the first data set. The data may be filtered from the first data set to a less invasive (e.g., the least invasive) combination of surgical data. The less invasive (e.g., the least invasive) combination of surgical data may be the second data set. The less invasive (e.g., the least invasive) combination of surgical data may be data that uses a lower number of resources, has a lower processor capacity, and/or has a lower memory capacity. The less invasive (e.g., the least invasive) combination of surgical data may include data that is transferred, stored, or resource consuming (e.g., processing capacity, memory capacity, etc.). The less invasive (e.g., the least invasive) combination of surgical data may balance facility information technology constraints with the need to collect data to perform surgical tasks. This may include the optimal combination of complied data, raw data, and which algorithmic reductions were used on the data to maximize optimal utilization of the available computing assets. The identified less invasive (e.g., least invasive) combination may help limit processing costs and data storage costs. The identified less invasive (e.g., the least invasive) combination may help limit transfer protocols and bandwidth (e.g., sensors can take measurements super rapidly), but Bluetooth transfer protocols and data buffers may not be able to handle large amounts of data which may then lead to dropped bits and lost packets). Pre-processing (e.g., lower level running of algorithms on less powerful hardware) may (e.g., may also) help utilize the available computing assets.

Public available datasets (e.g., procedural or published data) may be used which may allow neural networks to identify potential relationships that may enable the system to setup an initial set minimum collectable dataset for analysis. The minimum collectable dataset may be adjusted as neural networks expand their understanding of what is potentially useful relative to how private it is.

Figure 44:
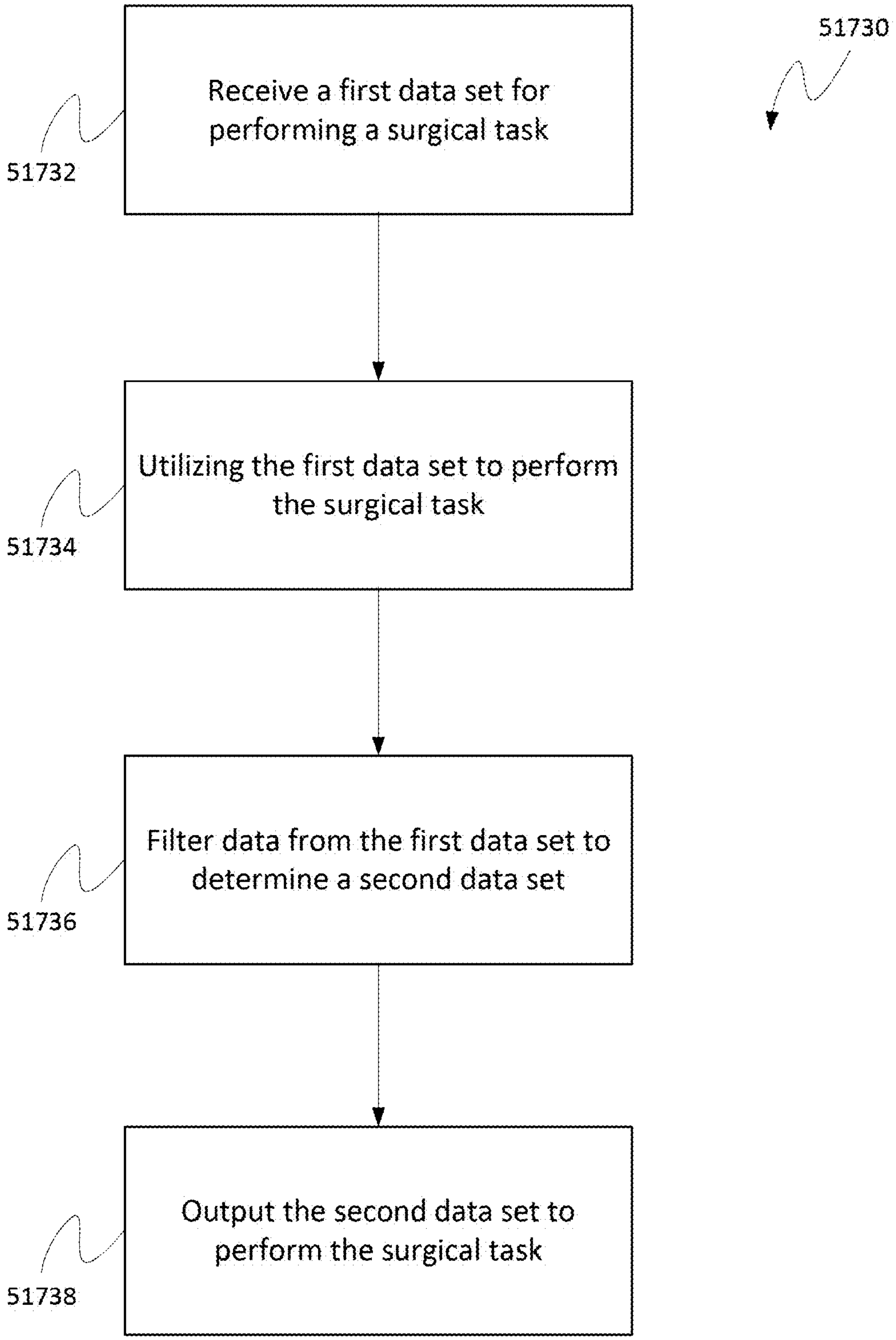
FIG. 44 illustrates an example flow chart for filtering data within a data set when performing a surgical task.

FIG. 44 illustrates an example flow chart 51730 for filtering data within a data set when performing a surgical task. At 51732, a first data set may be received for performing a surgical task. At 51734, the first data set may be utilized to perform the surgical task. In examples, the first data set may be evaluated to determine how the first data set performs the surgical task. At 51736, based on the evaluation of the first data set performing the surgical task, data from the first data set may be filtered to determine a second data set for performing the surgical task via a neural network. The neural network may be trained to filter the data (e.g., adjust the amount of data filtered) from the first data set to determine the second data set for performing the surgical task. The second data set may have a lower amount of data than the first data set. At 51738, the second data set for performing the surgical task may be outputted.

Examples herein may balance data reduction level with physical system capacities. Neural network(s) may monitor the physical resources of the hub system as well as the data being collected within the surgery in real time. Neural network(s) may balance the level of data reduction or combinations at the site of collection to minimize its effect on the overall system while also gathering as much data as possible.

The local hub server may supplement its processing capabilities with available edge computing resources. The local hub server may be combined with facility server capacity to determine the usable functions of the local hub or instruments. The excess capacity of the local edge may be segmented to determine what portions the local hubs can share. The maximum resources or available resources of the local hub server may change with time, for example, based on the number of hubs in operation, criticalness or location of each hub within a procedure, time of day, or importance of department within the facility.

In examples, a first data set may be received for performing a surgical task. The first data set may be generated by one or more surgical data sources associated with the performance of the surgical task by a surgical computing system. The first data set may have first data volume. The first data set may require may use a first level of resources of the surgical computing system to perform the surgical task. The first data volume and a first amount of resources used by the surgical computing system associated with performing the surgical task may be evaluated to determine a second data volume via a neural network. The neural network may be trained to determine the second data volume. The second data volume may maximize a quantity of data associated with performing the surgical task without exceeding the first level of available resources of the surgical computing system. A control signal may be sent to the one or more surgical data sources to generate a second data set associated with performing the surgical task at the second data volume.

Figure 45:
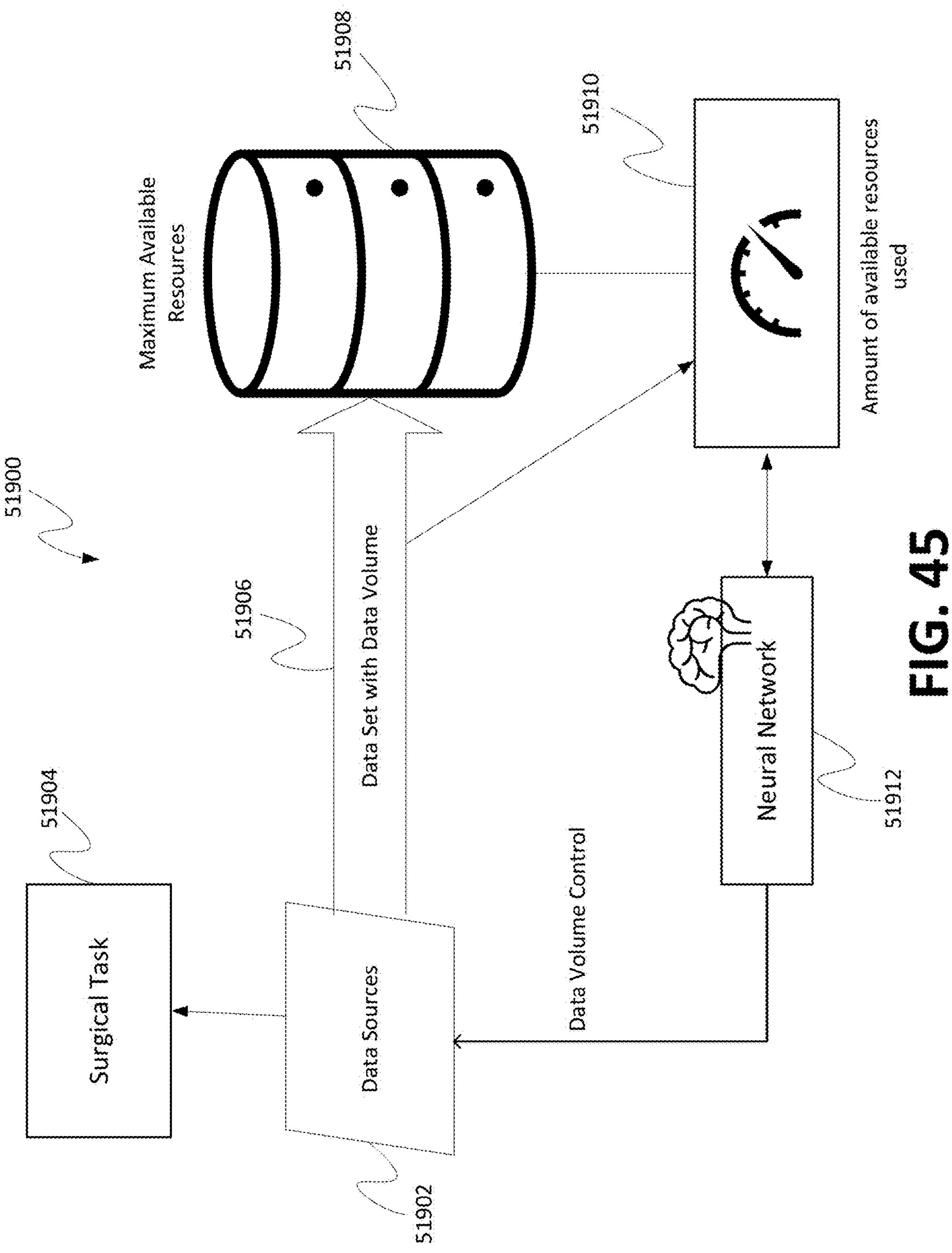
FIG. 45 illustrates an example block diagram for determining a data set maximizing the quantity of data for performing a surgical task without exceeding a maximum amount of available resources of a surgical computing system.

FIG. 45 illustrates an example block diagram 51900 for determining a data set maximizing the quantity of data for performing a surgical task without exceeding a maximum amount of available resources of a surgical computing system. The block diagram 51900 may include a data set with data sources 51902. The data sources 51902 may be received for performing a surgical task 51904. A data set 51906 (e.g., a first data set) may be generated by the data sources 51902 associated with performing the surgical task 51904. The surgical task 51904 using the data set 51906 may be performed by a surgical computing system 51908. The data set 51906 (e.g., the first data set) may have a data volume (e.g., a first data volume). The data set 51906 (e.g., the first data set) may require using a first level of available resources (e.g., a maximum amount of available of resources) of the surgical computing system 51908 to perform the surgical task 51904. The first amount of resources of the first level of available resources used by the surgical computing system 51908 to perform the surgical task 51904 using the first data volume may be provided at 51910. A neural network 51912 may be trained to evaluate the first amount of resources of the first level of available resources used by the surgical computing system 51908 at 51910 to determine an updated data volume (e.g., a second data volume) for performing the surgical task 51904. The neural network 51912 may determine the updated data volume (e.g., the second data volume) by determining a maximum amount of data associated with performing the surgical task without exceeding the first level of available resources (e.g., the maximum amount of available of resources) of the surgical computing system 51908. A control signal may be sent to the data sources 51902 to generate an updated data set (e.g., a second data set) associated with performing the surgical task 51904 at the updated data volume (e.g., the second data volume). The second data volume may be associated with a second level of available resources that is adequate to perform the surgical task. The second data volume may be less than the first data volume.

Figure 46:
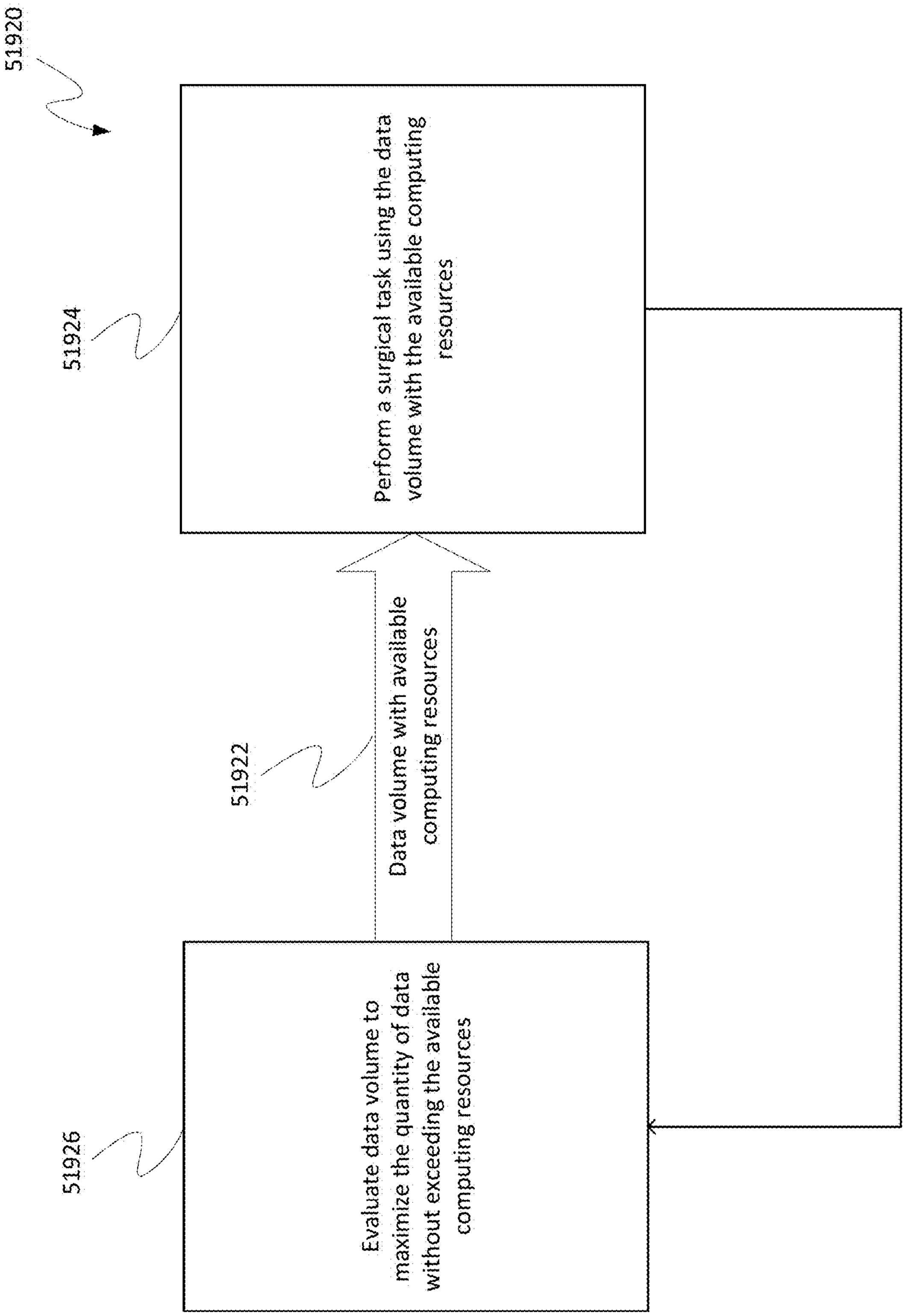
FIG. 46 illustrates an example block diagram for evaluating a data volume for performing a surgical task.

FIG. 46 illustrates an example block diagram 51920 for evaluating a data volume for performing a surgical task. The block diagram 51920 may include a data volume (e.g., a first data volume) with an amount of available level of computing resources (e.g., a first level of available resources) for performing a surgical task at 51922. At 51924, a surgical task may be performed using the first data volume with the first level of available resources. At 51926, the first data volume may be evaluated to determine a maximum quantity of data for performing the surgical task without exceeding the available amount of computing resources (e.g., a second data volume) for performing the surgical task via a neural network (e.g., the neural network 51912 shown in FIG. 45). The neural network may evaluate the first data volume and a first level of available resources used by the surgical computing system associated with performing the surgical task to determine a second data volume.

Neural networks (e.g., the neural network 51912 shown in FIG. 45) may be trained to monitor patient outcomes using the first data volume and the first amount of resources used by the surgical computing system associated with performing the surgical task to determine the second data volume for performing the surgical task. Patient monitoring intervals and their impact on mitigating risks or improving outcomes may be developed, bracketed, or optimized.

Neural networks (e.g., the neural network 51912 shown in FIG. 45) may be trained to track patient monitoring to determine the most efficient frequency, type, and in-person follow ups following a surgical task. Outcomes, impacts, and adverse events following a surgical task may be correlated with the type and frequency of biomarker monitoring to balance health care providers in-person follow up timing with automatable tracking. This may provide the minimal amount of staff to provide the most efficient amount of interaction and monitoring for the events or circumstances where they could prevent adverse events or catch approaching events to improve patient outcomes.

Neural networks (e.g., the neural network 51912 shown in FIG. 45) may be trained to track staffing allocations associated with performing the surgical task at certain data volumes by the surgical computing system. An optimal range may be determined for HCPs to follow up for the patient to have the most desirable outcome. Patterns may be identified to determine the ideal target monitoring frequency or range of follow ups. The follows ups may depend on the data volume and the amount of resources used by the surgical computing system associated with performing the surgical task. In examples, the outcomes and interactions of the HCPs may (e.g., may continue) to be tracked to confirm the ideal range or adapt the range or target based on the data volume associated with performing the surgical task, the amount of resources used by the surgical computing system for performing the surgical task, and the capacities of the staff. In examples, the outcomes and interactions of the HCPs may (e.g., may continue) to improve with new relationships determined by surgical outcomes. The outcomes and interactions of the HCPs may adjust the targets associated with the new relationships determined by the surgical outcomes.

Monitoring frequency may be baselined on standard practices and physician preferences (e.g., input by the physician, such as "for this patient I want blood pressure taken every hour post-op and then 4 times a day when the patient is released" rather than the standard practice of blood pressure every 4 hours post-op). Tracking staffing allocations between active tasks and monitoring tasks may be determined and optimized to balance between monitoring and action tasks and frequencies. Tracking staffing allocations may depend on the data volume and the amount of resources used by the surgical computing system associated with performing the surgical task.

Neural networks (e.g., the neural network 51912 shown in FIG. 45) may be trained to calculate or suggest monitoring and screening intervals based on individual patient data/risk factors and limited resource availability (e.g., staff, equipment). Aspects of the patient, their disease state, or treatment may be used to identify risk ratios that could be used to determine staff limitations. The ideal monitoring interval for the group may be different than for an individual patient due to these differences in patient risk. The balance of monitoring and frequency for the staff or system may be adapted based on these differing factors. In examples, the data volume may be higher for performing surgical tasks with high patient risk factors. The data volume may be greater than the amount of available resources used by the surgical computing system for performing the surgical task. In these instances, a greater amount of staff may be needed in addition to the surgical computing resources for performing the surgical task. In examples, the data volume may be lower for performing surgical tasks with low patient risk factors.

The data volume may be less than (e.g., much less than) the amount of available resources used by the surgical computing system for performing the surgical task. In these instances, a lesser amount of staff may be needed in addition to the surgical computing resources for performing the surgical task.

Example factors that could lead to higher risk ratios may be the time since surgery, number or intensity of comorbidities, most current biomarker measurement relative to the normal range for the patient, complications in the treatment, aggressiveness of the treatment, or personal characteristics (e.g., age, weight, gender, etc.). In these instances, the data volume may be higher for performing surgical tasks with high patient risk factors. The data volume may be greater than the amount of available resources used by the surgical computing system for performing the surgical task. In these instances, a greater amount of staff may be needed in addition to the surgical computing resources for performing the surgical task.

For example, some patients may require a more advanced or monitored standard of care. With respiratory monitoring, the caregiver may require a more specialized training or certification to properly care for and identify issues when they arise. This linking of staff qualification or experience may be a part of their employment record and is often designated on shift organization. If a patient is identified as part of the specialized classification by the neutral network, the caregiver may receive a push notification and reminders of the patient needs and status. These push notifications may include algorithm flagging or highlighting of monitored biomarkers or behavior that the algorithm has flagged as uncommon, which may allow the caregiver to spread their time more efficiently. If the procedure or care is reviewed by the neutral network, dynamic scheduling adjustments may (e.g., may also) be made if the staff with the appropriate skill is unavailable or not on schedule. This may allow the system to organize the schedule shifts and people relative to the changing needs of the facility.

Neural networks (e.g., the neural network 51912 shown in FIG. 45) may be trained to aggregate performances of a plurality of similar surgical tasks to the current surgical task for determining the second data volume. In examples, surgeon monitoring and aggregation of performance and behavioral data may be implemented to distill interactions/interrelationships, best combinations, best techniques (e.g., surgical steps order, access approaches, instrument efficacies, minimization of complications, efficacies of motion, efficacies of staff utilization, and costs) of procedure improvement. Local facility data set conclusions may be compared with regional and global conclusions to identify key local configurations or boundaries that may change the interrelationships or prioritizations.

In examples, outcome performance data may be compared to other physicians. This comparison may be to other physicians across global datasets, within a geographic region, or within healthcare network. In examples, procedure data may be compiled. The compiled procedure data may be interrelated to at least one of: the need for unintended surgical interventions, patient status throughout operation, complications, time to complete surgery, or tools used. In examples, patient outcomes as a result of surgical factors and the surgeon outcomes may be complied to determine an amount of data volume for performing a surgical task.

Ergonomic aspects (e.g., postures, instrument gripping, orientations, etc.) and behavioral aspects (e.g., attention, communications between HCPs, reliance on automation/technology assistance) of the surgeon may be monitored. In examples, the neural network may be trained to assess surgeon attention and focus (e.g., based on eye-tracking data) and compare the results to other (e.g., expert) surgeons.

Neural networks (e.g., the neural network 51912 shown in FIG. 45) may be trained to determine the second data volume based on historical data sets including volume data and surgical procedure data. Neural networks may utilize known interdependencies to identify what data to reduce or combine. Assumptions may be utilized based on known inputs (e.g., such as procedure plans, video indications through scopes feed to hub, surgeon identification, and/or classification of disease type or pre-operation information). For example, there may be an integration with the surgical suite tools and the room itself. Systems that know when to be used or interfaced with during a procedure, may indicate a flag or error that says, "I don't have xyz piece of data yet from the patient, please come back so we can go on the next step." The system may have the ability of overriding or bypassing fast or easy enough to ensure a patient never suffers a negative outcome from the delay, but irritating or annoying enough to encourage staff to actually gather (e.g., all the) requested data/biomarkers in order to benefit patient outcomes. This integrated system may (e.g., may also) be used to say, "I've got all my data that is important, now is a good time to stop gathering 'extra' or 'extraneous' data and now start the procedure."

Neural networks (e.g., the neural network 51912 shown in FIG. 45) may be trained to make assumptions based on unknown inputs that (e.g., that also) have known interrelationships to determine an amount of data volume for performing a surgical task. For example, for clamping tissue, monitoring the force over the rate of change in tissue may be utilized to determine which subset of data to pull from the cloud locally or for further procedure indications. The initial firing may indicate that the tissue rate of change of force over time is most equivalent to the stomach. As such, (e.g., all) the stomach firing data may be pulled locally from the cloud so (e.g., all) substantial firing decisions are run locally rather than sent out to the cloud. The disease state of tissue may be utilized. In examples, pre-op data may reveal or predict a tissue type or disease type to target data. Visual indications and/or the initial clamp rate of change in compression may (e.g., may further) determine the data set to pull from the cloud to local.

In examples, a neural network may have 100 variable inputs to derive the given output to provide the surgeon with the necessary surgeon risk threshold. Limitations in time or data collection availability may process at lower input variables until a minimum surgeon threshold is met. In examples, computing time, data collection, and frequency may be limited. In examples, computing location (e.g., edge, cloud, local) may be limited. In examples, storage capacity or location may be limited. In examples, data retrieval availability may be limited. In examples, patient consent (HIPAA) may be limited. In examples, the data gathered may be tracked and analyzed (e.g., such as where and when it has been used and for what kind of outcomes). If this data is used a lot more frequently than another piece of data, that piece of data may be prioritized for gathering if there are limitations related to storage space, bandwidth, time, etc.

Local hub processing may be supplemented with edge network processing (e.g., local facility edge network processing) if the local hub signals it has insufficient processing resources to produce the complied data results in a timely enough manner for utilization by the local smart instrumentation within the procedure. The edge network edge may provide the second data volume associated with the second level of available resources to perform the surgical task (e.g., as described above). Determinization and linking of distributing processing capabilities from the local edge network and the hubs connected to the network may maximize the processing resources available to the edge network based on the occupancy and active utilization of the associated hubs.

With robotic surgical systems, advanced visualizations, and sophisticated control algorithms for the advanced energy, stapling, and ablations technologies, the hub may become overwhelmed with its processing requirements. In examples, the hub may share the processing load with co-located other hubs. In examples, if a facility local edge computing solution exists within the facility secured network, the hub may be supplemented with facility local edge computing. Data and metadata may be sent to a facility local edge computing center. Results may be received back from the facility local edge computing center which may (e.g., may then) be integrated into parallel processed local elements.

In examples, real-time processing of data may be handled for use within the smart devices within the operating room at the time. In examples, real-time processing of data may be handled between the surgery complications of department, facility, divisions, etc. to improve control algorithms and setups for those future procedures or treatments.

At least partially combined resources of the hub(s) and the local network processing capacities may be utilized for determining the capabilities of a surgical hub attached smart systems (e.g., sampling rate, communication frequency, data packet size, processes/sec for controlling local smart devices, magnitude of coupled data). In examples, a test of network speeds and processing capabilities may be performed prior to the procedure and periodically throughout the procedure. If the surgical hub detects that the data is not coming back at the expected rates or quality, then tests may be run to assess if there is an issue or some portion(s) are too busy at that moment. Such a test may be a "ping" and speed test, which may provide the surgical hub with information on the health of the network, the processing time for downstream connected elements, etc.

Figure 47:
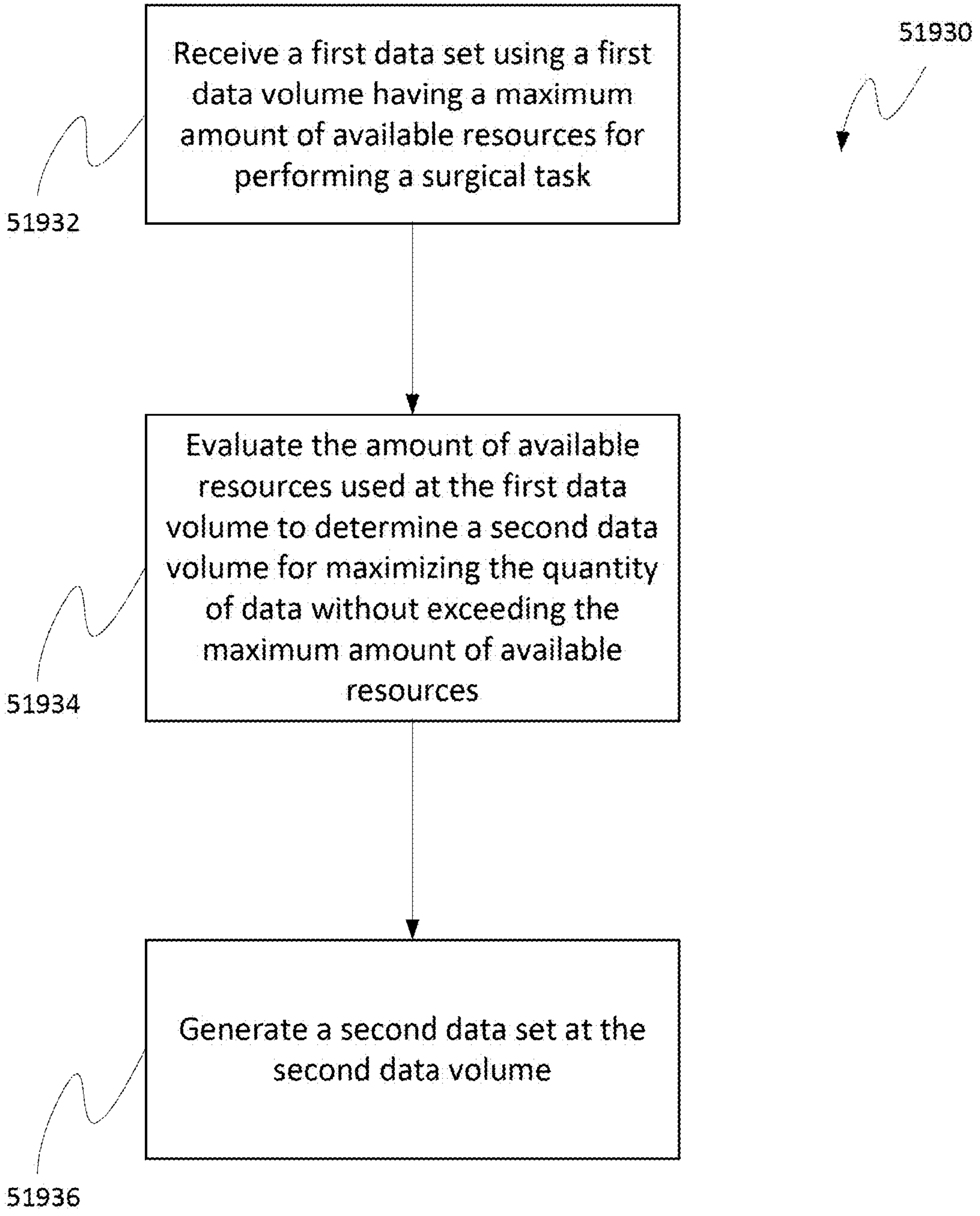
FIG. 47 illustrates an example flow chart for determining a data set maximizing the quantity of data for performing a surgical task without exceeding a maximum amount of available resources of a surgical computing system.

FIG. 47 illustrates an example flow chart 51930 for determining a data set maximizing the quantity of data for performing a surgical task without exceeding a maximum amount of available resources of a surgical computing system. At 51932, a first data set may be received for performing a surgical task. The first data set may be generated by one or more surgical data sources associated with the performance of the surgical task by a surgical computing system. The first data set may have a first data volume. The first data set may require the use of a first level of available resources of the surgical computing system to perform the surgical task. At 51934, the first data volume and a first amount of resources used by the surgical computing system associated with performing the surgical task may be evaluated by a neural network to determine a second data volume. The neural network may be trained to determine the second data volume. At 51936, a control signal may be sent to the one or more surgical data sources to generate a second data set associated with performing the surgical task at the second data volume.

There may be distinctly different (e.g., two distinctly different) machine learning resource loading needs based on its operation. In examples, the loading needs of using neural networks may be dramatically less than the training of neural networks. There may be a hybrid model where trained neural networks may (e.g., may still) look for adjustments to make to themselves to better identify patterns. This hybrid model may be a combination of train and use. In these situations, the processing load needed to sustain the learning portion of the model may be much higher than the use portion of the model. In examples, the system may (e.g., may then) link itself for more resources or compartmentalize the learned portion of the model and run (e.g., only run) a magnitude of the learned portion of the model that is not over burdensome to the resources available.

Neural network(s) may be trained to find coefficients for variables on the left side of the equation in order to produce the right side of the equation. During training, these coefficients may be determined by the learning model, and may (e.g., may then) in practice be given data and spit out predictions based on its previous training. If basic process parameters are known, the neural network(s) may be run with a subset of inputs that are expected, and a searchable outcome map may be generated for a specific procedure. Should the inputs be out of specification for whatever reason, the neural network(s) themselves may be executed to find the predicted answer. As such, it may be very easy for the system to run out of resources if you were trying to train and build a model, but it would most likely have enough resources to execute the program itself once it has been built.

Neural network(s) working on bad data could result in an incorrect answer. Some portions of the data may induce "drift" in the result. The neural network(s) themselves or the comparison of their results may highlight the stability, correctness level, etc. of the result in addition to the result itself. A nested algorithm may self-identify issues with its conclusions or patterns.

Neural network(s) may be using bad data in both the training and in the running of the algorithm. Training of the model with bad data may be difficult to fix. If the model is used in the training of the algorithm, the actual algorithm may be generating erroneous answers when running predictions. The neural network(s) may not be as reliable or robust as a system that was trained properly, even if the data being put in for evaluation is good. If bad data is being put into a trained model, the output may be unexpected or wrong, even if there is a chance it still may be usable. If bad data is being used, the algorithms themselves may not be able to detect the bad data without some system of evaluation of the quality of the data (e.g., identifying good data is being used or if bad data is being used). In examples, the bad data may behave and look like good data. As such, a layer may be added to the neural networks to identify whether good data or bad data is being used.

Figure 48:
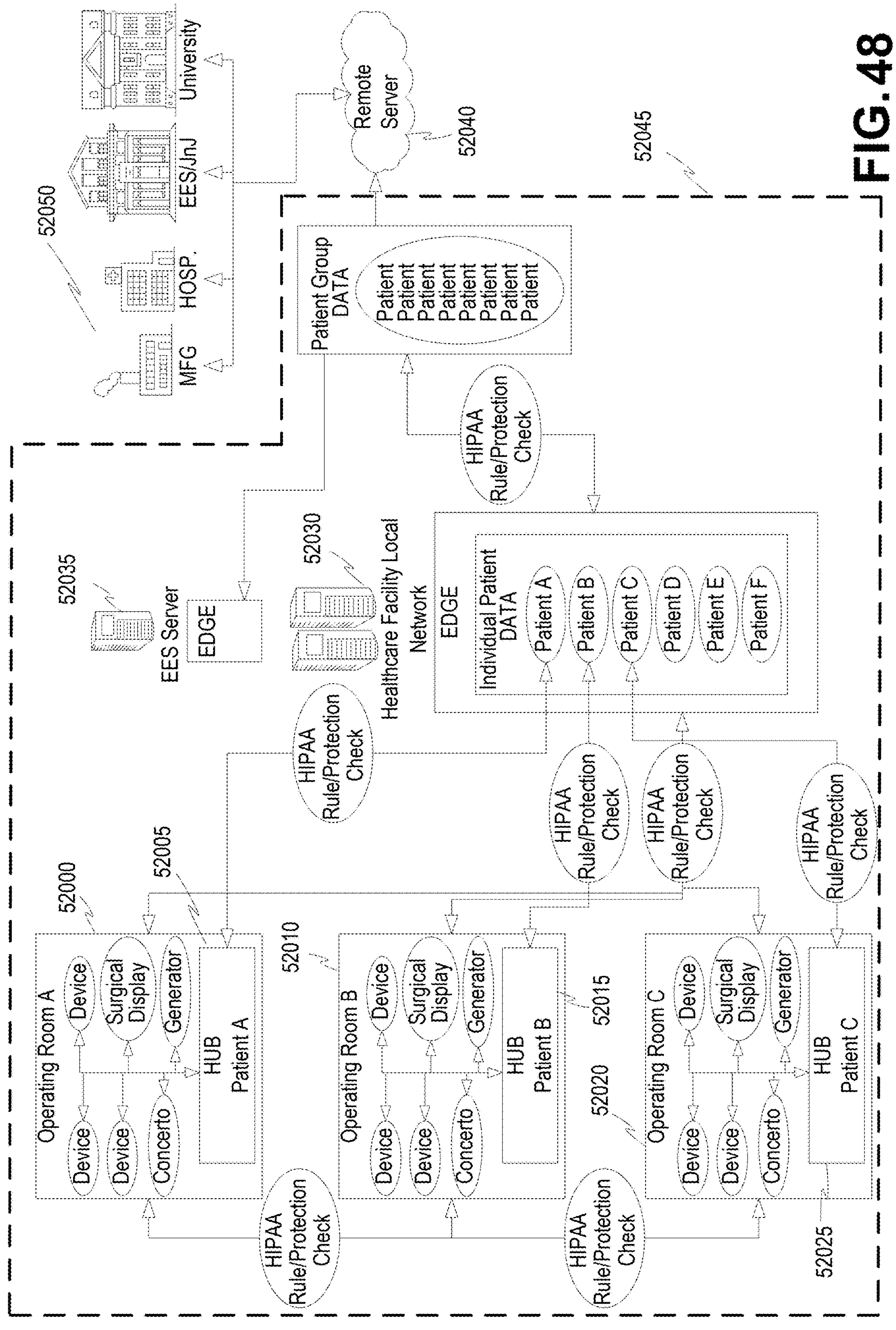
FIG. 48 is a block diagram of an example surgical system.

FIG. 48 is a block diagram of an example surgical system. The system may enable the communication of information among one or more operating rooms 52000, 52010, 52020, a corresponding hospital local network 52030, an edge server 52035, and one or more other entities 52050.

In an example, each of the operating rooms 52000, 52010, 52020 may include a respective surgical computing device (e.g., surgical hub 52005, 52015, 52025). The surgical hubs 52005, 52015, 52025, as illustrated, may include instances of the surgical computing device 704 for example, disclosed here. For example, the surgical hubs 52005, 52015, 52025 may include instances of the hub described in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Each surgical hub 52005, 52015, 52025 may be associated with one or more devices to be used during a surgery, such as surgical generators, intelligent surgical instruments, surgical robots, surgical displays, sensors, and the like. Example intelligent surgical instruments may include those described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example. An example robotic system may include that described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety. Such devices may be used in a surgical procedure as part of the surgical system.

Such devices and the corresponding surgical hubs 52005, 52015, 52025 may generate, process, send, and/or receive information, such as surgical information disclosed in FIG. 7A for example. In an example, the surgical information may include that associated with one or more patient biomarkers (e.g., information disclosed U.S. patent application Ser. No. 17/156, 28, filed Nov. 10, 2021, the disclosure of which is herein incorporated by reference in its entirety). This surgical information may be analyzed For example, such analysis may include that disclosed in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

A respective patient may be undergoing a surgical procedure in each of the operating rooms 52000, 52010, 52020. As illustrated, patient A may be undergoing a surgical procedure in operating room A 52000. Patient B may be undergoing a surgical procedure in operating room B 52010. And patient C may be undergoing a surgical procedure in operating room C 52020. The surgical information generated, processed, sent, an/or received by each of the hubs 52005, 52015, 52025 may be associated with the patient undergoing surgery in the corresponding operating room. Surgical information associated with different patients in a common network and/or networked devices, such as the hospital local network 52030, the edge server 52035, and/or other entities for example, may pose data privacy challenges and may promote the use of data privacy protection approaches such as those disclosed herein.

Surgical information, such as patient specific surgical information, may be communicated via a common network and/or networked devices, such as the hospital local network 52030, the edge server 52035, and/or other entities. To illustrate, surgical information associated with the surgical procedure performed on patient A in operating room A 52000 may be communicated between the surgical hub device 51005 in operating room A 52000 and the edge server 52035 via the hospital local network 52030. Similarly, surgical information associated with the surgical procedure performed on patient B in operating room B 52010 may be communicated between the surgical hub device 51015 in operating room B 52010 and the edge server 52035 via the hospital local network 52030. Likewise, surgical information associated with the surgical procedure performed on patient C in operating room C 52020 may be communicated between the surgical hub device 51025 in operating room C 52020 and the edge server 52035 via the hospital local network 52030.

Such surgical information may have the characteristic of individuality (e.g., data individuality). Data individuality or data individuality level may represent how likely the surgical information is to be linked to an individual patient. For example, surgical information with high data individuality level may have a high likelihood of being traced back to a specific patient. For example, surgical information with low data individuality level may have a low likelihood of being traced back to a specific patient. And surgical information with moderate data individuality level may have a moderate likelihood of being traced back to a specific patient.

Data individuality level may be highly correlated with particular data types. For example, biographical data (e.g., patient's name, patient ID, surgical procedure date/time, etc.) and/or surgical information tagged with biographical data may be associated with high data individuality. Likewise, data types associated with relatively generic medical data (e.g., data types with values common to many patients) may have low data individuality level. For example, patient weight may be data type with low data individuality level (because, for example, many patients may have the same body weight).

Data individuality level may be correlated with the specificity of the data taken as a whole. For example, data elements, viewed individually, may have a low data individuality to the extent that any such element taken alone would not likely reveal the patient from whom the data originated. However, such data elements, taken together as a whole, may be more likely to reveal the patient from whom the data originated. Such data elements, taken together as a whole, may exhibit high data individuality.

Data individuality level of a surgical data set associated with a patient may reflect the patient specificity of its subsets. For example, a surgical data set may have high data individuality level because most or all of its subsets may contain information that would reveal the patient source of information. In this example, a surgical data set may have high data individuality level because a small subset of the data has a relatively high likelihood of revealing the patient source of information and the remaining large complement subset of the data has a relatively low likelihood of revealing the patient source of information.

The data individuality surgical of surgical information may be changed (e.g., lowered). Anonymization techniques may be used to reduce the data individuality of surgical information. Anonymization techniques may include any logical processing of information that makes it less likely to decern its patient source. For example, anonymization techniques may include techniques such as redaction, randomization, aggregation and/or averaging, and/or the like. Redaction may include removing subsets of surgical data with high data individuality and preserving subsets of surgical data with low data individuality. In an example, redacting patient name and patient's ID from a data set may reduce the data individuality of a data set. Randomization may include modifying certain aspects of data with noise to conceal the origin of the data without significantly changing the surgical and/or analytical value of the information. For example, randomizing the time-of-day information for certain surgical information may help conceal the patient origin of such data without affecting the broader analytical value of the information in view of a larger population study. Data averaging an aggregate of common values across similarly situated patients reduces the likelihood that such an average may be traced back to a particular patient.

In a system, a desired data individuality level may be related to the data's use and/or location in the system. For example, data individuality for surgical information being analyzed within an operating room during a patient procedure may be left unchanged. Here, a reduction in data individuality may not be desired. Here, the privacy concern associated with such a high data individuality is minimal because the use and/or location of the data in the system is localized to the patient's surgical operation and operating room. For example, data individuality level for surgical information being analyzed in a university and/or academic setting may be reduced. Here, a reduction in data individuality level is desired because the privacy concern associated with such a high data individuality is greater because the use and/or location of the data in the system is distant from the patient's surgical operation and operating room.

A hierarchy may be used to determine a desired data individuality level in a system. For example, a surgical system may have one or more hierarchical levels. The levels may be logical levels, for example. The levels may be physical levels, for example. The levels may each, for example, based on the location in the hierarchy, be associated with a corresponding data individuality. In an example, uses and/or locations of surgical data that are more localized to the healthcare of a particular patient may have a level associated with a desired high data individuality. And uses and/or locations of surgical data that are distant to the healthcare of a particular patient may have a level associated with a desired low data individuality level. To illustrate, the use of data and systems when performing analytical research across many patients and/or many surgical procedures may be distant from the healthcare of any one particular patient and, therefore, may be associated with a desired low data individuality.

Data individuality level may change based on the location of a processing device in system hierarchy where the surgical information may be processed or sent for processing, as described herein. In example, data individuality level associated with surgical information may be changed from high data individuality level to low data individuality level, if/when the surgical information is sent for processing from the local entity that is located inside a protected boundary to a remote processing device that is located outside the protected boundary (e.g., a remote enterprise server). The transformation of the individuality level of the surgical information from a high data individuality level to low data individuality level may be performed using one of the anonymization techniques, as described herein.

In an example, data individuality may be transformed from high data individuality to medium data individuality, for example, if surgical information is sent from a processing (e.g., a surgical hub) located inside a protected boundary to a processing device that is located in an intermediate network with moderate protection. The intermediate hierarchical level may be located within a healthcare professional's network, but outside the protected boundary, as described in FIG. 49.

Transforming surgical information by changing its data individuality level may include anonymizing at least a portion of the surgical information or a data set. Surgical information, surgical data set, or data set may be used interchangeably herein. For example, by redacting a subset of data points of high data individuality level thereby changing the data individuality level from high data individuality to low data individuality level. In an example, changing data individuality level may include processing data sets (e.g., aggregating data sets) into a form where the data points of a data set are aggregated or pooled into one total data set. Data points in the total data set may not be tied to individual data sets.

Edge processing may balance privacy and comprehensiveness using balancing protocols to package the surgical data for sharing within differing levels of the system hierarchy. The surgical data sets may experience allometry (e.g., growth of the parts at different rates resulting in changes in proportions) of data individuality. The allometry of surgical data (e.g., growth or reduction of the size of surgical data or surgical information) may be directly proportional to the level of protection provided by a system hierarchy level. Surgical data packages (e.g., surgical data sets) may change the surgical data magnitude and the surgical data comprehensiveness as they are processed and/or passed through different levels of the system hierarchy. The growth or reduction of the surgical data or surgical data portions (e.g., separable surgical data portions) not be linear. In an example, the growth or decay of the surgical data or surgical data portions may be proportional to the protection level associated with the surgical data, for example, the protection level provided by the surgical data protection rules (e.g., HIPAA rules) or protection level associated with the networks within which the surgical data resides. In an example, the higher level of surgical data protection may result in more individuality of the surgical data points or a surgical data set.

Constitution of individual constituent data components may be based on the level of the data within the overall system hierarchy or protection level of the system. In examples, the data and/or algorithms may undergo assimilation and/or aggregation as the data is pushed down from higher levels of the system hierarchy (e.g., a remote server) to a lower levels of the system hierarchy (e.g., the surgical hub).

In an example, as illustrated in FIG. 48, the data may maintain the same data individuality level (e.g., high data individuality level which may include each of the data points within a data set) if it is sent to a processing device, for example, an edge server 52035 that is located within the hospital local network 52030, where the network is within a protected boundary 52045 (e.g., health insurance portability and accountability act (HIPAA) protection boundary). In such a case, data with high individuality level may be allowed since the data is less vulnerable to be traced back to a patient.

In an example, a local processing device may determine that instead of processing the data at an edge server 52035 that is located within a protected boundary of a hospital local network 52030, the data should be processed on a processing device that is located outside the protected boundary of the healthcare facility's network. Data individuality level of surgical information in such a case may be reduced (e.g., from high data individuality level to low data individuality level) before the surgical information is sent from a processing device (e.g., edge server 52035) that is located inside the protected boundary 52045 of a healthcare facility to a processing device (e.g., remote sever 52040) that is located outside the protected boundary 52045 of the healthcare facility.

Determining the individuality of the data as it passes through different levels of the system hierarchy may be determined based on a rule check (e.g., HIPPA rule check located within the analysis subsystem of the surgical hub/edge device). The rule check may be implemented as a check whether surgical information or a portion of surgical information is associated with a patient and/or the surgical information can be traced back to the patient. In an example, the rule check may be implemented using a machine learning model that may be trained to generate a data individuality based on an analysis and/or comparison of the data points within a surgical data set. The machine learning technique utilized may be based on a supervised learning framework, for example, as described in FIG. 8A. In such a case, the training data (e.g., training examples 802, as illustrated in FIG. 8A) may consist of a set of training examples (e.g., input data mapped to labeled outputs, for example, as shown in FIG. 8A). The training data used in training the local machine learning model 52090 may include surgical data sets gathered from previous surgical procedures, surgical parameters associated with those surgical procedures and/or simulated surgical procedures. The training data may include resource availability (e.g., memory and/or processing capacity availability) of various processing devices from previous surgical procedures, control algorithms associated with the surgical instruments (e.g., stored locally or received from other entities, e.g., a remote server).

In an example, machine learning utilized may be unsupervised (e.g., unsupervised learning), as described in FIG. 8B. As illustrated in FIG. 8B, in an unsupervised learning framework-based machine learning model may train on a dataset that may contain inputs and may find a structure or a pattern in the data. For example, the inputs may include parameters associated with data set to be processed (e.g., size of the data set, acceptable latency values, etc.), a rule set (e.g., based on the local privacy laws where the surgical procedure is performed), and parameters associated with various potential processing devices where the data set may be sent for processing. The outcome may be identification of one or more processing devices and/or system hierarchy levels where the data set may be sent for processing and/or the data individuality level that may be applied to the data set before sending it to the selected processing device. The data individuality level may be selected based on where the data set is sent for processing.

In an example, a machine learning algorithm may be trained to determine the individuality level of the data. For example, a histogram (or other method of estimate a probability distribution) may be generated to work out the standard deviation of the historical data. The deviation from the mean of a given data point can then be compared to the standard deviation or other predetermined range to classify the data point with a predetermined data individuality level.

In an example, the machine learning model may assign risks to each of the data points of the dataset based on previous data a machine learning model may have been trained with. The model may suggest a total data individuality level to be applied the dataset, for example, based on the accumulation of the risks of the data points within the data set. This individuality may be compared with the local applicable rule set to identify: (1) the system hierarchy level and/or the processing device the dataset may be sent for processing; (2) the data individuality level that may be applied to the data set (e.g., before sending it out from processing). The rule set may be derived from the protection rules (e.g., HIPAA rules) the healthcare facility where the surgical procedure is being performed may have to adhere to.

In an example, a surgical hub/edge device may identify the processing device and/or the system hierarchy level where a surgical data set may be sent for processing. The processing device and/or the system hierarchy level may be identified based on, for example, the surgical data set magnitude (e.g., size of the surgical data set), capabilities of the processing server, performance metrics associated with the data set, etc. Capabilities and characteristics may be used interchangeably herein. In an example, a surgical hub/edge device, for example, based at least on the size of a surgical data set to be processed, may determine that the surgical data set should be processed at a remote server with a processing power that is higher than the processing power of the surgical hub or the edge server. In such a case, the surgical hub/edge device may send the surgical data set to a remote server. Based on the identification of the processing device and/or the system hierarchy level, the surgical hub/edge device may perform a rule check to determine the data individuality level at which the data set should be sent to the processing device.

In an example, a surgical hub/edge device may identify the processing device and/or the system hierarchy level based on at least one of the capabilities of the processing device, the data magnitude of the surgical data, the sensitivity to latency in processing the surgical data, the data individuality level of the surgical data, or the intended use of the surgical data. Identifying the processing device may be performed using one or more look-up tables which may be combined, with optional prioritization between the look-up tables. For example, a look-up table may associate data magnitude with processing device capabilities to identify a suitable processing device for a given data magnitude. Similarly, intended use of data could be associated with the capabilities of the processing devices, e.g., if the intended use is for treatment of the patient this may be associated with a processing device with lower capability, whereas the intended use being analysis of data alongside other similar data for trend or correlation analysis, may be associated with a processing device of higher capability. Another look-up table may associate data individuality level with the location of the processing device. For example, a processing device located inside a protected boundary may have higher individuality level associated with it than a processing device that is located outside the protected boundary.

Combining the look-up tables, data with an intended use associated with a lower capability and lower individuality level may be sent to a processing device of higher capability if the data magnitude requires it. The processing device may be located outside a protected boundary. The capabilities of the processing devices may increase when moving from the operating room, e.g., with the operating room processing device (e.g., the surgical hub) having a lower capability than a hospital processor, which has a lower capability than a hospital network processing device, which has a lower capability than a remote processing device.

In an example, performance metrics (e.g., along with the rule set) may be considered by the surgical hub/edge device to determine the processing device and/or system hierarchy level where the data may be sent for processing. Determining the performance metrics for the data may involve using simulations which may output approximations for performance metrics associated with the data. Simulation framework may be described in "Method for Surgical Simulation" in U.S. patent application Ser. No. 17/332,593, filed May 27, 2021, the disclosure of which is herein incorporated by reference in its entirety. In an example, based on a determination whether or not the data set to be processed is sensitive to latency (e.g., the processing/transit delays), the data set may be sent for processing to an edge server that may be located within a healthcare's providers local network and therefore associated with lower latency level or to a remote server that may be associated with a higher latency level as is described herein.

In an example, a surgical data set may be prepared to be sent for processing to a processing device with the result to be utilized for a post-surgical follow-ups, recovery, monitoring etc. of the patient. In such a case, the latency or time taken for processing the data set may not be of importance. The surgical hub/edge device in such a case, based on at least the latency not being a factor and/or the benefit the diverse data set at a remote server (e.g., a centrally located server) may determine to send the surgical data set for processing to a remote server.

In an example, data magnitude of a surgical data set may be associated with a data individuality level. Data magnitude may be used in determining a data individuality level that may be applied to the surgical data set before sending it for processing to a processing device. In an example, a surgical data set of high data magnitude may be associated with high data individuality level, and low data magnitude may be associated with low data individuality level.

Transforming a data individuality level from one level to another may include anonymizing (e.g., redacting, randomizing, averaging, etc.) at least a portion of a surgical data set. Anonymizing a surgical data set may result in the surgical data set being less likely or impossible to be traced back to an individual patient. In an example, a local hub may determine to send a surgical data set associated with a surgical procedure to a remote server 52040 based on the remote server 52040 being the best candidate for processing the data, as described herein. Based on this determination, the local hub may anonymize (e.g., redact, randomize, average, etc.) the data. For example, data associated with patient A 52005 may be randomized, in a manner that the randomized data cannot be traced back to patient A 52005.

As described herein, anonymization techniques such as redaction, summarization, and/or compilation of data may be used on the surgical data set as the surgical data set is pushed up to a higher system hierarchy level (e.g., a cloud server), where there may be decreasing levels of protectivity of the privacy of the data. In an example, as the surgical data set is prepared to be sent to and/or shared with a processing device located in a higher system hierarchy level, the security of the data may be considered by the machine learning algorithm, for example. In an example, one or more parameters associated with the surgical data set may be categorized with respect to their relevance or need to have individual aspects viewable. In such a case, the system may combine specific individual surgical data points of a surgical data set and average or summarize surgical data points together within the surgical data set (e.g., data structure), which may result in not losing the trends and preventing individualization of datasets from specific patients. As described herein, portions of the data may be summarized and/or aggregated to produce pools of data that may be mixed, homogenized and/or aggregated, and may allow them to convey the same average result while preventing the individual constituent parts of a surgical data set to be separated.

In an example, encryption (e.g., a high-grade encryption) may be used to secure surgical data associated with a patent. The level of encryption used may depend on whether or not a surgical data set is being sent for processing to device that is located within a healthcare provider's protected boundary.

Determining where to process a surgical data set associated with a patient and/or a healthcare professional may be based on the degree of advantage the surgical data set may obtain from being processed at a certain hierarchical level. For example, a centrally located remote server 52040 may have access to diverse data sets it may have received from multiple locations of same or different healthcare providers. The level of the diversity of data may be proportional to the degree of advantage it may provide while processing a data set. In an example, a remote server may be capable of analyzing certain surgical data sets within a specific time frame. In an example, determining where to process a surgical data set may be based on the speed at which the surgical data set can be processed at a processing device that is located at certain level of the system hierarchy (e.g., data sent to a remote server 52040 may be processed faster than data sent locally).

Data individuality level may change based on anonymization of some or all of the data points within a surgical data set. Anonymization may include removing or altering one or more data points from a surgical data set, as described herein with respect to FIG. 49. The anonymization of the surgical data points that may be anonymized may be associated with an assigned high risk, for example, as determined by the machine learning model located in the surgical hub. For example, an identifying characteristic data point may be associated with a high risk and, therefore, may be anonymized from the surgical data set before sending the transformed surgical data set to a processing device (e.g., a remote server). In an example, the same data point may be included in a surgical data set if the surgical data set is sent to a processing device (e.g., an edge server 52035) that is located within a hospital's local network 52030 that is within the protective boundary 52045.

In an example, the surgical hub may weigh individualized surgical data set against privacy risks associated with the surgical data set, when determining the system hierarchy level that may be selected for sending the surgical data set for processing. Privacy risks may be pre-configured and/or may be a part of a machine learning model. In an example, the magnitude of a surgical data set may be derived based on the level of data individuality applied to that surgical data set.

In an example, a surgical data set that is generated within a healthcare facility's network (e.g., locally within the operating rooms of a healthcare facility) may allow for the surgical data set to be checked based on a protection rule (e.g., HIPAA rule). A surgical data set sent from a healthcare facility's edge network to a remote server (e.g., cloud server) may combine each of the surgical data points into one output. In such a case, the surgical data set sent may combine the distribution of all the patients' surgical data in a manner such that it may not be tied or tracked back to a particular patient.

In an example, during a surgical procedure, a surgical data set may be collected on each of the patient biometrics, supplies used, complications, and/or outcomes (e.g., locally within a healthcare facility for any follow-ups, recovery, and/or monitoring). If the information is to be sent outside the healthcare facility, the data may be combined into one combined surgical data set and sent to the remote server (e.g., cloud or any edge network that may not be a part of the healthcare facility). The information may be sent outside the healthcare facility using a distribution, a range, a minimum and a maximum value, so that the combined surgical data set may not be tied back to an individual patient.

Figure 49:
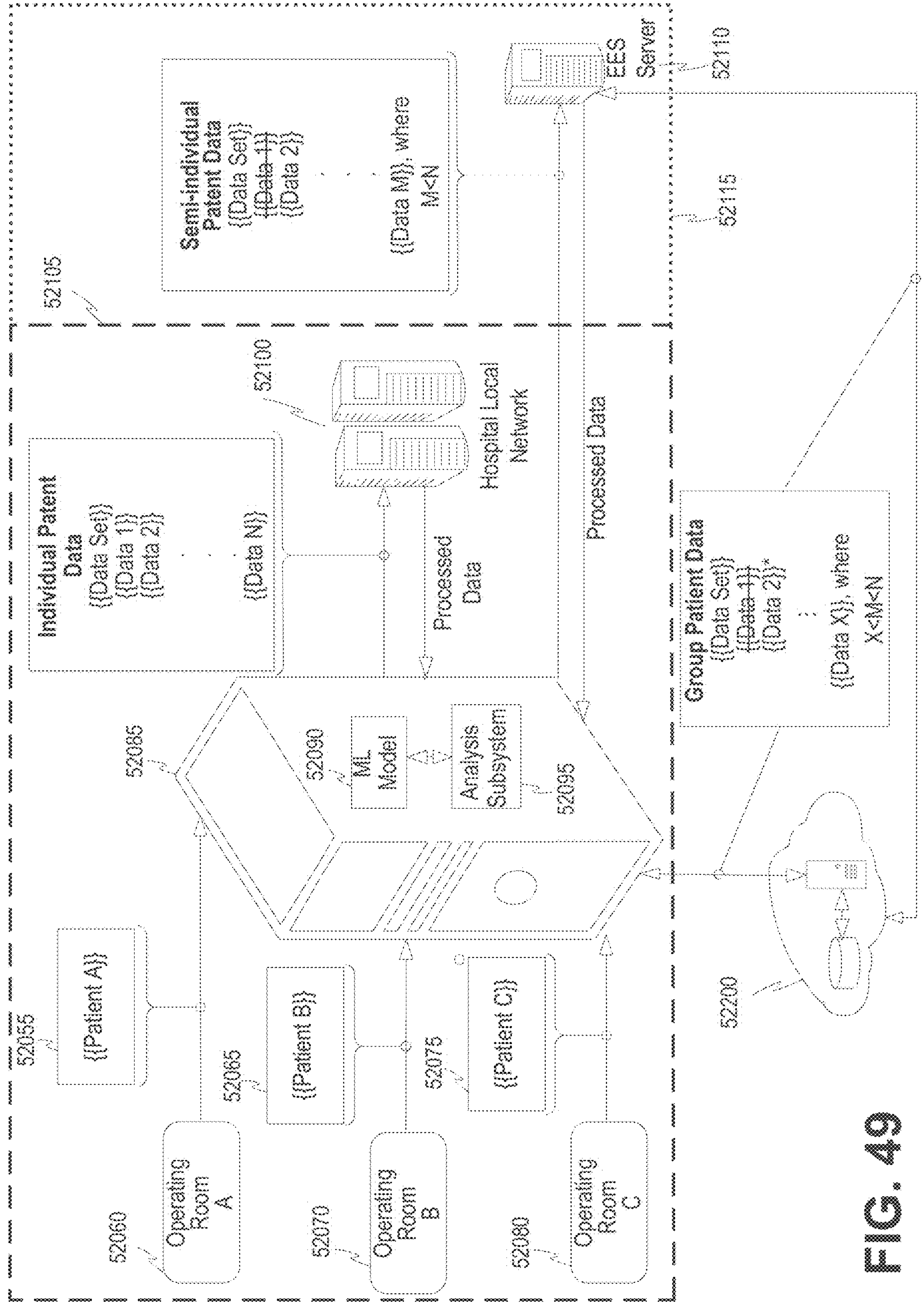
FIG. 49 illustrates an example of determining data individuality level based on a system hierarchy level where the surgical data may be sent for processing.

FIG. 49 illustrates an example of determining data individuality level based on a system hierarchy level where the surgical data may be sent for processing. As shown in FIG. 49, surgical data may be associated with patient A 52055 having a surgical procedure being performed on the patient in operating room A 52060, associated with patient B 52065 having a surgical procedure being performed in operating room B 52070, and/or associated with patient C 52075 having a surgical procedure being performed in operating room C 52080. The surgical data may be sent (e.g., sent via messages) to a local surgical hub/edge device 52085. The surgical data may be generated from one or more surgical instruments located in each of the operating rooms. The surgical data may be generated based on measurements taken using sensors, actuators, robotic movements, biomarkers, surgeon biomarkers, visual aids, billing, and/or the like. In an example, surgical data to be processed may be generated based on a visual tracking system located within each of the operating rooms. For example, the visual tracking system may include facial recognition system, which may produce data related to the status of the patient and/or surgeon during the surgical procedure.

The surgical data sent from the surgical instruments in the operating rooms to respective local surgical hubs may be in raw form (e.g., without any processing done to it). The raw measurement data may be converted by the local surgical hub into data points. A machine learning model 52090 and/or the analysis subsystem 52095 that are a part of the local surgical hub/edge device 52085, may be used to predict the location of a processing device (e.g., a processing device in a system hierarchy level) where the surgical data may be sent for processing. For example, the local hub 52085 may determine to send the surgical data to a processing device (e.g., an edge server 52100) that is located within the hospital's local network. The hospital's local network may be a part of a protected boundary 52105. In such a case, the local hub 52085 may send the surgical data with high data individuality and data magnitude to the server 52100 located with the protected boundary 52105.

As described with respect to FIG. 49, data sent from the surgical hub/edge device 52085 to the edge server 52100 may be organized into one or more surgical data sets. A surgical data set may include surgical data points (e.g., parameters associated with a patient, healthcare provider, and/or a surgical instrument) 1, 2, . . . . N, where N is a finite number. Surgical data points 1 through N may be associated with patients A 52055, B 52065, and/or C 52075. In an example, a surgical data set with surgical data points 1 through N may be associated with a high data individuality due to surgical data points 1 and 2 having a high risk of being linked back to patient A 52055. As illustrated in FIG. 49, in a case where the surgical data is being sent to a processing device located within the protected boundary 52105 (e.g., an edge server 52100), surgical data points 1 and 2 may be included in that surgical data set. In an example, surgical data points 11 through 20 may be associated with patient B 52065 and surgical data points 19 and 20 may be of type that may have a risk of being traced to patient B. Since the surgical data is being sent within the protective boundary 52105, the surgical data may be included within the surgical data set. In an example, surgical data points 30 through 40 may be associated with patient C 52075. Surgical data points 35 and 36 may be traced to patient C 52075. Since this surgical data is being sent within the protected boundary 52105, it may be included in the data set that may be sent to the edge server 52100.

In an example, the local surgical hub/edge device 52085 may determine that a surgical data set, for example, surgical data set associated with patient A 52055, patient B 52065 and/or patient C 52075 may be sent for processing to a processing device (e.g., server 52110) that may be located within an intermediate system hierarchy level. The intermediate system hierarchy level 52110 may be associated with a semi-protected boundary 52115. Server located at the intermediate system hierarchy level 52110 may have moderate processing power when compared to local servers 52100 (e.g., has least processing power) and remote servers 52200 (e.g., most processing power). In an example, the server may be located within an extended healthcare facility network. For example, the healthcare facility may have an agreement with some partner healthcare facilities about sharing the patient data. In such a case, the network shared by these hospitals may be considered within the semi-protected boundary 52115. Surgical data set sent to server(s) within this network may adhere to a moderate data individuality level. Surgical data set with moderate individuality level may have less individuality than the surgical data set that is located within a healthcare facility's protective boundary and more individuality than the surgical data set that may be sent outside of the protected/intermediate boundary. The different individuality levels may be achieved by anonymizing the data (e.g., redacting, randomizing, averaging, etc.), as described herein.

As shown in FIG. 49, the surgical data set sent to the intermediate system hierarchy level 52110, for example, may include M out of N surgical data points, where M is less than N (e.g., N is the total number of surgical data points that were generated within a healthcare facility's protective boundary 52105). The surgical data points that were removed or anonymized may be the surgical data points that may have high risk of being traced to an individual patient. Surgical data form and surgical data individuality may be used interchangeably herein.

In an example, as illustrated in FIG. 49, out of the surgical data points 1 through N associated with patient A 52055, surgical data points 1 and 2 may have high individuality and may reveal information that may trace it back to patient A 52055. In an example, surgical data point 1 may be the patient's name, patient ID, identification of the surgical procedure performed in the patient, etc. In such a case, because of the high individuality level, the surgical data point 1 may be redacted before a surgical data set it is a part of is sent for processing to any of the processing devices that are located outside the protected boundary 52105. In an example, surgical data point 2 may be associated with patient's physical features, for example, height, weight, etc. In such a case, surgical data point 2 may be deemed as not as likely to be traced back to patient A 52055 and may be sent in non-anonymized form to a device located in an intermediate hierarchical level, for example, within a healthcare facility's network 52115, but outside the protected boundary 52105. As illustrated in FIG. 49, in this case, the data magnitude M comprising the number of surgical data points M (data points N minus data point 1 that was anonymized and therefore not available for the processing device for analysis) may be less than the number of data magnitude N.

In an example, the data magnitude and/or the data individuality level associated with a hierarchical level may be related to the proportion of algorithm that may be utilized to process the data at that hierarchical level. For example, the proportion of algorithm used for processing surgical data points 1 through N of higher data individuality at the surgical hub/edge device 52085 may be higher than the proportion of algorithm used for processing surgical data points 1 through M (where M<N) at the server 52115 that is located within an intermediate hierarchical level, for example, within a healthcare facility's network 52115, but outside the protected boundary 52105.

In an example, the surgical hub/edge device may determine to send a surgical data set to a remote server 52200 located outside of the protective boundary 52105 and intermediate boundary 52115. The local surgical hub/edge device 52085 may identify the processing device using the machine learning model 52090 and/or analysis subsystem 52095 as described herein. For example, the machine learning model may identify a remote server 52200 based at least on the diversity of data sets available on the remote server 52200, performance metrics associated with the data, etc., as described herein. In such a case, in addition to anonymizing the surgical data point 1, the surgical hub/edge device 52085 may also anonymize the surgical data point 2 before sending both the surgical points for processing to the remote server 52200. As illustrated in FIG. 49, in this case, the data magnitude X comprising the number of surgical data points X (data points N minus 2) may be less than the data magnitude M (N minus 1), which may be lesser than the data magnitude N. As illustrated in FIG. 49, as the surgical data set associated with a patient may be sent to various processing devices for processing, the data magnitude may grow or shrink based on the protection level provided by the hierarchical level where the processing device is located, or the data individuality level associated with that hierarchical level.

In an example, as described here, the surgical hub/edge device 52085 may send a surgical data set of magnitude M (N minus 1) to the processing device (server 52110) that is located in the intermedia hierarchical level and/or associated with an intermediate individuality level. The server may send the surgical data for further processing to the remote server 52200. In such a case, the server 52110 my further anonymize the surgical data set by, for example, randomizing data point 2 before sending the surgical data set of magnitude X (N minus 2, and where X<M<N) to the remote server 52200. In this case, the proportion of algorithm used for processing surgical data points 1 through X (e.g., at remote server 52200) of lower data individuality may be lower than the proportion of algorithm used for processing surgical data points 1 through M (where X<M<N) at the server 52115 that is located within an intermediate hierarchical level, for example.

In an example, surgical data points 1 through 10 may be associated with patient A 52055 with surgical data point 1 and surgical data point 2 being traceable back to patient A 52055. In an example, the surgical data point 1 may be removed and data point 2 may be anonymized. In an example, these surgical data points may be fully anonymized (e.g., fully redacted, randomized, averaged, etc.) to where they are unable to be traced back to patient A 52055. In examples, the surgical data points of dataset X may be aggregated to a level where the surgical data cannot be traced back to any of patient A 52055, B 52065 and/or C 52075. In an example, surgical data points 10 through 20 may be associated with patient B 52065 and surgical data points 19 and 20 may be specific to B 52065 and may be traced back to patient B 52065. Both the surgical data points 19 and 20 may be redacted. In an example, the surgical data point 20 may be sent for processing in the surgical data set after being fully anonymized. Surgical data points 30 to 40 may be associated with patient C 52075. Surgical data points 35 and 36 may be specific to patient C 52075 and may be traced back to patient C 52075. Both data points may be removed (e.g., redacted). In such a case, the transformed surgical data may be associated with low data individuality and low data magnitude.

In an example a mathematical operation may be used to manipulate surgical data to change data individuality (e.g., remove any risk of the surgical data being associated or linked back to the patient). For example, an average and/or median may be taken among the surgical data points. Some of the surgical data points within the surgical data set may be manipulated to where they cannot be linked back to an individual patient, while other surgical data points within the surgical data set may be left unaltered. This may reduce the data individuality associated with the surgical data set while allowing the surgical data set to be sent to either the intermediate system hierarchy level 52110 or the remote level 52200.

Figure 50:
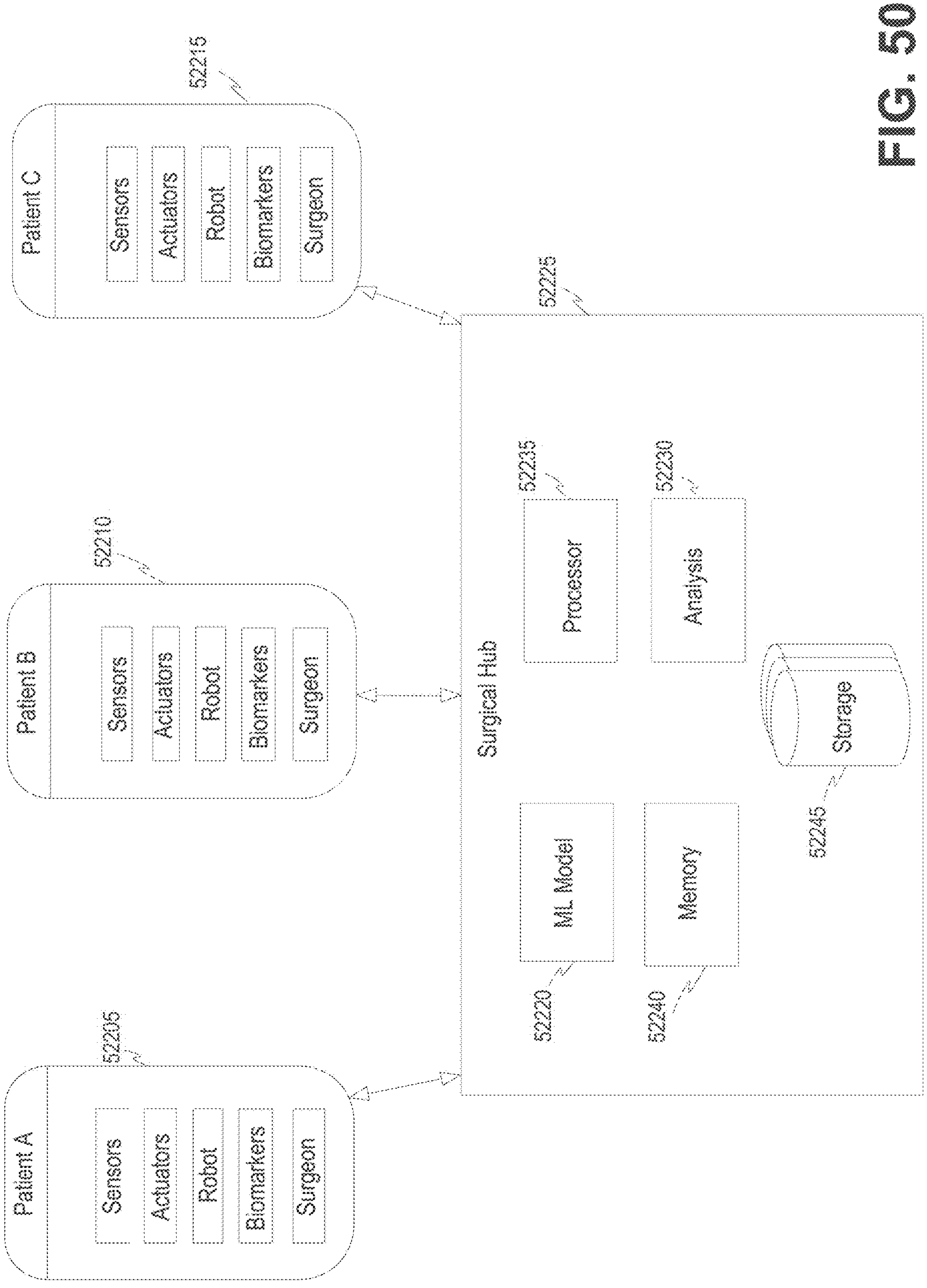
FIG. 50 illustrates an example of a surgical system where measurements taken within in operating rooms are received for processing by one or more respective the surgical hub/edge devices.

FIG. 50 illustrates an example of a surgical system where measurements taken within in operating rooms are received for processing by one or more respective the surgical hub/edge devices. As illustrated in FIG. 50, a surgical hub 52225 may include a processor 52235, a memory 52240 (e.g., a non-removable memory and/or a removable memory), an analysis subsystem 52230, a machine learning model 52220, and/or a storage subsystem 52245, among others. It will be appreciated that a surgical hub 52225 may include any sub-combination of the foregoing elements/subsystems while remaining consistent with an embodiment.

The processor 52235 in the surgical hub 52225 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), a state machine, and the like. The processor 52235 may perform data processing of surgical information it may receive from various surgical device and instruments attached to the surgical hub. The processor 52235 may perform data processing, authentication, input/output processing, and/or any other functionality that may enable the surgical hub 52225 to operate in an environment that is suitable for performing surgical procedures. The processor 52235 in the surgical hub 52225 may be coupled with a transceiver (not shown). The processor 52235 in the surgical hub 52225 may use the transceiver to communicate with other edge servers and/or remote servers, as described with respect to FIG. 48 and FIG. 49.

The processor 52235 in the surgical hub 52225 may access information from, and store data in, any type of suitable memory (e.g., a non-removable memory and/or the removable memory). The non-removable memory may include random-access memory (RAM), read-only memory (ROM), a hard disk, a solid-state drive or any other type of memory storage device. The removable memory may include secure digital memory.

The processor 52235 in the surgical hub 52225 may access information from, and store data in an extended storage 52245. (e.g., a non-removable memory and/or the removable memory). In an example, the processor 52235 in the surgical hub 52225 may process data points associated with a patient and determine a risk level associated with the data points and apply an individuality level associate with the risk level and/or a hierarchical level where the data points may be sent for further processing.

As described with respect to FIG. 49, a surgical data set may include multiple surgical data points. Surgical data points may be obtained from measurement data associated with a patients, a healthcare professional, etc. For example, a surgical data point may be associated with a measurements taken from a sensor, an actuators, a robotic movement, a patient biomarkers, a surgeon biomarker, a visual aid, and/or the like. Wearable devices could be used for those measurements. The wearable devices or wearables are described in greater detail under the heading "Monitoring Of Adjusting A Surgical Parameter Based On Biomarker Measurements" in U.S. Patent Application No. US 17/156, 28, filed Nov. 10, 2021, the disclosure of which is herein incorporated by reference in its entirety. Each surgical data point may have a data individuality level associated with it. The data individuality level may be associated with a risk level. The risk level may indicate whether or not a surgical data point can be traced or linked back to the patient. An overall risk level may be attributed to the surgical data set. The overall risk level, among other things, may be based on the aggregation of the risk levels of each of the surgical data points within a surgical data set.

In an example, the measurements may be associated with one of more actuators located within the operating room. For example, measurements may be generated based on potentiometer readings located on a surgical instrument used by a surgeon operating on the patient, for example, patient A 52205, patient B 52210, and/or patient C 52215 located within respective operating rooms as shown in FIG. 50. The potentiator readings received by the local surgical hub/edge device 52225 may be then provided to the machine learning model 52220 located in the local surgical hub/edge device 52225. The machine learning model 52220 may be trained to associate a potentiometer reading with a risk level (e.g., a low risk level). For example, the machine learning model 52220 may determine that the potentiometer readings are unlikely to be linked back to an individual patient, and therefore can be associated with low risk level. Accordingly, a surgical data set that includes potentiometer readings, for example, may be associated with an overall low risk level and may be sent by the local surgical hub/edge device 52225 to an intermediate system hierarchy level or a remote server for further processing.

In an example, one of a surgical data points of a surgical data set may be a cortisol level of a patient. The surgical data point may be generated or calculated based on measurements taken from a wearable that may be worn by the patient during a surgical procedure. For example, the patient may wear a wristwatch which may determine the cortisol level of the patient based on a reading of the sweat produced by the patient. The data point may be generated by the surgical instrument or the local surgical hub/edge device 52225. The local surgical hub/edge device 52225 may determine that the cortisol level may uniquely identify the patient and may assign a risk level (e.g., a high risk level) with the surgical data point. The local surgical hub/edge device 52225 may utilize machine learning model 52220 to assign a risk level to a surgical data point. The machine learning model 52220 may recommend to remove or anonymize the cortisol data point before sending it to a device that may be located outside the protected boundary. The input to the machine learning model may be the surgical data points that may be generated within an operating room, and the output of the machine learning model may be identification of a processing device and/or the system hierarchy level where a surgical data point or a surgical data set containing that surgical data point may be sent for processing.

Figure 51:
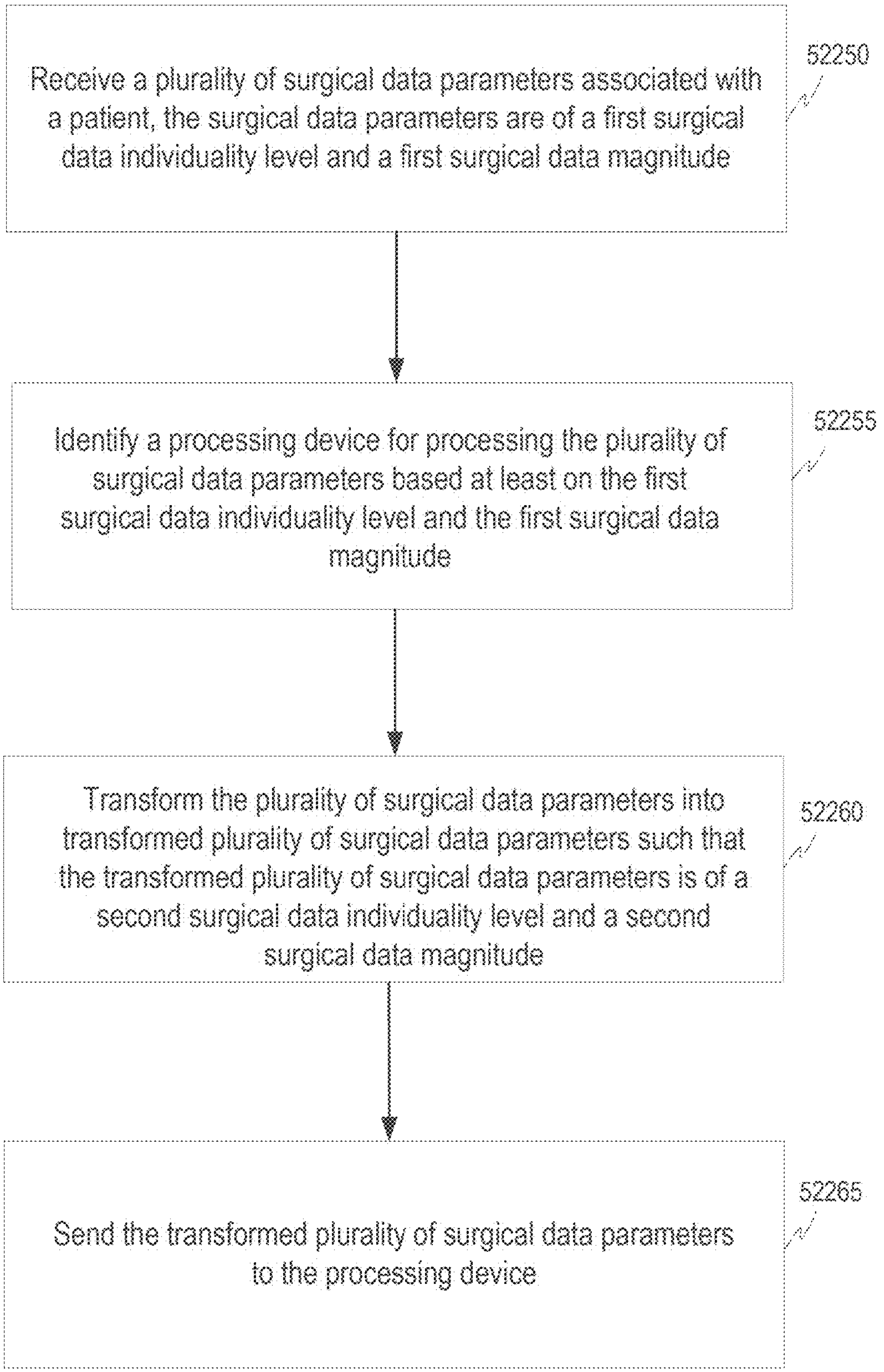
FIG. 51 illustrates an example of transformation of surgical data parameters associated with a patient based on data individuality and the system hierarchy level.

FIG. 51 illustrates an example of transformation of surgical data parameters associated with a patient based on data individuality and the system hierarchy level. At 52250, a surgical device (e.g., a surgical hub) may receive a plurality of surgical data parameters associated with a patient. The plurality of surgical data parameters may be of a first data magnitude (e.g., data size) and of a first data individuality level.

At 52255, the surgical device may identify a processing device for processing the plurality of surgical data parameters. The processing device may be identified based on one or more of: a the first surgical data individuality level, a first surgical data magnitude, a sensitivity to latency in processing the surgical data parameters, the intended use of the first surgical data parameters, characteristics of the first processing server, or a rule set.

At 52260, the surgical device may transform the plurality of surgical data parameters into a transformed plurality of surgical data parameters such that the transformed plurality of surgical data parameters is of a second surgical data individuality level and a second surgical data magnitude. In an example, the second surgical data individuality level may be lower than the first surgical data individuality level. The transformation of the first plurality of surgical data parameters may include anonymization or anonymization of a subset of the plurality of surgical data parameters. The anonymization may include at least one of redaction, randomization, aggregation, setting a range, or averaging.

At 52265, the transformed plurality of surgical data parameters are sent for processing to the processing device identified at 52250.

Figure 52:
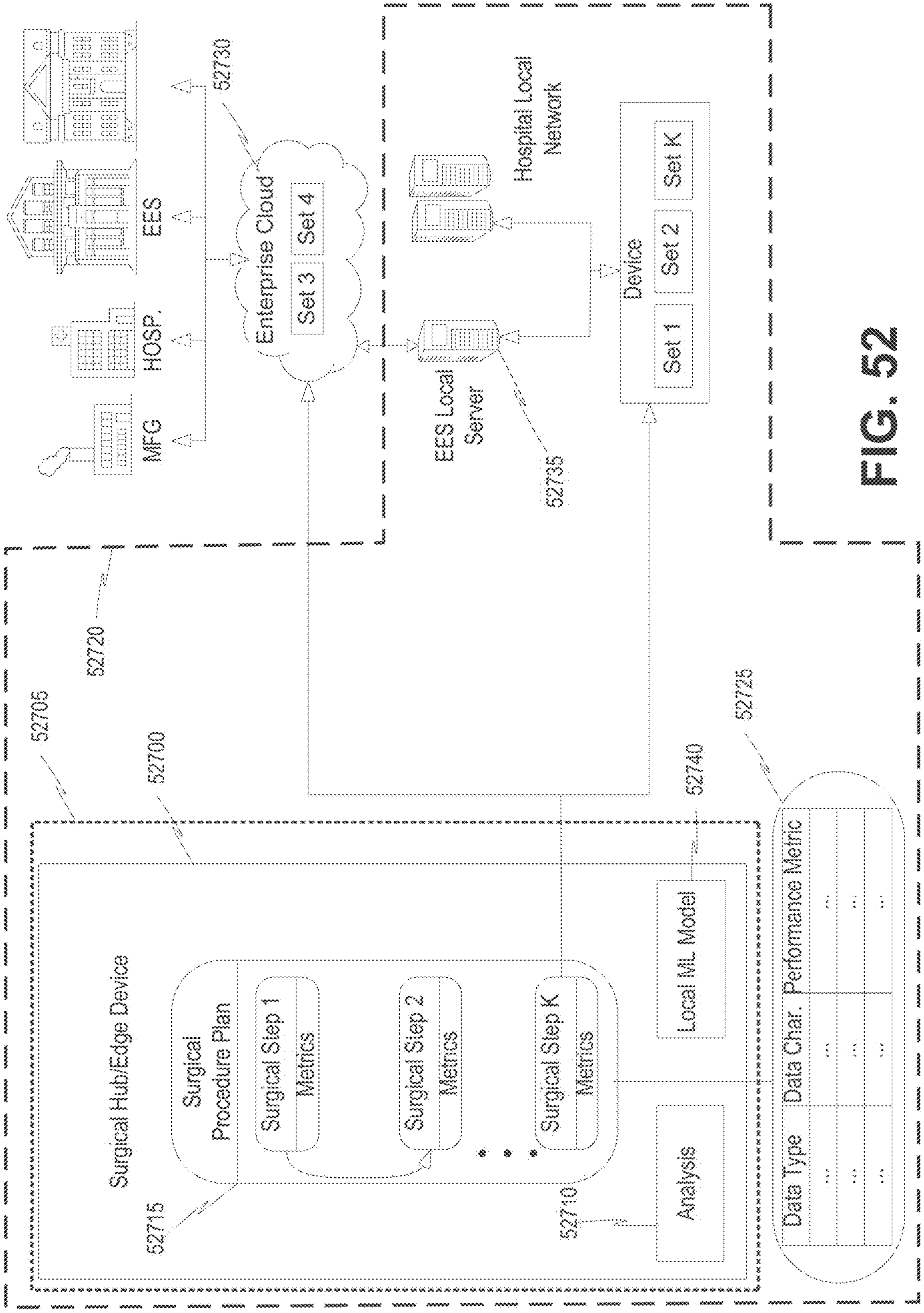
FIG. 52 shows an example of an overview of sending data to multiple system hierarchical levels.

Referring to FIG. 52, an overview of the surgical system may be provided. Surgical instruments may be used in a surgical procedure as part of the surgical system. The surgical hub/edge device may be configured to coordinate information flow to a surgical instrument (e.g., the display of the surgical instrument). For example, the surgical hub/edge device may be described in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Example surgical instruments that are suitable for use with the surgical system are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 52 shows an example of an overview of sending data to multiple system hierarchical levels. The surgical hub/edge device 52700 may be used to perform a surgical procedure on a patient within a surgical operating room 52705. A robotic system may be used in the surgical procedure as a part of the surgical system. For example, the robotic system may be described in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. The robotic hub may be used to process the images of the surgical site for subsequent display to the surgeon through the surgeon's console.

Other types of robotic systems may be readily adapted for use with the surgical system. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

Various examples of cloud-based analytics that are performed by the cloud, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, an imaging device may be used in the surgical system and may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (e.g., can be detected by) the human eye and may be referred to as visible light or simply light. A typical human eye will respond to wavelengths in air that are from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device may be configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngoneproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device and its attachments and components. It will be appreciated that the sterile field may be considered a specified area, such as within a tray or on a sterile towel that is considered free of microorganisms, or the sterile field may be considered an area, immediately around a patient, who has been prepared for a surgical procedure. The sterile field may include the scrubbed team members, who are properly attired, and all furniture and fixtures in the area.

As shown in FIG. 52, a surgical hub/edge device 52700 may be associated with and/or located in a surgical operating room 52705. The operating room(s) 52705 other than a surgical hub may also include one or more surgical instruments and surgical devices. The surgical instruments and surgical devices may be used (e.g., autonomously or manually by the surgeon) to perform the surgery on the patient. For example, the surgical device may be an endocutter. The surgical device may be in communication with the surgical hub/edge device 52700 that may be located within or close to the operating room 52705. The surgical hub/edge device 52700 may instruct the surgical device about information related to the surgery being performed on the patient. In examples, the surgical hub/edge device 52700 may set a settings parameter to a surgical instrument or surgical device by sending a message to the surgical instrument or the surgical device. For example, the surgical hub/edge device 52700 may send the surgical device information indicative of a firing rate for the endocutter to be set at or during a stage of the surgery. The message may be sent to the surgical instrument in response to the surgical instrument sending a request message to the surgical hub/edge device 52700 for the instrument.

Surgical information related to the surgery may be generated. For example, the information may be based on the performance of the surgical instrument. For example, the data may be associated with physical measurement physiological measurements, and/or the like. The measurements are described in greater detail under the heading "Monitoring Of Adjusting A Surgical Parameter Based On Biomarker Measurements" in U.S. patent application Ser. No. 17/156,28, filed Nov. 10, 2021, the disclosure of which is herein incorporated by reference in its entirety.

Surgical information associated with a surgical procedure being performed in an operating room may be sent to the local surgical hub/edge device 52700. In an example, surgical information associated with measurement(s) taken during a surgical procedure from a surgical display may be sent to the surgical hub/edge device 52700 where it may be further analyzed (e.g., analyzed by the analysis subsystem 52710).

As shown in FIG. 52, a surgical hub/edge device 52700 may track a progression of surgical steps in a surgical procedure and may coordinate functioning of surgical instruments based on such progression as indicated by a surgical procedure plan 52715. The surgical hub/edge device 52700 may determine the surgical steps (e.g., surgical steps 1, 2, through K) associated with the surgical procedure plan 52715. In an example, the surgical procedure tracked by the surgical hub/edge device 52700 may be a colectomy. The surgical procedure plan 52715 for the colectomy may include various surgical steps including, for example, mobilization of the colon. The surgical procedure plan 52715 may be obtained by the surgical hub/edge device or manually entered by a healthcare provider, such as the surgeon. The surgical steps associated with colectomy may be performed by one or more surgical instruments associated with the surgical hub/edge device 52700 and located in the operating room 52705. In an example, each of the surgical instruments may perform respective tasks associated with a surgical step. Surgical instruments may perform the surgical step autonomously. How the surgical instruments operate autonomously is described in greater detail under the heading "METHOD OF CONTROLLING AUTONOMOUS OPERATIONS IN A SURGICAL SYSTEM" in U.S. Patent Application No. U.S. Ser. No. 17/747,806, filed May 18, 2022, the disclosure of which is herein incorporated by reference in its entirety.

A surgical instrument involved in executing a surgical step may generate surgical data or surgical information associated with a surgical step. The terms data, surgical data, surgical data set, surgical information, surgical metrics set may be used interchangeably herein. Data or surgical data may include the data associated with the surgical hub/edge device 52700, a surgical instrument, data associated with a patient or a healthcare professional, and/or performance of the surgical step, for example as described herein. The surgical information or surgical data may be described in greater detail under the heading "Monitoring Of Adjusting A Surgical Parameter Based On Biomarker Measurements" in U.S. patent application Ser. No. 17/156,28, filed Nov. 10, 2021, the disclosure of which is herein incorporated by reference in its entirety. The surgical data may include a data type, data characteristics, and a performance metric. A surgical data characteristic may be associated with how sensitive the data (e.g., data form and/or individuality) is (e.g., in other words, what is the risk that the data be traced back to an individual patient). For example, surgical data that is highly sensitive may be likely to be tied back to an individual patient. Such surgical data may not be sent outside of a protected boundary 52720.

Health data is a special category of personal data which is subject to a higher level of protection (see Art. 9 GDPR or the HIPPA Privacy Rule), requiring heightened security considerations due to its cognitive content. Breaches of sensitive personal data can result in the accidental or unlawful destruction, loss, alternation, unauthorized disclosure of, or access to, sensitive data, which can have significant human consequences. For example, the permanent deletion of medical records of a person potentially has significant and long-lasting consequences for the health of said person.

Surgical data processing may be hybridized based on location, for example the location where the data is generated. Hybridization of data may include processing portions of surgical data locally (e.g., on a surgical hub/edge device 52700 or a local network processing), using one or more fog computing devices, and/or using cloud processing. The cloud processing may include analysis of surgical data sets that may be larger than the data sets that are analyzed by, for example, an edge server.

Figure 53A:
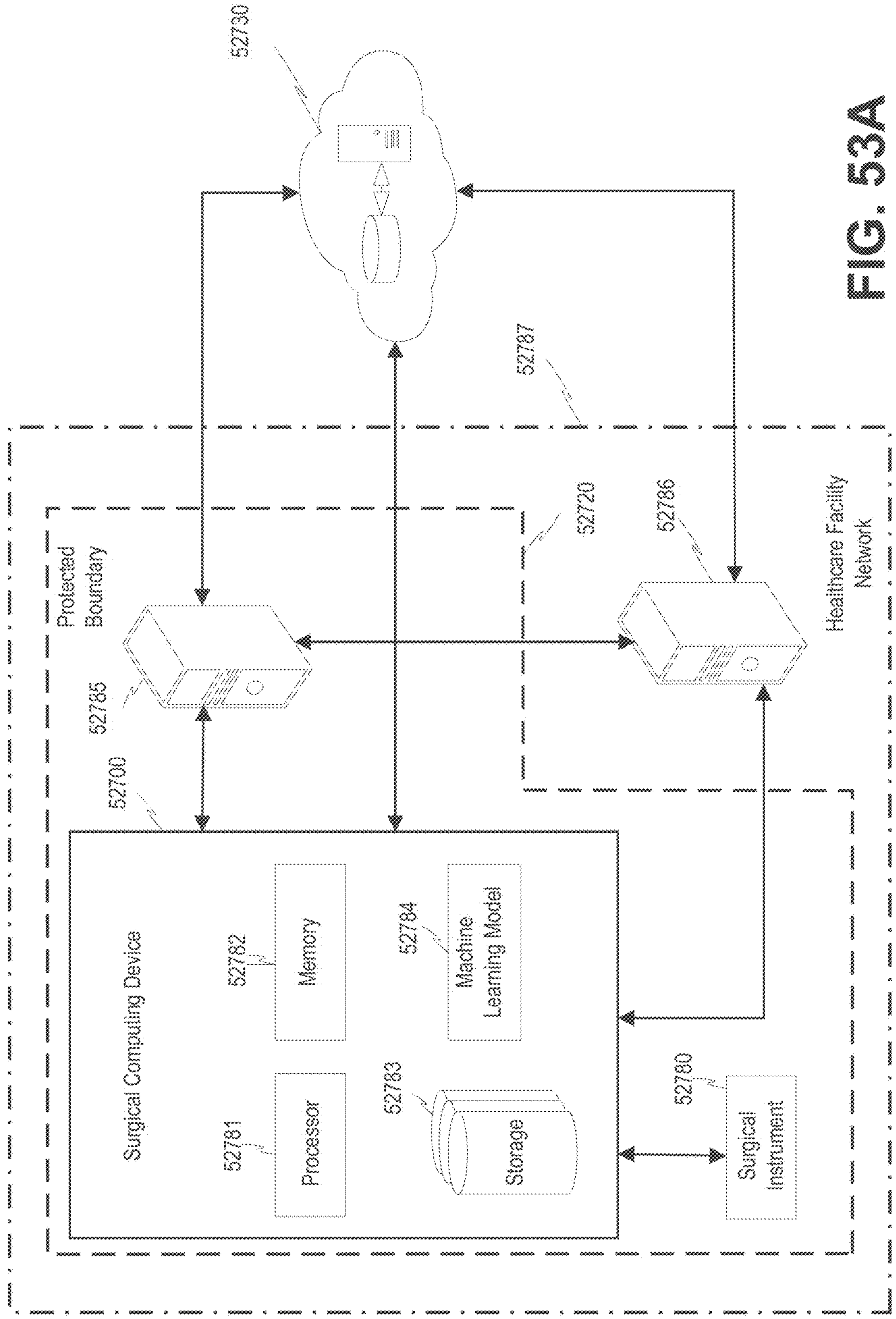
FIG. 53A shows an example of different system hierarchical levels.

Surgical data may be sent (e.g., in surgical data sets) to entities (e.g., entities with processors) located at different system hierarchical levels, as further described with respect to FIG. 52 and FIG. 53A. The systems and/or subsystems at various hierarchical levels may be divided based on one or more of the following: the location (e.g., whether the system or the subsystem is inside or outside the protected boundary 52720), the processing capability (e.g., processing power), the available memory (e.g., size and/or type of the memory), etc. Various hierarchical levels may include: (1) the surgical hub system; (2) the edge or the fog networking system; (3) and/or the cloud enterprise server system. In an example, the surgical hub system and the edge system may be located in the same hierarchical level. The surgical hub/edge device system including the surgical hub/edge device 52700, surgical devices and/or surgical instruments, etc. may be located in an operating room 52705. The edge or the fog networking system may include edge servers. The edge or the fog networking system may include server systems that may be co-located within a healthcare facility and/or distributed within a healthcare facility's network. As illustrated in FIG. 52, the surgical hub/edge device system and the edge or fog networking system may be located within a protected boundary 52720, for example, protected boundary based on the HIPAA rules. The enterprise cloud server system 52730 may include one or more enterprises cloud servers.

The surgical hub/edge device 52700 may determine a processing device in a system hierarchical level that may be suitable for processing the surgical data set or a portion or subblock of the surgical data set. The surgical hub/edge device 52700 may send the surgical data set to the determined processing device. For example, the surgical data set 52725 may be sent locally for processing, for example, to an edge server 52735 that is located within the protected boundary 52720. In an example, the surgical data set 52725 may be sent to an enterprise cloud server 52730 that may be located outside of the protected boundary 52720. In an example, the surgical data set 52725 may be sent to a server located within an intermediate system hierarchical level. For example, the intermediate system hierarchical level may be a location that is within a hospital network but is not within the protected boundary 52720.

The proportion of processing the surgical data at different hierarchical levels may be determined using system aspects, a parameter associated with the surgical data to be processed, and/or a result associated with the surgical data. System aspects, for example, inherent system aspects or the patterns needed may be utilized to determine the location where the surgical data may be processed or sent for processing. The system aspects and/or the patterns may be utilized to determine the extent the surgical data should be processed at different hierarchical levels of a system. For example, a high frequency surgical data set may be modified (e.g., decimated) to send (e.g., only send) a portion (e.g., a useful portion) of the surgical data for processing at different system levels of hierarchy of a system. In an example, the portions of subblocks of the surgical dataset may include calculated impedance spectrum instead of the complete set of voltage and current samples.

In an example, the parameters (e.g., only the parameters) of the algorithms may be transferred back to the main repository. The parameters may be used by ML models 52740 to enhance tissue characterization and performance. The ML models 52740 may be run inside a smart device (e.g., a smart instrument or a smart surgical hub/edge device 52700), an edge computing device, or a fog computing device (not shown) that may be located within the protected boundary 52720 of a healthcare facility. In an example, the processing capability of an edge or a fog computing device may be lower than a cloud-based server or an enterprise server.

In an example, ML models, e.g., light version of a local ML model may be used on a smart surgical hub/edge device 52700 or a fog or edge computing device. The local ML model may be utilized to calculate a smaller number and/or simpler calculations using, for example, devices with lower processor power than the cloud-based server devices. For example, gradient-enhanced kriging surrogate modeling may be utilized to provide a low computational cost mechanism of evaluating processor intensive functions. Gradient-enhanced kriging models may be utilized to reduce the number of function evaluations for the desired accuracy when efficient gradient computation, such as an adjoint method, is available. Such gradient-enhanced kriging models may be run on a smart surgical instrument itself to predict an output. In an example, the gradient-enhanced kriging models may be run on a smart surgical hub/edge device 52700 or a fog computing device.

In an example, a machine learning model and/or a trained machine learning model may be utilized as part of a supervised learning framework. Supervised learning model is described herein in FIG. 8A. The training data (e.g., training examples 802, as illustrated in FIG. 8A) may consist of a set of training examples (e.g., input data mapped to labeled outputs, for example, as shown in FIG. 8A). The training data used in training the local machine learning model 52515 may include data gathered from previous surgical procedures and/or simulated surgical procedures. The training data may include attributes or parameters associated with a patient and/or parameters associated with surgical instrument(s). In an example, the local ML model as an output may provide measurable outcomes associates with a surgical procedure. For example, a ML model may be utilized to detect low risk interpretations including for example, a prediction that hemostat may be required during a colorectal surgical procedure, prediction of post-operative leaks after a surgical procedure (e.g., colorectal surgical procedure), prediction of post-operative air leaks after a thoracic surgical procedure, etc. These predictions may be made based on various surgical data inputs including, for example whether the patent was irradiated before the surgical procedure and/or whether the patient consumed a certain type of drug. One or more of the attributes associated with a patient may be redacted before sending the surgical data for further processing to an enterprise cloud server location. In an example, the attributes selected for redaction may be performed in a manner to have minimum impact on a measured outcome.

In an example, a condensed parameterization mechanism may be utilized by a system (e.g., a system located in lower hierarchical level hierarchy) to filter out, condense interrelated data, or filter data that may have less significant probabilities of impacting a measured outcome. The lower hierarchical level system or a device located at a lower hierarchical level may perform condensed parameterization of surgical data, for example, before sending it to a higher level for further processing. The condensed parameterization of surgical data may be performed based on one or more of the following: limitations in communication, memory storage, processing resources by one or more higher level systems, etc.

In an example, surgical data collected in a device or a system that is located at a lower hierarchical level may be reduced before transferring it to the next hierarchical level (e.g., higher). For example, as illustrated in FIG. 53A, surgical data collected at the surgical instrument 52780 or processed at the surgical computing device 52700 or an edge server 52785 located within the protected boundary 52720 may be reduced before sending it to next hierarchical level (e.g., an enterprise cloud server 52730 located outside the protected boundary 52720).

The locally compiled parameterization, signal processing, and/or data reduction may be performed at a lower (e.g., lowest) branch of a hierarchical tree (e.g., the collection device or a smart instrument). The lower branch may be a smart surgical instrument 52780 or the surgical computing device 52700. The selective data parameterization, signal processing, and/or surgical data reduction may be performed based on at least one of the following: the processing limitations of the next hierarchical level, importance of surgical data, surgical data that may have minimal or no effect on a measured outcome or result, risk or severity of the surgical data or its implications, time relative to an event (e.g., failure, technical irregularity, communication issue, etc.).

In an example, a surgical instrument 52780 or a surgical subsystem that is located at a lower level in the computational hierarchy may perform decimation of data before transferring the surgical data to a device or a subsystem that is located at a next or higher level in the computational hierarchy, for example, the surgical computing device 52700 or an edge server 52785. In an example, data decimation may include removal of every tenth data point in the surgical data set. In the case of signal processing, decimation by a factor (e.g., a factor of 10) may include saving/keeping every tenth sample. Specialized, purpose-built and/or customized processing units (e.g., an application specific integrated circuit (ASIC) based processing unit or a reduced instruction-set computing (RISC) based processing unit) may be used in such devices (e.g., an end effector, shaft or handle of the instrument) to decimate the surgical data and/or process/condition signals so that the output from such computing devices (e.g., only the output from such devices) may be handled by another computing device that is located at a higher level in the computational hierarchy.

A mid-level device or a system may reduce and/or limit transferred data up the computational hierarchical levels based on the communication parameters, network conditions to the next node in the computational hierarchy (e.g., the next higher node in computational hierarchical levels), and/or processing capabilities of the system located higher in the computational hierarchy. For example, the surgical computing device 52700 may reduce and/or limit transferred surgical data to the enterprise cloud server 52730 based on the link condition between the surgical computing device 52700 and the enterprise cloud server 52730. The reduction and/or limitation of data at a mid-level computational hierarchical system may provide combined parameters or parameter data by eliminating or limiting the surgical data or a portion of the surgical data that may have a minimal or no impact on the measured outcome. The reduction and/or limitation of data may be performed based on the directionality of decomposition of the data with leading trending but inconclusive results. This may result in finding high signal patterns or relationships among data (e.g., by sacrificing more detailed interactions) in order to maximize benefit of cost, time, bandwidth, and/or processing resources.

In an example, edge computing processes running on an edge device 52785 or a fog computing device residing in healthcare facility's network 52720 may be utilized for providing edge processing of data locally, for example, using artificial intelligence. In an example, federated learning may be utilized to enable collaborative training of machine learning models on the edge device. Edge computing may process data away from centralized storage or a cloud server 52730 and may keep information on the local parts of the network edge devices 52785. Surgical data sent to an edge device 52785, or a fog computing device may be processed directly on the device, for example, without sending it to a centralized enterprise cloud server 52730. Processing of surgical data on an edge server device 52785 or a fog computing device may mean minimal or no delays in data processing. The data may be stored on the edge of a network, for example, an Internet of Things (IoT) network and may be processed immediately.

In an example, an edge device 52785 or a fog computing device may be utilized for performing real-time data analysis on data that the edge device 52785 or the fog computing device may receive from a smart device or a smart surgical instrument that is located lower in computational hierarchy or a device or a system that is located higher in computational hierarchy than the edge device 52785 or the fog computing device. The edge device 52785 or the fog computing device may be utilized to process substantial amounts of data, it may receive form a smart computing device or a smart surgical instrument that is located lower in computational hierarchy or a device or a system that is located higher in computational hierarchy than the edge device 52785 or the fog computing device. The edge device 52785 or the fog computing device may have capability of processing data immediately.

In an example, the network congestion between a surgical computing device 52700 or a surgical instrument 52780 that is located lower in a computational hierarchy than an enterprise server 52730 may be minimal. Such an edge device 52785 or a fog computing device may be utilized (e.g., utilized first) to process data locally (e.g., at the edge device 52785 or the fog computing device) and send the processed data to the main storage (e.g., storage at the enterprise server 52730). In an example, various prioritized data types may be sent for processing to the edge device or the fog computing device in order, for example, based on a priority value associated with each of the data types.

In an example, a device or a surgical instrument 52780 (e.g., with limited resources and/or higher down time) that is located lower in the computational hierarchy than the edge device 52785 or the fog computing device may utilize the edge device 52785 or the fog device to pre-process or completely process its data. The edge device 52785 or the fog computing device may send results (e.g., results in simpler conclusion form) back to the surgical device or surgical instrument 52780 that is located lower in the computational hierarchy than the edge device 52785 or the fog computational device. The edge device 52785 or the fog computational device may send the results through a link that may be experiencing network congestion.

Utilizing the edge device 52785 or the fog computational device for data management and/or data processing may result in reduced operating costs. Data management takes less time and computing power because the operation may have a single destination, for example, instead of circling from the center to local drives.

A device, for example, a smart surgical hub/edge device 52700 may consider one or more of the following to determine where to send surgical data for processing and/or to what extent to process the surgical data: the surgical data type, portion of surgical data to be processed, surgical data characteristics (e.g., surgical data form, surgical data magnitude, etc.), the performance metric, the processor's capabilities, network characteristics (e.g., congestion in the network), etc., as described herein. For example, one of the surgical data characteristics associated with a surgical data set 52725 may be that the surgical data set 52725 includes surgical data that is highly likely to be traced back to an individual patient. In such a case, the surgical data may be processed locally within the protected boundary 52720 and may not be sent to the enterprise cloud server 52730.

In an example, a smart surgical hub/edge device 52700, for example, based on a processor's and/or a processor device's capabilities, may determine that a surgical data set 52725 is to be processed at an enterprise cloud server 52730 that is located outside the protected boundary 52720. If the surgical data set 52725 includes surgical data that is highly sensitive, the surgical hub/edge device 52700 may anonymize the surgical data set 52725 or a portion of the surgical data set 52725, for example, using one or more of the anonymization mechanisms (e.g., redaction, randomization, aggregation, etc.). The surgical data set 52725 or a portion of the surgical data set 52725 may be anonymized in order to reduce the likelihood of the surgical data set being traced back to a patient, as described herein.

A mix of a centralized data storage system and cloud computing may be provided. Computing may be performed at local networks (e.g., although servers themselves may be decentralized). In such a case, the surgical data may be accessed offline, for example, because some portions of the surgical data may also be stored locally. Fog computing and cloud computing may be provided. Low latency may be associated with the fog network, where large volumes of data may be processed with little-to-no delay. Because a significant amount of data may be stored locally, the computing may be performed faster. Better data control may be associated with cloud computing. In cloud computing, third-party servers may be fully disconnected from local networks, leaving little to no control over data. In fog computing, users may manage surgical information locally and rely on their security measures. A flexible storage system may be associated with fog computing. For example, fog computing may not use (e.g., require) constant online access. The data may be stored locally or pulled up from local drives. The storage may combine online and offline access. Connecting centralized and decentralized storage may be described herein. Fog computing may build a bridge between local drives and third-party cloud services, allowing a smooth transition to fully decentralized data storage.

Referring to FIG. 52, the location where a surgical data set 52725 is sent for processing and/or the extent of surgical data set 52725 to be sent for processing may be determined based on a metric (e.g., performance metric) associated with the surgical data set 52725, such as latency, network congestion, etc. In an example, a system may weigh urgency of the need of the surgical data results against the magnitude of the surgical data and compare it with the capabilities within the system's local protected network to determine where and how the data may be sent for processing. For example, a surgical data set 52725 associated with a low latency metric may indicate its timeliness or criticality. Such surgical data may be sent for processing with the least latency (e.g., in order to perform the next surgical step in time). In such a case, the surgical hub/edge device 52700 may determine to send the surgical data locally to a processor or processing device that may process the surgical data in timely fashion with low latency (e.g., rather than sending the data to enterprise cloud server 52730). For example, the surgical data set 52725 may be sent to an edge network comprising an edge device 52735 or a fog computing device (not shown in the figure). The edge device 52735 or the fog computing device may be located within a protected boundary 52720. The edge device may, therefore, process large volumes of data within an acceptable time interval. In examples, if the surgical data set 52725 is associated with a high latency performance metric, the server hub 52700 may send the surgical data for processing to an enterprise cloud server 52730 that is located outside the protected boundary 52720. The surgical data or a portion of the surgical data may be anonymized before being sent to the enterprise cloud server for processing, as described herein.

In examples, the edge device 52275 after performing analysis on the surgical data may further anonymize the surgical data (e.g., as described in FIG. 49) send it for further comprehensive processing to the enterprise server 52730 that is located outside the protected boundary 52720.

In an example, results and/or conclusions associated with surgical data obtained within a local healthcare facility network may be sent to an enterprise cloud server for further processing. A portion of the surgical data may be sent to the enterprise cloud server in clear and/or redacted form, as described herein. The results and/or conclusions associated with the surgical data, for example, with other portions of the surgical data may be utilized to determine relationships with one or more measured outcomes. For example, in prolonged air leak (PAL) a section of a lung is removed. After the surgical procedure, there may be an air leak that may stop in a few days. A lung collapse may occur if the chest cavity is filled up. PAL may depend on one or more of the following pieces of surgical data: the transection device that was used during lobectomy, location the removed lobe, artifact of the patient (e.g., state and/or stage of the disease that calcified the lung, whether the patient was exposed to irradiated or experienced chemo therapy before the surgical procedure, and/or whether the patient was taking any medication, which may cause air leaks or enhance healing), kind of surgical procedure and/or risk associated with the surgical procedure (e.g., whether a small or a big piece of lung was removed). When the surgical data associated with a thoracic surgical procedure, for example, is sent from a device within the protected boundary to the enterprise cloud server, a portion of the surgical data associated with the patient may be anonymized before sending it to the enterprise cloud server. The portion of surgical data may include, for example, stage of the disease of the calcified lung, whether the patient was irradiated or experienced chemotherapy before the surgical procedure, and/or whether the patient was taking any medication. Other portions of the surgical data may be sent in non-anonymized form.

In an example, a measured outcome may be characterization of a disease state. Such a measured outcome may be determined by eliminating a portion of personal data associated with a patient. The selection of the data portion to be eliminated or redacted may be based on the relevance of the data portion in determining the measured outcome.

Variance analysis may be conducted, for example, to compare, an actual outcome of a surgical procedure with an expected or standard outcome. The differences may be investigated, for example, in order to address the performance inefficiencies. In an example, variance analysis may be conducted using a decision model. Variances may be identified that are statistically significant and require further investigation.

In an example, surgical data associated with a surgical procedure may be transferred (e.g., automatically transferred from a surgical hub/edge device 52700 to an enterprise cloud server 52730 (e.g., an enterprise server). The enterprise server may collect surgical data from various healthcare facilities of diverse geographical locations. In an example, the surgical hub/edge device 52700 may send surgical data periodically to an enterprise cloud server 52730. In an example, the surgical data may be sent aperioidcally, for example, based on the surgical hub/edge device 52700 receiving a request from the enterprise cloud server 52730.

In an example, a surgical hub/edge device 52700 may determine the system hierarchical level where the surgical data may be sent for processing. The system hierarchical level where the surgical data may be sent for processing may be determined by using a machine learning model 52740 (e.g., which may be located in the surgical hub/edge device 52700). In an example, a machine learning model and/or a trained machine learning model may be utilized as part of a supervised learning framework, for example, as described herein in FIG. 8A. The training data (e.g., training examples 802, as illustrated in FIG. 8A) may include a set of training examples (e.g., input data mapped to labeled outputs, for example, as shown in FIG. 8A). The training data used in training the local machine learning model 52515 may include data type associated with surgical data, characteristics and at least one of performance metrics, processor capabilities, etc. associated with a particular target processing device where the surgical data may be sent for processing. The output may include a hierarchical level that may be suitable for processing the surgical data. The output may also include identification of a server and/or location of the server where the surgical data may be sent for processing.

As described with respect to FIG. 52 and FIG. 53A, the surgical data set 52725 may be divided into data chunks portions or subblocks and sent to different levels of the system hierarchy. Surgical data chunks or surgical data portions or surgical data subblocks may be used interchangeably herein. The surgical data subblocks may be sent to various processing devices in parallel at the same time interval or in series at different time intervals. In an example, a machine learning model 52740 may be used to predict how the surgical data set 52725 may be divided into data subblocks. The machine learning model 52740 may also be used to predict where and when the divided data subblocks (e.g., each of the data subblocks) may be sent for processing. In an example, a machine learning model 52740 may predict how to divide the surgical data set 52725 in a way that results in a data subblocks without highly sensitive data. The machine learning model 52740 may predict where to send each of the data subblocks for further processing. For example, the machine learning model 52740 may predict that a first data subblock comprising non-sensitive data may be sent to enterprise cloud server 52730 for processing. The machine learning model 52740 may also predict that data subblock that comprises highly sensitive data may be sent locally to an edge server that is located within the protected boundary 52720.

The surgical hub/edge device 52700 may consider a potential benefit of sending the data to a particular system hierarchical level when determining where to send it. For example, the surgical hub 52700 may assess that a surgical data set 52725 may benefit from being processed at an enterprise cloud server 52730 rather than locally (e.g., based on the enterprise cloud server 52730 having access to a more diverse data pool than a local edge server). The surgical hub/edge device 52700 may determine to send the surgical data set 52725 to the enterprise cloud server 52730. Accordingly, surgical hub/edge device 52705 may send the surgical data set 52725 to the enterprise cloud server 52730 or a local edge server.

In an example, the surgical hub/edge device 52700 may consider the capabilities of the processors located at the different system hierarchical levels when determining where to send the surgical data set 52725. For example, the enterprise cloud server 52730 may have a capability of having higher processing power as compared to processing power of a local surgical hub or even an edge server. A surgical data set 52725 may have high data magnitude (e.g., included in the data characteristics). In such a case, surgical hub/edge device 52700 may determine that the surgical data set 52725 is to be processed at the enterprise cloud server 52730, which has a more power. In examples, the surgical data set 52725 may be of smaller data magnitude. In such a case, the surgical hub/edge device 52700 may send the surgical data set 52725 locally (e.g., to one of the local servers with less processing power than the enterprise cloud server).

In an example, the surgical hub/edge device 52700 (e.g., via the machine learning model 52740) may consider surgical data granularity (e.g., included in the data characteristics) when determining where to send the surgical data set 52725. Surgical data granularity may be associated with a measure of comprehensiveness or a degree of the surgical data set 52725 (e.g., all of the relevant data points versus a subset of the relevant data points). The surgical hub/edge device 52700 may determine that for a particular surgical data set 52725, data granularity may be given more importance than data diversity. In such a case, the surgical hub/edge device 52700 may send the surgical data or a portion of the surgical data to a local server for processing (e.g., if none of the data points of the surgical data set need to be anonymized such as redacted, resulting in the surgical data set 52725 having higher data granularity). In examples, the surgical hub/edge device 52700 may determine that for a particular surgical data set 52725, data diversity may be give higher importance than data granularity. In such a case, the surgical hub/edge device 52700 may send the surgical data set 52725 to an enterprise cloud server 52730 located outside of the protected boundary 52720 (e.g., where the data granularity (e.g., the amount of the data that may be included with the request) is lower and data diversity is higher than that of the surgical hub/local edge device).

As illustrated in FIG. 52, the surgical hub/edge device 52700 may send surgical data sets three and four to the enterprise cloud server 52730. These surgical data sets may be less granular than surgical data sets one, two and/or K. The surgical hub/edge device 52700 may send data sets one, two and/or K to a local server 52735 located within the protected boundary 52720.

A feedback mechanism may be used to evaluate the machine learning model's predictions or decision-making. For example, a score may be generated based on a surgical instrument's performance, for example, when the machine learning model selects a local server 52735 over an enterprise cloud server 52730 for data processing. The score may be used to improve the machine learning model's predictions or decision making when it determines where to send the surgical data sets 52735 for processing.

As described herein, capabilities of the processors (e.g., each of the processors) may be considered by the surgical hub/edge device 52700 when determining where to send the surgical data sets 52725 for processing. Data individuality level may also considered by the surgical hub/edge device 52700, as described herein. For example, the surgical hub/edge device 52700 may be aware of the processors' capabilities (e.g., each of the processors' capabilities). The surgical hub/edge device 52700 may be configured with capabilities, for example, as part of a surgical procedure plan 52715 or prior to initiating a surgical procedure. For example, the surgical hub/edge device 52700 may determine that the processing power of a remote cloud server 52730 is more than the processing power of a surgical hub 52700 or a local edge server 52735. The surgical hub/edge device 52700 may also consider the data individuality level associated with the device where the surgical data 52725 may be sent for processing. These factors may be used as input by the machine learning model 52740 when determining where to send the surgical data set 52725 for processing. In an example, the capabilities of various devices (e.g., an edge server located inside a protected boundary, an edge server located within a healthcare facility's network, or an enterprise cloud server located centrally at a global or a regional level) may be determined by exchanging discovery request/response messages.

The network traffic may be considered when determining where to send the surgical data set 52725. For example, the surgical hub/edge device 52700 may send a test signal through the network to each of the processors that are a part of servers or devices located at different system hierarchical levels. The test signal may be utilized for requesting an acknowledgement message (e.g., an ACK message). Based on the latency of the ACK message, the surgical hub/edge device 52700 may determine and assign a network quality score to each of the processing devices located across various system hierarchical levels. The network quality score may then be utilized by the machine learning model 52740 in predicting where to send the surgical data set for processing.

In an example, a simulation may be generated by the surgical hub/edge device 52700. The simulation may be used (e.g., in combination with the machine learning model 52740) to determine the device or the processor associated with a device where surgical data set 52725 may be sent for processing. A simulation may be used to determine the threshold (e.g., an ideal threshold). Simulation framework may be described in "Method for Surgical Simulation" in U.S. patent application Ser. No. 17/332,593, filed May 27, 2021, the disclosure of which is herein incorporated by reference in its entirety. The simulation may output a score associated with sending the data to each of the processing servers. The surgical hub/edge device 52700, based on the simulations, may choose the processing device for surgical data processing in a manner to maximize the score. The simulations with a score less than the determined threshold may be excluded from considering the simulation as a candidate for choosing a processing device.

In an example, a surgical data set's property to be controlled may be considered by the machine learning model 52740 when determining where to send the surgical data for processing. For example, if the surgical data set 52725 is sent to an enterprise cloud server 52730, the surgical hub/edge device 52700 may have little control or no control of managing the data. The surgical hub/edge device 52700 may be able to manage and control the surgical data, for example, if the surgical data set 52725 is sent to a local server 52735.

Figure 53B:
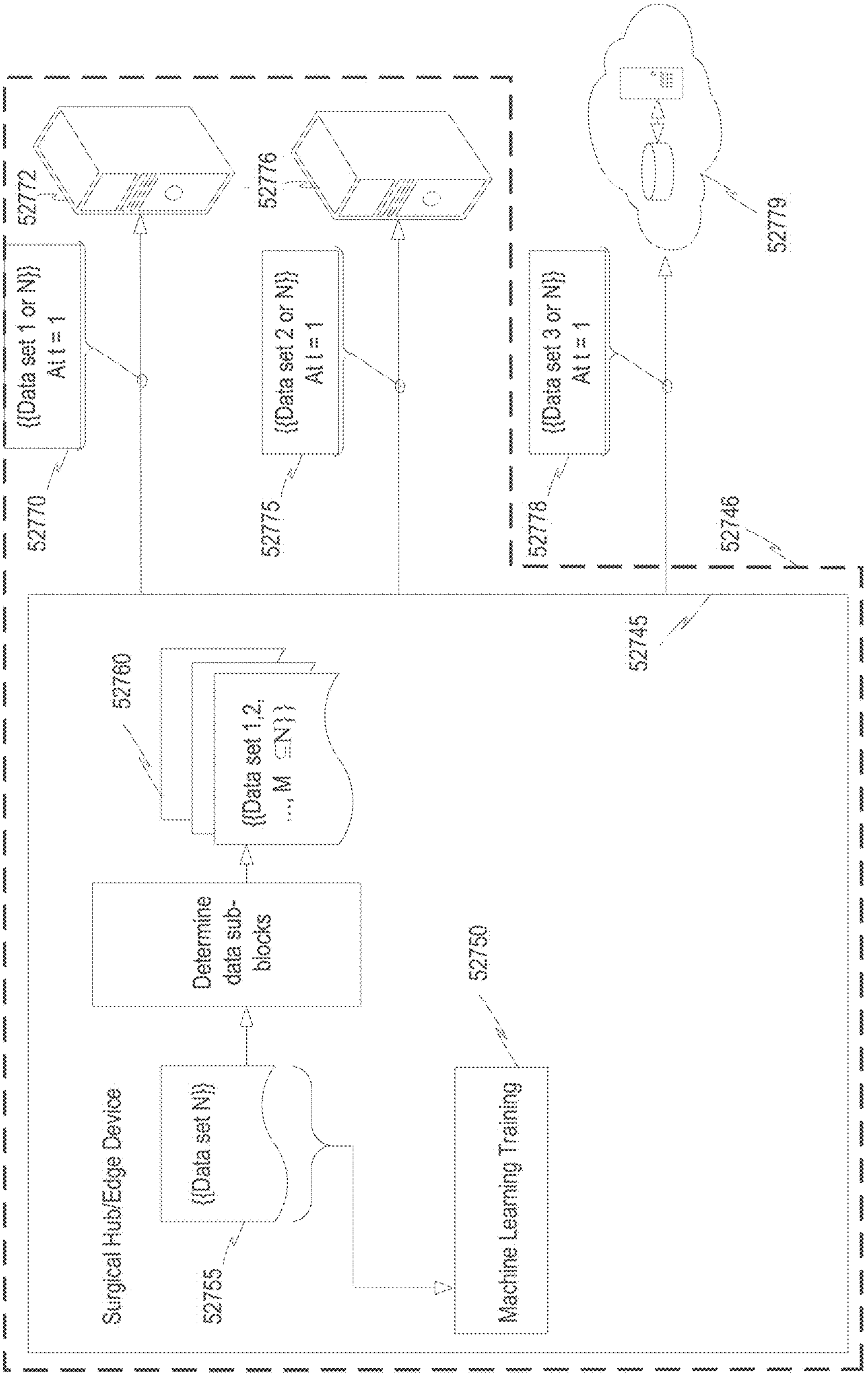
FIG. 53B shows an example of dividing the surgical data sets and sending the divided surgical data sets to different system hierarchical levels.

FIG. 53B shows an example of a surgical hub/edge device 52745 dividing surgical data sets 52755 in various surgical data subsets and sending the divided surgical data subsets to different system hierarchical levels. In an example, a machine learning model 52750 may be used to adjust the surgical data set 52755 before sending it for processing. For example, the surgical hub/edge device 52745 may determine that a given surgical dataset 52755, such as surgical dataset N, should be adjusted and/or manipulated and split into data subblocks 52760 (e.g., as illustrated in FIG. 53B) before sending it out for processing. The surgical hub/edge device 52745 may run a simulation with different combinations of dividing the surgical dataset 52755 into data subblocks. The surgical hub/edge device 52745 may then obtain how the surgical data set 52755 may be split and determine how the surgical data sets 52755 may be divided.

In an example, the machine learning model 52750 may be trained to take a surgical data set 52755 as an input and a combination of multiple data sub blocks 52760 as an output. In an example, a machine learning model and/or a trained machine learning model may be utilized as part of a supervised learning framework, for example, as described herein in FIG. 8A. The training data (e.g., training examples 802, as illustrated in FIG. 8A) may include a set of training examples (e.g., input data mapped to labeled outputs, for example, as shown in FIG. 8A). The training data used in training the local machine learning model 52515 may include surgical dataset(s). The output may include data subblocks, and an indication of where, when, and to what extent the data subblocks should be processed or sent for processing.

In an example, the machine learning model 52750 may predict and indicate that surgical data set N 52755 is to be divided into surgical data subsets one, two, through M (e.g., wherein each of the surgical data sets may include a number of the data points originally in dataset N). As illustrated in FIG. 53B, the machine learning model 52750 may be utilized to indicate that at time T equal to 1, the surgical data subset one 52770 and the surgical data subset two 52775 are to be processed locally, while the surgical data subset three 52778 is to be sent remotely to an enterprise cloud server.

In an example, the processing of the surgical data subset one 52770, the surgical data subset two 52775, and the surgical data subset three 52778 may occur in parallel. In such a case, the surgical data subsets may be sent for processing to various processors or processing devices in parallel, e.g., at the same time interval.

In an example, a machine learning model may be used to predict sending various surgical data subsets or subblocks (e.g., subblocks associated with a surgical dataset) to the same processor such as a local processor. The machine learning model may also predict the time intervals (e.g., different time intervals) at which the data subsets or subblocks may be processed by the processors or the processing devices.

Referring to FIG. 53B, the surgical hub/edge device 52745 may determine that at least because of the sensitivity associated with the surgical data subsets 52770 and 52775, they may not be sent to an enterprise cloud server for processing. In such a case, the surgical hub/edge device 52745 (e.g., using the machine learning model 52750) after splitting or dividing the surgical data sets 52755 into multiple surgical data subsets or subblocks may be processed locally either by the surgical hub/edge device 52745 or sent for processing to the edge servers 52772 and 52776, or at least one fog computing device (not shown in FIG. 53B). The surgical hub/edge device 52745, edge servers 52772 and 52776, and the fog computing device(s) may be located within the protected boundary 52746. In an example, the two surgical data subsets or subblocks may be sent for processing to the same edge server or a fog computing device that is located within the protected boundary 52746.

In an example, the surgical hub/edge device 52745, based at least on a performance metric associated with the surgical data subset or a surgical data subblock, may determine the manner in which the surgical data subblocks may be processed. For example, surgical data subset one 52770 may be associated with a low latency and surgical data subset three 52778 may be associated with a high latency. In such a case, surgical data subset one 52770 may be sent to a local server capable of processing the data with low latency, while surgical data subset three 52778 may be sent to an enterprise cloud server 52779.

In an example, location (e.g., level in computational hierarchy) of a device or a processor where surgical data may be sent for processing may be determined based on various surgical data characteristics, for example, intended utilization of results associated with surgical data, or the type of metadata associated with the surgical data. For example, a local device (e.g., a surgical hub/edge device 52745 or a smart surgical instrument) may be utilized for interactive or repetitive accessing, updating, or aggregation surgical data processing. In such a case, the surgical data may be added or extracted repeatedly. Accordingly, the conclusions or results may be updated (e.g., updated periodically). The conclusions or results may be updated, for example, after each surgical data addition or extraction. The portion of the surgical data processing algorithm that processes such repeated operations may reside on a device or a smart surgical instrument that is located within a protected boundary or a healthcare facility's premises or network.

In an example, surgical hub/edge device 52745 may use metadata or portions of metadata associated with surgical data to determine the location where the surgical data may be sent for processing, stored, and/or utilized. Metadata or a portion of metadata may indicate the network where the data was collected or stored (e.g., in a hospital network level micro-cloud network.) The network may retain control of the confidential patient information. Patient specific information may be utilized to train a new control algorithm. The training of a control algorithm may be conducted from a base surgical data set (e.g., acting as a seed surgical data set) or using data that is collected in the hospital network.

In an example, a metadata or a portion of metadata may include sensitivity of surgical data, for example, a confidentiality flag or an identifier of the surgical data designating the confidentiality level of the data. Such metadata or portion of metadata may be used to determine or control the level of surgical data processing.

In an example, surgical hub/edge device 52745 may use the amount of redaction of surgical data as a factor to control the level within a system where certain type of analysis of the surgical data may be performed. For example, low level analyses that may benefit from all the interrelated but identifiable personal surgical data may be performed within a protected boundary 52746 of a healthcare providers network. In an example, high level analyses that may performed with a portion of underlying surgical data anonymized may be performed by an enterprise cloud server 52779 that is located outside the protected boundary 52746.

In an example, higher level aggregations of regional or world-wide surgical procedure outcomes and/or surgical procedure step data may be performed on enterprise cloud servers. The enterprise cloud servers may be located outside the protected healthcare facility's network. Such enterprise cloud servers may have capability of processing large amounts of data. The data that may be processed at the enterprise cloud servers may be of type where personal biomarker data may not be needed. The data to be processed may be redacted before transferring it out from the protected network to other storage locations.

In an example, one or more of resources available in a processing device, system or a network, risk associated with surgical data, and a need for processing surgical data within a protected network may be utilized to determine priority, processing depth, and/or storage of the data and/or algorithmic results.

Figure 54:
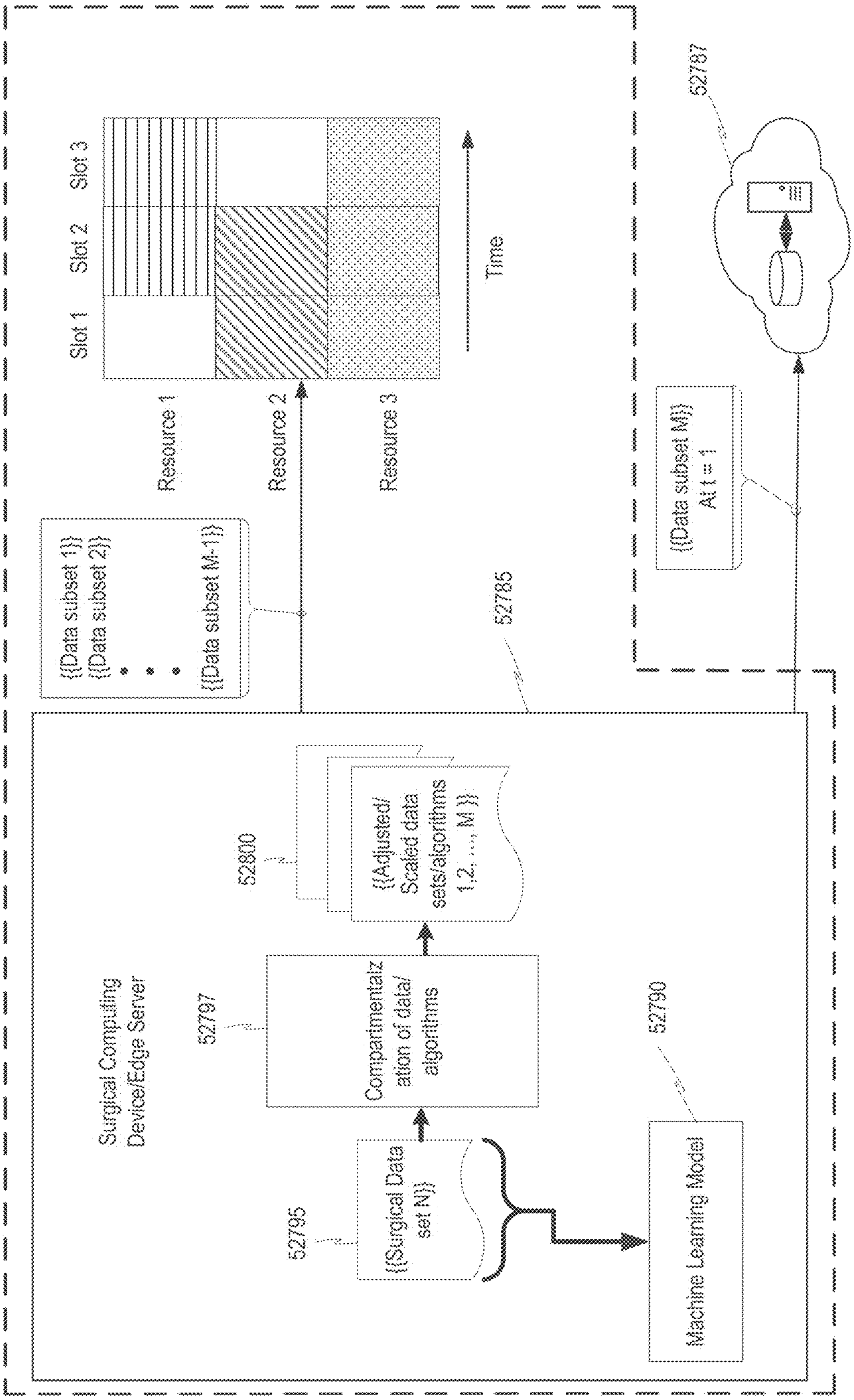
FIG. 54 illustrates compartmentalization of data and/or algorithms.

As described with respect to FIG. 54, a priority may be assigned to the surgical data subsets or subblocks (e.g., each of the surgical data subblocks) to determine the time and/or the resource that may be used for processing a particular surgical data subset or a subblock. The availability of at least one resources may be used in determining the resource that may be a particular data subset or a subblock of a particular priority level, as described herein.

FIG. 54 illustrates compartmentalization of surgical data and/or algorithms. Machine learning (ML) model 52790 may be utilized to process surgical data at local devices/systems and/or cloud servers. Compartmentalization (e.g., selective compartmentalization) of ML algorithm processing of local surgical data may be performed.

In an example, adjustment/scaling of the breadth, depth, and/or reduction of local surgical data may be performed on a local surgical computing device (e.g., a surgical hub) or an edge server based on the local available resource-time dependency relationship. Adjustments/scaling may include adjustment/scaling of the one or more of the following: amount of data or the variables that may be processed, the frequency or accuracy level of the surgical data, the algorithm type, the tolerable error of the algorithm, stacking levels of the algorithm, or validation (e.g., verification and/or checking) of a measured outcome or result.

As illustrated in FIG. 54, various resources of a processing device (e.g., a surgical hub or an edge server device) may have varied availability. For example, Resources 1 and 2 may be available for only two time out of three time slots (e.g., time slot 2 and 3 for Resource 1 and time slots 1 and 2 for Resource 2), and Resource 3 may be available in all the three slots. In such a case, compartmentalization and scaling may be performed in a such a way that the breadth and/or depth of surgical data subsets or subblocks to be processed by Resources 1 and 2 may the ones that need lesser resources (e.g., lesser amount of data, lesser number of variables, etc.) than the surgical data subset or subblock to be processed by Resource 3.

In an example, as illustrated in FIG. 54, local surgical data (e.g., surgical data set 52795) may be adjusted and/or scaled 52800 based on at least one of the following: timeliness of the needed result, processing and memory available, network bandwidth or communication parameters (e.g., throughput, latency, etc.), risk level of functioning without the answer, importance of the data or task, availability of other surgical data to be used in substitution. In an example, if a surgical data set 52795 to be analyzed is associated with timeliness of the needed result, the compartmentalization may be performed in a way that the time sensitive surgical data is scaled to be processed by Resources 2 and 3 (e.g., with all three time slots available for processing) and not Resource 1 (with the first time slot not being available for processing immediate or in slot 1). In an example, scaling of the breadth, depth, and/or reduction of local surgical data may be performed to balance the level of results achieved within a time interval and the resources that may be needed.

In an example, as illustrated in FIG. 54, surgical data or ML algorithms may be compartmentalized or clustered 52927. ML algorithms may be compartmentalized into smaller portions, for example, based on magnitude or level of processing. In an example, complexity of an ML algorithm may be determined based on the available local computing resource levels. A ML algorithm may be utilized between a cloud and edge processing networks. An algorithm pre-processing component may use a system and its resources on which it resides as a means for determining the following: the factors to be considered for diversity of a surgical dataset, a level of compartmentalization of surgical data, and/or analyses of surgical data.

ML algorithms used for analyzing surgical data may be scaled based on the computing resources (e.g., computational power, size of memory of the computing resource) associated with the surgical system 52785, on which the ML algorithm is running, the competing processing needs associated with various processes running on the surgical system 52785, and/or the breadth of the surgical dataset 52795. The computing resources associated with the surgical system, the competing processing needs by various processes running on the system, and/or the breadth of the surgical dataset may vary based on time, as illustrated in FIG. 54.

In an example, in a surgical computing device (e.g., a surgical hub) where the computing resources are being utilized for processing and/or analyzing surgical data received from various surgical devices (e.g., including video feeds from various cameras in an operating theater), the surgical device may scale an ML algorithm based on the level of the computing resources available (e.g., available during a time slot).

In an example, in a surgical computing device where availability of the computing resources of the surgical computing device are being utilized for processing surgical data received from various surgical devices may vary with time. The scaling of the ML algorithm may change dynamically (e.g., change dynamically with time) based on the resources available on the surgical computing device where the ML algorithm resides and/or us running.

As illustrated in FIG. 54, in time slot 1, only computing resource 1 and computing resource 2 may be available to be utilized by a ML algorithm, whereas in time slot 2, all the three computing resources 1, 2, and 3 may be available. only for time slots. Based on the availability of computing resources, the surgical device may scale the ML algorithm accordingly. For example, in time slot 1, the ML algorithm may be scaled down (e.g., simplified by ignoring, removing, or combining certain surgical data aspects). This may be done to accommodate the non-availability of computing resource 1, which, for example, may be processing critical piece of surgical data. And, as an example, in time slot 2 with all the three resources being available, the ML algorithm may be scaled up (e.g., by using a more comprehensive surgical dataset and/or performing more complex and comprehensive analyses of surgical dataset).

As described herein, various types of ML algorithms may include supervised algorithms, unsupervised learning algorithms, semi-supervised learning algorithms, reinforcement learning algorithms, etc. Some of the specific types of ML algorithms may include a linear regression, a logistic regression, a decision tree, an SVM algorithm, a Naive Bayes algorithm, an KNN algorithm, a K-means, etc. A respective algorithm complexity level may be associated with each of the ML algorithms. For example, the KNN algorithm may be computationally more complex and, therefore, may have higher algorithm complexity level than the decision tree algorithm.

An ML algorithm complexity level may be associated with the computing resources available. In an example, an ML algorithm of higher computational complexity may be utilized on an edge processing device, or a cloud-based enterprise server with higher computational/processing power and/or memory resources. In another example, an ML algorithm of lower computational complexity may be utilized on a device (e.g., a surgical hub) with lower computational/processing power and/or memory resources.

One or more of the scaling of ML algorithm complexity, the ML algorithm method or processing method applied, and/or the magnitude of the dataset on which the ML algorithm is applied may be determined based on the resources (e.g., computational resources, network resources, etc.) that are available on a surgical system or a surgical computing device, where the ML algorithm may reside and/or one or more attributes of the dataset. The attributes of the dataset may include size of the dataset, complexity of the dataset, depth at which the dataset may be processed, etc.

In an example, an ML algorithm may be compartmentalized into various parts that may be processed on an edge processing device (e.g., and edge processing device within a protected network) and a cloud-based enterprise server (e.g., an enterprise server located outside the protected network). In an example, an algorithm on a computing device (e.g., a pre-processing component of an algorithm) may consider at least the resources associated with the computing device to determine the factors that may be used to obtain magnitude of a dataset that may be analyzed by an ML algorithm. The resources associated with the computing device may include computational/processing power and/or memory resources.

In an example, ML algorithm scaling on a surgical computing system or a surgical computing device may be based on at least one of: the total amount of the surgical data to be analyzed, the depth at which the computing system compiles the surgical data, the serialization of the different processing stages (e.g., which may provide an indication of how long it may take to process the surgical data), or the simplicity of the surgical data or surgical data compilation. The scaling may ignore surgical data aspects, remove or combine categories, or aggregate datasets before removing individual paired comparisons.

In an example, scaling of an ML algorithm may result in simplifying the analysis to be performed on a surgical data. The simplification of the analysis may be performed, for example, by excluding certain surgical data aspects, or anonymizing, removing, or combining certain surgical data categories.

In an example, scaling of local analyses may be performed. As illustrated in FIG. 54, additional processing of surgical data or a surgical data subset or subblock (e.g., data subset M) may be performed on one or more enterprise cloud servers 52787. The enterprise cloud servers 52787 may be co-located or geographically separated. In another example, additional surgical data processing may be performed later in time or in combination with the current surgical data processing.

A device or a system may be configured to prioritize local sub-processing. The local sub-processing may process the part of the surgical data that may be personalized data. The non-personalized portion of surgical data may be processed on remote systems or servers. The non-personalized portion of surgical data may be processed simultaneously with local processing of the personalized portion of surgical data or in sequence.

In an example, a device or a system (e.g., a system located within a healthcare facility) may scale the analyses associated with time dependent aspects of the surgical data that may require immediate returned results within a surgical procedure. The surgical device may perform a more complete or thorough processing of the complete surgical dataset 52795 offline to the procedure. The offline processing may be performed by the device or the system or by a remote cloud-based server or service.

In an example, dynamic reallocation of ML compartments may be performed. For example, in case of a disconnected device or a disconnected element in the computing chain dynamic, reallocation of ML compartments may occur based on reallocation of processing resources. For example, if a communication channel is disrupted due to a failure in the chain (e.g., power interruption, disconnected or damaged instrument or cable during surgery or other hardware/software failure), one of the other surgical computing devices or computing elements may be configured to share the load associated with the failed surgical computing device or computing element. A notification, for example, a warning notification may be sent to a healthcare provider or a user indicating the failure of the device or the computing element and/or an indication that the processing of surgical data may be slowed down.

In an example, the compartmentalization of the ML algorithm may be dynamically scaled or adjusted with the resource availability. One or more ML compartments may be designated as related. In an example, such a relationship may be dynamic and may be updated (e.g., periodically updated). In an example, such a relationship may be defined prior to the surgical data processing, enabling the system to combine or separate the related ML aspects, as needed.

In an example, breadth and/or depth of surgical data on a surgical computing device (e.g., a surgical hub) may be altered or reduced, and at least one surgical data attribute to be analyzed by a ML algorithm may be scaled or adjusted. The alteration or reduction of surgical data and adjusting/scaling of at least one surgical data attribute to be analyzed by a ML algorithm may be based on availability of resource-time availability of the surgical computing device.

The availability of the resource-time relationship on a surgical computing device may be determined based on at least one of timeliness of a needed result, computational processing level associated with the surgical computing device or a computational memory associated with the surgical computing device, a network bandwidth between the surgical computing device and where the needed result it to be sent, one or more communication parameters (e.g., a throughput rate at the surgical computing device or a latency experienced by the surgical computing device), a risk level of functioning without obtaining the needed result, importance level of the surgical data or a surgical task associated with the surgical task, and/or availability of other data that may be used as a substitution.

The alteration or reduction of surgical data and adjusting/scaling of at least one surgical data attribute may be performed on the surgical computing device, for example, to balance the level of results achieved within a time slot and the resources the surgical computing device may make available, for example, within a time slot, as described herein.

The surgical computing device may scale at least one attribute associated with the ML algorithm based on balance of a level of a needed result, a time associated with the needed result, and availability of the computing resource within the time associated with the needed result. The at least one attribute may include a size of the surgical data, a number of surgical data variables, a frequency associated with the surgical data, an accuracy level associated with the surgical data, an ML algorithm type, a tolerable error associated with the ML algorithm, a number of stacking levels associated with the ML algorithm, and/or verification or checking of results.

In an example, the ML algorithm on a surgical computing device may be compartmentalized or clustered into a plurality of portions or parts. A magnitude and/or level of processing required may be determined for each of the small portions or parts of the ML algorithm.

Figure 55:
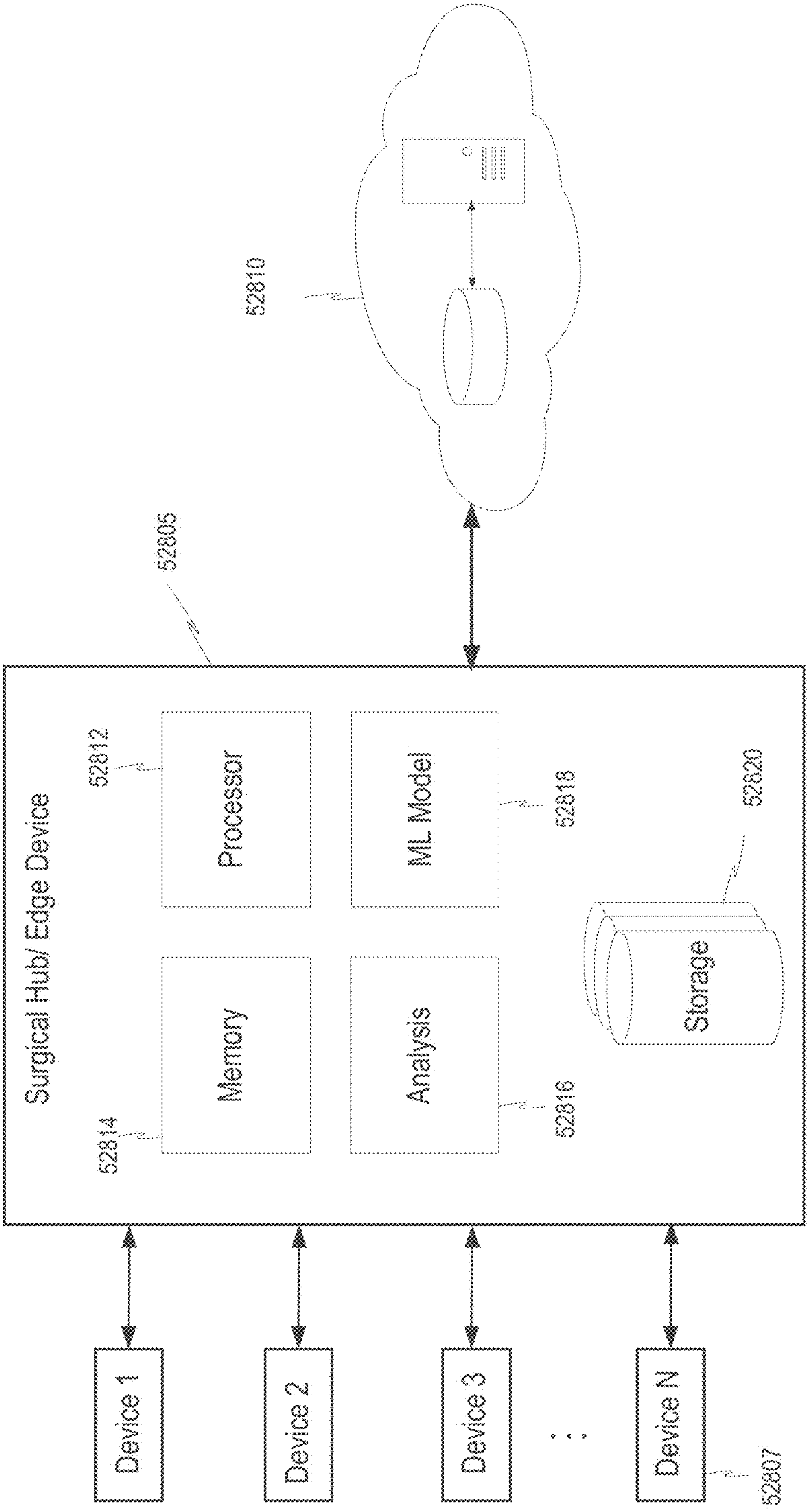
FIG. 55 shows an example of the surgical hub/edge device/edge device and the enterprise cloud server.

FIG. 55 illustrates an example of connectivity between the surgical computing device/edge computing device 52805 and the enterprise cloud server 52810 (e.g., enterprise cloud server). As illustrated in FIG. 55, the surgical computing device/edge computing device 52805 may include a processor 52812, a memory 52814 (e.g., a non-removable memory and/or a removable memory), an analysis subsystem 52816, a local machine learning model 52818, and/or a local storage subsystem 52820, among others. It will be appreciated that the surgical computing device/edge computing device 52805 may include any sub-combination of the foregoing elements/subsystems while remaining consistent with an embodiment.

The processor 52812 in the surgical computing device/edge computing device 52805 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), a state machine, and the like. The processor 52812 may perform data processing, authentication, input/output processing, and/or any other functionality that may enable surgical computing device/edge computing device 52805 to operate in an environment that is suitable for performing surgical procedures. The processor 52812 may be coupled with a transceiver (not shown). The processor 52812 may use the transceiver (not shown in the figure) to communicate with the enterprise cloud server 52810.

The memory 52814 in the surgical hub/edge device 52805 may be used to store where data was sent. For example, the memory may be used to recall that data was sent to an enterprise cloud server 52810. The memory may include a database and/or lookup table. The memory may include virtual memory which may be linked to servers located within the protected network.

The processor 52812 in the surgical computing device/edge computing device 52805 may access information from, and store data in, any type of suitable memory (e.g., a non-removable memory and/or the removable memory). The non-removable memory may include random-access memory (RAM), read-only memory (ROM), a hard disk, a solid-state drive or any other type of memory storage device. The removable memory may include secure digital memory.

The processor 52812 in the surgical computing device/edge computing device 52805 may access information from, and store data in an extended storage 52820. (e.g., a non-removable memory and/or the removable memory). In an example, the processor 52812 may access information from, and store data in, memory that is not physically located on the surgical computing device/edge computing device 52805, such as on a server or a secondary edge computing system (not shown).

An enterprise cloud server 52810 may include a processor, a memory (e.g., a non-removable memory and/or a removable memory), and/or a storage subsystem, among others. It will be appreciated that the enterprise cloud server 52810 may include any sub-combination of the foregoing elements/subsystems while remaining consistent with an embodiment.

The analysis module 52816 in the surgical hub/edge device 52805 may be used to determine when and where to send surgical data for processing, as described herein with respect to FIGS. 52, 53A, 53B, and 54. The analysis module 52816 may be used to determine when and how to perform compartmentalization of surgical data and ML algorithms, as described here with respect to FIG. 55.

Storage 52820 used in the surgical hub/edge device 52805 may be used to archive the results of what happened when data was sent to a particular processor. The storage 52820 may be a module included in the surgical hub/edge device 52805. In examples, the storage may be hardware (e.g., off-disk storage) accessible by the surgical hub/edge device 52805.

The local machine learning model 52818 in the surgical hub/edge device 52805 may be trained to determine where to send the data (e.g., to which processor) and/or how to divide the data for processing, as described with respect to FIGS. 52, 53A, and 54.

As illustrated in FIG. 55, Surgical hub/edge device 52805 may send data to and/or receive surgical data from the enterprise cloud server 52810. Surgical data may be based on measurements taken from sensors, actuators, robotic movements, biomarkers, surgeon biomarkers, visual aids, and/or the like. The wearables are described in greater detail under the heading "Monitoring Of Adjusting A Surgical Parameter Based On Biomarker Measurements" in U.S. patent application Ser. No. 17/156,28, filed Nov. 10, 2021, the disclosure of which is herein incorporated by reference in its entirety.

The measurements may be associated with one of more actuators located within the operating room. For example, measurements may be generated based on potentiometer readings located on a surgical instrument used as described with respect to FIG. 53B. Surgical data may relate to the cortisol level of surgeon. Surgical data may be collected based on these measurements and may help define the power, force, functional operation or behavior of a surgical instrument such as a smart hand-held stapler, which may be described in greater detail under the heading "Techniques for adaptive control of motor velocity of a surgical stapling and cutting instrument" in U.S. Patent No. U.S. Pat. No. 10,881,399, filed Jun. 20, 2017, the disclosure of which is herein incorporated by reference in its entirety. The data may be used to provide situation awareness to a smart instrument such as a smart energy device, which may be described in greater detail under the heading "Method for smart energy device infrastructure" in U.S. Patent No. U.S. Ser. No. 16/209,458, filed Dec. 4, 2018, the disclosure of which is herein incorporated by reference in its entirety.

For example, the surgeon may wear a sensing device (e.g., a wristwatch) that may determine the cortisol level of the surgeon based on a reading of the sweat produced by the surgeon. Such data may be anonymized (e.g., redacted, randomized, summarized, averaged, etc.) from being sent to the remove server.

Smart interconnected systems may be provided to define their relationship, cooperative behavior, or monitoring/storage of procedure details or the data described herein, which may be aggregated to develop better algorithms, trends, or procedure adaption based on the comparison of the outcomes with the choices. Such techniques may be described in greater detail under the heading "Method of hub communication, processing, display, and cloud analytics" in U.S. Patent No. U.S. Ser. No. 16/209,416, filed Dec. 4, 2018, the disclosure of which is herein incorporated by reference in its entirety.

Figure 56:
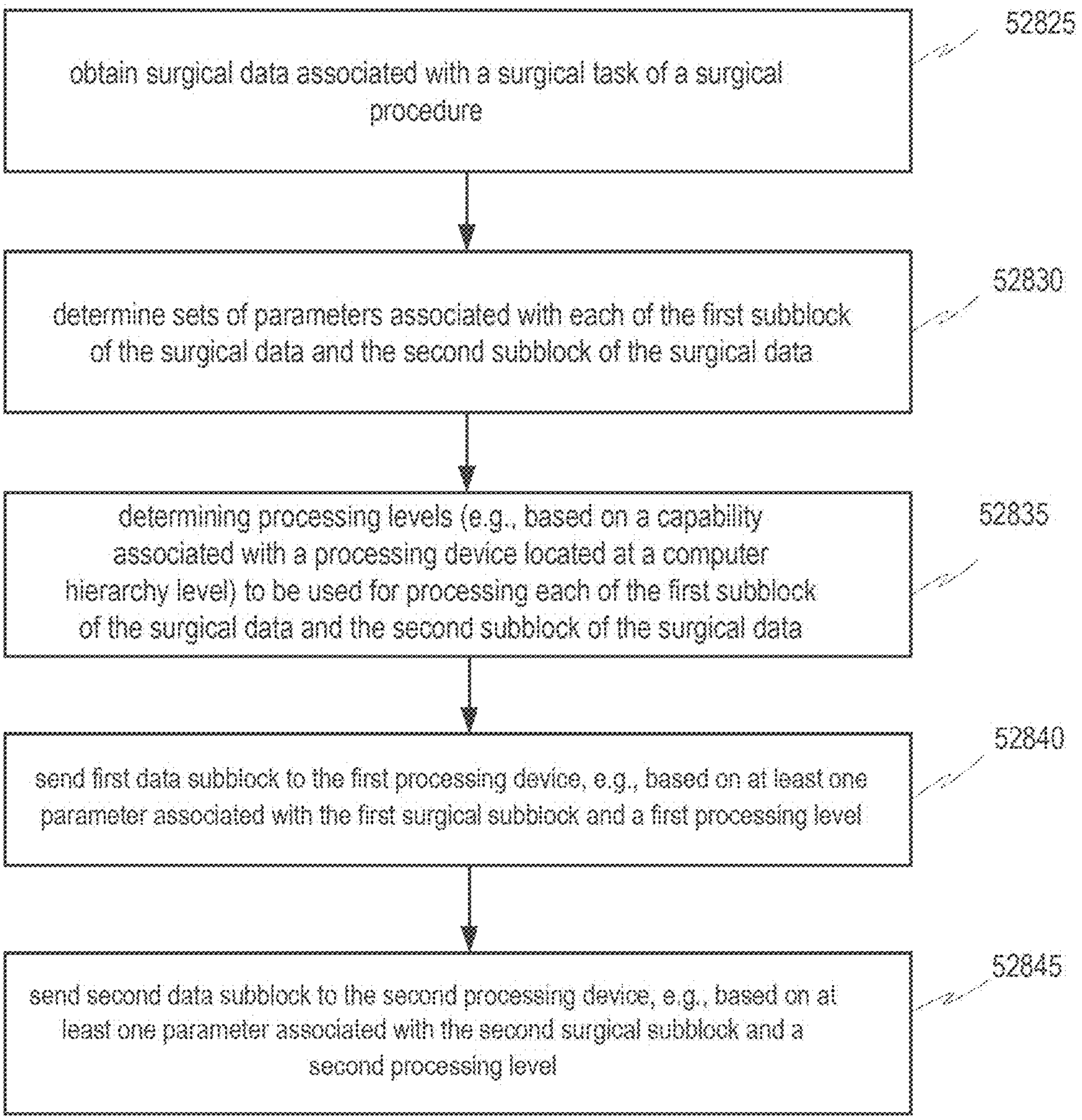
FIG. 56 shows an example of a flow chart of determining where to process data.

FIG. 56 shows an example of a flow chart for determining the location where surgical data may be sent for processing. At 52825, a device (e.g., a surgical hub, an edge server, a fog computing device, etc.) may obtain surgical data associated with a surgical task. The surgical data may be of a surgical data magnitude and a surgical data individuality level. The surgical data magnitude may be the extent the surgical data may be processed. The surgical data individuality level may be the individuality level of the surgical data to be processed.

At 52830, the surgical hub/edge device may determine sets of parameters associated with a first surgical data subblock of the surgical data and a second surgical subblock of the surgical data. For example, the surgical hub/edge device may determine a first set of parameters associated with a first surgical data subblock of the surgical data and a second set of parameters associated with a second surgical data subblock of the surgical data.

At 52835, the surgical hub/edge device may determine processing levels to be used for processing each of the first subblock of the surgical data and the second subblock of the surgical data. For example, the surgical hub/edge device may determine a first processing level to be used for processing the first surgical data subblock. The first processing level may be obtained based on a first capability associated with a first processing device located in a first computational hierarchal level of a healthcare provider's network. The surgical hub/edge device may also determine a second processing level to be used for processing the second surgical data subblock. The second processing level may be obtained based on a second capability associated with a second processing device located in a second computational hierarchy of the healthcare provider's network.

At 52840, the surgical hub/edge device may send the first surgical data subblock to the first processing device, for example, based on at least one of the first set of parameters associated with the first surgical data subblock and the first processing level. The first set of parameters associated with the first surgical data subblock may include, for example, a first surgical data magnitude associated with the first surgical data subblock, a first data granularity associated with the first surgical data subblock, a timeliness of a result associated with the first surgical data subblock.

At 52845, the surgical hub/edge device may send the second subblock to the second processing device, for example, based on at least one of the second set of parameters associated with the second surgical data subblock and second first processing level. The second set of parameters associated with the second surgical data subblock may include, for example, a second surgical data magnitude associated with the second surgical data subblock, a second data granularity associated with the second surgical data subblock, a timeliness of a result associated with the second surgical data subblock.

Figure 57:
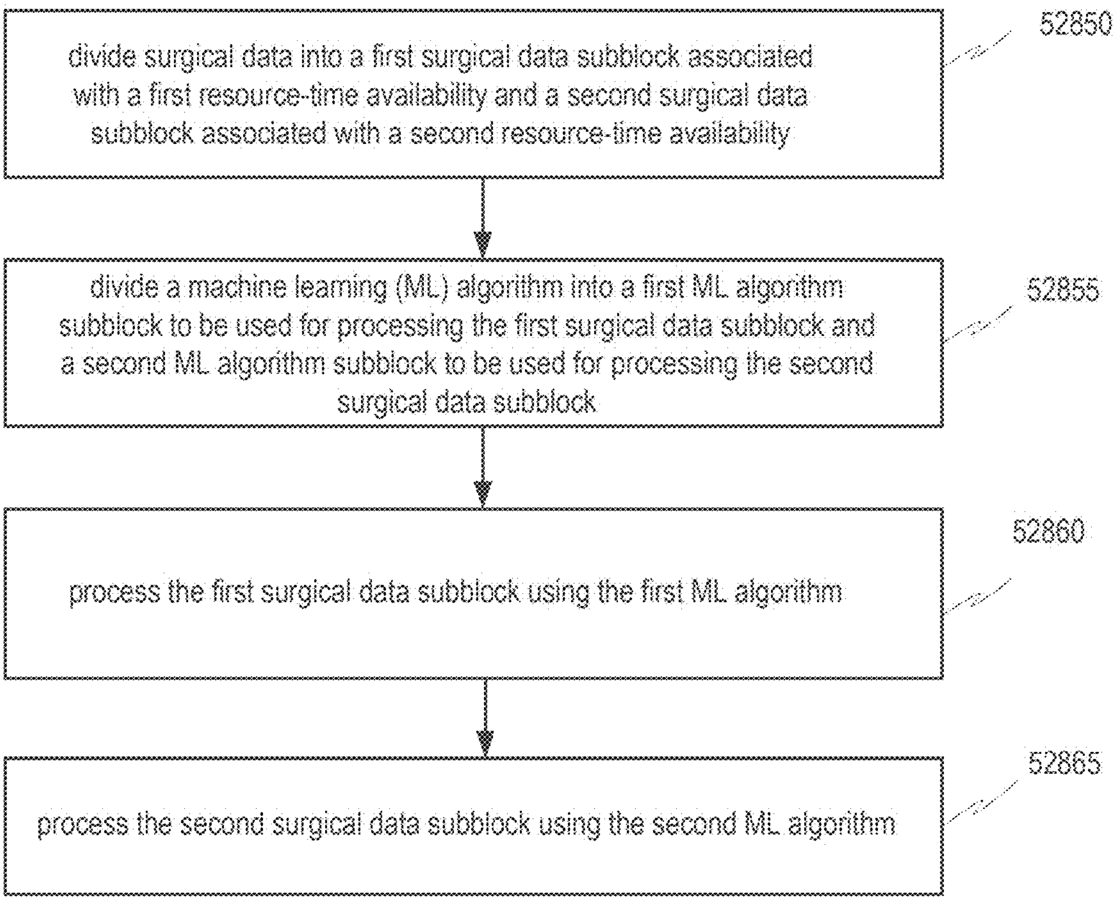
FIG. 57 shows an example of a flow chart of dividing ML algorithm into various subblocks for processing various parts of a dataset.

FIG. 57 shows an example of a flow chart of dividing ML algorithm into various subblocks for processing various parts of a dataset. At 52850, surgical data may be divided into a first surgical data subblock and a second surgical data subblock. The first portion of the surgical data may be associated with a first resource-time availability of a first device. The second portion of the surgical data may be associated with a second resource-time availability of a second device.

At 52855, a machine learning (ML) algorithm may be divided into a first ML algorithm subblock and a second ML algorithm subblock. The first portion of the ML algorithm may be used for processing the first portion of surgical data in accordance with the first resource-time availability. The second portion of the ML algorithm may be used for processing the second portion of surgical data in accordance with the second resource-time availability.

At 52860, the first portion of the surgical data may be processed using the first portion of the ML algorithm. At 52860, the second portion of the surgical data may be processed using the second portion of the ML algorithm.

Figure 58:
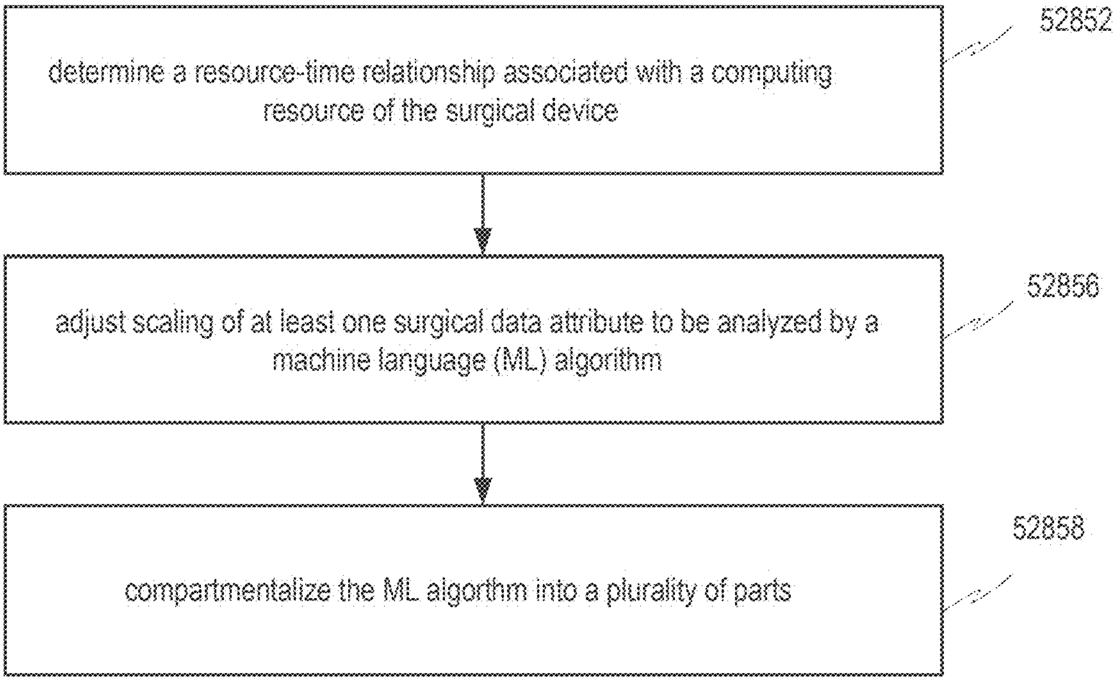
FIG. 58 shows an example of a flow chart of compartmentalization of ML algorithm processing of local data.

FIG. 58 shows an example of a flow chart of compartmentalization of ML algorithm processing of local data. At 52852, a surgical device may determine a resource-time relationship associated with a computing resource of the surgical device. The availability of the resource-time relationship on a surgical computing device may be determined based on at least one of timeliness of a needed result, computational processing level associated with the surgical computing device or a computational memory associated with the surgical computing device, a network bandwidth between the surgical computing device and where the needed result it to be sent, one or more communication parameters (e.g., a throughput rate at the surgical computing device or a latency experienced by the surgical computing device), a risk level of functioning without obtaining the needed result, importance level of the surgical data or a surgical task associated with the surgical task, and/or availability of other data that may be used as a substitution.

At 52856, the surgical device may adjust scaling of at least one data attribute to be analyzed by a machine language (ML) algorithm. The adjusting scaling of at least one surgical data attribute may be performed on the surgical computing device, for example, to balance the level of results achieved within a time slot and the resources the surgical computing device may make available, for example, within a time slot.

At 52858, the surgical computing device may compartmentalize the ML algorithm into a plurality of parts. A magnitude and/or level of processing required may be determined for each of the small portions or parts of the ML algorithm. For example, the magnitude and/or the level of processing required may be based on the computing resources available.

Figure 59:
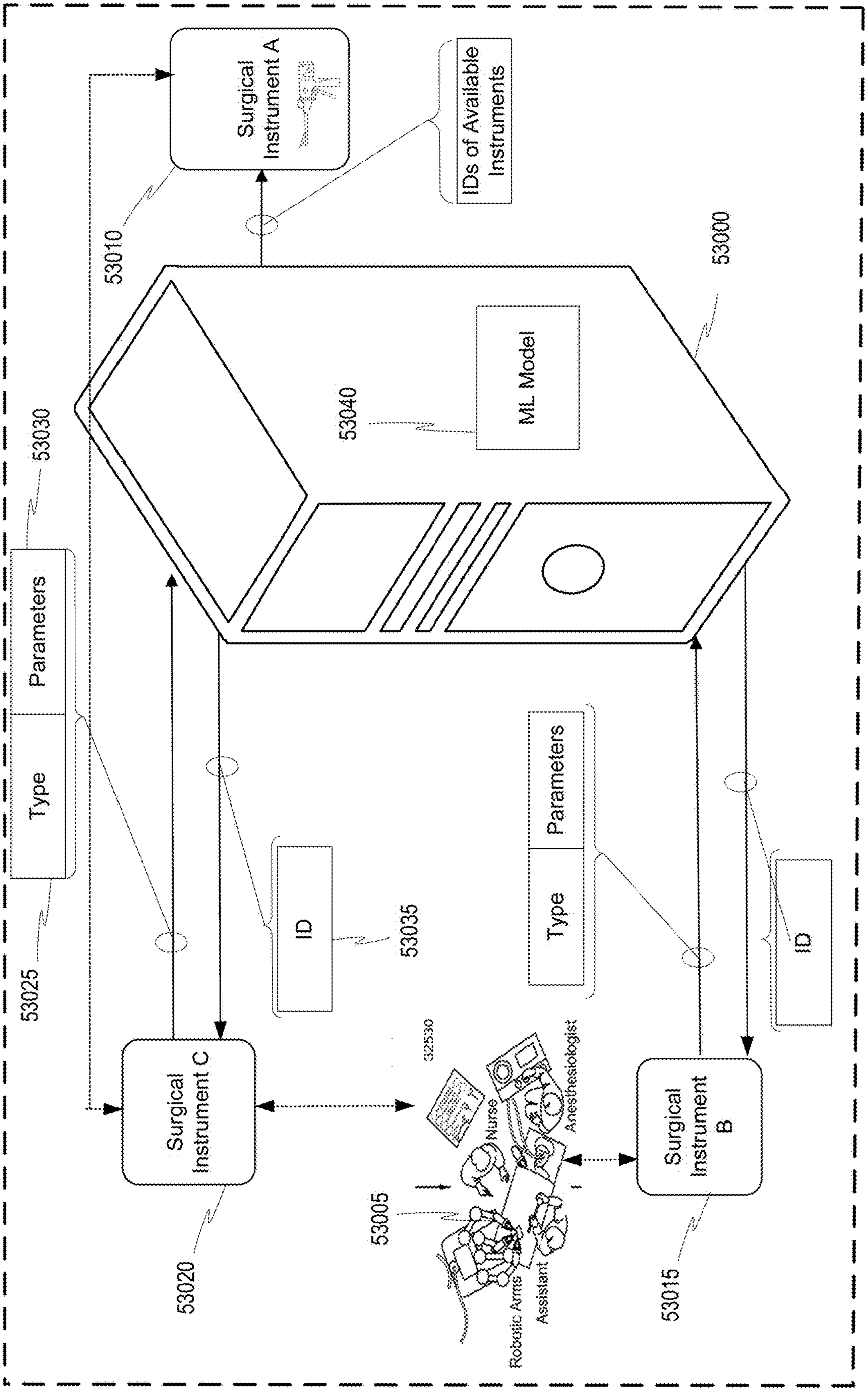
FIG. 59 shows an example of an overview of data flow within a peer-to-peer interconnected surgical system.

Referring to FIG. 59, an overview of the surgical system may be provided. Surgical devices or surgical instruments may be used in a surgical procedure as part of the surgical system. The surgical hub/edge device 53000 may be configured to coordinate information flow to a surgical device or a surgical instrument (e.g., the display of the surgical device). For example, the surgical hub/edge device 53000 may be described in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Example surgical instruments that are suitable for use with the surgical system are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 59 shows an example of an overview of data flow within a peer-to-peer interconnected surgical system. The surgical hub/edge device 53000 may be used to perform a surgical procedure on a patient within a surgical operating room. A robotic system may be used in the surgical procedure as a part of the surgical system. For example, the robotic system may be described in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. The robotic hub may be used to process the images of the surgical site for subsequent display to the surgeon through the surgeon's console.

Other types of robotic systems may be readily adapted for use with the surgical system. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CONTROL, filed Dec. 4, 2018, the disclosure of which is herein incorporated by reference in its entirety.

In an example, could-based analytics may be deployed to analyze surgical information and/or perform various surgical tasks. Various examples of cloud-based analytics that are performed by the cloud, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, the disclosure of which is herein incorporated by reference in its entirety.

In various aspects, an imaging device may be used in the surgical system and may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (e.g., can be detected by) the human eye and may be referred to as visible light or simply light. A typical human eye will respond to wavelengths in air that are from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device may be configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and ureteroscope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgery. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

As shown in FIG. 59, a surgical hub/edge device may be a part of a surgical operating room. The operating room may be located within a protected boundary designated by the dashed enclosure. The protected boundary may be based on (e.g., The Health Insurance Portability and Accountability Act (HIPAA) Privacy Rule or Art. 9 General Data Protection Regulation (GDPR). The privacy rules may be used to protect health data, which is a special category of personal data and, therefore, subject to a higher level of protection that other personal data.

In an example, multiple surgical hub/edge devices maybe associated with respective operating rooms. A patient 53005 may be undergoing a surgery in the operating room. The operating room(s) may include one or more surgical devices (e.g., surgical instruments A 53010, B 53015, and C 53020). The terms surgical devices and surgical instruments may be used interchangeably herein. The surgical devices may be used (e.g., autonomously or manually used by a healthcare professional) to perform various tasks associated with a surgical procedure on a patient. How a surgical instruments operates autonomously is described in greater detail under the heading "METHOD OF CONTROLLING AUTONOMOUS OPERATIONS IN A SURGICAL SYSTEM" in U.S. Patent Application No. U.S. Ser. No. 17/747,806, filed May 18, 2022, the disclosure of which is herein incorporated by reference in its entirety. For example, the surgical device may be an endocutter. The surgical device may be in communication with the surgical hub/edge device 53000 located within the operating room. The surgical hub/edge device 53000 may instruct the surgical device about information related to the surgery being performed on the patient 53005. In examples, the surgical hub/edge device 53000 may set a parameter of the surgical instrument (e.g., device) via sending the surgical device a message, which may be in response to the surgical instrument sending a request message to the surgical hub/edge device 53000 for the parameter. For example, the surgical hub/edge device 53000 may send the surgical device information indicative of a firing rate for the endocutter to be set at on during a stage of the surgery.

Surgical information (e.g., surgical data associated with a patient/healthcare professional/surgical device) that is associated with a surgical procedure may be generated (e.g., by a monitoring subsystem located at the surgical hub/edge device 53000 or locally by the surgical device). For example, the surgical information may be based on the performance of the surgical instrument. For example, the surgical data may be associated with physical measurement physiological measurements, and/or the like. The measurements are described in greater detail under the heading "Monitoring Of Adjusting A Surgical Parameter Based On Biomarker Measurements" in U.S. patent application Ser. No. 17/156,28, filed Nov. 10, 2021, the disclosure of which is herein incorporated by reference in its entirety.

Surgical information related to a surgical procedure being performed in the operating room may be sent to the local surgical hub/edge device 53000. For example, the operating room may include a surgical display. As the surgical procedure is being performed (e.g., by the healthcare professionals), surgical data (e.g., surgical data associated with measurements taken from a surgical display) may be sent to the surgical hub/edge device 53000 where it may be analyzed. The surgical hub/edge device 53000 may further send the surgical information for analysis to an enterprise cloud server (not shown in FIG. 59).

As shown in FIG. 59, one or more surgical instruments may be communicatively coupled with a surgical hub/edge device 53000. For example, surgical instrument A 53010, surgical instrument B 53015, and/or surgical instrument C 53020 may be connected with the surgical hub/edge device 53000. The surgical hub/edge device 53000 may perform a discovery operation (e.g., at the start of a surgical procedure or during a transition phase from one surgical step of the surgical procedure to the subsequent surgical step) to discover the surgical devices that may be located within an operating room. The surgical instruments may be associated with the surgical procedure being performed.

The surgical hub/edge device 53000 based on a surgical procedure, for example, may break down the surgical procedure into surgical tasks or surgical steps. The surgical hub/edge device 53000 may maintain the sequence of the surgical tasks or surgical steps in a subsystem or a module (e.g., surgical plan module) located locally at the surgical hub/edge device 53000. The surgical hub/edge device 53000 (e.g., as a part of discovery process) may perform discovery of surgical devices or surgical instruments that are associated with the surgical procedure and/or the surgical steps of the surgical procedure. For example, the surgical hub/edge device 53000 may identify that a colectomy is being performed and that the first step of the colectomy is severing tissue that is attached to the colon, thereby mobilizing the colon. Based on this information, the surgical hub/edge device 53000 may send one or more discovery request messages to various surgical devices or surgical instruments that are to be used for during the surgical procedure. The surgical hub/edge device 53000, in response to the request messages, may receive response messages from various surgical instruments. The response messages from the surgical instruments may include respective identification (e.g., which may be referred to as type 53025) and surgical instrument capabilities (e.g., which may be referred to as parameters 53030), as described with respect to FIG. 10. The surgical hub/edge device 53000, in response to the discovery request messages, may also receive information indicating capabilities of the surgical device or surgical instrument. For example, the information may indicate that the surgical instrument is an energy device with a set of surgical instrument capabilities (e.g., standard surgical instrument capabilities). The surgical hub/edge device 53000 may determine that this surgical instrument should be used for the first step of the colectomy and may establish a connection with the surgical instrument. The hub 53000 may receive information in the response message from an instrument that indicates that the instrument is an endocutter with standard surgical instrument capabilities. The terms surgical devices or surgical instruments may be used interchangeably herein.

The discovery request message may include an indication that the surgical hub/edge 53000 is requesting information (e.g., characteristics and capabilities) associated with the surgical instrument. In response, the surgical instrument may include the requested information (surgical characteristics and/or surgical parameters 53030) associated with the surgical instrument. For example, the characteristics may include a range of frequencies that the surgical instrument is capable of operating in. The surgical characteristics may include a power ratings associated with the surgical instrument. In an example, the surgical hub/edge device 53000 may perform discovery of instruments based on a surgical procedure plan associated with the current surgical procedure.

The surgical hub/edge device 53000, based on the characteristics or parameters, and the type of the surgical instrument, for example, may determine whether to establish a connection with the surgical instrument. For example, the surgical hub/edge device 53000 may determine that one of the responsive surgical instruments is an endocutter with frequency operating range that is to be used for the anastomosis step of the colectomy. Based on this determination, the surgical hub/edge device 53000 may determine not to establish a connection with the endocutter.

In an example, as a part of discovery process, the surgical hub/edge device 53000 may assign an identification to the surgical instruments (e.g., each of the surgical instruments) that are involved in a surgical procedure and the surgical hub/edge device 53000 may establish a connection with. For example, after determining whether to establish a connection with a surgical instrument based on the surgical type 53025 and the parameters 53030, the surgical hub/edge device 53000 may assign an identification tag 53035 to the surgical instrument and may send the identification tag 53035 to the surgical instrument. As described herein, the identification tag 53035 may be used by the surgical hub/edge device 53000 and/or by the monitoring surgical instrument when requesting data associated with a surgical instrument.

In an example, a surgical hub/edge device 53000 may determine a role (e.g., monitoring surgical instrument or a peer surgical instrument that is being monitored) associated with each of the surgical instruments that are part of a surgical ecosystem. For example, the surgical hub/edge device 53000 may assign one surgical instrument to be a monitoring surgical instrument and another surgical instrument a peer surgical instrument that is being monitored by the monitoring surgical instrument. The assignment of a role may include assignment of respective privileges associated with a surgical instrument, as described with respect to FIG. 10. For example, if the surgical instrument is determined to be a monitoring surgical instrument, the monitoring surgical instrument may monitor, record, and/or access surgical information (e.g., surgical data) associated with a surgical task being performed at a peer surgical instrument. In an example, the surgical instrument that is assigned a role of a peer surgical instrument may have the privilege of sending surgical data to the monitoring surgical instrument. With respect to FIG. 10, the monitoring surgical instrument and the peer surgical instrument may be connected either directly or via the surgical hub/edge device 53000.

In an example, a surgical instrument may be preconfigured with configuration that may enable it to assume the role of a monitoring surgical instrument or a peer surgical instrument that is being monitored. The surgical instrument may be configured and enabled as a monitoring surgical instrument or a peer surgical instrument. In an example, a surgical instruments may determine or select its role based on one or more of the following: type of the peer surgical instrument or the role assumed by the peer surgical instrument, the surgical instrument capabilities of the peer surgical instrument, the surgical step being performed, the surgical procedure being performed and/or the like. In an example, the surgical instrument may be configured with such information or may request such information from the surgical hub it has established a connection with. After selecting or enabling a particular role, the surgical instruments may send an indication of its selected role to one another surgical instrument and/or the surgical hub.

In an example, if two or more of the surgical instruments indicate that they have assumed the monitoring role, the surgical instruments involved may negotiate to determine which of the surgical instruments should stay in the monitoring role and which of the surgical instruments should change its role to a peer role or have no role. The negotiation may be based at least on the type of the surgical instruments involved, the surgical instrument capabilities of the surgical instruments involved, the surgical step being performed, the surgical procedure being performed and/or the like. In an example, multiple surgical instruments may agree that both can operate in a monitoring role. In an example, a surgical instrument may not have a capability of assuming a monitoring role or as a peer role. In such a case, no role may be assigned to the surgical instrument and the surgical instrument may not be connected with another surgical instrument.

In an example, the negotiation between the two surgical instruments may comprise transfer of data between the two devices and the application of one or more rules to determine the assignment of roles (e.g., the monitor role vs the monitored role or peer role). The determination may depend on speed or capability of each of the devices, memory capacity of the devices, timing (for example, which device sent the discovery request), an attribute of connectivity between the surgical instruments or surgical devices, etc. The determination may be based on whether the surgical instrument type or surgical device type is used in a surgical task of the surgical procedure and, optionally, the capabilities of the surgical device type required for that task, or the capabilities of the monitoring surgical instrument (e.g., higher processing speed for processing the data, more up-to-date models for processing the data, greater memory, etc.).

In an example, a surgical instrument may be powered on during a surgical procedure in a surgical operating room, for example, after one of the surgical instruments in the surgical operating room has been configured as a monitoring surgical instrument. In such a case, the newly powered surgical instrument may determine that one of the surgical instruments is acting as a monitoring surgical instrument and it may then assume its role as a peer surgical instrument and establish a connection with the existing monitoring surgical instrument. In an example, the existing monitoring surgical instrument may indicate to the newly added surgical instrument its status of being a monitoring surgical instrument.

In an example, once a surgical instrument assumes its role as a monitoring surgical instrument, it may then have the ability to directly monitor the performance and pull data directly from the surgical instruments without the use of the surgical hub/edge device 53000. In an example, a monitoring surgical instrument may request information about peer surgical instruments from the surgical hub/edge device 53000. For example, as shown in FIG. 59, surgical instrument A 53010 may be configured (e.g., based on the surgical instrument capabilities of surgical instrument A 53010) as a monitoring surgical instrument. Assuming that surgical instruments B 53015 and C 53020 are configured as or assume roles as peer surgical instruments, the surgical instrument A 53010 may be capable of directly monitoring and/or recording the surgical information and/or performance of surgical instruments B 53015 and C 53020.

In an example, the surgical instrument A 53010 may monitor surgical data (at surgical instruments B 53015 and/or C 53020) that is associated with a surgical step of a surgical procedure. In an example, surgical instrument A 53010 may request surgical information or surgical data (e.g., send a message requesting for data) associated with the performance of surgical tasks being performed on each of the of the surgical instruments B 53015 and C 53020 directly from surgical instruments B 53015 and C 53020 without involving the surgical hub/edge device 53000. In an example, surgical instrument A 53010 may request data associated with the performance of surgical tasks being performed on each of the surgical instrument B 53015 and surgical instrument C 53020 from the surgical hub/edge device 53000 or via the surgical hub/edge device 53000. As described with respect to FIG. 10, the surgical hub/edge device 53000 may determine whether the monitoring surgical instrument is able to monitor a surgical instrument directly or indirectly, for example, via the surgical hub/edge device 53000.

Monitoring a surgical device or a surgical instrument may include the monitoring surgical device (e.g., the monitoring surgical instrument on its own or the monitoring surgical instrument in collaboration with the surgical hub/edge device 53000) gathering surgical information associated with the patient, the healthcare provider, and/or a surgical task being performed by a surgical instrument that is being monitored). The surgical information associated with the patient, the healthcare professional may include measurements related to physical conditions, physiological conditions, and/or the like. The surgical information associated with the surgical instrument may include performance metrics associated with the surgical instrument or a task being performed by the surgical instrument.

Determining whether the monitoring surgical instrument is capable of directly interacting with the peer surgical instruments may be determined by a machine learning model 53040 located at the surgical hub/edge device 53000, as described herein in FIG. 12. The machine learning model 53040 may be trained to consider the type 53025 of the peer surgical instrument, the surgical instrument capabilities of the peer surgical instrument, the surgical step being performed, and/or the surgical procedure being performed when determining whether the monitoring surgical instrument may directly interact with the peer surgical instrument.

In an example, the monitoring surgical instrument may receive (e.g., receive from the surgical hub/edge device 53000) a list of potential peer surgical instruments it may monitor. The monitoring surgical instrument may also receive indication identifying the peer surgical instruments that the monitoring surgical instrument may be able to monitor directly and the peer surgical instrument that the monitoring surgical instrument may be able to monitor in collaboration with the surgical hub/edge device 53000.

In an example, the monitoring surgical instrument may receive an indication for the monitoring a set of peer surgical instruments. The indication may include a list of the identification tags 53035 associated with the peer surgical instruments. The monitoring surgical instrument may store the list of the peer surgical instruments to be monitored locally (e.g., in local memory).

In an example, the surgical hub/edge device 53000 may obtain a list of surgical instruments that may be utilized during a surgical. As part of the surgical procedure, for example, the surgical hub/edge device 53000 may assign roles to be assigned to the surgical instruments. The surgical hub/edge device 53000 may communicate the roles to the devices involved, for example, by sending messages to the surgical instruments.

In an example, the surgical hub/edge device 53000 may update roles and/or privileges assigned to the surgical instruments. For example, the roles may be updated during transitioning from one surgical step of a surgical procedure to another surgical step of the surgical procedure. In an example, a surgical instrument that may have been previously assigned a monitoring role may be updated to a peer surgical instrument and may be monitored by another surgical instrument, for example, a newly powered surgical instrument. The surgical hub/edge device 53000 may send an update message to the surgical instrument indicating for the surgical instrument to change its role from a monitoring surgical instrument to a peer surgical instrument. The surgical hub/edge device 53000 may also indicate to the surgical instrument an identification of a new monitoring surgical instrument.

In an example, surgical instrument A 53010 may receive surgical information directly from surgical instrument C 53020. The surgical instrument A 53010 may receive the surgical information periodically or aperiodically (e.g., based on completion of a surgical task at the surgical instrument B 53015 or C 53020 or based on a triggering condition being met (for example, commencing and/or finishing certain instrument operations such as clamping, firing etc. or when a derived parameter falls outside of an expected range/threshold)). For example, surgical instrument A 53010 may request and/or receive surgical parameters related to a tissue it may be dissecting or mobilizing. In an example surgical instrument, A 53010 may request and/or receive surgical information associated with a surgical task of a surgical procedure from surgical instrument B 53015 indirectly via the surgical hub/edge device 53000.

In an example, as described with respect to FIG. 59, a machine learning model and/or a trained machine learning model may be utilized as part of a supervised learning framework. Supervised learning model is described herein in FIG. 8A. The training data (e.g., training examples 802, as illustrated in FIG. 8A) may consist of a set of training examples (e.g., input data mapped to labeled outputs, for example, as shown in FIG. 8A). The training data used in training the local machine learning model 53040 may include surgical data gathered from previous surgical procedures and/or simulated surgical procedures. The training data may include attributes or parameters associated with a patient and/or parameters associated with surgical instrument(s). In an example, machine learning model as an output may provide parameters associated with another surgical instrument. For example, a machine learning model may be utilized to identify size and color of cartridge to be used for in a smart stapling device as an output. As an input, the machine learning model may be provided various parameters collected by a surgical instrument (e.g., power, time, impendence values collected by an energy device), and parameters associated with the patient (e.g., tissue thickness, as measured by jaw of a surgical instrument, area of dissection, age of the patient, etc.). The machine learning model based at least on the surgical instrument parameters collected by a surgical instrument and the parameters associated with the patient may predict the size and color of the cartridge to be used by a surgical stapling device.

In an example, a local machine learning model 53040 located within the surgical hub/edge server device 53000 may use surgical information and surgical parameters associated with a patient, a healthcare professional and/or a surgical instrument to predict settings for a surgical instrument or identify a surgical instrument part (e.g., a cartridge) as an outcome. The surgical hub/edge device 53000 may send the predicted outcome to the monitoring surgical instrument.

In an example, a local machine learning model may reside in a peer surgical instrument, as described herein in FIG. 12. The local machine learning model in the peer surgical instrument, based on surgical instrument parameters and/or patient parameters, my predict the size and color of a cartridge as an outcome. The peer surgical instrument may send that outcome for use to the monitoring surgical instrument.

In an example, a local machine learning model may reside in a monitoring surgical instrument as described herein in FIG. 12. In such a case, the peer surgical instrument may directly or indirectly send surgical information and parameters associated with a patient, a healthcare professional or a surgical task being performed by the peer surgical instrument to the monitoring surgical instrument. The local machine learning model located within the monitoring surgical instrument may predict settings for a surgical instrument or identify a surgical instrument part (e.g., a cartridge) as an outcome. The monitoring surgical instrument may use the predicted outcome including the surgical instrument settings and/or selection of a surgical instrument part.

In an example, the surgical procedure to be performed may be a colectomy. At the anastomosis step of the surgical procedure, an endocutter may be configured or configure itself to be the monitoring surgical instrument, while an. energy device may be configured to be a peer surgical instrument, to be monitored by the monitoring surgical instrument. The energy device (being a surgical instrument that is being monitored) may send surgical information to the endocutter (the monitoring device). The surgical information may include information about the anatomy of the tissue it observes such as the tissue's thickness. In an example, the energy device may send the surgical data based on a request it receives from the endocutter. In an example, the energy device may send surgical information to the endocutter based on a triggering condition being met, as described herein. In an example, the surgical information may be sent periodically to the endocutter (e.g., based on timer configured at the energy device). The endocutter may store the surgical data and perform analysis on the surgical data, as described herein. In examples, the monitoring surgical instrument (e.g., endocutter) may provide recommendations to the surgical instrument being monitored (e.g., the energy device) to adjust one or more of its parameters (e.g., surgical instrument parameters) based on the analysis of the tissue thickness. For example, the endocutter may analyze the tissue thickness and determine a uniqueness in the tissue thickness. Based on this analysis, the endocutter may send a recommendation (e.g., an updated recommendation) to the energy device to set its power settings accordingly, for example, when performing a surgical task of the surgical procedure.

Analysis performed in in the endocutter may involve a machine learning model 53040, which may take the data (e.g., measurements) from the energy device as input and output recommendations for setting one or more instrument parameters. The endocutter may, based on the surgical data (e.g., surgical measurements) received from the energy device, send a recommendation to a third device performing or assisting in performing the surgical step at hand. For example, measurements from the energy device may be received by the endocutter, which indicate that the tissue thickness of the patient is larger than average. Based on this, the endocutter may send a message to a third device, such as robotic arm or a clamp, to reorient itself in a different position (e.g., based on the tissue large tissue thickness), which may allow the energy device more freedom to operate within the surgical site. The endocutter may, based on the surgical information (e.g., surgical measurements) received from the energy device, send a recommendation to a device performing or assisting in performing a surgical task (e.g., a future surgical task).

Figure 60:
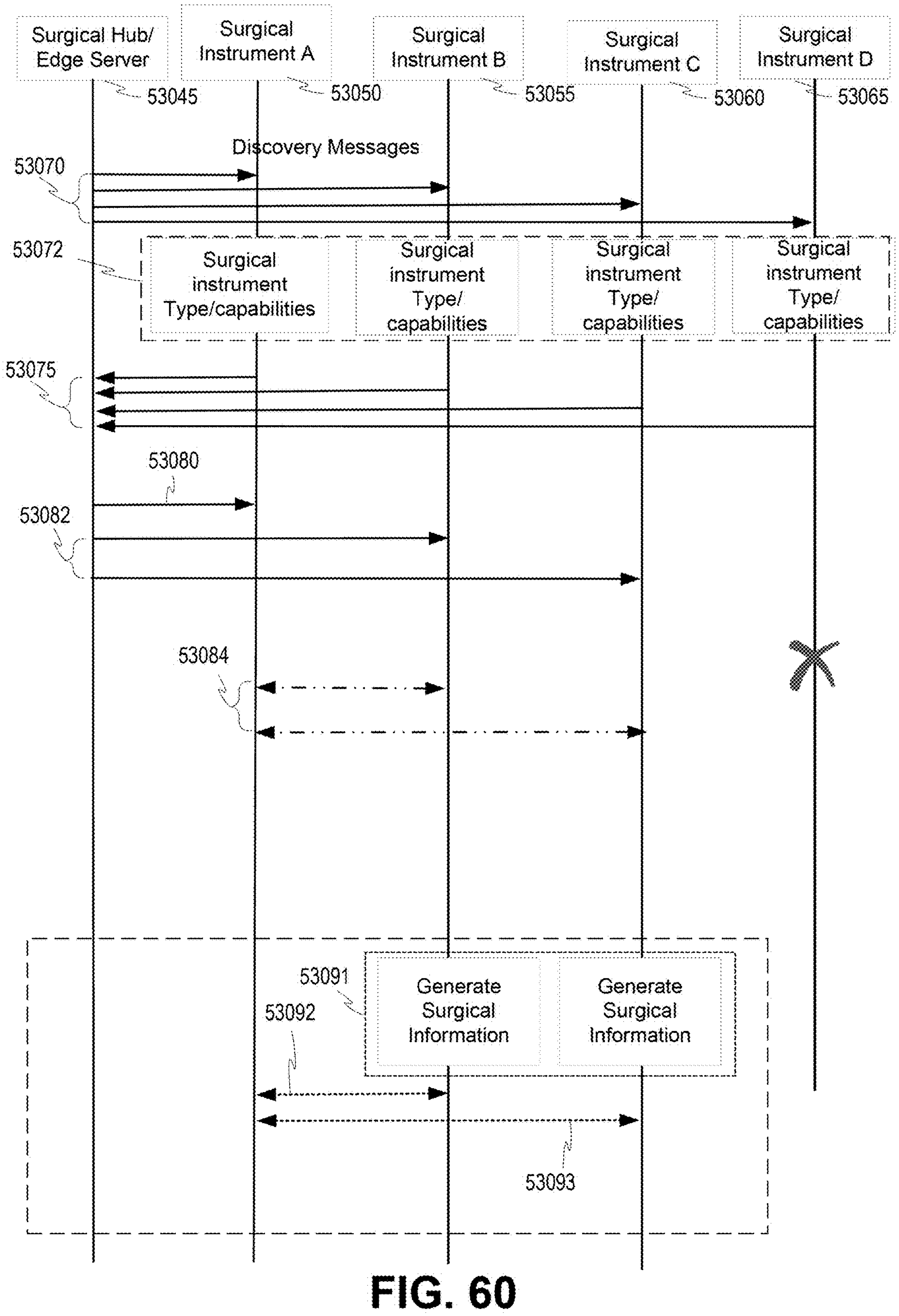
FIG. 60 shows an example of a sequence of interconnecting the surgical hub/edge device and the surgical device.

FIG. 60 shows a message sequence diagram illustrating one surgical instrument (e.g., surgical instrument A 53050) monitoring other surgical instruments (e.g., surgical instrument B 53055 and surgical instrument C 53060) in collaboration with the surgical hub/edge device 53045.

In an example, the surgical hub/edge device 53045 may statically obtain a list of surgical instruments present in the operating room and information about their respective surgical instrument type and/or surgical instrument capabilities from a surgical procedure plan or a surgical instrument list associated with a surgical procedure (e.g., a list of surgical instruments that have been activated and are to be used in a surgical procedure).

In an example, as illustrated in FIG. 60, a surgical hub/edge device 53045 (e.g., a local surgical hub/edge device) may dynamically obtain the surgical instruments involved in a surgical procedure by initiating a discovery procedure. For example, at 53070 the surgical hub/edge device 53045 may send a discovery message(s) to the surgical instruments A/B/C/D within an operating room where a surgical procedure being performed. The surgical hub/edge device 53045 may be configured (e.g., pre-configured) have a list surgical instruments and time stamps when the surgical instruments may be powered on and available for communication.

At 53072, each of the surgical instruments may determine its surgical instrument type and surgical instrument capabilities. In an example, the surgical instrument may be configured (e.g., pre-configured) with a surgical instrument type and a set of surgical instrument capabilities. At 53072, each of the surgical instruments may generate surgical instrument type and surgical instrument capabilities.

At 53075 each of the surgical instrument, in response to the discovery request message 53070, may send a response message 53075 to the surgical hub/edge server 53045. The response message 53075 may include an indication of the surgical instrument type and the surgical instrument capabilities associated with the surgical instrument sending the response message. The surgical instrument capabilities may include qualities related to the performance and/or the intelligence of the surgical instrument. Qualities related to the performance and/or intelligence of the surgical instrument are described in greater detail under the heading "Monitoring Of Adjusting A Surgical Parameter Based On Biomarker Measurements" in U.S. patent application Ser. No. 17/156,28, filed Nov. 10, 2021, the disclosure of which is herein incorporated by reference in its entirety.

The surgical hub/edge device 53045, for example, based on the response message 53075 from the surgical instruments (e.g., each of the surgical instruments), may assign roles to the available surgical instruments B or C. A surgical instrument may be assigned a role as a monitoring surgical instrument (e.g., surgical instrument A) or a peer surgical instrument (e.g., surgical instrument B or C) that is being monitored by the monitoring surgical instrument.

In an example, a surgical instrument (e.g., surgical instrument D 53065) based on its surgical instrument type and/or surgical instrument capabilities information may not be assigned a monitoring or a peer surgical instrument role. For example, the surgical instrument D 53065 may lack a capability of establishing a point-to-point connection with another surgical instrument. In an example, the surgical hub/edge device 53045 after receiving a response from the surgical instrument D 53065 may determine that a capability of the surgical instrument (e.g., operating power) is not within an acceptable operational range and therefore may not be assigned a monitoring or a peer role.

In an example, based on a surgical instrument's capabilities, the surgical hub/edge device 53045 may determine that this surgical instrument (e.g., surgical instrument A 53050) is a smart surgical instrument and, therefore, may be assigned the role of a monitoring surgical instrument. Based on at least the determination that the surgical instrument is a smart surgical instrument (e.g., has sufficient processing capability and memory capability of performing monitoring and recording of a surgical task being performed at a peer surgical instrument), the surgical hub/edge device 53045 may determine and/or assign the surgical instrument as the role of a monitoring surgical instrument.

At 53080, the surgical hub/edge device 53045 may send an assignment message to the surgical instrument 53050 indicating that it has been assigned the role of a monitoring surgical instrument. In the assignment message, the surgical hub/edge device 53045 may include an indication that surgical instrument A 53050 can establish a direct peer-to-peer connection with the surgical instrument B 53055. The surgical hub/edge device 53045 may send another assignment message 53082 to surgical instruments B 53055 and C 53060 indicating that the respective surgical instruments has been assigned the role of a peer surgical instrument. The assignment message 53082 may indicate to surgical instrument B 53055 to establish a direct peer-to-peer connection with the surgical instrument A 53050. The assignment message 53082 may indicate to surgical instrument C 53060 to establish a direct peer-to-peer connection with the surgical instrument A 53050.

As described with respect to FIG. 60, the privileges associated with a role assigned may be included in the assignment message. For example, the surgical instrument A 53050, which has been assigned as the monitoring surgical instrument, may be assigned read and write privileges with respect to surgical instrument B's a peer data. Surgical instrument A 53050 may record surgical instrument B's 53055 data in surgical instrument A's local memory. The privileges of a monitoring surgical instrument A 53050 may include sending an instruction and/or recommendation to a peer surgical instrument 53085 as it relates to the performance of a surgical step. Surgical instrument B 53055, which has been assigned as the peer surgical instrument 53085, may be assigned privileges of sending surgical information to the monitoring surgical instrument.

In an example, the local surgical hub/edge device 53045 may indicate to the monitoring surgical instrument may connect indirectly to a peer surgical instrument, for example, the monitoring surgical instrument may access the peer surgical instrument's data via the surgical hub/edge device 53045. As described with respect to FIG. 60, the surgical hub/edge device 53045 may indicate the surgical instrument A 53050 to establish a connection with the surgical instrument C 53060 indirectly via the surgical hub/edge device 53045, which may be based on the surgical instrument capabilities of surgical instrument C 53060. This message may be sent to the surgical instrument C 53060 as well.

At 53084 the monitoring surgical instrument 53050 may establish peer-to-peer connections with the peer surgical instrument B 53055 and surgical instrument C 53060. The established peer-to-peer connection may be utilized monitor and/or record surgical information associated with a surgical task being performed on the peer surgical instrument 53055.

In an example, the monitoring surgical instrument may establish connections with the peer surgical instruments at the beginning of a surgical procedure. For example, if the surgical procedure includes surgical steps 1 through K, the peer-to-peer connection establishment may occur as a part of surgical step 1.

In an example, the roles assigned to a surgical instrument may be altered at a transition from one surgical step to a subsequent surgical step. For example, during the transition from surgical step one to surgical step two of the surgical procedure, that the assigned role of surgical instrument A 53050 may be altered from a monitoring surgical instrument to a peer surgical instrument. In such a case, during surgical step two, surgical instrument A 53050 with new assigned role may no longer have the privileges of a monitoring surgical instrument.

As the surgical instruments perform their respective surgical tasks associated with the surgical step, they may generate surgical information related to how they are performing their surgical tasks. This surgical data may be sent to or accessed by the monitoring surgical instrument 53050, either directly without involving the surgical hub/edge device 53045 or indirectly via the surgical hub/edge device 53045.

At 53091, a peer surgical instruments B 53055 and C 53060 may generate surgical information associated with a patient, healthcare professional, or a surgical task performed by a surgical instrument. At 53092, the peer surgical instrument B 53055 may send the surgical information to the monitoring surgical instrument A 53050 using the established peer-to-peer connections at 53084, for example. At 53093, the peer surgical instrument C 53060 may send the surgical information to the monitoring surgical instrument A 53050 using the established peer-to-peer connections at 53084, for example. The surgical information transfer between the monitoring surgical instrument A 53050 and the peer surgical instruments B 53055 and/or C 53060 may be performed under supervision of the surgical hub/edge device 53045.

Figure 61:
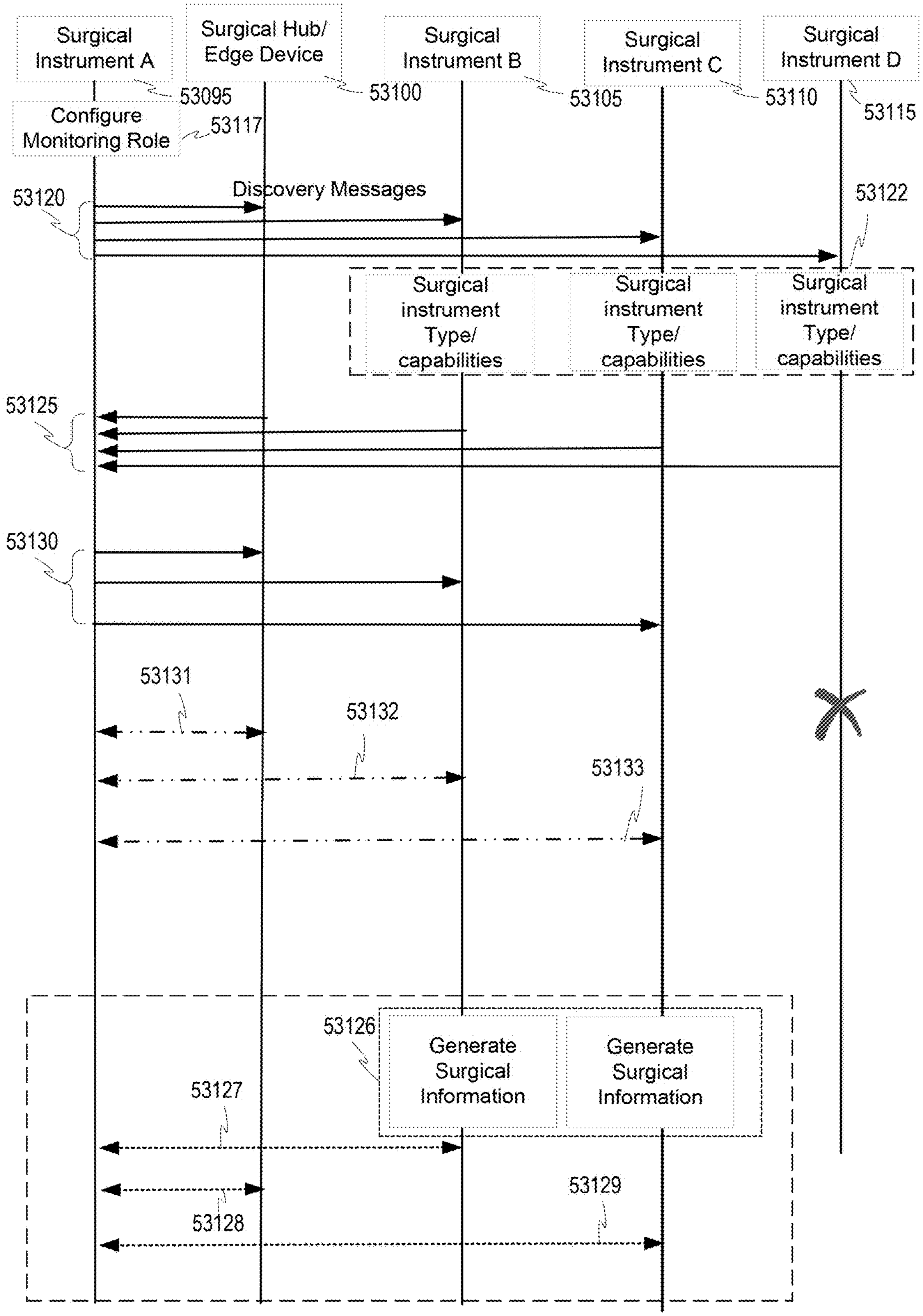
FIG. 61 a shows an example sequence of interconnecting the surgical hub/edge device and the surgical device.

FIG. 61 a shows an exemplary message sequence diagram of establishing a peer-to-peer connection with one or more surgical hub/edge device 53100 and the surgical instrument (e.g., surgical instrument A 53095, B 53105, C 53110, and D 53115) without involving any centralized surgical computing device. The surgical instrument A 53095, at a part of a surgical procedure initiation may obtain information (e.g., capability information) about other surgical instruments B/C/D as well as the surgical hub that may be active and/or connected to the ecosystem in a surgical operating room, for example. The smart surgical instrument may identify the other surgical instruments and the surgical hub are connected with the ecosystem and determine that other surgical instruments and the surgical hub are capable of establishing a peer-to-peer connection during the surgical procedure.

As illustrated in FIG. 61, at 53117, a surgical instrument (e.g., surgical instrument A 53095) may determine, for example based on its capabilities, whether it can assume the monitoring surgical instrument role, as described herein. For example, the surgical instrument A 53095 may determine that it is smart surgical instrument (e.g., a smart surgical stapler) and/or that it is the only or one of the smart surgical instruments to be utilized in the surgical procedure. In an example, the surgical instrument A 53095 may determine that it is operating within an interconnected network that is capable of monitoring other surgical instruments (e.g., surgical instrument B 53105 or C 53110) by establishing a peer-to-peer connection with those surgical instruments.

In an example, the surgical instrument A 53095 may be a smart surgical instrument. For example, the surgical instrument may determine that it is capable of operating independently, identifying surgical instruments other than itself, and communicating with the identified surgical instruments over a network. The network may be a local area network (LAN), a wireless interface (e.g., a WiFi interface (WiFi 6, WiFi6E, etc.), a Bluetooth X interface, etc.), and/or an optical interface (e.g., a fiber optic-based LAN). The devices in the network may include a smart computing device (e.g., a smart surgical hub) or a server (e.g., an edge server) at the center of the network. The network may be located inside a secured boundary (e.g., a HIPAA boundary).

In an example, the surgical instrument may identify and/or monitor other devices without utilizing the centralized computing device. In such a configuration, surgical information (e.g., surgical information associated with a surgical task) may be exchanged directly between the smart surgical instruments without utilizing a central surgical computing device or a server. In an example, the surgical instrument may determine that it has a capability of being a monitoring device, i.e., monitoring and/or recoding surgical information associated with one or more surgical tasks being performed at other surgical instruments (e.g., other peer surgical instruments). In an example, the surgical instrument may be capable of monitoring communication between two smart devices and recording aspects of their interaction or streams to monitor their operation. In an example, the surgical instrument may be capable of monitoring its own operation. Based on at least these determination, the surgical instrument A 53095 may configure itself as monitoring surgical instrument.

In an example, the surgical instrument A 53095 may analyze the surgical instrument capabilities information it may receive from a set of peer surgical instruments (e.g., surgical instrument B 53105 and surgical instrument C 53110). Based on the analysis of the surgical instrument capabilities information (e.g., limitations of the peer surgical instrument) associated with the set of peer surgical instruments, the surgical instrument A 53095 may determine that it is the only or one of the smart surgical instrument to be utilized during the surgical procedure. Accordingly, the surgical instrument A may configure itself as a monitoring surgical instrument.

In an example, one of the smart surgical instruments being utilized in a surgical procedure may determine that a plurality of other smart surgical instruments is also being utilized in the surgical procedure. The smart surgical instrument, as a part of discovery procedure for example, may obtain the firmware/software versions (e.g., version of ML software) running on each of the smart surgical instruments being utilized in the surgical procedure. The smart surgical may compare its firmware/software version with the firmware/software versions of the other surgical instruments and determine that it is running the latest version of firmware/software. Based on this determination, the smart surgical instrument may configure itself as a monitoring surgical instrument.

The surgical instrument A 53095 may initiate a discovery procedure. The surgical instrument A 53095 may obtain (e.g., obtain from a pre-configuration or obtain from a surgical hub/edge device 53100) a list of the surgical instruments that may be utilized during a surgical procedure. At 53120, the instrument A 53095 may send discovery message(s) to one or more surgical instruments and/or surgical hub/edge devices that may be part of a surgical procedure, for example.

In an example, the surgical hub/edge device 53100 may assign the roles of the surgical instruments (e.g., as described with respect to FIG. 60). After the roles have been assigned, the monitoring surgical instrument may take control and perform the other actions described herein. For example, the monitoring surgical instrument may send out the discovery requests to determine which of the surgical instruments it can directly establish connections with.

At 53122, the surgical instruments may determine their respective surgical instrument type and surgical instrument capabilities. In an example, the surgical instrument may be configured (e.g., pre-configured) with a surgical instrument type and/or a set of surgical instrument capabilities. The surgical instrument type and surgical instrument capabilities may be stored in the surgical instrument's local memory.

At 53125, each of the surgical instruments and the surgical hub that received a discovery message from a monitoring surgical device may respond with a response message. The response message sent by each of the surgical instruments or received by the monitoring surgical device may include an indication of the surgical instrument type and surgical instrument capabilities, e.g., as determined at 53122. The surgical instrument capabilities may include qualities related to the performance and/or the intelligence of the surgical instrument, which may be described in greater detail under the heading "Monitoring Of Adjusting A Surgical Parameter Based On Biomarker Measurements" in U.S. patent application Ser. No. 17/156,28, filed Nov. 10, 2021, the disclosure of which is herein incorporated by reference in its entirety.

The monitoring surgical instrument (e.g., surgical instrument A 53095, for example, based on the response message from the surgical instruments, may assign a role of a peer surgical instrument to the available surgical instruments A/B/C/D, and/or the surgical hubs/edge device 53100. The peer surgical instrument role assignment may be based on a selection criteria that may include the surgical instrument type, the surgical instrument capabilities, the surgical step of the surgical procedure, the surgical procedure, etc.

In an example, a surgical instrument (e.g., surgical instrument D 53115) based on its surgical instrument type and/or surgical instrument capabilities information may not be assigned a peer surgical instrument role. For example, the surgical instrument D 53065 may lack a capability of establishing a point-to-point connection with another surgical instrument. In an example, the surgical monitoring instrument 53095 after receiving a response from the surgical instrument D 53115 may determine that a capability of the surgical instrument (e.g., operating power) is not within an acceptable operational range and therefore may not be assigned a peer role.

At 53130, the monitoring surgical instrument A 53095 may send an assignment message to each of the surgical instruments B/C and surgical hub/edge device 53100 indicating that each of the surgical instruments B/C and surgical hub/edge device 53100 has been assigned the role of a peer surgical instrument. In an example, the assignment message may include the privileges associated with the peer role that has been assigned to a surgical instrument and/or the surgical hub. For example, the monitoring surgical instrument may assign surgical instrument B 53105 and surgical instrument C 53110 as a peer surgical instruments.

In an example, the assignment message, the surgical monitoring surgical instrument A 53095 may include an indication that surgical instrument may establish a peer-to-peer connection with surgical instrument A 53095. In an example, as part of the establishment of the peer-to-peer connection, the surgical instrument A 53095 and the peer-to-peer surgical instrument may optimize various parameters of the peer-to-peer connection (e.g., surgical data sharing, data transfer speeds, etc.)

At 53131, the monitoring surgical instrument A 53095 may establish a peer-to-peer connection with a surgical computing device/edge server 53100. The established peer-to-peer connection may be utilized to monitor and/or record surgical information on the surgical computing device/edge server 53100.

At 53132, the monitoring surgical instrument A 53095 may establish a peer-to-peer connection with a peer surgical instrument B 53105. The established peer-to-peer connection may be utilized to monitor and/or record surgical information on the peer surgical instrument B 53105.

At 53133, the monitoring surgical instrument 53095 may establish a peer-to-peer connection with a peer surgical instrument C 53110. The established peer-to-peer connection may be utilized monitor and/or record surgical information on the peer surgical instrument C 53110.

In an example, the monitoring surgical instrument A 53095 may establish direct peer-to-peer connections with the peer surgical instruments at the beginning of a surgical procedure. For example, if the surgical procedure includes surgical steps 1 through K, the peer-to-peer connection establishment may occur as a part of surgical step 1.

At 53126, peer surgical instruments B 53105 and C 53110 may generate surgical information associated with a patient, healthcare professional, or a surgical instrument. At 53127, the surgical instrument may send the surgical information to the monitoring surgical instrument A 53095.

In an example, a monitoring surgical instrument, for example, a smart surgical stapling device may identify a surgical energy device to be used during a surgical procedure in an operating room. The smart surgical stapling device may retrieve capabilities of the surgical energy device and configure it as a peer surgical instrument to be monitored by the smart energy stapler. The smart surgical stapling device may establish a peer-to-peer connection with the surgical energy device. As part of a surgical task, the surgical energy device may be used for dissecting and/or mobilizing a tissue. During this surgical task, the energy device may record and/or process the tissue viability, for example, based on feedback of the various surgical parameters collected by the surgical energy device. The surgical parameters may include power, time, impedance, etc. The smart surgical stapling device may directly obtain the information collected by the energy device (e.g., parameters including power, time, impedance) via the established peer-to-peer connection. In an example, the energy device may calculate surgical instrument settings like initial starting speed of the motor for firing the staples and send it to the smart surgical stapling device. In an example, based on the information directly obtained from the energy device, the smart surgical stapling device may calculate the initial starting speed of the motor for firing the staples. In an example, based at least on the information directly obtained from the energy device, the smart surgical stapler may identify an optimal location for tissue dissection with a stapling device. The location for tissue dissection may be based on tissue properties/disease state of tissue or areas with minimization of vessels avoidance. In an example, based at least on the area dissected, the energy device may identify the cartridge (e.g., the size of the cartridge (45 mm or 60 mm) and/or the color of the cartridge (e.g., blue) based on tissue thickness collected on jaw). The energy device may communicate the cartridge identification information directly to the smart energy device using the peer-to-peer connection between the energy device and the smart stamping device.

In an example, the interconnections may be altered at a transition from one surgical step to a subsequent surgical step. For example, from surgical step one to surgical step two, the interconnections and the assignments of the privileges may be adjusted. For example, with respect to FIG. 61, during the transition from surgical step one to surgical step two, the monitoring surgical instrument A 53095 may determine that surgical instrument B 53105 may no longer be a peer surgical instrument.

In an example, as the surgical instruments are performing their respective surgical tasks associated with the surgical step, they may generate surgical data related to how they are performing their surgical tasks., which may be described in greater detail under the heading "Monitoring Of Adjusting A Surgical Parameter Based On Biomarker Measurements" in U.S. patent application Ser. No. 17/156,28, filed Nov. 10, 2021, the disclosure of which is herein incorporated by reference in its entirety. This surgical data may be accessed by the monitoring surgical instrument, either directly as described here with respect to FIG. 61 or indirectly via the surgical hub/edge device 53100, as described herein with respect to FIG. 60.

Figure 62:
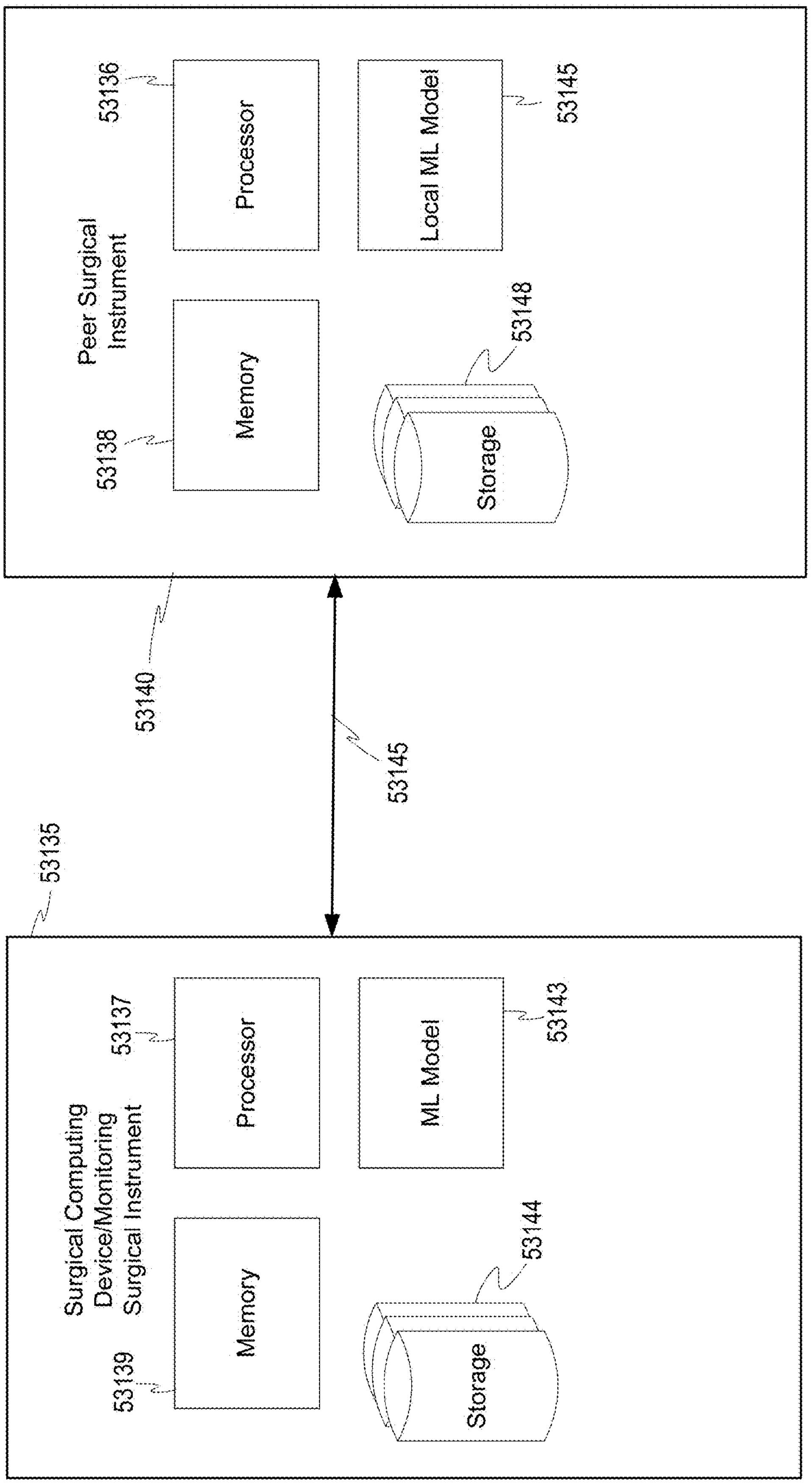
FIG. 62 shows an example of the relationship between the surgical hub/edge device and the surgical device.

FIG. 62 shows an example of the relationship between a surgical computing device (e.g., as surgical hub/edge device) or a monitoring surgical device 53135 and the surgical instrument 53140. Surgical information (e.g., surgical data) may be sent from the surgical computing device or a monitoring surgical device 53135 to the surgical instrument 53140 and vice versa. In examples, the surgical information may be communicated over a network interface 53145. The network interface may be of many types, as described herein. Surgical information may include surgical data associated with a surgical task being performed on a surgical instrument 53140. The surgical data may include data based on measurements taken from sensors, actuators, robotic movements, biomarkers, surgeon biomarkers, visual aids, and/or the like. The measurements are described in greater detail under the heading "Monitoring Of Adjusting A Surgical Parameter Based On Biomarker Measurements" in U.S. patent application Ser. No. 17/156,28, filed Nov. 10, 2021, the disclosure of which is herein incorporated by reference in its entirety.

The surgical information or surgical data measurements may be associated with one of more actuators located within the operating room. For example, surgical information may be generated from measurements on potentiometer readings. This surgical information may be associated with an orientation of the surgical instrument. The surgical information may be used in evaluating how the surgical instrument is performing its individual surgical tasks as described with respect to FIGS. 59 and 60. The surgical information may be used when determining roles of the surgical instruments as described with respect to FIGS. 60 and 61.

As illustrated in FIG. 62, surgical computing device or monitoring surgical device 53135 may include a processor 53137, a memory 53139 (e.g., a non-removable memory and/or a removable memory), a machine learning model 53143, and/or a local storage subsystem 53144, among others. It will be appreciated that the surgical computing device or the monitoring surgical instrument 53135 may include any sub-combination of the foregoing elements/subsystems while remaining consistent with an embodiment.

The processor 53137 in the surgical computing device or a monitoring surgical device 53136 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), a state machine, and the like. The processor 53137 may perform data processing, authentication, input/output processing, and/or any other functionality that may enable the surgical computing device or a monitoring surgical device 53136 to operate in an environment that is suitable for performing surgical procedures. The processor 53137 may be coupled with a transceiver (not shown). The processor 53137 may use the transceiver (not shown in the figure) to communicate with the peer surgical instrument 53140.

The memory 53139 in the surgical computing device or the monitoring surgical instrument 53135 may be used to store where surgical information was sent. For example, the memory may be used to recall that surgical information was sent to the peer surgical instrument 53140. The memory may include a database and/or lookup table. The memory may include virtual memory which may be linked to servers located within the protected network.

The processor 53137 in the surgical computing device or the monitoring surgical instrument 53135 may access information from, and store data in, any type of suitable memory (e.g., a non-removable memory and/or the removable memory). The non-removable memory may include random-access memory (RAM), read-only memory (ROM), a hard disk, a solid-state drive or any other type of memory storage device. The removable memory may include secure digital memory.

The processor 53137 in the surgical computing device or a monitoring surgical device 53135 may access information from, and store data in an extended storage 53144. (e.g., a non-removable memory and/or the removable memory). In an example, the processor 53137 may access information from, and store data in, memory that is not physically located on the surgical computing device or the monitoring surgical instrument 53135, such as on a server or a secondary edge computing system (not shown).

The processor 53137 in the surgical computing device or a monitoring surgical device 53135 may utilize the machine learning model 53143 to predict parameters associated with a surgical instrument or identify a part of a surgical instrument (e.g., a stapler cartridge), as described herein. The processor 53137 may use the transceiver (not shown in the figure) to directly communicate the surgical information or the predicted surgical parameters or the predicted identification of a surgical part to the peer surgical instrument 53140. The directly communication between the surgical computing device or the monitoring surgical instrument 53135 and the peer surgical instrument 53140 may occur using the established peer-to-peer connection 53145.

As further illustrated in FIG. 62, the peer surgical instrument 53140 may include a processor 53136, a memory 53138 (e.g., a non-removable memory and/or a removable memory), a local machine learning model 53145, and/or a local storage subsystem 53148, among others. The local machine learning model may be simpler than the machine learning mode used in the surgical computing device or the surgical monitoring device 53135. In an example, the local machine learning model may be provided with a training model that it may utilize, for example, to predict parameters associated with a surgical instrument or identify a part of a surgical instrument. It will be appreciated that the peer surgical instrument 53140 may include any sub-combination of the foregoing elements/subsystems while remaining consistent with an embodiment.

The processor 53136 in the peer surgical instrument 53140 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), a state machine, and the like. The processor 53136 may perform data processing, authentication, input/output processing, and/or any other functionality that may enable the peer surgical instrument 53140 to operate in an environment that is suitable for performing surgical procedures. The processor 53136 may be coupled with a transceiver (not shown). The processor 53136 may use the transceiver (not shown in the figure) to communicate with the surgical computing device or the monitoring surgical instrument 53135.

The memory 53138 in peer surgical instrument 53140 may be used to store where surgical information was sent. For example, the memory may be used to recall that surgical information was sent to the peer surgical instrument 53140. The memory may include a database and/or lookup table. The memory may include virtual memory which may be linked to servers located within the protected network.

The processor 53136 in the peer surgical instrument 53140 may access information from, and store data in, any type of suitable memory (e.g., a non-removable memory and/or the removable memory). The non-removable memory may include random-access memory (RAM), read-only memory (ROM), a hard disk, a solid-state drive or any other type of memory storage device. The removable memory may include secure digital memory.

The processor 53136 in the peer surgical instrument 53140 may access information from, and store data in an extended storage 53148. (e.g., a non-removable memory and/or the removable memory). In an example, the processor 53136 may access information from, and store data in, memory that is not physically located on the peer surgical instrument 53140, such as on a server or a secondary edge computing system (not shown).

The processor 53136 in in the peer surgical instrument 53140 may utilize the local machine learning model 53145 to predict parameters associated with a surgical instrument or identify a part of a surgical instrument (e.g., a stapler cartridge), as described herein. The processor 53136 may use the transceiver (not shown in the figure) to directly communicate to the monitoring surgical instrument 53135 the surgical information or the predicted surgical parameters or the predicted identification of a surgical part. The direct communication between the peer surgical instrument 53140 and the surgical computing device or the monitoring surgical instrument 53135 may occur using the established peer-to-peer connection over interface 53145.

Figure 63:
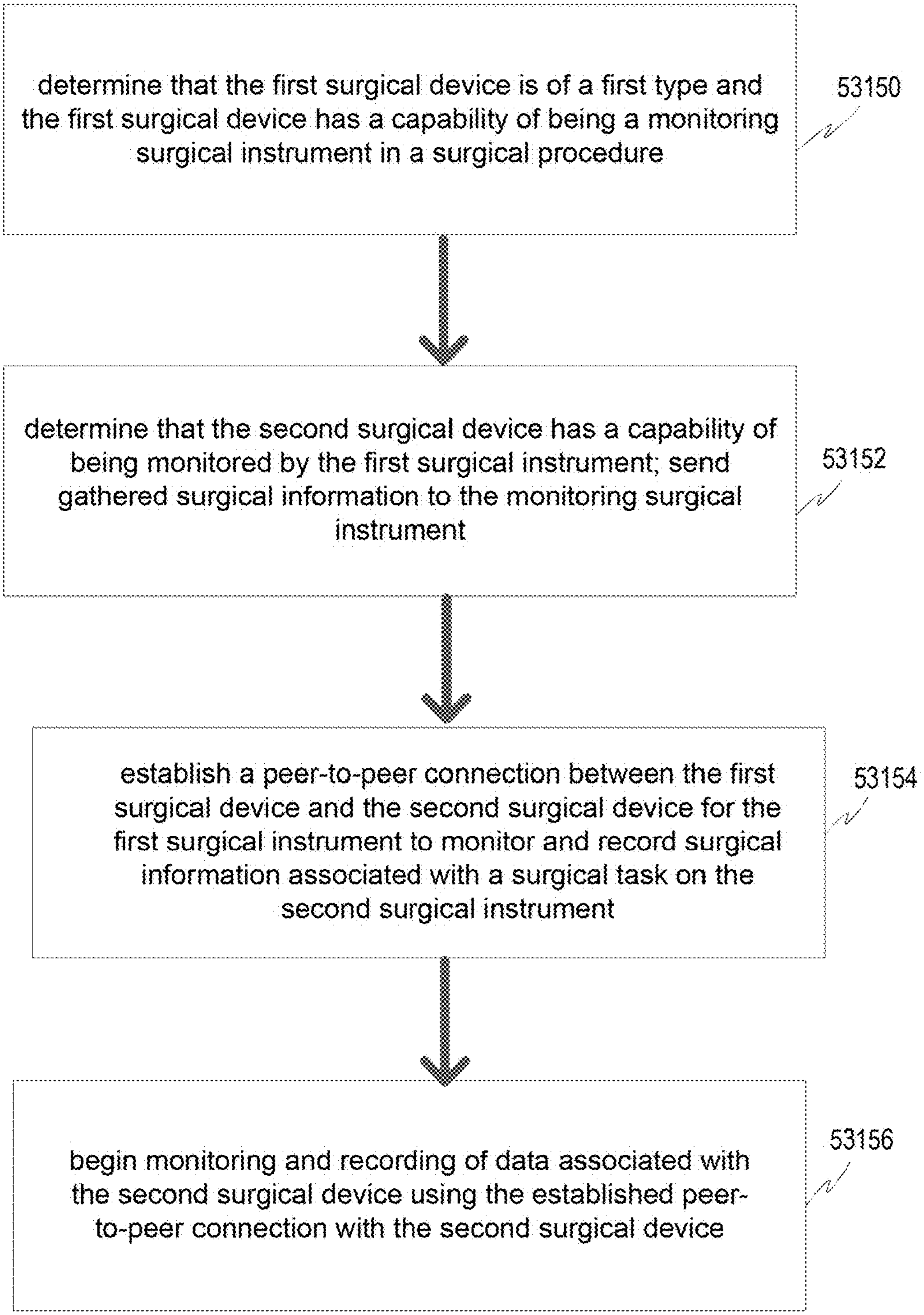
FIG. 63 shows an example of a peer-to-peer interconnected surgical system devices utilized for remote monitoring/recording, for example, without using a central surgical hub.

FIG. 63 shows a peer-to-peer interconnected surgical instruments or surgical devices without using a central surgical hub for remote monitoring/recording. At 53150, a surgical device or a surgical instrument may determine that it has capability of monitoring and recording surgical data associated with a surgical task of a surgical procedure being performed at a second surgical instrument. The capability of the surgical instrument being the monitoring surgical instrument may include the monitoring surgical instrument having a capability of accessing surgical data from the second surgical instrument and/or a capability of setting (e.g., remotely setting) a parameter on the second surgical instrument based on the accessed surgical data. The surgical data may include surgical data associated with a patient, a healthcare professional, or a surgical instrument. Based on the determination, the surgical instrument may configure itself as a monitoring surgical instrument. In an example, the surgical instrument being a monitoring surgical instrument and the second surgical instrument being a peer surgical instrument that is being monitored by the monitoring surgical instrument is based on a negotiation between the surgical instrument and the second surgical instrument.

At 53152, the surgical instrument may determine that the second surgical instrument has capability of being a peer surgical instrument that may be monitored by it. The capability of being a peer surgical instrument may include having a capability to establish a peer-to-peer connection with a monitoring surgical instrument and/or having a capability of gathering surgical data associated with a patient, a healthcare professional, or a surgical instrument and sending gathered surgical information to the monitoring surgical instrument. The surgical instrument may configure the second surgical instrument as a peer surgical instrument.

At 53154, the surgical instrument may establish a peer-to-peer connection with the second surgical instrument. The peer-to-peer connection is established between the first surgical instrument and the second surgical instrument for the first surgical instrument to monitor and record surgical information surgical task on the second surgical instrument.

At 53156, the surgical instrument may begin monitoring and recording of surgical data associated with the second surgical instrument using the established peer-to-peer connection with the second surgical instrument.

Figure 64:
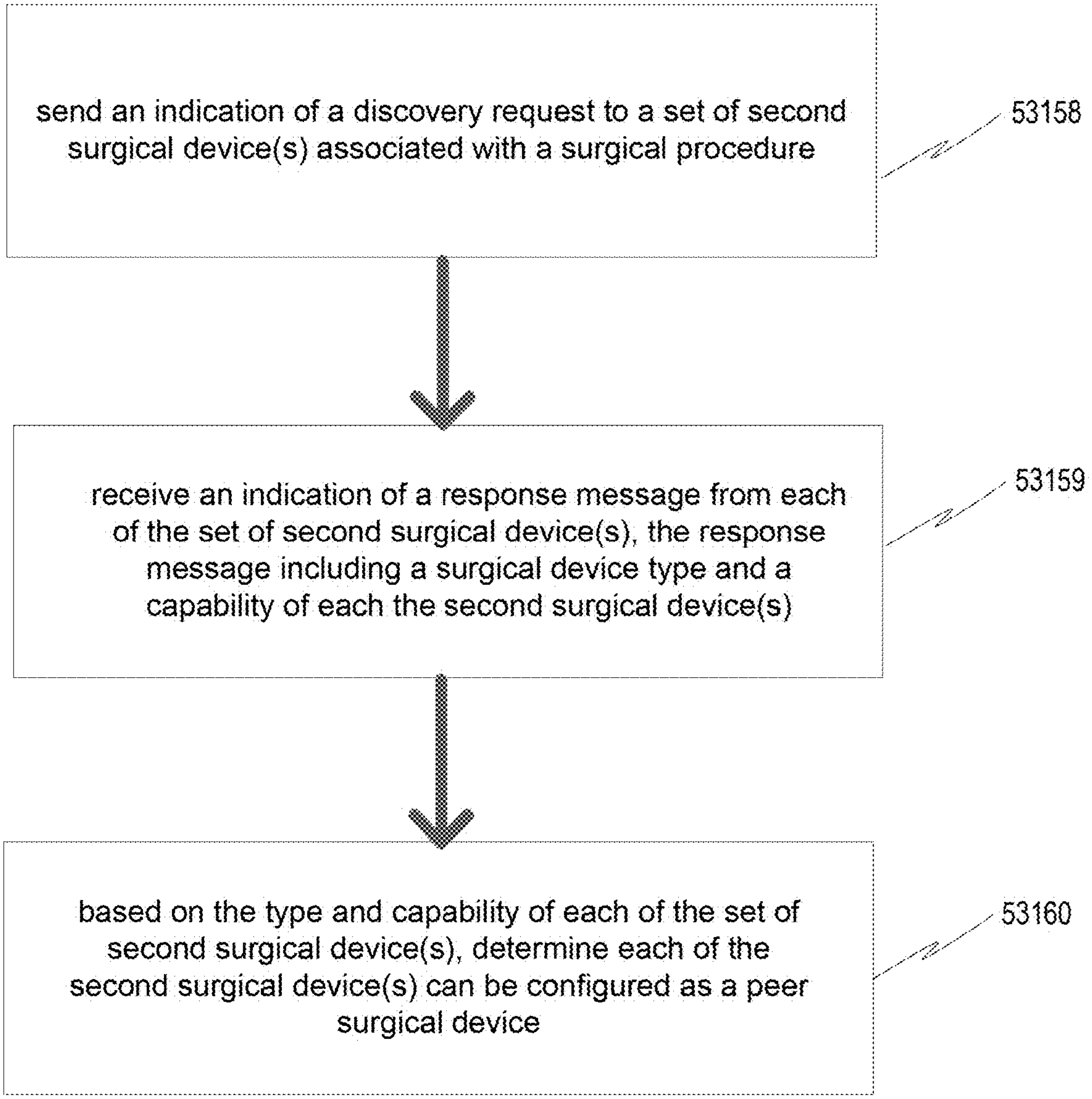
FIG. 64 illustrates a discovery mechanism used for assigning roles (e.g., a monitoring role and/or a peer role) to surgical devices that may be utilized in a surgical procedure.

FIG. 64 illustrates a discovery mechanism used for assigning roles (e.g., a monitoring role and/or a peer role) to surgical instruments that may be utilized in a surgical procedure. At 53158, a first surgical instrument may send an indication of a discovery request to a set of second instrument(s) associated with a surgical procedure.

At 53159, the first surgical instrument may receive an indication of a response message from each of the set of second surgical instrument(s). The indication of the response message may include indication of a surgical instrument type and indication of a capability of each of the second surgical instruments. Based on the surgical instrument type and the capability of the surgical instrument, the first surgical instrument may determine each the second surgical instrument(s) to be a peer surgical instrument. The indication of the response message from the first surgical instrument to each of the set of second surgical instrument(s) may indicate an assigned role.

At 53160, based at least on the surgical instrument type and capability of each of the second surgical instruments, the first surgical instrument may determine that each of the set of second surgical instrument(s) is a peer surgical instrument.

The first surgical instrument may be able to monitor one of the second surgical instruments. The first surgical instrument may be a monitoring surgical instrument and may be able to access data of the one of the second surgical instruments that has been assigned the role of a peer surgical instrument. In an example, the first surgical instrument may be able to set a parameter of the second surgical instrument based on the accessed surgical data.

In an example, the roles of the first surgical instrument and the second surgical instrument may be determined based on a negotiation between the surgical instrument and each of the second surgical instrument(s).

In an example, the first surgical instrument, based at least on its own surgical instrument type and capabilities information may assume the role of a monitoring surgical instrument.

In an example, the first surgical instrument may be a smart surgical instrument (e.g., operating within an interconnect network may be capable of understanding the limitations of the second surgical instrument used in the surgical procedure. This may include the instrument realizing it is the only smart instrument in the procedure as well as identifying other instruments have surgical instrument capabilities of sharing data.

In an example, a set of surgical instruments may be utilized in performing a surgical procedure. Some of the surgical instruments, for example, a smart stapling device may be smarter and/or more advanced than an energy device, for example. The advancement of the smart stapling device over the energy device may be based on revision or level of software (e.g., machine learning software) installed on each of the surgical devices.

In an example, during the startup of the procedure, the smart surgical stapler may obtain information about other surgical instruments that may be active and/or inter-connected to the ecosystem. The smart surgical stapler may have confirmation of other device availability which may be identified based on the instruments available and what operations would be capable of being performed during the surgery based on the instruments in the operating room. Based on identification of the available instruments identified, the smart surgical stapler may attempt to connect directly to the other instruments to have a peer-to-peer connection which may optimize data sharing, transfer speeds, and/or the like. For example, an energy device may be used for dissecting and mobilizing tissue. During a process, it may be recording/processing the tissue viability based on feedback of the parameters collected by the energy device (e.g., power, time, impendence, etc.). The information collected from the energy device may communicate to the surgical stapler to indicate the initial starting speed of the motor for firing the staples. This data may be sent to the surgical stapler directly which may identify an optimal location for tissue dissection with a stapling device based on tissue properties and/or a disease state of tissue or areas with minimization of vessels avoidance. For example, based on the area dissected, the device may process and communicate to the surgical stapler what cartridge should be use e.g., 45 mm or 60 mm and/or color based on tissue thickness collected on jaw.

Figure 65:
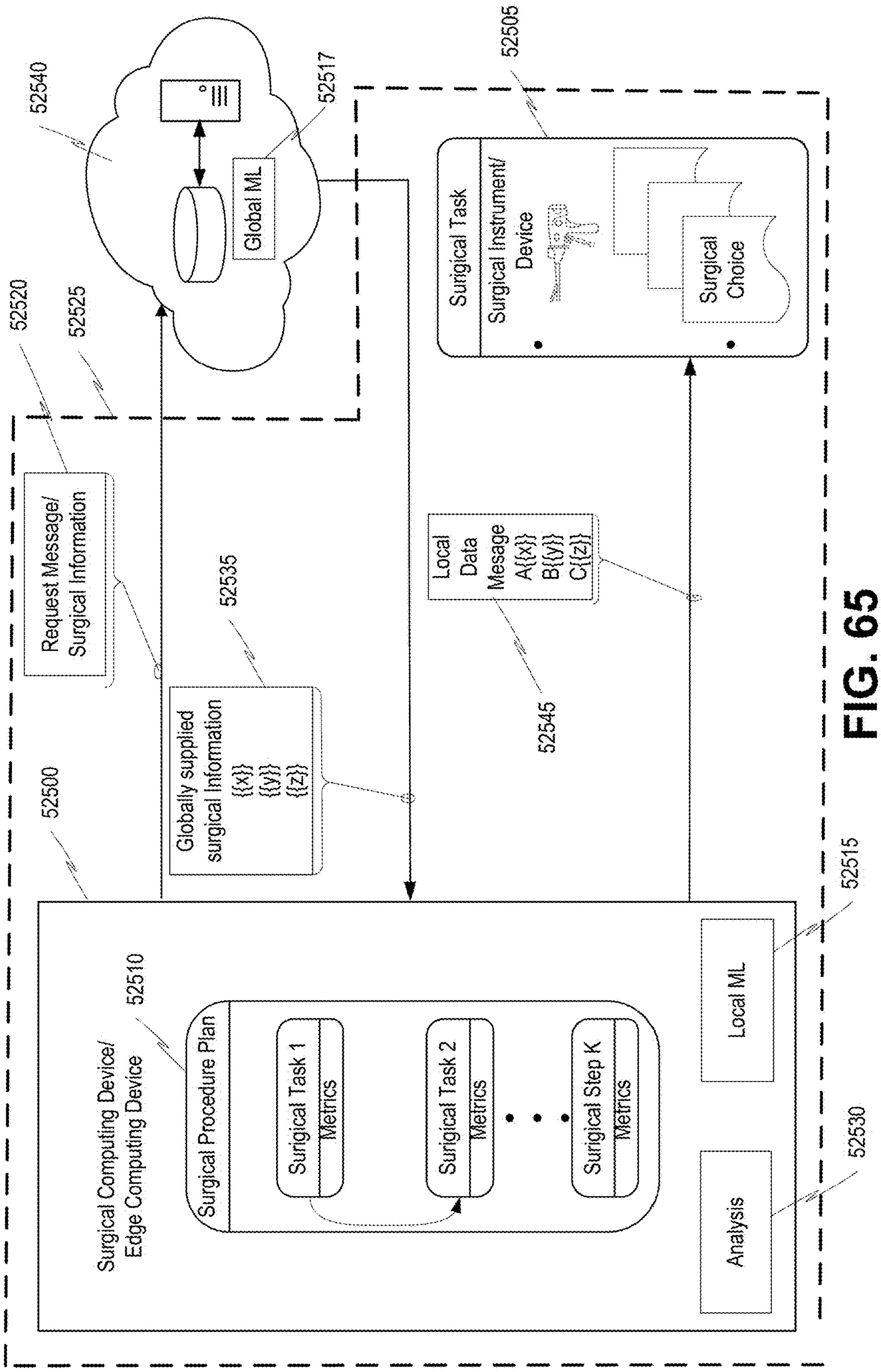
FIG. 65 shows an example of an overview of receiving global or regional information and modifying the global or regional information based on local information.

Referring to FIG. 65, an overview of the surgical system may be provided. Surgical instruments may be used in a surgical procedure as part of the surgical system. The surgical computing device/edge computing device may be configured to coordinate information flow to a surgical instrument (e.g., the display of the surgical instrument). For example, the surgical computing device/edge computing device may be described in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Example surgical instruments that are suitable for use with the surgical system are described under the heading "Surgical Instrument Hardware" and in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety, for example.

FIG. 65 shows an example of an overview of receiving global or regional information and modifying the global or regional information based on local information. The surgical computing device/edge computing device may be used to perform a surgical procedure on a patient. A robotic system may be used in the surgical procedure as a part of the surgical system. For example, the robotic system may be described in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. The robotic hub may be used to process the images of the surgical site for subsequent display to the surgeon through the surgeon's console.

Other types of robotic systems may be readily adapted for use with the surgical system. Various examples of robotic systems and surgical tools that are suitable for use with the present disclosure are described in U.S. Patent Application Publication No. US 2019-0201137 A1 (U.S. patent application Ser. No. 16/209,407), titled METHOD OF ROBOTIC HUB COMMUNICATION, DETECTION, AND CON- TROL, filed Dec. 4, 2018, the disclosure of which is herein incorporated by reference in its entirety.

Various examples of cloud-based analytics that are performed by the cloud, and are suitable for use with the present disclosure, are described in U.S. Patent Application Publication No. US 2019-0206569 A1 (U.S. patent application Ser. No. 16/209,403), titled METHOD OF CLOUD BASED DATA ANALYTICS FOR USE WITH THE HUB, filed Dec. 4, 2018, U.S. Patent Application Publication No. US2019-0201119 A1 (U.S. patent application Ser. No. 15/940,694), titled CLOUD-BASED MEDICAL ANALYTICS FOR MEDICAL FACILITY SEGMENTED INDIVIDUALIZATION OF INSTRUMENT FUNCTION, filed Mar. 29, 2018, U.S. Patent Application Publication No. US2019-0201144 A1 (U.S. patent application Ser. No. 15/940,679), titled CLOUD-BASED MEDICAL ANALYTICS FOR LINKING OF LOCAL USAGE TRENDS WITH THE RESOURCE ACQUISITION BEHAVIORS OF LARGER DATA SET, filed Mar. 29, 2018, U.S. Patent Application Publication No. US2019-0206555 A1 (U.S. patent application Ser. No. 15/940,660), titled CLOUD-BASED MEDICAL ANALYTICS FOR CUSTOMIZATION AND RECOMMENDATIONS TO A USER, filed Mar. 29, 2018, the disclosure of which are herein incorporated by reference in their entirety.

In various aspects, an imaging device may be used in the surgical system and may include at least one image sensor and one or more optical components. Suitable image sensors may include, but are not limited to, Charge-Coupled Device (CCD) sensors and Complementary Metal-Oxide Semiconductor (CMOS) sensors.

The optical components of the imaging device may include one or more illumination sources and/or one or more lenses. The one or more illumination sources may be directed to illuminate portions of the surgical field. The one or more image sensors may receive light reflected or refracted from the surgical field, including light reflected or refracted from tissue and/or surgical instruments.

The one or more illumination sources may be configured to radiate electromagnetic energy in the visible spectrum as well as the invisible spectrum. The visible spectrum, sometimes referred to as the optical spectrum or luminous spectrum, is that portion of the electromagnetic spectrum that is visible to (e.g., can be detected by) the human eye and may be referred to as visible light or simply light. A typical human eye will respond to wavelengths in air that are from about 380 nm to about 750 nm.

The invisible spectrum (e.g., the non-luminous spectrum) is that portion of the electromagnetic spectrum that lies below and above the visible spectrum (i.e., wavelengths below about 380 nm and above about 750 nm). The invisible spectrum is not detectable by the human eye. Wavelengths greater than about 750 nm are longer than the red visible spectrum, and they become invisible infrared (IR), microwave, and radio electromagnetic radiation. Wavelengths less than about 380 nm are shorter than the violet spectrum, and they become invisible ultraviolet, x-ray, and gamma ray electromagnetic radiation.

In various aspects, the imaging device may be configured for use in a minimally invasive procedure. Examples of imaging devices suitable for use with the present disclosure include, but not limited to, an arthroscope, angioscope, bronchoscope, choledochoscope, colonoscope, cytoscope, duodenoscope, enteroscope, esophagogastro-duodenoscope (gastroscope), endoscope, laryngoscope, nasopharyngo-neproscope, sigmoidoscope, thoracoscope, and uretero-scope.

The imaging device may employ multi-spectrum monitoring to discriminate topography and underlying structures. A multi-spectral image is one that captures image data within specific wavelength ranges across the electromagnetic spectrum. The wavelengths may be separated by filters or by the use of instruments that are sensitive to particular wavelengths, including light from frequencies beyond the visible light range, e.g., IR and ultraviolet. Spectral imaging can allow extraction of additional information the human eye fails to capture with its receptors for red, green, and blue. The use of multi-spectral imaging is described in greater detail under the heading "Advanced Imaging Acquisition Module" in U.S. Patent Application Publication No. US 2019-0200844 A1 (U.S. patent application Ser. No. 16/209,385), titled METHOD OF HUB COMMUNICATION, PROCESSING, STORAGE AND DISPLAY, filed Dec. 4, 2018, the disclosure of which is herein incorporated by reference in its entirety. Multi-spectrum monitoring can be a useful tool in relocating a surgical field after a surgical task is completed to perform one or more of the previously described tests on the treated tissue. It is axiomatic that strict sterilization of the operating room and surgical equipment is required during any surgical procedure. The strict hygiene and sterilization conditions required in a "surgical theater," i.e., an operating or treatment room, necessitate the highest possible sterility of all medical devices and equipment. Part of that sterilization process is the need to sterilize anything that comes in contact with the patient or penetrates the sterile field, including the imaging device and its attachments and components. It will be appreciated that the sterile field may be considered a specified area, such as within a tray or on a sterile towel, that is considered free of microorganisms, or the sterile field may be considered an area, immediately around a patient, who has been prepared for a surgical procedure. The sterile field may include the scrubbed team members, who are properly attired, and all furniture and fixtures in the area.

As shown in FIG. 65, a surgical computing system surgical hub/edge computing device 52500 may be linked to a surgical operating room. In examples, multiple surgical computing devices/edge computing devices maybe associated with respective operating rooms. The operating room(s) may include one or more surgical computing devices and one or more surgical instruments or devices 52505 or other modules and/or subsystems that may be utilized during a surgical procedure, for example, as described herein in FIG. 2, FIG. 3, and FIG. 7B. The surgical computing device or an edge computing device may include an analysis subsystem 52530 and a local machine learning (ML) model or subsystem 52515. The surgical devices may be used by a healthcare professional to perform a surgical procedure on a patient. For example, a surgical device may be an endocutter.

In an example, the surgical computing device and the edge computing device may be two different devices. In such a case, the surgical computing device or the edge computing device may send parameters associated with a surgical instrument or other modules, or control algorithms to the surgical instrument or other modules via the surgical computing device (e.g., a surgical hub).

A surgical device may be in communication with the surgical computing device/edge computing edge device 52500. The surgical computing device or the computing edge device may be located within the operating room where the surgical procedure is being performed or within a healthcare facility where the operating room is located. Surgical step and surgical task may be used interchangeably herein. The surgical computing device or the computing edge device may send one or more algorithms (e.g., control algorithms) or parameters to be used by the surgical instruments or other modules connected with the surgical computing device or the computing edge device. The surgical computing device/edge computing device 52500 may instruct the surgical device about information related to the surgical procedure being performed on the patient.

In an example, the surgical computing device or the edge device 52500 may indicate to the surgical instrument 52505 on how to set parameters (e.g., patient data, healthcare provider data, surgical instrument data, etc.) in order to perform the surgical procedure (e.g., or a surgical task of the surgical procedure), for example, perform the surgical procedure autonomously. How the surgical instruments operate autonomously is described in greater detail under the heading "METHOD OF CONTROLLING AUTONOMOUS OPERATIONS IN A SURGICAL SYSTEM" in U.S. Patent Application No. U.S. Ser. No. 17/747,806, filed May 18, 2022, the disclosure of which is herein incorporated by reference in its entirety. Determining the surgical information used for setting the parameters (e.g., patient data, healthcare provider data, surgical instrument data, etc.) may be based on an output from a local machine learning model 52515 located within the surgical computing device or the edge computing device 52500. In an example, a machine learning model and/or a trained machine learning model may be utilized as part of a supervised learning framework. Supervised learning model is described herein in FIG. 8A. The training data (e.g., training examples 802, as illustrated in FIG. 8A) may consist of a set of training examples (e.g., input data mapped to labeled outputs, for example, as shown in FIG. 8A). The training data used in training the local machine learning model 52515 may include data gathered from previous surgical procedures and/or simulated surgical procedures. The training data may include previous control algorithms associated with the surgical instruments (e.g., stored locally or received from the enterprise server 52540). The training data may also include parameters associated with a patient, a healthcare professional, and/or a surgical instrument. In an example, the local ML model as an output may provide a surgical instrument parameter (e.g., firing rate of a surgical instrument) or a control algorithm associated with the surgical instrument. In an example, the surgical instrument parameter or the control algorithm associated with the surgical instrument may be utilized to instruct a surgical instrument to set (e.g., autonomously set) a parameter, for example, firing rate at a certain frequency to perform anastomosis. The surgical computing device/edge computing device 52500 may set a parameter (e.g., patient data, healthcare provider data, surgical instrument data, etc.) of the surgical instrument or device 52505 by sending the surgical instrument a message. In an example, the message for setting a parameter may be in response to the surgical instrument 52505 sending a request message 52520 to the surgical computing device/edge computing device 52500 requesting the parameter.

Surgical information (e.g., surgical data) related to a surgical procedure may be generated (e.g., by a monitoring module located at the surgical computing device/edge computing device surgical computing device/edge computing device 52500 or locally by the surgical instrument 52505). For example, the surgical information may be based on the performance of the surgical instrument 52505. For example, the surgical information associated with a patient may include physical measurement physiological measurements, and/or the like. The measurements are described in greater detail under the heading "Monitoring Of Adjusting A Surgical Parameter Based On Biomarker Measurements" in U.S. patent application Ser. No. 17/156,28, filed Nov. 10, 2021, the disclosure of which is herein incorporated by reference in its entirety.

The surgical computing device/edge computing device surgical computing device/edge computing device 52500 may receive local measurements based on measurements from one or more surgical instruments 52505 located in the operating room where the surgical computing device/edge computing device surgical computing device/edge computing device 52500 is located. The measurements may be related to a surgical procedure being performed on a patient within the operating room. For example, the surgical procedure may be a colorectomy. The surgical computing device/edge computing device surgical computing device/edge computing device 52500 may have a module that may include a surgical procedure plan 52510. By using the surgical plan 52510, the surgical computing device/edge computing device surgical computing device/edge computing device 52500 may determine the surgical tasks to be performed that may be a part of the surgical procedure, for example, as described herein in FIG. 7D. For example, the surgical procedure may be a lung segmentectomy. In such a case, the surgical tasks may include surgical tasks 1 through K. For example, surgical task 1 may include pulling electronic medical records associated with the patient and surgical task K may include reversing anesthesia and removing all the monitors. While the surgical tasks 1 through K are being performed by healthcare professionals, the surgical instruments 52505 within the operating room, along with other devices capable of measuring data related to the surgical procedure, may send data (e.g., related to the surgical procedure) to the surgical computing device/edge computing device surgical computing device/edge computing device 52500.

When highly sensitive surgical information associated with a patient is sent to a remote entity (e.g., an enterprise cloud server) located (physically or virtually) outside the protected boundary 52525, it may be first anonymized. Anonymization of patient data may include one or more of the following operations: redaction, randomization, transformation of data into a shorter format (e.g., summarizing, or averaging). Redaction may include removing data from a data set, for example, prior to sending it to the remote server (e.g., enterprise cloud server). Randomization may include applying a random value to the data, which may be reversed if the receiver receives a private key. Transformation of data into a shorter format may include summarization and/or averaging. Summarization, for example, may include representing a patient data by a range, and sending the data range that represents the data. Averaging may include representing the data with an average value instead of the exact value.

The analysis subsystem 52530 in the surgical computing device or the edge computing device. may be used by the surgical computing device/edge computing device 52500 to gather and/or analyze surgical data associated with a surgical procedure. Surgical data may include data associated with a surgical procedure plan 52500 (e.g., comprising a set of surgical tasks), patient-related data, healthcare professional-related data, and/or other data (e.g., metrics associated with various surgical devices and/or instruments utilized during the surgical procedure). The analysis subsystem 52530, based the surgical data associated with a surgical procedure) may determine whether to request global or regional surgical information 52535 from a global cloud enterprise server 52540. For example, during a surgical procedure (e.g., at the beginning of a surgical procedure), the analysis subsystem 52530 associated with a surgical computing device/edge computing device 52500 may determine to send a request to the global cloud enterprise 52540 for receiving recommendations regarding surgical information related to a surgical procedure (e.g., default parameters, control algorithms, etc.) The global cloud enterprise 52540 may be located outside of the protected boundary 52525. In such a case, information located at the surgical computing device/edge computing device 52500 (e.g., in the database accessible by the surgical hub/edge device) that is sent outside of the protected boundary 52525 to the cloud server 52540 may be anonymized (e.g., redacted, randomized, summarized, averaged, etc.), as described herein. In determining whether a request may be sent to the enterprise global server 52540, the surgical computing device/edge computing device 52500 (e.g., via the analysis subsystem 52530) may consider one or more of the following: the surgical information (e.g., metrics) linked to the surgical task, the surgical task itself, the overall surgical procedure plan 52510, performance criteria related to the surgical task (e.g., overall latency needed for the endocutter to perform (e.g., autonomously perform) anastomosis successfully), capabilities of the surgical computing device/edge computing device 52500 and of the global cloud enterprise server 52540 the type of surgical data, etc.

The request message 52520 may include one or more of the following: an indication of the surgical procedure being performed, the current surgical task (e.g., if the request is sent during a surgical procedure), the request is associated with, and/or the surgical data (e.g., parameters associated with various surgical instruments and/or device and metrics gathered by the surgical computing device/edge computing device 52500 during a surgical task), anonymized patent-related information, etc. The request sent to the global cloud enterprise server 52540 may be for one or more global algorithms or default parameters that may be used for various surgical instruments and device relevant to the current surgical procedure being performed.

In an example, the information gathered by the surgical computing device/edge computing device 52500 and related to one or more surgical tasks of a surgical procedure and/or algorithms used by the local surgical systems may be sent to the enterprise cloud server 52540 prior to or after sending the request message 52520. The enterprise cloud server 52540 may use the surgical information received from various surgical computing device/edge computing device spread globally to train a global machine learning subsystem, as described with respect to FIG. 66. The global machine learning subsystem may learn which global or regional surgical information 52535 (e.g., recommendation) to send to the surgical computing device/edge computing device 52500 based on receiving a certain set of data related to a certain surgical task as input.

The surgical computing device/edge computing device 52500 may anonymize (e.g., redact, randomize, summarize, average, etc.) at least some of the data before sending it to the enterprise cloud server 52540. The surgical computing device/edge computing device 52500 may perform anonymization of data based on rules (e.g., privacy rules) of the location where the surgical computing device/edge computing device 52500 is located. When sending data outside of the protected boundary 52525 (e.g., outside of the protected network boundary), the surgical computing device/edge computing device 52500 may determine that the data has to be altered based on the rules. The surgical computing device/edge computing device 52500 may anonymize (e.g., redact, randomize, summarize, average, etc.) the data based on a set of rules. In examples, a subset of the data (e.g., subset of the data likely to be tied back to a patient) may be anonymized while another subset of the data may be sent in non-anonymized form to the enterprise cloud server 52540 or any other device in the surgical system hierarchy for processing, for example, as described in U.S. patent application Ser. No. 18/092,047, the disclosure of which is herein incorporated by reference in its entirety.

An enterprise cloud server 52540 located outside the protected boundary 52525 may receive the request message 52520 along with the patient surgical information and/or surgical instrument information related to a surgical procedure. The enterprise cloud server 52540 may maintain a global or regional data structure (e.g., global or regional database) of information associated with surgical procedures that were performed globally. In an example, the enterprise cloud server 52540 may compare the received information associated with a surgical procedure with one or more entries present in the data structure (e.g., an entry already in the database). Based on the comparison, the enterprise cloud server 52540 may generate global or regional surgical information 52535 (e.g., algorithm(s) and/or recommendation(s) to be sent to the surgical computing device/edge computing device 52500. The surgical information stored in the enterprise cloud server 52540 may include diverse surgical information received from healthcare facilities across the globe or a geographic region. The global or regional surgical information 52535 provided by the global enterprise cloud sever 52540 may include algorithms and parameters (e.g., patient data, healthcare provider data, surgical instrument data, etc.) for a surgical instrument 52505 that is performing the surgical task autonomously to be set at. For example, the global or regional surgical information 52535 may include algorithm(s) to be pushed to a surgical instrument/device (e.g., a smart surgical instrument/device). The global or regional surgical information 52535 may also include identification of the model of the surgical instrument/device to be used, and/or settings to be used by the surgical instrument/device. For example, the surgical instrument identified may be a specific model of an endocutter device, for example, for performing anastomosis in a surgical procedure. A setting to be used for the endocutter may be the firing rate setting.

In an example, the global or regional surgical information 52535 may include coordinates of a starting position for the surgical instrument 52505. In an example, the global or regional surgical information 52535 may include a sequence of coordinates that may be sent to the surgical computing device/edge computing device 52500. The surgical computing device/edge computing device 52500 may consider when setting parameters (e.g., patient data, healthcare provider data, surgical instrument data, etc.) associated with the movement of the surgical instrument 52505.

In an example, machine learning may be used by the enterprise cloud server 52540 to generate the global or regional surgical information 52535, for example, using global machine learning model or subsystem 52517. In an example, the machine learning model 52517 (e.g., using deep learning) may use the surgical task and surgical information (e.g., surgical information associated with the surgical task) as input to predict a set of parameters (e.g., parameters associated with patient information, healthcare provider information, surgical instrument information, etc.) to be used in a surgical procedure. The machine learning may also provide global or regional algorithm that may then be pushed to surgical instruments and/or devices via the surgical computing device or edge computing device 52500. The machine learning prediction may be based on a plurality of (e.g., a large number of) diverse datasets associated with surgical procedures that may have been performed on a variety of patients across various globally diverse locations. The global machine learning model 52517 may use a global machine learning model and/or a global trained machine learning model may be utilized as part of a supervised learning framework, for example, as described herein in FIG. 8A. The training data (e.g., training examples 802, as illustrated in FIG. 8A) may include a set of training examples (e.g., input surgical information mapped to labeled outputs, for example, as shown in FIG. 8A). The training data used in training the global machine learning model may include surgical information gathered from surgical procedures and/or simulated surgical procedures from across the globe or a region. The training data may include previous control algorithms associated with the surgical instruments (e.g., stored globally and/or received from various healthcare facilities across the globe or a region). The training data may also include parameters associated with a patient, a healthcare professional, and/or a surgical instrument. In an example, the global ML model as an output may provide control algorithms and/or surgical instrument parameters associated with the surgical instrument (e.g., firing rate of a surgical instrument).

The surgical computing device/edge computing device 52500 (e.g., using the analysis subsystem 52530) may analyze the global surgical information 52535 it received from the enterprise cloud server. When assessing the global surgical information 52535, the surgical computing device/edge computing device 52500 may access and/or consider the local information. The local information may include the information that was anonymized before being sent to the enterprise cloud server 52540. As described with respect to FIGS. 66 and 68, the surgical computing device/edge computing device 52500 may modify the received global surgical information 52535, for example, using the local information.

In an example, the surgical computing device/edge computing device 52500 may have access to local surgical information including the information that may have been anonymized (e.g., redacted, randomized, summarized, averaged, etc.) before sending it to the enterprise cloud server 52540 (e.g., enterprise cloud server). For example, the local data may be associated with a patient's fat percentage. This data may have been anonymized from the data set that was sent to the remote server 52540 (e.g., enterprise cloud server) due to a privacy rule (e.g., The Health Insurance Portability and Accountability Act (HIPAA) Privacy Rule, Art. 9 General Data Protection Regulation (GDPR), or Data Protection Act in the United Kingdom. The privacy rules may be used to protect health data, which is a special category of personal data and, therefore, subject to a higher level of protection that other personal data.

After the surgical computing device/edge computing device 52500 receives global or regional surgical information 52535 related to performing a surgical task, the surgical computing device/edge computing device 52500 may consider the local data related to the patient's fat percentage. The surgical computing device/edge computing device 52500 may adjust the global or regional surgical information 52535 based on the patient's fat percentage. The global or regional surgical information 52535 may include a recommendation to set one or more parameters (e.g., patient data, healthcare provider data, surgical instrument data, etc.) of a surgical instrument 52505 to a certain value. For example, the surgical computing device/edge computing device 52500 may receive global or regional surgical information 52535 associated with setting an endocutter to a recommended firing rate. Considering the fat percentage (e.g., high fat percentage which was not sent to the remote server), the surgical computing device/edge computing device 52500 may increase the firing rate before sending it (e.g., as local a local surgical information message 52545) as a parameter (e.g., patient data, healthcare provider data, surgical instrument data, etc.) to the surgical instrument 52505. Modifying the global or regional surgical information 52535 may involve adding weights (e.g., coefficients). For example, as shown in FIG. 65, A may be a constant value of 1.2, which may increase the firing rate of X by 0.2 or 20%.

In an example, the surgical computing device/edge computing device 52500 may override (e.g., completely override) the global or regional information (e.g., global recommendation or algorithm changes) based on the additional local information that may have been anonymized and therefore not available to the enterprise cloud server. For example, the surgical computing device/edge computing device 52500 may determine that one of the patient related parameters (e.g., patient's blood pressure) was sent to the enterprise cloud server 52540 in redacted form. The surgical computing device/edge computing device 52500 may also determine that the population of the locality where the surgical procedure is taking place is known to have fat percentages that are different than the global averages. Based on one or more of these determinations, the surgical computing device/edge computing device 52500 may determine that the global or regional surgical information 52535 received from the enterprise cloud server associated with the firing rate of a surgical instrument may not be suitable for the patient and, for example, may pose a serious risk to the patient. The surgical computing device/edge computing device 52500 may, therefore, revise the surgical information supplied by the enterprise cloud server 52540. The surgical computing device/edge computing device 52500 may then update the surgical information, for example, change the firing rate or update the algorithm based on the local patient information and/or demographic factors. In such a case, surgical computing device/edge computing device 52500 may override the recommended firing rate with its own firing rate, which may be based on private local data (e.g., data that was anonymized prior to sending it to the cloud) to the enterprise cloud server 52540. In an example, overriding the global recommendation or algorithm changes may be made based on the global recommendation not being compatible with the value generated by local machine learning within the surgical computing device/edge computing device 52500.

The parameters (e.g., patient data, healthcare provider data, surgical instrument data, etc.) or modified parameters may be sent from the surgical computing device/edge computing device 52500 to the surgical instrument 52505 in order for the surgical instrument to perform a surgical task (e.g., autonomously perform a surgical task). This may involve a local machine learning model 52515 located either at the surgical computing device/edge computing device 52500 or locally on the surgical instrument 52505. The machine learning model 52515 may use the parameters (e.g., patient data, healthcare provider data, surgical instrument data, etc.) to set the instructions for the surgical instrument 52505.

The request message 52520 may be sent at the beginning of performing the surgical tasks (e.g., each of the surgical tasks). For example, the surgical computing device/edge computing device 52500 may recognize a transition phase from a first surgical task to a second surgical task and may determine, via the analysis subsystem 52530, to send the request message 52520. In examples, the request message 52520 may be sent at periodic intervals throughout the performance of the surgical task. Sending the request message 52520 may be based on a trigger. For example, an error may be determined by the surgical computing device/edge computing device based on the performance of the surgical instrument. Determining the error is described in greater detail under the heading "METHOD OF CONTROLLING AUTONOMOUS OPERATIONS IN A SURGICAL SYSTEM" in U.S. Patent Application No. U.S. Ser. No. 17/747,806, filed May 18, 2022, the disclosure of which is herein incorporated by reference in its entirety. A simulation may be used to determine the threshold (e.g., an ideal threshold). Simulation framework may be described in "Method for Surgical Simulation" in U.S. patent application Ser. No. 17/332,593, filed May 27, 2021, the disclosure of which is herein incorporated by reference in its entirety. If the error crosses a threshold (e.g., configured threshold), the surgical computing device/edge computing device 52500 may trigger the request message 52520 to be sent to the remote server 52540 (e.g., enterprise cloud server). A cost analysis of the value of sending the request message 52520 and receiving globally supplied recommendation may be considered by the surgical computing device/edge computing device 52500. The surgical computing device/edge computing device 52500 may weigh the benefits and costs of sending the request message 52520 and receiving the global or regional surgical information 52535. The global or regional surgical information 52535 may be more accurate due to it being generated from a global machine learning model with a more diverse training set.

In an example, the surgical computing device/edge computing device 52500 may take recommendations received from the enterprise cloud server 52540 and modify (e.g., customize) them with the patient specific, population specific, or surgeon specific needs based on the individualized data (e.g., local surgical data, as described herein) available to it within the protected network.

In an example, the local machine learning model 52515 may be capable of making local modifications (e.g., customizations) to a globally supplied recommendation or algorithm, for example, by adjusting for a surgical instrument or surgical device based on local processing and local data.

In an example, the surgical computing device/edge computing device 52500 may have access to the private interrelation data of the patients, staff, and other confidential information. It may use that data to review and modify (e.g., customize) more global or regional algorithms supplied to it before the modified algorithms are pushed to the local surgical instruments or surgical devices 52505. In such a case, the global algorithm may benefit from the local private data without the data having to leave the protected local boundary 52525.

The global recommendations or algorithm changes may have pre-identified parameters or variables that may benefit from local procedure modifications, specific surgeon techniques, or sub-group patient data. These parameters may be identified within the pushed algorithm including the programs or manner needed to compile the local private data and insert them into the overarching algorithm update. For example, during a colonecomy surgical procedure, the surgical computing device/edge computing device 52500 may identify that it will be performing a defined procedure. As a part of the surgical procedure, the surgical computing device/edge computing device 52500 may reach out to an enterprise cloud server 52540 to request the surgical information that is used (e.g., required) during the surgical procedure, and one or more sets of default parameters associated with one or more surgical instruments or surgical devices. The surgical computing device/edge computing device 52500 may also obtain local parameters specific to patient and/or demographics or local healthcare facility procedures or supply/inventory availability. Such parameters may include characteristics that may be unique because of the demographics associated with the patient. Such parameters may also be unique because of the procedures adopted by local healthcare facilities and/or supply/inventory available in those healthcare facilities.

A described herein, the surgical computing device/edge computing device 52500 may 52500 may override, adjust, or modify the global or regional information or parameters received from the enterprise cloud server 52540 with local variables. The global or regional information or parameters may be modified for example, based on laws, procedures, techniques and/or devices available within a healthcare facility. In an example, the device targets/limits may be altered based on demographics associated with the patient and/or other patient information to modify (e.g., alter/shift) a surgical instrument's or surgical device's initial or default settings. The global/regional parameters may be set based on the surgical information collected from surgical procedures conducted across the globe or a region. The surgical computing device/edge computing device may modify (e.g., shift, weight or alter) the global variables with locally available information, for example, to optimize performance.

In an example, the surgical computing device/edge computing device 52500 may provide anonymized surgical information (e.g., datasets) to the enterprise cloud servers 52540. Based on the surgical information provided by various surgical computing devices/edge computing devices around the globe or a region, such surgical information enable enterprise cloud server to determine that there is a pattern and relationship between, for example, the orientation of two linear staple lines with respect to each other relative to the next step of the circular staple approximation and firing. This relationship may be highlighted in the colorectal leak rates relative to the surgical procedure plan 52510 or approach and the circular device force to fire (FTF) or force to clamp (FTC) being elevated. By reviewing further surgical information (e.g., an annotated video), the system may determine the pattern of the staple lines correlated well to the force to fire anomaly that may be correlated to the increased leak rate.

The enterprise cloud server 52540 may determine that in addition to alignment, additional factors may contribute to the outcome (e.g., because of the statistical probabilities accounted for a portion of the variance in the results. In such a case, the enterprise cloud server 52540 may determine recommendations (e.g., new recommendations) for staple line alignment (e.g., as seen through the scope) and for the force to fire thresholds and responses from the smart circular staple. The enterprise cloud server 52540 may push the parameter values and/or control algorithm updates to the surgical computing devices/edge computing devices 52500 for pushing or transferring them to the smart surgical instruments or smart surgical devices that may be connected with the surgical computing device or the edge computing device or when they connect with the surgical computing device or the edge computing device. The enterprise cloud server 52540 may indicate to the surgical computing device or the edge computing device 52500 that there may be relational data that the server may not have accounted for. The enterprise cloud server 52540 may recommend to the surgical computing device or the edge computing device 52500 to look for the sources of these issues and modify or adjust them (e.g., if possible).

A surgical computing device or an edge computing device 52500 located in a healthcare facility's network may identify additional relationships between various parameters that may be part of non-anonymized surgical information. Non-anonymized surgical information may include more complete patient medical record access than what is available to the enterprise cloud server (e.g., the redacted patient medical records that were sent to the cloud). In an example, the surgical computing device or an edge computing device 52500 may determine that combination of surgical information associated with a patient (e.g., the patient's blood pressure) and healthcare professional's techniques around mobilization of the colon may be correlated with an outcome. In an example, the surgical computing device or an edge computing device 52500, for example based on their usage or population, may modify or adjust the global parameters or control algorithm adjustments with the additional local updates, resulting in local modification (e.g., customization) of the pushed algorithm.

In an example, a healthcare facility may identify extenuation circumstances that may result in local modification or alteration of the received global or regional surgical parameter value updates and/or control algorithm updates. In an example, surgical computing devices/edge computing device 52500 may send the modified (e.g., customized) control algorithms to the enterprise cloud server 52540, without including any private patient information. The enterprise cloud system may then push it (e.g., automatically push or push based on a request) to other surgical computing devices/edge computing devices. In an example, the enterprise cloud system t may compare the modified or altered surgical information or control algorithm with the one it pushed earlier to determine the additional modifications (e.g., customizations), allowing it to start the learn process of looking for these interrelationship with the data it has access to.

Figure 66:
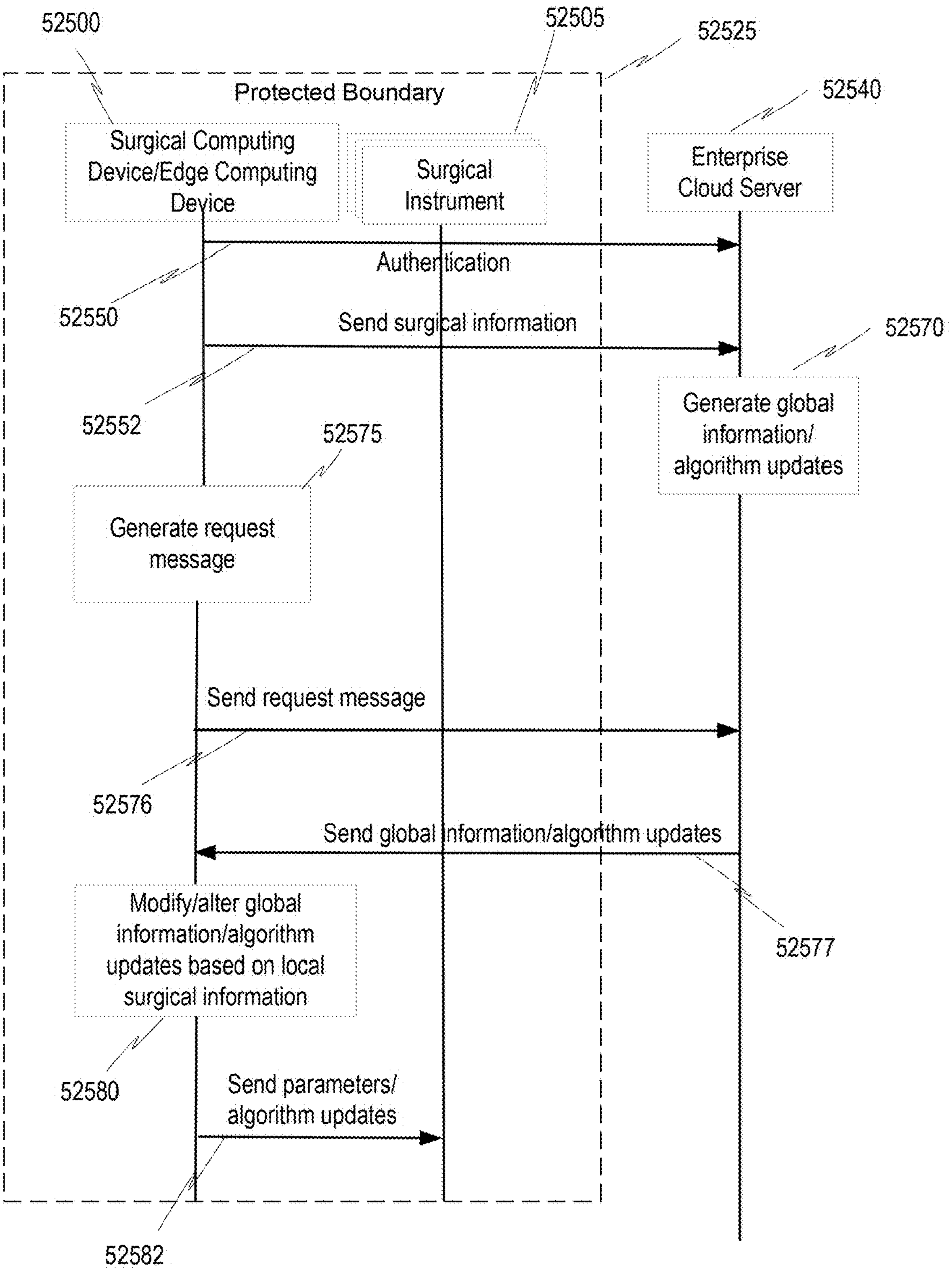
FIG. 66 shows an example of a message sequence diagram depicting communication and modification of global or regional information at a local device.

FIG. 66 illustrates an example of a message sequence diagram depicting communication (e.g., reception and/or transmission) and modification/customization/alternation of global or regional information at a local device, for example, a surgical computing device/edge computing device 52500 that is located within a protected boundary 52525. Global or regional information and globally or regionally supplied information may be used interchangeably herein.

As illustrated in FIG. 66, a surgical computing device/edge computing device 52500 may be provided, which may be the same as the surgical computing device/edge computing device 52500 described with respect to FIG. 65. The surgical computing device/edge computing device 52500 may be located within a hospital's internal network 52525 that is protected (e.g., based on HIPAA rules, as described herein).

A surgical instrument 52505 associated with the surgical computing device/edge computing device 52500 may be used to perform a surgical procedure (e.g., perform the surgical procedure autonomously). The surgical instrument 52505 may also be located within the protected boundary 52525, as described herein. The enterprise cloud server 52540 may be located outside of the protected boundary 52525. Surgical information (e.g., surgical information associated with a patient, a healthcare professional, or surgical instruments, etc.) sent to the enterprise cloud server 52565 may be vulnerable to exploitations. Such data within a protected network 52525 (e.g., data exchanged between a surgical instrument 52505 and a surgical computing device/edge computing device 52500) may be exchanged without being altered, whereas data that is sent outside of the protected boundary 52525 may be altered. For example, as described with respect to FIG. 66, the surgical information sent to an entity (e.g., an enterprise cloud server 52540) may be anonymized (e.g., redacted, summarized, etc.), randomized, encrypted, and/or manipulated. The surgical information may be anonymized such that the data cannot be traced back to the patient.

At 52550, a surgical computing device or a surgical edge computing device 52500 may establish an authenticated session with an enterprise cloud server 52540. To establish an authenticated session, the surgical computing device or a surgical edge computing device 52500 may register and perform authentication with the 52540. In an example, the authentication may be performed by using a message hash model-based encryption to achieve desired network latency and security during surgical information exchanges between the surgical computing device or a surgical edge computing device 52500 and the enterprise cloud server 52540. In an example, the surgical computing device or a surgical edge computing device 52500 may be pre-configured with authentication information, therefore, minimizing end-to-end delay to create a secure communication interface between the devices.

At 52552, the surgical computing device/edge computing device 52500 (e.g., surgical computing devices/edge computing devices spread across a region or across globe) may send surgical information to the enterprise cloud server 52540. The surgical information may include surgical information associated with one or more surgical instruments/devices 52505, patient-related surgical information, healthcare professional-related surgical information, etc. In an example, the surgical computing device/edge computing device 52500 may send the surgical information periodically, for example, based on a configured time period. In an example, the surgical computing device/edge computing device 52500 may send the surgical information aperiodically, for example, as an update based on a newly obtained local surgical information, for example, a parameter or a control program algorithm associated with a surgical instrument or device that is related to a surgical procedure outcome. In an example, the surgical computing device/edge computing device 52500 may send the surgical information aperiodically, for example, based on a request from the enterprise cloud server 52540.

At 52575, the surgical computing device/edge computing device 52500 may generate a request for receiving recommendations regarding surgical information related to a surgical procedure (e.g., default parameters, control algorithms, etc.) The surgical computing device/edge computing device 52500 may generate the request as a part of a surgical procedure (e.g., first step of a surgical procedure). At 52576, the surgical computing device/edge computing device 52500 may send the request to the enterprise cloud server 52540. The request may include identification of a surgical task, surgical instrument At 52577, the surgical computing device/edge computing device 52500 may receive from the enterprise cloud server 52540, recommendations regarding surgical information (instrument/device settings parameters, related to a surgical procedure. In an example, the recommendations may be received in response to the request sent by the surgical computing device/edge computing device 52500 or autonomously pushed (e.g., pushed periodically) by the enterprise cloud server 52540.

At 52580, the surgical computing device/edge computing device 52500 may modify/alter the received recommendations based on local surgical information, as described herein. At 52582, the surgical computing device/edge computing device 52500 may send the modified/altered recommendations to one or more of the surgical instruments/devices 52505.

Figure 67:
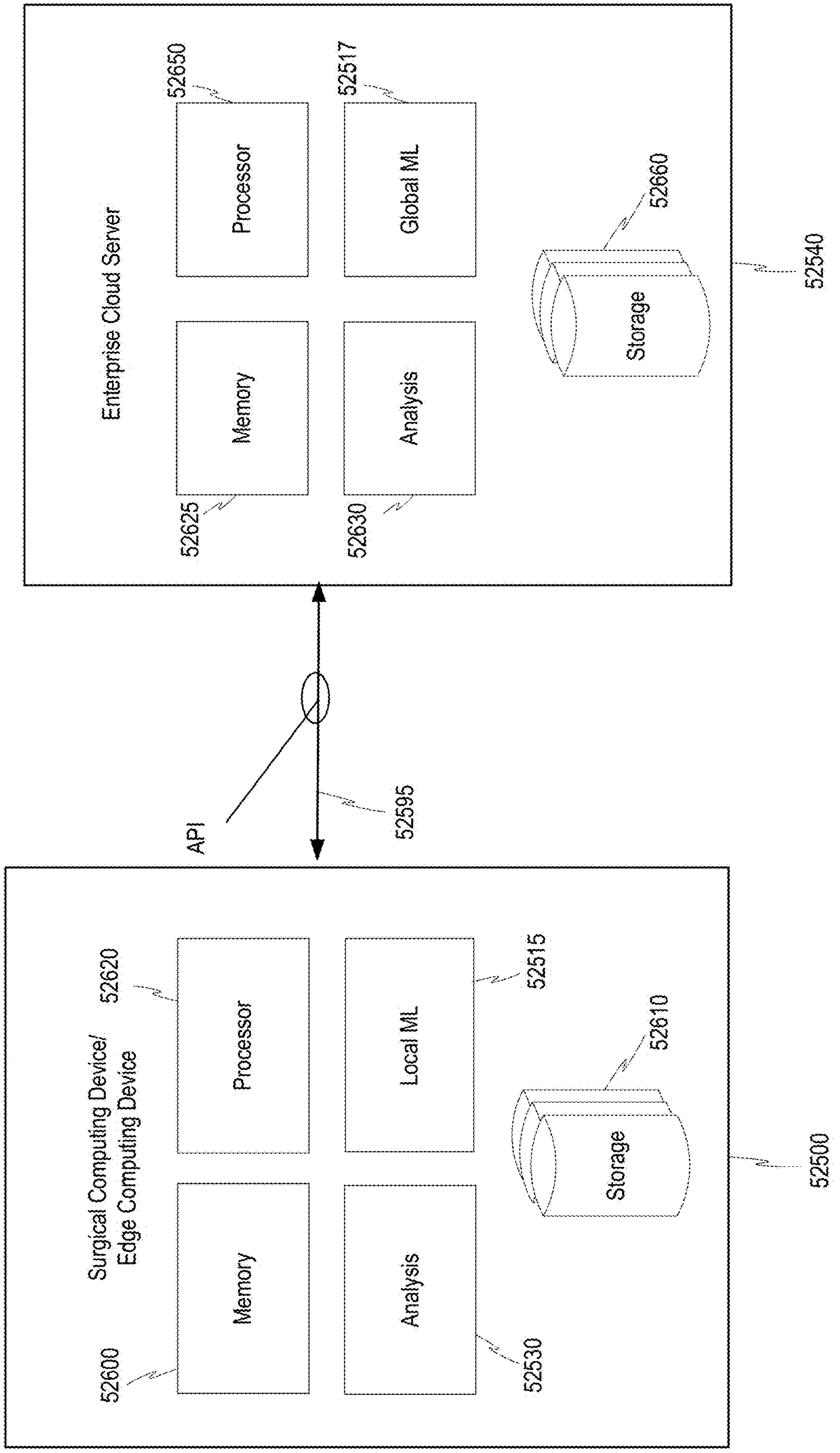
FIG. 67 shows an example of the relationship between the surgical computing device/edge computing device and the remote server.

FIG. 67 illustrates an example of the relationship between the surgical computing device/edge computing device 52500 and the enterprise cloud server 52540 (e.g., enterprise cloud server). As illustrated in FIG. 67, the surgical computing device/edge computing device 52500 may include a processor 52620, a memory 52600 (e.g., a non-removable memory and/or a removable memory), an analysis subsystem 52530, a local machine learning model 52515, and/or a local storage subsystem 52610, among others. It will be appreciated that the surgical computing device/edge computing device 52500 may include any sub-combination of the foregoing elements/subsystems while remaining consistent with an embodiment.

The processor 52620 in the surgical computing device/edge computing device 52500 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), a state machine, and the like. The processor 52620 may perform data processing, authentication, input/output processing, and/or any other functionality that may enable surgical computing device/edge computing device 52500 to operate in an environment that is suitable for performing surgical procedures. The processor 52620 may be coupled with a transceiver (not shown). The processor 52620 may use the transceiver (not shown in the figure) to communicate with the enterprise cloud server 52540.

The processor 52620 in the surgical computing device/edge computing device 52500 may access information from, and store data in, any type of suitable memory (e.g., a non-removable memory and/or the removable memory). The non-removable memory may include random-access memory (RAM), read-only memory (ROM), a hard disk, a solid-state drive or any other type of memory storage device. The removable memory may include secure digital memory.

The processor 52620 in the surgical computing device/edge computing device 52500 may access information from, and store data in an extended storage 52610. (e.g., a non-removable memory and/or the removable memory). In an example, the processor 52620 may access information from, and store data in, memory that is not physically located on the surgical computing device/edge computing device 52500, such as on a server or a secondary edge computing system (not shown).

As further illustrated in FIG. 67, an enterprise cloud server 52540 may include a processor 52650, a memory 52625 (e.g., a non-removable memory and/or a removable memory), an analysis subsystem 52630, a global machine learning model 52517, and/or a storage subsystem 52660, among others. It will be appreciated that the enterprise cloud server 52540 may include any sub-combination of the foregoing elements/subsystems while remaining consistent with an embodiment.

The processor 52650 in the enterprise cloud server 52540 may be a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Arrays (FPGAs) circuits, any other type of integrated circuit (IC), a state machine, and the like. The processor 52650 may perform data processing, authentication, input/output processing, and/or any other functionality that may enable the enterprise cloud server 52540 to operate in an environment that is suitable for performing surgical procedures. The processor 52650 in the enterprise cloud server 52540 may be coupled with a transceiver (not shown). The processor 52650 in the enterprise cloud server 52540 may use the transceiver to communicate with the surgical computing device/edge computing device 52500, for example, a secured interface, as described herein).

The processor 52650 in the enterprise cloud server 52540 may access information from, and store data in, any type of suitable memory (e.g., a non-removable memory and/or the removable memory). The non-removable memory may include random-access memory (RAM), read-only memory (ROM), a hard disk, a solid-state drive or any other type of memory storage device. The removable memory may include secure digital memory.

The processor 52650 in the enterprise cloud server 52540 may access information from, and store data in an extended storage 52660. (e.g., a non-removable memory and/or the removable memory). In an example, the processor 52650 in the enterprise cloud server 52540 may access information from, and store data in, memory that is not physically located on the in the enterprise cloud server 52540, such as on a server or a secondary edge computing system (not shown).

As further illustrated in FIG. 67, surgical information (e.g., including surgical instrument settings parameter values, control program algorithms, and/or updates associated with the control program algorithms) may be sent to and/or received from the surgical computing device/edge computing device 52500 to enterprise cloud server 52540. In examples, the surgical information may pass through an application programming interface 52595 (API) that may available, for example, after establishing a secured interface between the surgical computing device/edge computing device 52500 and the enterprise cloud server 52540, as described herein. The surgical information may include measurements taken from sensors, actuators, robotic movements, biomarkers, surgeon biomarkers, visual aids, and/or the like. The surgical information may also include healthcare professional-related information, and/or patent-related information, for example, obtained from a billing subsystem or database. The wearables are described in greater detail under the heading "Monitoring Of Adjusting A Surgical Parameter Based On Biomarker Measurements" in U.S. patent application Ser. No. 17/156,28, filed Nov. 10, 2021, the disclosure of which is herein incorporated by reference in its entirety.

Figure 68:
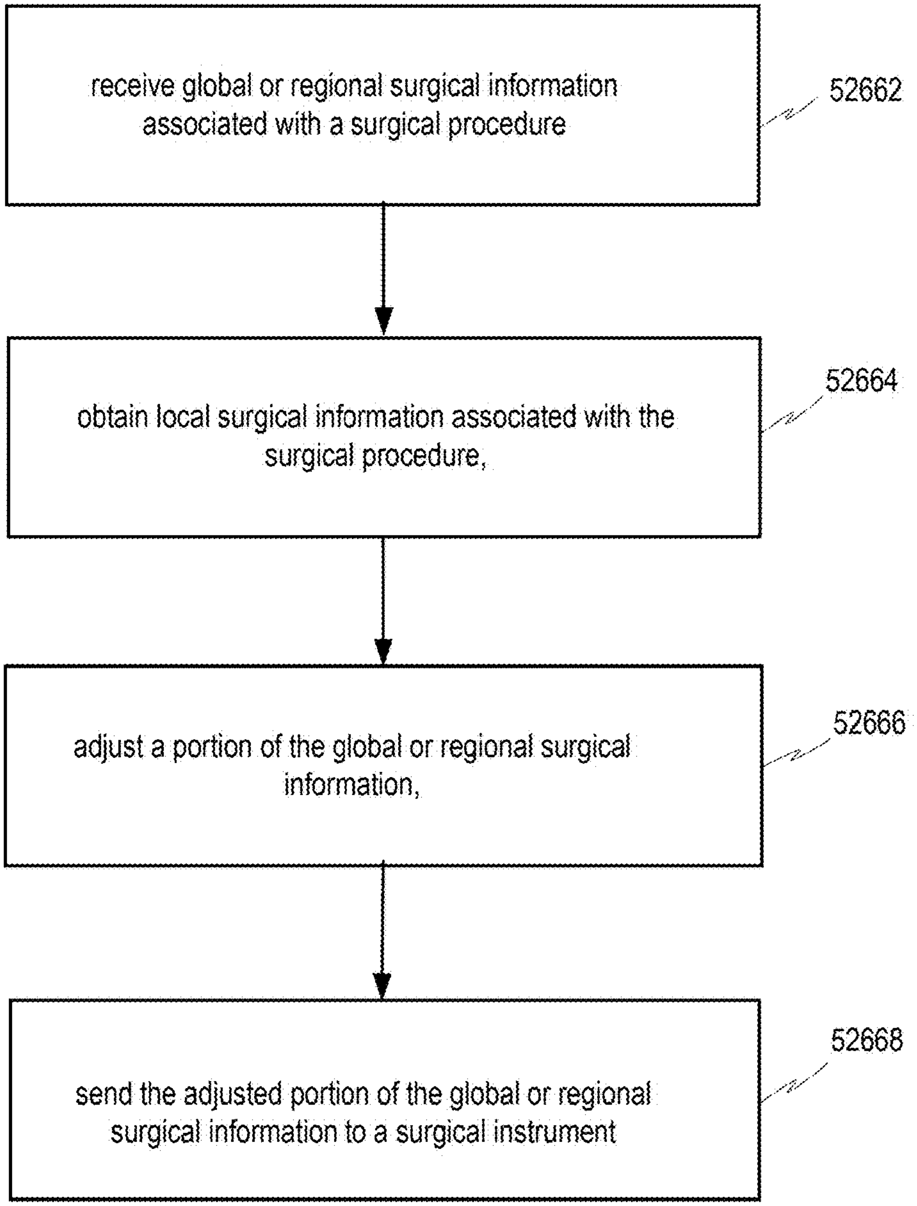
FIG. 68 shows an example of a flow chart of modifying globally or regionally supplied information

FIG. 68 shows an example of a flow chart of a surgical computing device/edge computing device 52500 adjusting or modifying global or regional surgical information provided by an enterprise cloud server 52540. The surgical computing device/edge computing device 52500 may be located inside a protected network (e.g., a HIPAA protected network) and the enterprise cloud server 52540 may be located outside the protected network.

At 52662, a surgical computing device/edge computing device 52500 may receive global or regional surgical information associated with a surgical procedure (e.g., one or more surgical tasks of a surgical procedure) from an enterprise cloud server 52540. In an example, the surgical computing device/edge computing device 52500 may receive the global or regional surgical information in response to a request message sent by the surgical computing device/edge computing device 52500 to the enterprise cloud server 52540. The request message may be generated based on a trigger event occurring.

At 52664, the surgical computing device/edge computing device 52500 may obtain (e.g., from a surgical instrument) local surgical information. The local surgical information may be associated with a patient and/or a patient's location. The local surgical information may include at least one of the following: demographics, a local healthcare procedure, supply or inventory status, or control algorithm associated with a surgical instrument. The local surgical data may be based on characteristics of a local surgical procedure.

At 52666, the surgical computing device/edge computing device 52500 may adjust or modify at least a portion of the global or regional surgical information associated with a local surgical procedure and/or the patient. In an example, adjusting or modifying a portion of the global or regional surgical information may include adjusting or modifying a global control algorithm using at least one local update. In an example, the portion of the global or regional surgical information portion may be adjusted or modified based on at least one of the following: privacy laws, procedures, techniques or device availability within a healthcare facility where the surgical procedure is being performed. In an example, adjusting at least a portion of the global or regional surgical information may be based on a neural network analysis of the global or regional surgical information, the local surgical data and/or the patient-related data. A neural network may be trained using global or regional surgical information, local surgical information, and patient-related surgical information to determine how to adjust at least a portion of the global or regional surgical information.

At 52668, the surgical computing device/edge computing device 52500 may send the adjusted global or regional surgical information to a surgical instrument. In an example, the adjusted global or regional control algorithm received from the enterprise server 52540 may be sent to the surgical instrument.

The invention claimed is:

1. A computer-implemented method, where the computer performs each of the steps of the method, the steps comprising:

receiving surgical operation data associated with a surgical operation, based on the surgical operation data, identifying a surgical device to be used for the surgical operation and a surgical step associated with the surgical operation;

based on the identified surgical device and surgical step, accessing surgical device data and surgical step data that comprises operation range data for the surgical device corresponding to the surgical step;

training a first machine learning model based on the surgical device data, the surgical step data, and the surgical operation data, determining an allowable operation range associated with the surgical device using the first machine learning model, wherein the allowable operation range is an operation range to control the surgical device for the surgical step;

training a second machine learning model based on the surgical device data, the surgical step data, and the surgical operation data;

generating an adjustment input configuration using the second machine learning model, wherein the adjustment input configuration is configured to control the surgical device for the surgical step;

determining whether the adjustment input configuration is within the determined allowable operation range;

based on a determination that the adjustment input configuration is within the allowable operation range, adjusting an input to control the surgical device for the surgical step using the adjustment input configuration; and based on a determination that the adjustment input configuration is outside of the allowable operation range, blocking the adjustment input configuration to control the surgical device.

2. The method of claim 1, further comprising:

receiving updated surgical operation data associated with the surgical operation;

updating the first machine learning model based on the updated surgical operation data; and changing the allowable operation range associated with the surgical device based on the updated first machine learning model.

3. The method of claim 1, further comprising:

configuring the second machine learning model to have a magnitude limit or a frequency limit associated with the adjustment input configuration.

4. The method of claim 3, wherein the magnitude limit or the frequency limit is based on an aspect of the surgical operation.

5. The method of claim 3, wherein the magnitude limit or the frequency limit is based on an effect or a frequency of at least one previous adjustment.

6. The method of claim 3, wherein the magnitude limit or the frequency limit is based on a historic adaptation.

7. The method of claim 1, wherein the trained first machine learning model provides a range of control inputs that have a high success rate for the surgical step, and wherein the determination of the allowable operation range associated with the surgical device is based on the range on control inputs.

8. The method of claim 1, wherein the surgical operation data is data associated with at least one of a patient, a health care provider, the surgical device, a risk involved in the surgical operation, a user input, a magnitude of a risk of failure, a risk of an anticipated consequence, or a risk or an unanticipated consequence.

9. The method of claim 8, wherein the data associated with the patient includes data associated with at least one of a body mass index, height, weight, or medical history.

10. The method of claim 8, wherein the data associated with the health care provider includes data associated with at least one of a number of times performing a surgical procedure, a success rate, a preferred setting for using the surgical device, or other health care providers performing the surgical operation.

11. A surgical device, comprising: a processor configured to:

receive surgical operation data associated with a surgical operation, wherein the surgical operation data comprises information associated with at least one of a patient, a healthcare professional (HCP), or a surgical device to be used for the surgical operation;

based on the surgical operation data, identify a surgical device to be used for the surgical operation and a surgical step associated with the surgical operation;

based on the identified surgical device and surgical step, access surgical device data and surgical step data that comprises operation range data for the surgical device corresponding to the surgical step;

train a first machine learning model based on the surgical device data, the surgical step data, and the surgical operation data;

determine an allowable operation range associated with the surgical device using the first machine learning model, wherein the allowable operation range is an operation range to control the surgical device for the surgical step;

train a second machine learning model based on the surgical device data, the surgical step data, and the surgical operation data;

generate an adjustment input configuration using the second machine learning model, wherein the adjustment input configuration is configured to control the surgical device for the surgical step;

determine whether the adjustment input configuration is within the determined allowable operation range;

based on a determination that the adjustment input configuration is within the allowable operation range, adjust an input to control the surgical device for the surgical step using the adjustment input configuration; and based on a determination that the adjustment input configuration is outside of the allowable operation range, block the adjustment input configuration to control the surgical device.

12. The surgical device of claim 11, wherein the processor is further configured to:

receive updated surgical operation data associated with the surgical operation;

update the first machine learning model based on the updated surgical operation data; and change the allowable operation range associated with the surgical device based on the updated first machine learning model.

13. The surgical device of claim 12, wherein the processor is further configured to:

configure the second machine learning model to have a magnitude limit or a frequency limit associated with the adjustment input configuration.

14. The surgical device of claim 13, wherein the magnitude limit or the frequency limit is based on an aspect of the surgical operation.

15. The surgical device of claim 13, wherein the magnitude limit or the frequency limit is based on an effect or a frequency of at least one previous adjustment.

16. The surgical device of claim 13, wherein the magnitude limit or the frequency limit is based on a historic adaptation.

17. The surgical device of claim 11, wherein the trained first machine learning model provides a range of control inputs that have a high success rate for the surgical step, and wherein the determination of the allowable operation range associated with the surgical device is based on the range on control inputs.

18. The surgical device of claim 11, wherein the surgical operation data is data associated with at least one of a patient, a health care provider, the surgical device, a risk involved in the surgical operation, a user input, a magnitude of a risk of failure, a risk of an anticipated consequence, or a risk or an unanticipated consequence.

19. The surgical device of claim 18, wherein the data associated with the patient includes data associated with at least one of a body mass index, height, weight, or medical history.

20. The surgical device of claim 18, wherein the data associated with the health care provider includes data associated with at least one of a number of times performing a surgical procedure, a success rate, a preferred setting for using the surgical device, or other health care providers performing the surgical operation.

* * * * *